(12) United States Patent
Ricciardi et al.

(10) Patent No.: US 11,324,845 B1
(45) Date of Patent: May 10, 2022

(54) HEATED AIRFLOW AND AIR FILTRATION APPARATUS FOR MULTI-FUNCTION SANITIZATION, DISINFECTION AND STERILIZATION

(71) Applicants: Jonathan J. Ricciardi, Wausau, WI (US); Carl L. Ricciardi, Tomahawk, WI (US); Jonathan D. Yoder, Goshen, IN (US); Jim Gerend, Cedar Grove, WI (US)

(72) Inventors: Jonathan J. Ricciardi, Wausau, WI (US); Carl L. Ricciardi, Tomahawk, WI (US); Jonathan D. Yoder, Goshen, IN (US); Jim Gerend, Cedar Grove, WI (US)

(*) Notice: Subject to any disclaimer, the term of this patent is extended or adjusted under 35 U.S.C. 154(b) by 0 days.

(21) Appl. No.: 17/156,689

(22) Filed: Jan. 25, 2021

Related U.S. Application Data

(63) Continuation of application No. 16/935,132, filed on Jul. 21, 2020, and a continuation-in-part of application No. 16/136,221, filed on Sep. 19, 2018.

(60) Provisional application No. 62/560,895, filed on Sep. 20, 2017.

(51) Int. Cl.
*A61L 2/22* (2006.01)
*A61L 2/06* (2006.01)
*A61L 2/26* (2006.01)

(52) U.S. Cl.
CPC ............... *A61L 2/22* (2013.01); *A61L 2/06* (2013.01); *A61L 2/26* (2013.01); *A61L 2202/121* (2013.01); *A61L 2202/122* (2013.01); *A61L 2202/13* (2013.01)

(58) Field of Classification Search
CPC ............... A61L 2/22; A61L 2/06; A61L 2/26
See application file for complete search history.

(56) References Cited

U.S. PATENT DOCUMENTS

| | | | | |
|---|---|---|---|---|
| 4,898,713 | A * | 2/1990 | Picard | A61L 2/204 422/3 |
| 5,965,087 | A * | 10/1999 | Caracciolo, Jr. | A61L 2/202 119/300 |
| 7,641,130 | B2 | 1/2010 | Ricciardi et al. | |
| 7,871,016 | B2 | 1/2011 | Ricciardi et al. | |
| 8,062,590 | B1 | 11/2011 | Baumgartner | |
| 8,074,896 | B2 | 12/2011 | Ricciardi et al. | |
| 8,110,156 | B2 | 2/2012 | Ricciardi et al. | |
| 8,177,142 | B2 | 5/2012 | Ricciardi et al. | |
| 8,196,604 | B1 | 6/2012 | Ricciardi et al. | |
| 9,439,991 | B2 | 9/2016 | Schwartz et al. | |
| 9,551,996 | B2 | 1/2017 | Ricciardi et al. | |
| 2005/0013726 | A1* | 1/2005 | Hill | A61L 2/28 422/3 |
| 2006/0286921 | A1* | 12/2006 | Arts | F24F 8/10 454/187 |
| 2010/0226821 | A1* | 9/2010 | Ricciardi | A61L 2/04 422/33 |
| 2011/0256041 | A1* | 10/2011 | Ho | C23C 16/4402 423/210 |
| 2015/0113927 | A1* | 4/2015 | Wright | B01L 1/04 55/385.2 |

* cited by examiner

*Primary Examiner* — Kevin Joyner
(74) *Attorney, Agent, or Firm* — Donald J. Ersler

(57) ABSTRACT

Methods and apparatus for the sanitization, detoxification, disinfection, high level disinfection, or sterilization of both the interior and exterior surfaces of at least one object.

15 Claims, 100 Drawing Sheets

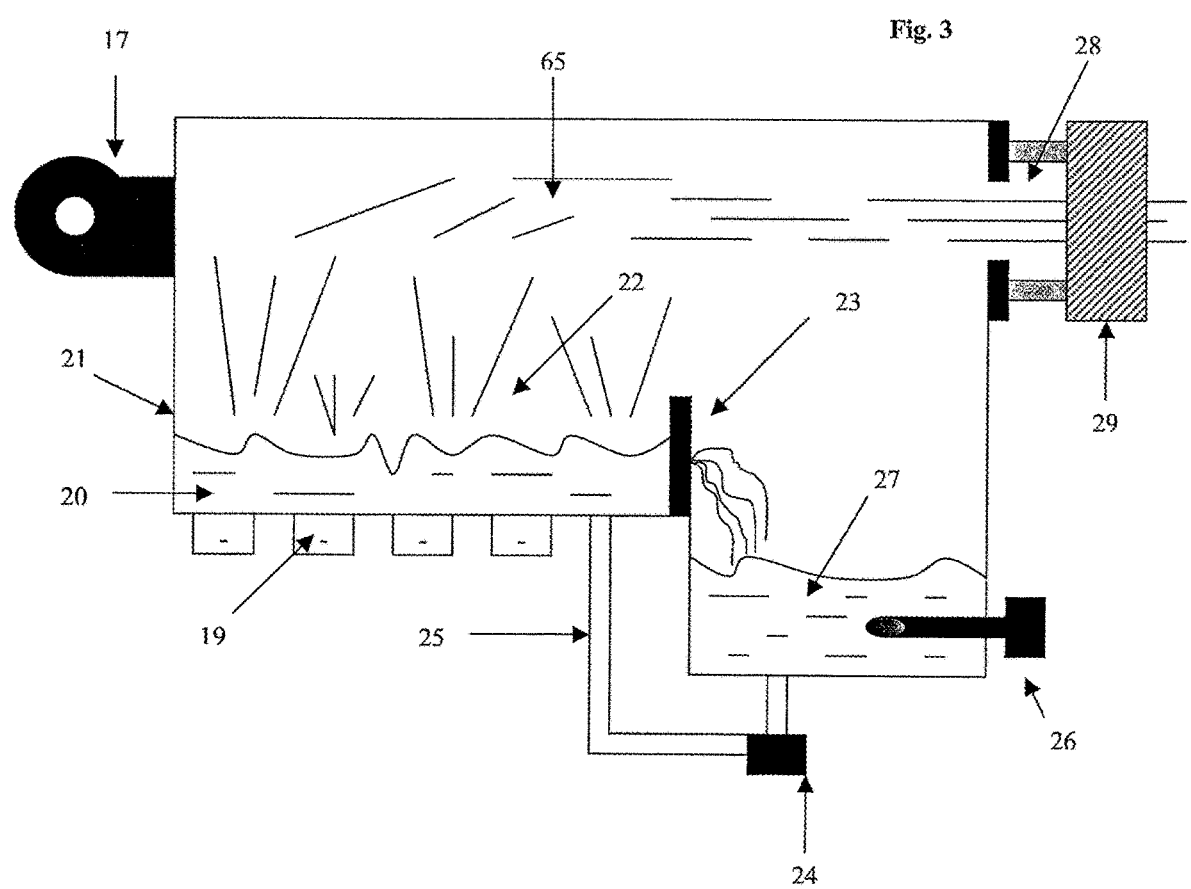

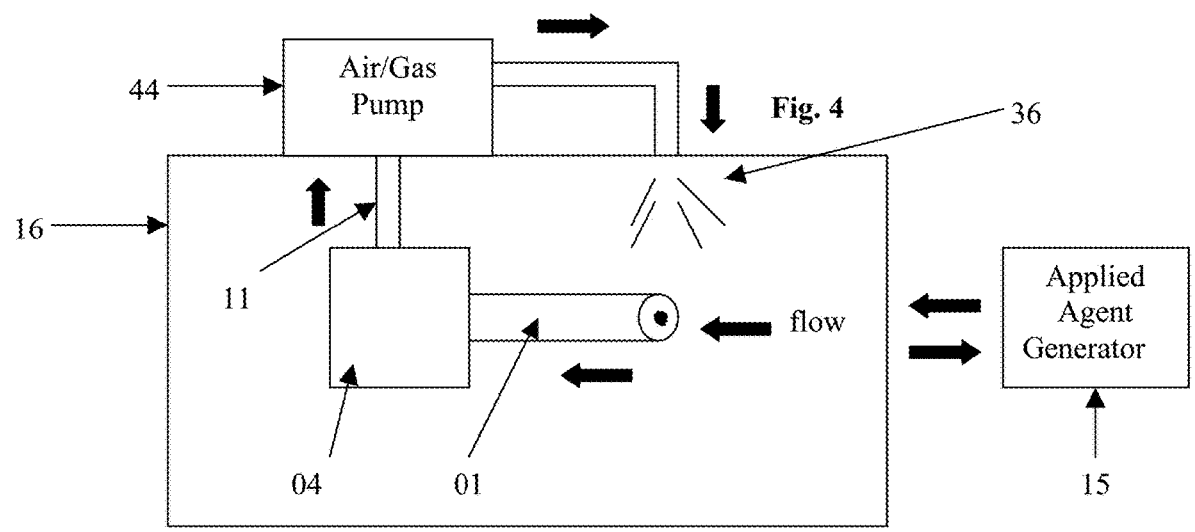
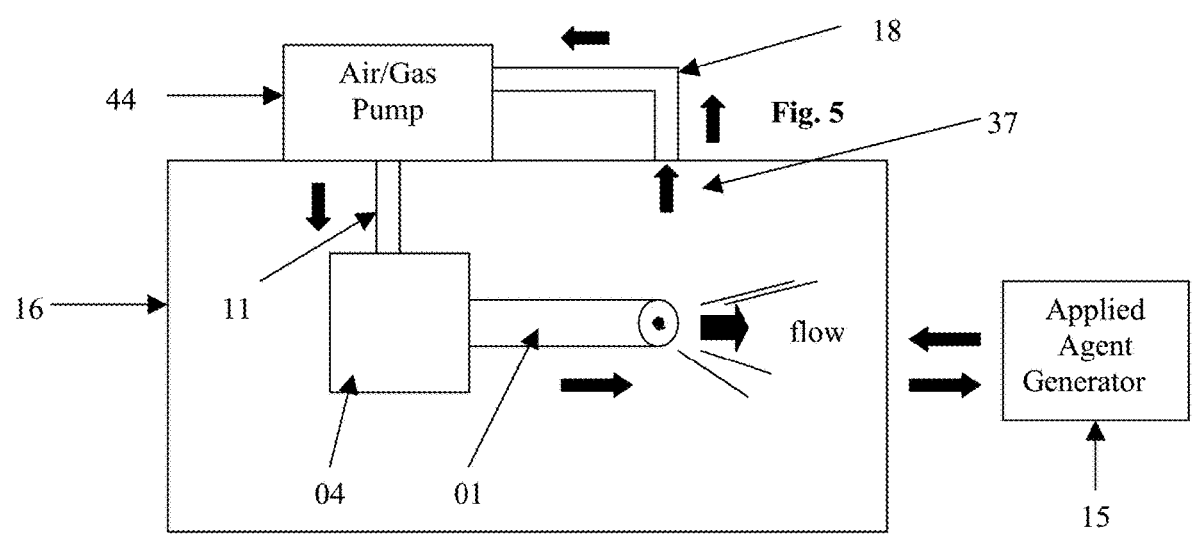

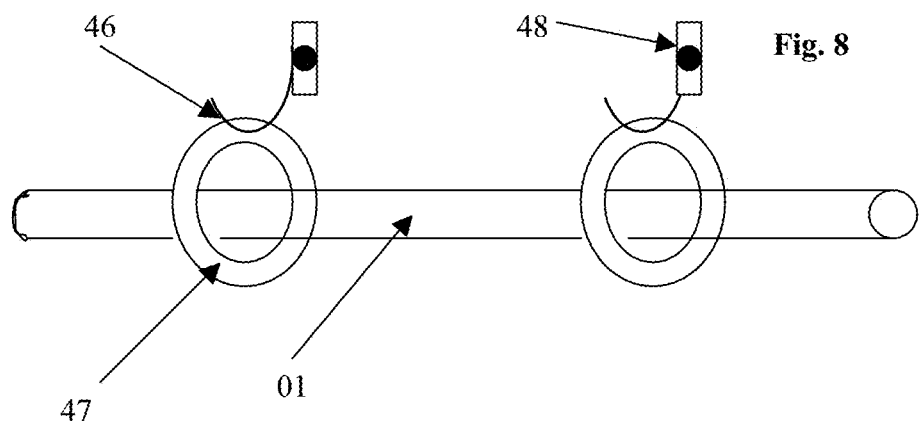
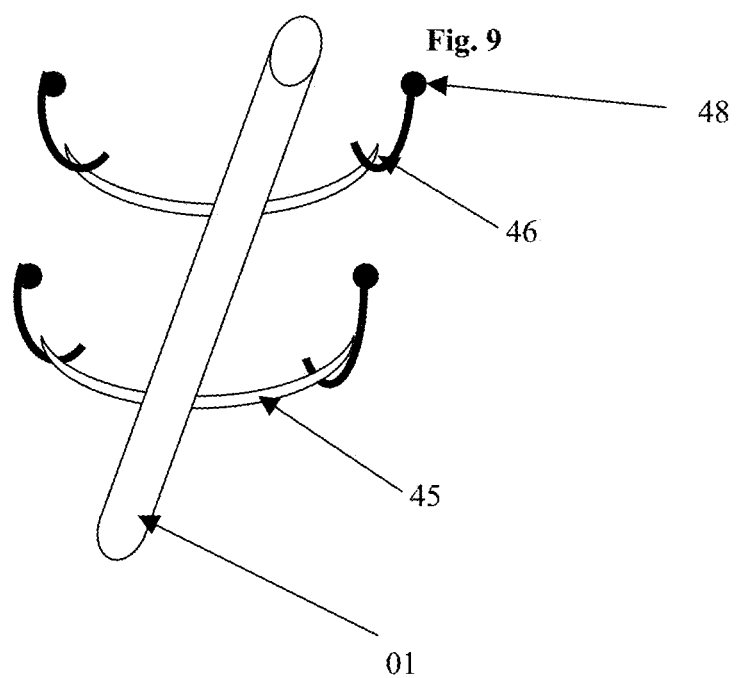

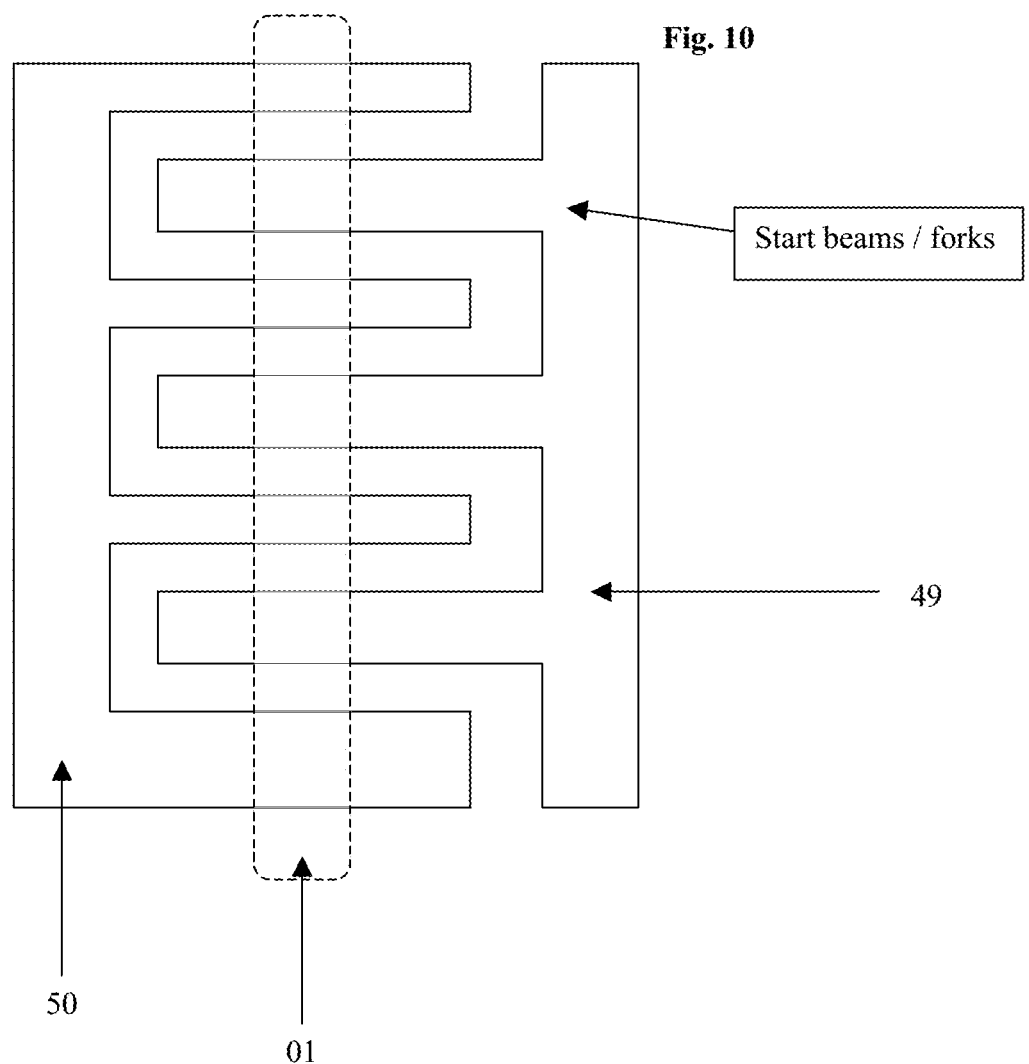
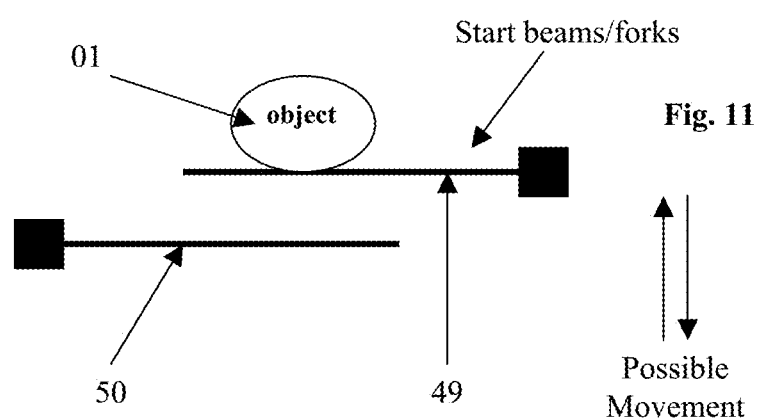

FIG 108
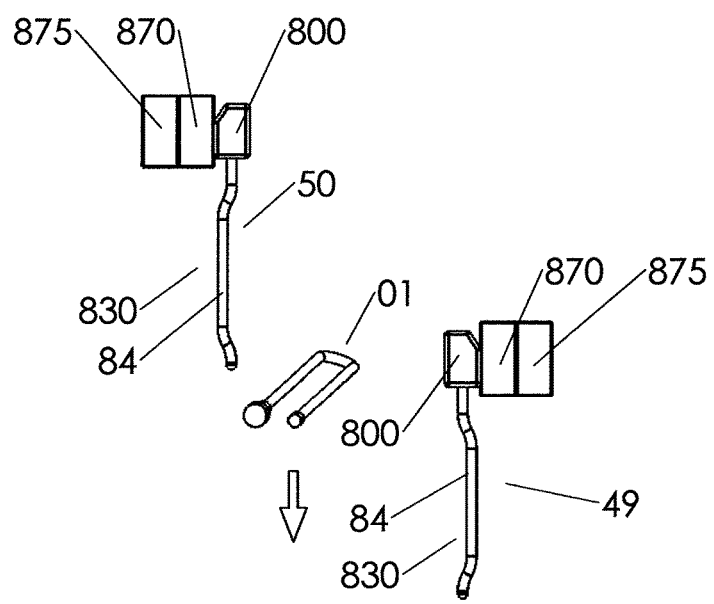
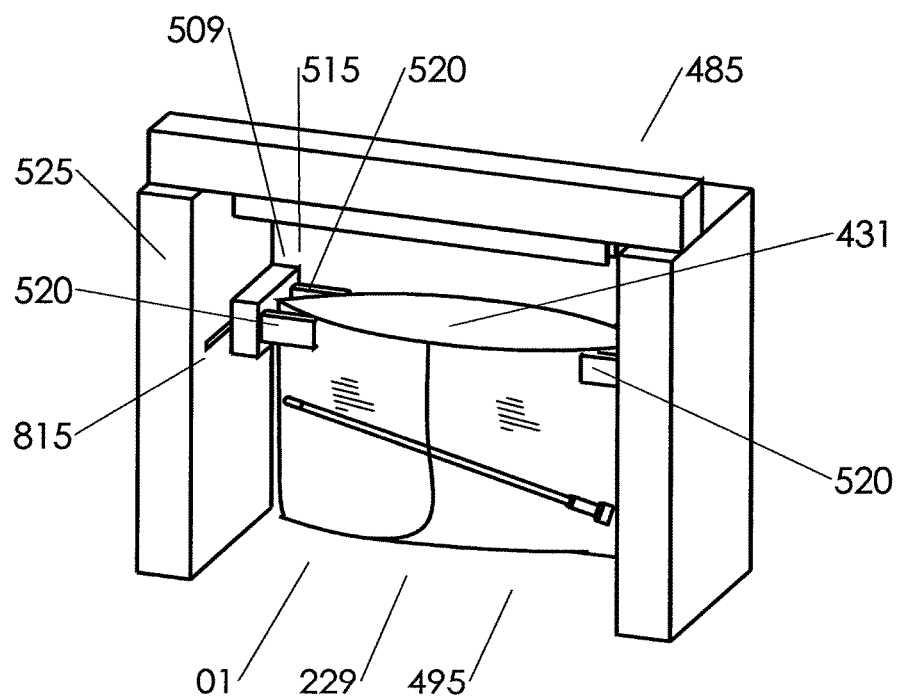

HEATED AIRFLOW AND AIR FILTRATION APPARATUS FOR MULTI-FUNCTION SANITIZATION, DISINFECTION AND STERILIZATION

CROSS-REFERENCES TO RELATED APPLICATIONS

This is a continuation in part application, which claims priority from patent application Ser. No. 16/136,221, filed on Sep. 19, 2018, which claims the benefit of provisional application No. 62/560,895 filed on Sep. 20, 2017; and which claims priority from patent application Ser. No. 16/935,132, filed on Jul. 21, 2020, which are herein incorporated by reference in their entirety.

RELATED APPLICATIONS

The following patent applications and patents are herein incorporated by reference in their entirety: U.S. Pat. Nos. 7,641,130, 7,871,016, 8,074,896, 8,110,156, 8,177,142, 8,196,604, 8,506,900, 8,821,807, 9,408,931, 9,551,996, 10029274, 10195632 and 10213803.

TECHNICAL FIELD OF THE INVENTION

The present invention relates to improved disinfection apparatuses and methods for use of those apparatuses, including but not limited to the simultaneous or non-simultaneous, sanitization, disinfection, high-level disinfection, or sterilization of one or more internal and exterior surfaces, or areas, of objects or spaces, as well as the airborne delivery of various types of agents, for various purposes, to an area, and without limitation, their surfaces. These areas may include one or more surfaces that are interfaced or articulated.

Additionally, the present invention relates to an improved means to support or hold one or more of any objects such as, but not limited to any endoscope(s), and ultrasonic probe(s), including any attached objects such as, but not limited to any, tube(s), pipes, cable(s), fiber optic line(s), cable(s), plug(s), connector(s), and/or wire(s), within any suitable enclosure(s) and/or removable enclosure(s), and to treat the one or more of any surfaces of any of the supported object(s), including any surfaces of any object(s) that are interfaced or connected with the one or more of means to support or hold the various object(s).

The present invention also relates to an improved means of treating various surfaces within one or more of any removable treatment enclosure(s), including any surfaces of any treated object(s) within the removable treatment enclosure(s), whereby any treatment agent(s), air, and/or gas(s), that are moved into the removable treatment enclosure(s), are used for purposes such as, but not limited to, to treat and/or decontaminate, dry, remove any vapor(s) and/or undesired gas(s), and/or process, the various surfaces within the enclosure(s), are all flowed into, through, and then out of, the removable treatment enclosure(s). Also, the removable treatment enclosure(s) can be optionally and effectively sealed upon the disconnection of the removable enclosure(s) from any connecting tube(s), pipe(s), cable(s), fiber optic line(s), cable(s), wire(s), plug(s), connector(s), and/or wire(s), or the like. The removable treatment enclosure can also, and without limitation, include various means to support and/or hold one or more of any object(s). The removable treatment enclosure can also, and without limitation, include any effective means to suspend the one or more of any object(s) within the removable treatment enclosure(s) so that there is a complete or at least efficacious treatment and/or decontamination of any of the targeted surface(s) of the treated object(s).

The present invention also relates to an improved means to treat the surfaces of one or more objects positioned inside of, and more preferably that is effectively hung and/or suspended inside of, including with any of their one or more of any connected objects such as but not limited to any, tube(s), pipe(s), cable(s), fiber optic line(s), cable(s), wire(s), plug(s), connector(s), and/or wire(s), one or more of any enclosure(s) and/or removable enclosure(s), where various new means are described to hold, position, or hang the various object(s) within the enclosure(s) and/or removable enclosure(s), so that they do not contact various other surfaces within the enclosed space(s) resulting in one or more surface(s) that are shadowed or unable to be suitably treated. Also, once the one or more object(s) are treated, the one or more of any effective apparatus(s) holding the one or more of the said object(s) can automatically or manually release the object(s) so they can fall via the force of gravity through at least one suitable opening(s) in at least one suitable package(s) located below the said object(s), and be effectively held in that package(s) where the package(s) can then be optionally and effectively sealed with the said object(s) contained inside the package.

The present invention also relates to improved means for treating one or more of any suspended object(s) suitably located effectively above and/or within one or more of any suitable and effective open package(s) in at least one of any suitable enclosure(s) and/or removable enclosure(s). Without limitation, the package(s) can be open on the top, bottom, or both top and bottom, for exposure to the treatment agent, but at least on one or more of any suitable side(s) of the package.

The present invention also relates to various apparatuses that are used to release the one or more object(s) that are suspended, supported, and/or held, within any suitable enclosure(s) and/or removable enclosure(s), so they can be effectively moved and/or located, preferably and without limitation, moved and/or fall, via the force of gravity after being released by any suitable, holding, suspension, and/or supporting, apparatus(s), through at least one suitable opening(s) in any suitable and effective package(s), and into at least one suitable package(s) located preferably, and without limitation, below the said object(s).

The present invention also relates to an improved means for packaging one or more treated object(s) within one or more enclosure(s), where the package and/or packaging material is moved up from underneath the one or more object(s) that are effectively held, located, and/or suspended within the enclosure(s) until the package and/or packaging material suitably and effectively surrounds the one or more object(s). The one or more of any effective apparatus(s) holding the one or more of the said object(s) can automatically or manually release the object(s) so they can fall via the force of gravity through at least one suitable opening(s) in at least one suitable package(s) located below the said object(s), and be effectively held in that package(s) where the package(s) can then be optionally and effectively sealed with the said object(s) contained inside the package.

The present invention also relates generally to the sanitization, disinfection, high level disinfection, sterilization, cooling, and/or drying, of any contaminated and/or biological contaminated, object(s), equipment(s), machine(s), device(s), accessory(s), and/or tool(s), such as those found, and without limitation, in any, medical, governmental, food, pharmaceutical, medical device, military, dental, scientific, life science(s), and/or industrial, commercial fields and/or industries, such as, but not limited to any, object(s), such as, but not limited to any, instrument(s), equipment(s), packaging equipment(s), packaging material(s), food(s), sensor(s), power supply(s), medical equipment(s), dental equipment(s), industrial equipment(s), military equipment(s), product(s), accessory(s), device(s), tool(s), sensor(s), probe(s), ultrasonic probe(s), ultrasonic imaging device(s), esophageal imaging device(s), component(s), parts(s), component(s), cable(s), conduit(s), wire(s), dental device(s), object(s), equipment(s), accessory(s), tool(s), cord(s), tube(s), pipe(s), wire(s), hose(s), conduit(s), scope(s), endoscope(s), medical device(s), ultrasonic device(s), imaging device(s), imaging device(s) component(s), scope(s), medical scope(s), dental scope(s), scientific scope(s), electronic(s), cable(s), cutting tool(s), irrigation device(s), suction device(s), vacuum device(s), drilling device(s), stethoscope(s), umbilical connector(s), computer mouse(s) and attached cable(s), clamp(s), cord(s), blood pressure measuring and reporting device(s), stethoscope(s), ECG device(s), SPO2 device(s), temperature sensing device(s), TOCO device(s), and/or patient monitoring equipment or device(s), including, but not limited to, any of their or associated, part(s), accessory(s), device(s), and component(s), (Herein after called "object(s)" or "treated object(s)"), and more specifically to a multi-function surface treatment chamber(s) and/or enclosure(s).

More specifically, and without being limited, the improved cabinet mounted treatment chamber processing system and improved chamber and/or enclosure mobile processing system, described in the present invention, can treat, process, sanitize, disinfect, high-level disinfect, sterilize, dry, and/or cool, one or more of any suitable and effective enclosure(s) and/or chamber(s) that can be used for various purposes such as, but not limited to any, production and/or packaging of any, food, medical product(s), pharmaceuticals, and/or medical devices, as well as the treatment, processing, sanitization, disinfection, high-level disinfection, sterilization, and/or drying, of one or more of any suitable object(s) such as, but not limited to any, tool(s), mask(s), hospital PPE, N95 mask(s), P100 mask(s), face shield(s), endoscope(s), scope(s), blood pressure cuff(s) and any attached device(s), imaging device(s), device(s) and any of their attached cable(s) and/or cord(s), medical device(s), medical product(s), cable(s), cord(s), wire(s), patient monitoring cable(s) and any attached electronic(s), food product(s), pharmaceutical product(s), that can be located, held, suspended, and/or supported, at any suitable and effective location(s) within the said treatment enclosure(s) and/or treatment chamber(s), all in a manner known to those skilled in the art.

Even more specifically, and without limitation, the current invention relates generally to an improved multi-function decontamination, sanitization, disinfection, high-level disinfection, and/or sterilization cabinet(s), for one or more of any surface(s) of one or more of any object(s), which provides and allows for preferably, but not limited to, the decontamination, sanitization, disinfection, high-level disinfection, sterilization, drying, and/or cooling, of various object(s), preferably, and without limitation, at any suitable and effective temperature(s), and more preferably and without limitation, at any suitable and effective low temperature(s), while achieving, without limitation, at least any suitable, effective, and/or efficacious, log reduction of one or more of any bio-burden, virus(s), bacteria(s), spore(s), and/or any pathogen(s), and more preferably and without limitation, at least a greater than 2 log reduction of one or more of any bio-burden, virus(s), bacteria(s), spore(s), and/or any pathogen(s), in less than 10 minutes, but at least and without limitation, within less than 60 minutes, and even more preferably and without limitation, at least a 3 log reduction or greater of one or more of any bio-burden, virus(s), bacteria(s), spore(s), and/or any pathogen(s), in less than 10 minutes, but at least and without limitation, within less than 60 minutes, and very preferably and without limitation, at least a 6 log reduction or greater of one or more of any bio-burden, virus(s), bacteria(s), spore(s), and/or any pathogen(s), in less than 10 minutes, but at least and without limitation, within less than 60 minutes.

Still even more specifically, and without limitation, the present invention also relates generally to an improved enclosure and/or chamber treatment and processing system for treating, sanitizing, disinfecting, high-level disinfecting, sterilizing, drying, and/or cooling, one or more of any object(s) and/or surface(s), suitably and effectively located within one or more of any suitable and effective enclosure(s) and/or treatment chamber(s). Without being limited, the present invention describes an improved cabinet mounted chamber and/or enclosure treatment and processing system, and an improved mobile processing system for the treatment and processing of both fixed and mobile treatment chamber(s).

Without being limited, the improved cabinet mounted treatment chamber processing system and improved chamber and/or enclosure mobile processing system, described in the present invention, provide various improvements to the current art including but not limited to, a novel push and pull filtered air/gas(s) system that first takes fresh air and/or air/gas(s) that is sourced from the environment outside of the one or more treatment enclosure(s), treatment chamber(s), and/or cabinet housing(s), effectively filter(s) the said air/gas(s) and/or fresh air/gas(s) with one or more of any suitable and effective filter(s), but preferably, and without limitation a plurality of any suitable and effective air/gas(s) filter(s), and effectively pushes, flows, and/or blows, any effective amount of the said fresh air/gas(s) and/or air/gas(s) into and through the conduit(s) of the airflow system with one or more suitable and effective fan(s) and/or blower(s), and where the said air/gas(s) and/or fresh air/gas(s) can be, and without limitation, effectively heated to one or more of any suitable and effective temperature(s), before moving or flowing into and through one or more of any treatment chamber(s) and/or treatment enclosure(s), and where the said fresh air/gas(s) and/or air/gas(s) are moved and/or flowed into and through the said treatment chamber(s) and/or enclosure(s) for various purposes such as, but not limited to, effectively drying, effectively removing, and/or effectively reducing, any effective quantity(s) and/or amount(s) of any, deployed agent(s), vapor(s), water, and/or water vapor, from one or more of any surface(s) and/or area(s) inside of the treatment chamber(s) and/or enclosure(s) such as, but not limited to, one or more of any object(s) surface(s) and/or any treated object(s) surface(s), as well as effectively removing the deployed agent(s) from the inside of the treatment chamber(s) and/or enclosure(s) and/or removing the deployed agent(s) from the atmosphere(s) inside of the treatment chamber(s) and/or enclosure(s), at one or more of any suitable and effective time(s), and where the said fresh air/gas(s), air/gas(s), heated fresh air/gas(s), and/or heated air/gas(s), are then effectively filtered once they have exited the treatment chamber(s) and/or enclosure(s) to effectively remove one or more of any substance(s) such as, but not limited to any, deployed agent(s), vapor(s), and/or water vapor(s), that was moved, flowed out, and/or removed, from the said treatment chamber(s) and/or enclosure(s).

Also, without being limited, the movement and/or flow of these said fresh air/gas(s), air/gas(s), heated fresh air/gas(s), heated air/gas(s), and/or deployed agent(s), at least through and then out of the said enclosure(s) and/or treatment chamber(s), is also effectively assisted with one or more of any effective fan(s) and/or blower(s) located on the side of the enclosure(s) and/or treatment chamber(s) where the fresh air/gas(s), air/gas(s), heated fresh air/gas(s), heated air/gas(s), and/or deployed agent(s), exit from, and effectively near, at, and/or close to, the exhausting end of the airflow system, where that part of the airflow system effectively communicates with the said enclosure(s) and/or treatment chamber(s), and where the said fan(s) and/or blower(s) push, blow, move, and/or flow, and/or assist with flowing and/or moving, the fresh air/gas(s), air/gas(s), heated fresh air/gas(s), heated air/gas(s), and/or deployed agent(s), out of the said airflow system, and exhausted back into the surrounding environment that is exterior to the treatment enclosure(s), treatment chamber(s), and/or the environment outside of the treatment enclosure(s), treatment chamber(s), and/or cabinet housing.

More specifically, and without limitation, the improved cabinet mounted treatment chamber processing system and improved chamber and/or enclosure mobile processing system, described in the present invention, provide various improvements to the current art including but not limited to, a novel push and pull air/gas(s) system (Herein also called "airflow system" and/or "air/gas(s) flow system"), that first takes fresh air and/or air/gas(s) that is sourced from the environment outside of the one or more treatment enclosure(s), treatment chamber(s), and/or cabinet housing(s), and where one or more of any suitable and effective first filter(s), fan(s), air/gas pump(s), and/or blower(s), are suitably and directly and/or indirectly connected to and/or located effectively, in one or more of any suitable and effective combination(s), at, near, approximate to, and/or effectively close to, one or more of any, air/gas(s) inlet(s), air/gas(s) inlet port(s), and/or air/gas(s) inlet duct(s), of the said air/gas(s) flow system and/or airflow system(s), and where the said first fan(s), air/gas pump(s), and/or blower(s), preferably and without limitation, effectively pulls air/gas(s) and/or fresh air/gas(s) through one or more of any suitable and effective first filter(s) located preferably, but not limited to, before the said fan(s) and/or blower(s) in the airflow system, and then pushes, flows, moves, and/or pressurizes with any effective positive pressure(s), this air/gas(s) and/or fresh air/gas(s) through one or more of any suitable and effective second air/gas(s) filters where it is effectively filtered to any suitable and effective, filter rate(s), filtration amount(s), filter performance(s), and then the said air/gas(s) and/or fresh air/gas(s) are moved and/or flowed past one or more of any suitable and effective air/gas(s) heaters, where the one or more air/gas(s) heater(s) can effectively heat the air/gas(s) and/or fresh air/gas(s), at one or more of any suitable and effective time(s), to any suitable and effective temperature(s), before the said air and/or fresh air/gas(s) is moved into and then through one or more of any suitable and effective valve(s) that can control its flow at any suitable and effective times, and the said air/gas(s) and/or fresh air/gas(s) are then moved into and then through one or more of any suitable and effective enclosure(s) and/or treatment chamber(s) for various purposes such as, but not limited to, effectively drying the various surfaces within the said enclosure(s) and/or treatment chamber(s) and/or effectively removing any suitable and effective amount(s) of any liquid(s) and/or deployed agent(s) from any one or more surface(s) inside the treatment chamber(s) and/or enclosure(s) and/or any one or more surface(s) of any one or more object(s) within the said enclosure(s) and/or treatment chamber(s), at one or more of any suitable and effective time(s). Once the any fresh air/gas(s), air/gas(s), heated fresh air/gas(s), heated air/gas(s), vapor(s), water vapor(s), and/or deployed agent(s), have left or have moved and/or have flowed out of the said enclosure(s) and/or treatment chamber(s), the said any fresh air/gas(s), air/gas(s), heated fresh air/gas(s), heated air/gas(s), vapor(s), water vapor(s), and/or deployed agent(s), are flowed and moved through an improved system of one or more of any suitable and effective combination(s) of any suitable and effective fan(s), blower(s), and/or filter(s), including, but not limited to one or more of any, suitable and effective air/gas(s) filter(s) for removing and/or absorbing any deployed vapor(s), deployed agent(s), vapor(s), humidity(s), and/or gas(s), and/or one or more of any suitable and effective filter(s) for filtering one or more of any, particle(s), debris, airborne particle(s), airborne dust(s), filter particle(s), and/or airborne filter material(s), and effectively filter any flow(s) of any fresh air/gas(s), air/gas(s), heated fresh air/gas(s), heated air/gas(s), vapor(s), water vapor(s), humidity(s), and/or deployed agent(s), before it leaves the said air/gas processing system or otherwise the said airflow system, and is exhausted back into the surrounding environment that is exterior to the treatment enclosure(s), treatment chamber(s), and/or the environment outside of the treatment enclosure(s), treatment chamber(s), and/or cabinet housing.

More specifically, and without limitation, the said any fresh air/gas(s), air/gas(s), heated fresh air/gas(s), heated air/gas(s), vapor(s), water vapor(s), and/or deployed agent(s), can be and/or is also moved, flowed, drawn, sucked, and/or pulled, through the air/gas(s) processing system and/or airflow system, including any of the one or more conduits, filters, and treatment chamber(s), with a negative pressure and/or is effectively drawn, pulled, flowed, moved, and/or sucked, through the one or more of any conduit(s), filter(s), treatment chamber(s), and/or airflow system(s), and exhausted back into the surrounding environment that is exterior to the one or more treatment enclosure(s), treatment chamber(s), and/or environment(s) outside of the treatment chamber and/or cabinet housing(s), by using one or more second and/or additional fan(s), air/gas pump(s), and/or blower(s), that are suitably and directly and/or indirectly connected to and/or located effectively, at, near, approximate to, and/or effectively close to, one or more of any, outlets, exhaust outlet(s), exhaust portal(s), and/or exhaust duct(s), connected to and/or of the said air/gas(s) flow system and/or airflow system(s), that pushes, flows, and/or moves, the air/gas(s) and/or deployed agent(s) out of the said outlet(s), exhaust portal(s), exhaust outlet(s), and/or exhaust duct(s), that communicates with the one or more of any, conduits, filter(s), treatment enclosure(s), treatment chamber(s), airflow processing system(s), and/or airflow system(s). The flow of air/gas(s) and/or fresh air/gas(s), and even more preferably and without limitation, the flow of air/gas(s) and/or fresh air/gas(s) that is then heated if needed, is sourced from outside of the one or more of any suitable and effective, treatment enclosure(s), treatment chamber(s), cabinet(s), and/or the surrounding environment(s) of these said parts and components, and can be used for purposes such as, but not limited to, removing any suitable and effective amount(s) of any deployed agent(s) and/or liquid(s) from any surface(s) inside of the treatment chamber(s) and effectively drying the various surfaces within the treatment chamber(s) including, but not limited to the various surface(s) of the treated object(s) located inside of the treatment chamber(s). Without being limited, the fresh air/gas(s) can also be suitably and effectively sourced from any suitable and effective location(s) within the one or more cabinet(s), but preferably, and without limitation, at least one or more of any suitable and effective location(s) outside of the treatment enclosure(s) and/or treatment chamber(s).

The flow and/or movement of the said any, fresh air/gas(s), air/gas(s), heated fresh air/gas(s), heated air/gas(s), vapor(s), water vapor(s), and/or deployed agent(s), into and out of the treatment enclosure(s) and/or treatment chamber(s), at one or more of any suitable and effective time(s), can be controlled with one or more of any suitable and effective valve(s) that is suitably and effectively connected to both the one or more entrance(s) and exit(s) of the treatment chamber(s) and/or enclosure(s) and can effectively seal the treatment chamber(s) and/or enclosures when the various object(s) and/or surfaces within the treatment chamber(s) are treated with airborne agent(s) or deployed agent(s) that are deployed by one or more of any suitable and effective means to generate and/or deploy any effective airborne deployed agent(s) and/or any suitable and effective agent generator(s).

The design of the one or more treatment cabinet(s), and more specifically and without limitation, the treatment chamber(s), treatment enclosure(s), and/or enclosure(s), is also improved in the present invention by including one or more of an improved means to suitably and effectively dry, reduce, and/or remove, the one or more deployed agent(s) and/or any other liquid(s) from one or more of any surface(s) such as, but not limited to any, floor(s), horizontal surface(s), and/or horizontal shelve(s), inside of the said, treatment chamber(s), treatment enclosure(s), and/or enclosure(s), and whereby one or more of any suitably and effectively sized and shaped air/gas(s), outlet(s), orifice(s), nozzle(s), and/or one or more of any suitable and effective air/gas(s) director(s) and/or diffuser(s), can suitably and effectively point and/or direct any, fresh air/gas(s), air/gas(s), heated fresh air/gas(s), heated air/gas(s), and/or deployed agent(s), that is moved with at least one or more of any suitable and effective, fan(s), air/gas pump(s), and/or blower(s), at, about, along, towards, horizontal to, angled along, and/or angled towards any of the said, floor(s), surface(s), and/or horizontal shelve(s), inside of the treatment chamber(s), at any suitable and effective speed(s), velocity(s), quantity of air/gas(s), and/or cubic feet per minute (CFM), and can also be used for any other purposes such as, but not limited to, effectively circulating, stirring, mixing, and/or homogenizing, any deployed agent(s), air/gas(s), and/or atmosphere(s), that is or may be present within the treatment chamber(s) at any suitable and effective time(s) such as, but not limited to, during one or more of any suitable and effective processing and/or treatment step(s) for the various surface(s) and/or atmosphere(s) within the treatment chamber(s), during one or more of any step(s) to move and/or deploy the deployed agent(s) into the treatment chamber(s), during one or more of any step(s) where the deployed agent(s) "dwell" inside of the treatment chamber(s), during one or more of any step(s) to reduce and/or remove the deployed agent(s) from the various surface(s) inside of the treatment chamber(s), during one or more of any step(s) to dry any surface(s) within the treatment chamber(s).

Without being limited, the various parts and components described in the present invention, can be suitably and effectively, located, affixed, and/or connected, to, on, inside of, outside of, and/or at, one or more of any suitable and effective, location(s), structure(s), apparatus(s), and/or surface(s), such as, but not limited to, one or more of any suitable and effective mobile, means, structure(s), and/or apparatus(s), known to those skilled in the art such as, but not limited to any, mobile cabinet(s), mobile chassis(s), mobile frame(s), mobile surface(s), mobile wall(s), mobile bulkhead(s), mobile and/or wheeled apparatus(s), portable device(s), carriage(s), cart(s), mobile apparatus(s), and/or mobile structure(s). Also, and without being limited, the various parts and components described in the present invention, can also be suitably and effectively, located, affixed, and/or connected, to, on, inside of, outside of, and/or at, one or more of any suitable and effective, location(s), structure(s), apparatus(s), and/or surface(s), such as, but not limited to, one or more of any suitable and effective static, means, structure(s), and/or apparatus(s), known to those skilled in the art such as, but not limited to any, static cabinet(s), static chassis(s), static frame(s), static surface(s), static wall(s), static bulkhead(s), static apparatus(s), static device(s), static carriage(s), static structure(s).

Also, and without limitation, the flow and/or movement of the various air/gas(s), fresh air/gas(s), heated air/gas(s), heated fresh air/gas(s), water vapor(s), vapor(s), and/or deployed agent(s), into, through, and/or out of one or more of various locations such as, but not limited to any, one or more treatment chamber(s), means to filter the supply of any air/gas(s) and/or fresh air/gas(s) to the treatment chamber(s), means to heat the supply of any air/gas(s) and/or fresh air/gas(s), means to filter any, air/gas(s), fresh air/gas(s), heated air/gas(s), heated fresh air/gas(s), deployed agent(s), water vapor(s), and/or vapor(s), that is being exhausted from the said treatment chamber(s), means to generate and/or deploy the deployed agent(s), and/or means to recirculate the various air/gas(s), fresh air/gas(s), heated air/gas(s), heated fresh air/gas(s), water vapor(s), vapor(s), and/or deployed agent(s) through the treatment chamber(s) and/or to stir, mix, and/or homogenize the deployed agent(s) inside of the treatment chamber(s), can also be controlled by a unique system of multiple suitable and effective valves. This is another improvement to the current art.

For example, and without limitation, a plurality of any suitable and effective valves known to those skilled in the art, that are suitably and effectively open, can also be effectively closed for one or more of any suitable and effective duration of time(s) and used to effectively seal the one or more airflow entry opening(s) and/or port(s) and airflow exit opening(s) and/or port(s), that communicate with the treatment chamber(s), for and/or during one or more of any situation(s) and/or step(s) such as, but not limited to, when one or more object(s) and/or surfaces within the said treatment chamber(s) are being treated, sanitized, disinfected, high-level disinfected, and/or sterilized. These same said valves can also be suitably and effectively opened to allow the flow of any, air/gas(s), fresh air/gas(s), heated air/gas(s), heated fresh air/gas(s), deployed agent(s), water vapor(s), and/or vapor(s), into and out of the one or more treatment chamber(s) for various purposes including, but not limited to, removing the deployed agent(s) from within the treatment chamber(s) and/or drying the various surfaces and object surfaces within the treatment chamber(s).

Without being limited, a plurality of valves, and more particularly at least one of any suitable and effective valve(s) that effectively communicates with at least one of any suitable and effective outlet(s) from which any air/gas(s) and/or deployed agent(s) flows out of the said outlet(s) from the at least one of any suitable and effective agent generator(s) and/or one or more of any suitable and effective means to emit and/or disperse one or more of any airborne deployed agent(s) into the treatment chamber(s), and at least one of any suitable and effective valve(s) that communicates with at least one of any suitable and effective inlet(s) that can also effectively communicate with the treatment chamber(s) and through which any air/gas(s) and/or deployed agent(s) can flow from inside of the treatment chamber(s) and into the said inlet(s) and to and/or into the one or more said agent generator(s) and/or means to emit and/or disperse one or more of any airborne deployed agent(s), can remain suitably and effectively open at one or more of any suitable and effective time(s) for purposes including, but not limited, the deployment and/or movement of the deployed agent(s) into and/or circulated into and/or through the treatment chamber(s) from the said agent generator(s) and/or means to emit and/or disperse one or more of any airborne deployed agent(s), and can also, and without limitation, remain suitably and effectively closed at one or more of any suitable and effective time(s), when the various air/gas(s), fresh air/gas(s), and/or heated fresh air/gas(s) are flowed into and through the treatment chamber(s) for purposes such as, but not limited to, removing the deployed agent(s) from within the treatment chamber(s) and/or drying the various surfaces and object surfaces within the treatment chamber(s), and/or after the entire processing cycle(s) for the various surfaces, object surface(s), and/or atmosphere(s), within the treatment chamber(s), is complete. Without being limited, the one or more of any, decontamination system(s), deployed agent(s) generator(s), and/or one or more of any suitable and effective means to deploy, emit, and/or disperse, one or more of any airborne deployed agent(s) into the treatment chamber(s), can also suitably and effectively interface directly with and/or into the one or more treatment chamber(s).

The present invention also includes, and without limitation, locating at least one, but more preferably and without limitation, a plurality, of any suitable and effective air/gas(s) filter(s) in one or more of any airflow path(s) that are located before and connect with the treatment chamber(s) so that any air/gas(s) that enter the treatment chamber(s) is effectively filtered. In addition, and without limitation, at least one, but more preferably and without limitation, a plurality, of any suitable and effective air/gas(s) filter(s) are also located in one or more of any airflow paths after the treatment chamber(s) so that any, air/gas(s), fresh air/gas(s), heated air/gas(s), heated fresh air/gas(s), water vapor(s), vapor(s), and/or deployed agent(s), that exit the treatment chamber(s) is at least suitably and effectively filtered before it enters and/or is exhausted back into the surrounding environment that is exterior to the treatment enclosure(s), treatment chamber(s) and/or the environment outside of the treatment enclosure(s), treatment chamber(s), and/or cabinet housing, but preferably, and without limitation, effectively filtered for various purposes such as, but not limited to, suitably and effectively removing and/or filtering any, deployed agent(s), filter media particle(s), filter particle(s), particle(s), and/or deployed agent(s), from any, air/gas(s), fresh air/gas(s), heated air/gas(s), heated fresh air/gas(s), water vapor(s), vapor(s), and/or deployed agent(s), that are flowed or moved out of the treatment chamber(s) and into into the surrounding environment that is exterior to the treatment enclosure(s), treatment chamber(s) and/or the environment outside of the treatment enclosure(s), treatment chamber(s), and/or cabinet housing.

Without being limited, a unique push and pull filtered airflow system taught in the present invention is another improvement to the current art, and preferably, and without limitation, is used in the present invention for various purposes including, but not limited to, overcoming any airflow resistance that is created by various sources such as, but not limited to, the one or more of any filters used to effectively filter any, air/gas(s), fresh air/gas(s), heated air/gas(s), and/or heated fresh air/gas(s), before it enters the treatment chamber(s), as well as the one or more of any filters used to effectively filter any, air/gas(s), fresh air/gas(s), heated air/gas(s), heated fresh air/gas(s), water vapor(s), humidity(s), vapor(s), and/or deployed agent(s), after being flowed, moved, and/or exhausted, out of the treatment chamber(s), before the said any, air/gas(s), fresh air/gas(s), heated air/gas(s), heated fresh air/gas(s), water vapor(s), humidity(s), vapor(s), and/or deployed agent(s), are flowed, moved, and/or exhausted, into the surrounding environment and/or the environment that surrounds the treatment chamber(s), entire apparatus(s), system enclosure(s), system outer enclosure(s), cabinet(s), outer cabinet(s), and/or the improved cabinet mounted treatment chamber processing system.

It is preferred, without limitation, that at least one or more of any suitable and effective, fan(s), air/gas pump(s), and/or blower(s) (Herein called Inbound Blower(s)), that supplies, flows, and/or moves any, air/gas(s), fresh air/gas(s), heated air/gas(s), and/or heated fresh air/gas(s), into the one or more treatment chamber(s), is suitably and effectively located in one or more of any suitable and effective location(s) in the one or more of any airflow path(s) and/or filtered and heated inbound air/gas(s) assembly(s) that communicates with the one or more treatment chamber(s) and is also located before the said treatment chamber(s), and the said inbound blower(s) communicates with the one or more treatment chamber(s) and moves the said air/gas(s), fresh air/gas(s), heated air/gas(s), and/or heated fresh air/gas(s), with one or more of any suitable and effective positive pressure(s) into the one or more treatment chamber(s) and, at least one or more of any suitable and effective, fan(s), air/gas pump(s), and/or blower(s) (Herein called Outbound Blower(s)), is also suitably and effectively located in one or more of any suitable and effective location(s) in the one or more of any exhaust airflow path(s) and/or filtered exhaust assembly(s) that communicates with the one or more treatment chamber(s) and is also located after the said treatment chamber(s), and the said outbound blower(s) communicates with, and more preferably and without limitation, is located effectively near, the one or more exhaust outlet(s) for the one or more exhaust airflow path(s) from the said treatment chamber(s), and moves, suctions, and/or pulls, any, air/gas(s), fresh air/gas(s), heated air/gas(s), heated fresh air/gas(s), water vapor(s), humidity(s), vapor(s), and/or deployed agent(s), with one or more of any suitable and effective negative pressure(s) from one or more of any suitable and effective location(s) such as, but not limited to any, treatment chamber(s), and then pushes the said any, air/gas(s), fresh air/gas(s), heated air/gas(s), heated fresh air/gas(s), water vapor(s), humidity(s), vapor(s), and/or deployed agent(s), out of the exhaust outlet(s), filtered exhaust assembly(s), airflow system(s), and/or the improved cabinet mounted treatment chamber processing system(s), and into the surrounding environment and/or the environment that surrounds the treatment chamber(s), entire apparatus(s), system enclosure(s), system outer enclosure(s), cabinet(s), outer cabinet(s), and/or the improved cabinet mounted treatment chamber processing system.

BACKGROUND OF THE INVENTION

The complete and assured sanitization, disinfection, high-level disinfection, or sterilization of devices, tools and other objects in industries such as but not limited to the health care industry, has always been a challenge in terms of processing time, cost, engineering trade-offs, toxicity, safety, and overall effectiveness. Currently, the available choices are liquid disinfection, typically referred to as a "wet" method, and various airborne methods, typically referred to as a "dry" method. The dry method can include, but is not limited to, gases, aerosols, and processes that use steam as a carrier gas for the disinfecting composition or solution. All processes that do not include liquid immersion are generally considered to constitute a dry method even if the agent used has a liquid phase.

Immersion of an object in liquids known in the art for sterilization or disinfection is a relatively simple method that is cost effective, and offers fast cycle times that are typically measured in hours. However, it also presents problems related to reproducibility and quality assurance due to the potential for bubbles to form on the inner surfaces of complex instruments, including endoscopes, which prevent cleaning solution contact with interior surfaces, such as lumens or channels. Another method for cleaning devices such as endoscopes is known to those skilled in the art, but generally involves several sequential steps or activities such as, but not limited to, wiping the device to remove any unwanted debris or contaminants and then placing the endoscope in a washer and interfacing it with a hose, or other means known to those skilled in the art (herein called "supply tube"). The supply tube enables various liquids including but not limited to, surfactant, high purity rinse water, and disinfectant/sterilant, to be moved through the various channels and lumens of the endoscope at various stages of the cleaning process. The outside of the endoscope is also exposed, preferably simultaneously, to these same liquids at various stages of the cleaning process. After the final rinse stage, the endoscope is dried in a manner known to those skilled in the art including, but not limited to, being dried within the processing chamber, or removed from the washer and dried outside of the processing chamber.

The current art can be improved in various ways including, but not limited to: (1) decreasing the time required to achieve the desired anti-pathogen/toxin/fungal/sporicidal effect on both the internal and external surfaces as well as any interfacing/articulating surfaces of an object or endoscope (2) reducing the risk that "air bubbles" will prevent full contact of the disinfectant/sterilant solution with all inner surfaces of an object or endoscope (3) reducing the drying time for an object or endoscope, and (4) reducing or eliminating the deleterious effect of the disinfectant solution and/or disinfecting process on the materials that are used to construct the object or endoscope. The methods and apparatuses of the present invention address these needs by decreasing the time to efficaciously complete the essential steps while achieving a satisfactory result.

In general, liquid disinfection/sterilization creates a major corresponding drawback in that the finished product remains wet, and therefore unsuitable for packaging and/or storage. The deployed or applied disinfecting agent(s) or substance(s) must have limited toxicity, be reasonably safe as well as compatible with those materials comprising the instruments and devices to be disinfected/sterilized.

Gaseous agents used in the prior art for sterilization are very limited in terms of medical applicability. Steam or dry heat sterilization is effective, but many medical devices and instruments are incompatible with the degree of heat required for this process. So-called "cold sterilization" is an alternative, but the only currently available cold sterilization agents in use in hospitals are ethylene oxide and hydrogen peroxide in various forms that include, but are not limited to plasma. U.S. Pat. No. 4,512,951 (Koubek, 1983), which is incorporated herein by reference in its entirety, including any references cited therein, teaches using hydrogen peroxide to sterilize medical articles by causing hydrogen peroxide-water vapors to deposit a film of liquid on the medical devices. The liquid film is then caused to be evaporated. Hydrogen peroxide vapor is susceptible to humidity that can reduce the efficacy of the process.

Ethylene oxide (EtO) is carcinogenic, toxic and dangerous and, although effective, is only used as a last resort for instruments and devices that cannot be subjected to other modalities. In addition, after being exposed to EtO, items cannot be used for long periods to allow "off-gassing" or aeration of the EtO. According to the UNC School of Dentistry, the complete EtO cycle, including aeration, can last as long as 24 hours. The newer technology utilizing hydrogen peroxide plasma is an alternative, however, it is very expensive, and the technology requirements have translated to only small size sterilization chambers. To date, it has not been capable of sterilizing certain instruments including, but not limited to, endoscopes. Endoscopes generally contain small lumens and/or channels and the hydrogen peroxide plasma has difficulty in maintaining its effectiveness throughout the length of the lumen.

Without being limited to a mechanism, method, or chemical, it is believed that chemically reactive liquids are necessary in sterilization processes to contact contaminants including but not limited to toxins, bacteria, virus, fungus, and spores (both fungal and bacterial), prions or protein structures, within a target area(s) to kill the bacteria, virus, fungus, spores, neutralize a toxins, or render a virus, or protein structure incapable of replication or to otherwise interfere with the target's cellular physiology, or to destroy or neutralize the toxin. These chemically reactive liquids may be provided as an aerosol.

Prior art has taught that relatively quick disinfection and sterilization of objects can be achieved by their exposure to an aerosol of a disinfectant/sterilizing agent created by ultrasonic nebulization. U.S. Pat. No. 4,366,125 (Kodera et al., 1980), which is incorporated herein by reference in its entirety, including any references cited therein, teaches that an aerosol, created by ultrasonic transducers and consisting of hydrogen peroxide, can contact surfaces targeted for sterilization. Ultraviolet-ray lamps are then synergistically used in concert with the applied aerosol to achieve sterilization of the targeted surfaces. Generally, the prior art also describes apparatuses and methods where the aerosol is generated by one or more ultrasonic transducers located below the surface of a reservoir containing a liquid. The output of the transducers is focused to either a point and/or directed toward an area near the surface of the liquid to cause a surface disturbance, which results in the formation of an aerosol from the liquid. The transducers used in these apparatuses are typically made from lead-zirconate-titanate-four (PZT-4) or other piezoelectric materials. This material is coated with a conductive coating (i.e., an electrode material) that enables an electrical signal to energize the transducer and causes it to emit high frequency pressure (energy).

G.B. Patent No. 1,128,245, (Rosdahl et al., 1968) which is incorporated herein by reference in its entirety, including any references cited therein, describes a device for disinfecting apparatuses and instruments, including medical instruments. This apparatus also generates a mist of disinfectant, including hydrogen peroxide, by means of an ultrasonic aerosol generator. According to Rosdahl et al., this patent was "primarily adapted for the disinfection of small medical instruments such as scalpels, tongs, syringes, or the like, positioned on a grid in a container" (pg 3 col. 23-30). However, another separate intended use for a second described apparatus was for disinfecting interior surfaces of objects such as the interior of tubing used for "breathing apparatuses" and "heart lung machines" (pg 1 ln 30-36 and pg 2 ln 95-101).

Rosdahl et al. is clearly distinguished from the present invention in that it is silent with respect to simultaneously disinfecting both the interior and exterior surfaces of an object Rosdahl et al. also does not teach a method for simultaneously sterilizing/disinfecting and drying the outside and interior surfaces/lumen of an object. Most importantly, Rosdahl et al. does not teach how the apparatus could effectively and efficaciously be "connected" to the object (pg 2 ln 95-101) in a way that enables all of the interfaced/articulated surfaces to be sanitized, disinfected, high level disinfected, or sterilized. The pressurized air in Rosdahl et al. is supplied by way of a fan etc. or carrier gas, (pg 2 ln 48-49) and is used to both move the generated aerosol to perform the disinfection function, and to dry the objects placed within the enclosed area of their described apparatus after disinfection. Rosdahl et al. incorporated "a heating element to dry the air in the flow path of the carrier gas, to increase drying efficiency" (pg 3 ln. 123-127). The use of a heating element in the flow path of a gas stream taught in U.S. Pat. No. 6,379,616 (Sheiman, 1999), is incorporated herein by reference in its entirety, including any references cited therein. Sheiman also teaches the use of ultrasonic transducers to generate aerosol. The heater is located about the inlet conduit of the apparatus and is designed to heat the aerosol, which encourages its condensation on or within the article. It is important to note that Sheiman is silent regarding the use of the apparatus or a secondary apparatus to interface and sanitize, disinfect, high-level disinfect, or sterilize, the interior of an object or device, as well as the simultaneous or non-simultaneous cleaning of both the interior and exterior of objects.

Ultrasonic nebulizers have a unique advantage in that they can create small aerosol droplets less than 5 microns in size. The size of the droplets enables them to penetrate small cracks and crevices and to behave like a gas due to Brownian movement and diffusion. In addition, the cloud is able to form a very thin coating, deposition, or film over various surfaces that are inherent to this technology and method. The thin coating, film, or deposition of sterilant or disinfectant is able to dry much faster than coatings created by aerosol containing droplets that are much larger in diameter. It is also theorized that the vapor component resulting from the evaporation of the droplets, contributes to the overall efficacy of the process.

U.S. Pat. No. 4,366,125, (Kodera et al., 1980), which is incorporated herein by reference in its entirety, including any references cited therein, teaches that heated H2O2 is more efficacious than H2O2 used at room temperature (col. 1, line 19-25). In other words, (Kodera et al., 1980) teaches that the efficacious nature of a liquid agent can be increased as it is heated to temperatures higher than ambient temperature. THIS is desired, without limitation, in the present invention. The text entitled, "Aerosol Technology" by William C. Hinds (1982), which is incorporated herein by reference in its entirety, including any references cited therein, also taught that the size of the aerosol particles produced by ultrasonic means are not only affected by the frequency of the transducer operation, but also by the surface tension and density of the liquid.

It is commonly known that heating a liquid to a temperature less than its boiling point will reduce its surface tension. William C. Hinds (1982) established that the higher the temperature of the liquid, the lower the liquid's surface tension, resulting in smaller sized aerosol particles. This principal is incorporated without limitation, in the present invention. In the same text he also taught that smaller diameter particles demonstrate characteristics such as but not limited to, a lower settling velocity, a higher diffusion coefficient, and a higher Brownian displacement (movement), which is desired, without limitation, in the present invention. Hinds further taught that ultrasonic aerosol generating transducers can heat the surrounding liquid (page 382). This is also desired, without limitation, in the present invention.

It has been difficult and time consuming applying current devices and methods to disinfect or sterilize both the exterior and interior surfaces of tools or equipment, e.g., endoscopes, in a single cleaning cycle or process due to their complex construction including narrow lumens of various lengths. The limitations of the prior art are further indicated by the failure or problems, which various anti-pathogen/toxin/fungal/sporicidal agents or substances have in contacting, and/or rapidly achieving an efficacious result on the surfaces of the endoscope or object that are interfaced/articulated with any coupling(s) or other device.

"Flash" sterilization is also needed in industries such as, but not limited to the health care industry. It is commonly used for quick sterilization and turn around of various objects immediately needed for or during surgery. Flash sterilization methods that include the use of steam under pressure at recommended temperatures of approximately 270 degree Fahrenheit for approximately three to ten (3 to 10) minutes, are generally representative of the current art. The object that is flash sterilized must then cool down before it is used, taking valuable time. A need exists in the industry to further reduce the total amount of time it takes to clean, sterilize or disinfect, and deliver a surgical tool on demand within a reasonable period of time. The present invention can, without limitation, decrease the total cycle time needed for rapid sterilization of medical devices by providing a means to quickly sterilize or disinfect objects whose construction materials are thermally sensitive and cannot be flash sterilized by current means.

The methods and apparatuses of the present invention address the need for a quick and effective way to fully sanitize, detoxify, disinfect, high level disinfect, or sterilize both the interior and exterior of medical devices, and objects. In addition, this may without limitation, be accomplished while still enabling all surfaces of the object or endoscope to have contact with the anti-pathogen/toxin/fungal/sporicidal agent(s) or substance(s) including surfaces of the object or endoscope that are interfaced/articulated with any coupling(s) or other device.

There is a continued need to increase both the efficacy and effectiveness of a system that offers shortened cycle times. The present invention addresses these issues. One such means in the present invention utilizes thermal forces by cooling or decreasing the temperature of the objects themselves, the atmosphere in which they reside, or the targeted area for the administration of an aerosol as well any surfaces in that area, prior to the administration of the aerosol.

Prior art has taught the step of cooling an enclosed area and its surfaces before the administration of a hydrogen peroxide disinfectant, however the hydrogen peroxide was first vaporized into a gaseous state before its administration, and the cooling step was intended to condense the vaporized hydrogen peroxide onto the intended surfaces, as taught in U.S. Pat. No. 4,512,951 (Koubek et al., 1983), which is incorporated herein by reference in its entirety, including any references cited therein. More specifically, Koubek et al., teaches a method of sterilization where a liquid of aqueous hydrogen peroxide is vaporized, and the vapors are delivered into an evacuated sterilizer chamber. The articles to be sterilized are cooled prior to the introduction of the vapor (or are cooled by the evacuation of air from the sterilizing zone) to a temperature below the dew point of the entering vapors. The condensing vapor deposits a film of liquid on all such cool surfaces (col 2, line 40-51). Koubek et al., also mentions in claim 2 that the result of vaporization was a mixed "gaseous vapor" consisting of hydrogen peroxide and water vapor free of solid contaminants.

U.S. Pat. No. 4,952,370 (Cummings et al., 1988), which is incorporated herein by reference in its entirety, including any references cited therein, teaches a similar method of sterilization where a liquid of aqueous hydrogen peroxide is also vaporized into a gaseous state before its administration into an evacuated sterilizer chamber. However, Cummings et al., teaches improvements to the art where the hydrogen peroxide-water vapor is applied under vacuum to surfaces that are below 10 degree centigrade, or surfaces in an environment that are both below 10 degree centigrade and above 10 degree centigrade. The cold surfaces mentioned in Cummings et al., were not cooled to accentuate or enhance the process, but were surfaces of components that were inherently cold for their own operational purposes. This is mentioned in sections such as (col 2, line 4-9), (col 2, line 29-33), and (col 4, line 67 to col 5, line 2).

U.S. Patent Application No. 2005/0042130 A1 (Lin et al., 2003), which is incorporated herein by reference in its entirety, including any references cited therein, claims the use of an applied vacuum to move an ultrasonically derived aerosol, consisting of a sterilant, throughout the area of an enclosed chamber. The use of vacuum pressures below atmospheric pressure was also mentioned as well as the possibility that vacuum pressures lower than 5 torrs lower than atmospheric pressure would likely "enhance the results", and that using a vacuum pressure low enough to vaporize the sterilant generally enhances sterilization (pg. 2, paragraph 28). However, Lin et al, was silent with respect to how the lower vacuum pressures would "enhance the results" other than any enhancement that vaporization of the aerosol might bring. Lin et al, was also silent with respect to the amount of time that is needed to elapse between lowering the pressure within the enclosed chamber and the application of an aerosol, in order to obtain the needed or desired level of efficacy. (Lin et al., 2003) was silent with respect to cooling any surfaces within the sterilization chamber or applying the aerosol to any cooled surfaces.

It is important to note that Lin et al, did not mention any process or method to heat the liquid of the aerosol or cool the surfaces in the sterilization chamber before or during the delivery of the aerosol, or any means to encourage condensation if the liquid was vaporized. In fact, the 5 torr negative pressure that was used by Lin et al. to generate their findings was reported to be sufficient enough to disperse the mist within the sterilization chamber (pg. 2, paragraph 28), but was never mentioned to have cooled the surfaces within the sterilization chamber or to have that intended effect.

In addition, it is important to note that the cooling of a targeted environment(s) and/or the surfaces contained therein addressed by the present invention is intended, without limitation, for a completely different application and purpose. The present invention utilizes the principals of aerosol behavior to increase the performance of the process of the present invention, and not the condensation of a gas as taught in the prior art. This is further addressed in the present invention.

By comparison, the current invention utilizes, without limitation, the cooling of the targeted environment(s) and its surfaces to enhance the performance and efficacy of the aerosol administration process and not to condense a gas as taught by the prior art.

U.S. Pat. No. 8,821,807 B2 (Schwartz et al., 2003), which is incorporated herein by reference in its entirety, including any references cited therein, describes "retaining" an object such as an endoscope in a "pouch", and later in a "package" or "enclosure", and then moving an aerosol created from a liquid chemical agent via a high pressure nozzle apparatus, through a port located in a wall of a pouch and into the pouch to decontaminate or disinfectant the various surfaces inside of the pouch, including the treated object. However, this patent is problematic for various reasons.

The first problem with Schwartz et al., 2003, and other similar methods and apparatuses taught in the art, is that surfaces that contact each other, especially as a medical device(s) rests in a pouch, package, or enclosure, is that any contacting surfaces between the medical device and itself, and/or the medical device and any surfaces within the interior of it's packaging, can be difficult and/or impossible to efficaciously treat or decontaminate with airborne agents that are delivered such as, but not limited to any, aerosol and/or vapor. This is especially true without using the assistance of any effective positive pressure and heat cycling that is common with ethylene oxide (EtO) gas/vapor systems, all in a manner known to those skilled in the art.

Schwartz et al., 2003, and the current art, is silent as to how to effectively, locate, hang, and/or suspend, and effectively treat and process, one or more of an entire medical device(s) such as, but not limited to any, endoscope(s), and/or ultrasonic probe(s), including any associated parts and components such as, but not limited to any, tube(s), pipe(s), conduit(s), fiber optic line(s), cable(s), wire(s), plug(s), and/or connector(s), especially that are connected to the said medical device(s), in any suitable chamber, pouch, enclosure, package, removable enclosure, and/or removable package, in an effective manner, to prevent the targeted surfaces of the medical device(s) and any associated parts and components, as well as any interior surfaces of the chamber, pouch, enclosure, package, and/or removable enclosure and/or removable package, from having any contacted and covered surfaces that cannot be effectively treated, decontaminated, sterilized, high-level disinfected, disinfected, processed, and/or treated.

Schwartz et al., 2003, and the current art, is also silent regarding releasing the one or more hung and/or suspended medical device(s) such as, but not limited to any, endoscope(s), and/or ultrasonic probe(s), including any associated parts and components such as, but not limited to any, tube(s), pipe(s), conduit(s), fiber optic line(s), cable(s), wire(s), plug(s), and/or connector(s), especially that are connected to the said medical device(s), after they are treated or decontaminated, so that once automatically and/or manually released they fall and/or released into any effectively open, pouch, enclosure, package, removable enclosure, and/or removable package, that is effectively sized and constructed, and then preferably and effectively closing and/or sealing the said open, pouch, enclosure, package, removable enclosure, and/or removable package. The open, pouch, enclosure, package, removable enclosure, and/or removable package, can be located under the treated object at any time, before, during, and/or after the treatment or decontamination process(s).

The second problem with Schwartz et al., 2003, and other similar methods and apparatuses taught in the art, is that the aerosol is created outside of the pouch or enclosure, and then flowed through a port located in a wall of a pouch, package, and/or removable package, and then flowed into the pouch, package, and/or removable package to decontaminate or disinfectant the various surfaces inside. This is problematic for various reasons including, but not limited to, (1) the pouch, package, and/or removable package can become over pressurized with the air/gas flow that delivers the aerosol, (2) the pouch, package, and/or removable package can become over pressurized with the air/gas flow that delivers the aerosol before the surfaces within the pouch or package are effectively treated, (3) turbulent air/gas flow and/or air/gas vortices can form within the pouch, package, and/or removable package preventing full and effective coverage of all of the various surfaces within the pouch, package, and/or removable package, which would result in a failure of the decontamination process.

Schwartz et al., 2003, and the current art, is also silent to designing a removable enclosure in which surfaces inside can be treated and/or decontaminated that effectively seals upon removal, that has a second port opening, preferable on an opposite end of the said enclosure from the first port opening, that allows the decontamination agent and/or the air/gas that carries it, to flow effectively into the removable enclosure, filling the said enclosure, and then flow through the removable enclosure, where the decontamination agent and/or carrier air/gas can flow back to the apparatus that generates the decontamination agent, thus forming a closed circuit or circular flow path between the treatment agent generator area and the removable enclosure through which the decontamination agent and/or carrier air/gas can flow. In addition, numerous other closed circuit or circular flow paths that flow through the removable enclosure can also be used for purposes such as, but not limited to, removing any vapor or humidity from the inside of the treatment enclosure. This is also not disclosed by Schwartz et al., 2003, or in the current art.

There is also a need in the current art to improve the means for holding objects in any enclosure or package, for an efficacious treatment or decontamination of the various surfaces of the object being held. This need has especially presented itself as the type of objects being held can include various medical devices such as, but not limited to any, endoscope(s), and/or ultrasonic probe(s), including any associated parts and components such as, but not limited to any, tube(s), pipe(s), conduit(s), fiber optic line(s), cable(s), wire(s), plug(s), and/or connector(s), especially that are connected to the said medical device(s).

The prior art does not teach or suggest, and without limitation, a multi-function enclosure and/or chamber product, for the decontamination, sanitization, disinfection, high-level disinfection, and/or sterilization, of various surface(s) within its chamber(s) (Hereinafter called "Treatment Chamber(s)"), that can provide any suitable and effective, decontamination, sanitization, disinfection, high-level disinfection, and/or sterilization, of various one or more of any object(s) located in the said treatment chamber(s), and without limitation, also any, directly and/or indirectly connected, handle(s), signal and/or electrical connector(s), and/or cable(s) and/or cord(s), and that can achieve a greater than 6 log reduction of any pathogens found on the various treated surface(s) such as, but not limited to any, viruses, *Staphylococcus aureus, Salmonella enterica, Pseudomonas aeruginosa*, MRSA, VRE, CRE, *C. Auris*, and/or *C. difficil* spores, preferably and without limitation, in less than 10 minutes, and also without being limited, at any suitable "low cost", and preferably, and without limitation, at a cost less than twenty dollars USD per operation cycle, and more preferably, and without limitation, less than two dollars USD per operation cycle, and even more preferably, and without limitation, less than one dollar USD per operation cycle, and very preferably, and without limitation, less than thirty cents USD per operation cycle, and where the temperatures for both the various surface treatment(s) and drying activity(s) are both, and without limitation, "suitable and effective low temperature(s)", and preferably, and without limitation, at temperatures of 200 degree Fahrenheit or less, and more preferably, and without limitation, at temperatures of 150 degree Fahrenheit or less, and even more preferably, and without limitation, at temperatures of 125 degree Fahrenheit or less, and very preferably, and without limitation, at temperatures between 50 to 125 degree Fahrenheit, and extremely preferably, and without limitation, at temperatures between 85 to 120 degree Fahrenheit.

There are various systems described and in use in the prior art that treat, decontaminate, sanitize, disinfect, high-level disinfect, and/or sterilize, the surfaces of various objects in a treatment chamber such as, but not limited to any, ultrasound probes, and/or topical ultrasonic imaging devices, with at least one or more suitable and effective airborne treatment agent(s) such as, but not limited to any, vapor(s) and/or aerosol(s), specifically, and without limitation, any ultrasonically generated aerosol(s) and/or any effective means to generate any effective vapor(s) and/or gas(s), containing one or more of any suitable and effective chemical(s) and/or substance(s) such as, but not limited to any, silver, metal(s), chlorine dioxide, hydrogen peroxide, and/or ozone, and more specifically, and without limitation, any ultrasonically generated aerosol(s) containing hydrogen peroxide and then effectively dry the various object surface(s) in the same treatment chamber. However these systems are fully closed and/or sealed. These sealed and/or fully closed systems can increase the time to effectively dry the various surface(s) of the object(s), and can also require the use of high heat to effectively dry the surface(s) of the treated object(s) in a duration of time that is acceptable to the customer. The use of high heat for drying the various surfaces within the treatment chamber and the surfaces of the treated object(s) can potentially damage the various materials and/or components from which the treated object(s) are constructed. This potential damage can increase various costs for the customer including repair costs and/or replacement costs for the thermally damaged treated object(s). In addition, and without limitation, the sizes and/or shapes of the treatment chamber(s) used in the current art are limited for reasons known to those skilled in the art, and this reduces the number(s), size(s), shape(s), and/or dimension(s), of the various object(s) that can be located, treated, and/or dried, inside of the said treatment chambers.

Without limitation, the prior art does not, and without limitation, teach, suggest, and/or describe, and the present invention teaches as an improvement to the current art, an enclosure and/or chamber treatment and processing system for treating the various surfaces of one or more of any suitable object(s) that are located within one or more of any suitable and effective enclosure(s) and/or treatment chamber(s), with any suitable and effective deployed airborne agent(s) such as, but not limited to any, vapor(s)

and/or aerosol(s), and then drying and/or removing the deployed agent(s) from those same treated surfaces, where fresh air, air/gas(s), and/or fresh air/gas(s), is sourced from the environment outside of the airflow system(s), treatment chamber(s), cabinet(s), and/or cabinet housing(s) of the object treatment and drying and/or deployed agent(s) removal apparatus, and is flowed and/or moved, through at least one or more preliminary air/gas(s) filter(s) for purposes such as, but not limited to, preventing the blower(s) from accumulating unwanted foreign object debris or dust, through and/or past at least one blower(s) that pushes, flows, and/or moves, the sourced fresh air, air/gas(s), and/or fresh air/gas(s), into and through a plurality of various locations such as, but not limited to any, airflow system(s), various parts and component(s), air/gas(s) heater(s), air/gas(s) filter(s), treatment chamber(s), and any communicating conduit(s), then the fresh air, air/gas(s) and/or fresh air/gas(s), are flowed and/or moved through one or more primary air/gas(s) filters to effectively filter the said fresh air, air/gas(s) and/or fresh air/gas(s) before it is moved into the treatment chamber(s), the said fresh air, air/gas(s) and/or fresh air/gas(s), is then pushed, flowed, and/or moved, past and/or through at least one air/gas(s) flow heater(s), through at least one treatment chamber(s), through at least one first exhaust air/gas(s) filter(s) to prohibit any particles and/or foreign object debris (FOD) from entering the treatment chamber(s) at any time(s) through or by way of any exhaust conduit(s), through at least one of any deployed agent(s), vapor(s), and/or gas(s) absorption filter(s), through at least one or more additional exhaust filter(s) to prohibit the movement of any, foreign object debris (FOD), virus(s), spore(s), bacteria(s), and/or particles, especially and without limitation, any particles from one or more of any vapor absorption filter(s) such as but not limited to any charcoal and/or carbon dust, to be released into the surrounding environment that is exterior to the treatment chamber(s) and/or environment outside of the treatment chamber and/or cabinet housing, then through and/or past at least one blower(s) that pulls, suctions, flows, and/or moves any, air/gas(s), fresh air/gas(s), heated air/gas(s), heated fresh air/gas(s), water vapor(s), humidity(s), vapor(s), and/or deployed agent(s), from one or more of any location(s) such as, but not limited to any, airflow system(s), treatment chamber(s), and/or any communicating conduit(s), and is flowed and/or moved, through at least one or more exhaust air/gas(s) filter(s) for purposes such as, but not limited to, preventing the blower(s) from accumulating unwanted foreign object debris or dust, and where the said any, air/gas(s), fresh air/gas(s), heated air/gas(s), heated fresh air/gas(s), water vapor(s), humidity(s), vapor(s), and/or deployed agent(s), are exhausted into the surrounding environment outside of the airflow system(s), treatment chamber(s), cabinet(s), and/or cabinet housing(s) of the object treatment and drying and/or deployed agent(s) removal apparatus.

The prior art also does not, and without limitation, teach, suggest, and/or describe, and the present invention teaches as an improvement to the current art, the use of a unique push and pull filtered airflow system that is described in the present invention to move air/gas(s) and/or fresh air/gas(s) through various parts, components, and locations, of the present invention such as, but not limited to any, plurality of air/gas(s) filters, air/gas(s) heater(s), air/gas(s) flow conduits, airflow system(s), and treatment chamber(s), and overcome the difficulty to flow air/gas(s) through the entire airflow system(s) with all of its various parts and components, and overcome the air/gas(s) flow resistance and/or overcome any drop in air/gas(s) flow pressure(s) that is created by all of the various parts, equipments, attributes, variables, and/or components, of the airflow system(s) such as, but not limited to one or more of any, filters, valves, airflow conduits, length of airflow conduits, various angles of airflow conduits, diameter of airflow conduits, conduit designs, airflow control valve design(s), and/or heater element(s). Without being limited, this unique push and pull filtered airflow system also provides an effective means to effectively move any effective volume(s) and/or quantity(s) of any air/gas(s), fresh air/gas(s), heated air/gas(s), and/or heated fresh air/gas(s), through the entire airflow system(s) including, but not limited to any, treatment chamber(s and/or enclosed area(s), air/gas(s) filters, filtered and heated inbound air/gas(s) assembly(s), and filtered exhaust assembly(s), for purposes including, but not limited to, effectively removing the deployed agent(s) from the treatment chamber(s) and any connected conduit(s), as well as effectively dry and/or effectively remove the deployed agent(s) from all of the various surfaces and treated object surfaces within the treatment chamber(s), and where this unique push and pull filtered airflow system also flows and moves fresh air/gas(s) that is brought into the airflow system from outside of the airflow system from one or more location(s) such as, but not limited to, the surrounding environment(s), any one or more locations outside of any external cabinet(s) that may house the one or more airflow system(s), treatment chamber(s), and any associated parts and equipment(s), and/or the room(s) or area(s) in which the various equipment and airflow system(s) of the present invention is located.

Without being limited, the said push and pull filtered and heated airflow system(s) that is described in the current invention, is also an improvement to the current art for other reasons including, but not limited to, (a) it effectively moves the fresh air/gas(s) and heated fresh air/gas(s) into, through, and then out of, the treatment chamber(s) and the entire airflow system(s), (b) the air/gas(s) that move through the treatment chamber(s) and the entire airflow system(s) are effectively heated to effectively dry and/or effectively remove the deployed agent(s) from the various surfaces and treated object(s) surface(s) within the treatment chamber(s) within an effective duration of time, (c) it can effectively overcome any, airflow resistance(s), airflow restriction(s), and air/gas(s) flow rate(s) reduction(s), presented by the entire airflow system(s), and supply any effective quantity of fresh air/gas(s) and heated fresh air/gas(s) per any number(s) and unit(s) of time(s) and at at one or more of any effective airspeed(s) for the flow of the said air/gas(s) through the entire air flow system(s) and the treatment chamber(s), and (d) it can effectively overcome any reduction(s) in the quantity(s) and/or speed(s) of the fresh air/gas(s) and/or heated fresh air/gas(s) that is flowed and moved into, through, and out of, the airflow system(s), that is created by sources such as, but not limited to, the various air/gas(s) filters used to effectively filter the fresh air/gas(s) and/or heated fresh air/gas(s) flowing into, through, and out of, the treatment chamber(s), as well as the various air/gas(s) filters used to effectively filter the fresh air/gas(s), air/gas(s), heated air/gas(s), heated fresh air/gas(s), vapor(s), water vapor(s), humidity(s), and/or deployed agent(s), that are flowed or moved out of the treatment chamber(s) and into the environment that surrounds the treatment chamber(s), entire apparatus(s), system enclosure(s), system outer enclosure(s), cabinet(s), and/or outer cabinet(s), as well as other sources known to those skilled in the art.

It is preferred, without limitation, that this improved push and pull filtered and heated airflow system(s) includes at least one or more of any suitable and effective, fan(s), air/gas pump(s), and/or blower(s) (Herein called Inbound Blower(s)) that supplies, flows, and/or moves fresh air/gas(s) and/or air/gas(s), that can also, and without being limited, be effectively heated, to, into, and, through, various locations such as, but not limited to any, airflow system(s) and the treatment chamber(s), and is suitably and effectively located in one or more of any suitable and effective location(s) in the one or more airflow path(s) that is located before and communicating with the one or more treatment chamber(s), but more preferably, and without limitation, the said inbound blower(s) can be located effectively near or effectively in close proximity to, the one or more air/gas(s) and/or fresh air/gas(s) inlet(s) for the one or more airflow path(s) that connect to and feed into the treatment chamber(s). It is also preferred, without limitation, that the inbound blower(s) also communicates with and moves the air/gas(s), fresh air/gas(s), heated air/gas(s), and/or heated fresh air/gas(s), with any suitable and effective positive pressure(s), into, through, and out of, the treatment chamber(s) for various purposes such as, but not limited to, drying and/or removing the deployed agent(s) from the various surfaces and/or treated object surfaces and/or atmosphere(s) located inside of the treatment chamber(s) and/or assisting with the removal of any substance(s) from the inside of the treatment chamber(s) such as, but not limited to any, vapor(s), water vapor(s), humidity(s), and/or deployed agent(s).

In addition, and without limitation, at least one or more of any suitable and effective, fan(s), air/gas pump(s), and/or blower(s) (Herein called Outbound Blower(s)), is also suitably and effectively located in one or more of any suitable and effective location(s) in the one or more airflow path(s) of the airflow system(s) located after the one or more treatment chamber(s), and the outbound blower(s) communicates with, and more preferably, and without limitation, is located effectively near or effectively close proximity to, the one or more exhaust outlet(s) for the one or more exhaust airflow path(s) connecting from the said treatment chamber(s) and preferably, and without limitation, operates at the same time as the the said inbound blower(s), and moves, suctions, and/or pulls, any, fresh air/gas(s), air/gas(s), heated fresh air/gas(s), heated air/gas(s), vapor(s), water vapor(s), humidity(s), and/or deployed agent(s), with any effective negative pressure(s) from and/or through at least the treatment chamber(s) and any other connecting parts of the airflow system(s) and then pushes the said fresh air/gas(s), air/gas(s), heated fresh air/gas(s), heated air/gas(s), vapor(s), water vapor(s), and/or deployed agent(s), out of the exhaust outlet(s), airflow system(s), and/or improved chamber processing system(s) and into the environment outside of the airflow system(s), treatment chamber(s), cabinet(s), and/or cabinet housing(s) of the object treatment and drying apparatus, for various purposes such as, but not limited to, drying and/or removing the deployed agent(s) from the various surfaces and/or treated object surfaces and/or atmosphere(s) located inside of the treatment chamber(s) and/or assisting with the removal of any substance(s) from the inside of the treatment chamber(s) such as, but not limited to any, vapor(s), water vapor(s), humidity(s), and/or deployed agent(s).

Without limitation, the prior art also does not, teach, suggest, and/or describe, and the present invention teaches as an improvement to the current art, flowing fresh air/gas(s) sourced from the surrounding environment that is exterior to the treatment chamber(s) and/or the environment outside of the treatment chamber(s) and/or cabinet housing(s), using one or more of any suitable and effective blower(s) to push the fresh air/gas(s) into the airflow system(s), effectively filtering the said fresh air/gas(s) with at least one or more suitable and effective air/gas(s) filter(s), before they are flowed into to the one or more treatment chamber(s), and preferably, and without limitation, effectively heating the said fresh air/gas(s) to any significantly lower effective temperature(s) and/or temperature range(s) compared to the prior art, and more preferably, and without limitation, heating the said fresh air/gas(s) to one or more of any effective temperature(s) between 50 to 150 degree Fahrenheit, and more preferably, and without limitation, between 80 to 120 degree Fahrenheit, before flowing and/or moving the said heated fresh air/gas(s) and/or unheated fresh air/gas(s) into the treatment chamber(s), and then exhausting and/or moving or flowing the said fresh air/gas(s), air/gas(s), heated fresh air/gas(s), heated air/gas(s), vapor(s), water vapor(s), and/or deployed agent(s), out of the treatment chamber(s) and through one or more of any effective particle capturing filter(s) and/or deployed agent(s) and vapor(s) capturing filter(s), as well as through the one or more exhaust conduits with the assistance of one or more of any suitable and effective exhaust blower(s) that also pushes the said fresh air/gas(s), air/gas(s), heated fresh air/gas(s), heated air/gas(s), vapor(s), water vapor(s), and/or deployed agent(s), out of the airflow system(s) and into the surrounding environment. More specifically, and without being limited, the said fresh air/gas(s), air/gas(s), heated fresh air/gas(s), heated air/gas(s), vapor(s), water vapor(s), and/or deployed agent(s), is moved or flowed out of the one or more exhaust outlet(s), airflow system(s), filtered exhaust assembly(s), and/or improved chamber processing system(s) and into the surrounding environment and/or the environment outside of the airflow system(s), treatment chamber(s), cabinet(s), and/or the surrounding environment that is exterior to the treatment chamber(s) and/or the environment outside of the treatment chamber(s) and/or cabinet housing(s). Without limitation, this provides various advantages such as, but not limited to: (a) the size of the treatment chamber(s) does not have to be limited in size to effectively and quickly remove the deployed agent(s), vapor(s), water vapor(s), gas(s), and/or humidity(s), from the treatment chamber(s), (b) the size of the treatment chamber(s) does not have to be limited in size to effectively and quickly dry the various surfaces and object(s) surfaces inside of the treatment chamber(s), (c) larger treatment chamber(s) can provide and/or allow for the treatment of one or more long length object(s) such as, but not limited to any, cord(s) wire(s), cable(s), entire endoscope(s) and their attached cable(s), patient monitoring cable(s), (d) the time to effectively dry the various surfaces and treated object(s) surfaces within the treatment chamber(s) is significantly reduced, (e) the total process time to effectively treat and then dry and/or remove the deployed agent(s) from the various surfaces and object(s) surfaces within the treatment chamber(s) and allow the operator to remove the effectively treated and processed object(s) from the treatment chamber(s), is significantly reduced, (f) the present invention reduces the total processing time for the treated object(s) because significantly less time and/or even no time, is needed for effectively cooling the various surfaces of the treated object(s) after being dried and/or the deployed agent(s) are removed from the surfaces of the treated object(s), (g) more object(s) can be treated in the larger treatment chambers provided by the present invention, (h) flowing air/gas(s) that is heated to much higher temperatures than those used in the present invention, through sealed or closed treatment chamber(s) and processing systems, as shown in the prior art for purposes including, but not limited to, drying the various surfaces and object(s) surfaces inside of the treatment chamber(s) and/or removing the deployed agent(s) from the various surface(s) inside of the treatment chamber(s) such as, but not limited to any, surface(s) of the treated object(s), is not needed in the present invention, and the present invention avoids thermally damaging the treated object(s), (i) flowing air/gas(s) that is heated to much higher temperatures than those used in the present invention, to thermally degrade the deployed agent(s) into benign chemical components in area(s) such as, but not limited to, the treatment chamber(s), is not needed in the present invention and the present invention avoids thermally damaging the treated object(s).

Without limitation, the prior art also does not, teach, suggest, and/or describe, and the present invention teaches as an improvement to the current art, controlling the flow or movement of air/gas(s) and/or fresh air/gas(s) into and out of the treatment chamber(s) where the airflow can be controlled by a plurality of any suitable and effective valves to effectively seal the treatment chamber(s) suitably and/or effectively before the deployed agent(s) are moved and/or flowed into the treatment chamber(s), and then to effectively reopen the said valves to effectively unseal any sealed treatment chamber(s) to allow the flow and/or movement of any fresh air/gas(s), air/gas(s), heated fresh air/gas(s), and/or heated air/gas(s), into and through the said treatment chamber(s) and airflow system(s), for various purposes including, but not limited to, effectively removing the deployed agent(s), vapor(s), humidity(s), gas(s), and/or water vapor(s), from the one or more area(s) inside of the treatment chamber(s) and airflow system(s) and/or effectively drying and/or effectively removing the deployed agent(s) from the various surface(s) and/or object surface(s) within the treatment chamber(s), where the fresh air/gas(s), air/gas(s), heated fresh air/gas(s), and/or heated air/gas(s), that are flowed into, through, and out of, the said airflow system(s) and treatment chamber(s) is then flowed and/or moved out of the filtered exhaust assembly(s), airflow system(s), and exhaust outlet(s), and into the surrounding environment outside of the airflow system(s), treatment chamber(s), treatment enclosure(s), and/or any other enclosure(s), cabinet(s), and/or cabinet housing(s), that can, and without limitation, house and/or enclose the present invention.

Without limitation, the prior art also does not, teach, suggest, and/or describe, and the present invention teaches as an improvement to the current art, the inclusion and/or use of one or more improved means to effectively dry and/or quickly dry one or more of any floor(s) and/or horizontal surface(s) located inside of the treatment chamber(s), whereby one or more of any suitable and effective, air/gas(s) outlet(s), air/gas(s) director(s), and/or diffuser(s) for air/gas(s), that effectively communicates with one or more of any suitable and effective fan(s), air/gas pump(s), and/or blower(s), to move and/or flow any fresh air/gas(s), air/gas(s), heated fresh air/gas(s), heated air/gas(s), vapor(s), water vapor(s), gas(s), humidity(s), and/or deployed agent(s), that is sourced from and recirculated from the one or more of any suitable and effective location(s) inside of the treatment chamber(s), can be suitably and effectively located within and/or interfaced with the treatment chamber(s), and the said any fresh air/gas(s), air/gas(s), heated fresh air/gas(s), heated air/gas(s), vapor(s), water vapor(s), gas(s), humidity(s) and/or deployed agent(s) can be effectively recirculated and emitted into the said treatment chambers at one or more of any suitable and effective speed(s), volume(s) of air/gas(s) flow(s), velocity(s), and/or cubic feet per minute (CFM), and can be directed at, about, horizontal to, along, and/or towards, one or more of any area(s) and/or location(s) of and/or near any floor(s) and/or horizontal surface(s) inside of the treatment chamber(s), and can also be used, without limitation, at one or more of any suitable and effective time(s) and for any suitable and effective duration(s) of time(s), but at least, and without limitation, at any suitable and effective time(s) such as, but not limited to, (a) during one or more of any suitable and effective processing and/or treatment step(s) for the various surface(s) and/or atmosphere(s) within the treatment chamber(s), (b) during one or more of any surface drying step(s) for any surface(s) located within the treatment chamber(s) and/or any step(s) to remove any deployed agent(s) from any surface(s) and/or object(s) surface(s) located inside of the treatment chamber(s), (c) during one or more of any step(s) to effectively mix and/or homogenize any deployed agent(s) located within the atmosphere(s) inside of the treatment chamber(s) such as, but not limited to, during the one or more step(s) when the deployed agent(s) are moved and/or deployed into the treatment chamber(s) and/or during one or more of any step(s) to allow the deployed agent(s) to dwell inside of the treatment chamber(s) after the deployed agent(s) are moved and/or deployed into the treatment chamber(s). Without being limited, the said mixing and/or homogenizing activities of the deployed agent(s) can serve various purposes such as, but not limited to, helping the deployed agent(s) to effectively fill the treatment chamber(s) and/or prevent the deployed agent(s) from stratifying inside of the treatment chamber(s).

SUMMARY OF THE INVENTION

The present invention generally relates to a combination of various apparatuses and methods for the sanitization, disinfection, high level disinfection, or sterilization of both the interior and exterior surfaces of an object or medical device, including any articulating surfaces of interest, or plurality of objects within one or more closed space(s), closed system of space(s), or chamber(s), of any space, size, shape, configuration, or construction, that is either sealed or unsealed (Hereinafter called "sterilization chamber"). In order to accomplish this, anti-pathogen/toxin/fungal/sporicidal agent(s) or substance(s) are first created, generated, and/or administered into the sterilization chamber. It is preferred without limitation, that the objects, e.g., endoscopes, are washed according to the manufacturer's recommendations or methods common to the industry, before being placed inside of the sterilization chamber. However, the washing and cleaning activities can also take place within the sterilization chamber prior to the application of the anti-pathogen/toxin/fungal/sporicidal agents(s) or substance(s).

According to an embodiment, any anti-pathogen/toxin/fungal/sporicidal agent(s) or substance(s) to be applied or used (hereinafter "applied agent" or "applied agent(s)"), may be in the form of a gas, vapor, plasma, or aerosol. It is preferred, without limitation, in the present invention that the "applied agent" is an aerosol, including, but not limited to, any acidic oxidizer, generated by one or more ultrasonic nebulizer(s). Transducers of any geometry, frequency, or construction may be used. The aerosol may be created by any means and may be of any concentration, number, size, or density; however it is preferred, without limitation, that the aerosol generally includes droplets whose size is five micron or less. It is preferred without limitation that the aerosol has a higher rather than lower mass concentration or density of droplets. In addition, any substance may be applied to neutralize any chemical residue on the interior or exterior of an object and/or device.

As previously discussed, the prior art is limited because of the difficulty that an "applied agent" has in reaching the interior surfaces of objects, lumen or channels found in an endoscope in a short period of time. Quicker turn-around times may be accomplished by improving the current art by means including, but not limited to: decreasing the processing time or exposure time to the "applied agent", and decreasing the drying time of the object.

The prior art is further limited because of the difficulty of the "applied agent" or substance to reach surfaces that are interfaced/articulated with a coupling(s) or other devices or components.

The present invention addresses the failure of the prior art to treat the articulating surfaces of an endoscope and coupling by incorporating an innovative porous and/or permeable interface between the endoscope and coupling. This innovative porous and/or permeable interface assures that the "applied agent" is able to reach the entirety of the internal spaces and surfaces, including endoscope lumens, channels, internal and external spaces and surfaces. One of the critical features of this solution is the design of the interface between the supply of negative or positive air/gas pressure used to bring the "applied agent"(s) and the surfaces of the endoscope. The porous and/or permeable interface of the present invention not only provides the necessary positive or negative air/gas pressure, but more importantly, it is able to do so while still insuring that all of the surfaces including the interface have sufficient exposure to the "applied agent". While this innovative system and method could be applied to other forced air sterilization systems/ "applied agent(s)", it is preferred in the present invention that transducer based ultrasonic nebulization is utilized. It is also important to note that this particular aspect of the present invention could easily be adapted for use with any "applied agent" that can be applied to any surfaces of a device or endoscope in liquid form such as, but not limited to, a jet or stream of disinfecting or sterilizing liquid or mixture of liquids as taught by U.S. Pat. No. 5,425,815, (Parker et al., 1995) incorporated herein by reference in its entirety.

These advantages include, but are not limited to: 1) the ability to offer large chambers in which the devices to be disinfected can be positioned and treated without the technical challenges and costs associated with EtO and plasma; 2) the ability to build simple glass or plastic see-through chambers; 3) the ability to incorporate the addition of one or more polymer glove(s) or finger(s), built into the wall(s) of the closed space or sterilization chamber (similar in purpose and design to what is found in common laboratory or industrial glove boxes); 4) a very rapid processing times associated with the ultrasonically-generated aerosols, and 5) the ability to utilize a wide range of liquid disinfection or sterilization agents or mixtures of agents.

The aerosol created by the ultrasonic nebulizer(s) is generated by one or more ultrasonic transducers located below the surface of a liquid agent. The transducer(s) energy output is focused to either a point and/or an area near the surface of the liquid causing a surface disturbance, which results in the formation of an aerosol of the agent. Each transducer used in this apparatus is made from lead-zirconate-titanate-four (PZT-4), or other piezoelectric materials. The transducer(s) are operated in the frequency range of 0.001 to 10.0 MHz. The resultant aerosol is then evacuated from the reservoir and/or chamber in which it is generated, by a blower or other source of pressurized air, and moved into the designated or targeted space or closed area or chamber (hereinafter "sterilization chamber"). After its utilization in disinfecting or sterilizing a tool/device, the aerosol can then be circulated back to the aerosol generation chamber. This is taught in Kodera et al. U.S. Pat. No. 4,366,125 and Sheiman, U.S. Pat. No. 6,379,616. Recirculation can also be applied to any gas, plasma, vapor, aerosol, or other form of an "applied agent" or substance. The aersolized agent within the sterilization chamber may be moved within the chamber by a blower, fan, or other source of pressurized air.

U.S. Pat. No. 4,366,125, (Kodera et al., 1980), which is incorporated herein by reference in its entirety, including any references cited therein, describes an improved method and device involving ultrasonic nebulization that includes a means to heat the liquid which is nebulized. Kodera et al. teaches that heated H2O2 was more efficacious than H2O2 used at room temperature (col. 1, line 19-25). In other words, the efficacious nature of a liquid agent can be increased as it is heated to temperatures higher than ambient temperature. It is preferred, without limitation, that this advancement in the art is incorporated into the present invention.

Sheiman, U.S. Pat. No. 6,379,616 also improves upon the art by incorporating a heating element operatively coupled to the inlet of the closed area or sterilization chamber. According to Sheiman, the purpose of the heating element is to provide a means for effecting condensation of the aerosol within or on the article. This could also be incorporated into the present invention as described.

An embodiment of the present invention includes, without limitation, a possible means for radiating heat that is either operatively coupled to and/or about the outlet(s) of the closed area or sterilization chamber, or anywhere past the said outlet(s) and along the path of the air and aerosol as it is recirculated from the closed space or sterilization chamber back into the aerosol generation chamber(s). The purpose of this embodiment is to further diminish the diameter of the aerosol droplets before they reach the interior of the aerosol generation chamber(s). Heating, or other means to encourage rapid evaporation of the aerosol droplet will reduce the possibility of coalescence.

Another embodiment of the present invention includes, without limitation, the possible addition of a means to heat the floor within the closed space or sterilization chamber. A heated plate(s) could also be placed in this location. The purpose of having a heated surface at the bottom of the closed space or sterilization chamber is to repel the downward trajectory of the aerosol droplets as a result of gravity or thermal forces. In addition, droplets that contact the heated surface(s) may be re-energized or transformed into a vapor. This will contribute to the efficacious nature of the overall process and further decrease aggregate settling velocity. It is important to note that care should be taken in the placement of this heated surface so that an item(s) placed in the chamber is not itself heated. Increased heat of an object or device will cause the droplets to be repelled and will correspondingly reduce the efficacy of the process.

An apparatus and method of another embodiment of the present invention comprises placing one or more endoscope(s), tool(s) or object(s), in a closed space or sterilization chamber with the addition of a means to enable the sanitization, detoxification, disinfection, high level disinfection, or sterilization of the interior area or surfaces, lumen(s), and/or channel(s) of the endoscope(s) or object(s). This means is able to interface or connect positive air/gas pressure or negative air/gas pressure (vacuum) line(s) with an object or endoscope inside of the sterilization chamber, and move "applied agent"(s) or substance(s) through the entire object or endoscope with sufficient volume and velocity without compromising the ability to treat contaminated areas or surfaces under or between that interface or connection and the medical device. It is preferred, without limitation, that the aforementioned object be washed, cleaned, or rinsed, prior to being placed into the sterilization chamber.

This particular embodiment utilizes an innovative pressure interface assembly including a coupling and interface or interface material combination that is unique for this application. This assembly is interfaced/articulated with the open end of the object or the distal end of the endoscope where the lumen/ports/working channels exit.

The pressure interface assembly has a number of components that include, without limitation, a porous and/or permeable interface or interface material (hereinafter called "interface") and a coupling. The coupling may be constructed from various materials such as but not limited to stainless steel, glass, cellulose, polyolefin, paper, polymer, natural or manufactured fibers or materials, that may be coated or uncoated, or constructed with combinations of these materials, or other materials known in the art. The coupling may be rigid, semi-rigid, or flexible. The coupling may have one or more ports or other means for attaching tubes, hose, pipes, duct, tunnels, conduit etc. (hereinafter called "delivery pipe") that supply air, gas, or the "applied agent" to the various spaces and surfaces of the pressure interface assembly and endoscope, including without limitation their internal spaces and surfaces, under positive or negative pressure.

The interface assembly may be used, without limitation, to dry the endoscope or to push or pull the "applied agent"(s) or substance(s) through any of its internal spaces, lumen or channels. The coupling can be designed so that one end is able to fit over an end of the endoscope and the other end of the coupling is designed to interface or connect with the delivery pipe. The coupling may also have various opening sizes on one end and various opening sizes on the other. The end of the coupling that is designed to fit over an end of an endoscope can also have one or more openings of various shapes and geometries. This opening can control the negative or positive air/gas flow or pressure in or out of the coupling. The internal dimensions of the coupling are designed to allow it to fit over the end of the endoscope and interface/articulate with the interface that is positioned between the coupling and the endoscope. The thickness of the coupling as well as the material(s) from which it is constructed, may also contribute to the efficacious performance of the interrelationship between the coupling, interface and endoscope, and their surfaces.

The interface is designed so that its internal dimensions provide a sufficiently tight fit with the outside dimensions of the endoscope or object. Attributes such as, but not limited to the width, thickness, porosity and/or permeability, flow of "applied agent" or gas, absorbency, as well as other chemical, mechanical, and physical (including durometer) properties of the interface may also contribute to an effective interface. The interface is either slipped over the end of the endoscope or at least a portion is mounted inside of the coupling, or combinations thereof. The coupling is then fitted over the end of the endoscope so that the endoscope interfaces sufficiently with the interface material and the interface material interfaces sufficiently with the coupling. The coupling is designed so that its internal dimensions provide a sufficient fit with both the contacted interface material and the endoscope. In certain situations, the thickness of the coupling material may also contribute to a sufficiently sealed or interfaced system.

Attributes such as but not limited to the interface material utilized, porosity and/or permeability of the interface, absorbency of the interface, as well as other chemical, mechanical, and physical (including durometer) properties, the interface thickness and width, the fit of the interface to the endoscope or object, the pressure exerted by the fit of the coupling to the interface and endoscope or object, and the distance the coupling overlaps on the interface material, control the rate of air/gas flow through the interface which then directly impacts the air/gas pressure differential between the inside and outside of the coupling.

It is important that the air/gas pressure differential be controlled so that a sufficient air/gas pressure differential exists to achieve an anti-pathogen/toxin/fungal/sporicidal effect on both the area and surfaces under the interface and the internal surfaces inside of the endoscope. These variables can be optimized for each object or endoscope configuration and coupling configuration based on, but not limited to, its external and interior dimensions, choice of permeable and/or porous material, internal area, and number, size and length of their interior areas.

There are two main components or features of an effective interface in this assembly. First, the interface must be porous or permeable. This allows the "applied agent" to pass through it. The air/gas, as well as the "applied agent" (if applicable) may also, without limitation, pass through the interface at a controlled and/or limited, but effectual rate. The passage of the "applied agent" through the interface material allows the area and surfaces under the interface material to be exposed to, and acted upon, by the "applied agent" in order to achieve the desired level of sanitization, detoxification, disinfection, high level disinfection, or sterilization. The interface may have absorbent characteristics to improve its efficacy. The composition of the interface material is not limited to but could be as simple as cotton gauze or some other substrate made of natural or manufactured fibers. The interface may also be constructed from one or more layers of various materials or combinations of materials such as but not limited to, cloth, gauze, manufactured fibers, synthetic fibers, natural fibers or materials, cellulose, polyolefin, polymer, or other materials known in the art, in order to control attributes such as, but not limited to, absorbency, and the flow rate or passage of the "applied agent" through the interface material as desired.

The limitation and/or control of the rate of flow of air/gas and/or "applied agent" allows the present invention to create an effective negative or positive air/gas pressure to move the "applied agent" through the interior space, lumens, and/or channels of the endoscope, as well as through the interface. For instance, if a vacuum is applied to the coupling interfaced/articulated with the interface material, the "applied agent" will be pulled through both the interface material and/or the areas of articulation as well through the interior space and/or lumens or channels with sufficient velocity to assure anti-pathogen/toxin/fungal/sporicidal activity on the surfaces throughout the length of the interior area, lumen, or working channels of the object or endoscope and in the area and on the surfaces under the interface.

The second feature of an effective interface involves the application and/or control of an effective pressure exerted on the interface as it contacts the object or endoscope. This assures a sufficient flow of "applied agent" through all areas of the interface and results in obtaining the desired level of sanitization, detoxification, disinfection, high level disinfection, or sterilization of the entire area and surfaces under the interface. It is preferred without limitation that the pressure exerted on the interface is evenly distributed.

According to another embodiment, the applied pressure is effectual and efficacious. The exerted pressure on the interface can result from the interface/articulation of the coupling and interface material with the endoscope. The effectiveness of the interface/articulation may also be augmented or optimized by the application, bonding, or interposition of one or more layers of various materials or combinations of materials such as but not limited to, cloth, gauze, manufactured fibers, synthetic fibers, natural fibers or materials, cellulose, polyolefin, polymer, or other materials known in the art. The exerted pressure on the interface material can result from, or be further controlled or optimized, by the interface/articulation of the coupling and interface material with the object or endoscope. It may be further controlled or optimized by the use of an inflatable pillow, balloon, bladder, reservoir, or other inflatable or expandable means or material (hereinafter called "balloon") between the coupling and interface material, between the endoscope and the interface material, between the endoscope and the coupling, on the internal surface of the interface, and/or around the coupling. The balloon can be constructed of and/or have its outermost layer constructed of this interface material and function as the interface layer. In either case involving the balloon, varying the amount of pressure inside of the balloon controls the pressure exerted on the interface. Additional means may be used to exert pressure on the coupling, interface material, and endoscope in order to create at least a minimum working interface. For example, a clamp that fits over and is used to apply pressure to the coupling, interface material and endoscope may be used to create a sufficient working interface. In another example, a ring of material can be incorporated into the coupling and the ring in a manner to exert evenly distributed pressure on the interface material.

It is also possible to exclude the interface component of the pressure interface assembly, and cause the coupling to function as an interface to the endoscope; this feature represents an embodiment of the pressure interface assembly in its simplest form. In this alternative, the entire coupling, part of the coupling, or the end of the coupling that interfaces with the object or endoscope, is constructed from, or is laminated, glued, cemented, adhered, or otherwise attached, to the interface. Effective and preferably evenly distributed pressure can be exerted on the interface material by means previously discussed, and can include, but not limited to the exertion of pressure by the inflation of an inflatable pillow, balloon, bladder, reservoir, or other inflatable or expandable means or material (balloon) either between the interface layer and the coupling, inside of the coupling walls, or on the exterior surfaces of the coupling. Everything previously discussed pertaining to the coupling and seal material applies to this embodiment. In general, the coupling is designed, constructed, treated, or processed, so that a pressure differential is able to be established that results in the effective flow of an applied agent or substance through both the interior space of the endoscope and the interface that is in contact with the endoscope, resulting in an anti-pathogen/toxin/fungal/sporicidal effect on areas and surfaces that include, but are not limited to, the areas and surfaces surrounding and under the seal material.

Another embodiment of the present invention includes the supply of air/gas, that is under either negative or positive pressure, to the pressure interface assembly by using a means such as, but not limited to, a vacuum pump, air/gas pump, pressurized air source, fan, or blower. This air pressure serves several functions. First, the positive and/or negative air/gas pressure can be applied to the pressure interface assembly at the beginning and/or end of the treatment, sanitization, detoxification, disinfection, high level disinfection, or sterilization cycle, or at any time during the entire cycle, in order to move air/gas or dry and/or heated air/gas through the interior space, lumens, and/or channels of the endoscope. This will remove any moisture present in these areas. One or more heating element(s) placed in the air stream before the pressure interface assembly can also, without limitation, provide heated air (Rosdahl et al. pg 3 Col. 123-127). It is preferred, without limitation, that any air from outside of the sterilization chamber that is pulled, drawn, pushed, or otherwise moved into the sterilization chamber and/or the endoscope be filtered before its entry into the sterilization chamber and endoscope. Any high efficiency filter such as a HEPA filter(s) or other filter(s) that is known to those skilled in the art and/or is acceptable in the industry may be used. The air/gas may be filtered with any type of filter acceptable to those skilled in the art before its exit from the sterilization chamber. The object or endoscope may be dried by heated and/or dehumidified air within the sterilization chamber and/or before its entry into the sterilization chamber.

The positive air/gas pressure or negative air/gas pressure is also intended, without limitation, to move the "applied agent" or substance through the interior space of the endoscope as well as through the interface and the area under the interface. It is preferred, without limitation, that if a negative air/gas pressure is supplied to the coupling that a pressure differential is established. This will cause, without limitation, the flow of air/gas and "applied agent" or substance from the sterilization chamber, to pass through the interface material, the area under the interface, the internal space within the endoscope, and into the coupling. Once in the coupling, the air/gas and/or "applied agent" flows into the attached tubes, hose, pipes, duct, tunnels, conduit, or delivery pipe, where it is eventually vented back into the sterilization chamber, or through a filter and into the outside environment.

The "applied agent" may also, without limitation, flow into the coupling under positive air/gas pressure. It is preferred, without limitation, that the "applied agent" or substance is pulled from the sterilization chamber, or a chamber where it is generated, and flowed into the coupling via the attached tubes, hose, pipes, duct, tunnels, conduit, or delivery pipe. It then flows, without limitation, out of the interface material, the area under the interface material, and through the internal space within the object or endoscope, and into the sterilization chamber. If generated in a chamber separate from the sterilization chamber, the "applied agent" or substance in this case, can without limitation, be separately delivered into the sterilization chamber.

Another embodiment of the current invention is the incorporation, positioning, or placement, of one or more biological indicator(s) and/or chemical exposure indicator(s) in or articulated with the pressure interface assembly. It is preferred in the present invention that the indicator(s) is placed or positioned inside the coupling. The indicator(s) provides a method of assuring that proper sanitization, detoxification, disinfection, high level disinfection, or sterilization has occurred within the pressure interface assembly.

An apparatus and method of another embodiment of the invention comprises the incorporation of a means to flow or circulate either filtered or unfiltered air/gas from outside of the apparatus into the sterilization chamber. This air/gas can also be flowed through the interior space, lumens, and/or channels of the endoscope inside of the sterilization chamber by using the same means that is used to supply positive or negative air/gas pressure to the pressure interface assembly that is interfaced with the endoscope. This air may be heated to remove moisture from any of the surfaces of the endoscope(s) within the sterilization chamber as well as the surfaces of their interior areas, lumen or channel(s). This activity can occur at any time including, but not limited to, before the application of the "applied agent" or substance. In addition, and without limitation, the completion of this activity at the end of the sanitization, detoxification, disinfection, high level disinfection, or sterilization cycle can reduce the entire cycle/processing time. When an "applied agent" or substance is applied, such as but not limited to an aerosol, this activity can also reduce the relative humidity in the sterilization chamber to ambient or below ambient levels. The incoming air can be, without limitation, effectively filtered with the use of any high efficiency filtering process, or other filtering means known in the art. The sterilization chamber can also be, without limitation, coupled to a filtered exhaust system to allow the incoming filtered air to replace air inside the chamber.

An apparatus and method of another embodiment of the present invention comprises the incorporation and use of any apparatus or methods know to those skilled in the art, to remove humidity from within the sterilization chamber(s) or other targeted area(s). This should not be confused with a fan or blower that was previously mentioned. The dehumidification apparatus may, without limitation, be placed or interface with or within the sterilization chamber(s) or other connected areas or spaces. The dehumidification apparatus may be operated any time after the application of the "applied agent". After the endoscope processing steps are completed and the sterilization chamber(s) or other targeted area(s) are dehumidified, the air/gas within these spaces may be filtered to remove substances such as, but not limited to, any remaining odors, chemicals, smells, vapors, aerosols, or gases. Any filtering means or level of filtering may be utilized that is known to those skilled in the art. The processed air/gas may be, without limitation, returned back to the sterilization chamber(s) or any space(s) connected to the sterilization chamber(s). This feature allows, without limitation, the system or process to be self-contained until the sterilization chamber is opened at the end of the operation cycle.

An apparatus and method of another embodiment of the present invention comprises the incorporation of a means for holding or positioning the endoscope so that all of its surfaces are exposed to the "applied agent" and drying cycle. An apparatus and method of another embodiment of the present invention comprises the inclusion of a means for holding or positioning the endoscope during the sterilization cycle. Currently many sanitization, detoxification, disinfection, high level disinfection, or sterilization systems cannot adequately address the problem with shadowing, or inadequate coverage, when one hard or impenetrable surface contacts another.

According to one embodiment of the present invention, the endoscope is held about its circumference with a loop, band or it is cradled, in one or more places with a porous, permeable, semi-permeable and/or absorbent material and the remaining material is then placed on hooks or other holding mechanisms positioned within the sterilization chamber so that the object or endoscope can hang in free space within the sterilization chamber. Without limitation, previous tests have shown that certain porous materials like glassine have shown sufficient permeability with this process to obtain a high level of disinfection on the internal side of the barrier material.

According to another embodiment of the present invention, the endoscope is placed on one or more beams or forks (hereinafter "Start Beams") that are located within the sterilization chamber. These beams or forks can be of various sizes and shapes and interplay or loosely interlock with opposing beams or forks (hereinafter "Opposing Beams") that can be of similar shape and size. During the application of the "applied agent" either the "Start Beam(s)" or "Opposing Beam(s)" move by way of various mechanical means know in the art, and take hold of the endoscope so that it is transferred from the Start Beams to the Opposing Beams or from the Opposing Beams to the Start Beams. This process can be reversed during the drying cycle(s). This process can be timed so that all surfaces receive a sufficient or efficacious exposure to both the "applied agent" and drying cycle.

According to an embodiment, it is more preferred, without limitation, that one or more endoscopes is placed within an enclosed area, chamber, or sterilization chamber, and the internal and external surfaces of the endoscope are simultaneously or non-simultaneously subjected to various combinations of activities including, but not limited to, washing, cleaning, rinsing, drying, disinfection/sterilization, in various orders, frequency, and duration. Some of these activities may not be undertaken. This embodiment improves the current methodology for the disinfection or sterilization of an endoscope.

The initial processing or cleaning of an endoscope in this embodiment incorporates activities already known to those skilled in the art. These activities may include, but are not limited to, (1) Wiping, or otherwise cleaning the endoscope in various ways known to those skilled in the art, to remove liquids, debris, contaminants, blood, mucus, feces, urine, or any other substances that are unwanted or undesirable; (2) Placing the endoscope into a chamber, washer, or other device or means for cleaning, washing, or otherwise disinfecting/sterilizing endoscopes or other objects (hereinafter called "washer"); (3) Securing or holding the endoscope within the washer, (4) Interfacing the endoscope with a hose, tube, or other delivery means known to those skilled in the art (hereinafter "supply tube") in which the supply tube enables various liquids including, but not limited to, surfactants, and high purity rinse water, to be moved through the various channels and lumen of the endoscope at various stages of the cleaning process; (5) Operating the washer to spray, cover, flood, or any combination thereof, of the inside or outside surfaces of an endoscope with liquids or compounds such as, but not limited to, surfactants or other cleaning liquids; (6) Operating the washer to subject, spray, cover, flood, or any combination thereof, various surfaces such as but not limited to, the inside and outside surfaces of the endoscope, with liquids or compounds such as, but not limited to, any liquid rinse (hereafter "rinse" or "rinse water"), which may be formed of any liquids or combination of liquids such as, but is not limited to, high purity water.

In order to improve the art and decrease the endoscope processing time, improvements are made after this particular "rinse" activity to the current art and are shown in the following embodiments. The endoscope processing or cleaning is completed in the current art by the following activities: (7) Applying a disinfectant to both the interior and exterior surfaces of the endoscope in various ways known to skilled in the art such as, but not limited to, pumping or spraying onto the various internal and external endoscope surfaces; (8) Rinsing the interior and exterior surfaces of the endoscope in various ways known to skilled in the art such as, but not limited to, pumping or spraying high purity water onto the various internal and external endoscope surfaces; (9) In many applications the endoscope surfaces may also, without limitation, be rinsed in a manner known to those skilled in the art, with a volatile solution such as, but not limited to, alcohol, and this can also replace the high purity rinse water mentioned above; (10) Drying the internal and external surfaces in a manner known to those skilled in the art; (11) Removal of the endoscope from the washer or chamber.

According to an embodiment, after the endoscope is treated with surfactant and, without limitation, rinse water, its internal and external surfaces may, without limitation, be dried before application of the "applied agent". The internal surfaces may, without limitation, be dried with air/gas flow through one or more supply tubes in a manner known to those skilled in the art, and the external surfaces may be dried with various means known to those skilled in the art. The application of the "applied agent" may be, without limitation, followed by another rinse water cycle, volatile liquid rinse cycle, and/or drying cycle. However, to further reduce processing time, it is preferred, without limitation, that the internal and external surfaces of the endoscope are dried in a final drying activity in a manner known to those skilled in the art, after the application of the "applied agent"(s). It is possible, without limitation, to skip the final rinsing activity(s) for reasons including, but not limited to, aerosols such as, but not limited to, ultrasonically derived aerosols, are able to be administered to the endoscope's surfaces as a thin film of a low concentration of peroxyacetic acid, which then breaks down into harmless components as it dries. This particular embodiment will improve the current art by significantly decreasing the overall processing time, as well as increasing the efficacy of the process.

According to an embodiment, after the endoscope is cleaned with surfactant and/or rinsed, the inside and outside surfaces of the endoscope are treated with one or more "applied agent"(s) in the form of an aerosol. It is preferred, without limitation, that the internal and external surfaces of the endoscope be dried in a manner known to those skilled in the art, before the applied agent(s) is applied. The "applied agent"(s) are created, generated, and/or administered in or into the sterilization chamber. It is preferred, without limitation, that the aerosol is any aqueous aerosol that is generated or created by any transducer or ultrasonic nebulizer of any construction and design. The "applied agent"(s) may be pushed or pulled through the endoscope with various means known to those skilled in the art. The agents may be, without limitation, first administered or deployed into the sterilization chamber and then pulled through the endoscope with a vacuum or negative air/gas pressure. This particular embodiment will improve the current art by significantly decreasing the processing time.

According to an embodiment, the "applied agents" may also be, without limitation, in the form of any gas, vapor, plasma, or aerosol. The prior art includes the use of pumping, jetting/spraying, or flowing agents as a liquid over the external surfaces as well as through the lumens and channels of an endoscope for disinfection/sterilization purposes, and are not claimed in the present invention.

According to another embodiment, after the various endoscope surfaces are treated with an agent, the internal surfaces, as well as external surfaces of the object or endoscope may be, without limitation, exposed to another rinse liquid comprising one or more liquids that include, but not limited to high purity water, all in a manner known to those skilled in the art. After the "applied agent" or final rinse liquid is applied, all of the endoscope surfaces may also, without limitation, be rinsed with a volatile solution such as, but not limited to an alcohol solution. The endoscope can then be removed from the washer and hung to dry.

According to another embodiment, and without limitation, the internal and external surfaces of the endoscope may be dried with means including but not limited to, dehumidification of the air within the chamber before the endoscope is removed from the washer. The supply tube may, without limitation, provide the air/gas that is used to dry the internal surfaces, and the various external surfaces are dried in a manner known to those skilled in the art.

An apparatus and method of an embodiment of the present invention, briefly summarized, comprises cooling or decreasing the temperature of the objects, the atmosphere in which they reside, or any or all targeted surfaces or areas, including the internal surfaces of an object(s) such as, but not limited to an endoscope, within the sterilization chamber(s). This is accomplished in the present invention via the use of one or more, or the combination of one or more, of any thermoelectric and/or refrigeration cooling system(s) to cool or chill any air or gas within the sterilization chamber, before and/or during the administration of the aerosol into the sterilization chamber(s) or other to targeted area(s). Cool air may also, without limitation, be moved through the endoscope or any other object by various means known to those skilled in the art, as well as addressed in the present invention, before or during the "applied agent" phase or applied aerosol. This cooling activity or process enables the present invention to utilize the principals of aerosol behavior to increase the efficacy or performance of the process of the present invention. Aerosol particles experience a force in the direction of decreasing temperature. By decreasing the surface temperature of the targeted surfaces, the administered aerosol, and especially an aerosol where the liquid was heated, is drawn towards those cooled surfaces forming a microfilm.

According to another embodiment of the present invention, the one or more structures, pillars, members, beams, forks, clamps, or other means to support, hold, cradle, suspend, position, or support the object(s) or endoscope(s) within the sterilization chamber, can have, without limitation, one or more means incorporated into their construction to disperse, or even pull in, any substances used for processing the object(s) or endoscope(s) such as, but not limited to, surfactant, rinse water, high purity rinse water, alcohol solution, "applied agent"(s) in any form, heated air/gas, and dehumidified air/gas. These substances may flow at any quantity, rate, or pressure. In addition, any part of the one or more structures, members, beams, forks, or other means to hold or support the endoscope(s) within the sterilization chamber can be, without limitation, effectively covered with any interface material or combination of interface materials, through which these substances may move or flow. This can help to insure that all of the surfaces of the object(s) or endoscope(s) including the interface material(s), have sufficient exposure to any substances used in the processing steps used inside of the sterilization chamber.

An apparatus and method of another embodiment of the present invention comprises a new and novel way to administer the "applied agent"(s) into one or more sterilization chamber(s) in which the object(s) or endoscope(s) are positioned. The sterilization chamber(s) can be, without limitation, effectively sealed or enclosed when used, and each has one or more valves, airlocks, or other effectively sealing door known to those skilled in the art (hereinafter called "valve(s)"). The valve(s) either directly or indirectly connect the sterilization chamber to a secondary chamber, as well as control the flow of any aerosol or "applied agent" from the secondary chamber into the sterilization chamber.

One or more object(s) or endoscope(s) are placed within the sterilization chamber(s), where they can, without limitation, be washed and dried in a manner known to those skilled in the art. The object(s) can, without limitation, also include any package(s) that are sealed, partially sealed, or hermetically sealed. The package(s) can also, without limitation, be constructed from, or include in its construction, at least an effective amount of Tyvek or other similar material. The package(s) can be, without limitation, placed on or and secured to any type of racks inside of the sterilization chamber(s). Before the application of the "applied agent" all surfaces, and environment, within the sterilization chamber(s) can be cooled to any temperature, in a manner known to those skilled in the art. Before application of the "applied agent"(s), the pressure within the sterilization chamber(s), or any connecting or shared areas or atmospheres, is reduced to a pressure including, but not limited to, any effective negative pressure, but preferably a full, or close to complete, vacuum. The sterilization chamber(s) can be, without limitation, positioned inside a larger sealed or at least effectively sealed chamber, enclosed area, or one or more interconnected areas (hereinafter called "Secondary Chamber"). The "secondary chamber" can be any size, shape, or geometry. The secondary chamber can, without limitation, be located anywhere outside of the sterilization chamber, and effectively connected to the sterilization chamber in one or more places. The pressure within this "secondary chamber" can be any pressure including, but not limited to ambient pressure.

However, it is preferred, without limitation, that the pressure within the secondary chamber is at least effectively greater than the pressure inside of the sterilization chamber(s). The pressure within the sterilization chamber may, without limitation, be maintained at any ambient or outdoor pressure, or even be slightly pressurized, and the "secondary chamber" can be effectively pressurized in addition to being filled with the "applied agent(s)". The secondary chamber is filled with the "applied agent"(s), either directly or indirectly. Any or all surfaces, or the environment, within the secondary chamber can be, without limitation, cooled with refrigerated or chilled air before, during, or after the application of the "applied agent(s)".

It is preferred, without limitation, that the "applied agent" be an aerosol containing substances including, but not limited to, any acidic oxidizer. Once the secondary chamber is sufficiently and effectively filled, the valve(s) are opened and the "applied agent"(s) is allowed to flow into and fill the sterilization chambers(s). The "applied agent"(s) can also flow, without limitation, through one or more of any filter(s) as it moves from the secondary chamber to the sterilization chamber. At this point, the air or gas pressure within the sterilization chamber(s) can be, without limitation, increased to any effective pressure. The air or gas pressure can also be increased in the secondary chamber as well. After the valve(s) are opened, additional amounts of "applied agent"(s) can, without limitation, be administered into the sterilization chamber(s) and any interconnected areas for any desired time period. The temperature of the air or gas(s) within the sterilization chamber(s) and any interconnected areas can also be increased to any effective temperature after the valve(s) are opened. Following an effective amount of time, the sterilization chamber(s) can be, without limitation, dried, dehumidified, and deodorized, before removal of the object(s) or endoscope(s).

According to another embodiment of the present invention, and without limitation, an object or endoscope may be initially interfaced with one or more means to hold, grip, clamp, or otherwise support the object or endoscope (hereinafter "primary grip(s)") in any angeled, or more preferably a vertical, position or orientation within the closed space or sterilization chamber. Before, during, or after, any processing activities that the object or endoscope may experience inside of the sterilization chamber, the object or endoscope may be transferred to, or interfaced with, one or more separate or different means to hold, grip, clamp, or otherwise support the object or endoscope (hereinafter "secondary grip(s)") in any angeled, or more preferably a vertical, position or orientation within the sterilization chamber. The "secondary grip(s)" shall interface with the object or endoscope in a different location than the "primary grip(s)" at least once, for each processing activity. The object or endoscope may be, without limitation, transferred or passed back and forth between the "primary grips" and "secondary grips" one or more times, during any processing activity inside of the sterilization chamber. Processing activities can include, but are not limited to, the object or endoscope being washed, dried, subjected to the "applied agent", and dried again. This embodiment provides an additional way to insure that all surfaces or targeted surfaces of the object or endoscope are efficaciously exposed to the various processing activities, and to prevent untreated or shadowed surfaces. The time that the object or endoscope is held by either the "primary grips" or "secondary grips" during each processing activity may vary, but is at least an efficacious amount of time. The pressure interface assembly may also be, without limitation, interfaced or attached to the object or endoscope when the various "grips" or more specifically, the "primary grips" and "secondary grips", are utilized.

The present invention also provides, without limitation, an improved system for decontaminating, sanitizing, disinfecting, high-level disinfecting, and/or sterilizing, effectively drying, and effectively cooling, one or more of any object(s) and/or various surfaces located in one or more of any suitable and effective treatment enclosure(s) and/or treatment chamber(s) (Herein called "treatment chamber(s)").

Without being limited, the treatment chamber(s) can also be one or more of any suitable and effective, size(s), shape(s), design(s), construction(s), geometry(s), length(s), width(s), height(s), and depth(s), all in a manner known to those skilled in the art. Also, and without being limited, a plurality of treatment chamber(s), if used, can suitably and effectively interconnect and communicate with one another. Further, and without limitation, the treatment chamber(s) can be used in any suitable industries and for one or more of any suitable and effective purposes and/or activities and/or in a manner known to those skilled in the art, and therefore can contain various item(s), object(s), equipment(s), machine(s), component(s), device(s), apparatus(s), part(s), and/or component(s), known to those skilled in the art. For example, and without limitation, the interior of the said treatment chamber(s) can include one or more of any means and/or apparatus(s) to suitably and effectively hold, support, and/or grip, one or more of any object(s) and/or treated object(s) located inside of the treatment chamber(s), all in a manner known to those skilled in the art. In another example, and without limitation, the interior of the said treatment chamber(s) can also include one or more of any suitable and effective means and/or apparatus(s) to package one or more of any of the said object(s) and/or treated object(s) located inside of the treatment chamber(s), all in a manner known to those skilled in the art.

The improved cabinet mounted treatment chamber processing system and improved chamber and/or enclosure mobile processing system, described in the present inventions, includes, and without limitation, first, one or more of any suitable and effective means known to those skilled in the art that can treat, decontaminate, sanitize, disinfect, high-level disinfect, and/or sterilize, the various surface(s) within one or more of any suitable and effective enclosure(s) and/or treatment chamber(s), such as, but not limited to any suitable and effective, apparatus(s), system(s), device(s), means, and/or decontamination system(s), that can create, generate, deploy, and/or emit (Herein called "Decontamination System(s)), one or more of any airborne agent(s) such as, but not limited to, any one or more, and/or one or more of any suitable and effective combination(s) of one or more, of any suitable and effective, vapor(s), gas(s), aerosol(s), plasma(s), molecule(s), particle(s), ion(s), metal(s), and/or chemical(s), such as, but not limited to any, acids, quaternary ammonium, bleach, chlorine, alcohol, ozone, hydrogen peroxide, chlorine dioxide, acetic acid, peracetic acid, peroxyacetic acid, silver, copper, nickel, anti-microbial agent(s), anti-viral agent(s), anti-bacterial agent(s), and/or any other suitable and effective, molecule(s), chemical(s), ion(s), metal(s), compound(s), particle(s), and/or chemical compound(s), known to those skilled in the art (Herein called (deployed agent(s)").

Without being limited, the current inventions can also be used with one or more of any suitable and effective means known to those skilled in the art and/or one or more of any suitable and effective decontamination system(s), to create, produce, and/or generate, one or more of any suitable and effective, aerosol(s), gas(s), plasma(s), vapor(s), and/or one or more of any suitable and effective combination(s) of one or more of any aerosol(s), gas(s), plasma(s), and/or vapor(s), such as, but not limited to any, means to create, produce, and/or generate, any aerosol(s) using one or more of any aerosol producing ultrasonic and/or transducer apparatus(s) known to those skilled in the art, means to create, produce, and/or generate, any vapor(s), plasma(s), and/or gas(s), using one or more of any apparatus(s) for heating any suitable and effective chemical(s) and/or liquid chemical(s) and turning and/or transitioning them into any vapor(s), plasma(s), and/or gas(s), all in manner known to those skilled in the art, means to create, produce, and/or generate, any vapor(s), plasma(s), and/or gas(s), using one or more of any vapor(s), plasma(s), and/or gas(s), creating and/or generating apparatus(s) known to those skilled in the art, means to create, produce, and/or generate, any aerosol(s) using one or more of any pressurized air and/or pressurized gas(s) apparatus(s) known to those skilled in the art, means to create, produce, and/or generate, any aerosol(s) using any pressurized liquid(s) apparatus(s) known to those skilled in the art, and/or means to create, produce, and/or generate, any aerosol(s) using one or more of any pressurized air and/or pressurized liquid(s), and/or any effective combination(s) of pressurized air and pressurized liquid(s), and one or more of any suitable and effective aerosol(s) generating nozzle(s) and/or emitter(s) apparatus(s) known to those skilled in the art. Without being limited, the one or more of any suitable and effective decontamination system(s) that can create, produce, generate, deploy, and/or emit, the said aerosol(s), gas(s), and/or vapor(s), can be controlled by one or more of any suitable and effective microcontroller(s) all in a manner known to those skilled in the art.

Also, and without being limited, the various parts and components described in the present invention, improved cabinet mounted treatment chamber processing system, and/or improved chamber and/or enclosure mobile processing system, such as, but not limited to any, motor(s), equipment(s), device(s), packaging machinery, packaging device(s), sensor(s), pressure sensor(s), liquid sensor(s), liquid level sensor(s), liquid presence sensor(s), strain sensor(s), proximity sensor(s), temperature sensor(s), light(s), electronic(s), pump(s), blower(s), fan(s), air pump(s), liquid heater(s), valve(s), air/gas(s) heater(s), valve(s) that control the flow of liquid(s), valve(s) that control the flow of air/gas(s), human machine interface(s) (HMI), means to create, produce, generate, deploy, and/or emit, any aerosol(s), gas(s), and/or vapor(s), decontamination system(s), communication equipment device(s) and/or apparatus(s), airflow sensing and monitoring device(s) and apparatus(s), inbound blower(s), heater element(s), chamber inlet valve(s), chamber outlet valve(s), exhaust blower(s), can suitably and effectively communicate with and/or be controlled by one or more of any suitable and effective, computer(s), microcomputer(s), processor(s), controller(s), microcontroller(s), programmable logic circuit(s) and/or computer(s) (PLC), and/or software(s), (Herein called "Microcontroller(s)"), all in a manner known to those skilled in the art.

Second, the present inventions includes, and without limitation, one or more of any suitable and effective means to flow, blow, supply, and/or or move, any suitable and effective quantity of air/gas(s) and/or fresh air/gas(s) at and/or with one or more of any suitable and effective, speed(s), velocity(s), quantity of air/gas(s), and/or cubic feet per minute (CFM), into and through the said one or more enclosure(s) and/or treatment chamber(s), and where the said air/gas(s) and/or fresh air/gas(s) are sourced from any suitable and effective location(s) outside of the treatment chamber(s), and preferably, and without limitation, the said air/gas(s) and/or fresh air/gas(s) are sourced and/or supplied from any suitable and effective environment(s) and/or atmosphere(s) that surrounds the improved cabinet mounted treatment chamber processing system(s) and improved chamber and/or enclosure mobile processing system(s) (Herein called "Surrounding Environment"), and more preferably, and without limitation, the said air/gas(s) and/or fresh air/gas(s) are sourced and/or supplied from any suitable and effective environment(s), atmosphere(s), and/or external atmosphere(s), that surrounds the present inventions, and even more preferably, and without limitation, the said air/gas(s) and/or fresh air/gas(s) are sourced and/or supplied from any suitable and effective environment(s) and/or atmosphere(s) that surrounds any cabinet(s) and/or enclosure(s) that houses and/or encompasses one or more of any parts and components such as, but not limited to any, treatment chamber(s), agent generator(s), airflow control valve(s), and/or airflow filter(s) (Herein also called "Surrounding Environment"), and very preferably, and without limitation, the said air/gas(s) and/or fresh air/gas(s) are sourced and/or supplied from one or more of any suitable and effective source(s) of fresh air/gas(s) that is external to the one or more airflow system(s) of the present inventions, (Herein called "fresh air/gas(s)").

Third, the present invention generally includes, and without limitation, one or more of any suitable and effective means for both pushing and pulling effectively filtered fresh air/gas(s) and/or air/gas(s), that can also be, and without limitation, effectively heated if needed to one or more of any suitable and effective temperature(s) one or more of any suitable and effective time(s), effectively through the one or more airflow system(s) and treatment chamber(s), and where this said means includes, but is not limited to, one or more of any suitable and effective "supply", fan(s), air pump(s), and/or blower(s), that can flow, blow, pump, supply, and/or move, any effective quantity of the fresh air/gas(s) and/or air/gas(s) at and/or with, one or more of any suitable and effective, velocity(s), speed(s), quantity of air/gas(s), and/or cubic feet per minute (CFM), into and through the said one or more treatment chamber(s) and/or airflow system(s), preferably and without limitation, with at least one or more of any effective positive pressure(s), and where the said air/gas(s) and/or fresh air/gas(s) are sourced from the surrounding environment(s) and/or outside of any area(s) and/or component(s) such as, but not limited to any, treatment chamber(s) and/or any cabinet(s) and/or enclosure(s) containing, encompassing, and/or partially encompassing, the various parts of the present inventions such as, but not limited to any, air/gas(s) filter(s), means to create, produce, and/or generate any deployed agent(s), valve(s), decontamination system(s), and/or treatment chamber(s). Without being limited, the movement, flow, and/or supply, of the said fresh air/gas(s) and/or air/gas(s) into and through the said treatment enclosure(s) and/or treatment chamber(s) can be used for purposes such as, but not limited to, effectively removing the deployed agent(s) from the various surface(s) and/or treated object(s) surface(s) located inside of the treatment chamber(s), effectively drying various surfaces and/or treated object(s) surfaces within the said treatment enclosure(s) and/or treatment chamber(s), and/or effectively purging, flowing, moving, and/or exhausting, any deployed agent(s), gas(s), vapor(s), and/or humidity, from the inside of the said treatment enclosure(s) and/or treatment chamber(s), and also where this said means can also work in concert or combination with another one or more means such as, but not limited to one or more of any, suitable and effective "exhaust", fan(s), air pump(s), and/or blower(s), that can also assist with moving and/or flowing, any, fresh air/gas(s), air/gas(s), heated air/gas(s), heated fresh air/gas(s), humidity, deployed agent(s), gas(s), and/or vapor(s), out of the treatment chamber(s) and/or airflow system(s), and effectively exhaust the said fresh air/gas(s), air/gas(s), heated air/gas(s), heated fresh air/gas(s), humidity, deployed agent(s), gas(s), and/or vapor(s), out of the treatment chamber(s) and/or the entire airflow system(s), by being oriented and/or positioned in a manner known to those skilled in the art, so that it can exert one or more of any effective negative pressure(s) on the said treatment chamber(s) and/or various parts of the airflow system(s), and blow, flow, push, and/or move, the said fresh air/gas(s), air/gas(s), heated air/gas(s), heated fresh air/gas(s), humidity, deployed agent(s), gas(s), and/or vapor(s), out of the airflow system(s), filtered exhaust assembly(s), and/or modified filter exhaust assembly(s), and out of one or more of any exhaust outlet(s) for the airflow system(s), filtered exhaust assembly(s), and/or modified filter exhaust assembly(s), and/or it can also assist with blowing, flowing, pushing, and/or moving the said fresh air/gas(s), air/gas(s), heated air/gas(s), heated fresh air/gas(s), humidity, deployed agent(s), gas(s), and/or vapor(s), out of the airflow system(s), filtered exhaust assembly(s), and/or modified filter exhaust assembly(s), and out of one or more of any exhaust outlet(s) for the airflow system(s), filtered exhaust assembly(s), and/or modified filter exhaust assembly(s). Without being limited, the said "supply", fan(s), air pump(s), and/or blower(s), and the said "exhaust", fan(s), air pump(s), and/or blower(s), effectively connect and communicate with each other and/or the same airflow system(s).

Fourth, the present invention generally includes, and without limitation, one or more of any suitable and effective means to effectively heat (Herein called "Heated Air/gas(s) System(s)") the said air/gas and/or fresh air/gas(s) to one or more of any suitable and effective temperatures before it is flowed into the one or more treatment chamber(s), and the said air/gas and/or fresh air/gas(s) can be effectively heated to any suitable and effective temperature(s) at one or more of any effective time(s) and for any effective duration of time(s).

Fifth, the present invention also includes, and without limitation, one or more, but preferably, and without limitation, a plurality, of any suitable and effective means to effectively filter the said air/gas(s) and/or fresh air/gas(s) before it reaches the treatment chamber(s), and where the said means for filtering the air/gas(s) and/or fresh air/gas(s) is located in one or more of any suitable and effective locations in and/or of the airflow system(s), filtered and heated inbound air/gas(s) assembly(s), and/or modified filtered and heated inbound air/gas assembly(s), that is suitably and effectively located before the treatment chamber(s), as well as one or more, but preferably, and without limitation, a plurality, of any suitable and effective means to suitably and effectively filter the said fresh air/gas(s), air/gas(s), heated air/gas(s), heated fresh air/gas(s), humidity, deployed agent(s), gas(s), and/or vapor(s), after it is leaves the treatment chamber(s), and where the said means for filtering the fresh air/gas(s), air/gas(s), heated air/gas(s), heated fresh air/gas(s), humidity, deployed agent(s), gas(s), and/or vapor(s), is located in one or more of any suitable and effective locations in and/or of the airflow system(s), filtered exhaust assembly, and/or modified filtered exhaust assembly, that is suitably and effectively located after the treatment chamber(s), and can include but is not limited to:

(a) effectively locating and/or positioning one or more of any suitable and effective filters within the airflow system(s), that filters the fresh air/gas(s) and/or air/gas(s) before and/or after the first and/or airflow system "supply", fan(s), air pump(s), and/or blower(s), and preferably, and without limitation, the said filter(s) can be located and/or positioned approximate to, near, and/or at, the one or more airflow inlet(s) for the said airflow system(s), (b) effectively locating and/or positioning one or more of any suitable and effective filters within the airflow system(s), that filter the air/gas(s) and/or fresh air/gas(s) before it enters the said treatment chamber(s), it is preferred, without limitation, that this filter(s) is at least a HEPA type performing and/or rated filter(s), (c) effectively locating one or more of any suitable and effective filters within the airflow system(s), immediately after, approximate to, and/or effectively near or at, one or more of any, exit(s), outlet(s), exhaust port(s), and/or chamber outlet(s), of, connected to, and/or at, the treatment chamber(s) to effectively filter any, fresh air/gas(s), air/gas(s), heated air/gas(s), heated fresh air/gas(s), humidity, deployed agent(s), gas(s), and/or vapor(s), that may travel through, enter, and/or exit, the treatment chamber(s) via or through the one or more of any, exit(s), outlet(s), exhaust port(s), and/or chamber outlet(s), of, interfaced with, designed into, and/or connected to, the treatment chamber(s), (d) effectively locating and/or positioning one or more of any suitable and effective filter(s) at any suitable and effective location(s) within the airflow system(s), and/or at any suitable and effective location(s) after the treatment chamber(s), where the said filter(s) can effectively, filter, absorb, adsorb, and/or remove, one or more of any, substance(s), gas(es), vapor(s), aerosol(s), molecule(s), chemical(s), and/or particle(s), such as, but not limited to any, deployed agent(s) and/or any effective and/or targeted amount(s) and/or quantity(s) of the deployed agent(s) (Herein called "Absorption Filter(s)"), where the said filter(s) can suitably and effectively filter, absorb, adsorb, and/or remove, any of the, said, deployed agent(s), substance(s), gas(es), vapor(s), aerosol(s), molecule(s), chemical(s), and/or particle(s), from any of the, fresh air/gas(es), air/gas(es), heated air/gas(es), heated fresh air/gas(es), humidity, deployed agent(s), gas(es), and/or vapor(s), that exit and/or flow out of the treatment chamber(s), and suitably and effectively filter the said any, fresh air/gas(s), air/gas(s), heated air/gas(s), heated fresh air/gas(s), humidity, deployed agent(s), gas(s), and/or vapor(s), before they are exhausted into the surrounding environment and/or outside of the airflow system(s), (e) effectively locating and/or positioning one or more of any suitable and effective filter(s) that can effectively filter any, fresh air/gas(s), air/gas(s), heated air/gas(s), heated fresh air/gas(s), humidity, deployed agent(s), gas(s), and/or vapor(s), traveling within the airflow system(s), after the said one or more filter(s) that can effectively filter, absorb, adsorb, and/or remove, the said any, deployed agent(s), substance(s), gas(s), vapor(s), aerosol(s), molecule(s), chemical(s), and/or particle(s, from any, fresh air/gas(s), air/gas(s), heated air/gas(s), heated fresh air/gas(s), humidity, deployed agent(s), gas(s), and/or vapor(s), that are moved through the airflow system(s), and where this said one or more filter(s) can also be effectively located within the airflow system(s) before and/or after the one or more last fan(s), air pump(s), and/or blower(s) and/or the airflow system "exhaust", fan(s), air pump(s), and/or blower(s) and/or the one or more exhaust blower(s), and where it is preferred, without limitation, that this one or more filter(s) is at least any suitable and effective MERV 6 or higher rated filter(s), and it is more preferred, without limitation, that this one or more filter(s) is at least any suitable and effective HEPA or higher rated performing and/or rated filter(s), and where it is even more preferred, without limitation, that the said filter(s) can at least suitably and effectively filter and/or remove any particles and/or foreign object debris that may be released by any previous filter(s) located in the airflow system(s), (f) effectively locating and/or positioning one or more of any suitable and effective filter(s) that can effectively filter any, fresh air/gas(s), air/gas(s), heated air/gas(s), heated fresh air/gas(s), humidity, deployed agent(s), gas(s), and/or vapor(s), within the airflow system, after the last fan(s), air pump(s), and/or blower(s) and/or the airflow system "exhaust", fan(s), air pump(s), and/or blower(s), that exhaust the said air/gas(s) and/or fresh air/gas(s) into the surrounding environment and/or outside of the airflow system(s), and preferably, and without limitation, the said filter(s) are located and/or positioned approximate to, near, and/or at, the one or more exhaust outlet(s).

Sixth, the present invention also includes, and without limitation, a plurality of various suitable and effective means such as, but not limited to any, suitable and effective valve(s), known to those skilled in the art, that can, and without limitation, suitably and effectively control and/or assist in controlling, in a manner known to those skilled in that art, the flow and/or movement of any, fresh air/gas(s), air/gas(s), heated air/gas(s), heated fresh air/gas(s), humidity, deployed agent(s), gas(s), and/or vapor(s), into, through, and/or out of, the treatment chamber(s) for various purposes such as, but not limited to, (i) treating the various surface(s) and treated object(s) surface(s) located inside of the treatment chamber(s) with the deployed agent(s), (ii) cooling the various surface(s) and treated object(s) surface(s) located inside of the treatment chamber(s) with any suitable and effective air/gas(s) and/or fresh air/gas(s) after they are exposed to one or more of any substance(s) such as, but not limited to any, heated deployed agent(s), heated air/gas(s), and/or heated fresh air/gas(s), (iii) drying the various surface(s) and treated object(s) surface(s) located inside of the treatment chamber(s), (iv) removing the deployed agent(s) from various surface(s) and treated object(s) surface(s) located inside of the treatment chamber(s), (v) circulating, homogenizing, mixing, and/or recirculating, one or more of any substance(s) such as, but not limited to any, humidity, deployed agent(s), gas(s), and/or vapor(s), located inside of the treatment chamber(s), for purposes such as, but not limited to, effectively exposing all of the various surfaces and treated object(s) surface(s) located inside of the treatment chamber(s) to the deployed agent(s) and/or fully and effectively conditioning all of the various, space(s), surface(s), area(s), and atmosphere(s), located inside of the treatment chamber(s), (vi) circulating, mixing, and/or recirculating, any, fresh air/gas(s), air/gas(s), heated air/gas(s), heated fresh air/gas(s), inside of the treatment chamber(s) for purposes such as, but not limited to, drying the various surfaces and treated object(s) surface(s) located inside of the treatment chamber(s), removing the deployed agent(s) from various surfaces and the treated object(s) surfaces located inside of the treatment chamber(s), and moving and flowing the output of the various circulated and/or recirculated fresh air/gas(s), air/gas(s), heated air/gas(s), and/or heated fresh air/gas(s), at, to, above, parallel to, and/or along, the various floor(s) surface(s) located inside of the treatment chamber(s) to effectively dry them and/or remove the deployed agent(s) from these various surface(s), (vii) venting one or more location(s) such as, but not limited to any, treatment chamber(s), chamber circulation apparatus(s), and/or decontamination system(s), at any suitable and effective, time(s), number of time(s), and duration(s) of time(s). Also, and without being limited, the said treatment chamber(s) and the various said valve(s) can be, and without limitation, effectively connected to, indirectly connected to, and/or communicate with, the same airflow system(s), interconnected airflow system(s), airflow path(s), and/or interconnected airflow path(s).

In one aspect of this part, and without limitation, at least one of any suitable and effective valve(s) can control the flow and movement of any, fresh air/gas(s), air/gas(s), heated air/gas(s), heated fresh air/gas(s), flowing through the airflow system(s) and into the one or more treatment chamber(s) (Herein called "Chamber Inlet Valve(s)"). In a second aspect of this part, and without limitation, at least one of any suitable and effective valve(s) can control the flow of any, fresh air/gas(s), air/gas(s), heated air/gas(s), heated fresh air/gas(s), humidity, deployed agent(s), gas(s), and/or vapor(s), out of the one or more treatment chamber(s) (Herein called "Chamber Outlet Valve(s)") and into, through, and out of the one or more other connecting and communicating part(s) of the airflow system(s) and into the surrounding environment.

In still another aspect of this part, and without limitation, at least one valve(s), but preferably, and without limitation, a plurality of valve(s) (Herein called "Deployed Agent(s) Inlet Valve(s) and Deployed Agent(s) Outlet Valve(s)") can suitably and effectively connect to and communicate with both the one or more treatment chamber(s) and the one more means to generate, create, emit, and/or deploy, the deployed agent(s), and/or the one or more of any suitable and effective decontamination system(s), and preferably, and without limitation, where the one or more deployed agent(s) inlet valve(s) can control the flow and movement of one or more of any, fresh air/gas(s), air/gas(s), heated air/gas(s), heated fresh air/gas(s), humidity, deployed agent(s), gas(s), air, and/or vapor(s), from the inside of the treatment chamber(s) into, through, and/or out of, the one or more decontamination system(s), and the one or more deployed agent(s) outlet valve(s) can also control the flow and movement of one or more of any, fresh air/gas(s), air/gas(s), heated air/gas(s), heated fresh air/gas(s), humidity, deployed agent(s), gas(s), air, and/or vapor(s), from the inside of the treatment chamber(s) and into, through, and/or out of, the decontamination system(s), and also preferably, and without limitation, the deployed agent(s) outlet valve(s) can control the flow and movement of any, deployed agent(s), gas(s), and/or vapor(s), from and/or out of the decontamination system(s) and into treatment chamber(s).

Without being limited, the flow and/or movement of any, fresh air/gas(s), air/gas(s), heated air/gas(s), heated fresh air/gas(s), humidity, deployed agent(s), gas(s), and/or vapor(s), can flow and move into, through, and out of, the said decontamination system(s) and can be controlled by means such as, but not limited to any one or more, deployed agent(s) inlet valve(s), deployed agent(s) outlet valve(s), and microcontroller(s), and can be suitably and effectively opened and closed at one or more of any suitable and effective time(s) and for any suitable and effective duration(s) of time(s). Also, and without being limited, the said various decontamination system(s) can suitably and effectively directly and/or indirectly interface and/or communicate with the interior space(s) and area(s) of the treatment chamber(s). For example, and without limitation, one or more of any suitable and effective pressurized air and/or pressurized liquid(s) aerosol(s) generating nozzle(s), outlet(s), and/or apparatus(s), and/or ultrasonic aerosol(s) generator(s) and/or apparatus(s), known to those skilled in the art, can also directly interface with and communicate with the interior space(s) and area(s) of the treatment chamber(s), and emit and/or deploy any one or more aerosol(s) into the treatment chamber(s), all in a manner known to those skilled in the art.

Without being limited, the deployed agent(s) inlet valve(s) and deployed agent(s) outlet valve(s) that suitably and effectively connect to and communicate with the decontamination system(s) and the treatment chamber(s) can suitably and effectively, interconnect with, communicate with, function in concert with, and/or function together with, various part(s), component(s) and/or system(s), of the present invention such as, but not limited to one or more of any, decontamination system(s), agent blower(s), chamber inlet valve(s), chamber outlet valve(s), airflow system "supply", fan(s), air pump(s), and/or blower(s), inbound blower(s), heated air system(s), heater element(s), airflow system "exhaust", fan(s), air pump(s), and/or blower(s), exhaust blower(s), and circulation blower(s).

For example, and without limitation, the deployed agent(s) inlet valve(s) and deployed agent(s) outlet valve(s) that effectively connect to and/or communicate with both the said decontamination system(s) and the treatment chamber(s), can be effectively positioned and located, and remain effectively open at one or more of any suitable and effective time(s) and for any suitable and effective number and duration(s) of time(s) such as, but not limited to, when any deployed agent(s) are moved or flowed into the treatment chamber(s) from the one or more decontamination system(s) while the one or more chamber inlet valve(s) and the one or more chamber outlet valve(s) that directly and/or indirectly connect to and/or communicate with the one or more of any, treatment chamber(s) and/or any, entry point(s), inlet(s), outlet(s), entry(s), exit(s), exhaust port(s), and/or chamber outlet(s), of the treatment chamber(s), remain effectively closed.

Alternatively, and without limitation, the deployed agent(s) inlet valve(s) and deployed agent(s) outlet valve(s) that effectively connect to and/or communicate with both the said decontamination system(s) and the treatment chamber(s), can be suitably and effectively positioned and located, and remain effectively closed at one or more of any suitable and effective time(s) and for any suitable and effective number and duration(s) of time(s) such as, but not limited to, when the one or more chamber inlet valve(s) and chamber outlet valve(s) that connect to and communicate with various parts and components such as, but not limited to any, airflow system(s), filtered and heated inbound air/gas(s) assembly(s), filtered exhaust assembly(s), and/or the treatment chamber(s), are open and any, fresh air/gas(s), air/gas(s), heated air/gas(s), heated fresh air/gas(s), are flowed through the said treatment chamber(s) for purposes such as, but not limited to, to effectively dry the various surfaces within the treatment chamber(s) and/or to effectively remove any deployed agent(s) from any surface(s) and/or treated object(s) surface(s) located inside of the said treatment chamber(s).

However, and without limitation, at times it may also be desired and/or necessary to open all of the various said valves such as, but not limited to one or more of any, chamber inlet valve(s), chamber outlet valve(s), circulation input valve(s), circulation output valve(s), deployed agent(s) inlet valve(s), and deployed agent(s) outlet valve(s), and operate a plurality of any suitable and effective part(s) and component(s) of the present invention such as, but not limited to any, airflow system "supply", fan(s), air pump(s), and/or blower(s), and/or inbound blower(s), circulation blower(s), agent blower(s), air/gas(s) flow or movement apparatus(s) that are a part of any decontamination system(s), heated air/gas(s) system(s), heater element(s), and airflow system "exhaust", fan(s), air pump(s), and/or blower(s), and/or exhaust blower(s), to flow any suitable and effective quantity(s) of fresh air/gas(s), air/gas(s), heated air/gas(s), heated fresh air/gas(s), into, through, and out of, one or more of any part(s), component(s), space(s), area(s), and location(s), such as, but not limited to any, airflow system(s), airflow path(s), filtered and heated inbound air/gas(s) assembly(s), treatment chamber(s), filtered exhaust assembly(s), decontamination system(s), treatment agent deployment apparatus(s), chamber circulation apparatus(s), and connected conduit(s), part(s), and component(s), for any suitable and effective time(s) and for any suitable and effective number and duration(s) of time(s), for any purposes including, but not limited to, effectively drying and/or removing the deployed agent(s) from the various, area(s), surface(s), apparatus(s), space(s), part(s), and component(s), of or within the said any, apparatus(s), part(s), component(s), space(s), area(s), and location(s), of the present invention such as, but not limited to any, airflow system(s), airflow path(s), filtered and heated inbound air/gas(s) assembly(s), treatment chamber(s), filtered exhaust assembly(s), decontamination system(s), treatment agent deployment apparatus(s), chamber circulation apparatus(s), and connected conduit(s), part(s), and component(s). It is preferred, without limitation, that both the deployed agent(s)

inlet valve(s) and deployed agent(s) outlet valve(s) are effectively closed at the end of any operation cycle(s), processing cycle(s), and/or when the present invention is not in use.

In another aspect of this part, and without limitation, various valve(s) can be used in the present invention and the improved chamber and/or enclosure mobile processing system(s), to control the flow of any, fresh air/gas(s), air/gas(s), heated air/gas(s), heated fresh air/gas(s), humidity, deployed agent(s), gas(s), and/or vapor(s), into, through, and/or out of, the one or more of any, treatment chamber(s), and/or separate and/or standalone treatment chamber(s), and these said various valves are preferably, and without limitation, located separately from and/or in and/or on one or more of any different suitable and effective location(s) from, the one or more said treatment chamber(s) and the one or more of any suitable and effective, housing(s), enclosure(s), cabinet(s), frame(s), mounting structure(s), mobile mounting structure(s), and/or cart(s), that holds, supports, interfaces with, and/or encloses, the said treatment chamber(s). More specifically, it is preferred, without limitation, that the various said valves for the improved chamber and/or enclosure mobile processing system(s), are suitably and effectively located in, to, and/or on, one or more of any suitable and effective location(s), housing(s), enclosure(s), cabinet(s), frame(s), mounting structure(s), mobile mounting structure(s), and/or cart(s), that is different from one or more location(s), housing(s), enclosure(s), cabinet(s), frame(s), mounting structure(s), mobile mounting structure(s), and/or cart(s), that the treatment chamber(s) is suitably and effectively located in, to, and/or on.

Without limitation, the various said valves for the present invention and the improved chamber and/or enclosure mobile processing system(s), can also be included in one or more of any suitable and effective, housing(s), enclosure(s), cabinet(s), frame(s), mounting structure(s), mobile mounting structure(s), and/or cart(s), that suitably and effectively, directly and/or indirectly, interfaces with, connects with, and/or communicates with, one or more of any suitable and effective mobile enclosure(s), mobile treatment chamber(s), stand alone treatment chamber(s), independent treatment chamber(s), and/or isolated treatment chamber(s). Without being limited, the various said valves for the improved chamber and/or enclosure mobile processing system(s), can also be suitably and effectively located in, to, and/or on, one or more of any suitable and effective location(s), housing(s), enclosure(s), cabinet(s), frame(s), mounting structure(s), mobile mounting structure(s), and/or cart(s), that is the same and/or different from the one or more location(s), housing(s), enclosure(s), cabinet(s), frame(s), mounting structure(s), mobile mounting structure(s), and/or cart(s), that the treatment chamber(s) is suitably and effectively located in, to, and/or on.

In another example of this aspect of this part, and without limitation, the said valves described in the present invention, and/or the improved cabinet mounted treatment chamber processing system(s), can be located in, to and/or on, one or more of any suitable and effective location(s) such as, but not limited to any, housing(s), enclosure(s), frame(s), cabinet(s), mounting structure(s), mobile mounting structure(s), and/or cart(s), that contains, interfaces with, and/or houses, various parts and components such as, but not limited to any, (a) treatment chamber(s), (b) means to filter any, fresh air/gas(s), air/gas(s), heated air/gas(s), and/or heated fresh air/gas(s), before it flows and/or moves into and/or through any, treatment chamber(s) and any means to heat any, fresh air/gas(s), air/gas(s), heated air/gas(s), and/or heated fresh air/gas(s), (c) means to generate, emit, disperse, create, and/or deploy, any deployed agent(s), and move and/or flow the deployed agent(s) into the treatment chamber(s) such as, but not limited to any, decontamination system(s), (d) means to move and/or flow any deployed agent(s) into the treatment chamber(s), (e) means to flow, move, and/or supply, any, fresh air/gas(s), air/gas(s), heated air/gas(s), heated fresh air/gas(s), into, through and out of, the treatment chamber(s), such as, but not limited to any, inbound blower(s), (f) means to circulate, mix, and/or homogenize, any one or more substance(s) such as, but not limited to any, fresh air/gas(s), air/gas(s), heated air/gas(s), heated fresh air/gas(s), humidity, deployed agent(s), gas(s), and/or vapor(s), inside of the treatment chamber(s), (g) means to flow, move, and/or exhaust, any, fresh air/gas(s), air/gas(s), heated air/gas(s), heated fresh air/gas(s), humidity, deployed agent(s), gas(s), and/or vapor(s), into, through, and out of, the treatment chamber(s) and airflow system(s), and into the surrounding environment, such as, but not limited to any, exhaust blower(s), (h) means to effectively filter any, fresh air/gas(s), air/gas(s), heated air/gas(s), heated fresh air/gas(s), humidity, deployed agent(s), gas(s), and/or vapor(s), after it leaves the treatment chamber(s) and before it is moved and/or flowed out of the airflow system(s) and into the surrounding environment. Without being limited, these various parts and components can be suitably and effectively located in the same location(s) and/or any suitable and close proximity of location(s), to the said treatment chamber(s), and preferably, and without limitation, these various parts and components can also share the same, housing(s), enclosure(s), cabinet(s), frame(s), mounting structure(s), mobile mounting structure(s), and/or cart(s), that holds, interfaces with, and/or encloses, the said treatment chamber(s).

In still another example, and without being limited, the said valves described in the present invention, and/or the improved chamber and/or enclosure mobile processing system(s), can be located in, to, and/or on, one or more of any suitable and effective, housing(s), enclosure(s), frame(s), cabinet(s), mounting structure(s), mobile mounting structure(s), and/or cart(s), that can contain, interface with, and/or house, various parts and components such as, but not limited to any, (a) means to filter any, fresh air/gas(s), air/gas(s), heated air/gas(s), and/or heated fresh air/gas(s), before it flows and/or moves into and/or through any, treatment chamber(s) and any means to heat any, fresh air/gas(s), air/gas(s), heated air/gas(s), and/or heated fresh air/gas(s), (b) means to generate, emit, disperse, create, and/or deploy, any deployed agent(s), and move and/or flow the deployed agent(s) into the treatment chamber(s) such as, but not limited to any, decontamination system(s), (c) means to move and/or flow any deployed agent(s) into the treatment chamber(s), (d) means to flow, move, and/or supply, any, fresh air/gas(s), air/gas(s), heated air/gas(s), heated fresh air/gas(s), into, through and out of, the treatment chamber(s), such as, but not limited to any, inbound blower(s), (e) means to circulate, mix, and/or homogenize, any one or more substance(s) such as, but not limited to any, fresh air/gas(s), air/gas(s), heated air/gas(s), heated fresh air/gas(s), humidity, deployed agent(s), gas(s), and/or vapor(s), inside of the treatment chamber(s), (f) means to flow, move, and/or exhaust, any, fresh air/gas(s), air/gas(s), heated air/gas(s), heated fresh air/gas(s), humidity, deployed agent(s), gas(s), and/or vapor(s), into, through, and out of, the treatment chamber(s) and airflow system(s), and into the surrounding environment, such as, but not limited to any, exhaust blower(s), (g) means to effectively filter any, fresh air/gas(s), air/gas(s), heated air/gas(s), heated fresh air/gas(s), humidity, deployed agent(s), gas(s), and/or vapor(s), after it leaves the treatment chamber(s) and before it is moved and/or flowed out of the airflow system(s) and into the surrounding environment, and where the one or more of any suitable and effective treatment chamber(s) and/or treatment enclosure(s) is, held, located, interfaced with, and/or enclosed, in, to, and/or at, one or more of any suitable and effective separate location(s), housing(s), enclosure(s), cabinet(s), frame(s), mounting structure(s), mobile mounting structure(s), and/or cart(s), than these various said parts and components. It is preferred, without being limited, that these said various parts and components can be suitably and effectively located in one or more of any, different, remote, and/or separate locations, than the said treatment chamber(s), and more specifically, and without limitation, these said various parts and components can be suitable and effectively located in one or more of any, different, remote, and/or separate, housing(s), enclosure(s), cabinet(s), frame(s), mounting structure(s), mobile mounting structure(s), and/or cart(s), than the one or more of any suitable and effective, housing(s), enclosure(s), cabinet(s), frame(s), mounting structure(s), mobile mounting structure(s), and/or cart(s), that holds, locates, interfaces with, and/or encloses, the said treatment chamber(s).

Also, and without limitation, the one or more of any suitable and effective, housing(s), enclosure(s), cabinet(s), frame(s), mounting structure(s), mobile mounting structure(s), and/or cart(s), that holds, interfaces with, and/or encloses, the said treatment chamber(s), can also hold, interface with, and enclose, one or more of any suitable and effective means such as, but not limited to any, one or more of any suitable and effective means to circulate, mix, and/or homogenize, any one or more substance(s) such as, but not limited to any, fresh air/gas(s), air/gas(s), heated air/gas(s), heated fresh air/gas(s), humidity, deployed agent(s), gas(s), and/or vapor(s), inside of the treatment chamber(s), and the one or more of any suitable and effective means to, generate, emit, disperse, create and/or deploy, any deployed agent(s), and move and/or flow the deployed agent(s) into the treatment chamber(s) such as, but not limited to any, decontamination system(s).

Without being limited, the present invention can have various suitable and effective valves and these various valves can have various purposes such as, but not limited to any, (a) inbound filtered and/or heated air/gas(s) control valve(s) such as, but not limited to any, chamber inlet valve(s), that can have various purposes such as, but not limited to, controlling the flow and/or movement of any, air/gas(s), fresh air/gas(s), heated air/gas(s), and/or heated fresh air/gas(s), into the said treatment chamber(s), (b) agent generator and/or decontamination system(s) inbound air/gas(s) control valve(s), such as, but not limited to any, deployed agent(s) inlet valve(s), that can have various purposes such as, but not limited to, controlling the flow of any deployed agent(s) and/or any accompanying air/gas(s) and/or one or more of any other, fresh air/gas(s), air/gas(s), heated air/gas(s), heated fresh air/gas(s), humidity, gas(s), and/or vapor(s), out of the said treatment chamber(s) and into, through, and/or out of, the decontamination system(s), and sealing the decontamination system(s) from the treatment chamber(s) when needed and/or at one or more of any suitable and effective time(s), (c) outbound deployed agent(s) control valve(s), such as, but not limited to any, deployed agent(s) outlet valve(s), that can have various purposes such as, but not limited to, controlling the flow of any deployed agent(s) and/or any accompanying air/gas(s) and/or one or more of any other, fresh air/gas(s), air/gas(s), heated air/gas(s), heated fresh air/gas(s), humidity, gas(s), and/or vapor(s), into the said treatment chamber(s) from the decontamination system(s), and sealing the decontamination system(s) from the treatment chamber(s) when needed and/or at one or more of any suitable and effective time(s), (d) circulation of any, fresh air/gas(s), air/gas(s), heated air/gas(s), heated fresh air/gas(s), humidity, deployed agent(s), gas(s), and/or vapor(s), control valve(s) such as, but not limited to any, circulation input valve(s) and circulation output valve(s), that can have various purposes such as, but not limited to, controlling the flow of any, air/gas(s), heated air/gas(s), fresh air/gas(s), heated fresh air/gas(s), humidity, vapor(s), and/or deployed agent(s), into, through, and out of the treatment chamber(s) and into, through, and/or out of, the one or more chamber circulation apparatus(s), and sealing the circulation blower(s) and chamber circulation apparatus(s) from the treatment chamber(s) when needed, (e) exhaust control valve(s) such as, but not limited to any, chamber outlet valve(s), that can have various purposes such as, but not limited to, controlling the movement and flow of any, air/gas(s), heated air/gas(s), fresh air/gas(s), heated fresh air/gas(s), humidity, vapor(s), and/or deployed agent(s), out of the treatment chamber(s), and into and through the various location(s) such as, but not limited to any, air/gas(s) filter(s), airflow path(s), airflow system(s), and/or filtered exhaust assembly(s), and into the surrounding environment. Without being limited, the various said valve(s) can all be suitably and effectively located in the same and/or different housing(s), enclosure(s), cabinet(s), frame(s), and/or mounting structure(s), mobile mounting structure(s), and/or cart(s), that is remote and/or separate from the said treatment chamber(s) and/or shared with and the same as the treatment chamber(s).

Sixth, the present invention also includes, and without limitation, at least one or more of any suitable and effective means to direct one or more of any suitable and effective air/gas(s) flows at one or more of any suitable and effective angle(s) and/or direction(s) towards, above, horizontal to, and/or along, one or more of any surface(s), angled surface(s), and/or horizontal surface(s), located inside of the treatment chamber(s) such as, but not limited to any, floor(s) located inside of the said treatment chamber(s). Without being limited, one or more of any suitable and effective, fan(s), air pump(s), and/or blower(s), and more preferably, and without limitation, one or more of any suitable and effective circulation blower(s), can provide, generate, move, flow, and/or source, any air/gas(s), such as, but not limited to any, heated air/gas(s), fresh air/gas(s), and/or heated fresh air/gas(s), that can be flowed or moved suitably and effectively, onto, into, and/or over, the said horizontal surface(s), chamber surface(s), and/or floor(s), located inside of the said treatment chamber(s), at one or more of any suitable and effective, speed(s), velocity(s), quantity(s) of air/gas(s), and/or cubic feet per minute (CFM). Without being limited, this flow of air/gas(s) can be preferably and without limitation, sourced from one or more of any suitable and effective location(s) within the treatment chamber(s). It is also preferred, without limitation, that at least one of any suitable and effective, fan(s), air pump(s), and/or blower(s), is dedicated solely for this application.

Seventh, the present invention also includes, and without limitation, at least one of any suitable and effective means to generate and direct one or more of any suitable and effective air/gas(s) flows into the treatment chamber(s) in which any suitable and effective quantity of deployed agent(s) has been flowed, moved, deployed, and/or dispensed, into the said treatment chamber(s), and where the said air/gas(s) flow(s)

are generated, moved, and/or flowed, by one or more of any suitable and effective fan(s), air pump(s), and/or blower(s), such as, but not limited to one or more of any suitable and effective, circulation blower(s) and/or agent blower(s), and where the said air/gas(s) enter the said treatment chamber(s) with one or more of any suitable and effective, direction(s), angle(s), speed(s), velocity(s), quantity(s) of air/gas(s), and/or cubic feet per minute (CFM), so as to cause any deployed agent(s) that are present inside of the treatment chamber(s) to suitably and effectively, homogenize, stir, mix, move, and/or flow, within the said treatment chamber(s) and effectively fill the treatment chamber(s), and the one or more said air/gas(s) flow(s) can be generated, moved, and/or flowed, into the said treatment chamber(s) at any suitable and effective time(s) and for any suitable and effective number and duration(s) of time(s). It is preferred, without limitation, that the said one or more of any air/gas(s) flow(s) that is intended, outputted, and/or deployed, for purposes such as, but not limited to any, stirring, mixing, homogenizing, flowing, and/or moving, the said deployed agent(s) within the treatment chamber(s), are generated, moved, and/or flowed, by at least one of any dedicated fan(s), air pump(s), and/or blower(s), that is suitable and effective, such as, but not limited to any suitable and effective, circulation blower(s), however, and without limitation, the one or more decontamination system(s) and/or agent blower(s), can also generate, provide, flow, move, and/or deploy, the said one or more of any suitable and effective air/gas(s) flow(s) that can cause the deployed agent(s) that are inside of the treatment chamber(s) to effectively stir, mix, homogenize, move, and/or flow, within the said treatment chamber(s) and suitably and effectively fill the said treatment chamber(s).

Generally, and without limitation, two variations of the current invention are described. Without being limited, the first variation is an improved cabinet mounted treatment chamber processing system that includes at least one of any suitable and effective treatment chamber(s) that is accessed by the machine operator with and/or through one or more of any suitable and effective door(s) and/or any suitable and effective hermetically resealable treatment chamber(s) access means known to those skilled in the art. The said improved cabinet mounted treatment chamber processing system includes effectively locating and/or positioning at least one of any suitable and effective treatment chamber(s) and the various associated and related parts and components to effectively operate the said improved cabinet mounted treatment chamber processing system, such as, but not limited to any, plurality of any suitable and effective, fan(s), air pump(s), and/or blower(s) such as, but not limited to any, inbound blower(s) and exhaust blower(s), plurality of any suitable and effective valve(s), one or more of any suitable and effective decontamination system(s) and any associated part(s) and component(s), various of any suitable and effective air/gas(s) flow conduits, and/or pipe(s), at least one of any suitable and effective system control part(s) and/or microcontoller(s) and any associated part(s) and component(s), to effectively automate and control the various operations, part(s), component(s), device(s), apparatus(s), motor(s), light(s), system(s), of the improved cabinet mounted treatment chamber processing system, all in a manner known to those skilled in the art, one or more of any suitable and effective means to hold and/or support one or more object(s) within the treatment chamber(s), one or more of any suitable and effective means to move and/or stir the deployed agent(s) within the treatment chamber(s) at one or more of any suitable and effective time(s), at least one of any suitable and effective heated air/gas(s) system(s) to effectively heat the air/gas(s) and/or fresh air/gas(s) before they enter the said treatment chamber(s), and/or a plurality of any various suitable and effective filter(s) located at any various suitable and effective location(s) within and/or along the airflow system(s) and/or one or more various air/gas(s) flow(s) path(s) before and after the said treatment chamber(s) of the improved cabinet mounted treatment chamber processing system(s).

The operation of the first variation, which is the improved cabinet mounted treatment chamber processing system, can be summarized, and without limitation, as follows. Without limitation, one or more of any suitable object(s) are effectively located and sealed inside of one or more treatment chamber(s) for any suitable and effective number(s) and duration(s) of time(s) within the said treatment chamber(s). Without limitation, the said treatment chamber(s) can be accessed through and/or by one or more of any suitable and effective means known to those skilled in the art such as, but not limited to one or more of any, door(s), portal(s), window(s), and/or hatch(s), that can be repeatedly and effectively hermetically sealed and later reopened at any suitable and effective times, by the machine operator, all in a manner known to those skilled in the art. It is preferred without limitation, that the said object(s) are suitably and effectively dry before they are positioned within the said treatment chamber(s).

Without limitation, the one or more of any suitable and effective valve(s) and/or chamber inlet valve(s), that effectively control the flow of any, fresh air/gas(s), air/gas(s), heated air/gas(s), heated fresh air/gas(s), into the one or more treatment chamber(s), and the one or more of any suitable and effective valve(s) and/or chamber outlet valve(s), that effectively control the flow of any, fresh air/gas(s), air/gas(s), heated air/gas(s), heated fresh air/gas(s), humidity, gas(s), deployed agent(s), and/or vapor(s), out of the same said one or more treatment chamber(s), are all effectively closed, preferably, and without limitation, at least while the said decontamination system(s) are operating and deployed agent(s) are moved, flowed, and/or deployed into, the treatment chamber(s) and/or during any one or more dwell steps where the deployed agent(s) are allowed to dwell inside of the treatment chamber(s) to effectively interact with the various surface(s) inside of the said treatment chamber(s). Also, and without limitation, the one or more of any suitable and effective valve(s) that can control the flow of at least any, fresh air/gas(s), air/gas(s), heated air/gas(s), heated fresh air/gas(s), humidity, gas(s), deployed agent(s), and/or vapor(s), into and/or through the one or more treatment agent(s) deployment apparatus(s) and/or decontamination system(s), and the one or more suitable and effective valve(s) that can control the flow of at least any, fresh air/gas(s), air/gas(s), heated air/gas(s), heated fresh air/gas(s), humidity, gas(s), deployed agent(s), and/or vapor(s), through and/or out of the one or more treatment agent(s) deployment apparatus(s) and/or decontamination system(s), are all effectively open, preferably, and without limitation, at least while the said decontamination system(s) are operating and deployed agent(s) are moved, flowed, and/or deployed into, the treatment chamber(s) and/or during any dwell steps where the deployed agent(s) are allowed to dwell inside of the treatment chamber(s) for any suitable and effective number(s) and duration(s) of time(s) to effectively interact with the various surface(s) inside of the said treatment chamber(s).

Without limitation, the treatment agent(s) deployment apparatus(s) and/or decontamination system(s) can deploy and/or move any suitable and effective quantity(s) and/or concentration(s) of one or more of any suitable and effective deployed agents(s) and/or one or more of any other effective substance(s), into the said treatment chamber(s), that are preferably, and without limitation, suitably and effectively sealed, for one or more of any suitable and effective number(s) and duration(s) of time(s), and at any suitable and effective time(s).

In addition, and without limitation, the one or more treatment chamber circulation apparatus(s) can be activated and operated for one or more of any suitable and effective number(s) and duration(s) of time(s), and at any suitable and effective time(s), and can effectively, stir, move, homogenize, and/or mix, the deployed agent(s) within the said treatment chamber(s), with one or more of any suitable and effective treatment chamber circulation apparatus(s) that can effectively communicate with the said treatment chamber(s) with one or more of any suitable and effective conduit(s) and/or orifice(s) so that the deployed agent(s) can be suitably and effectively, moved, stirred, homogenized, dispersed, and/or mixed, within the said treatment chamber(s).

Also, and without being limited, one or more of any suitable and effective valve(s) such as, but not limited to any circulation input valve(s) and circulation output valve(s) (Herein called "Circulation Valve(s)"), can control the flow and/or movement of one or more of any substance(s) such as, but not limited to any, fresh air/gas(s), air/gas(s), heated air/gas(s), heated fresh air/gas(s), humidity, deployed agent(s), gas(s), and/or vapor(s), from, to, into, and/or out of, the one or more of any treatment chamber(s). It is preferred, without limitation, that these said circulation valve(s) are effectively located at least at and/or effectively near the one or more orifice(s) and/or opening(s) of both the one or more circulation inlet(s) and the one or more circulation outlet(s) that communicate with at least one or more of any, treatment chamber(s) and the one or more circulation blower(s). It is also preferred, without limitation, that the said circulation valve(s) if used, are effectively open at, any one or more of any suitable and effective time(s), and/or at any suitable and effective number(s) and duration(s) of time(s), such as, but not limited to, when the deployed agent(s) within the treatment chamber(s) need to be stirred, homogenized, and/or mixed, and/or when various surface(s) within the treatment chamber(s) need to be effectively dried and/or the deployed agent(s) need to be effectively removed from various surface(s) and object surface(s), located inside of the treatment chamber(s), and/or when any area(s), space(s), and/or surface(s), located within the treatment chamber circulation apparatus(s) need to be effectively dried and/or purged of any deployed agent(s). Without being limited, the said circulation valve(s) can also be effectively closed at one or more of any suitable and effective number(s) and duration(s) of time(s), and at any suitable and effective time(s), such as, but not limited to, at the end of the one or more processing cycle(s).

Without being limited, the deployment and/or movement of the said deployed agent(s) into the said treatment chamber(s) can be stopped and/or terminated for various reasons, situations, and/or steps, such as, but not limited to, when any effective, quantity, density, concentration, and/or amount, of the said deployed agent(s) is reached, met, achieved, recorded, observed, and/or sensed, within the said treatment chamber(s). It is preferred, without limitation, that the deployed agent(s) are flowed and/or moved into the said treatment chamber(s) for at least any suitable and effective amount(s) of time(s). Also, and without limitation, the deployed agent(s) that are emitted, flowed, moved, and/or deployed, into the treatment chamber(s), can remain in the treatment chamber(s) and can dwell inside of the said treatment chamber(s), for any suitable and effective number(s) and duration(s) of time(s). Still also, and without being limited, after the various surface(s) of the said one or more treated object(s) and/or any other surface(s) and/or atmosphere(s) located in the treatment chamber(s), are effectively treated and/or effectively exposed to the said deployed agent(s), the deployed agent(s) and any other, humidity, gas(s), and/or vapor(s), can be suitably and effectively removed from the treatment chamber(s), and the various surfaces and any treated object(s) surface(s) located inside of the treatment chamber(s) can be suitably and effectively dried and any, deployed agent(s), gas(s), vapor(s), and/or humidity, can also be suitably and effectively removed from any, surfaces inside of the treatment chamber(s), treated object(s) surface(s), space(s), and/or area(s), located inside of the treatment chamber(s).

Without limitation, after the said object(s) are effectively, treated, decontaminated, sanitized, disinfected, high-level disinfected, and/or sterilized, the one or more of any suitable and effective valve(s) and/or chamber inlet valve(s), that can effectively control the flow of any, fresh air/gas(s), air/gas(s), heated air/gas(s), and/or heated fresh air/gas(s), into the one or more treatment chamber(s), and the one or more of any suitable and effective valve(s) and/or chamber outlet valve(s), that effectively control the flow of any, fresh air/gas(s), air/gas(s), heated air/gas(s), heated fresh air/gas(s), humidity, deployed agent(s), gas(s), and/or vapor(s), out of the same said one or more treatment chamber(s), can all be effectively opened. In addition, and without limitation, the one or more of any suitable and effective valve(s) that can control the flow of any, fresh air/gas(s), air/gas(s), heated air/gas(s), heated fresh air/gas(s), humidity, deployed agent(s), gas(s), and/or vapor(s), into and/or through the one or more of any treatment agent(s) deployment apparatus(s) and/or decontamination system(s), and the one or more of any suitable and effective valve(s) that control the flow of any, fresh air/gas(s), air/gas(s), heated air/gas(s), heated fresh air/gas(s), humidity, deployed agent(s), gas(s), and/or vapor(s), through and/or out of the one or more treatment agent(s) deployment apparatus(s), can also be either effectively closed and/or effectively open, for any suitable and effective number(s) and duration(s) of time(s).

Without being limited, the one or more of any surface(s), object surface(s), treated object surface(s), and/or targeted surface(s), located within one or more of any suitable and effective locations such as, but not limited to any, treatment chamber(s), can also be suitably and effectively dried by moving any suitable and effective, fresh air/gas(s), air/gas(s), heated air/gas(s), heated fresh air/gas(s), through a plurality of location(s) such as, but not limited to any, treatment chamber(s), airflow system(s), filtered and heated inbound air/gas assembly(s), and filtered exhaust assembly(s).

More particularly, and without limitation, at least one of any suitable and effective, fan(s), air pump(s), and/or blower(s) (Herein called "Inbound Blower(s)"), can flow and/or move any suitable and effective quantity(s), concentration(s), and/or amount(s), of any, fresh air/gas(s), air/gas(s), heated air/gas(s), heated fresh air/gas(s), into the one or more airflow system(s) and treatment chamber(s), with which they effectively communicate with. It is preferred, without limitation, that the said air/gas and/or fresh air/gas(s) are pulled into and through the one or more airflow inlet(s) of the one or more filtered and heated inbound air/gas(s) assembly(s), by the said inbound blower(s), and then pulled into and through at least one suitable and effective initial filter(s) (Herein called "Airflow Inlet Pre-Filter(s)"), where the said air/gas and/or fresh air/gas(s) then flow or move into and through the said inbound blower(s), where the said air/gas and/or fresh air/gas(s) is then pushed through at least one of any suitable and effective filter(s) (Herein called "Inbound Air Filter(s)".

It is preferred, without limitation, that the one or more of any suitable and effective inbound air filter(s) is at least any suitable and effective, high efficiency, effectively high rated, high level filtering, and/or ultra high level filtering, filter(s) such as, but not limited to any, MERV rated filter(s), HEPA rated filter(s), and/or ULPA rated filter(s), all in a manner known to those skilled in the art.

It is also preferred, without limitation, that these said air/gas(s) filter(s) are at least any suitable and effective filter(s) that can provide any air and/or gas(s) filtering performance(s) that is acceptable to the United States Food and Drug Administration (FDA) for flowing filtered air/gas(s) into various treatment chamber(s), area(s), and/or space(s), for and/or used in any industries such as, but not limited to any, medical industries, medical device(s) industries, life sciences industries, pharmaceutical industries, clean room industries, biotechnology industries, and/or food industries, all in a manner known to those skilled in the art. It is also preferred, without limitation, that the one or more of any airflow inlet prefilter(s) is any suitable and effective air/gas(s) filter(s) that can effectively perform as one or more prefilter(s) for any air/gas(s) that enter the airflow system(s) and filtered and heated inbound air/gas(s) assembly(s), all in a manner known to those skilled in the art. More particularly, it is preferred, without limitation, that the airflow inlet prefilter(s) is any suitable and effective filter(s) that can at least suitably and effectively filter the airflow(s) and/or gas flow(s) with any one or more of any suitable and effective attribute(s) such as, but not limited to any, airflow and/or gas flow resistance(s), filtering efficiency(s), filtering performance(s), particle size(s) filtration, particle concentration(s) filtration, filtering level(s), airflow and/or gas flow speed(s), and/or airflow and/or gas flow velocity(s), for any substance(s) such as, but not limited to any, dust(s), foreign object debris, and/or particulate(s), that may be present in the atmosphere of the surrounding environment that is pulled into the airflow system(s) and filtered and heated inbound air/gas(s) assembly(s), by the said inbound blower(s).

Without limitation, that the various filter(s) used in the present invention, such as, but not limited to any, airflow inlet prefilter(s), inbound air filter(s), first outlet filter(s), vapor absorbing outlet filter(s), primary post absorption filter(s), secondary post absorption filter(s), exhaust outlet filter(s), can have any suitable and effective, amount(s), level(s), efficiency(s), performance(s), and/or rating(s), of airflow resistance, and more preferably, and without limitation, as low of an airflow resistance as possible.

Also, without being limited, the various filter(s) used in the present invention, such as, but not limited to any, airflow inlet prefilter(s), inbound air filter(s), first outlet filter(s), vapor absorbing outlet filter(s), primary post absorption filter(s), secondary post absorption filter(s), exhaust outlet filter(s), can have any suitable and effective, amount(s), level(s), efficiency(s), performance(s), and/or rating(s), of and/or for any airflow and/or gas flow filtering, and can also have any one or more of any suitable and effective attribute(s) such as, but not limited to any, airflow and/or gas flow resistance(s), filtering efficiency(s), filtering performance(s), particle size(s) filtration(s), particle concentration(s) filtration(s), filtering level(s), airflow and/or gas flow speed(s) performance(s) and/or compatibility(s), and/or airflow and/or gas flow velocity(s) performance(s) and/or compatibility(s), for any substance(s) such as, but not limited to any, chemical(s), air(s), molecule(s), vapor(s), gas(s), aerosol(s), dust(s), foreign object debris, and/or particulate(s). It is preferred, without limitation, that these said filters also have any suitable and effective amount(s) of airflow resistance(s), and more preferably, and without limitation, as low of an airflow resistance(s) as possible.

Without being limited, the said air/gas and/or fresh air/gas(s) pass through the said inbound air filter(s) and enter any suitable and effective means known to those skilled in the art to effectively heat the said air/gas(s) and/or fresh air/gas(s) to one or more of any suitable and effective temperature(s) before the said air/gas and/or fresh air/gas(s) is pushed by the said inbound blower(s) through one or more of any suitable and effective valve(s) and/or open chamber inlet valve(s), and into and then through the said treatment chamber(s). It is preferred, without limitation, that the said means to heat the said flow of air/gas(s) and/or fresh air/gas(s) is one or more of any suitable and effective heater element(s) known to those skilled in the art.

Also, and without being limited, the said any, fresh air/gas(s), air/gas(s), heated air/gas(s), heated fresh air/gas(s), humidity, deployed agent(s), gas(s), and/or vapor(s), can be pushed, blown, moved, and/or flowed, into, through, and/or out of, the said treatment chamber(s), at various steps during the processing cycle(s), with one or more of any suitable and effective positive pressure(s) generated by the said inbound blower(s), at one or more of any suitable and effective time(s) and for any suitable and effective duration(s) of time(s). However, and without limitation, these same said air/gas(s), fresh air/gas(s), gas(s), vapor(s), deployed agent(s), and/or humidity, that can be present in the said treatment chamber(s), can also be pulled, sucked, flowed, and/or moved, out of the said treatment chamber(s) with the one or more of any suitable and effective fan(s), air pump(s), and/or blower(s) (Herein called "Exhaust Blower(s)"), that can preferably and without limitation, operate at the same time and/or simultaneously as and/or with the said inbound blower(s). Without being limited, the one or more exhaust blower(s) can also create and/or exert any suitable and effective negative pressure(s), suction(s), and/or vacuum(s), at various steps during the processing cycle(s), and at one or more of any suitable and effective time(s) and for any suitable and effective duration(s) of time(s).

Without being limited the said any, fresh air/gas(s), air/gas(s), heated air/gas(s), heated fresh air/gas(s), humidity, deployed agent(s), gas(s), and/or vapor(s), can be moved out of the said treatment chamber(s), through one or more of any suitable and effective valve(s) and/or open chamber outlet valve(s), where the said exhausted any, fresh air/gas(s), air/gas(s), heated air/gas(s), heated fresh air/gas(s), humidity, deployed agent(s), gas(s), and/or vapor(s), can first pass through one or more of any suitable and effective filter(s) that can effectively filter one or more of any dust(s) and/or particle(s) (Herein called "First Outlet Filter(s)") that may exit the treatment chamber(s).

Without limitation, this first said filter(s) or first outlet filter(s) can effectively filter any of the said fresh air/gas(s), air/gas(s), heated air/gas(s), heated fresh air/gas(s), humidity, deployed agent(s), gas(s), and/or vapor(s), either exiting the said treatment chamber(s) and/or any air/gas(s) that may try to enter the said treatment chamber(s) via any conduits(s) and/or pipe(s) that provide an exhaust path from the said treatment chamber(s) to one or more of any filtered exhaust assembly(s). It is preferred, without limitation, that the first outlet filter(s) is any suitable and effective filter(s) that can at least effectively filter any effective quantity and/or concentration(s) of any, dust(s), particle(s), foreign object debris, and/or particulate(s), from one or more of any sources such as, but not limited to, that may be present in the treatment chamber(s), that may be leaving the treatment chamber(s), may be present in any of the said, fresh air/gas(s), air/gas(s), heated air/gas(s), heated fresh air/gas(s), humidity, deployed agent(s), gas(s), and/or vapor(s), that moves out of said treatment chamber(s), and/or that moves from any one or more parts of the filtered exhaust assembly(s) and into the said treatment chamber(s). It is preferred, without limitation, that the first outlet filter(s) has any suitable and effective amount(s) of airflow resistance, and more preferably, and without limitation, as low of an airflow resistance as possible.

Also, and without limitation, after passing through the said one or more first outlet filter(s), the said any, fresh air/gas(s), air/gas(s), heated air/gas(s), heated fresh air/gas(s), humidity, deployed agent(s), gas(s), and/or vapor(s), can be passed through another one or more of any suitable and effective filter(s) (Herein called "Vapor Absorbing Outlet Filter(s)") that can effectively filter and/or remove one or more of any substance(s) such as, but not limited to any, deployed agent(s), mist(s), aerosol(s), vapor(s), particle(s), chemical(s), substance(s), compounds(s), molecule(s), and/or gas(s), that are exhausted, flowed, and/or moved out, from the treatment chamber(s). It is preferred, without limitation, that the said vapor absorbing outlet filter(s) are any suitable and effective filter(s) that contains activated carbon, charcoal, and/or any other suitable and effective filter media(s) and/or filter material(s), known to those skilled in the art, that can, and without limitation, absorb, adsorb, and/or remove, one or more of any substances such as, but not limited to any, deployed agent(s), mist(s), aerosol(s), vapor(s), particle(s), chemical(s), compound(s), substance(s), molecule(s), and/or gas(s), from the flow and/or movement of any, fresh air/gas(s), air/gas(s), heated air/gas(s), heated fresh air/gas(s), humidity, deployed agent(s), gas(s), vapor(s), mist(s), aerosol(s), and/or particle(s), that are moved through and/or pass through the said vapor absorbing outlet filter(s).

Without being limited, after passing through the said vapor absorbing outlet filter(s), the said any, fresh air/gas(s), air/gas(s), heated air/gas(s), heated fresh air/gas(s), humidity, deployed agent(s), gas(s), and/or vapor(s), pass through one or more of any suitable and effective filter(s) that can effectively filter and/or remove any substance(s) such as, but not limited to any, dust(s), particle(s), and/or particulate(s). The first said filter is called the "Primary Post Absorption Filter(s)" and the second said filter(s) that is located after the first said primary post absorption filter(s), is called the "Secondary Post Absorption Filter(s)". It is preferred, without limitation, that the primary post absorption filter(s) and the secondary post absorption filter(s) is at least any suitable and effective, high efficiency, effectively high rated, high level filtering, and/or ultra high level filtering, filter(s) such as, but not limited to any, MERV rated filter(s), HEPA rated filter(s), and/or ULPA rated filter(s), all in a manner known to those skilled in the art.

Without being limited, after passing through the said first primary post absorption filter(s) and the second, if used, secondary post absorption filter(s), the said any, fresh air/gas(s), air/gas(s), heated air/gas(s), heated fresh air/gas(s), humidity, deployed agent(s), gas(s), and/or vapor(s), is preferably, and without limitation, suitably and effectively, vacuumed, sucked, and/or pulled, into and through the one or more of any suitable and effective, fan(s), air pump(s), and/or blower(s) (Herein called "Exhaust Blower(s)"), and then expelled, moved out, forced out, flowed, and/or moved, through one or more of any suitable and effective filter(s) (Herein called "Exhaust Outlet Filter(s)") with one or more of any suitable and effective positive pressure(s) and/or air and/or gas(s) flows created by the one or more exhaust blower(s). It is preferred, without limitation, that the said exhaust blower(s) exert one or more of any suitable and effective negative pressure(s) and/or suction(s) on the said any, fresh air/gas(s), air/gas(s), heated air/gas(s), heated fresh air/gas(s), humidity, deployed agent(s), gas(s), and/or vapor(s), that is present in one or more of any suitable and effective location(s) such as, but not limited to any, treatment chamber(s), filtered exhaust assembly(s), and/or any effective location(s) of and/or in any conduit(s) and/or pipe(s) that are located past the treatment chamber(s), but located before the said exhaust blower(s).

It is also preferred, without limitation, that the exhaust outlet filter(s) is any suitable and effective filter(s) that can effectively perform as any suitable and effective exhaust filter(s) that can perform various functions such as, but not limited to, preventing any, dirt, dust, particles, and any foreign object debris, from entering the airflow system(s) and/or moving inward past the exhaust outlets and into the filtered exhaust assembly(s), all in a manner known to those skilled in the art. More particularly, it is preferred, without limitation, that the exhaust outlet filter(s) is any suitable and effective filter(s) that can at least effectively filter any effective quantity and/or amounts of any dust(s) and/or particulate(s) that may be present in the atmosphere of the surrounding environment that might flow into the airflow system(s), but also has any suitable and effective amount of airflow resistance, and more preferably, and without limitation, as low of an airflow resistance as possible. Without being limited, after the air/gas(s) and/or fresh air/gas(s) move through, out of, and past, the said exhaust outlet filter(s), the said air/gas(s) and/or fresh air/gas(s) are effectively vented into the surrounding environment and/or outside of the said airflow system(s).

Without being limited, a second variation of the present invention is an improved chamber and/or enclosure mobile processing system that includes, and without limitation, at least one of any suitable and effective separate and/or stand-alone treatment chamber(s) and/or treatment enclosure(s), and at least one of any suitable and effective other separate and/or stand-alone, structure(s), enclosure(s), wall(s), frame(s), cabinet(s), bulkhead(s), mounting structure(s), mobile mounting structure(s), mobile cabinet(s), mobile surface(s), mobile wall(s), mobile bulkhead(s), mobile frame(s), mobile and/or wheeled apparatus(s), portable device(s), carriage(s), mobile structure(s), mobile mounting structure(s), mobile enclosure(s), and/or cart(s), on, within, and/or to which, the various associated and related, parts and components to effectively operate the said improved chamber and/or enclosure mobile processing system can be suitably and effectively positioned, mounted, and/or located, such as, but not limited to any, modified airflow system(s), treatment and processing system(s), processing system outer enclosure(s), cabinet(s), shell(s), enclosure(s), means to filter any air/gas(s) and/or fresh air/gas(s) before it enters the treatment chamber(s) and/or treatment enclosure(s), means to effectively filter any, fresh air/gas(s), air/gas(s), heated air/gas(s), heated fresh air/gas(s), humidity, deployed agent(s), gas(s), and/or vapor(s), after it has left the treatment chamber(s) and/or treatment enclosure(s), modified treatment agent deployment apparatus(s), modified filtered and heated inbound air/gas(s) assembly(s), modified filtered exhaust assembly(s), inbound air/gas(s) valve(s) control system(s), outbound air/gas(s) and agent(s) valve(s) valve control system(s), plurality of any suitable and effective fan(s), air pump(s), and/or blower(s), plurality of any suitable and effective valve(s), one or more of any suitable and effective decontamination system(s) and any associated part(s) and component(s), various of any suitable and effective air/gas(s) flow conduits, and/or pipes, at least one of any suitable and effective system control part(s) and/or microcontoller(s) and any associated part(s) and component(s), to effectively automate and control the various operations, part(s), component(s), device(s), apparatus(s), motor(s), light(s), and system(s), of the improved chamber and/or enclosure mobile processing system(s), all in a manner known to those skilled in the art, at least one of any suitable and effective heated air/gas(s) system(s), means, and/or apparatus(s), that can effectively heat any air/gas(s) and/or fresh air/gas(s) before they enter the said treatment chamber(s) and/or treatment enclosure(s), and/or a plurality of any various suitable and effective filter(s) located at various suitable and effective location(s) within and/or along the airflow system(s) and/or one or more various air/gas(s) flow(s) path(s) of the improved chamber and/or enclosure mobile processing system such as, but not limited to any, modified filtered and heated inbound air/gas(s) assembly(s), treatment and processing system(s), and/or modified filtered exhaust assembly(s).

Without limitation, one or more of any suitable and effective means to hold and/or support one or more object(s) can also be suitably and effectively located and/or positioned within the at least one separate and/or stand-alone treatment chamber(s) and/or treatment enclosure(s), all in a manner known to those skilled in the art. Also, and without limitation, one or more of any suitable and effective means to package one or more object(s) located inside of the treatment chamber(s) and/or treatment enclosure(s), after they have been suitably and effectively treated with the deployed agent(s) and/or suitably and effectively dried and/or the deployed agent(s) have been suitably and effectively removed from the various surfaces of the said treated object(s), can also be included in the present invention, all in a manner known to those skilled in the art.

In addition, and without limitation, one or more of any suitable and effective means to effectively, move, mix, homogenize, and/or stir, any, fresh air/gas(s), air/gas(s), heated air/gas(s), heated fresh air/gas(s), humidity, deployed agent(s), gas(s), and/or vapor(s), inside of the said at least one separate and/or stand-alone treatment chamber(s) and/or treatment enclosure(s), at any suitable and effective time(s) and/or for any suitable and effective duration(s) of time(s), can also be suitably and effectively, interfaced with, mounted to, positioned with, and/or effectively located near, function with, and/or communicate with, the said at least one separate and/or stand-alone treatment chamber(s) and/or treatment enclosure(s). Without being limited, the one or more decontamination system(s) and agent blower(s), can also be suitably and effectively, interfaced with, mounted to, positioned with, and/or effectively located near, function with, and/or communicate with, the said at least one separate and/or stand-alone treatment chamber(s) and/or treatment enclosure(s).

Without being limited, the said one or means to stir the deployed agent(s) and/or dry and/or assist with drying any surface(s) such as, but not limited to any, floor(s) surface(s), treated object(s) surface(s), and/or horizontal surface(s), located within the said at least one separate and/or stand-alone treatment chamber(s) and/or treatment enclosure(s), such as, but not limited to one or more of any, chamber circulation apparatus(s), can draw, suction, and/or pull in any, fresh air/gas(s), air/gas(s), heated air/gas(s), heated fresh air/gas(s), humidity, deployed agent(s), gas(s), and/or vapor(s), from and/or at one or more of any suitable and effective location(s) within the said treatment chamber(s) and/or treatment enclosure(s), and deploy, disperse, dispense, flow out, blow out, the same said any, fresh air/gas(s), air/gas(s), heated air/gas(s), heated fresh air/gas(s), humidity, deployed agent(s), gas(s), and/or vapor(s), to and/or at one or more of any suitable and effective location(s) within the said treatment chamber(s) and/or and/or treatment enclosure(s), as previously mentioned in the present invention.

It is preferred, without limitation, that any of the, fresh air/gas(s), air/gas(s), heated air/gas(s), heated fresh air/gas(s), humidity, deployed agent(s), gas(s), and/or vapor(s), that can be circulated, recirculated, deployed, and/or emitted, by the chamber circulation apparatus(s) and into the treatment chamber(s), and/or separate and/or stand-alone treatment chamber(s) and/or treatment enclosure(s), for various purposes such as, but not limited to, mixing, homogenizing, and/or stirring, the deployed agent(s) within the said treatment chamber(s) and/or treatment enclosure(s), drying the floor(s) within the said treatment chamber(s) and/or treatment enclosure(s), and/or removing the deployed agent(s) from the various surface(s) and/or treated object(s) surface(s) located inside of the treatment chamber(s) and/or treatment enclosure(s), can be drawn, suctioned, and/or pulled, from one or more of any suitable and effective location(s) effectively near the top(s) and/or ceiling(s) inside of the said any, treatment chamber(s), treatment enclosure(s), and/or separate and/or stand-alone treatment chamber(s) and/or treatment enclosure(s), and the same any, fresh air/gas(s), air/gas(s), heated air/gas(s), heated fresh air/gas(s), humidity, deployed agent(s), gas(s), and/or vapor(s), can also be deployed, blown out, and/or flowed out, at one or more of any suitable and effective location(s) effectively near the floor(s) and/or bottom(s) of the said treatment chamber(s), treatment enclosure(s), and/or separate and/or stand-alone treatment chamber(s) and/or treatment enclosure(s).

Without being limited, the improved chamber and/or enclosure mobile processing system(s), and more specifically, and without being limited, the one or more treatment and processing system(s), can have at least six or more paths through which any substances such as, but not limited to any, fresh air/gas(s), air/gas(s), heated air/gas(s), heated fresh air/gas(s), humidity, deployed agent(s), gas(s), and/or vapor(s), can move and/or flow through (Herein called "Modified Airflow System(s)"). Without limitation, these paths can constitute the modified airflow system(s) of the improved chamber and/or enclosure mobile processing system.

The first airflow path includes, and without limitation, the one or more modified filtered and heated inbound air/gas(s) assembly(s), that effectively connects the surrounding environment and/or the surrounding outside environment to the one or more outbound filtered and heated air/gas(s) control valve(s) (Herein called "First Air/gas(s) Control Valve(s)"). The second airflow path includes, without limitation, the one or more chamber connection input conduit(s) that effectively connects the one or more treatment chamber(s) and/or treatment enclosure(s) to the treatment and processing system(s), and more specifically directly and/or indirectly to the first air/gas(s) control valve(s) and the one or more outbound deployed agent(s) control valve(s) (Herein called "Fourth Air/gas(s) Control Valve(s)"). The third airflow path includes, without limitation, the one or more treatment chamber(s) and/or treatment enclosure(s) that effectively connects with both the one or more chamber connection input conduit(s) and the one or more chamber connection output conduit(s). The fourth airflow path includes, without limitation, the one or more chamber connection output conduit(s) that connects the one or more treatment chamber(s) and/or treatment enclosure(s) to the treatment and processing system(s), and more specifically directly and/or indirectly to the one or more exhaust control valve(s) (Herein called "Second Air/gas(s) Control Valve(s)") and to the one or more agent generator inbound air/gas(s) control valve(s) (Herein called "Third Air/gas(s) Control Valve(s)"). The fifth airflow path includes, without limitation, the one or more modified treatment agent deployment apparatus(s) that connects with both the third air/gas(s) control valve(s) and the fourth air/gas(s) control valve(s). The sixth airflow path includes, without limitation, the one or more modified filter exhaust assembly(s) that effectively connects with the second air/gas(s) control valve(s) and the surrounding environment.

Without being limited, the various part(s) and component(s) of the at least one of any, improved chamber and/or enclosure mobile processing system(s), packaging system(s), decontamination system(s), heated air/gas(s) system(s), chamber circulation apparatus(s), valve(s), blower(s), fan(s), treatment and processing system(s), and/or separate and/or stand-alone treatment chamber(s) and/or treatment enclosure(s), can be controlled from, communicate with, and/or send and/or receive any, power, information, data, controls, signals, directions, inputs, and/or communications, to and/or from the at least one of any suitable and effective system control part(s) and component(s) and/or any microcontroller(s), that can be located at and/or within any suitable and effective location(s) such as, but not limited to any, treatment and processing system(s), cabinet(s), enclosure(s), and/or separate and/or stand-alone treatment chamber(s) and/or treatment enclosure(s), and can effectively automate and control the various operations of the improved chamber and/or enclosure mobile processing system(s), through one or more of any suitable and effective, cable(s), wire(s), power cable(s), fiber optic line(s), and/or wire link(s) (not shown), all in a manner known to those skilled in the art. It is preferred, without limitation, that the one or more microcontroller(s) are suitably and effectively a part of and/or are located at, on, and/or with, any one or more treatment and processing system(s) of the improved chamber and/or enclosure mobile processing system(s). Also, and without being limited, the at least one separate and/or stand-alone treatment chamber(s) and/or treatment enclosure(s) can also be independently powered, and can also be controlled via one or more of any suitable and effective wireless means from one or more of any suitable and effective controller(s), microcontroller(s), and/or digital controller(s), located at one or more of any suitable and effective location(s), that can control all of the various parts and components of the improved chamber and/or enclosure mobile processing system(s), all in a manner known to those skilled in the art.

According to an embodiment of this part of the present invention, and without being limited, the treatment, sanitization, disinfection, high-level disinfection, sterilization, and/or decontamination, of the one or more of any, surface(s), treated object(s) surface(s), and/or targeted treated object(s) surfaces, located within the treatment chamber(s) is generally described. Without being limited, both the first air/gas(s) control valve(s) and the second air/gas(s) control valve(s) can be effectively closed, and both the the third air/gas(s) control valve(s) and the fourth air/gas(s) control valve(s) can be effectively open.

Also, and without limitation, at, after, and/or effectively about, the time(s) that both the third air/gas(s) control valve(s) and the fourth air/gas(s) control valve(s) are effectively open, and both the first air/gas(s) control valve(s) and the second air/gas(s) control valve(s) are effectively closed, the deployed agent(s), are generated within, created by, emitted by, and/or dispersed by, one or more of any suitable and effective decontamination system(s) that is a part of the modified treatment agent deployment apparatus(s) that is a part of the treatment and processing system(s) that is a part of the improved chamber and/or enclosure mobile processing system(s). Without limitation, one or more of any, deployed agent(s), air/gas(s), humidity, gas(s), and/or vapor(s), are then effectively, flowed, moved, flowed through, moved through, and/or sent, from the at least one decontamination systems(s) that can be a part of the at least one treatment and processing system(s), to the at least one separate and/or stand-alone treatment chamber(s) and/or treatment enclosure(s), through one or more of any suitable and effective hose(s) and/or conduit(s), and more particularly the one or more chamber connection input conduit(s).

More specifically, and without limitation, the said any, deployed agent(s), air/gas(s), humidity, deployed agent(s), gas(s), and/or vapor(s), can be suitably and effectively, flowed and/or moved, from the said one or more decontamination system(s), through the one or more open fourth air/gas(s) control valve(s), through the one or more chamber connection input conduit(s), into, through, and out of, the one or more treatment chamber(s) and/or treatment enclosure(s), through the one or more chamber connection output conduit(s), through the open third air/gas(s) control valve(s), and back into, through, and/or out of, the one or more decontamination systems(s). Without being limited, the said any, deployed agent(s), air/gas(s), humidity, deployed agent(s), gas(s), and/or vapor(s), can be suitably and effectively, moved, circulated, and/or recirculated, into, through, and out of, the treatment chamber(s) by the effective design and operation of one or more of any suitable and effective decontamination system(s) in a manner known to those skilled in the art and/or the effective operation of one or more of any suitable and effective agent blower(s).

Without being limited, the said deployed agent(s) can be flowed and/or moved into the treatment chamber(s) and/or treatment enclosure(s) and effectively, and without limitation, treat, sanitize, disinfect, high-level disinfect, sterilize, and/or decontaminate, any, surfaces, atmosphere(s), and/or any treated object(s) surface(s), located within the treatment chamber(s) and/or treatment enclosure(s), including, but not limited to any, various surfaces of any treated object(s) removably and effectively located within the said treatment chamber(s). Without being limited, the said, deployed agent(s), air/gas(s), humidity, deployed agent(s), gas(s), and/or vapor(s), are flowed, moved, and returned, from the at least one separate and/or stand-alone treatment chamber(s) and/or treatment enclosure(s), through one or more of any suitable and effective hose(s) and/or conduit(s), and more particularly the one or more chamber connection output conduit(s), back to the at least one treatment and processing system(s). Also, and without limitation, the said, deployed agent(s), air/gas(s), humidity, deployed agent(s), gas(s), and/or vapor(s), are flowed, recirculated, and/or moved, back into and through the said modified treatment agent deployment apparatus(s) and decontamination system(s), and then flowed, recirculated, and/or moved, back into the said treatment chamber(s) and/or treatment enclosure(s) along with any newly generated and/or dispensed deployed agent(s) for any suitable and effective, number(s) and duration(s) of time(s), but at least until the process of treating the various surfaces and treated object(s) surfaces located inside of the said treatment chamber(s) and/or treatment enclosure(s) is suitably and effectively complete and/or efficaciously complete. In addition, and without being limited, this process can continue until any suitable and effective, quantity(s), concentration(s), and/or amount(s), of the deployed agent(s) are delivered, dispensed, and/or deployed, into the said treatment chamber(s) and/or treatment enclosure(s) to effectively treat the various surfaces and treated object(s) surfaces located within the said treatment chamber(s) and/or any one or more of any suitable and effective, quantity(s), concentration(s), and/or amount(s), of the deployed agent(s) are moved into the said treatment chamber(s) and/or are detected inside of the treatment chamber(s), all in a manner known to those skilled in the art. Without being limited, the effective flow and movement of the said deployed agent(s), vapor(s), gas(s), humidity(s), mist(s), aerosol(s), and/or particle(s), within this particular embodiment, are controlled by, both the first air/gas(s) control valve(s) and the second air/gas(s) control valve(s) being effectively closed, and both the the third air/gas(s) control valve(s) and the fourth air/gas(s) control valve(s) being effectively open.

According to another embodiment of this part of the present invention, and without being limited, the suitable and effective drying and/or the suitable and effective removal of the deployed agent(s), of and/or from the various surface(s) located inside of the treatment chamber(s) and/or the various surface(s) of the one or more treated object(s) located inside of the treatment chamber(s), is generally described.

First, without being limited, the one or more of any, decontamination system(s), agent blower(s), and/or the modified treatment agent deployment apparatus(s), are turned effectively off and/or effectively cease operation(s), and the flow and movement of the said any, deployed agent(s), air/gas(s), humidity, deployed agent(s), gas(s), and/or vapor(s), into the treatment chamber(s) and/or treatment enclosure(s) can be stopped. Without being limited, the deployed agent(s) can also dwell and/or remain inside of the treatment chamber(s) and/or treatment enclosure(s) for any suitably and effective time(s) and number(s) of time(s) before they are removed and/or exhausted from the treatment chamber(s) and/or treatment enclosure(s).

Without being limited, after any, deployed agent(s), humidity, gas(s), atmosphere(s), and/or vapor(s), are effectively deployed into and are present and/or are effectively located inside of the treatment chamber(s) and/or treatment enclosure(s), for any suitable and effective duration(s) and/or length(s) of time(s), the said any, deployed agent(s), humidity, gas(s), atmosphere(s), and/or vapor(s), can be suitably and effectively, flowed, moved, evacuated, exhausted, circulated, replaced, and/or removed, from and/or out of, the said treatment chamber(s) and/or treatment enclosure(s).

Also, and without limitation, both the first air/gas(s) control valve(s) and the second air/gas(s) control valve(s) can be effectively opened, and both the the third air/gas(s) control valve(s) and the fourth air/gas(s) control valve(s) can be preferably, and without limitation, effectively closed. However, and without limitation, both the first air/gas(s) control valve(s) and the second air/gas(s) control valve(s) can be effectively opened, and both the third air/gas(s) control valve(s) and the fourth air/gas(s) control valve(s) can also be effectively open. In addition, and without limitation, both the one or more inbound blower(s) and the one or more exhaust blower(s) can then be preferably, and without limitation, both suitably and effectively powered and operated after at least the first air/gas(s) control valve(s) and the second air/gas(s) control valve(s) are effectively opened.

Without being limited, the operation, and preferably, and without limitation, the simultaneous operation, of the one or more inbound blower(s) and the one or more exhaust blower(s), can suitably and effectively flow and move any, fresh air/gas(s), air/gas(s), heated air/gas(s), heated fresh air/gas(s), into, through, and out of, the treatment chamber(s), and also suitably and effectively flow and move any, fresh air/gas(s), air/gas(s), heated air/gas(s), heated fresh air/gas(s), humidity, deployed agent(s), gas(s), and/or vapor(s), suitably and effectively out of the said one or more treatment chamber(s) and/or treatment enclosure(s), and into, through, and out of, the one or more modified filter exhaust assembly(s).

Without being limited, the fresh air/gas(s) and/or air/gas(s) can be sourced from any suitable and effective surrounding external environment(s) such as, but not limited to any, surrounding environment(s) that is outside of and/or surrounds the improved chamber and/or enclosure mobile processing system(s), treatment and processing system(s), treatment enclosure(s), and/or treatment chamber(s), and first enters the one or more of any suitable and effective modified filtered and heated inbound air/gas(s) assembly(s) where the air/gas(s) and/or fresh air/gas(s) is preferably, and without limitation, at least effectively filtered by one or more of any suitable and effective filter(s) and then suitably and effectively heated, if needed and/or desired, by one or more of any suitable and effective means to heat any air/gas(s) and/or moving air/gas(s) known to those skilled in the art such as, but not limited to, one or more of any heater element(s). Without being limited, various suitable and effective combinations, numbers, and/or orders, of any suitable and effective, inbound blower(s), air/gas(s) filters, and means to heat any air/gas(s) and/or fresh air/gas(s), can be used in the present invention as described earlier in the present invention for the improved cabinet mounted treatment chamber processing system(s).

Without limitation, the said filtered, air/gas(s), fresh air/gas(s), heated air/gas(s), and/or heated fresh air/gas(s), is flowed, moved, and/or sent, from the at least one treatment and processing system(s) to the at least one separate and/or stand-alone treatment chamber(s) and/or treatment enclosure(s), through one or more of any suitable and effective hose(s) and/or conduit(s), and more particularly the one or more chamber connection input conduit(s). Without limitation, the said filtered, air/gas(s), fresh air/gas(s), heated air/gas(s), and/or heated fresh air/gas(s), are flowed into and through the treatment chamber(s) and/or treatment enclosure(s) and effectively dry and/or suitably and effectively remove any, humidity, deployed agent(s), gas(s), and/or vapor(s), from various location(s), area(s), surface(s), and/or space(s), located inside of the treatment chamber(s) and/or any communicating area(s) and/or space(s) such as, but not limited to, any atmosphere(s) and/or various surfaces located within the said treatment chamber(s) and/or treatment enclosure(s) including, but not limited to any, surfaces of any one or more treated object(s) that are removably and effectively located within the said treatment chamber(s).

Also, and without being limited, the any, fresh air/gas(s), air/gas(s), heated air/gas(s), heated fresh air/gas(s), humidity, deployed agent(s), gas(s), and/or vapor(s), are flowed, moved, and returned, from the at least one separate and/or stand-alone treatment chamber(s) and/or treatment enclosure(s), through one or more of any suitable and effective hose(s) and/or conduit(s), and more particularly the one or more chamber connection output conduit(s), back to the at least one treatment and processing system(s). Without being limited, the said any, fresh air/gas(s), air/gas(s), heated air/gas(s), heated fresh air/gas(s), humidity, deployed agent(s), gas(s), and/or vapor(s), are then flowed and/or moved into and through the one or more open second air/gas(s) control valve(s) and then into and through the one or more modified filter exhaust assembly(s), where the said any, fresh air/gas(s), air/gas(s), heated air/gas(s), heated fresh air/gas(s), humidity, deployed agent(s), gas(s), and/or vapor(s), is effectively filtered with one or more of any suitable and effective filter(s), and then exhausted into the said surrounding external environment(s) through one or more suitable and effective exhaust outlet(s). Without being limited, this process can continue until any one or more of any suitable and effective, quantity(s), concentration(s), and/or amount(s), of any, humidity(s), deployed agent(s), gas(s), and/or vapor(s), are suitably and effectively removed, dried, and/or reduced, from any one or more surface(s) and/or area(s) such as, but not limited to any, treatment chamber(s), treatment enclosure(s), atmosphere(s) within the said treatment chamber(s) and/or treatment enclosure(s), and/or from the various surfaces and treated object(s) surfaces located within the said treatment chamber(s).

Without being limited, any suitable and effective substance(s) such as, but not limited to any, fresh air/gas(s), air/gas(s), heated air/gas(s), and/or heated fresh air/gas(s), can be flowed and/or moved into, through, and out of, the treatment chamber(s) and/or treatment enclosure(s), as described within this particular embodiment, for various purposes such as, but not limited to, suitably and effectively drying the various surfaces and/or treated object(s) surface(s) located inside of the treatment chamber(s), suitably and effectively removing and/or drying any, humidity(s), deployed agent(s), gas(s), and/or vapor(s), from the various surfaces and/or treated object(s) surface(s) located inside of the treatment chamber(s), and/or suitably and effectively removing any undesired and/or unwanted, quantity(s), concentration(s), and/or amount(s), of any, humidity(s), gas(s), vapor(s), and/or deployed agent(s), from the atmosphere(s) and/or various surface(s) and/or treated object(s) surface(s) located inside of the treatment chamber(s).

Also, and without being limited, the flow and/or movement of one or more of any substance(s) such as, but not limited to any, fresh air/gas(s), air/gas(s), heated air/gas(s), and/or heated fresh air/gas(s), deployed agent(s), humidity(s), gas(s), and/or vapor(s), out of the said treatment chamber(s) and/or treatment enclosure(s), at any suitable and effective time(s) and for any suitable and effective number(s) of time(s), can also be controlled by, and without limitation, both the one or more first air/gas(s) control valve(s) and the second air/gas(s) control valve(s) being effectively open, and both the one or more third air/gas(s) control valve(s) and the fourth air/gas(s) control valve(s) being effectively closed, and preferably and without limitation, the suitable and effective operation of both the one or more inbound blower(s) and exhaust blower(s). It is preferred, without limitation, that after the suitable and effective treatment of the one or more surface(s) and/or treated object(s) surface(s) located inside of the treatment chamber(s), and/or after the suitable and effective drying of the various surfaces located inside of the treatment chamber(s), and/or after the suitable and effective removal of the deployed agent(s) from the various surfaces located inside of the treatment chamber(s), both the first air/gas(s) control valve(s) and the second air/gas(s) control valve(s) can remain effectively open, and both the third air/gas(s) control valve(s) and the fourth air/gas(s) control valve(s) can remain effectively closed.

Without being limited, everything previously described and mentioned about the improved cabinet mounted treatment chamber processing system(s), such as, but not limited to any, (a) filtered and heated inbound air/gas(s) assembly(s) and their operation(s), description(s), and purposes, (b) filtered exhaust assembly(s) and their operation(s), description(s), and purposes, (c) treatment chamber(s) and their operation(s), description(s), and purposes, (d) treatment agent deployment apparatus(s) and their operation(s), description(s), and purpose(s), (e) decontamination system(s) and their operation(s), description(s), and purpose(s), (f) chamber circulation apparatus(s) and their operations(s), description(s), and purpose(s), (g) various valves and their operation(s), description(s), and purposes, (h) various treatment and processing steps, (i) various steps for treating, sanitizing, disinfecting, high-level disinfecting, and/or sterilizing, various surfaces and/or treated object(s) surface(s) located inside of the treatment chamber(s), (j) various steps for drying the various surfaces and/or treated object surface(s) located inside of the treatment chamber(s), (k) various steps for removing and/or reducing the deployed agent(s), vapor(s), gas(s), and/or humidity(s), from the various area(s), atmosphere(s) space(s), surface(s), and/or treated object surface(s), located from the various area(s), atmosphere(s), space(s), surface(s), and/or treated object surface(s), located inside of the treatment chamber(s), (l) and/or communications and controls of and/or with the various part(s) and component(s) of the present invention by one or more of any suitable and effective microcontroller(s), also pertains to, equates to, and/or is shared by, the improved chamber and/or enclosure mobile processing system(s) and its various parts, components, operations, methods, steps, and purposes, such as, but not limited to any, (a) modified filtered and heated inbound air/gas(s) assembly(s) and their operation(s), description(s), and purposes, (b) modified filtered exhaust assembly(s) and their operation(s), description(s), and purposes, (c) treatment chamber(s) and/or treatment enclosure(s) and their operation(s), description(s), and purposes, (d) modified treatment agent deployment apparatus(s) and their operation(s), description(s), and purpose(s), (e) treatment agent deployment apparatus(s) and their operation(s), description(s), and purpose(s), (f) decontamination system(s) and their operation(s), description(s), and purpose(s), (g) chamber circulation apparatus(s) and their operations(s), description(s), and purpose(s), (h) various valves and their operation(s), description(s), and purposes, (i) various treatment and processing steps, (j) various steps for treating, sanitizing, disinfecting, high-level disinfecting, and/or sterilizing, various surfaces and/or treated object(s) surface(s) located inside of the treatment chamber(s), (k) various steps for drying the various surfaces and/or treated object surface(s) located inside of the treatment chamber(s), (l) various steps for removing and/or reducing the deployed agent(s), vapor(s), gas(s), and/or humidity(s), from the various area(s), atmosphere(s) space(s), surface(s), and/or treated object surface(s), located inside of the treatment chamber(s), (m) and/or communications and control of the various part(s) and component(s) by the one or more of any suitable and effective microcontroller(s).

These and additional objects, advantages, features and benefits of the present invention will become apparent from the following specification.

BRIEF DESCRIPTION OF THE DRAWINGS

The drawing figures illustrate the best mode currently contemplated of practicing the present invention.

In the drawings:

FIG. 3 is a schematic view of an aerosol generator used in the apparatus of FIG. 1;

FIG. 4 is a schematic view of a first embodiment of a sterilization chamber used in the apparatus of FIG. 1;

FIG. 5 is a schematic view of a second embodiment of a sterilization chamber used in the apparatus of FIG. 1;

FIG. 8 is a front isometric view of a first embodiment of an object holder used in the apparatus of FIG. 1;

FIG. 9 is a top isometric view of a second embodiment of an object holder used in the apparatus of FIG. 1;

FIG. 10 is a top plan view of a third embodiment of an object holder used in the apparatus of FIG. 1;

FIG. 11 is an end view of the object holder of FIG. 10;

FIG. 108 is a schematic type view of, the start beam(s) (84)(49) and the secondary beam(s) (84)(50) pivoting and/or tilting effectively downward to cause the object(s) to fall down and into any, open removable package(s) (229) and/or packaging and open packaging material(s) (495), located below the object(s). The package sealer(s) (485) is shown which is used to package and seal the object(s) in their packages. More particularly, the open removable package(s) (229) and/or packaging and open packaging material(s) (495) can slide or be moved laterally out along any track or slide (815) and be positioned under the start beam(s) (84)(49) and/or the secondary beam(s) (84)(50), catch falling object, and then slide back in for any package sealing activities.

DETAILED DESCRIPTION OF THE PREFERRED EMBODIMENTS

Figure 1:
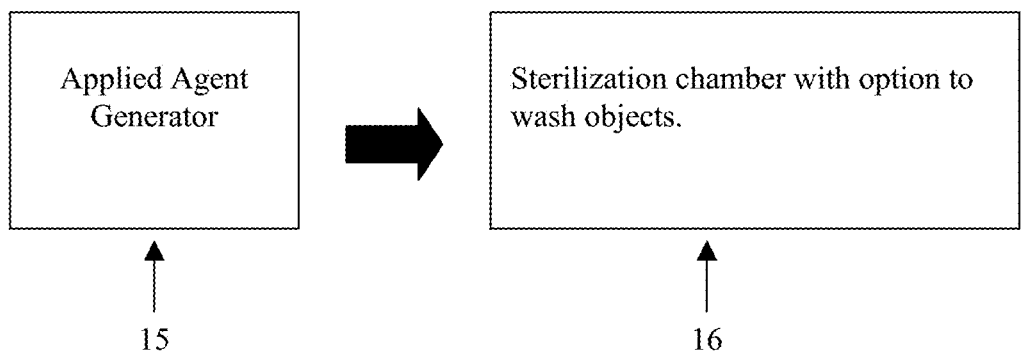
FIG. 1 is a schematic view of a first embodiment of a disinfecting apparatus constructed according to the present invention.
Figure 2:
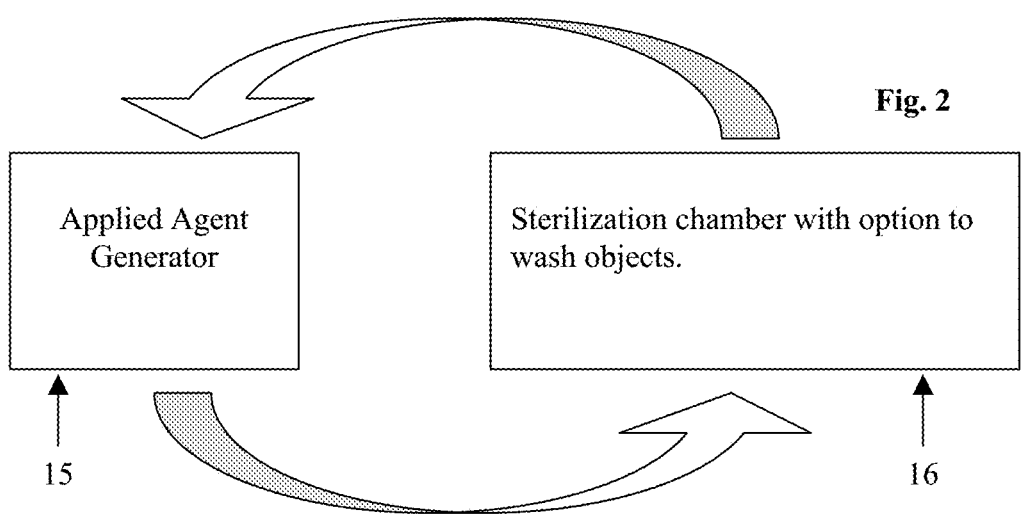
FIG. 2 is a schematic view of a second embodiment of the disinfection apparatus of FIG. 1.

With reference now to the drawing figures in which like reference numerals designate like parts throughout the disclosure, the invention broadly comprises methods and apparatuses for the sanitization, detoxification, disinfection, high level disinfection, or sterilization of both the interior and exterior surfaces of any object such as, but not limited to, an endoscope (01) or plurality of endoscopes (01) (FIG. 5) within one or more closed space(s), closed system of space(s), or chamber(s) (herein called "sterilization chamber") (16), as well as and, without limitation, their surrounding atmosphere.

U.S. Pat. Nos. 7,641,130 and 7,871,016 both to Ricciardi et al. and U.S. patent application Ser. Nos. 12/567,428 and 12/637,310 both to Ricciardi et al. are all herein incorporated by reference in their entirety.

This is achieved or attained by the generation and/or administration of an "applied agent", or mixtures of these agent(s) or substance(s), in or into the sterilization chamber (16) in which the object(s) or endoscope(s) (01) is positioned or placed. It is more preferred, without limitation, that the "applied agent" or substance is in the form of an aqueous aerosol (65) that is generated by way of one or more ultrasonic device(s) (19), an example of which is shown in FIG. 3 and disclosed in co-pending U.S. patent application Ser. No. 11/509,332, which is incorporate herein by reference in its entirety as part of the present specification. It is also preferred, without limitation, that the aerosol be formed of an aqueous solution that contains a suitable disinfecting, sanitizing or sterilizing agent(s) or substance(s) that contains an acidic oxidizer, such as hydrogen peroxide and peroxyacetic acid. Any chemical neutralizing agent(s) or substance(s) can also, without limitation, be used and can be in any form including, but not limited to any liquid, gas, vapor, plasma, or aerosol.

One aspect of the present invention, is an improvement to the current art involving an innovative pressure interface assembly (68) (FIGS. 14-19) for the application of a positive or negative air/gas pressure to the internal space, lumens, ducts, channels or fiber optic shafts or tunnels (herein called "ducts") (08), of an object or endoscope (01), in order to apply or administer the "applied agent" or substance(s) such as but not limited to any gas, plasma, vapor, or aerosol, to the internal spaces and surfaces within these locations as well as the areas and surfaces that interface or articulate with the pressure interface assembly (68). This innovative pressure interface assembly and its interface, assures that the agent(s) or substance(s) is able to reach and coat, sanitize, detoxify, disinfect, high level disinfect, or sterilize, the entirety of the internal spaces and surfaces that are inherent to various objects including, but not limited to, endoscope designs, diameters, and especially lengths. The assembly (68) includes an interface material (02) that also assures that all of the surfaces of the object or endoscope in contact with the interface have sufficient exposure to the aerosol (65) of an "applied agent" (20) through either direct and/or indirect contact, for their sanitization, disinfection, high-level disinfection, or sterilization, depending on the agent used and the exposure time. For example and without limitation, any absorbent interface material may also indirectly deploy/transmit the "applied agent" (20) that is aerosolized, to the articulated areas and surfaces by the interaction or movement of the "applied agent" (20) through the interface material (02) formed from the selected material. The present invention also incorporates various other improvements to the current art.

It is preferred, without limitation, that the endoscope (01) is washed according to the manufacturer's recommendations or methods common or prescribed in the industry or field of art, before being placed inside of the sterilization chamber (16) and the application of the "applied agent" or substance(s) (20) to the endoscope. However, the object or endoscope can also be placed within the sterilization chamber (16) and the washing and cleaning activities can, without limitation, take place within the same sterilization chamber (16) prior to the application of the "applied agent" (20).

According to an embodiment, any gas, vapor, plasma, aerosol, or aerosol, may be utilized or applied and be created from any chemical, mixture, compound, or anti-pathogen/toxin/fungal/sporicidal agent(s) or substance(s) (hereinafter ""applied agent"(s)") (20), and it can be created, stored, produced, or generated either inside the closed space, closed system of space, sterilization chamber (16), or inside a separate chamber (15) that is connected to the closed space, system of closed space, or sterilization chamber (16) as shown in FIGS. 1-2 and FIGS. 4-5, 12-13, 20-23, 26-33.

According to another embodiment, the "applied agent" (20) may be in any form including, but not limited to, one or more of any, gas, vapor, plasma, aerosol, or liquid. The "applied agent" (20) in liquid form does not include any liquid aerosols and is applied in a distinctly separate way. In particular, the "applied agent" (20) in liquid form is generally applied or administered in ways including, but not limited to, being pumped, poured, flowed, or sprayed, onto, or through various internal or external surfaces of an endoscope.

The "applied agent" (20) may be, without limitation, one or more or any combination of suitable compounds, mixtures, substances, or chemicals, in any concentration, number, size, or density. It is preferred, without limitation, that if an aerosol (65) is utilized, it is formed generally of droplets whose size is less than five microns. The aerosol (65) may have any mass concentration or density. It is further preferred, without limitation, that the aerosol (65) has droplets that are of a higher rather than lower mass concentration or density.

According to an embodiment, the atmospheric pressure within the sterilization chamber, or any connecting or shared areas or atmospheres, may be any negative pressure, including a full or close to full vacuum, before or during the deployment of any "applied agent" inside of the sterilization chamber, or through any pressure interface assembly or supply tube. This can also help to increase the efficacy of the process, and is known to those skilled in the art. Also, the "applied agent" can be either generated inside the sterilization chamber, or any separate, but connecting area to the sterilization chamber, that may or may not be controlled with a valve.

The amount of "applied agent" (20) that is generated and administered or applied can vary as necessary or desired. In addition, the application time and total exposure time of the "applied agent" (20) to the endoscope(s) (01) in the closed space or sterilization chamber (16) can also vary. The level of efficacy, result, outcome, or effect that is desired or needed, as well as the time needed to accomplish it, with the application of the "applied agent" (20) to any of the areas or surfaces within the closed space or sterilization chamber (16), pressure interface assembly (68), or endoscope (01), including, but not limited to, any exterior surfaces, any interface surfaces or areas, or any internal spaces and surfaces, can vary according to variables or any combination of variables such as, but not limited to, the total application time of the "applied agent" (20), total exposure time of the surfaces and areas to the "applied agent" (20), temperature of the "applied agent" (20), temperature of the targeted surfaces and/or areas, relative humidity within the area that the "applied agent" is deployed or administered, flow rate and velocity of the air/gas and "applied agent" (20) that are utilized, the amount or volume of "applied agent" (20) that is generated or produced, the amount of "applied agent" (20) that is applied or deployed to the targeted surfaces or areas, the properties and chemical characteristics of the "applied agent" (20), the amount of positive or negative air/gas pressure that is applied to the endoscope (01) or pressure interface assembly (68) and associated components, and the concentration, number, size, and density of the "applied agent" (20). The variables can vary, without limitation, to achieve the desired or needed results and/or processing time. Other variables may include, but are not limited to the number, shape, diameter, and length of the ducts (08), or size and number of interior spaces inside of the object or endoscope (01), and the selection of the materials used to form the interface (02) and the attributes of the interface material (02).

It is preferred, without limitation, that the gas, vapor, and/or aerosol (65) is generated and/or created in a separate generation (production) chamber (hereinafter "generation chamber") (15) (FIGS. 1-2) and flowed, blown, or otherwise moved into the sterilization chamber (16) via a blower, fan, or other source of pressurized air/gas (17), where it may then be recirculated back into the generation chamber (15) (FIG. 2) or, to any condenser or filter known to those skilled in the art. The respective chambers are interconnected with piping, tubing, or conduit (18), creating a common atmosphere or potential for a common atmosphere within the closed system. However, if the "applied agent" (20) is created, produced, or generated within the sterilization chamber (16), a blower, fan, or other source of pressurized air/gas, can without limitation, be used to disperse the said agent(s) or substance(s) within the sterilization chamber (16). The sterilization chamber (16) may be constructed so that it is any shape, size, or configuration and can also, without limitation, be any room, chamber, glove box, or connected system of one or more space(s) of any size that may, without limitation, be sealed or enclosed.

The purpose of the "applied agent" (20) such as, but not limited to any effective, gas, vapor, plasma, and/or aerosol, in the present invention is to coat, interface, interact, envelope, or have contact with, one or more contaminants including but not limited to toxins, bacteria, virus, fungus, spores (both fungal and bacterial), prions or other protein(s), chemicals, compounds, or other structures, within a target area(s) killing bacteria, fungus, spores, or neutralizing toxins or rendering a virus, or protein structure incapable of replication or otherwise interfering with the target's cellular physiology, or destroying or neutralizing the toxin and/or chemicals or chemical structures.

Figure 12:
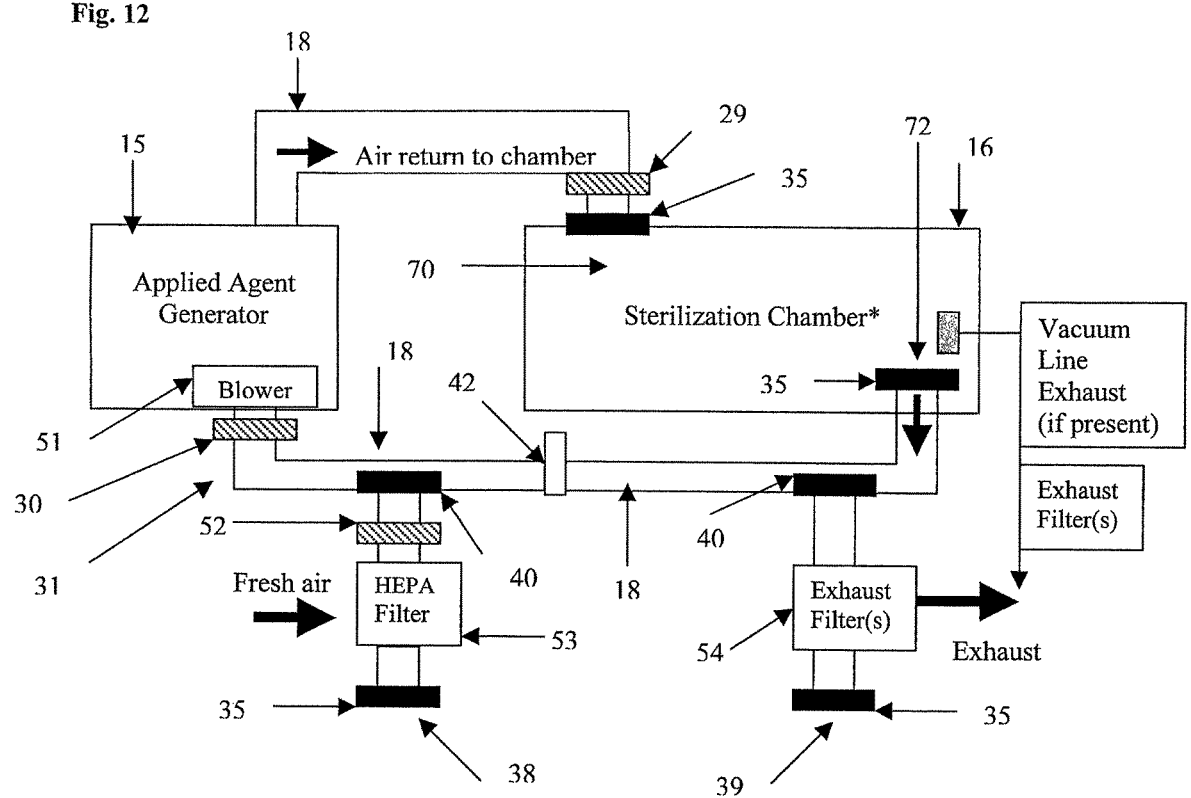
FIG. 12 is a schematic view of a third embodiment of the apparatus of FIG. 1.

It is preferred in the present invention that the aerosol (65) is generated by one or more aerosol generating ultrasonic transducers (19) located below the surface of an aqueous "applied agent" (20) in a reservoir (21), as shown in FIG. 3. Transducers (19),(22) of any design, frequency, or construction may, without limitation, be used. However, any other means to generate an aerosol, such as but not limited to, high pressure nozzle technology, (65) could potentially be used in the present invention, are not specifically set forth, but are known to those skilled in the art. The reservoir (21) may be made of any suitable material that is unaffected by the chemical action of the "applied agent" (20). One preferred "applied agent" (20) is a mixture of acidic oxidizing compounds including mainly hydrogen peroxide and peroxyacetic acid in an aqueous solution, however one or more of any other effective substance(s) or agent(s), in any effective forms, known to those skilled the art, may be used. Suitable materials for the reservoir (21) may include PVC, polypropylene, glass, and stainless steel, but many other suitable materials may be used. The aerosol (65) generated by operation of the transducers (19),(22) forms above the surface of the "applied agent" liquid (20) in the reservoir (21) and is, without limitation, transferred from the basin, reservoir, and/or chamber in which it is created, to the space (16) to be treated by a fan, blower, or other source of pressurized air/gas (17), as will be described in greater detail below.

The output of the transducers (19),(22) is either focused or directed to a point and/or an area near the surface of the "applied agent" (20) to cause a surface disturbance, which results in the formation of an aerosol (65) of the "applied agent" (20). This aerosol (65) is then blown, flowed, or otherwise moved, into the contaminated area, space, or target area, (16) in order to coat, interface, interact, envelope, or have contact with, contaminants including but not limited to toxins, bacteria, virus, fungus, spores (both fungal and bacterial), prions or other proteins, chemicals, compounds, or other structures, within a target area(s) killing the bacteria, fungus, and spores, neutralizing the toxins, or rendering the virus, or protein structure incapable of replication or otherwise interfering with the target's cellular physiology, or destroying or neutralizing the toxin and/or chemicals or chemical structures. The aerosol (65) droplets are of a defined size distribution of less than, but not limited to, 10 microns in diameter, allowing them to behave like a gas due to Brownian movement and diffusion. This enables the droplets to penetrate small cracks and crevices, and apply thin films on surfaces if desired. In addition, the aerosol (65) may effectively reach and disinfect, detoxify, high level disinfect/sterilize, areas of contamination and areas of otherwise limited accessibility. Each transducer (19),(22) used in this apparatus and method is preferably, without limitation, made from lead zirconate-titanate-four (PZT-4), or other suitable piezoelectric materials.

The present invention can include, but is not limited to, the electronic equipment mentioned in U.S. Pat. Nos. 5,878,355 and 6,102,992, which each are incorporated by reference herein in their entirety. A variable frequency oscillator is used to generate a high frequency sine or square wave. A preferred oscillator is a digital function generator/counter capable of producing sine, square, triangle, pulse and ramp waveforms. The unit has an adjustable frequency range from 0.001 hertz to 10 megahertz in seven ranges. It has variable output amplitude from 5 mv to 500 Vp-p, variable symmetry/duty cycle from 5% to 95% in the ramp or pulse mode, continuous or externally controlled outputs. A D.C. offset between −10 v to +10 v can be added to any of the output waveforms. A continuous wave power amplifier amplifies the wave generated by the oscillator. The preferred amplifier is a solid-state amplifier with a frequency response from 0.001 hertz to 10 megahertz. It provides up to 2500 watts of linear power with low harmonic and intermodulation distortion, however the number of watts could also be increased in order to provide enough power to drive the desired number of transducers (19),(22).

The amplified signal from the amplifier is used to drive one or a plurality of transducer(s) (19),(22), where each transducer in the present invention is operated at a frequency range between 0.001 to 10.0 megahertz. In addition, each transducer (19), (22) has a resonant frequency between 0.001 and 10.0 megahertz.

Referring to FIG. 3, there is shown an aerosol generator (15) to which the teachings of the present invention may be applied and used. A reservoir (21) contains a volume of "applied agent" (20), the level of which is controlled by a weir gate (23) operatively associated with a supply pump (24) and line (25) to maintain the level of the "applied agent" (20) at a preferred level above the transducers (19),(22) mounted on the bottom wall of the reservoir. The "applied agent" can vary in temperature when it is applied, however it has been found that the efficiency of aerosol generation is enhanced by heating the liquid "applied agent" (20) to at least 20° F. above ambient, but preferably to at least about 80° F. A heater element (26) mounted in the liquid agent supply sump (27) may be used for this purpose. The aerosolized (65) "applied agent" (20) is delivered to the space to be treated via an exit orifice (28) in one wall of the reservoir to which suitable piping or tubing (not shown) is attached for delivery. A heater element(s) (29) may, without limitation, be attached either to the exit orifice (28) or anywhere between the aerosol generator and the sterilization chamber as taught in prior art. This means for heating is intended to heat the aerosol to various temperatures as it is removed from the aerosol generator or before it reaches the closed space or sterilization chamber (16). A blower, fan, or other source of pressurized air (17) generates the air/gas flow necessary to deliver the aerosol (65), all in a manner well known in the art. As shown in FIG. 12, a return path of suitable piping or tubing (18) may also, without limitation, connect the area or sterilization chamber (16) in which the aerosol (65) is applied back to the air/gas intake of the blower (17) in order to create a closed system or common atmosphere of air/gas in order to prevent positive air/gas pressure from building in the sterilization chamber (16).

A means to radiate heat (30) may also, without limitation, be provided or otherwise operatively coupled to and/or about the outlet(s) of the sterilization chamber (16), or anywhere along the return path of the recirculated air/gas (31) and aerosol before it reenters the aerosol generator (15), in the present invention. This is shown in FIG. 12. The radiated heat provides the added benefit of heating the returning air/gas (31) and aerosol droplets to various temperatures. This may, without limitation, further reduce the diameter of the aerosol droplets (65) so as to lessen the possibility of an impact with droplets (65) within the aerosol generator (15) that would result in the coalescence and/or creation of larger droplets. The heat can vary in its temperature and intensity.

Figure 6:
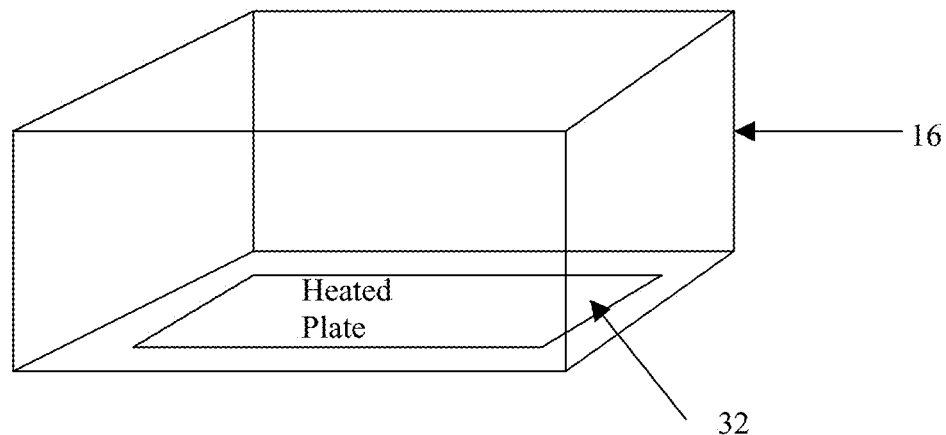
FIG. 6 is a schematic view of a third embodiment of a sterilization chamber used in the apparatus of FIG. 1.

A means to heat the floor and/or bottom area (32), of the sterilization chamber (16) may also, without limitation, be added to the present invention as shown in FIG. 6. A heated plate (32) placed on the floor of the sterilization chamber (16) may also be positioned in this location. The thermal, or convective forces emitted from the heated floor or bottom area (32) of the chamber is intended, without limitation, to both repel any aerosol droplets as they settle, and delay their downward path of travel. An added benefit is that any droplets that do touch or come in close proximity to the heated floor (32) can be turned to vapor or gain additional thermal energy, which can contribute to the efficacy of the process. The means (32) to heat the floor can, without limitation, vary in its temperature and intensity.

Figure 7:
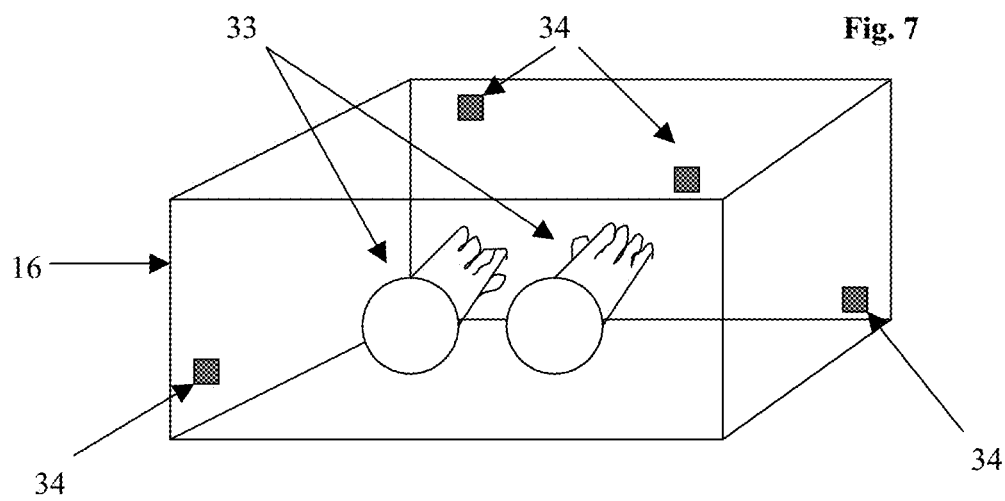
FIG. 7 is a schematic view of a fourth embodiment of a sterilization chamber used in the apparatus of FIG. 1.

One or more polymer glove(s) or fingers(s) (33) may be incorporated into the system of closed space, and/or the sterilization chamber (16) or an area that can access these spaces, as shown in FIG. 7. They can have a broad similarity in purpose, design, and concept as gloves(s) or finger(s) (33) that are commonly found in laboratory or industrial glove boxes. They can enable an operator to handle the endoscope (01) within the sterilization chamber (16) both before and after the cleaning cycle and related activities have occurred. In addition, the operator can use the glove(s) or finger(s) (33) to handle and place the endoscope (01) into packaging such as but not limited to trays, pouches, bags, or other means to otherwise hold the endoscope (01), and then sealing the packaging so as to keep the packaged endoscope (01) free from contamination or to insure that its properties or characteristics are unaltered. This allows the operator to handle and package the sanitized, detoxified, disinfected, high level disinfected, sterilized, or otherwise cleaned endoscope (01) without having to expose the endoscope (01) to the outside environment and risk contamination.

The endoscope (01) that is placed within the sterilization chamber (16) can be packaged before or after the present invention has completed its operational cycle for the sanitization, detoxification, disinfection, high level disinfection, or sterilization, of the objects, with methods, equipment, and materials which are not specifically set forth, but known to those skilled in the art. This can include packaging methods, equipment, and materials used in industries including but not limited to medical devices, and medical related products.

According to an embodiment, any package (not shown) containing one or more of any objects (not shown) can also be processed in the present invention, for the sanitization, detoxification, disinfection, high level disinfection, or sterilization, of the interior of the package as well as its contents. The package may or may not be connected to the pressure interface assembly (68). It is preferred, without limitation, that the package is constructed of polymer, and it has at least one or more sides or walls that is constructed from materials such as, but not limited to, Tyvek or a similar type of material, glassine, or any type of permeable or semi-permeable material. The packaging materials can be made from any material or combination of materials, and be of any thickness or polarity. It is preferred, without limitation, that the package is constructed in the form of a flexible pouch containing at least one wall that is constructed from a flexible layer of Tyvek whose construction and thickness is commonly used in the medical industry and is known to those skilled in the art. The package may be, without limitation, subjected to any combination and sequence of the following operational parameters such as: (a) Any temperature before exposure to the "applied agent" (b) Any negative atmospheric pressure or vacuum before or during the deployment of any "applied agent" inside of the sterilization chamber (16), (c) any exposure times of the package to the "applied agent", (d) any amount of "applied agent" (e) any temperature during exposure to the "applied agent", (f) any positive atmospheric pressure before, during, or after the deployment of any "applied agent" inside of the sterilization chamber (16), (g) any temperature after exposure to the "applied agent", (h) any temperature and pressure to dry the contents, interior, and exterior of the package, and (i) any drying time.

As also shown in FIG. 7, one or more chemical exposure indicator(s), and/or biological indicator(s) (hereinafter "indicator") (34) can be mounted, held, hung, positioned, or placed, anywhere inside of the closed space or sterilization chamber (16). The position of the indicator(s) (43) can vary both vertically and horizontally with respect to the object(s) in the closed space or sterilization chamber (16). The indicators (34) provide a means for assuring that proper sanitization, detoxification, disinfection, high level disinfection, or sterilization has occurred for the object (01) and/or the closed space or sterilization chamber (16). A detailed description of the construction and operation of suitable chemical exposure indicator(s) and/or biological indicator(s) (34) is not specifically set forth, but is known to those skilled in the art.

Figure 13:
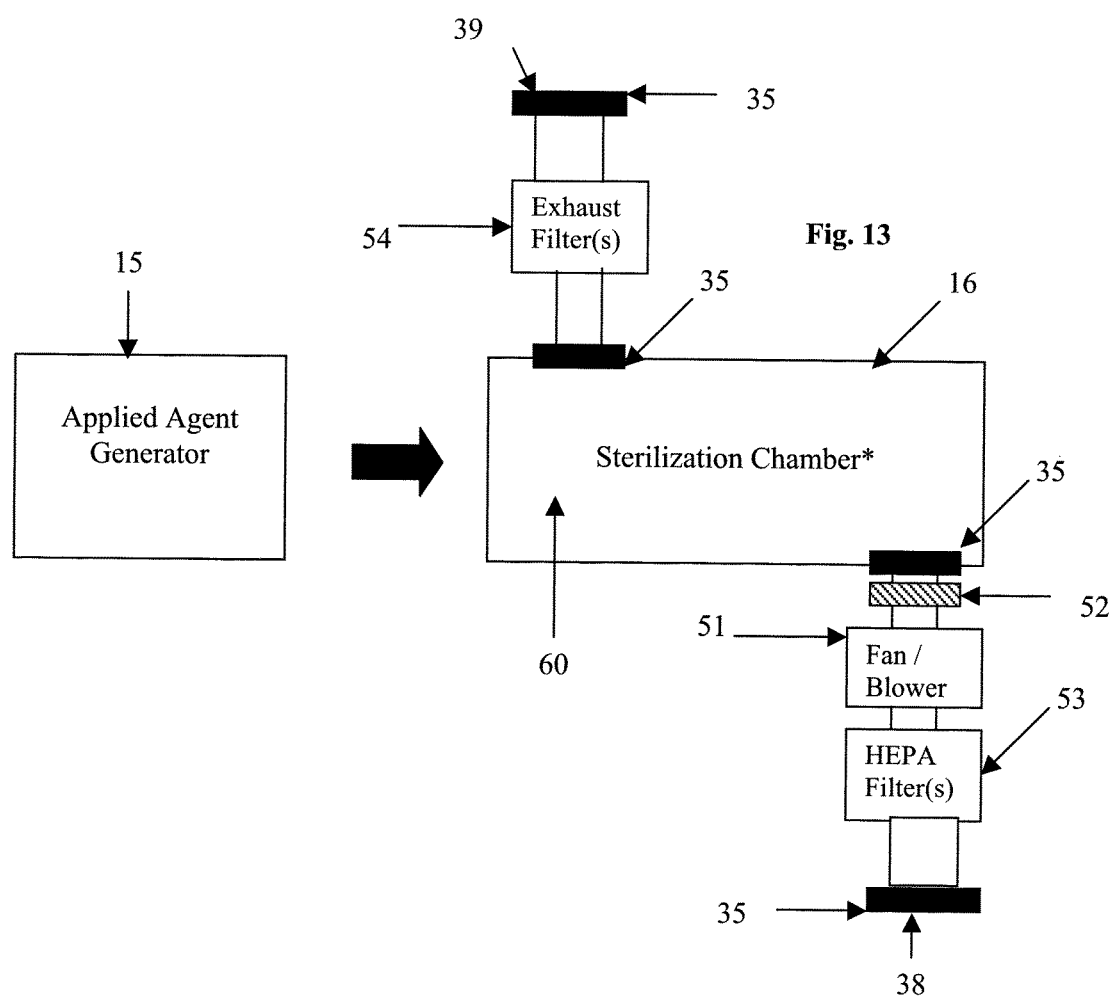
FIG. 13 is a schematic view of a fourth embodiment of the apparatus of FIG. 1.

Referring again to FIG. 12, one or more means (35) known to those skilled in the art may, without limitation, be operably connected to various components of the present invention to effectively close off, seal, or separate, the closed space or sterilization chamber(s) (16) from the "applied agent" (20) generation chamber(s) (15), and/or the tubes, ducting, channels, tunnels, etc. (18), that connect the "applied agent" (20) generator(s) (15) to the closed space or sterilization chamber(s) (16), at any time including, but not limited to, before or during any washing, cleaning, drying, or other processing activities of the endoscope (01). Referring to FIGS. 4, 5, and 12, a closure device (35) can, without limitation, be any cap or separating device implemented for operably sealing off various portions of the apparatus of the present invention including: a) any air/gas outlet (36) or air/gas inlet (37), or anywhere along the path, for any air/gas or "applied agent" (20) that is flowed through the pressure interface assembly (68); b) any inbound fresh air/gas inlet (38); c) any outbound or exhaust air/gas outlet (39); d) any opening, or inlet or outlet, to/from the sterilization chamber (16), including but not limited to, any air/gas inlet (70) or air/gas outlet (72) to/from the sterilization chamber (16); e) any other tubes, ducting, channels, tunnels, or other parts or components, etc., that would need, or be desired, to have a controlled connection or access, to the pressure interface assembly (68), sterilization chamber (16), or other connected or potentially connected closed space or system of closed space. The closure device (35) can be a door, flap, valve, lid, panel, or other physical means (hereafter called "valve") (35), to contain the chemicals, liquids, vapor, gases, or other substances used in the washing and/or processing activities, within the closed space or sterilization chamber(s). The valve 35 is constructed of any suitable material that is unaffected by the chemical action of the agents or substances used for the washing, cleaning, or processing activities, or the anti-pathogen/toxin/fungal/sporicidal agent(s) or substance(s) that is applied or administered. Referring to FIGS. 12-13, certain valves, covers, doors, flaps or other means known to those skilled in the art (herein called "system valve") (40) may be effectively used during the application or administration of the "applied agent" (20) in the sterilization chamber (16). Each system valve (40) can be actuated, closed, or operated to effectively stop the transfer, flow, or movement of air/gas or "applied agent" (20) through the inbound fresh air/gas inlet (38), the outbound or exhaust air/gas outlet (39), and/or the tubes, ducting, channels, tunnels, etc. (18), that connect the fresh air/gas inlet (38) or exhaust air/gas outlet (39) to the closed system of space or sterilization chamber (16). The various valves (35),(40) in the present invention can be actuated, opened, or operated so that any substances may flow through the valves (35),(40) when desired or needed. In addition, the various valves (35),(40) can be effectively utilized at various times to allow the fresh air/gas from outside of the present invention to flow through, without limitation, the inbound fresh air/gas inlet (38), the air/gas inlet(s) (37) for the air/gas that is flowed through the pressure interface assembly (68), the "applied agent" generator (15), the outbound or exhaust air/gas outlet (39), and/or the tubes, ducting, channels, tunnels, etc. (18), that connect the fresh air/gas inlet (38) or exhaust air/gas outlet (39) to the closed system of space or sterilization chamber (16). Referring to FIG. 12, an additional valve (42) can be utilized to separate the flow of inbound fresh air/gas from the outbound air, gas, or "applied agent" (20) as they are circulated through and from the closed system of space or sterilization chamber (16) and exhausted out of the present invention and into the external environment. The various valves (35),(40),(42) are designed, operationally controlled whether manually or automatically, and operationally sealed in a manner that is not specifically set forth, but known to those skilled in the art. This includes the possible operation, command, and control of the valves (35),(40),(42) via an electronic or electrical means.

Referring to FIGS. 1-2, 4-5, 12-13, 20-23, and FIGS. 26-33, the sanitization, detoxification, disinfection, high level disinfection, or sterilization of both the internal and external surfaces of an endoscope (01) begins with placing it in the closed space or sterilization chamber (16). The endoscope (01) can, without limitation, be washed, cleaned, rinsed, and/or processed after it is placed in the sterilization chamber (16), but prior to the application of the "applied agent" (20). It is preferred, without limitation, that the object or endoscope (01) is washed, cleaned, rinsed, and/or dried and processed before it is placed in the sterilization chamber (16). In either case, the washing, cleaning, rinsing, drying, and/or processing is performed according to methods that are common in the industry in which the object or endoscope (01) is used, and/or according to the recommendations of the object or endoscope's (01) manufacturer. A means for washing, cleaning, rinsing, and/or processing the object(s), such as endoscopes (01), within the sterilization chamber (16), which results in the endoscope (01) being clean, and/or removing contamination such as, but not limited to, blood, saliva, mucous, feces, or tissue, before the application of an "applied agent" (20), may also, without limitation, be added in the present invention and is known to those skilled in the art. After placing the endoscope (01) in the sterilization chamber (16), and the washing, cleaning, and/or processing steps are completed, if they were performed, an "applied agent" (20) such as, but not limited to, any gas, plasma, vapor, or aerosol, is generated and administered, moved, or blown into the closed space or sterilization chamber (16), covering all of the external and possibly the internal surfaces over time. Despite the ability of small droplets and gases to penetrate hard to reach places, it is still difficult and time consuming to disinfect or sterilize the interior surfaces of objects or instruments like endoscopes (01) due to the length and small diameter of features such as, but not limited to, their lumens or ducts (08), and their general construction. However, by using positive or negative air/gas pressure to move the "applied agent" (20) through these hard to reach areas, they can without limitation, be easily and quickly, sanitized, detoxified, disinfected, high level disinfected, or sterilized. The "applied agent" (20) may be pushed or pulled through the endoscope (01) by using the supplied positive or negative air/gas pressure for all endoscope (01) related applications including, but not limited to, all uses related to the pressure interface assembly (68) as well as all other general endoscope (01) interfaces already known to those skilled in the art. In addition, the "applied agent" (20) may, without limitation, be administered or deployed into the sterilization chamber (16) where it is then pulled into and through the endoscope (01) that is positioned within the sterilization chamber (16).

Figure 14:
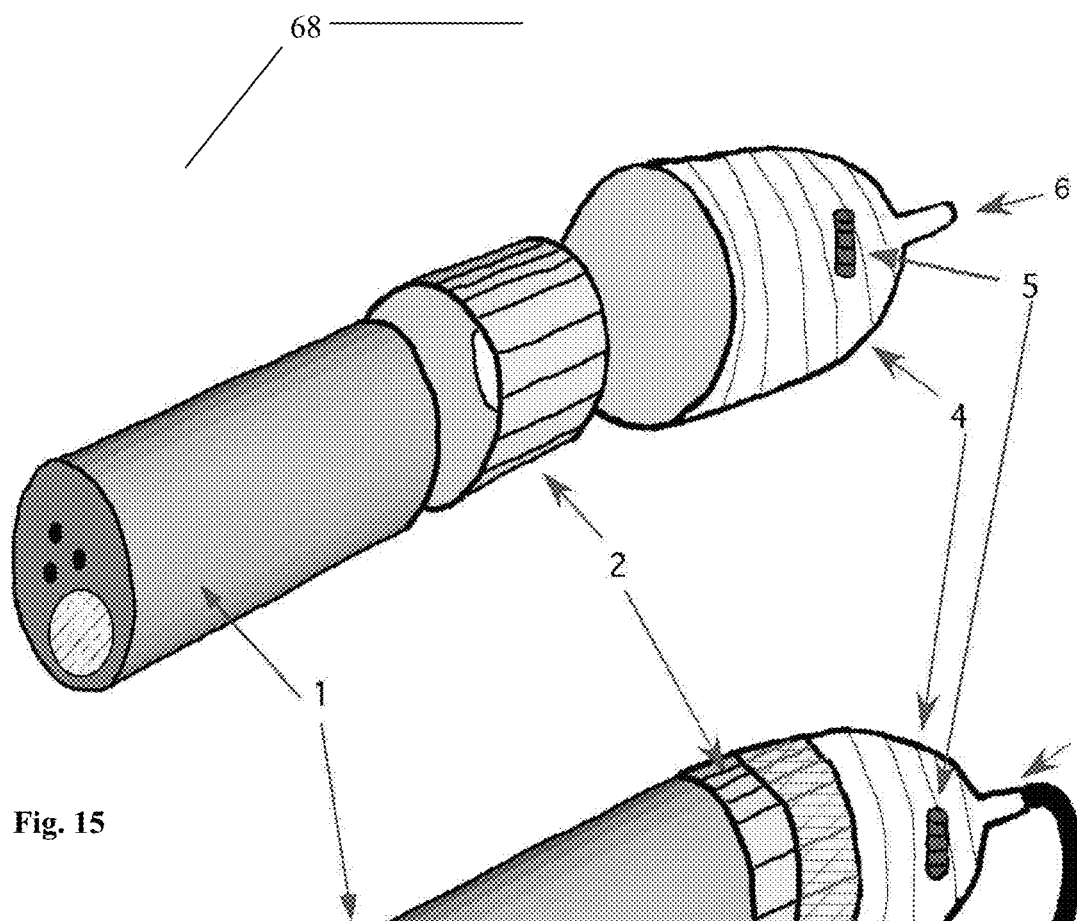
FIG. 14 is an exploded, perspective view of a first embodiment of a pressure interface assembly utilized with the apparatus of FIG. 1.
Figure 15:
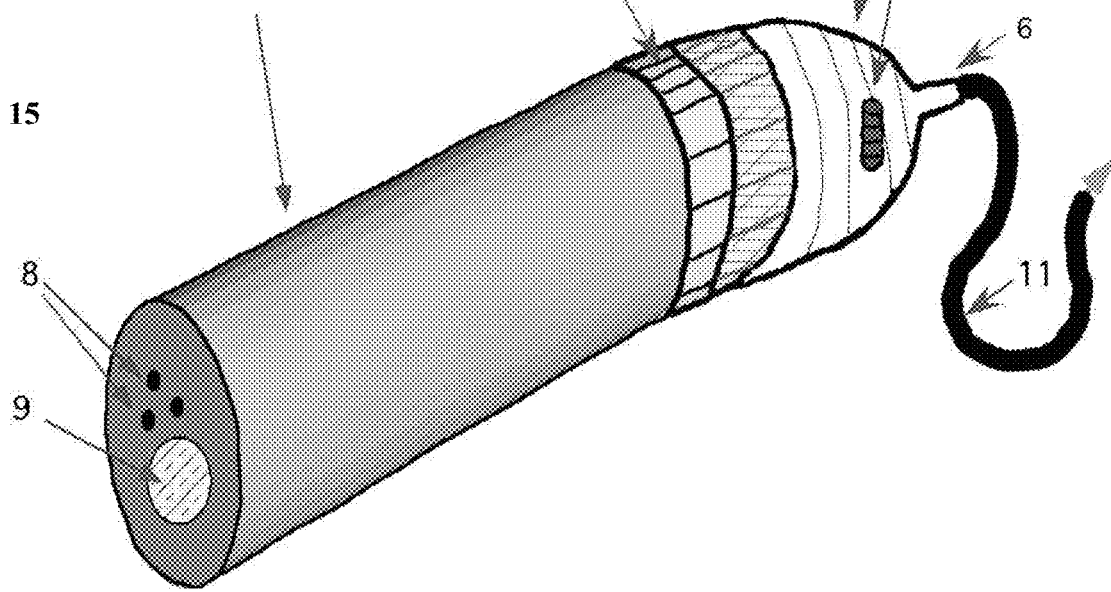
FIG. 15 is a perspective view of the assembly of FIG. 14.

Referring now to FIGS. 14 and 15, one or more open ends or openings of an endoscope (01) are interfaced with one or more pressure interface assembly(s) (68). The open end of an endoscope (01), can include, but is not limited to, the end of the endoscope (01) where the various ducts (08), or other ports end, exit, or are made visible or accessible. This unique and innovative pressure interface assembly (68) has parts including, but not limited to, a coupling (04), and an interface or interface material (02) combination. The coupling (04) can have one or more ports or other means (hereinafter "main port") (06) for attaching one or more tubes, hose, pipes, duct, tunnels, conduit, or other means (herein called "supply tube") (11) that can supply air, gas, liquid, or the "applied agent" (20) under positive or negative pressure, to the various spaces and surfaces of the pressure interface assembly (68) and endoscope (01), including without limitation, their interfacing surfaces and internal spaces and surfaces, under positive or negative pressure. The supply tube (11) can be any size. The main port (06) can, without limitation, connect the space within the pressure interface assembly (68) to the space within the supply tube (11) so that the spaces become connected.

Looking at FIGS. 4 and 5, the supply tube (11) can, without limitation, be effectively connected anywhere to the generation chamber (15) or any other effective area, which is in turn connected to any source of pressurized air/gas or vacuum. The pressure interface assembly (68) allows for any aerosol (65), air/gas, liquid, or "applied agent" (20) to be driven, pushed, or pulled through places such as, but not limited to, both the internal space and/or ducts (08), of the endoscope (01), as well as through the interface material (02) and/or interface location, for purposes including, but not limited to, rinsing the endoscope (01), drying the endoscope (01), or the sanitization, detoxification, disinfection, high level disinfection, or sterilization of these areas and their respective surfaces. It is preferred, without limitation, that the pressure interface assembly (68) is utilized inside of the sterilization chamber (16), but it could also be used outside of the sterilization chamber (16) in applications not specifically set forth but are known to those skilled in the art.

The supply of a positive or negative air/gas pressure to the pressure interface assembly (68) may originate from any vacuum pump, air/gas pump, pressurized air source, fan, or blower (44),(17). The air/gas pressure can vary depending on the situation and particular application and can serve several functions. First, the positive and/or negative air/gas pressure can, without limitation, be applied to the pressure interface assembly (68) at the beginning and/or end of the sanitization, detoxification, disinfection, high-level disinfection, or sterilization cycle, in order to move air/gas or dry and/or heated air through the interior space of the endoscope (01). This will remove any moisture if it is still present in these areas.

Referring now to FIGS. 12 and 13, one or more heating element(s) (29), (52) placed in the air stream before or after the pressure interface assembly (68) can provide the heated air (referenced Rosdahl et al. pg 3 Col. 123-127). It is preferred, without limitation, that air from outside of the sterilization chamber (16) that is pulled, drawn, pushed, or otherwise moved into the sterilization chamber (16) and/or the endoscope (01) be first filtered before its entry into the sterilization chamber (16) and/or endoscope with one or more high efficiency filter (53) such as, but not limited to, a HEPA filter or other filter that is known to those skilled in the art or is acceptable in the industry in which it is used. The air/gas stream may also, without limitation, be filtered by one or more filters (54) before it exits from the sterilization chamber (16); and the filter is known to those skilled in the art or its use is acceptable in the industry in which it is used. The air can, without limitation, be heated within the sterilization chamber (16) and/or before its entry into the sterilization chamber (16) from areas including, but not limited to, the outside atmosphere, or the atmosphere that surrounds the outside of the sterilization chamber (16), in order to help dry the endoscope (01) at the desired time or stage during processing.

Also, the positive air/gas pressure or negative air/gas pressure is intended to move the "applied agent" (20) through the interior space of the endoscope (01). It is preferred, without limitation, that, as shown in FIG. 4, if a negative air/gas pressure is supplied to the coupling (04) that is interfaced or attached to the endoscope (01), a pressure differential is established. This results in the flow of air/gas and the "applied agent" (20) from areas such as, but not limited to, the sterilization chamber (16), through "both" the interface material (02) and internal space within the endoscope (01), and into the coupling (04). Once in the coupling (04), the air/gas and the "applied agent" (20) flows into the attached pipes, tubes, conduits, etc. (11),(118), where it is eventually vented back into the sterilization chamber (16), or through a filter (54) and into the outside environment.

The "applied agent" (20) can, without limitation, flow into the coupling (04) under positive air/gas pressure, as shown in FIG. 5. It is preferred, without limitation, that in this situation, the air/gas and "applied agent" (20) is pulled from the sterilization chamber (16), or chamber where the "applied agent" is generated (15), and flowed into the coupling (04) via the attached pipes, tubes, conduits, etc. (18),(11). It is then flowed "both" out of the interface material (02) and through the internal space within the endoscope (01), and into the sterilization chamber (16). The "applied agent" (20) in this case, can also be separately delivered into the sterilization chamber (16), if it is generated in a chamber (15) separated from the sterilization chamber (16).

Without limitation, the apparatuses and methods can be used or take place in any type of rigid, semi-rigid, flexible container, or package (herein called "container"), and the container can function as the sterilization chamber (16). The container (16) can, without limitation, have the pressure interface assembly (68) or coupling (04) integrated into its design or construction. The container (16) can, without limitation, be designed so that it can be sealed and function as effective packaging or medical quality packaging after completion of the processing steps in a manner that meets or exceeds industry and regulatory standards.

Referring to FIG. 4-5, 14-16, the coupling (04) can be constructed from various materials such as, but not limited to, stainless steel, glass, polymer, polyolefin, cellulose, or even natural or manufactured fibers that are either coated or uncoated. The coupling (04) can, without limitation, be constructed from one or more polymers that meets or exceeds industry and regulatory standards. It is preferred without limitation, that the coupling (04) is constructed from one or more polymers that can include, but is not limited to PVC, polycarbonate, polypropylene, and HDPE. The coupling (04) surfaces can, without limitation, be electrically or electrostatically charged in order to attract the "applied agent" (20). It is preferred, without limitation, that the materials used to construct the coupling (04) may be rigid, semi-rigid, or flexible. A flexible polymer or tube roll is one example of a flexible material that could be used. The pressure interface assembly (68) can be designed and constructed for single or multiple uses. It is preferred, without limitation, that the coupling (04) is designed so that one end is able to fit over an end of an endoscope (01), and the other end of the coupling (04) is substantially closed. The coupling (04) can, without limitation, be designed so that one end is able to fit over an end of an endoscope (01), and the other end of the coupling (04) is designed to interface or connect with a supply tube (11) or other means to connect the coupling (04) to a source of negative or positive air/gas pressure in a suitable manner. For example, one end of the coupling (04) can be, without limitation, open and its exterior surface can have a hose barb, or a portion of its exterior surface can be molded into a barb of sufficient size to securely interface/articulate it with a supply tube (11). The end of the coupling (04) that is designed to fit over an end of an endoscope (01), can have an opening of various sizes and shapes. This opening can control the negative or positive air/gas flow in or out of the coupling (04).

One or more main ports (06) or means to connect the coupling (04) with a supply of positive and/or negative air/gas pressure that is used to drive, push, or pull the "applied agent" (20) through both the ducts (08) of the endoscope and the interface material (02), can be located on the closed end or "air/gas pressure interfacing end" of the coupling (04). This main port(s) (06) may be connected to a positive or negative air/gas pressure supply tube (11) in order to create a positive air/gas or negative air/gas pressure within the coupling (04). In the context of the present invention, "tube" or "tubing" includes pipes, ducts, conduits, tunnels, and the like.

One or more chemical contact or biological indicators (hereinafter "indicator(s)") (05) of any size type or construction may be mounted, held, hung, positioned, or placed, anywhere inside of the pressure interface assembly (68). The pressure interface assembly (68) is designed for the addition as well as possible removal of these accessories. The indicator (05) provides a means for communicating or assuring that proper sanitization, detoxification, disinfection, high level disinfection, or sterilization has occurred within the endoscope and/or the pressure interface assembly. A detailed description of the indicator (05) is not specifically set forth, because the details are well known to those skilled in the art.

The internal dimensions of the coupling (04) help provide for an interface/articulation between the endoscope (01), the interface or interface material (02) (if it is used), and the coupling (04), that permits the creation of at least a minimum working positive or negative air/gas pressure inside of the coupling (04) and endoscope (01), but still allows "applied agent" (20) to penetrate and sanitize, detoxify, disinfect, high level disinfect, or sterilize the areas and surfaces that interface/articulate or are between the endoscope (01) and the interface material (02) (if it is used), or the coupling (04). In certain circumstances, the inner diameter of the coupling (04) in addition to its thickness can contribute to the performance of the interface (02). This can include but is not limited to, coupling (04) designs where the part of the coupling (04) that interfaces with the endoscope (01) is constructed from materials that are flexible and may or may not have elastic properties. More specifically, the inside dimensions and thickness of the coupling (04) can change in order to accommodate various variables, including, but not limited to, pressures, temperatures, sizing, shape, fit, interface integrity, interface efficiency, thickness of the interface, as well as other variables to achieve efficacy with the process. The coupling (04) may not even touch the exterior or internal surfaces of the endoscope (01).

Referring to FIG. 14-19, the coupling (04) is preferably used in combination with an interface material (02) to interface/articulate with the external circumference or external surfaces of the endoscope (01). In addition, it is preferred that the interface material (02) is positioned between the coupling (04) and the endoscope (01). The interface material (02) can be, without limitation, porous, and/or permeable, and is constructed from materials that can provide effective performance and the desired level of efficacy for the process. The interface material (02) can be, without limitation, constructed of one or more layers of material. The interface material (02) may also have absorbent characteristics to improve its efficacy and performance. The interface material (02) is intended, without limitation, in the present invention to allow the air/gas and the "applied agent" (20) to move or flow through the interface layer at a controlled, but effectual rate, so that at least a minimum working positive or negative air/gas pressure is created or established inside of the coupling (04) and endoscope (01). This minimum working positive or negative air/gas pressure that is created or established inside of the coupling (04) and endoscope (01), moves or otherwise results in the movement or flow of the "applied agent" (20) through places such as, but not limited to, the interior space, or ducts (08), of the endoscope (01) and results in the sanitization, detoxification, disinfection, high level disinfection, or sterilization of these surfaces and areas. The minimum working positive or negative air/gas pressure that is created or established inside of the coupling (04) and endoscope (01), moves or otherwise results in the movement or flow of the "applied agent" (20) through the interface material (02) and areas of interface/articulation between the interface material (02) and endoscope (01), and results in the areas and surfaces under the interface material (02) to be exposed to, and acted upon, by the "applied agent" (20) in order to achieve the desired level of sanitization, detoxification, disinfection, high level disinfection, or sterilization. The interface material (02) can include, but is not limited to cloth, gauze, manufactured fibers, synthetic fibers, natural fibers or materials, cellulose, polymer, polyolefin, glass, metal, ceramic, carbon, combinations of these materials, or other materials know in the art. The interface material (02) can be coated with chemicals, materials, or substances including, but not limited to, polymer(s), polyolefin, wax, lipid, oil, enamel, paint, carbon, metal, combinations of these materials, or other materials known in the art. The interface material (02) as well as the coupling (04) surfaces can be electrically or electrostatically charged or uncharged in order to attract the "applied agent". The electrostatic potential or polarity of the various materials as well as the "applied agent" (20) can, without limitation, vary. Materials for the interface material (02), which are developed in the future, may be utilized to improve the efficacy of the design or its application to certain objects, endoscopes (01), or devices. The interface material (02) and its effectiveness can vary with variables including but not limited to, its size, width, surface area, shape, fit, thickness, density, hardness, elasticity, flow rate, porosity, permeability, evenness of air/gas flow, mechanical properties, physical properties, and other variables known to those skilled in the art. However, the effectiveness and efficacy of each interface material (02) can increase with attributes such as, but not limited to, the uniformity of these variables throughout the interface that is used. The interface material (02), coupling (04) and endoscope (01), can be planned, manufactured, or formed, to assure the proper placement, fit, or function of these components. The shape or physical parameters may include, but is not limited to, closing or tapering the ends of the interface material (02) to various amounts or increments, the presence of ribbings, pegs, grooves, studs, or clips, or other means known to those skilled in the art, that are indented or protrude from components including, but not limited to, the interface material (02), coupling (04) and/or endoscope (01), so that the interface material (02) can interlock or have a controlled or guided articulation/interface with the coupling (04) and/or object or endoscope (01). The interface material (02) may be connected to the coupling (04), or endoscope (01) in various ways that include, but is not limited to, welding, forming, molding, bonding, adhering, gluing, laminating, or cementing. The performance of the interface material (02) or the pressure interface assembly (68) may, without limitation, be improved by welding, forming, molding, bonding, adhering, gluing, laminating, or cementing, one or more layers of material with attributes such as, but not limited to any, width, surface area, shape, thickness, density, hardness, elasticity, flow rate, porosity, permeability, evenness of air/gas flow, mechanical properties, or physical properties, between the interface material (02) and the coupling (04), or between the endoscope (01) and the interface material (02). It is preferred, without limitation, that the material is pliable. The coupling (04) can also be constructed from, or otherwise be, the interface material (02) or interface material (02) and function as the interface (02), which negates the use of a separate interface material (02). This represents the pressure interface assembly (68) in its simplest form. In this case, the coupling (04) is designed and constructed so that it incorporates the purpose, performance, traits, attributes, and characteristics of both the interface material (02) and the coupling (04). Everything pertaining and related to the interface material (02), coupling (04), and exertion of pressure on these materials, in the present invention also pertains to this particular design/construction.

The performance of the interface material (02) is also impacted by the application, existence, and/or control of a pseudo constant or constant, and effectively distributed, pressure exerted on the interface material (02) (herein called "exerted pressure") as it contacts the endoscope (01). This exerted pressure provides, without limitation, an effective distribution of flow of the "applied agent" (20) through the interface material (02) and areas of interface/articulation between the interface material (02) and endoscope (01), and results in the areas and surfaces under the interface material (02) and surfaces of the endoscope (01) that interface/articulate with the material of the interface material (02), to be exposed to and acted upon, by the "applied agent" (20), in order to achieve the desired level of sanitization, detoxification, disinfection, high level disinfection, or sterilization. The application, existence, and/or control of a constant or relatively constant, and effectively distributed, pressure exerted on the interface material (02) as it contacts the endoscope (01), can also, without limitation, be sufficient to hold the endoscope (01) if it is suspended in the sterilization chamber (16) via the pressure interface assembly (68). The weight of the endoscope (01) and/or pressure interface assembly (68) can provide at least the minimum pressure/force needed to form and/or establish a usable and efficacious interface/articulation, and this can, without limitation, be accomplished in a manner known in the art.

It is preferred in the present invention that the exerted pressure is not only effective, but it is evenly distributed. In addition, this exerted pressure can also affect the balance of flow of the "applied agent" (20) through the interface material (02), as well as the interior space or ducts (08) of the endoscope (01). It is preferred in the present invention that the flow of air/gas and "applied agent" (20) through the interface material (02), as well as the interior space or ducts (08) of the endoscope (01), is adjusted so that a desired level of sanitization, detoxification, disinfection, high level disinfection, or sterilization can be achieved. The exerted pressure can vary due to variables related to the interface material (02), including but not limited to its, size, width, surface area, shape, fit, thickness, density, hardness, elasticity, mechanical properties, physical properties, and other variables known to those skilled in the art. The exerted pressure can also vary to control variables associated with the air/gas and "applied agent" (20), including but not limited to, flow rate, air/gas flow and pressure, permeability, and evenness of flow through the interface material (02), and balance of flow through both the interface material (02) and the interior space or ducts (08) of the endoscope (01). The exerted pressure can vary depending on the amount of force that is exerted on the interface material (02), and the amount of surface area of the interface material (02) that receives that force (force per unit area).

Figure 16:
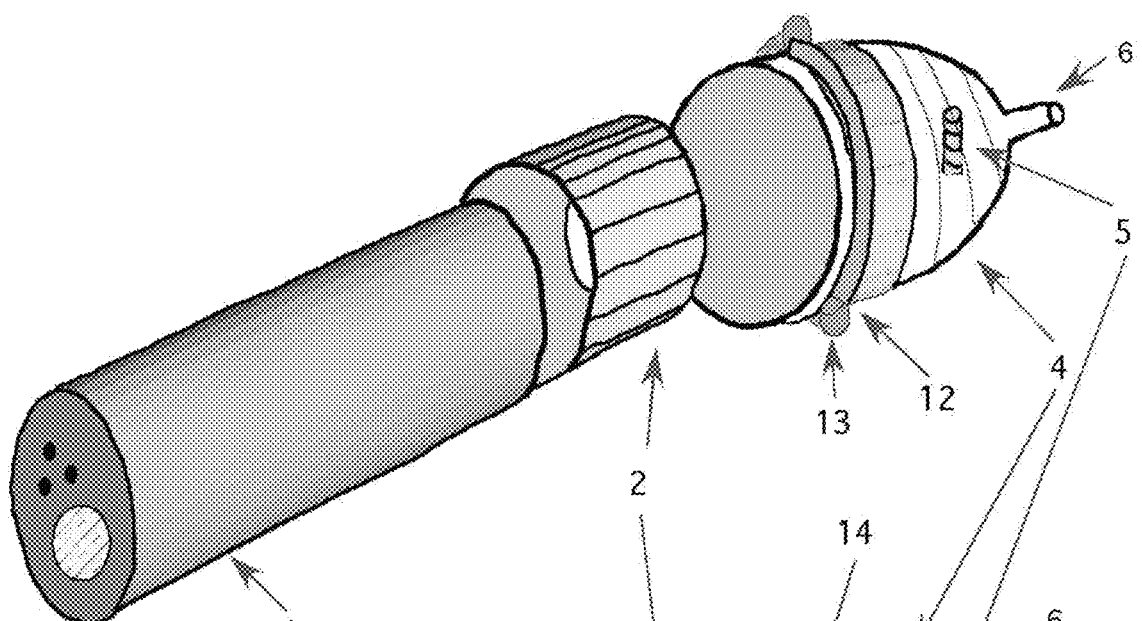
FIG. 16 is exploded, perspective view of a second embodiment of a pressure interface assembly utilized with the apparatus of FIG. 1.
Figure 17:
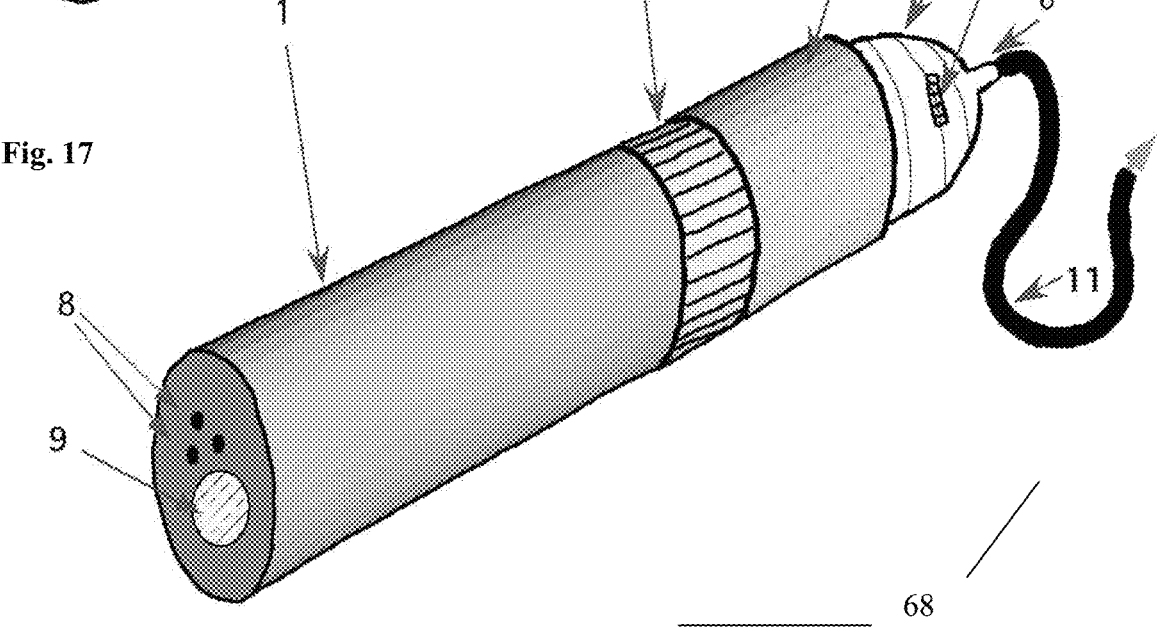
FIG. 17 is a perspective view of the assembly of FIG. 16.

The effective pressure that is exerted on the interface material (02) can result from the articulation/interface of the coupling (04), interface material (02), and endoscope (01). This can be accomplished by ways including, but not limited to, adjusting the designs, dimensions, and properties, of the coupling (04), interface material (02), and endoscope (01), to create a loose or tight fit and/or a weak or strong friction fit, with the interface material (02) and the endoscope (01). It can be accomplished through the use of additional means to exert pressure around the coupling (04), interface material (02) and endoscope (01) in order to create an effective articulation/interface, and includes but is not limited to positioning a clamp over or around the coupling (04) and applying pressure to the coupling (04), interface material (02), and endoscope (01), which creates an effective articulation/interface. It can also be accomplished by utilizing a coupling (04) where at least the part or area of the coupling (04) that interfaces/articulates with the endoscope (01) is constructed from material that is flexible, and may or may not have elastic properties, and one or more parts or areas of this coupling (04) that interface/articulate with the endoscope (01) have dimensions, an inner diameter or inner dimensions, and width, so that an effective pressure is exerted on the interface material (02) when the coupling (04) is interfaced/articulated with the endoscope (01). As shown in FIGS. 16 and 17, this can include, but is not limited to, a coupling (04) that is completely or partially constructed from a flexible material (12),(14) and/or one or more flexible rings (13) that are either built into the flexible material (12),(14) or positioned outside and around the coupling's flexible wall material (12),(14). For example, and without limitation, an effective or sufficient interface material (02) can be provided by, without limitation, one or more rings (13) that fit over, and are utilized to apply an effective or sufficient force or pressure to, the coupling (04), interface material (02), and endoscope (01). Various attributes including, but not limited to, the dimensions, thickness, interior dimensions or interior diameter, and width, of the rings (13) have tolerances so that the rings (13) exert effective pressure on the coupling (04), interface material (02), and endoscope (01), when the pressure interface assembly (68) interfaces/articulates with the endoscope (01). This can also include, but is not limited to, a coupling (04) that is constructed from a rigid or semi-rigid polymer and one or more rings (13) are built into the coupling's (04) interior wall where they can interface/articulate with the interface material (02), and endoscope (01). Various attributes including, but not limited to, the dimensions, thickness, interior dimensions or interior diameter, and width, of the rings (13) have tolerances so that the rings (13) exert effective pressure on the coupling (04), interface material (02), and endoscope (01), when the pressure interface assembly (68) interfaces/articulates with the endoscope (01).

According to an embodiment, one or more encircling geometric shapes or rings (not shown) can also be added to the exterior of an endoscope (01) and/or to the endoscope (01) interfacing/articulating surfaces of the pressure interface assembly (68). Without limitation, these encircling geometric shapes or rings can protrude outward or inward, and can be created without limitation by cutting, carving, engraving, molding, thermoforming, or laminating, gluing, cementing, adhering, or otherwise being attached, to the pressure interface assembly (68). Without limitation, the encircling geometric shapes or rings can also be partially or fully constructed from and have the same chemical, physical, and mechanical properties of the materials that can be used to construct the endoscope (01), the coupling (04), and/or one or more of the interface materials (02) that articulates between the pressure interface assembly (68) and the endoscope (01), and can also be made from a combination of these different materials.

These shapes or rings can, without limitation, interact with each other, the interface material (02), the endoscope (01), the coupling (04), and/or the pressure interface assembly (68). They can be connected to the interface material (02) in various ways that include, but are not limited to, welding, forming, molding, bonding, adhering, gluing, laminating, or cementing, and/or they can also function as the interface material (02). The encircling geometric shapes or rings can also interact or interlock with each other to securely engage the assembly (68) with the endoscope (01). For example, without limitation, the rings can slide past or over each other and into a static position, or be turned within a grove and lock into a static position. The interaction of these encircling geometric shapes or rings can create at least the minimum pressure/force needed to form and/or establish an efficacious and usable interface material (02) and interface/articulation. The interaction of these encircling geometric shapes or rings can also be used to bear the weight of the endoscope (01) if it is suspended in the sterilization chamber (16) via the pressure interface assembly (68). The weight of the endoscope (01) and/or pressure interface assembly (68), in this instance can also provide at least the minimum pressure/force needed to form and/or establish a usable and efficacious interface material (02).

Figure 18:
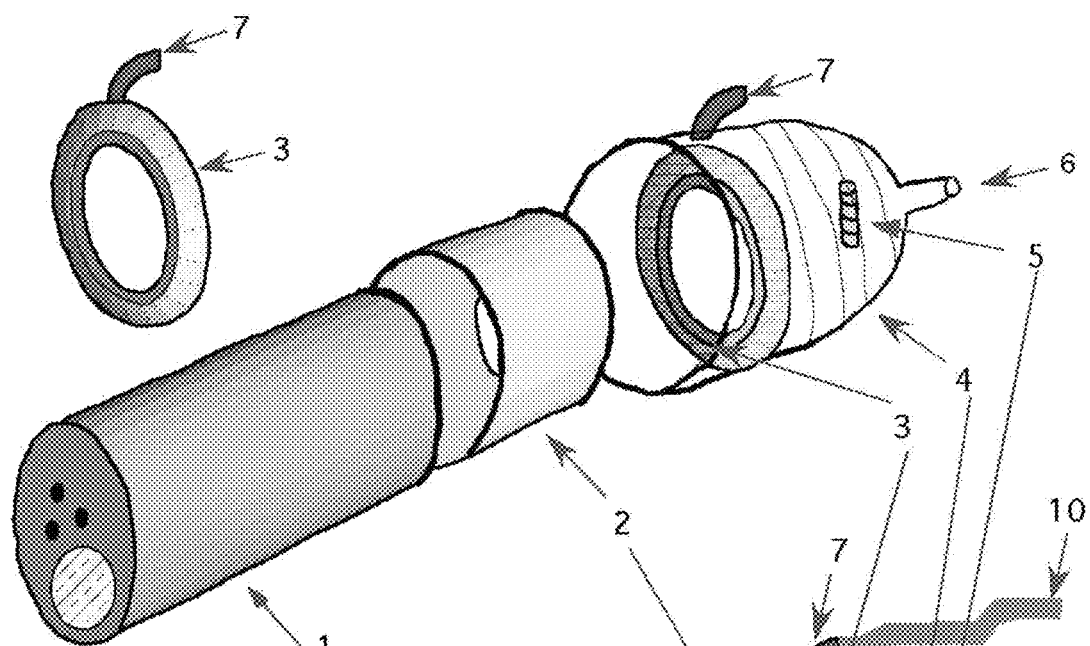
FIG. 18 is an exploded, perspective view of a third embodiment of a pressure interface assembly utilized with the apparatus of FIG. 1.
Figure 19:
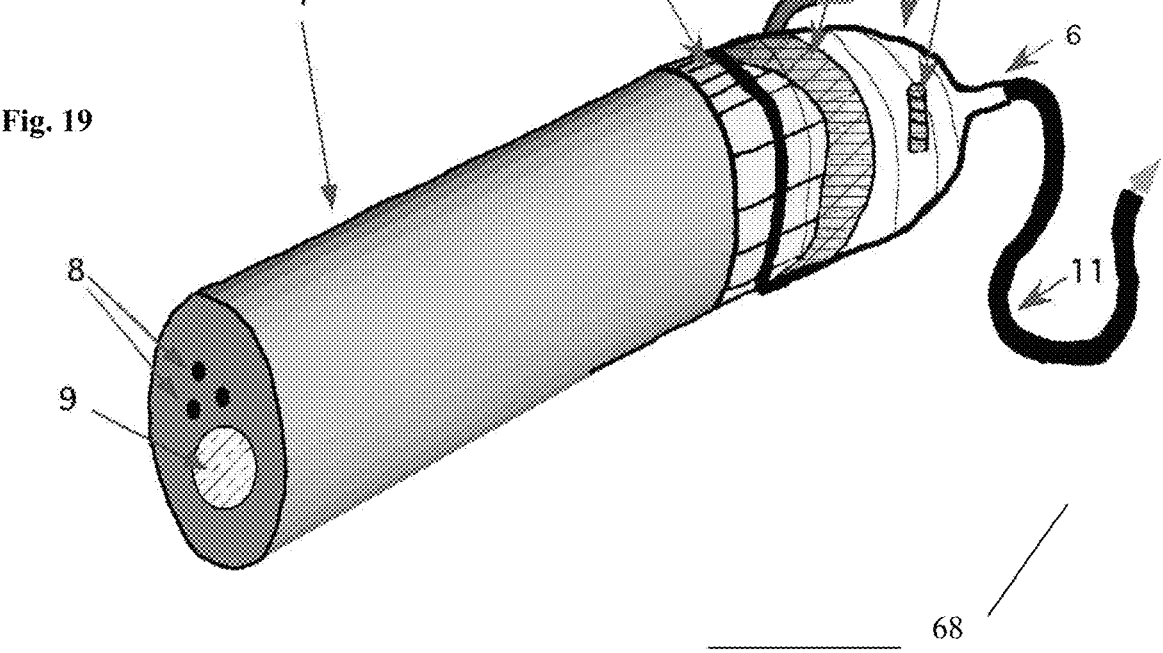
FIG. 19 is a perspective view of the assembly of FIG. 18.
Figure 20:
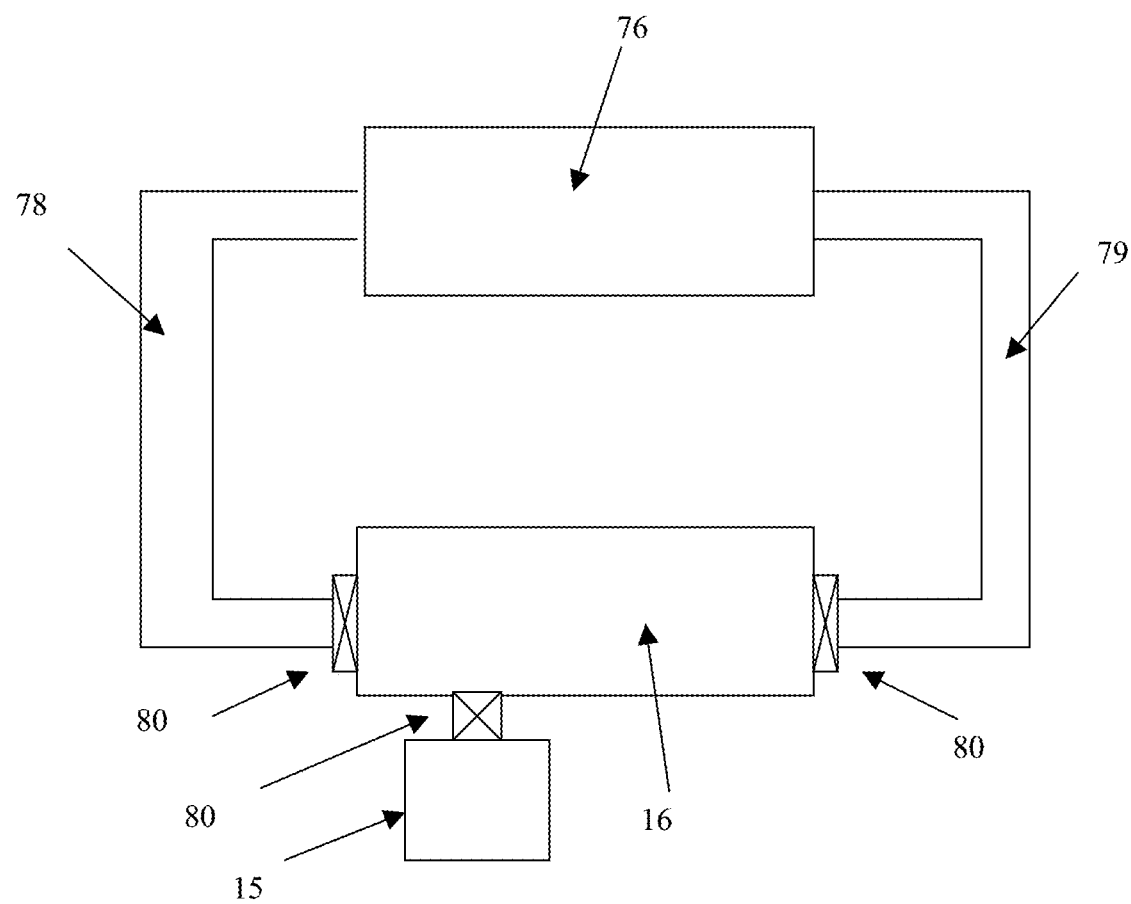
FIG. 20 is a schematic view of a sterilization chamber with a thermoelectric air or gas cooling system(s) and/or refrigerated air or gas system(s), connected to the sterilization chamber in a loop.
Figure 21:
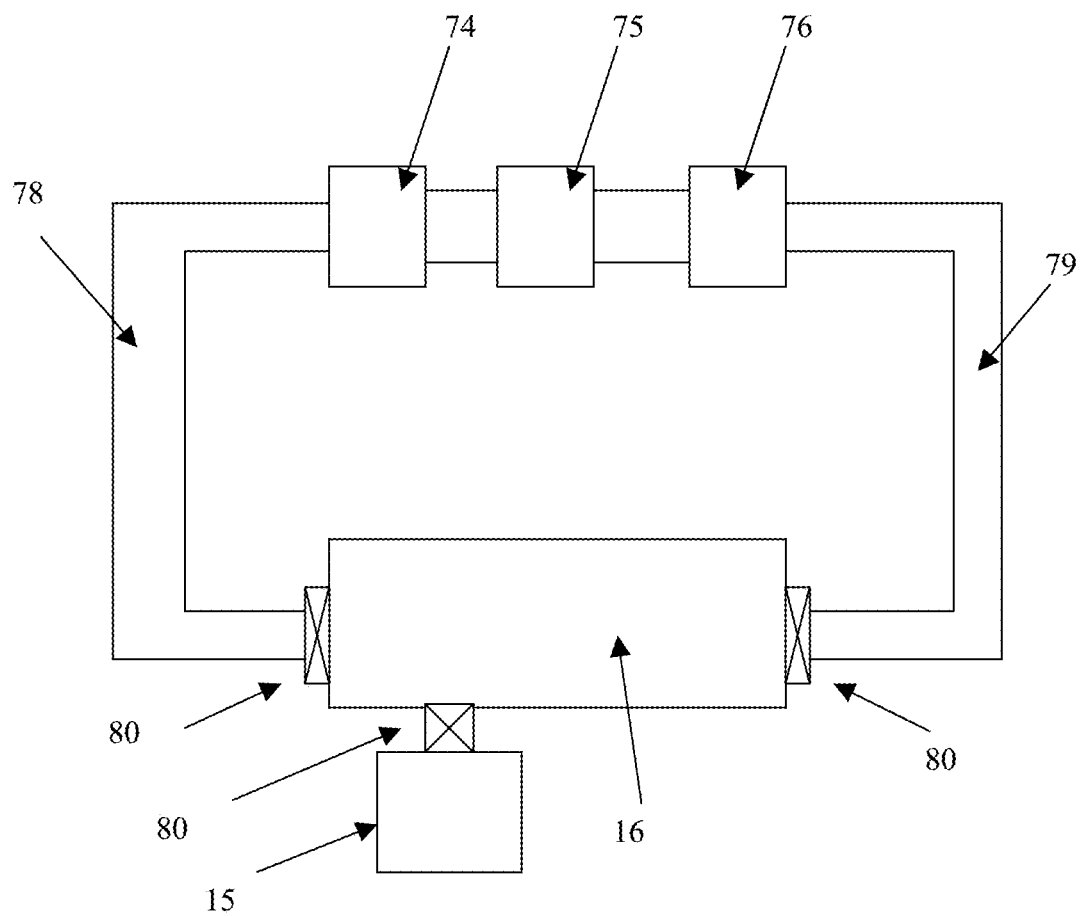
FIG. 21 is a schematic view of a sterilization chamber with a dehumidification apparatus, a filter, and a thermoelectric air or gas cooling system(s) and/or refrigerated air or gas system(s), connected to the sterilization chamber in a loop.

Referring to FIGS. 18-19, an inflatable pillow, balloon, bladder, reservoir, or other inflatable or expandable means or material (hereinafter "balloon") (03), can be used to exert an effective pressure on the interface material (02), as well as on the coupling (04). Varying the amount of exerted pressure inside of the balloon (03) can control the pressure that is exerted. The balloon (03) can be utilized in ways including, but not limited to, inserting or positioning the balloon (03) completely, or at varying positions or amounts, around the interface material (02), on the side of the interface material (02) that is furthest away from the endoscope (01) and closest to the interior wall of the coupling (04), and inflating the balloon (03) after the pressure interface assembly (68) is effectively positioned or has interfaced/articulated with the endoscope (01). The balloon (03) can also be positioned and effectively used inside of the coupling (04) wall material or on the exterior surfaces of the coupling (04). The size, width, thickness, inflation pressure, material of construction, and design of the balloon (03) can be influenced by many factors including, but not limited to the negative and positive pressure or air/gas pressure that can be exerted within the coupling (04), the temperatures of the "applied agent" (20), the amount of pressure that is needed inside of the balloon (03) in order to apply an effective pressure on the interface material (02), and the type of chemical interaction between substances such as, but not limited to, the "applied agent" (20), and various materials of construction. The balloon (03) may assume many different shapes including, but not limited to, a toroidal shape. The balloon (03) can also be constructed from, or have its outermost layer constructed from the interface material (02), and the balloon (03) can function as the interface material (02). The balloon (03) can have a port and/or valve (herein called "balloon port") (07) to connect with a source of pressurized fluid, and is inflated and deflated by way of a means that is known to those skilled in the art. The source of pressure can include, but is not limited to, the supply of air, gas, liquid, or foam under positive pressure. An effective pressure can also be created as the result of a chemical reaction inside of the balloon (03).

Parameters such as, but not limited to: a) the exerted pressure on the interface material (02); b) the positioning of the coupling (04) on or to the interface material (02); c) the surface area of the coupling (04) that interfaces/articulates with the interface material (02) or endoscope (01); d) any physical, chemical, or mechanical interactions between any components of the pressure interface assembly (68); d) the size, width, surface area, shape, fit, thickness, density, hardness, elasticity, flow rate, porosity, permeability, mechanical properties, physical properties, and other variables known to those skilled in the art, relative to various components of the pressure interface assembly (68) such as, but not limited to the interface material (02), the coupling (04), and endoscope (01); e) evenness of air/gas and "applied agent" flow (20); can all, without limitation, be varied and may help control the air/gas pressure differential between the outside and inside of the coupling (04). These parameters may also vary, without limitation, to help control the air/gas pressure differential between the endoscope's (01) ducts (08) and the outside and inside of the coupling (04). This in turn controls the balance of the "applied agent" (20) flow through the interface material (02) and any interfaced/articulated areas verses the interior space or ducts (08) of the endoscope (01). These variables are optimized for each endoscope (01) configuration based on the outside diameter of the endoscope (01), and the number, diameter, area, and length of the interior spaces or ducts (08), of the endoscope (01).

Referring to FIG. 4, for applications involving the movement of an "applied agent" (20), in form including but not limited to any gas, plasma, vapor, and/or aerosol, through the endoscope (01) with negative air/gas pressure (vacuum), the endoscope (01) is placed within the closed space or sterilization chamber (16), or other area within the closed system, and the pressure interface assembly (68) is interfaced with an end of the endoscope (01). The "applied agent" (20) is then generated and/or administered or applied, filling the closed space or sterilization chamber (16). The "applied agent" (20) that is in the sterilization chamber (16) is then pulled through one end of the endoscope (01), through its interior space or ducts (08) via a negative air/gas pressure (vacuum) that is created in the coupling (04). The negative air/gas pressure can vary. The "applied agent" (20) is then, without limitation, pulled through any supply tube (11) and is then, without limitation, vented into an area (36) either back into the sterilization chamber (16), or other area within the closed system. The vacuum is generated by one or more, without limitation, air/gas pump, vacuum pump, venturi apparatus, blower, fan, or other means (44),(17) that can create a negative air/gas pressure (vacuum) within the pressure interface assembly (68). The "applied agent" (20) that is pulled with vacuum can also vent into the outside environment after being filtered, if filtering is necessary. If the "applied agent" (20) is vented into the outside environment, a means to provide equalization in air/gas pressure between the closed system and the outside environment is provided and the movement of the air/gas is filtered. The resulting process is the sanitization, detoxification, disinfection, high level disinfection, or sterilization, of both the exterior of the endoscope (01) and its interior space or ducts (08).

Referring to FIG. 5, alternatively, for applications involving the movement of an "applied agent" (20) in the form including but not limited to any gas, plasma, vapor, and/or aerosol, through the object or endoscope (01) with positive air/gas pressure, the endoscope (01) is placed within the closed space or sterilization chamber (16), or other area within the closed system, and the pressure interface assembly (68) is interfaced with an end of the object or endoscope (01). The "applied agent" (20) is then generated and/or administered or applied, filling the closed space or sterilization chamber (16). The "applied agent" (20) that is in the closed space or chamber (16), or other area within the closed system, is then, without limitation, pulled through one end (37) of a tube (18) and forced out the other end of the same tube or any other connected tube(s), into the supply tube (11), under positive air/gas pressure, and then into the coupling (04) that interfaces/articulates with the endoscope (01), and then into and through the interior space or ducts (08) of the endoscope (01) where it is then vented back into the closed space, sterilization chamber (16), or other area within the closed system. The positive air/gas pressure is generated by one or more air/gas pump, vacuum pump, blower, fan, or other means (44),(17) that can create a positive air/gas pressure within the pressure interface assembly (68). The positive air/gas pressure can vary. The "applied agent" (20) in this case can also be pulled from a source that is separate from the sterilization chamber (16). The result of the whole process is the sanitization, detoxification, disinfection, high level disinfection, or sterilization, of both the exterior of the endoscope and its interior space, lumen(s), and/or channels.

The positive or negative air/gas pressure can also be supplied to the pressure interface assembly (68) and the interfaced/coupled or articulated object or endoscope (01), by one or more air/gas pump, vacuum pump, blower, fan, or other means (44),(17), at different times during the sanitization, detoxification, disinfection, high level disinfection, or sterilization cycle. For example, this can be performed, without limitation, either before or after the "applied agent" (20) is generated and/or administered or applied. The purpose is to move, without limitation, fresh filtered or non-filtered air/gas and/or dry air/gas through the interior space or ducts (08) of the endoscope (01), which removes any moisture, liquid, and/or "applied agent" (20) that is present, or cause the moisture, liquid, agent, "applied agent" (20) or substance that is present to be removed or evaporated.

One challenge with the application of an "applied agent" (20) by aerosol or other means, is that of obtaining full coverage on all surfaces of the endoscope (01) or the targeted space, areas, or surfaces. This is especially true when two surfaces touch each other, which prevents the contacted surfaces from being exposed to the "applied agent" (20). This causes a shadowing effect. Of course, this challenge does not apply to the use of ethylene oxide gas (EtO) with polymeric materials because EtO is able to penetrate that material and any shadowed surfaces over time.

Figure 30:
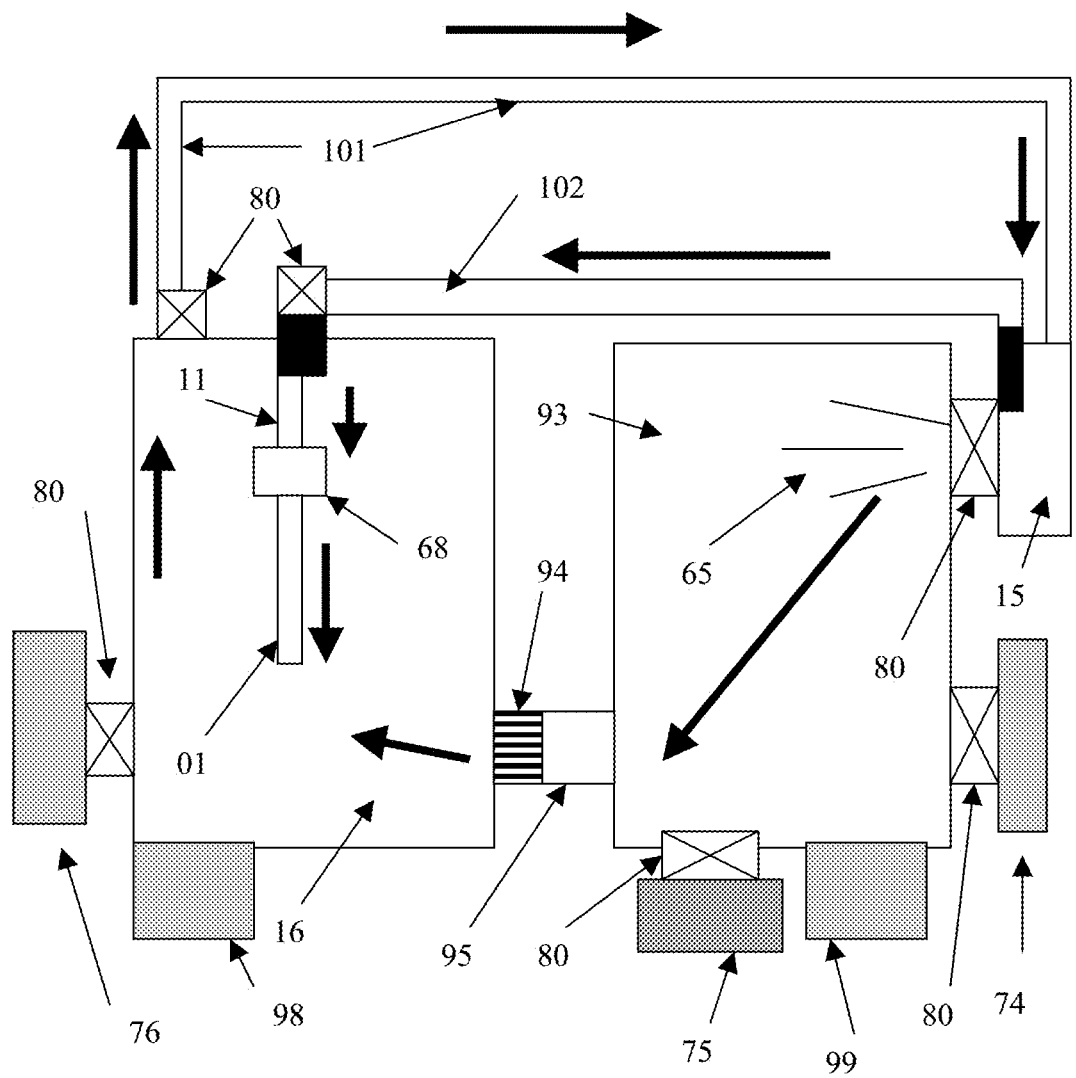
FIG. 30 is a schematic view of a sterilization chamber with a thermoelectric air or gas cooling system(s) and/or refrigerated air or gas system(s), and vacuum source, connected via a flow pipe, to a second chamber with a dehumidification apparatus, filter, and aerosol generator, and a pressure source. One pipe connects the aerosol generator to the pressure interface assembly positioned within the sterilization chamber, while the other pipe connects the sterilization chamber to the aerosol generator forming a loop for gas/aerosol flow back to the aerosol generator.

With reference to FIG. 30, the shadowing effect found with the delivery of "applied agent" (20) such as, but not limited to, aerosols (65), can be overcome in various ways. It is preferred, without limitation, that one way includes placing one or more endoscopes (01) in a sterilization chamber (16) and attaching each of them to a pressure interface assembly(s) (68) and then suspending the endoscopes (01) in the air within the sterilization chamber (16) via the pressure interface assembly(s) (68). This eliminates the chance for incomplete interaction, coating, or contact of the "applied agent" (20) with all of the surfaces of the endoscope (01). For example, the pressure interface assembly (68) may interface/articulate with either end of an endoscope (01), and the endoscope (01) may hang down toward the floor of the sterilization chamber (16) without touching anything.

Referring to FIGS. 8-9, an alternative embodiment for suspending the endoscope (01) within the chamber (16) includes, without limitation, placing the endoscope (01) in one or more cradles (45) within the sterilization chamber (16), or encircling the endoscope (01) in one or more places with a material (47), in order to hang it within the sterilization chamber (16). In either case, the material (47) that holds the endoscope (01) should be, without limitation, as thin and narrow as possible, as well as sufficiently, porous, and permeable. The material (47) can also have, without limitation, any sufficient number of pores of any effective size. This material (47) can, without limitation, include various layers of various materials suitable for these purposes and it can also be absorbent. Some of this material (47) is then interfaced, connected, or otherwise attached to a hook(s) or other means (46), which are additionally attached using a suitable attachment member (48) to the interior of the sterilization chamber (16), in order to hold the material (47). This results in the suspension of the endoscope (01) in free space above the floor of the closed space or sterilization chamber (16) in which it is placed. The intent is to maximize the external surface area of the endoscope (01) that is exposed to "applied agent" (20) as well as allowing the "applied agent" (20) to quickly achieve its desired effect on the areas and surfaces that interface between the endoscope (01) and the material that is holding it. Previous laboratory work with an ultrasonic aerosol generator has shown that materials like glassine have shown sufficient permeability with the administration of an aerosol (65) having the preferred disinfectant or "applied agent" (20) contained therein. A high level of disinfection on the opposing side of this example barrier material (47) was achieved.

With reference to FIGS. 10-11 and 24-25, the shadowing can also be overcome by the incorporation and use of movable fork(s) or beam(s) (49),(50) within the closed space or sterilization chamber (16) of the present invention, as shown in FIG. 10-11. The endoscope (01) is first placed or positioned on one or more beam(s) or fork(s) (herein "start beams") (49). One or more beam(s) or fork(s) (herein "opposing beams") (50) are also provided and they are intended to loosely interlock or intermesh with and/or oppose the start beams (49) without touching the start beams (49). The beams or forks (49),(50) can vary in size and shape as desired. The start beams (49) or opposing beams (50) can be designed or constructed so that the endoscope (01) will not roll or move off of the beams. In order to maintain the position of the endoscope (01) on the various beams (49), (50), they can have one or more, without limitation, indentations, ridges, bumps, or protrusions of various sizes, shapes, and heights. They may also, without limitation, slope or curve upward at various angles at locations including, but not limited to the ends of the beams (49),(50). During the application of the "applied agent" (20), the start beams (49) or opposing beams (50) move, by way of any mechanical means that are known in the art, resulting in the transfer of the endoscope(s) (01) so that it is moved from either the start beams (49) to the opposing beams (50) or from the opposing beams (50) to the start beams (49). This allows all of the endoscope (01) surfaces to be covered with the "applied agent" (20) as a result of exposing those portions of the surface of the endoscope (01) covered by the beams (49) when the endoscope (01) is moved onto the beams (50), or vice versa. These beams (49),(50) can then reverse their movement during the drying cycle to allow all of the endoscope (01) surfaces to dry if it is necessary. The beams (49),(50) can move in either direction, or reverse their motion, one or more times for various steps in any processing cycle. The movement of the beams (49),(50) can also vary, without limitation, in speed and range of motion, and are controlled in a manner well known in the art. It is preferred, without limitation, that the beams (49),(50) move at least at a speed or rate where the object can be effectively, efficaciously, or gently, transfer from one of the beams (49),(50) to the other. At least one of the beams (49), (50) moves vertically up or down relative to the other causing the object to transfer from one of the beams (49), (50) to the other and thus exposing an area of the object previously covered by one of the beams (49), (50). It is preferable that the object does not pivot or rotate, while transferred from one beam (49), (50) to the other or while resting on the beams (49), (50). Any digital or analog controller known to those skilled in the art can, without limitation, control the operation of the movable fork(s) or beam(s) (49),(50), as discussed later. A digital controller such as, but not limited to any programmable logic circuit (PLC) or other means known to those skilled in the art can, without limitation, control the operation of and be signaled the status of, the movable fork(s) or beam(s) (49),(50), all in way know. The status of the movable fork(s) or beam(s) (49),(50) can, without limitation, signal and initiate other processes such as, but not limited to, the commencement of any drying activities. The beams (49),(50) may be constructed from the same materials used to construct the sterilization chamber (16) or pressure interface assembly (68).

The closed space, closed system of space, or sterilization chamber (16) can be purged, flowed, and/or filled with air or other gas from the outside environment (fresh filtered air) either before and/or after the "applied agent" (20) or other liquids are administered or applied in the sterilization chamber (16). The fresh air/gas is moved into the closed space, closed system of space, or sterilization chamber (16) via any air/gas pump, vacuum pump, blower, fan, or other means to move air, or source of pressurized air or gas (hereafter transfer device) (17), (51) and can move the fresh air at various volumes, rates, or speed. In either case, this can contribute to the removal of moisture, liquids, and/or "applied agent" (20) from the surfaces of the endoscope (01), and other surfaces and areas within the closed space or sterilization chamber (16). The time needed to effectively remove the moisture, liquids, and/or "applied agent" (20) that had coated, interfaced, interacted, enveloped, or had contact with the surfaces, or filled areas, within the closed area or sterilization chamber (16), is dependent on variables such as, but not limited to, the application time, temperature, relative humidity, flow rate, volume, and velocity, of the fresh air. It can also include the temperature of the targeted surfaces or endoscope (01) and/or areas. The variables can vary in order to remove the moisture, liquids, and/or "applied agent" (20) from these surfaces and areas in a manner that is as quick and effective as possible. The air/gas from the outside environment (fresh filtered air) can also be used to remove moisture, liquids, and/or "applied agent" (20) present in the interior space or ducts (08) of the endoscope (01) within the sterilization chamber (16). This can, without limitation, be accomplished by operating the same air/gas pump, vacuum pump, blower, fan, or other means (44),(17) which is used to create a positive or negative air/gas pressure within the pressure interface assembly (68) that is attached to the object or endoscope (01), in order to flow fresh air/gas through places such as, but not limited to, the interior space or ducts (08) of the object or endoscope (01). This is shown in greater detail in FIGS. 4-5. The time needed to effectively remove the moisture, liquids, and/or "applied agent" (02) from the surfaces in this application will vary and is affected by variables including but not limited to the number, shape, diameter, and length of the interior spaces or ducts (08) of the endoscope (01), as well as the application time, temperature, relative humidity, flow rate and volume, and velocity, of the applied fresh air/gas. The variables such as, but not limited to, the fresh air/gas temperature, flow rate, volume, velocity, and relative humidity, can vary in order to remove the moisture, liquids, and/or "applied agent" (20) in a manner that is as quick and effective as possible. The fresh air/gas that is used in this particular application can be sourced from either the fresh air/gas from the outside environment that is flowed or moved into the sterilization chamber (16), or it can be sourced directly from the outside environment. The air/gas from the outside environment can be treated to reduce its relative humidity and can be heated to various temperatures before it enters the closed space, sterilization chamber (16), or endoscope (01). The means to heat the air/gas (52) (29) is not specifically set forth, but known to those skilled in the art. Heating the air/gas can contribute to the accelerated removal of any moisture, liquids, and/or "applied agent" (20) from the surfaces and areas within the closed space, closed system of space, or sterilization chamber (16), in addition to the external and internal surfaces or ducts (08) of the object(s) or endoscope(s) within the closed space or sterilization chamber (16). The air/gas from the outside environment can be filtered before it enters into the closed space, sterilization chamber, or endoscope (01). The fresh air/gas can be filtered with one or more filters (53) such as but not limited to a 99.9% HEPA filter or other high efficiency filter, or with other filters or means for filtering air/gas that is not specifically set forth, but known to those skilled in the art. The filter (53) can limit or prevent the contamination of the endoscope (01) within the closed space or sterilization chamber (16). The exhaust port (39) the air/gas within the closed system of space or sterilization chamber can also be incorporated into the present invention. The exhaust system and/or outlet or exhaust port (39), can also include the use of one or more filters (54) or combination of filters (54) such as, but not limited to, a gas filtering filter, 99.9% HEPA filter or other high efficiency filter, or other filters or means for filtering (54) that is not specifically set forth, but known to those skilled in the art. The exhaust is means for exhaust (39) can help to establish a flow of fresh air/gas through the closed system of space or sterilization chamber (16) and allows the incoming fresh air/gas to fully replace the air/gas inside of these areas which can prevent the buildup of positive pressure within the closed system of space or sterilization chamber (16). The exhausted flow of air/gas also helps to remove the "applied agent" (20) from the closed system of space or sterilization chamber (16). The filter(s) (54) can prevent the contamination of objects or endoscopes (01) within the closed system of space or sterilization chamber (16) by filtering any potential backflow of air and/or gases, as well as filter and remove any "applied agent" (20), or any contaminants, in the air/gas before they are exhausted out of the present invention and into the external environment. In many situations, air and gas filtering standards are dictated or impacted by regulatory entities, or by standards set within the industry in which the present invention operates. This may also affect the type or means of air and/or gas filters (53),(54) that are used in the present invention. The fresh air/gas can also be moved into and through the closed system of space or sterilization chamber (16) by locating a means to move the air/gas such as but not limited to an air/gas pump, vacuum pump, blower, fan or other transfer device (17),(51) as earlier described, at or near the exhaust port (39). The transfer device (17),(51) moves the air/gas can be located before or after any of the filter(s) (53),(54) that filters the inbound or exhausted air/gas.

Referring to FIG. 13, in bound air from the transfer device (17),(51) is passed through the filter (53), so that the inbound air/gas cannot contaminate the endoscope (01) inside of the closed space or sterilization chamber (16). The inbound fresh air/gas may also be heated by any means that can heat air/gas (52). The devices to move, filter, and heat the air/gas can be in any order. The air/gas is then circulated, moved, or flowed into the closed space or sterilization chamber (16). The transfer device (39) is used to ventilate the air/gas and the "applied agent" (20), out of the closed system of space or sterilization chamber (16). The vented air/gas can also pass through one or more filters (54) before it is ventilated into the external environment. One or more closure device (35) is also present to effectively close off, seal, or separate, the closed system of space or sterilization chamber(s) (16) from the inbound fresh air/gas inlet (38), the transfer port (39), and/or any of the tubes, ducting, channels, tunnels, etc., that connect the fresh air/gas inlet or exhaust air/gas outlet to the closed system of space or sterilization chamber (16). The transfer device (35) can be a door, flap, valve, lid, panel, or other physical means to contain the "applied agent" (20) or any air/gas that is utilized or applied or administered, as well as the agents or substances that are used to wash the endoscopes (01) as discussed earlier.

With reference to FIGS. 21, 22 and 26-32, the at least one dehumidification apparatus (74) within the sterilization chamber(s) (16) or other area(s) where the "applied agent" (20) in aerosol form (65) is applied may also, without limitation, be located within the sterilization chamber(s) (16) or other targeted area(s), or otherwise be operatively coupled or attached to and/or about the sterilization chamber (16), or anywhere along the path of any circulated or recirculated air/gas (31) and aerosol (65), or other connected spaces. It is preferred, without limitation, that the dehumidification activity occurs any time after the application of the "applied agent" (20) in aerosol form (65), which is unique in comparison to the prior art. The prior art teaches that dehumidification is a necessary activity for achieving efficacious results before the application of certain applied agent such as, but not limited to, vaporized hydrogen peroxide, and is therefore not claimed in the present invention. However, dehumidification activities can, without limitation, take place any time during or after the processing of the endoscope in the present invention. The use of one or more dehumidification apparatus(s) (74) in the present invention is beneficial in situations that include, but are not limited to, where the air/gas and/or the "applied agent" (20) in aerosol form (65) within the sterilization chamber(s) (16) or targeted area(s) cannot be evacuated for reasons known to those skilled in the art. The dehumidification apparatus (74) is constructed and operated in a manner known to those skilled in the art, and includes, but is not limited to a dehumidification means where air/gas from the targeted environment is moved over any chilled media, to remove the humidity. The dehumidification apparatus (74) may reduce or even sustain the humidity level to any desired level or percentage of humidity, and in a manner that is known to those skilled in the art. However, it is preferred, without limitation, that if the dehumidification apparatus (74) is operated, it reduces the humidity to a level that is at least efficacious or meets standards known to those skilled in the art. It is more preferred that the humidity is reduced to a level that is equal to or less than 50% relative humidity. It is even more preferred that the humidity is reduced to a level that is equal to or less than 20% relative humidity. After the sterilization chamber (16) or other targeted area(s) are dehumidified or reach the desired humidity level, the air/gas within these spaces may be, without limitation, processed in a manner known to those skilled in the art to remove any substances such as, but not limited to, any remaining odors, chemicals, smells, vapors, aerosols, or gases. This can be accomplished in ways that include, but are not limited to, passing the air/gas in the at least one sterilization chamber (16) or other targeted area(s) through at least one filter (75) that contains carbon, charcoal, or any other applicable filtering means known to those skilled in the art. The processed air/gas can be, without limitation, returned back to the sterilization chamber (16) or any space connected to the at least one sterilization chamber (16). The removal of any odors, chemicals, smells, vapors, aerosols, or gases, can also, without limitation, take place at any time. The at least one filter (75) can also be operated simultaneously with the dehumidification apparatus (74). It is preferred, without limitation, that the at least one filter (75) is utilized after the sterilization chamber (16) or other targeted area(s) are dehumidified to a desired or effective level. Without being limited, the processing of the atmosphere within the sterilization chamber (16) or other targeted area(s), with the at least one filter (75), can also be triggered in various ways including, but not limited to using any, timers, dew point levels, or humidity levels, to start the filtering (75) process.

The effective operation of the present invention can be accomplished using any electrical and/or electronic means to control the mechanisms that the present invention depends on for its proper function. The electrical and electronic means can be programmed or electrically designed to execute, manage, monitor, or control, the present invention and are not specifically set forth, but known to those skilled in the art. This means can monitor and control the function, as well as the timing of use, of any electrically dependent components such as, but not limited to, any valves, any means used for the production of the "applied agent" (20) used in the present invention as well as any related mechanisms or systems, any means used to flow or move the air/gas and/or "applied agent" (20) within or out of the present invention, any means to heat the aerosol, air/gas, or floor of the sterilization chamber, any means used to flow or move the air/gas and/or "applied agent" (20) through the internal spaces or ducts (08) of the object or endoscope (01), any packaging equipment or related systems, as well as any other microcomputers that are used, such as but not limited to, microcomputers or printers utilized to record and report the operating parameters of each cycle of use.

According to an embodiment, the present invention also improves the current art by decreasing the processing time for the simultaneous or non-simultaneous cleaning and disinfection/sterilization of both the interior and exterior surfaces of an object or plurality of objects such as, but not limited to, an endoscope (01). It is more preferred, without limitation, that the activities such as, but not limited to, the soaking, washing, cleaning, disinfection/sterilization, rinsing, and drying, of both the interior and exterior surfaces of an endoscope (01) or plurality of endoscopes (01) take place within the same sterilization chamber (16). The pressure interface assembly (68) of the present invention may or may not be used, without limitation, in this embodiment. However, it is preferred, without limitation, that the pressure interface assembly (68) is not used in this particular embodiment, and that the endoscope (01) is connected to a pipe, hose, tube, or other delivery means that can supply any surfactant, rinse liquid, or applied agent to the endoscope (01), or otherwise a supply tube (11).

Initially, processing steps utilized in the current art are followed in this embodiment and involve the use of a washer (72) or other device or means, known to those skilled in the art, for activities including, but not limited to, cleaning, washing, or disinfecting/sterilizing endoscopes (01) (herein called "washer") (72). The washer (72) may, without limitation, be integrated into the design or construction of the enclosed area, chamber, or sterilization chamber (16) of the present invention. These steps are known to those skilled in the art and include, but are not limited to, wiping or cleaning the endoscope (01) to remove, or attempt removal of, any unwanted liquid, debris, contaminants, or other substances, and then placing the endoscope (01) into a washer (72) and interfacing it with a supply tube (11). The endoscope (01) is placed on a rack, or other means known to those skilled in the art, to hold or position the endoscope (01) within the sterilization chamber (16) and/or washer (72). The supply tube (11) enables various liquids including but not limited to, surfactant, and high purity rinse water, to be moved through the various ducts (08) of the endoscope (01) at various stages of the cleaning process. The object or endoscope (01) may be, without limitation, soaked for any effective time period within liquids or compounds such as, but not limited to, any surfactants or any other combination of various cleaning liquids, within the washer (72). The washer (72) then subjects, sprays, covers, floods, or a combination thereof, the endoscope (01) with liquids or compounds such as, but not limited to, any surfactants or other cleaning liquids, both inside and outside of the object or endoscope (01) for an effective amount of time all in a manner known to those skilled in the art. After this cycle is completed, the inside as well as outside surfaces of the object or endoscope (01) may be exposed to a liquid rinse, which preferably comprises one or more liquids that includes high purity water. It is preferred, without limitation, that the endoscope (01) is rinsed with high purity water. Any surfactant solution and rinse liquid can be used and it may be any temperature when it is used. It is preferred, without limitation, that the surfactant used in the present invention is any surfactant that meets standards acceptable to the industry in which it is used, as well as any regulatory requirements. It is preferred, without limitation, that the rinse liquid used in the present invention is any high purity rinse water that meets standards acceptable to the industry in which it is used, as well as any regulatory requirements. The cycle time for the exposure of the endoscope (01) to any surfactant and rinse liquid can vary but is at least efficacious. In order to decrease the processing time, improvements are made at this point to the current art.

According to an embodiment, any or all attributes, functions, features, or designs of the endoscope washer (72) utilized in the current art may be integrated into the sterilization chamber (16) that is previously described in the present invention.

According to another embodiment after the endoscope (01) is treated with any surfactant and/or rinse water, its internal and external surfaces may be dried. Any drying technique previously described in the present invention or known to those skilled in the art can be utilized in this embodiment. It is preferred that any air/gas that may be heated and/or filtered is flowed or otherwise moved into the sterilization chamber (16) and/or washer (72) in which the endoscope (01) is positioned in order to dry it. The creation of a vacuum within the sterilization chamber (16), of various negative atmospheric pressures, but at least an efficacious level of vacuum, may also be used for drying purposes. The level or amount of dryness can vary. The drying of the internal and external surfaces of the endoscope (01) can be done simultaneously or at different times, or it can be treated as mutually exclusive activities that can or cannot be undertaken. It is preferred, without limitation, that all of the internal and external surfaces of the endoscope (01) are dried and that this activity is done simultaneously.

The internal surfaces of the endoscope (01) can be dried, without limitation, by flowing air/gas through the supply tube (11) and then through the endoscope (01). The air/gas can be heated and/or filtered. The air/gas, or other means used for surface drying, may be applied for any length of time to any surfaces of the endoscope (01).

According to an embodiment, the supply tube (11) is, without limitation, designed, manufactured, and incorporated, into the design of the sterilization chamber (16) and/or washer (72), and the endoscope (01) in a manner known to those skilled in the art. The supply tube (11) may also be effectively connected to any supply of, including, but not limited to, air/gas, liquid surfactant, liquid for rinsing, and source of applied agents, in a manner known to those skilled in the art. The various controlled access points or the valves (35) that control the exposure of the endoscope (01) to various substances such as, but not limited to, air/gas, liquid surfactant, liquid for rinsing, and anti-pathogen/toxin/fungal/sporicidal agent(s) or substance(s), to the supply tube (11) or endoscope (01) can be, without limitation, designed and controlled in a manner known to those skilled in the art.

According to a preferred embodiment, after the endoscope (01) undergoes various activities such as, but not limited to, cleaning with surfactant, rinsing with water and optionally alcohol in separate steps, and drying (if desired), the inside and outside surfaces of the endoscope (01) are treated with an anti-pathogen/toxin/fungal/sporicidal agent (s) or substance(s) that is, in the form of any aerosol. The applied agents are created, generated, and/or administered in or into the sterilization chamber (16) and/or the washer (72) in which the endoscope (01) are placed. It is preferred that the treated surfaces are dried before the anti-pathogen/toxin/fungal/sporicidal agent(s) or substance(s) is applied, such as by passing a drying gas over the surfaces of the endoscope (01). This may enhance the efficacy or cycle time of the process. It is preferred, without limitation, that the applied agent is an aqueous aerosol (65), consisting of, but not limited to, any acidic oxidizer, generated by one or more of any transducer (22) or ultrasonic nebulizer(s) (22) of any design or construction. However, any other means for generating an effective aerosol (65) may also be used. The aerosol (65) may be of any concentration, number, size, or density, however it is preferred, without limitation, that the aerosol (65) includes a plurality of droplets whose size is five micron or less. The aerosol (65) can be generated from any liquid that is at any temperature. The aerosol (65) is delivered to the internal surfaces, areas, or ducts (08) of the endoscope (01) via a supply tube (11). This particular embodiment may improve the current art by significantly decreasing the endoscope (01) processing time.

According to an embodiment, the applied agent that is used to treat the endoscope (01) may also be in the form of any gas, plasma, or vapor. The prior art includes the use of an applied liquid agent through the various internal spaces such as, but not limited to the ducts (08) of an endoscope (01), as well as over the various external surfaces of the endoscope (01), and is therefore not claimed in the present invention.

After this cycle is completed, the ducts (08) or internal, as well as external surfaces of the endoscope (01) may be exposed or subjected to a liquid rinse, which includes one or more liquids, substances, or compounds, that includes, but is not limited to high purity water or alcohol, all in a manner known to those skilled in the art. The endoscope (01) can then be removed from the sterilization chamber (16) and/or washer (72) and hung to dry.

According to another embodiment as an alternative to hanging the endoscope (01) to dry, the inside and outside surfaces of the endoscope (01) are dried with various means such as, but not limited to, the at least one dehumidification apparatus (74), formation of a negative atmospheric pressure or vacuum in the sterilization chamber (16), or air/gas or heated air/gas, before it is removed from the sterilization chamber (16) and/or washer (72). It is preferred that the air/gas is heated. The air/gas can be heated in a manner known to those skilled in the art. The supply tube (11) may be used to supply air or heated air to the inside surfaces or ducts (08) of the endoscope (01).

According to a preferred embodiment, after the endoscope (01) undergoes various activities such as cleaning with surfactant, rinsing, drying (if desired), and the inside and outside surfaces of the endoscope (01) are then treated with an applied agent, the final rinsing activity(s) are not utilized and the endoscope is instead subjected to the final drying activity. This offers the benefit of significantly reducing processing time. It is preferred that this is conducted with an "applied agent" (20) in the form of an aqueous aerosol (65), including, but not limited to, any acidic oxidizer, generated by one or more of any transducer (22) or ultrasonic nebulizer(s) (22) of any design or construction. However, this embodiment can also pertain to any "applied agent(s)" (20) such as, but not limited to one or more of any, gas(s), plasma(s), vapor(s), and/or aerosol(s) that is utilized.

According to an embodiment, any objects including, but not limited to endoscope(s) (01), the atmosphere in which they reside, any surfaces in the sterilization chamber (16) or any interconnected areas, can be, without limitation, cooled before, during, or after the aerosol (65) is introduced. This effect will apply to interfacing surfaces, as well as the inside surfaces of object(s) or endoscope(s) such as, but not limited, lumens or duct(s) (08). This embodiment should not be confused with what was taught by U.S. Pat. No. 4,512,951 (Koubek at al., 1983), which is incorporated herein by reference in its entirety, including any references cited therein. Koubek et al., 1983, taught a method of sterilization where a liquid of aqueous hydrogen peroxide is vaporized, and the uniformly vaporized mixed hydrogen peroxide-water vapors are delivered into an evacuated sterilizer chamber, and the articles to be sterilized are cooled prior to the introduction of the vapor (or are cooled by the evacuation of air from the sterilizing zone) to a temperature below the dew point of the entering vapors. The condensing vapor deposits as a film on the cool surfaces (col 2, line 40-51). Koubek et al., 1983, also mentions in claim 2 that the result of vaporization was a mixed "gaseous vapor" consisting of hydrogen peroxide and water vapor free of solid contaminants.

The present embodiment of "cooling" is intended to optimize the attraction of heated droplets of the "applied agent" to the targeted area in conformance with the laws of physics and not to create a condensate from a vapor as taught by Koubek. Here, the difference in temperate between the droplets and the object's surface causes the droplet to be attracted to the surface as if it were electrically charged.

Basic principles applied in this embodiment are taught in the text entitled, "Aerosol Technology" by William C. Hinds (1982), which is incorporated herein by reference in its entirety, including any references cited therein. Without limitation, the cooling of the said object(s), surfaces, or environment or atmosphere, within the sterilization chamber (16), in the present invention, can accentuate the performance or efficacy of the aerosol (65) generated by the aerosol generator (15) in the present invention. In addition, and without being limited to a mechanism or method, the aforementioned principles taught by William C. Hinds (1982), show that the efficacy, efficiency, and performance of the process in the present invention can be further enhanced by introducing an aerosol (65), consisting of a heated "applied agent" (20) into the sterilization chamber(s) (16) containing objects with cooled surfaces.

The cooling of any object(s) or endoscope(s) (01), surface(s), space(s), environment(s), or atmosphere(s), within the sterilization chamber(s) (16), can be accomplished by any means other than by decreasing the pressure or pulling a vacuum. Creating a vacuum in an enclosed area and applying an aerosol was taught in the prior art by U.S. Patent Application No. 2005/0042130 A1 (Lin et al., 2003). However, Lin et al., was silent with respect to cooling surfaces within the sterilization chamber or targeted area, and only mentioned the vaporization of the applied aerosol as being an enhancement or advantage that further vacuum past 5 torr would provide (pg. 2 paragraph 28). The vacuum utilized by Lin et al., (pg. 2 paragraph 28) to obtain data, was intended to move the aerosol through the sterilization chamber. In addition, using a vacuum to cool object(s), surfaces, or environment or atmosphere, within a enclosed area, would not be desired in this embodiment due to the complexity and expense involved in designing a chamber for the necessary vacuum and the expense of acquiring the necessary pump, which is all known to those skilled in the art. It is desired that another means for cooling object(s) or endoscope(s) (01), surfaces, or environment or atmosphere, within the sterilization chamber(s) (16), other than utilizing a vacuum, be utilized.

As shown in FIGS. 20-23 and 26-32, it is preferred, without limitation, that the sterilization chamber(s) (16) and its atmosphere, environment, objects, or any of the targeted surfaces within the sterilization chamber(s) (16), be cooled with air or gas that is cooled or chilled in a manner known to those skilled in the art. It is further preferred, without limitation, that the air or gas is cooled or chilled with one or more chill coils or refrigerated air systems (76) that are known to those skilled in the art. It is even more preferred, without limitation, that the air or gas within the sterilization chamber(s) (16), is cooled or chilled with any thermoelectric cooling means (76), or any means known in the art for reducing temperature that uses a Peltier effect (76). Any number, size, capacity, or combination, of the thermoelectric cooling system(s) (76) and/or the refrigerated air system(s) (76), which chill or cool the air or gas can be, without limitation, attached to the aerosol generating apparatus (15) in the present invention, be separate from the aerosol generating apparatus (15) and connect with at least one pipe (77) or outbound cooled air pipe(s) (78) or inbound air pipe(s) (79) that connect with the targeted area(s) or sterilization chamber(s) (16), or it can be part of, directly or indirectly connected to, or positioned anywhere within the targeted area(s) or sterilization chamber(s) (16) to be treated. It can be controlled by one or more PLC(s) or remote PLC(s) in a manner known to those skilled in the art. Without limitation, any pipe(s) that lead to (79) or from (78) the source of the thermoelectric or refrigerated cooled or chilled (76) air or gas, can be operably separated from the targeted area(s) or sterilization chamber(s) (16) with one or more of any door, valve, cap, or other separating device or valve (Herein called "valve(s)") (80) that can be controlled by one or more PLC(s) or remote PLC(s). It is preferred, without limitation, that the valve(s) (80) can effectively seal. Without limitation, one or more valve(s) (80) may also be positioned at any location between the location where the administered air/gas or aerosol enters any pipe(s) (78) (79) or targeted area(s) or sterilization chamber(s) (16) and the aerosol generating apparatus (15), and can be controlled by one or more PLC(s) or remote PLC(s). The said valve(s), pipe(s), or other related part(s) or component(s) can all be constructed from any material that is compatible, and suitable for use with the liquid (20). Without limitation, the amount or duration of air or gas that is flowed into or recirculated through the targeted area(s) or sterilization chamber(s) (16), the locations that the air or gas is flowed into or out of the targeted area(s) or sterilization chamber(s) (16), the temperature of the air or gas, as well as the temperature of the surfaces within the targeted area(s) or sterilization chamber(s) (16) can vary depending on variables such as, but not limited to, the application, the level of performance that is desired, desired application time, as well as the volume of the targeted area(s) or sterilization chamber(s) (16).

Without limitation, the temperature of the atmosphere, surfaces, or space(s) in the targeted area(s) or sterilization chamber(s) (16) can be cooled to at least nine degrees Fahrenheit below the temperature of the applied liquid (20). It is preferred, without limitation, that the temperature of the atmosphere, surfaces, or space(s) in the targeted area(s) or sterilization chamber(s) (16) be cooled to at least nine to twenty-five degrees Fahrenheit below the temperature of the applied liquid (20). However, it is more preferred, without limitation, that the temperature of the atmosphere, surfaces, or space(s) in the targeted area(s) or steriliztion chamber(s) (16) be cooled to at least forty degrees Fahrenheit or lower. It is further preferred, without limitation, that the temperature of the atmosphere, surfaces, or space(s) in the targeted area(s) or sterilization chamber(s) (16) be cooled to at least thirty-two degrees Fahrenheit or lower. It is very preferred, without limitation, that the temperature of the surfaces, or space(s) within the targeted area(s) or sterilization chamber(s) (16) be cooled at least to any effective temperature approximately near or below the dew point within the targeted area(s) or sterilization chamber(s) (16). The temperature of the applied liquid (20) of which the aerosol (65) is created or the temperature to which the aerosol (65) is heated with other means, can also vary.

The internal space(s) of an object including, but not limited to any, lumen(s), channel(s), or duct(s) (08), of an object or endoscope (01), as well as the areas and surfaces that interface or articulate with the pressure interface assembly (68) can also be, without limitation, cooled with air or gas that is cooled or chilled. The cooled or chilled air or gas can be delivered with means such as, but not limited to, the pressure interface assembly (68) which can be directly or indirectly connected to the source of the cooled or chilled air or gas. The pressure interface assembly (68) can be, without limitation, separated from the source of the cooled or chilled air by any PLC controlled valve (80).

According to an embodiment, any object(s) (01) processed in the sterilization chamber(s) (16) or other connected areas, can also include, without limitation, one or more of any package that is unsealed, partially sealed, or hermitically sealed. The package(s) can have one or more of any contents. Referring to FIGS. 22 and 26-28, it is preferred, without limitation, that the package(s) be placed in the sterilization chamber (16) on perforated rack(s) (90) containing perforations of any size, shape, or construction. It is also preferred, without limitation, that the packages incorporate at least an effective or efficacious amount of any sufficiently porous or permeable materials such as, but not limited to, Tyvek, or other similar functioning material, in their design. Furthermore, the package can be, without limitation, designed in manner known to those skilled in the art, so that it can allow free passage of any quantity of air, gas, and/or any agent(s) through the package.

Figure 22:
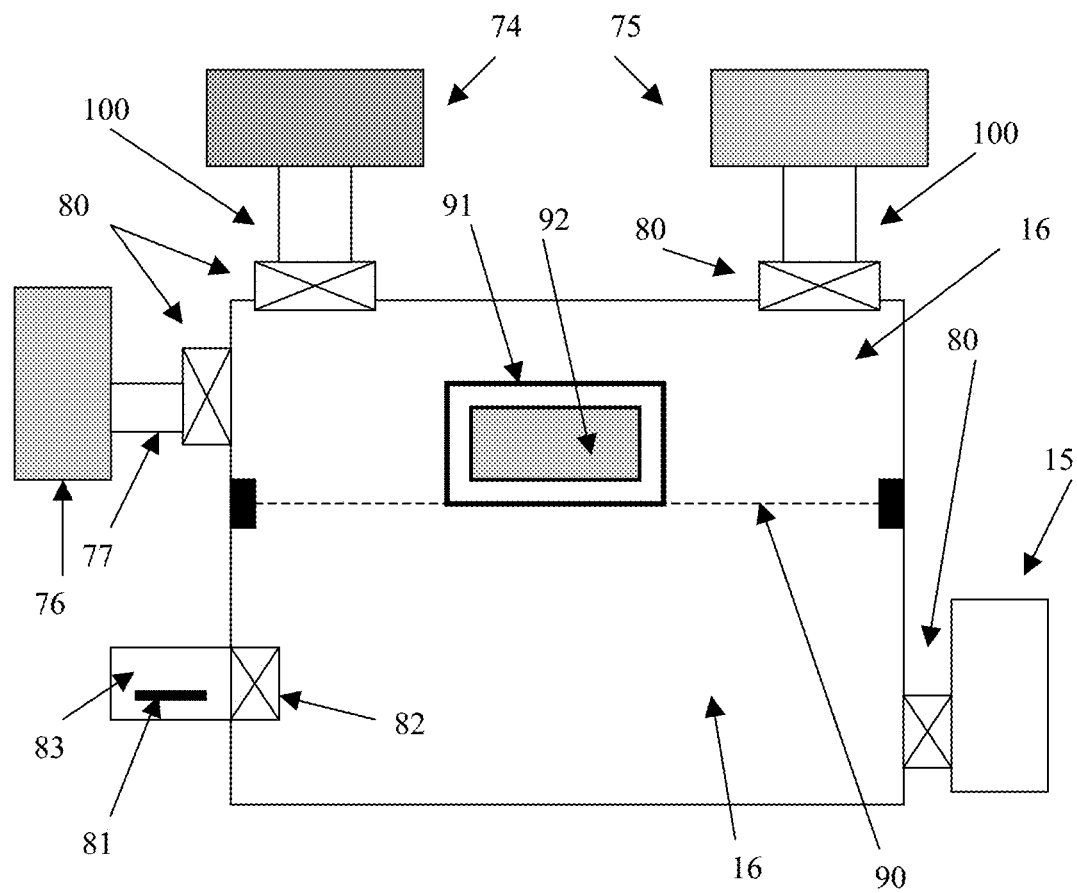
FIG. 22 is a schematic view of a sterilization chamber with a dehumidification apparatus, a filter, a thermoelectric air or gas cooling system(s) and/or refrigerated air or gas system(s), and a separate chamber connected to the sterilization chamber.
Figure 23:
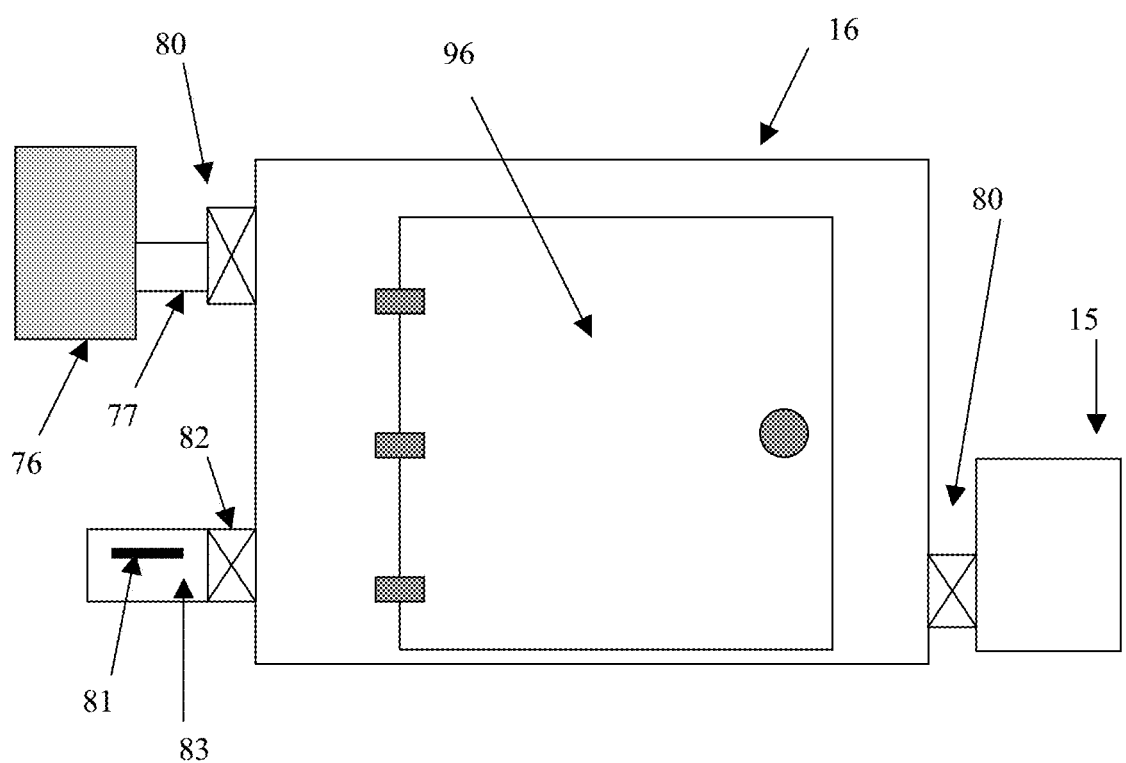
FIG. 23 is a schematic view of a sterilization chamber illustrating a sealed door.

With reference to FIGS. 22-23, according to another embodiment, and without limitation, any product used to measure or indicate the efficacy of the one or more processing steps utilized within the sterilization chamber (16) such as, but not limited to, chemical or biological indicator(s) used for validation of high level disinfection or sterilization (herein called "indicator(s)") (81), can be located anywhere within the sterilization chamber (16). It is more preferred, without limitation, that one or more of these indicator(s) (81) be located in a indicator enclosure (83) behind one or more valve(s), door(s), cap(s), or cover(s) (herein called "door(s)) (82). It is preferred, without limitation, that the door(s) (82) effectively seal the indicator enclosure (83) in which the indicator(s) (81) are located, to prevent any unwanted damage or changes to the indicator(s) (81) from any substance(s) or condition(s) that may be used in the sterilization chamber(s) (16) during various processing steps. Referring to FIGS. 22-23, the door(s) (82) can open at any time including, but not limited to, before or during the application of the applied agent(s) (20) inside the sterilization chamber(s) (16). The door(s) (82) can be opened, closed, or maintained in their desired position, at any time and for any duration of time. The movement of the door(s) (82) at any time can be, without limitation, PLC controlled, all in a manner known to those skilled in the art.

Figure 24:
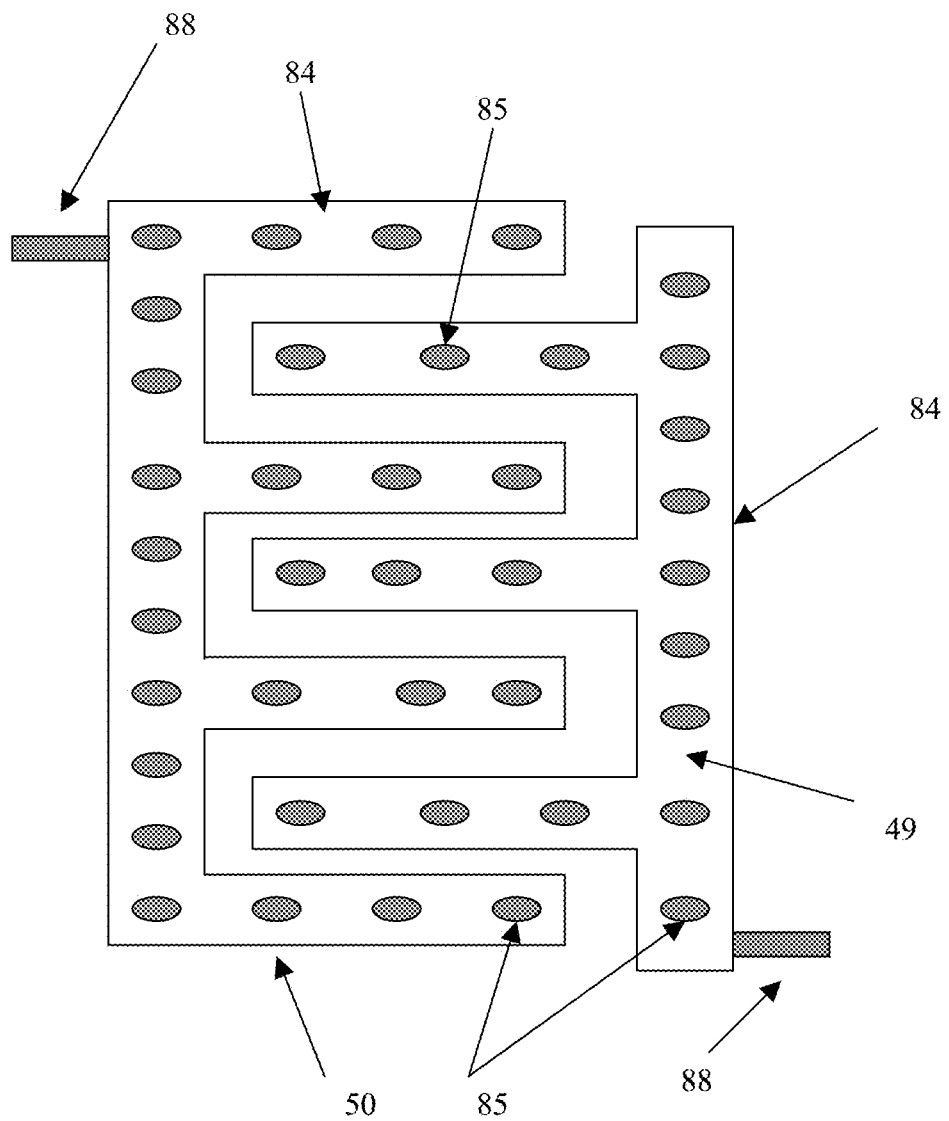
FIG. 24 is a top view of a pair of object supports with a plurality of openings formed therethrough.
Figure 25:
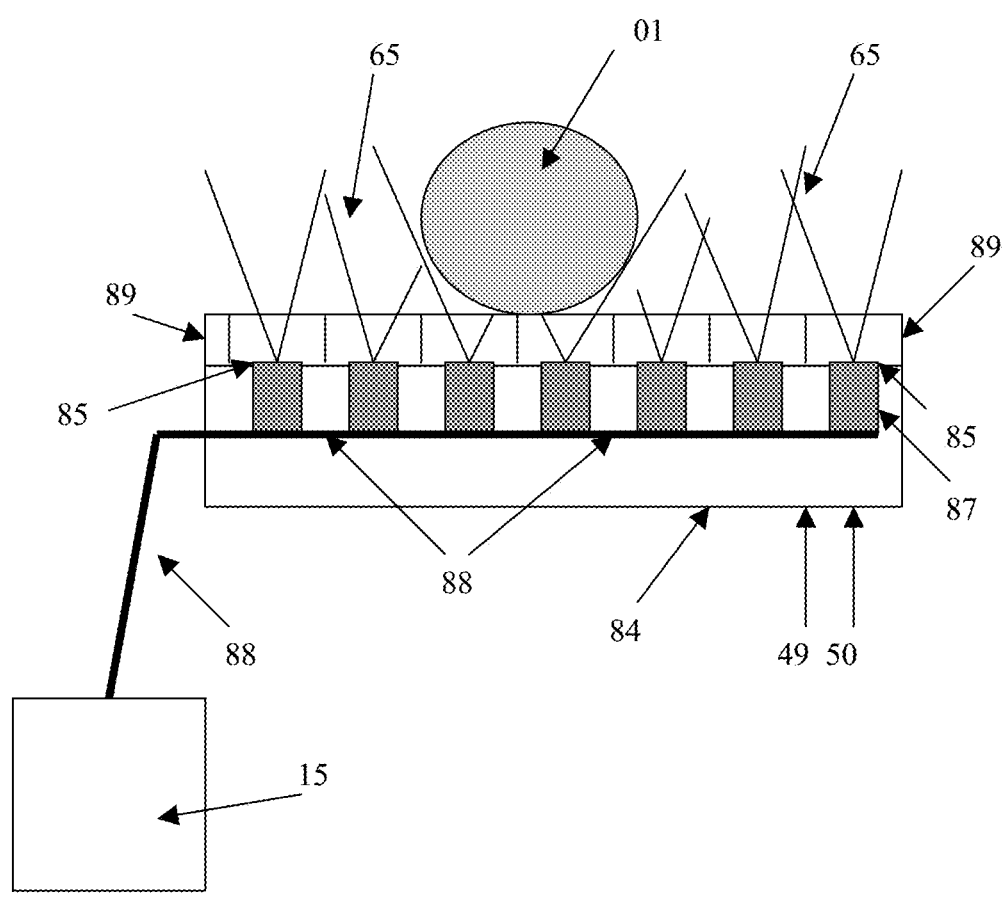
FIG. 25 is a cross sectional view of an endoscope or object resting on object supports with an aerosol passing through a plurality of openings in the object supports.

According to an embodiment, and referring to FIGS. 24-25, it is preferred, without limitation, that various objects or endoscope(s) (01) can be, without limitation, held, supported, hung, cradled, suspended, positioned, or supported, within the sterilization chamber(s) (16) by one or more of various devices including, but not limited to any, clamp(s), fork(s) (49)(50), beam(s) (49)(50), shelve(s), rack(s) (90), member(s), hook(s), ring(s), cradle(s), or support pillar(s) (herein called "object support(s)") (84). Furthermore, these object support(s) (84) can, without limitation, be designed to have one or more opening(s) (85), which can serve as either, or both, outlet(s) or inlet(s), through which various substances or materials used to process the object(s) or endoscope(s) (01) within the sterilization chamber (16) can flow such as, but not limited to any, surfactant, rinse water, high purity rinse water, alcohol solution, "applied agent(s)", air/gas, heated air/gas. These various substances or materials may flow either out of or into the one or more opening(s) (85), where by doing so, they can directly or indirectly contact or interact with various surfaces the object(s) or endoscope(s) (01). Any number of opening(s) (85) may be utilized and positioned anywhere on the object support(s) (84), but it is preferred, without limitation, that at least an effective number of object support(s) (84) are used, and they at least effectively face various surfaces of the object or endoscope (01). The opening(s) (85) may be any size, shape, geometry, or design, known to those skilled in the art. The various substances or materials used to process the object(s) or endoscope(s) (01) within the sterilization chamber (16) can flow or move at any quantity, rate, or pressure, at any time. These materials or substances can be, without limitation, supplied to the opening(s) (85) through one or more of various supply hose(s), pipe(s), conduit(s), or channel(s) (herein called "process hose(s)") (88), and are flowed or moved in a manner known to those skilled in the art. One or more of any opening(s) (85) can be, without limitation, dedicated and plumbed (87) with an aerosol generation device (15) to flow one or more of any substance(s) or material(s) at any time, or at any designated time(s), and for any duration of time, in order to process the object(s) or endoscope(s) (01).

Referring to FIGS. 24-25, an object interface material (herein called "object interface") (89) may also, without limitation, be positioned or maintained between the object support(s) (84) and the object(s) or endoscope(s) (01). This assures that all of the surfaces of the object(s) or endoscope(s) (01) in contact with the object interface (89) have sufficient exposure to the aerosol (65) of an "applied agent" (20) through either direct and/or indirect contact, for their sanitization, disinfection, high-level disinfection, or sterilization, depending on the agent used and the exposure time. For example and without limitation, any absorbent object interface (89) material may also indirectly deploy/transmit the "applied agent" (20) that is aerosolized, to the articulated areas and surfaces by the interaction or movement of the "applied agent" (20) through the interface formed from the selected material.

Referring to FIG. 25, the object interface (89) can be, without limitation, porous, and/or permeable, and be constructed from materials that can provide effective performance and the desired level of efficacy for the process. The object interface (89) can be, without limitation, constructed of one or more layers of material. The object interface (89) may also have absorbent characteristics to improve its efficacy and performance. The object interface (89) is intended, without limitation, to allow the various substances or materials used to process the object(s) or endoscope(s) (01) within the sterilization chamber (16), to move or flow through the interface layer at a controlled, but effectual rate.

Referring to FIG. 25, the object interface (89) can be manufactured from a variety of materials including, but not limited to, cloth, gauze, manufactured fibers, synthetic fibers, natural fibers or materials, cellulose, polymer, polyolefin, glass, metal, ceramic, carbon, combinations of these materials, or other materials know in the art. The object interface (89) can be coated with chemicals, materials, or substances including, but not limited to, polymer(s), polyolefin, wax, silver, lipid, oil, enamel, paint, carbon, metal, combinations of these materials, or other materials known in the art. The object interface (89) can be electrically or electrostatically charged or uncharged in order to attract the "applied agent" (20). The electrostatic potential or polarity of the various materials as well as the "applied agent" (20) can, without limitation, vary. Object interface materials (89) that are developed in the future, may be utilized to improve the efficacy of the design or its application to certain objects or endoscopes (01). The object interface (89) and its effectiveness can vary with variables including but not limited to, its size, width, surface area, shape, fit, thickness, density, hardness, elasticity, flow rate, porosity, permeability, evenness of air/gas flow, mechanical properties, physical properties, and other variables known to those skilled in the art. However, the effectiveness and efficacy of each object interface (89) that is used may, without limitation, increase with attributes such as, but not limited to, the uniformity of these variables throughout the interface that is used. The object interface (89) material can be, without limitation, permanently attached to the object support(s) (84), or it can be designed to be easily removed and replaced, all in a manner known to those skilled in the art. The "object support(s) (84) can also, without limitation, be constructed either partially or completely from the same materials, and in the same manner and concept, as the object interface (89).

According to an embodiment, one or more object(s) or endoscope(s) (01) can be placed inside of, and effectively sealed within, one or more sterilization chamber(s) (16). The sterilization chamber(s) (16), can be any size, shape, or geometry. The object(s) or endoscope(s) (01) can be, without limitation, located or positioned on any racks (90), object supports (84), cradle(s), or other effective materials (47) inside the sterilization chamber(s) (16). It is preferred, without limitation that the racks (90) are preferably perforated, and the perforations can be any size, number, and construction. The object(s) or endoscope(s) (01) can be, without limitation, washed, cleaned, and dried, inside of the sterilization chamber (16), all in a manner known to those skilled in the art.

Referring to FIGS. 22, 26-29, and 32, the object(s) or endoscope(s) (01) can also, without limitation, be one or more package(s) (91) of various types and construction. It is also preferred, without limitation, that the package(s) (91) are constructed from at least an effective or efficacious amount of any sufficiently porous film, sheet, or other material, such as, but not limited to any, woven or unwoven substrate, spun-bonded olefin, or microporous material (92). Any other effective packaging materials or package designs known to those skilled in the art may also be utilized. The package can be, without limitation, designed in manner known to those skilled in the art, so that it can allow free passage of any quantity of air, gas, and/or any agent(s) through the package. This can, without limitation, enable the passage of an efficacious or effective amount of the "applied agent" (20), which is administered into the sterilization chamber(s) (16), to move into the package(s) (91) and treat or interact with the various surfaces within the package(s) (91). The package(s) (91) does not have to be washed or cleaned, unless desired or needed. However, the various object(s) or endoscope(s) (01), including any package (91) can, without limitation, undergo any processing steps or cycle(s) that includes, but it not limited to any, soaking, washing, rinsing, drying, and/or temperature decrease or cooling, before they are treated with an "applied agent" (20). The various processing steps or cycle(s), can occur or transpire for any length of time. It is preferred, without limitation that the processing steps or cycle(s), occur or transpire for at least an effective amount of time, and in any effective order. The package(s) (91) can be, without limitation, sealed, partially sealed, or hermitically sealed. The package(s) (91) can be designed in various ways known in the art. The package(s) (91) may also have any, without limitation, interior volume, wall thickness, or permeability for various substances. It is preferred, without limitation, that at least an effective interior volume, wall thickness, or permeability, is used. The packages (91), object(s) or endoscope(s) (01) can also, without limitation, be designed in a manner known to those skilled in the art, so that they contain, hold, maintain, or are integrated with, one or more of any products used to measure the efficacy of the one or more processing steps utilized within the sterilization chamber such as, but not limited to, any indicator(s) (81). In addition, the packages (91), object(s) or endoscope(s) (01)

can also, without limitation, be designed in a manner known to those skilled in the art, so that the status of the indicator(s) (81) can be easily visible, or visible from outside of the package (91).

Referring to FIGS. 26-30, the sterilization chamber(s) (16) can directly or indirectly connect to one or more secondary chamber(s) (93). Both chambers (16),(93) should also be designed and constructed to withstand, without limitation, various positive and negative pressures, including pressures that are near a vacuum. The secondary chamber(s) (93) can be any size, shape, geometry, and have any number of connected areas. It is preferred, without limitation, that the secondary chamber(s) (93) is at least the same size, as the sterilization chamber(s) (16). It is more preferred that the secondary chamber(s) (93) is at least effectively larger than the than the sterilization chamber(s) (16). Without limitation, one or more of any valves, caps, airlocks, or other effectively sealing door(s) known in the art that can control the flow of any gas, (herein called "pressure valve(s)" (94)), can be positioned anywhere along the path of any moving air, gas, and/or "applied agent" (20) between the sterilization chamber(s) (16) and the secondary chamber(s) (93). One or more paths may be used to flow or move various material(s) or substance(s) including, but not limited to any, air, gas, and/or "applied agent" (20) between the sterilization chamber(s) (16) and the secondary chamber(s) (93). The pressure valve(s) (94) control the flow of any air, gas, and "applied agent" (20) between the sterilization chamber(s) (16) and the secondary chamber(s) (93). The pressure valve(s) (94) can have any effectual operation speed for opening and closing, means of sealing, size, and design. The valve(s) (94) can also be, without limitation, positioned or directly or indirectly connected anywhere on or to, the sterilization chamber (16).

Figure 26:
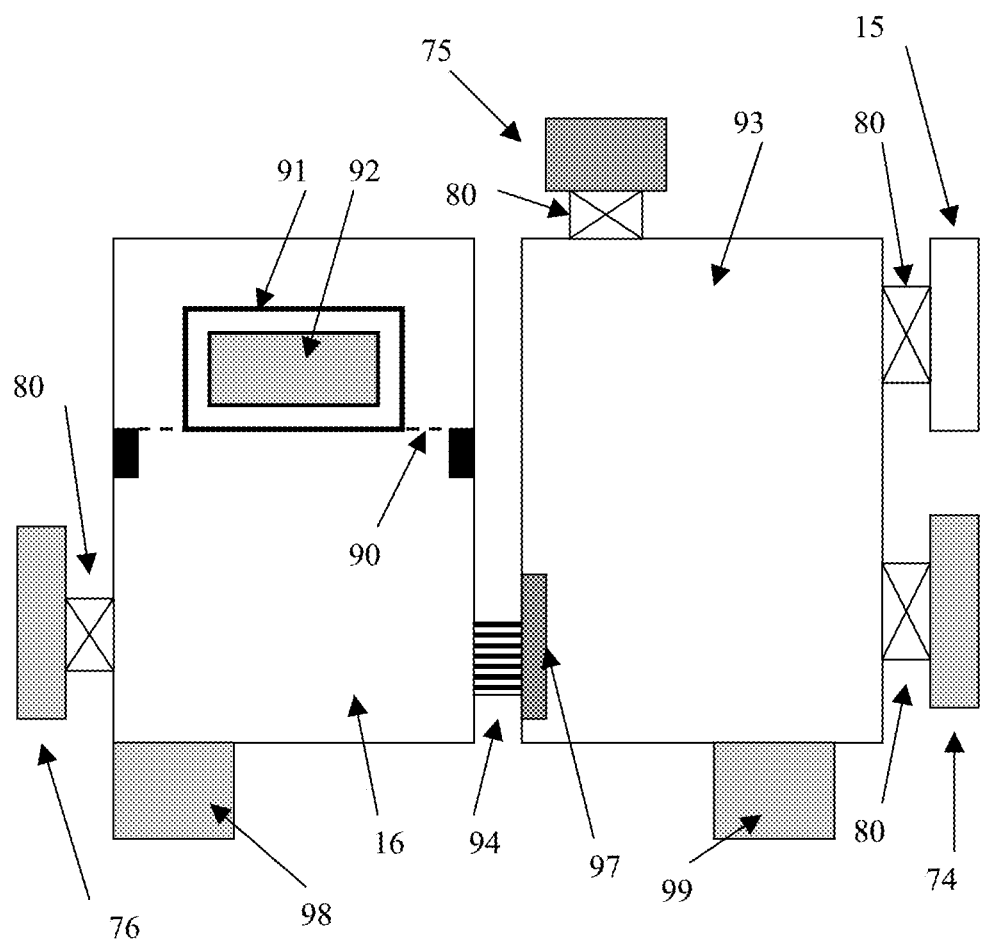
FIG. 26 is a schematic diagram of two sterilization chambers connected to each other with a pressure valve.
Figure 27:
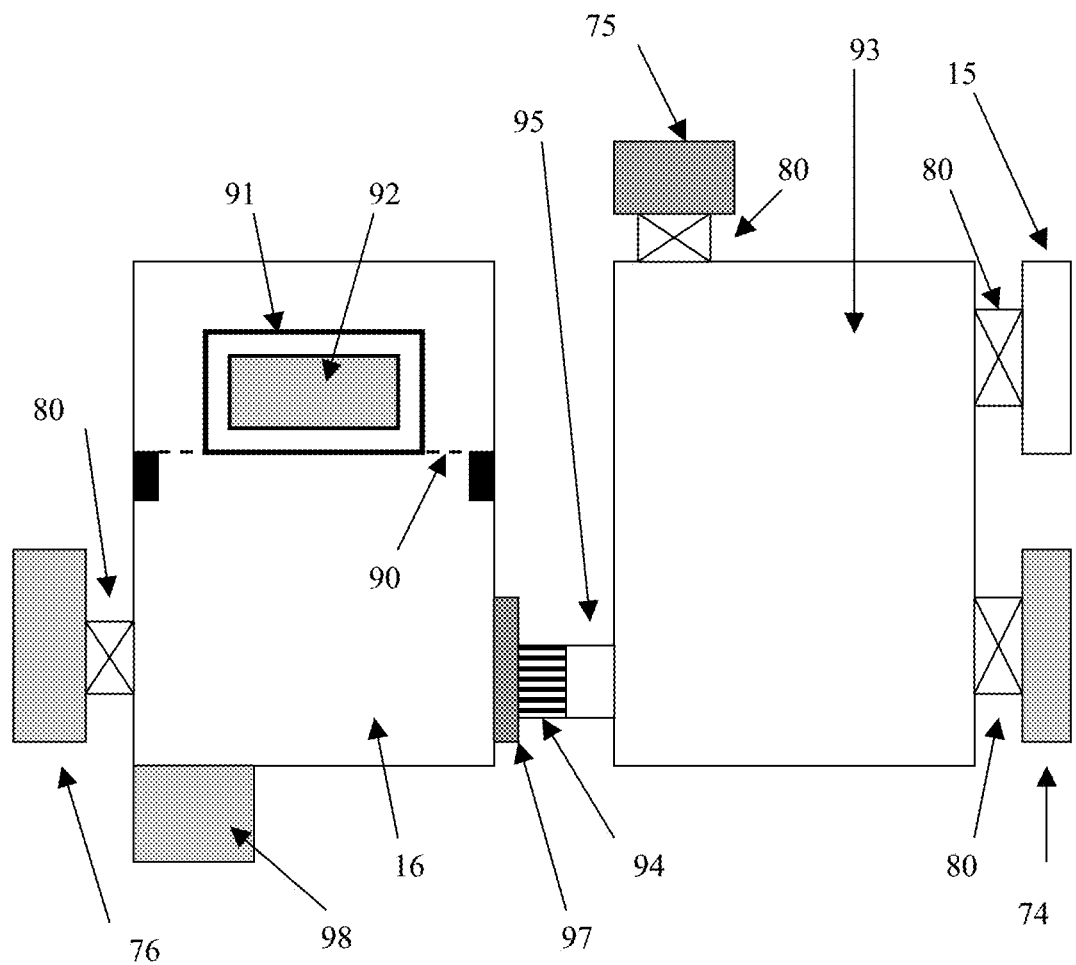
FIG. 27 is a schematic diagram of two sterilization chambers connected to each with a pressure valve and a flow pipe.
Figure 28:
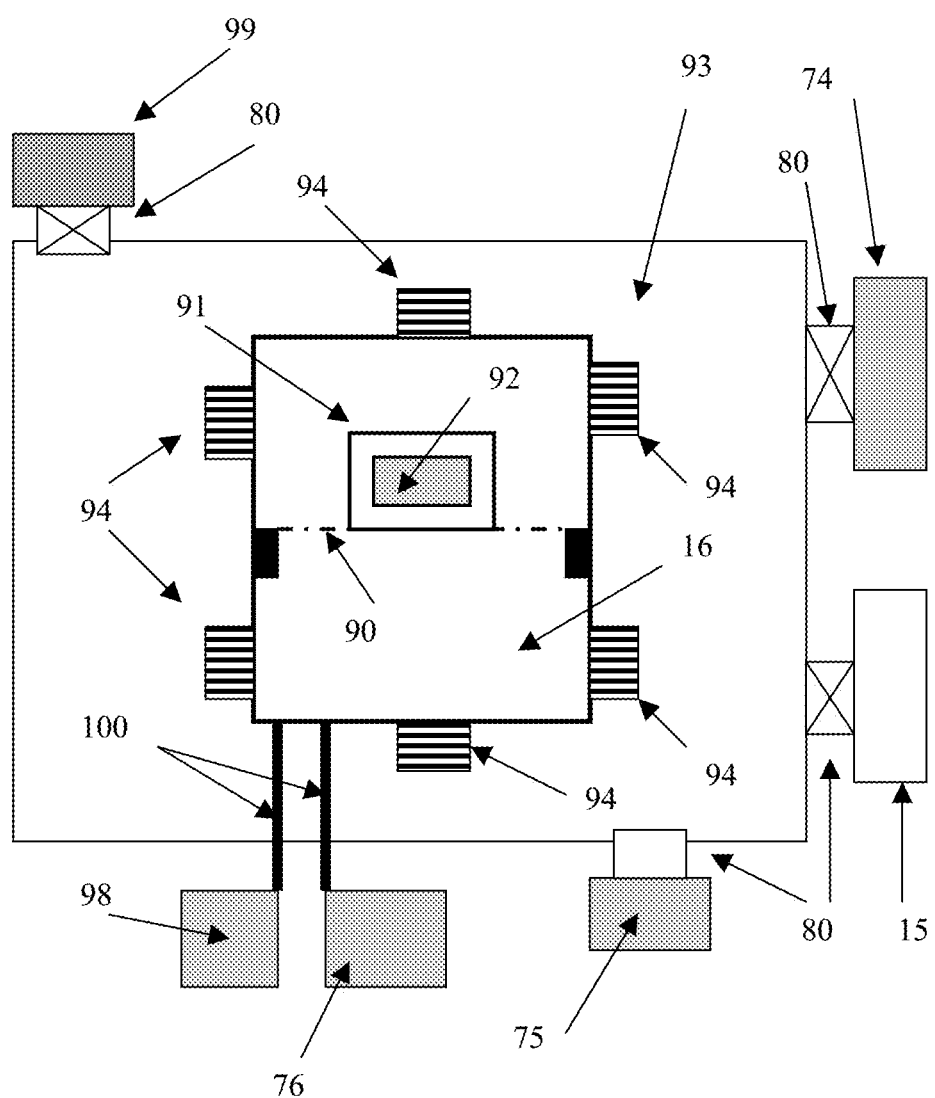
FIG. 28 is a schematic diagram of a first sterilization chamber located within a second sterilization chamber.
Figure 29:
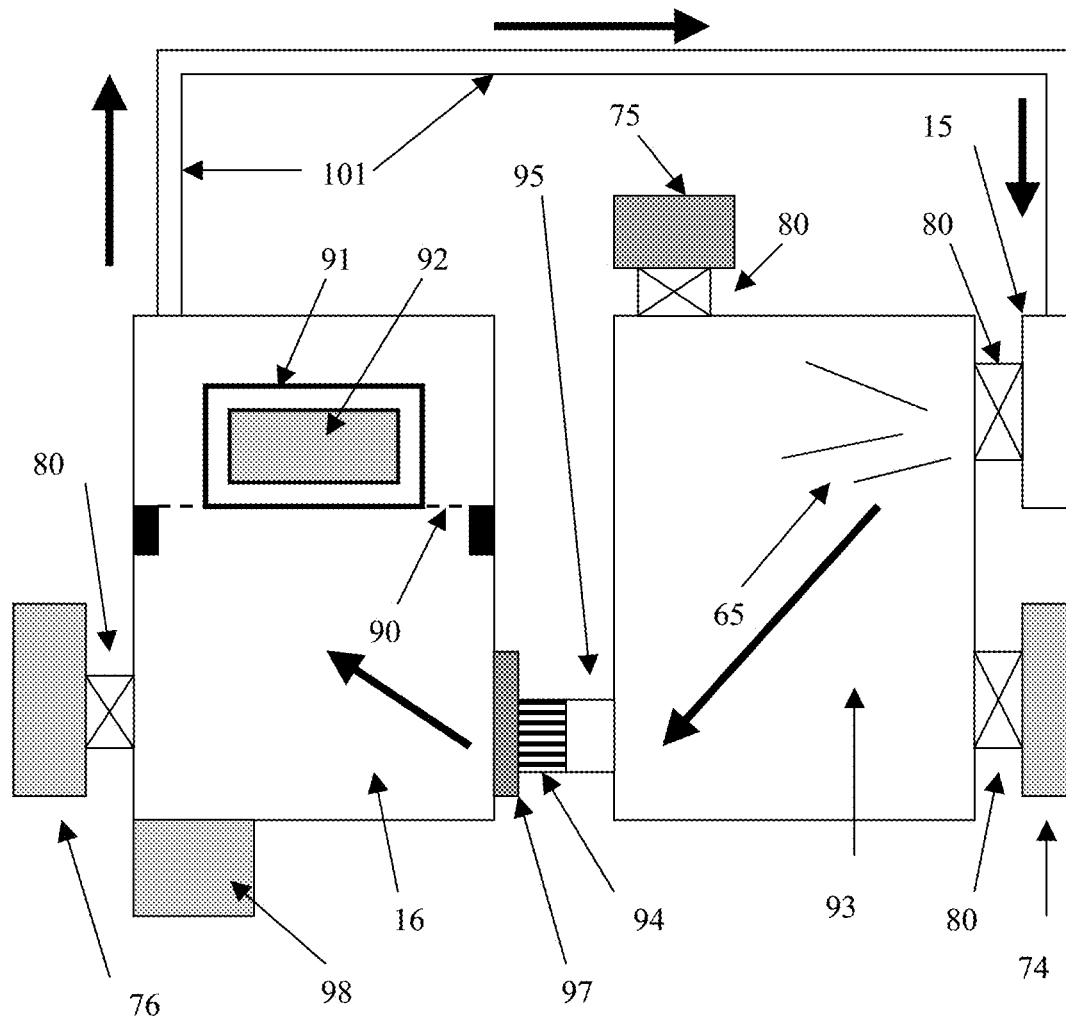
FIG. 29 is a schematic view of a sterilization chamber with a refrigerated air system and vacuum source, connected via a flow pipe and filter, to a second chamber with a dehumidification apparatus, filter, and aerosol generator. One pipe connects the sterilization chamber to the aerosol generator forming a loop for gas/aerosol flow back to the aerosol generator.

As shown in FIGS. 26-27 and 29, one or more of any filter(s) (97) of any size, filtering capacity, level of filtering, or construction, known in the art, may be, without limitation, utilized or positioned anywhere between the sterilization chamber(s) (16) and the secondary chamber(s) (93), to filter the flow of any air, gas, and "applied agent" (20). Any filter(s) (97) may be used, which may have any level of effective filtering, but is preferred, without limitation, that one or more filter(s) (97) is used that can filter out or remove airborne aerosol particles larger than or equal to, "three" micron in size. It is more preferred, without limitation, that one or more filter(s) (97) be used that can filter out or remove airborne aerosol particles larger than or equal to, "one" micron in size. It is even more preferred, without limitation, that one or more filter(s) (97) be used that can filter out or remove airborne aerosol particles larger than or equal to, "half or 0.5" micron in size. It is very preferred, without limitation, that one or more filter(s) (97) be used that can filter out or remove airborne aerosol particles larger than or equal to "a tenth or 0.1" micron in size.

As shown in FIGS. 26-27 and 29, filtering a generated or deployed aerosol was initially demonstrated by the inventors of the present invention in a public area at the Richland, Wash. Municipal Airport on Oct. 9, 2003. Staff from Washington State University, observed aerosol created by the aerosol generating apparatus described in the present invention, pass through a long tortuous path created with 150 feet of six inch diameter flex ducting, that terminated with various filter media including a HEPA filter and a furnace filter. This same system was used to dehumidify and dry the system of ductwork, after the aerosol was deployed. Any filter may also be used, without limitation, to filter any output from the means to generate and deploy the "applied agent" (20).

In a preferred part of this embodiment, the sterilization chamber(s) (16) can be located inside of a larger secondary chamber (93) that can also effectively seal. In this application, as shown in FIG. 28, it is advantageous that both chambers (16),(93) have one or more sealing doors (96), that are at least adequately sized and positioned, so that objects or endoscopes (01) may be easily moved from the sterilization chamber (16) for use.

In a very preferred part of this embodiment, and without limitation, the secondary chamber (93) can be located anywhere outside of the sterilization chamber (16), and effectively connect with the sterilization chamber (93) in one or more places. As shown in FIGS. 26-27 and 29-30, this connection can be made with one or more of various pipes, supply hose(s), conduit(s), or channel(s) (herein called "flow pipe(s)") (95). The sterilization chamber(s) (16) in this application should also have one or more sealing doors (96) that are at least adequately sized and positioned, so that objects or endoscopes (01) may be easily moved from the sterilization chamber (16) for use.

Referring to FIGS. 26 and 30, and according to an embodiment, the pressure within the sterilization chamber(s) (16) can be, without limitation, reduced with any suitable negative pressure device (98) known to those skilled in the art (such as a vacuum pump), to any effective pressure below atmospheric pressure, and more preferably near a vacuum. In comparison, the pressure within the secondary chamber(s) (93) can be, without limitation, increased with any positive pressure device (99) known to those skilled in the art (such as a positive pressure pump), to any effective pressure above standard atmospheric pressure. The secondary chamber(s) (93) is filled with the applied agent (20), and once it is effectively full or has reached an effective density, the one or more "pressure valve(s)" (94), can be opened to allow the "applied agent" (20) to flow or move into the sterilization chamber(s) (16) at any effective speed, quantity, or rate of flow to overwhelm the endoscope (01) or object in the sterilization chamber(s) (16). It is preferred, without limitation, that the one or more "pressure valve(s)" (94), are simultaneously opened within one second or less. The one or more "pressure valve(s)" (94) can be controlled by one or more PLC(s) or remote PLC(s) in a manner known to those skilled in the art.

Referring to FIGS. 26 and 30, and. according to another embodiment, the pressure within the sterilization chamber(s) (16) can be, without limitation, kept effectively near standard atmospheric pressure in a manner known in the art. In comparison, the pressure within the secondary chamber(s) (93) can be, without limitation, increased with the positive pressure device (99) known to those skilled in the art, to any effective pressure above standard atmospheric pressure. The secondary chamber(s) (93) is filled with the applied agent (20), and once it is effectively full or has reached an effective density, the one or more "pressure valve(s)" (94), can be opened to allow the "applied agent" (20) to flow or move into the sterilization chamber(s) (16) at any, effective speed, quantity, or rate of flow. It is preferred, without limitation, that the one or more "pressure valve(s)" (94), are simultaneously opened within one second or less. The one or more "pressure valve(s)" (94) can be controlled by one or more PLC(s) or remote PLC(s) in a manner known to those skilled in the art.

Referring to FIGS. 26-27 and 29-30 and, according to a preferred embodiment, the pressure within the sterilization chamber(s) (16) can be, without limitation, reduced with the negative pressure device (98) known to those skilled in the art, to any effective pressure below atmospheric pressure, and more preferably near a vacuum. In comparison, the pressure within the secondary chamber(s) (93) can be, without limitation, kept effectively near standard atmospheric pressure in a manner known to those skilled in the art. The secondary chamber(s) (93) is filled with the applied agent (20), and once it is effectively full or has reached an effective density, the one or more pressure valve(s) (94), can be opened to allow the "applied agent" (20) to flow or move into the sterilization chamber(s) (16) at any effective speed, quantity, or rate of flow. It is preferred, without limitation, that the one or more pressure valve(s)" (94), are simultaneously opened within one second or less. The one or more "pressure valve(s)" (94) can be controlled by one or more PLC(s) or remote PLC(s) in a manner known to those skilled in the art.

Referring to FIGS. 1-2, 4-5, 12-13, 20-23, and 26-32, the applied agent (20) in these embodiments can, without limitation, continue being deployed or applied into the secondary chamber(s) (93) and/or the sterilization chamber(s) (16) until effective exposure or coverage of the surfaces in the targeted area(s) is achieved. Any amount of time can transpire after the deployment of the applied agent (20) is terminated, and the next processing step(s) or cycle(s) is started. This period of time is called the "dwell time". It is preferred, without limitation, that the dwell time is at least three minutes. It is more preferred, without limitation, that the dwell time is at least six minutes. It is even more preferred, without limitation, that the dwell time is at least ten minutes. It is very preferred, without limitation, that the dwell time is at least fifteen minutes. With reference now to FIGS. 26 and 30, after the "pressure valve(s)" (94), are opened, the pressure within either, or both, the sterilization chamber(s) (16) and/or the secondary chamber(s) (93), can be increased to any effective pressure, with the positive pressure device (99) known to those skilled in the art, for any effective period of time. In addition, after the pressure valve(s)" (94), are opened, the temperature within either, or both, the sterilization chamber(s) (16) and/or the secondary chamber(s) (93), can also be increased to any effective elevated temperature for any effective period of time using one or more means known to those skilled in the art. The sterilization chamber(s) (16) and its contents, and/or the secondary chamber(s) (93), can be, without limitation, further processed in a manner previously discussed in the present invention, including, but not limited to, any drying, dehumidification, or deodorizing activities. These various processing step(s) or cycle(s) can occur or transpire for any length of time, and in any effective order. In addition, any number of the steps or cycles in the present invention, or combination of the steps or cycles in the present invention, may without limitation, be repeated any number of times at any time, to efficaciously process the one or more object(s) (01) or package(s) (91). The one or more endoscope(s) or object(s) (01), or package(s) (91), may also, without limitation, be processed multiple times with a complete processing cycle, including various steps, in order to obtain the needed or desired level of efficacy. The one or more "pressure valve(s)" (94), can remain open or closed at any time, and for any time period that is needed, to complete the various processing steps within either, or both, the sterilization chamber(s) (16) and/or the secondary chamber(s) (93). Any components in the sterilization chamber can also, without limitation, be effectively cooled anytime before any applied agent (20) is administered. The pressure interface assembly (68) may also, without limitation, be used at any time.

Referring to FIGS. 20-23 and 26-32, and according to an embodiment, the various means used to process the object(s) or endoscope(s) (01) such as, but not limited to dehumidify or with the dehumidification apparatus (74), chill or cool with any thermoelectric cooled or chilled air or gas system(s) (76) or refrigerated air or gas system(s) (76) the atmosphere, environment, objects, or any of the targeted surfaces, increase atmospheric pressure with the positive pressure pump (99) or decrease atmospheric pressure with the negative pressure pump (98), or remove substances with the filter(s) (75) such as, but not limited to, any remaining odors, chemicals, smells, vapors, or gases, within the one or more sterilization chamber(s) (16), secondary chamber(s) (93), or interconnected spaces, can be, without limitation, effectively interfaced or connected to these areas in various ways known to those skilled in the art. The thermoelectric air or gas cooling system(s) (76) and/or refrigerated air or gas system(s) (76), dehumidification apparatus (74), the filter(s) (75), the negative pressure device (98) and the positive pressure device (99) may also effectively interface or connect directly or indirectly to one or more areas such as, but not limited to any, targeted area(s) or sterilization chamber(s) (16), secondary chamber(s) (93), or connected space(s). The thermoelectric air or gas cooling system(s) (76) and/or refrigerated air or gas system(s) (76), dehumidification apparatus (74), the filter(s) (75), the negative pressure device (98) and the positive pressure device (99) may be, without limitation, separated from the one or more sterilization chamber(s) (16), secondary chamber(s) (93), or interconnected spaces with one or more valve(s) (80), that can all be controlled by one or more PLC(s) or remote PLC(s) in a manner known to those skilled in the art.

Figure 31:
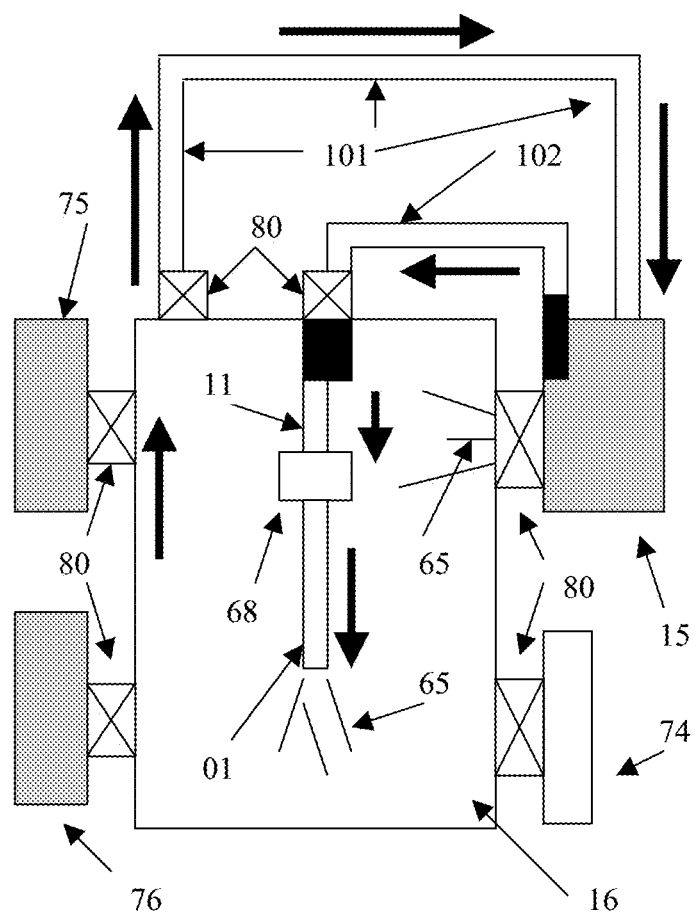
FIG. 31 is a schematic diagram of one sterilization chamber with a dehumidification apparatus, a filter, and a thermoelectric air or gas cooling system(s) and/or refrigerated air or gas system(s). The sterilization chamber is also connected to two separate pipes. One pipe connects the aerosol generator to the pressure interface assembly positioned within the sterilization chamber, while the other pipe connects the sterilization chamber to the aerosol generator forming a loop for gas/aerosol flow back to the aerosol generator.
Figure 32:
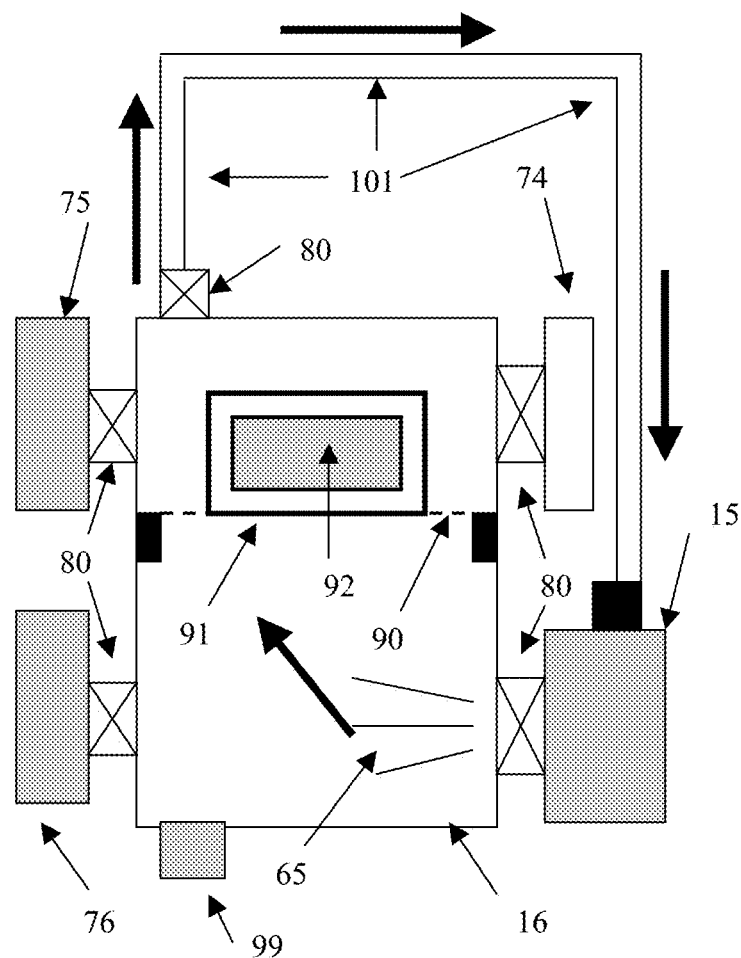
FIG. 32 is a schematic diagram of one sterilization chamber with a dehumidification apparatus, a filter, a thermoelectric air or gas cooling system(s) and/or refrigerated air or gas system(s), and a pressure source. The sterilization chamber is connected to one pipe that connects the aerosol generator directly to the sterilization chamber, forming a closed loop system for air/gas flow.

According to an embodiment, and with reference now to FIGS. 29-33, the sterilization chamber(s) (16) can, without limitation, directly or indirectly connect with the aerosol generator(s) (15) via one or more "return pipe(s)" (101). This connection can allow air/gas and any applied agent(s) (20) or aerosol(s) (65) delivered into the sterilization chamber (16) to flow or recirculate back to the aerosol generator (15) forming a loop. Referring to FIGS. 30 and 31, one or more "connector pipe(s)" (102) can also, without limitation, directly or indirectly connect with the aerosol generator (15) and one or more supply tube(s) (11) and/or one or more pressure interface assembly(s) (68) located within the sterilization chamber. It is preferred, without limitation, that the applied agent(s) (20) or aerosol(s) (65) are delivered via the connector pipe(s) (102) to the supply tube(s) (11) and/or pressure interface assembly(s) (68) from the aerosol generator (15). Without limitation, one or more valve(s) (80) may also be positioned at any location between the sterilization chamber (16) and the aerosol generator (15) for both the return pipe(s) (101), and/or the delivery pipe(s) (102). The valve(s) (80) can all be controlled by one or more PLC(s) or remote PLC(s) in a manner known to those skilled in the art.

Referring to FIGS. 26-27 and 29-30, the various gas(s), air, substances, or materials, used to process the object(s) or endoscope(s) (01) can flow or move at any quantity, rate, or pressure, at any time. These materials or substances can be, without limitation, supplied or moved through one or more of various supply hose(s), pipe(s), conduit(s), or channel(s) (herein called "process pipe(s)") (100), and are flowed or moved to or from the one or more sterilization chamber(s) (16), secondary chamber(s) (93), or interconnected spaces, to or from at least one of the thermoelectric air or gas cooling system(s) (76) and/or refrigerated air or gas system(s) (76), dehumidification apparatus (74), the filter(s) (75), the negative pressure device (98) and the positive pressure device (99) in a manner known to those skilled in the art.

According to an embodiment, it is preferred, without limitation, that the following processing steps or cycle(s), occur or transpire in the following order, for at least an effective amount of time. Delays of time may also, without limitation, exist between the various processing steps or cycle(s). If any delay of time does occur, it is preferred, without limitation, that it is at least an effective amount of time. The order of the one or more of these processing steps or cycle(s) can also, without limitation, be changed. In addition, one or more, or combinations of one or more, of these steps may also be, without limitation, utilized. One or more of these processing steps or cycle(s) can also, without limitation, be removed and not enacted. In addition, any number of the steps or cycles in the present invention, or combination of the steps or cycles in the present invention, may without limitation, be repeated any number of times at any time, to efficaciously process the one or more object(s) (01) or package(s) (91). The one or more endoscope(s) or object(s) (01), or package(s) (91), may also, without limitation, be processed multiple times with a complete processing cycle, including various steps, in order to obtain the needed or desired level of efficacy. Without being limited, the pressure interface assembly (68) can also be utilized when its application can provide an efficacious or desired outcome. The one or more processing steps or cycle(s) are as follows:

a) Soak object(s) or endoscope(s) (01) in a solution.
b) Wash object(s) or endoscope(s) (01).
c) Rinse object(s) or endoscope(s) (01).
d) Dry object(s) or endoscope(s) (01).
e) Cool or chill surfaces of object(s) or endoscope(s) (01).
f) If two interconnected chambers, separated by one or more valves(s) (94), are used, and the object(s) or endoscope(s) (01) are located within the sterilization chamber (16), and it is connected to a secondary chamber (93), the two chambers can each be subjected to various combinations of any pressure within the chambers. The one or more valve(s) (94) are opened once the secondary chamber (93) is effectively and sufficiently filled with the applied agent(s) (20).
g) Generate and deploy the applied agent(s) (20) to the various surfaces within sterilization chamber (16) for effective amount of time.
h) Terminate application of applied agent(s) (20)
i) Use effective dwell time if needed.
j) Heat and/or dehumidify sterilization chamber (16) and secondary chamber (93) (if used), to obtain an effective relative humidity.
k) Filter the atmosphere within the sterilization chamber (16) and secondary chamber (93) (if used), to remove any odor(s), gase(s), or vapor(s), with an effective filtering device(s) (75).

Figure 33:
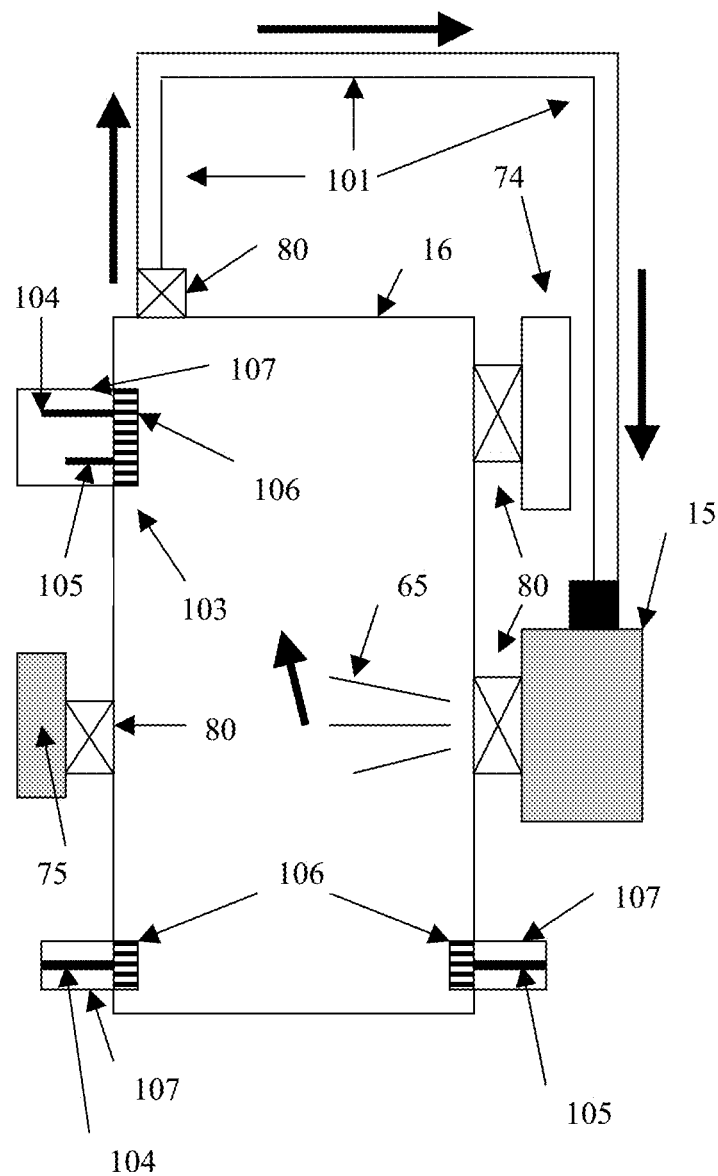
FIG. 33 is a schematic diagram of one sterilization chamber with a dehumidification apparatus, a filter, and also incorporates a sensor consisting of a light source and a light-sensing component. The sterilization chamber is connected to one pipe that connects the aerosol generator directly to the sterilization chamber, forming a closed loop system for air/gas flow.

With reference to FIG. 33, according to another embodiment, and without limitation, one or more sensors (103), or the means for indirect or direct communication with one or more sensor(s) (103) or any programmable logic circuit(s) or controller(s) which are connected to one or more sensor(s) (103), can be utilized to determine if an effective or sufficient amount of aerosol (65) has been delivered into the sterilization chamber(s) (16). This embodiment was initially taught in U.S. Pat. No. 7,871,016 and U.S. patent application Ser. No. 12/816,986, both entitled "Method and Apparatus For An Improved Aerosol Generator and Associated Uses and Equipment," which are expressly incorporated by reference herein in their entirety.

The at least one sensor(s) (103) can be located in any area that is targeted for treatment with the applied agent(s) (20) or aerosol (65). It is preferred, without limitation, that the sensor(s) (103) are located in an effective location within the sterilization chamber(s) (16). The one or more sensor(s) (103) can also be, without limitation, positioned outside of the treated area(s) or sterilization chamber(s) (16) behind any suitable window(s) (106) or in any other suitable location if they are optical sensor(s) (103), and monitor the conditions within these various areas through the window(s) (106). This can allow the sensor(s) (103) to properly function while being protected from the environment within the targeted area(s) or sterilization chamber(s) (16).

In another aspect of this embodiment, each sensor(s) (103) includes at least two parts including, but not limited to, a light source (104) and a light sensor (105), known to those skilled in the art. The light source (104) and light sensor (105) can be directly or indirectly connected, or they can be placed or positioned independent from one another. Without being limited, the distance between the light source (104) and light sensor (105) can also vary depending on the type of sensor (103) that is used. For various sensors (103) known in the art, the light source (104) and light sensor (105) can be, without limitation, separated. It is preferred, without limitation, that if sensor(s) like this are used, they are at least separated by an effective distance. It is preferred, without limitation, that the light source (104) and light sensor (105) components of sensors (103) like this are positioned at least two feet or more apart. Other types of sensor(s) (103) known in the art can also integrate both the light source (104) and the light sensor (105) into the same unit or housing (107). These types of sensor(s) (103) can also be, without limitation, utilized in the present invention. These units typically detect reflected light, and the distance between the light source (104) and light sensor (105) may not, without limitation, be an important variable for effective function since they point in a similar direction.

The emitted light or energy, or light source (104) can have, without limitation, any: (a) intensity, (b) brightness, (c) period, (d) frequency, (e) type of light, and (f) wavelength. The light source (104) can be controlled via any electronic system, programmable logic circuit, or other means known in the art. The light sensor (105) can, without limitation, vary widely in its sensitivity and ability to sense light of any: (a) intensity, (b) brightness, (c) period, (d) frequency, (e) type of light, and (f) wavelength. The means to sense the light (105) can also have various capabilities known in the art, including, without limitation, the ability to have adjustable sensitivity and trigger level(s), and the ability to communicate with any electronic system, programmable logic circuit, or other means known in the art. The light sensor(s) (105) can, without limitation, indicate or communicate with any electronic system, programmable logic circuit, or other means known in the art, if it either receives or ceases to receive a desired or set level of light stimulus, and the communication can be accomplished in various ways known in the art. It is preferred, without limitation that the electronic system, programmable logic circuit, or other means known in the art, is indicated or receives information by any means including, but not limited to, an electrical signal, lack of an electrical signal, or any analog signal, from the light sensor(s) (105) or any directly or indirectly connected hardware. This communication can result in various actions such as, but not limited to, shutting down the device used to generate and/or deploy the aerosol (65), or extending the amount of time that the aerosol generator(s) (15) operates and deploys the applied agent(s) (20) or aerosol (65) into the various areas targeted for treatment. Any amount of extended time can, without limitation, be utilized to deploy the applied agent(s) (20) or aerosol (65). It is preferred, without limitation, that the amount of extended time is at least an efficacious or effective amount of time in addition to any initial deployment time that may have been chosen or established in various ways to deploy the applied agent(s) (20) or aerosol (65).

Without limitation, an effective or sufficient amount of administered aerosol (65) in this embodiment can be indicated in various ways including, but not limited to, (a) causing the disruption, lowering, diminishment, or cessation, of the light that is emitted from the light source(s) (104) before it reaches the light sensor(s) (105), (b) causing an increased level of light as the light emitted from the light source(s) (104) is reflected by the sufficient amount of aerosol (65) back to the light sensor(s) (105), (c) causing a decreased level of the light as the light emitted from the light source(s) (104) is not reflected by a surface in front of the light source(s) (104) back to the light sensor(s) (105). The effective, sufficient amount, or specified quantity, of administered aerosol (65) can vary for intended or unintended reasons or designs, and the trigger or sensitivity levels for the light sensor(s) (105) can, without limitation, be varied, calibrated, or adjusted, for each situational circumstance.

According to an embodiment, and with reference to FIGS. 34-37 and FIGS. 40-43, shadowed surface(s) of the object(s) or endoscope(s) (01) or the absence of sufficient processing or treatment of one or more surfaces and/or targeted surface(s) of the object(s) or endoscope(s) (01), within the sterilization chamber(s) (16), can also be, without limitation, overcome or prevented by the incorporation and use of one or more of any means to apply effective pressure in order to hold, grip, clamp, or otherwise support, the object(s) or endoscope(s) (01) (hereinafter called "gripper(s)" or "gripping mechanism(s)") (135) within the closed space or sterilization chamber(s) (16). Various means known in the art may, without limitation, be utilized to effectively clamp, grip, hold, or support, the object(s) or endoscope(s) (01). Without being limited, the "gripping mechanism(s)" (135) used in the present invention can include, but is not limited to, the use of one or more "primary gripping mechanism(s)" (109) and "secondary gripping mechanism(s)" (110), which are "gripping mechanism(s)" (135) that can be, without limitation, used in various orders, timing, combinations, and/or sequences. Without being limited, the gripping mechanism(s) (135) can include, but is not limited to any, mechanical apparatus or means, electromechanical apparatus or means, or pneumatic apparatus or means, in its design or construction, to apply sufficient pressure in order to hold, grip, clamp, or otherwise support, the object(s) or endoscope(s) (01), or effectively open and release or detach from the object(s) or endoscope(s) (01). More specifically, and without being limited, the gripping mechanism(s) (135) includes, but is not limited to, the use of one or more of any means to directly or indirectly interface with the object(s) or endoscope(s) (01) (hereinafter called "gripping fingers" (108)) in order to either apply effective pressure to hold, grip, clamp, or otherwise support, the object(s) or endoscope(s) (01) when needed, or effectively open and release or detach from the object(s) or endoscope(s) (01). Without being limited, at least two gripping fingers (108) can either move, or even remain in a static or stationary position. It is preferred, without limitation, that the one or more gripping mechanism(s) (135), includes at least one movement mechanism (127) that with the assistance of any suitable motor or any other suitable movement device (125), is able to directly or indirectly actuate or move the at least two gripping fingers (108) so that the at least two gripping fingers (108) can either effectively close with sufficient force and hold, grip, or clamp, the object(s) or endoscope(s) (01), or effectively open and release or detach from the object(s) or endoscope(s) (01).

The object(s) or endoscope(s) (01) can be, without limitation, first placed, held, gripped, clamped, positioned, connected, interfaced, or supported, with one or more "primary gripping mechanism(s)" (109). It is preferred, without limitation, that the object(s) or endoscope(s) (01) is maintained in a vertical orientation during all of the processing activities within the sterilization chamber(s) (16), however any other angled, horizontal, or other orientation may also, without limitation, be used. The object or endoscope is then processed in one or more various ways or activities (hereinafter "processing activity(s)" or "activity(s)"), or any number of one or more combination(s) or order of processing activity(s), including, but not limited to being, washed, rinsed, dried, and/or subjected to the "applied agent", and/or dried again. After the surfaces and/or targeted surfaces of the object(s) or endoscope(s) (01) are efficaciously processed or treated with the one or more processing activity(s) or step(s), the object(s) or endoscope(s) (01) is then transferred, in one or more various ways, so that it is then placed, held, gripped, clamped, positioned, connected, interfaced, or supported, solely by one or more "secondary gripping mechanism(s)" (110) also located within the sterilization chamber(s) (16). It is preferred, without limitation, that the object(s) or endoscope(s) (01) is continued to be maintained in a vertical orientation during all of the processing activities within the sterilization chamber(s) (16), however any other angled, horizontal, or other orientation may also, without limitation, be used. The one or more "secondary gripping mechanism(s)" (110) interface with one or more surfaces of the object(s) or endoscope(s) (01) that were not covered or shadowed by the "primary gripping mechanism(s)" (109). The object(s) or endoscope(s) (01) is then, without limitation, further processed with the same one or more activity(s) or combination or order of activity(s), that were used to process the object(s) or endoscope(s) (01) when the one or more "primary gripping mechanism(s)" (109) were used. Once the processing of the object(s) or endoscope(s) (01) is completed, with the one or more processing activity(s), the object(s) or endoscope(s) (01) can be, without limitation, returned back to the "primary gripping mechanism(s)" (109) for purposes, including, but not limited to, the start of one or more additional processing activities(s) or step(s). However, any processing activity(s) may also, without limitation, be started while the object(s) or endoscope(s) (01) is being held, gripped, clamped, positioned, connected, interfaced, or supported, by one or more "secondary gripping mechanism(s)" (110). The one or more processing activity(s) are performed with each "gripping mechanism" until all surfaces of the object(s) or endoscope(s) (01) are efficaciously processed or treated. The time necessary to conduct each and/or all of the one or more processing activity(s) can vary, but it is at least an effective amount of time. In addition, the time that the object(s) or endoscope(s) (01) is held by either the "primary gripping mechanism(s)" (109) or "secondary gripping mechanism(s)" (110) during each processing activity(s) may vary, but it is at least an efficacious amount of time. The object(s) or endoscope(s) (01) can also, without limitation, alternate being placed, held, gripped, clamped, positioned, connected, interfaced, or supported, by the one or more "primary gripping mechanism(s)" (109) and "secondary gripping mechanism(s)" (110) one or more times, to complete all of the one or more processing activity(s), and efficaciously process or treat all of the surfaces and/or targeted surfaces of the object(s) or endoscope(s) (01). Any or all of the various processing activity(s) or step(s) for the object(s) or endoscope(s) (01) may also be, without limitation, repeated one or more times. The movement of the object(s) or endoscope(s) (01) between the one or more gripping mechanism(s) (135), or the "primary gripping mechanism(s)" (109) and "secondary gripping mechanism(s)" (110), can be, without limitation, performed at various times such as, but not limited to, during or after one or more processing activity(s) or combination of processing activity(s), or after all of the various processing activity(s) are completed for each contact of the object(s) or endoscope(s) (01) with the one or more gripping mechanism(s) (135).

One example of using various processing activity(s) or step(s) coupled with the use of one or more gripping mechanism(s) (135), to treat the object(s) or endoscope(s) (01) includes, without limitation, the following activity(s) or steps and details. The object(s) or endoscope(s) (01) is first interfaced with the one or more "primary gripping mechanism(s)" (109) within the sterilization chamber(s) (16), and it is then sufficiently dried with one or more of any drying activity(s). The interior of the sterilization chamber(s) (16) may also, without limitation, be subjected to one or more drying activity(s) before the object(s) or endoscope(s) (01) is initially placed within the sterilization chamber(s) (16) to insure that all of the various surfaces within the sterilization chamber(s) (16) such as, but not limited to any, gripping fingers (108), or object interface material(s) (89), are sufficiently dry. The object(s) or endoscope(s) (01) is then moved to or interfaced with the one or more "secondary gripping mechanism(s)" (110) where the object(s) or endoscope(s) (01) is then subjected to the same one or more drying activity(s) which are sufficient to dry the previously covered or shadowed areas of the object(s) or endoscope(s) (01). The object(s) or endoscope(s) (01) may be, without limitation, returned back to the one or more "primary gripping mechanism(s)" (109) to begin another processing activity cycle, after it is processed while being interfaced with the one or more "secondary gripping mechanism(s)" (110). However, this is, without limitation, not mandatory. An effective amount of one or more applied agent(s) (20) is then dispersed or applied into the sterilization chamber(s) (16) for a sufficient amount of time to effectively treat the various surfaces of the one or more object(s) or endoscope(s) (01) while it is still interfaced with the "secondary gripping mechanism(s)" (110). After the one or more surfaces of the object(s) or endoscope(s) (01) are sufficiently exposed to the one or more applied agent(s) (20), the object(s) or endoscope(s) (01) is then moved back to or interfaced with the one or more "primary gripping mechanism(s)" (109), where the one or more surfaces of the object(s) or endoscope(s) (01) are also sufficiently exposed to the one or more applied agent(s) (20). This process may be, without limitation, repeated for each processing activity(s) or step(s), as well as for any movement of the object(s) or endoscope(s) (01) between the various gripping mechanism(s) (135). All of the various processing activity(s) or step(s), and any movement of the object(s) or endoscope(s) (01) between the various gripping mechanism(s) (135), may be, without limitation, repeated one or more times. It is preferred, without limitation, that the object(s) or endoscope(s) (01) is connected to one or more pressure interface assembly(s) (68) while it is treated within the sterilization chamber(s) (16).

In another example, and without limitation, the one or more object(s) or endoscope(s) (01) is first interfaced with the one or more "primary gripping mechanism(s)" (109) within the sterilization chamber(s) (16), and it is then processed with one or more various processing activity(s) or step(s) that may include, but are not limited to, washing the various surfaces of the object(s) or endoscope(s) (01) in a manner known to those skilled in the art, drying the various surfaces of the object(s) or endoscope(s) (01), application or deployment of sufficient amounts of one or more applied agent(s) (20) into the sterilization chamber(s) (16), treating the various surfaces of the object(s) or endoscope(s) (01) with the applied agent(s) (20) for an effective amount of time, and drying the various surfaces of the object(s) or endoscope(s) (01). The object(s) or endoscope(s) (01) is then moved to or interfaced with the one or more secondary gripping mechanism(s)" (110) where the object(s) or endoscope(s) (01) is then subjected to the same one or more processing activity(s) or step(s). This insures that the surfaces of the object(s) or endoscope(s) (01) that were shadowed or covered by the "primary gripping mechanism(s)" (109), are effectively processed by the same various processing activity(s) or step(s). The object(s) or endoscope(s) (01) may be, without limitation, returned back to the one or more "primary gripping mechanism(s)" (109), after it is finished being processed with the one or more various processing activity(s) or step(s), while being interfaced with the one or more "secondary gripping mechanism(s)" (110). Once the object(s) or endoscope(s) (01) is returned back to the "primary gripping mechanism(s)" (109), it may also, without limitation, undergo one or more drying activity(s). The one or more of any processing activity(s) or step(s), and movement of the object(s) or endoscope(s) (01) between the various gripping mechanism(s) (135), may be, without limitation, repeated one or more times. It is preferred, without limitation, that the object(s) or endoscope(s) (01) is connected to one or more pressure interface assembly(s) (68) while it is treated within the sterilization chamber(s) (16).

Figure 36:
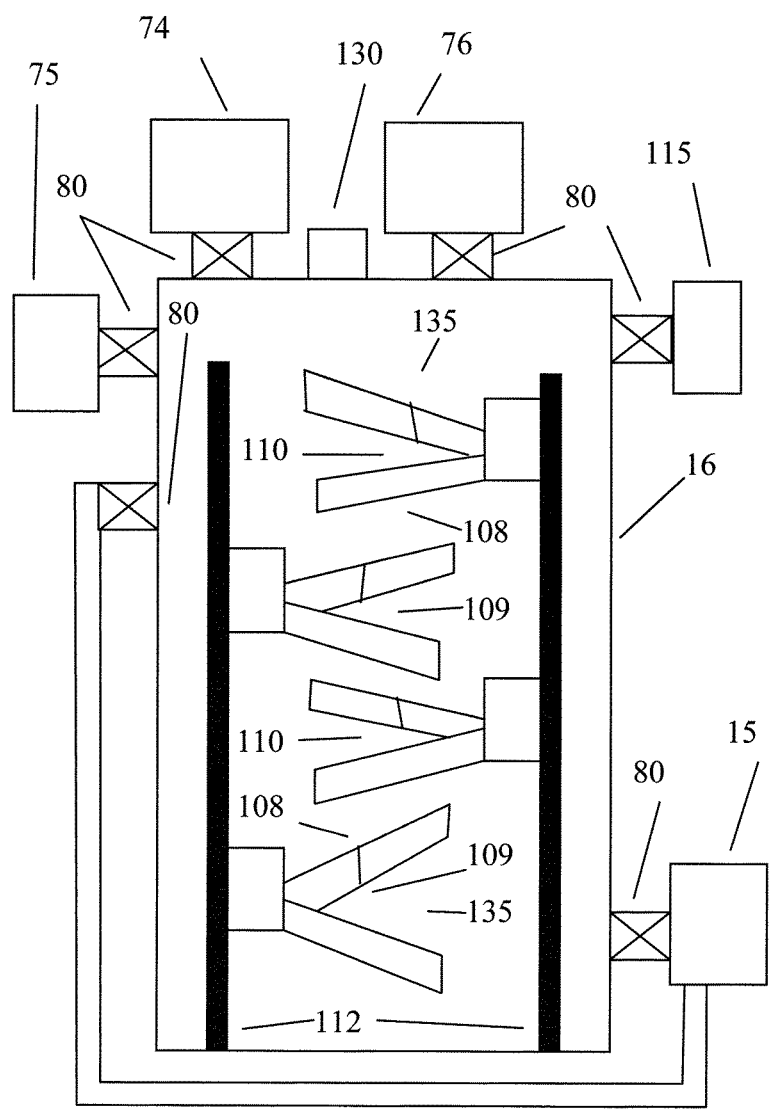
FIG. 36 is a schematic diagram of an enclosed chamber with two primary grips retained on a first linear positioning device and two secondary grips retained on a second linear positioning device for retaining an object to be treated.

According to an embodiment, and with reference to FIG. 36, one or more of any sensor(s) (130) may be, without limitation, utilized to verify that the object(s) or endoscope(s) (01) is sufficiently or effectively moved or transferred between the one or more gripping mechanism(s) (135), or between the "primary gripping mechanism(s)" (109) and the "secondary gripping mechanism(s)" (110). These sensor(s) (130) can include any sensor(s) (130) such as, but not limited to any, proximity sensor(s), light emitter(s) and light sensor(s), trigger mechanism(s), mechanical switch(s), weight or mass sensor(s), stress and strain gauge(s), signal emitter(s) and signal sensor(s), or any other applicable sensor(s) known to those skilled in the art. One or more of these sensor(s) (hereinafter called "verification sensor(s)") (130) can be located anywhere on or within the sterilization chamber(s) (16), but at least at an effective location. The verification sensor(s) (130) can communicate with one or more of any digital, electronic, or analog, controller(s) such as, but not limited to, any PLC, in order to determine the presence or absence of the object(s) or endoscope(s) (01). Depending on the location of the one or more verification sensor(s), any data, information, signal(s), or lack of signal(s) or data, received by the PLC or controller can be utilized for purposes such as, but not limited to, determining that the object(s) or endoscope(s) (01) has successfully or effectively moved or transferred between the one or more gripping mechanism(s) (135), or between the "primary gripping mechanism(s)" (109) and the "secondary gripping mechanism(s)" (110). If the PLC detects that the object(s) or endoscope(s) (01) has not successfully transferred at any time between the various gripping mechanism(s) (135), the PLC can, without limitation, shut the apparatus down or cause the entire machine to enter into a fault mode.

Referring to FIGS. 34-37 and FIGS. 40-41, it is preferred, without limitation, that once the object(s) or endoscope(s) (01) is fully transferred from one or more gripping mechanism(s) (135) to another one or more gripping mechanism(s) (135), or from the at least two gripping fingers (108) to another set of gripping fingers (108), the receiving one or more gripping mechanism(s) (135) or gripping fingers (108), are the only gripping mechanism(s) (135) or gripping fingers (108) that have contact with the object(s) or endoscope(s) (01). In addition, each time the object(s) or endoscope(s) (01) is moved from either the "primary gripping mechanism(s)" (109) to the "secondary gripping mechanism(s)" (110), or the "secondary gripping mechanism(s)" (110) back to the "primary gripping mechanism(s)" (109), the various "gripping mechanism(s)" (135), or gripping fingers (108), shall only, without limitation, interface with the one or more surfaces of the object(s) or endoscope(s) (01) that were not previously covered or shadowed. This insures that all surfaces and/or targeted surfaces of the object(s) or endoscope(s) (01) are efficaciously exposed to the various processing activities, and untreated or shadowed surfaces are prevented. It is also preferred, without limitation, that the object(s) or endoscope(s) (01), is effectively placed or positioned so that the one or more various gripping mechanism(s) (135) including, but not limited to, its gripping fingers (108), can apply effective pressure when needed, in order to effectively hold, grip, clamp, or otherwise support, the object(s) or endoscope(s) (01), within the sterilization chamber(s) (16).

Referring to FIGS. 34-41, the one or more various gripping mechanism(s) (135) including, but not limited to, its gripping fingers (108), can be any, without limitation, mechanical, electromechanical, or pneumatic, means or device known in the art that can not only apply any effective or sufficient pressure in order to place, hold, grip, clamp, position, connect, interface, or otherwise support, the object(s) or endoscope(s) (01) within the closed space or sterilization chamber(s) (16), but also perform functions such as, but not limited to any, unclamping, ungripping, releasing, or sufficiently decreasing their holding pressure so that the object(s) or endoscope(s) (01) can be released or disconnected for various purposes such as, but not limited to, it's removal from the sterilization chamber(s) (16), or to transfer the object(s) or endoscope(s) (01) back and forth between the various gripping mechanism(s) (135) or gripping fingers (108). The various gripping mechanism(s) (135) including, but not limited to, its gripping fingers (108), can also, without limitation, directly or indirectly move or pivot in one or more of any direction(s), in a manner known in the art. Without being limited, the various gripping mechanism(s) (135) including, but not limited to, its gripping fingers (108), may also be directly or indirectly moved, in any direction or orientation, and for any distance, within the sterilization chamber(s) (16), and this may be accomplished in a manner known to those skilled in the art.

Also, referring to FIGS. 34-41, it is preferred, without limitation, that the various gripping mechanism(s) (135) are constructed from or utilize any movable and/or adjustable gripping fingers (108), such as, but not limited to, any "clamp(s)" or "jaw(s)" (111), that can be sufficiently opened and closed when needed. The various gripping mechanism(s) (135), gripping fingers (108), clamp(s) or jaw(s) (111), can be, without limitation, opened or closed any distance, at any time, and for any purpose. The one or more gripping mechanism(s) (135) or gripping fingers (108) can be, without limitation, constructed in a manner known to those skilled in the art, so they can be manually or automatically adjusted or controlled, by any digital, electronic, or analog, controller(s), or PLC known in the art, so that the object(s) or endoscope(s) (01) can be sufficiently interfaced, held, supported, clamped, and/or gripped each time it is interfaced with or connected to any gripping mechanism(s) (135) or gripping fingers (108), as well as be effectively released. Without being limited, any, sensing, opening, closing, function, or movement, of any component(s) of the various gripping mechanism(s) (135), can be monitored and controlled via one or more of any digital, electronic, or analog controller(s) such as, but not limited to, any PLC. Without being limited, any component(s) of the various gripping mechanism(s) (135), including, but not limited to the gripping fingers (108), can be any, size, length, width, thickness, shape, consist of any construction, and/or be constructed from any suitable materials, known to those skilled in the art. Without being limited, any components of the gripping mechanism(s) (135), including, but not limited to any gripping fingers (108), can also be constructed from any of the same materials used to construct the sterilization chamber (16) and/or the pressure interface assembly (68). Without being limited, any components of the gripping mechanism(s) (135), including, but not limited to any gripping fingers (108), can be constructed from any material that is porous and/or permeable. Also, without being limited, any components of the gripping mechanism(s) (135), including, but not limited to any gripping fingers (108), can also be constructed from any material that is absorbent. In addition, any components of the gripping mechanism(s) (135), including, but not limited to any gripping fingers (108), can be, without limitation, designed and built in a manner known to those skilled in the art, so they can interface with one or more of any surface(s) of one or more object(s) or endoscope(s) (01) from any direction, distance, angle, or orientation, as well as be easily adjusted to effectively interface with object(s) or endoscope(s) (01) of any size, length, shape, or geometry. Any components of the gripping mechanism(s) (135) including, but not limited to any gripping fingers (108), can also, without limitation, undergo any number of one or more movement(s) or combinations of movement(s) within the sterilization chamber(s) (16). It is preferred, without limitation, that the one or more gripping mechanism(s) (135), or any other of its components that interface with the object(s) or endoscope(s) (01) such as, but not limited to, the gripping fingers (108) are positioned within sufficient proximity or distance to each other, so they can effectively move the one or more object(s) or endoscope(s) (01) back and forth between themselves.

Referring to FIGS. 34-41, the one or more various gripping mechanism(s) (135) including, but not limited to, its gripping fingers (108), can be can be, without limitation, located anywhere within the closed space or sterilization chamber(s) (16). However, they should at least be, without limitation, located in one or more locations within the sterilization chamber(s) (16), at sufficient height(s) and with sufficient surrounding space or area, to insure quick, efficient, and efficacious processing of the object(s) or endoscope(s) (01). It is also preferred, without limitation, that the object(s) or endoscope(s) (01) is placed, held, gripped, hung, clamped, positioned, connected, interfaced, supported, or suspended, via the various gripping mechanism(s) (135) in the sterilization chamber(s) (16), and it is done in a manner so that the only additional surfaces that the object(s) or endoscope(s) (01) contacts, is the one or more components of the pressure interface assembly (68) if it is used. In addition, if the pressure interface assembly (68) is used, the one or more supply tube(s) (11) that connect to it, may be any length, but at least an effective length. A sufficient amount of vertical and/or horizontal space should, without limitation, separate the various gripping fingers (108), so that the object(s) or endoscope(s) (01) with attributes such as, but not limited to various, sizes, geometry, construction, and lengths, may be processed. In addition, and without being limited, the gripping mechanism(s) (135) can be mounted in a manner known in the art, so their positions or locations anywhere within the closed space or sterilization chamber(s) (16) can be easily adjusted, changed, or modified in order to accommodate any object(s) or endoscope(s) (01) with attributes such as, but not limited to various, size, shape, width, and length.

Figure 34:
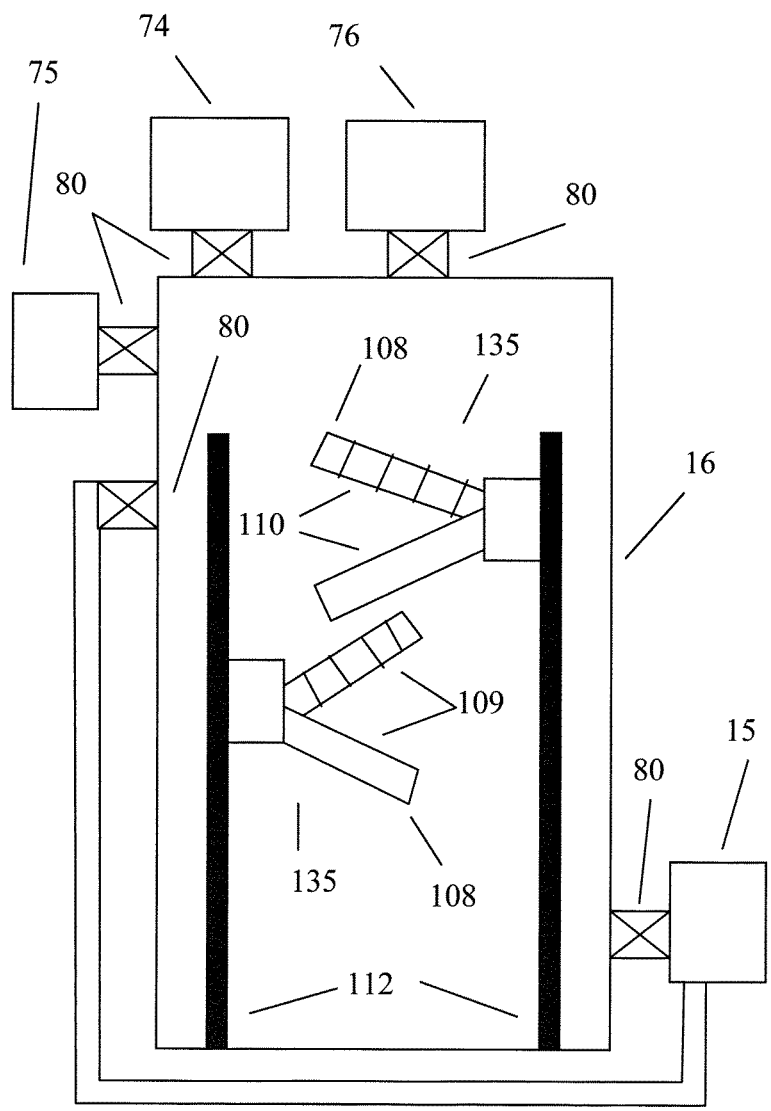
FIG. 34 is a schematic diagram of an enclosed chamber with a single primary grip retained on a first linear positioning device and a single secondary grip retained on a second linear positioning device for retaining an object to be treated.
Figure 35:
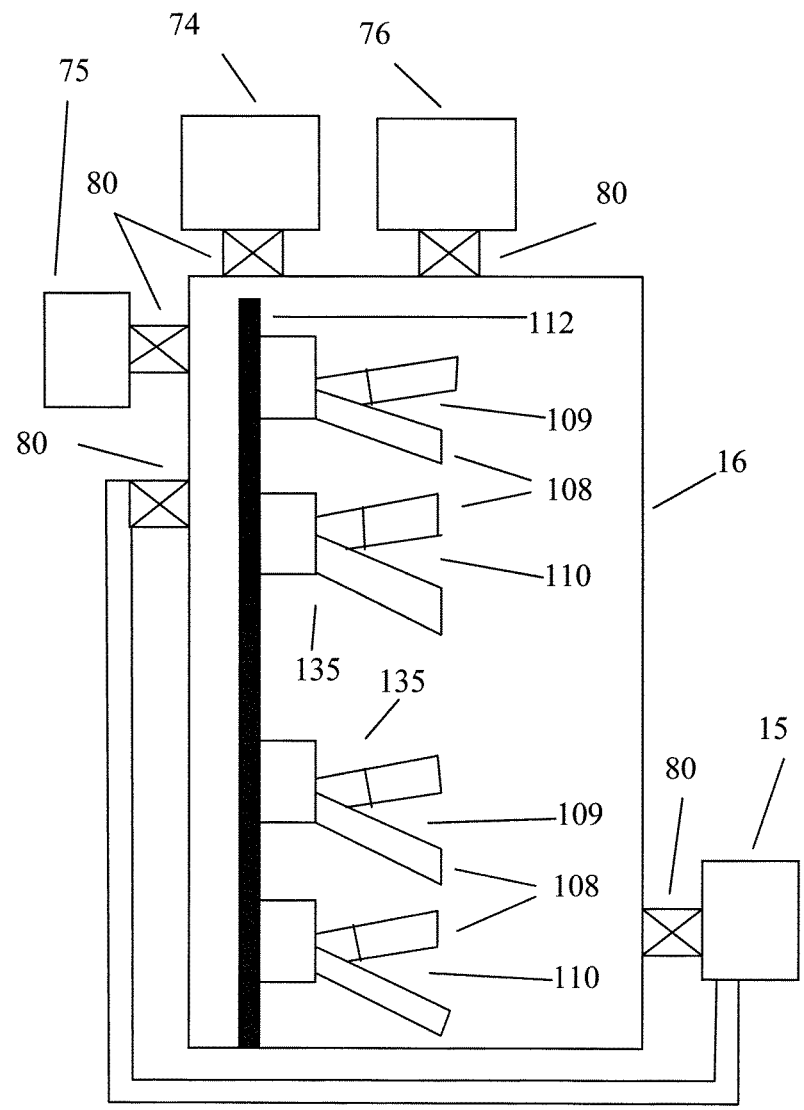
FIG. 35 is a schematic diagram of an enclosed chamber with two primary grips and two secondary grips retained on a single linear positioning device for retaining an object to be treated.

Referring to FIGS. 34 and 36, it is preferred, without limitation, that the one or more secondary gripping mechanism(s) (110) are at least partially staggered in a vertical fashion approximate to the primary gripping mechanism(s) (109), and the secondary gripping mechanism(s) (110) approximately face towards the primary gripping mechanism(s) (109). Now referring to FIG. 35 and FIGS. 40-41, it is even more preferred, without limitation, that the one or more secondary gripping mechanism(s) (110) are at least partially staggered in a vertical fashion approximate to the primary gripping mechanism(s) (109), and the secondary gripping mechanism(s) (110) approximately face out towards the same direction as the primary gripping mechanism(s) (109).

With reference to FIGS. 34-37 and FIGS. 40-41, the one or more various gripping mechanism(s) (135) including, but not limited to, its gripping fingers (108), should be, without limitation, positioned and spaced so that they do not touch, and their interface locations with the object(s) or endoscope(s) (01) do not overlap or create any shadowed areas that cannot be reached by the various processing activity(s). It is also preferred, without limitation, that any of the gripping mechanism(s) (135) components, including, but not limited to, gripping fingers (108), are designed or built so that the object(s) or endoscope(s) (01) cannot pivot, rotate, roll, or excessively move during the various processing activity(s).

Figure 39:
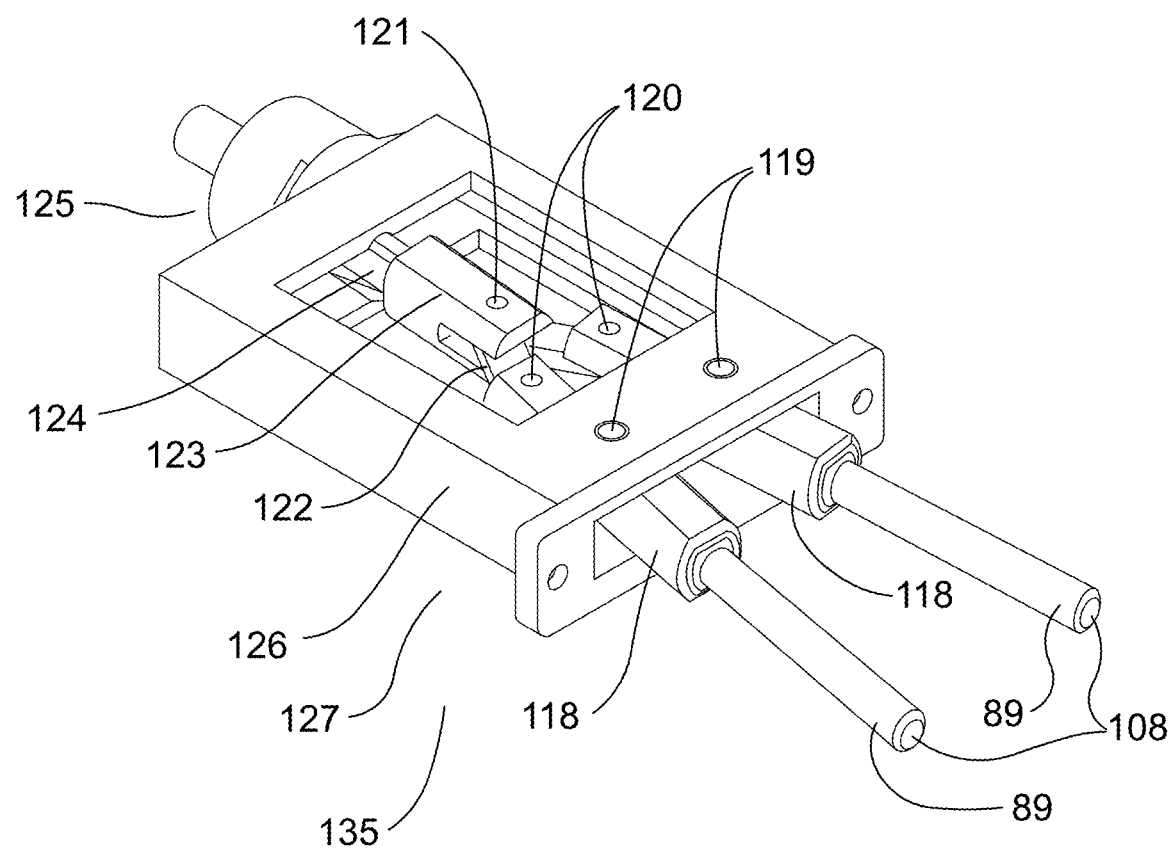
FIG. 39 is a perspective view of a grip for retaining an object to be treated.
Figure 40:
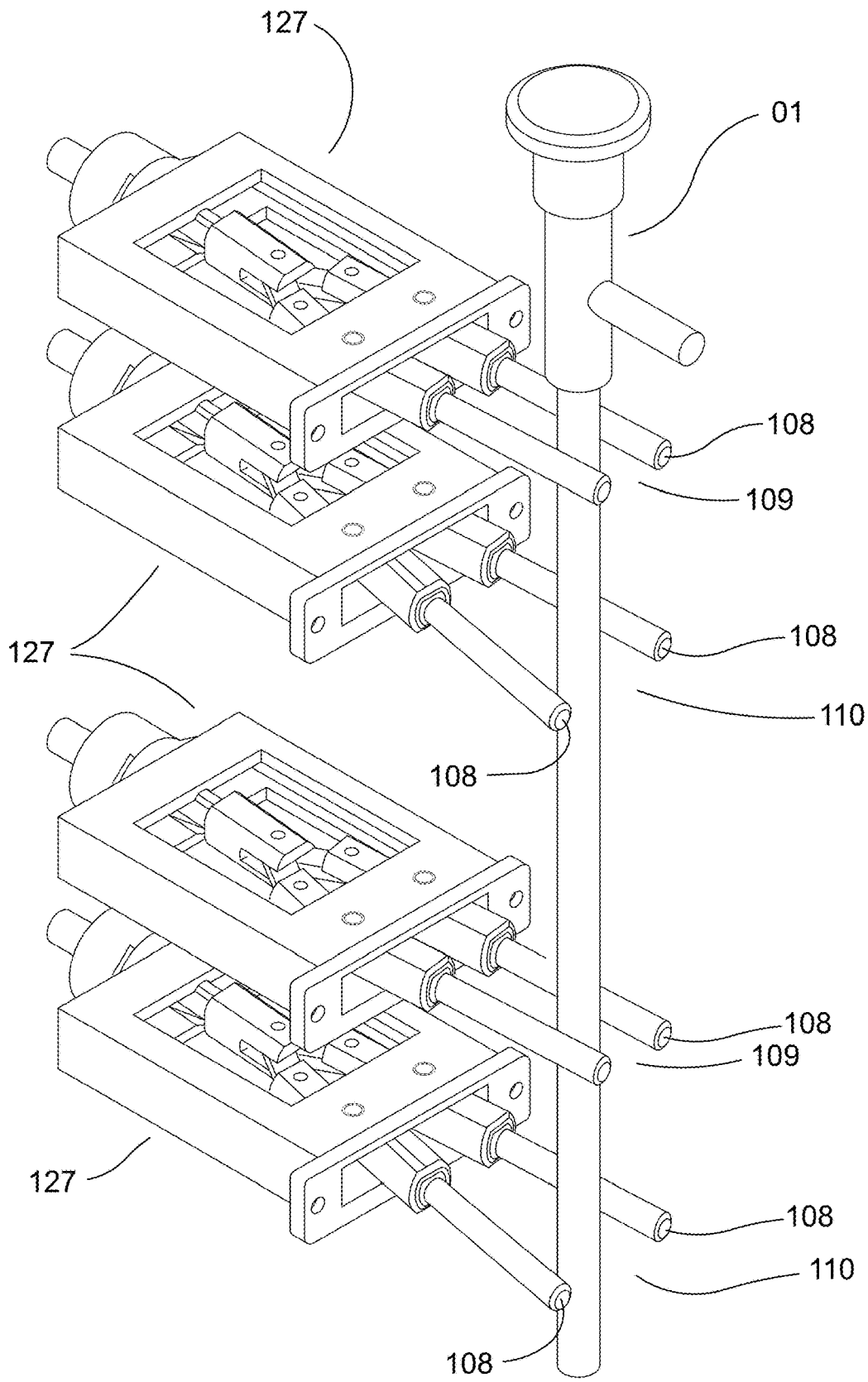
FIG. 40 is a perspective view of two primary grips retaining an object and a secondary grip positioned below each primary grip.
Figure 41:
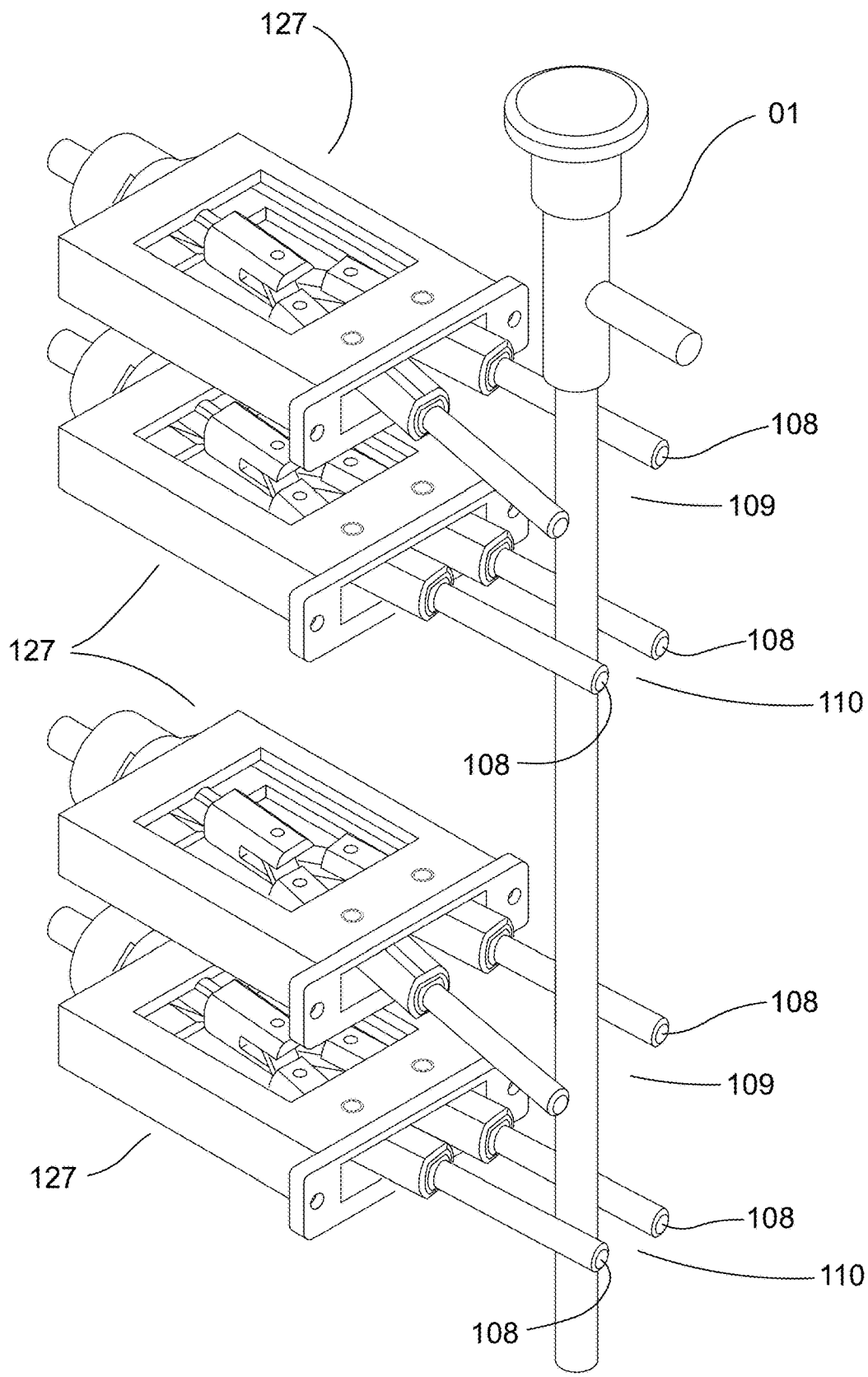
FIG. 41 is a perspective view of two secondary grips retaining an object and a primary grip positioned above each secondary grip.
Figure 42:
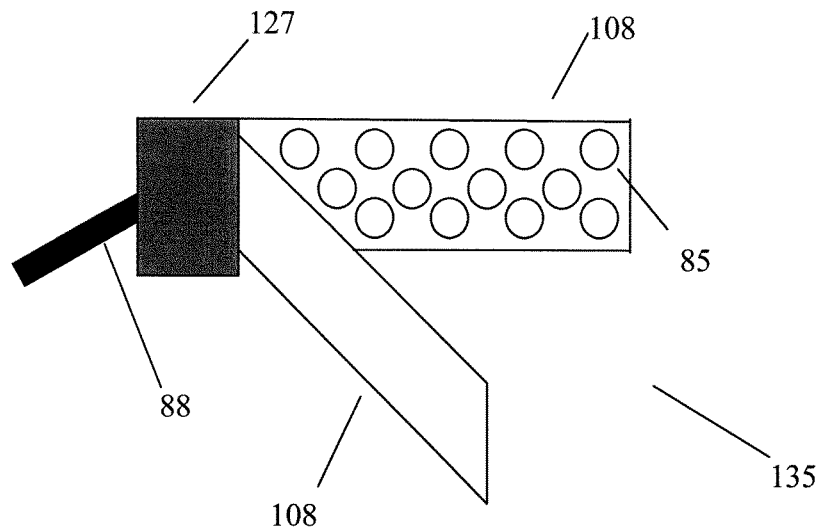
FIG. 42 is a perspective view of two gripping fingers with one or more openings.
Figure 43:
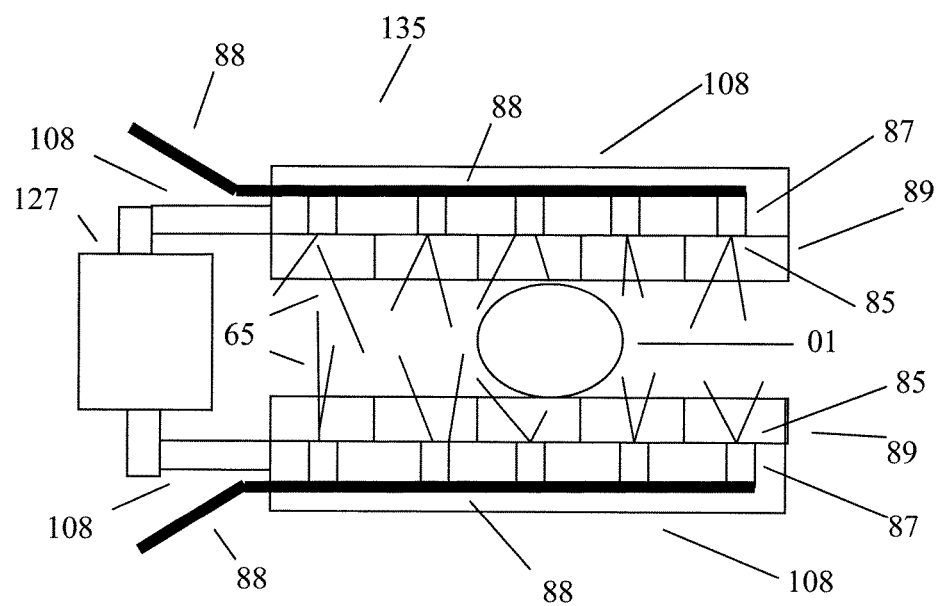
FIG. 43 is a side view of two gripping fingers with one or more openings and agent flowing through the one or more openings.

Without being limited, and according to a preferred embodiment and with reference to FIGS. 39-41, an even more specific description of the gripping mechanism(s) (135), including one or more of its mechanism(s) that is utilized to move or actuate (Herein called "movement mechanism(s)") (127), the one or more various gripping fingers (108), is given. It is preferred, without limitation, that the one or more movement mechanism(s) (127) is designed and constructed to include the at least two gripping fingers (108). However, the at least two gripping finger(s) (108) in addition to one or more of any other structures, braces, or supports, that are either static or movable, may also, without limitation, be utilized.

Each movable gripping finger (108) can be, without limitation, connected to, or interface with, one or more means to hold, support, or connect with the gripping finger(s) (108) (Herein called "socket interface(s)") (118). Each socket interface (118) can be directly or indirectly connected to one or more clevis(s) (123) that either directly or indirectly impart motion to the at least two gripping fingers (108). On the contrary, the at least two gripping fingers (108), can also be, without limitation, directly connected to any means that can cause it to move. The "socket interface(s)" (118) can be, without limitation, designed and constructed so that the at least two gripping finger(s) (108), can be removably retained. It is preferred, without limitation, that the gripping fingers (108) can be easily removed from the socket interface(s) (118) for applications where the gripping fingers (108) may need to be frequently replaced or even replaced after each use of the apparatus. The object interface material (89) and/or the various gripping fingers (108) can, without limitation, be designed and constructed so that the object interface material (89) that is utilized, can also be removably retained.

It is preferred, without limitation, that each socket interface (118) is connected to the clevis (123) via one or more linkage component(s) (122). Without being limited, each linkage component(s) (122), can connect directly or indirectly with the clevis(s) (123) via one or more "clevis pivot point(s)" (121), as well as directly or indirectly connect to each socket interface(s) (118) via one or more "socket interface pivot point(s)" (120). The "clevis pivot point(s)" (121) and the "socket interface pivot point(s)" (120) can, without limitation, consist of any vertical pin(s), rivet(s) or bolt(s) that effectively connect the various components together, and allow any effective movement of each socket interface(s) (118), or gripping fingers (108), all in a manner known to those skilled in the art.

However, for simplicity, the gripping fingers (108) can also, without limitation, connect directly to one or more clevis(s) (123). Without being limited, the gripping fingers (108), can connect directly or indirectly to the clevis(s) (123) via one or more "clevis pivot points" (121) that can, without limitation, consist of any vertical pin(s), rivet(s) or bolt(s) that connect the various components together, and allow any effective movement of each gripping finger (108), all in a manner known to those skilled in the art.

Each socket interface (118) can connect to the body or framework (126) of the movement mechanism(s) (127) via one or more pivot point(s) (119) that can, without limitation, consist of any vertical pin(s), rivet(s) or bolt(s) that connect the various components together, and allow any movement of each socket interface(s) (118), all in a manner known to those skilled in the art. The socket interface(s) (118) can be any suitable length.

The one or more clevis(s) (123) can be, without limitation, directly or indirectly connected to one or more means that can impart any effective motion to the clevis(s) (123). It is preferred, without limitation, that each clevis (123) is connected to one or more linear actuator rod(s) (124). It is also preferred, without limitation, that the linear actuator rod(s) (124) are able to cause the clevis(s) (123) to have an effective linear motion or close to an effective linear motion. The linear actuator rod(s) (124) are connected to one or means that can cause them to sufficiently move in a way to effectively open or close each of the various gripping fingers (108). It is preferred, without limitation, that the one or more linear actuator rod(s) (124) are connected to one or more of any linear actuator(s) (125) or stepper motor(s) that cause the linear actuator rod(s) (124) to move in an linear motion or close to a linear motion. Referring to FIGS. 39-41, it is preferred, without limitation, that when the clevis(s) (123) is moved outward, or away from the linear actuator(s) (125), the at least two gripping finger(s) (108) are able to close and effectively hold, grip, clamp, or otherwise support, the object(s) or endoscope(s) (01). Alternatively, and referring to FIGS. 39-41, it is preferred, without limitation, that when the clevis(s) (123) is moved inward, or towards the linear actuator(s) (125), the at least two gripping fingers (108) are able to open and effectively unhold, ungrip, unclamp, or otherwise lose or cease contact with, the object(s) or endoscope(s) (01). It is preferred, without limitation, that the one or more movement mechanism(s)") (127) are constructed from any suitable materials or combination of suitable materials such as, but not limited to, any compliant plastics and/or metals known to those skilled in the art.

Without being limited, the gripping mechanism(s) (135), movement mechanism(s) (127), socket interface(s) (118), gripping fingers (108), or any number of other structures, braces, or supports, that are either static or movable, can also be designed in a manner known in the art so they can pan, tilt, rotate, or be able to articulate, in any direction at any time, either mechanically or manually. Furthermore, any number of socket interface(s) (118), gripping fingers (108), or any other connecting parts, may have, without limitation, one or more hinges or sites of articulation, so that one or more of the socket interface(s) (118), gripping fingers (108), or any other connecting parts, can sufficiently move either manually or under any digital, electronic, or analog, controller or any PLC control, at any time, causing contact to cease with the object(s) or endoscope(s) (01), or causing the object(s) or endoscope(s) (01) to be effectively held, gripped, clamped, or otherwise supported. Any number of the gripping mechanism(s) (135), or movement mechanism(s) (127), utilized within the sterilization chamber(s) (16) can be, without limitation, directly or indirectly mounted or connected to one or more walls within the sterilization chamber(s) (16), or even structures within the sterilization chamber(s) (16) such as, but not limited to any, pipe(s), stand(s), or pole(s) (112), all in a manner known in the art.

Referring to FIGS. 34-41, one or more various components of the gripping mechanism(s) (135) such as, but not limited to, any gripping fingers (108), can also, without limitation, be designed and built so that they incorporate one or more sensors (hereinafter called "grip sensor(s)") (135), such as, but not limited to, any stress and strain gauge(s) or other measuring devices, known in the art, that can be connected to any digital, electronic, or analog, controller(s) such as, but not limited to, any PLC, in order to enable the PLC or controller(s) to sense, monitor, and adjust the amount of pressure that the at least two gripping fingers (108) may exert in order to not only sufficiently place, hold, grip, clamp, position, connect, interface, or otherwise support, the object(s) or endoscope(s) (01) within the closed space or sterilization chamber(s) (16), but also to perform functions such as, but not limited to any, unclamping, ungripping, releasing, or sufficiently decreasing or eliminating their holding pressure, so that the object(s) or endoscope(s) (01) can be released or disconnected. The grip sensor(s) (135) may be, without limitation, interfaced with or located anywhere on or within the structure, or any components of, the one or more various gripping mechanism(s) (135). It is preferred, without limitation, that if any grip sensor(s) (135) are utilized, they are at least interfaced with or located on or in any components of the movement mechanism(s)" (127) and/or the gripping fingers (108).

Referring to FIGS. 34-43, and as previously mentioned in the present invention, the at least two gripping fingers (108) can, without limitation, be sufficiently plumbed, and have one or more opening(s) (85), which can serve as either, or both, outlet(s) or inlet(s), through which various substances or materials used to process the object(s) or endoscope(s) (01) within the sterilization chamber (16) can optionally flow such as, but not limited to any, surfactant, rinse water, high purity rinse water, alcohol solution, "applied agent(s)", air/gas, heated air/gas. These various substances or materials may flow either out of or into the one or more opening(s) (85), where by doing so, they can directly or indirectly contact or interact with various surfaces of the object(s) or endoscope(s) (01). Any number of opening(s) (85) may be utilized and positioned anywhere on the object support(s) (84), but it is preferred, without limitation, that at least an effective number of object opening(s) (85) are used, and they at least effectively face various surfaces of the object or endoscope (01). The opening(s) (85) may be any size, shape, geometry, or design, known to those skilled in the art. Without being limited, the various substances or materials used to process the object(s) or endoscope(s) (01) within the sterilization chamber (16) can flow or move at any, quantity, rate, or pressure, at any time, for any duration of time, and can be used during one or more of any processing activity(s). These materials or substances can be, without limitation, supplied to the opening(s) (85) through one or more of various supply hose(s), pipe(s), conduit(s), or channel(s) or "process hose(s)" (88), and are flowed or moved in a manner known to those skilled in the art. One or more of any opening(s) (85) can be, without limitation, dedicated and plumbed (87) with any aerosol generation device (15) or any vapor generator, to flow one or more of any substance(s) or material(s) at any time, in order to process the object(s) or endoscope(s) (01). Agent (65) may be also be emitted through the openings 85 in the object interface 89 as supplied by one or more of various supply hose(s), pipe(s), conduit(s), or channel(s) or "process hose(s)" (88). The object interface 89 is retained on the gripping finger (108).

Also, referring to FIGS. 34-43, and as previously mentioned in the present invention, any object interface material (89) may also, without limitation, be positioned or maintained between the object(s) or endoscope(s) (01), and the at least two gripping fingers (108). The object interface material (89) may be, without limitation, permeable and/or absorbent. The at least two gripping fingers (108) may also be, without limitation, covered, coated, or constructed from one or more of any polymer(s), as well as any polymers that have a rubber-like durometer. It is preferred, without limitation, that the polymer(s) is chemically compatible with any agent(s) (20) that are used. The at least two gripping fingers (108) may also be, without limitation, constructed from any material that is porous and/or permeable. The at least two gripping fingers (108) may be, without limitation, constructed from any material that is absorbent.

According to an embodiment, and with reference to FIG. 34, one or more gripping mechanism(s) (135) can also, without limitation, be directly or indirectly mounted or connected to one or more walls within the sterilization chamber(s) (16), or even any structures within the sterilization chamber(s) (16) such as, but not limited to any, pipe(s), pole(s), or stand(s) (Hereinafter called "pole(s)") (or linear positioning device) (112), all in a manner known in the art. The pole(s) (112) may also be, without limitation, any tracks, channels, or other mounting structures known to those skilled in the art. The pole(s) (112) may, without limitation, directly or indirectly interface or be mounted on any walls within the sterilization chamber(s) (16). It is further preferred, without limitation, that the gripping mechanism(s) (135), can be adjusted, moved, or otherwise positioned or repositioned anywhere on the pole(s) (112), and locked or maintained in a static position with any locking or position maintaining mechanism (117), all in a manner known to those skilled in the art. It is also preferred, without limitation, that the pole(s) (112) are plumbed and connected to the necessary components in the present invention, so they can deliver various substances or materials such as, but not limited to any, surfactant, rinse water, high purity rinse water, alcohol solution, "applied agent(s)", air/gas, chilled air/gas, and/or heated air/gas, to the at least two gripping fingers (108). The one or more pole(s) (112) can also have, without limitation, one or more of any orifice(s) (113) of sufficient size, design, or construction, through which the various substances or materials such as, but not limited to any, surfactant, rinse water, high purity rinse water, alcohol solution, "applied agent(s)", air/gas, chilled air/gas, and/or heated air/gas, can be delivered to the at least two gripping fingers (108). The one or more orifice(s) may be located anywhere on the pole(s), but at least in one or more effective locations. Any unused orifice(s) can be, without limitation, temporarily or permanently plugged with any effective closure(s) (114) known in the art. Without being limited, the one or more gripping mechanism(s) (135), can be designed and constructed to effectively interface and/or seal (116) with the one or more orifice(s) (113).

According to an embodiment, and with reference to FIGS. 34-41, the one or more various gripping mechanism(s) (135), including, but not limited to, the primary gripping mechanism(s) (109) and secondary gripping mechanism(s) (110), and more specifically, the at least two gripping fingers (108), can, without limitation, sufficiently open and close in any order, at any time, and for any duration, provided that all of the surfaces that are shadowed or covered by the various gripping mechanism(s) (135), and more specifically the various gripping fingers (108), at any time during the various processing activity(s) that take place, are effectively and sufficiently processed by the end of all of the processing activity(s) or step(s) that are desired. In addition, the one or more of the various gripping mechanism(s) (135), and more specifically the various gripping fingers (108), can, without limitation, sufficiently open or close either independently, or as any group, in any order, at any time, and for any duration, provided that all of the surfaces that are shadowed or covered by the various gripping mechanism(s) (135), and more specifically the various gripping fingers (108), at any time during the various processing activities that take place, are effectively and sufficiently processed by the end of all of the processing activity(s) or step(s). Without being limited, the one or more of the various gripping mechanism(s) (135), and more specifically the various gripping fingers (108) may, without limitation, interface with the object(s) or endoscope(s) (01) at one or more of any effective location(s). It is preferred, without limitation, that at least one of the various gripping mechanism(s) (135), and more specifically the various gripping fingers (108), interfaces either directly or indirectly approximately at or near each end of the object(s) or endoscope(s) (01). It is even more preferred, without limitation, that at least one of the various gripping mechanism(s) (135), and more specifically the various gripping fingers (108), interfaces either directly or indirectly approximately at or near each end of the object(s) or endoscope(s) (01), and at least one or more of the various gripping mechanism(s) (135), and more specifically the various gripping fingers (108), also interfaces either directly or indirectly approximately at or near the middle or center of the object(s) or endoscope(s) (01).

According to an embodiment, and with reference to FIGS. 8-11, FIGS. 24-25, and FIGS. 34-43, all embodiments pertaining to the prevention of shadowing and the processing of the one or more surfaces and/or targeted surface(s) of the object(s) or endoscope(s) (01) may, without limitation, involve subjecting or exposing the object(s) or endoscope(s) (01) to any, one or more processing activity(s) or step(s), one or more combinations of processing activity(s) or step(s), as well as repeating one or more processing activity(s) or step(s), within the sterilization chamber (16). These processing activity(s) or step(s) may, without limitation, last for any length of time, but at least be or take part within, an efficacious amount of time. Without being limited, these processing activity(s) or step(s) are either addressed within the present invention, or are known to those skilled in the art. Furthermore, the object(s) or endoscope(s) (01) may be, without limitation, suspended, held, cradled, gripped, clamped, supported, in various ways, and in various orientations, within the sterilization chamber (16). The object(s) or endoscope(s) (01) may also be, without limitation, interfaced with one or more pressure interface assembly(s) (68), at any time, while they are suspended, held, cradled, gripped, clamped, transferred, supported, in various ways, and in various orientations, within the sterilization chamber (16). One or more of any processing activity(s) or step(s), substances, or materials may be, without limitation, used at any time, to process the object(s) or endoscope(s) (01) within the sterilization chamber (16) and may include, but not be limited to any, surfactant in aqueous solution, rinse water, high purity rinse water, alcohol solution, air/gas, chilled air/gas, "applied agent(s)", dehumidified air/gas, and/or heated air/gas, which can be used one or more times during any processing activities, for any duration, with any amount, at any concentration, with any temperature of substance used, and can be used in any order or with any combination of processing activities needed.

Figures 37A, 37B:
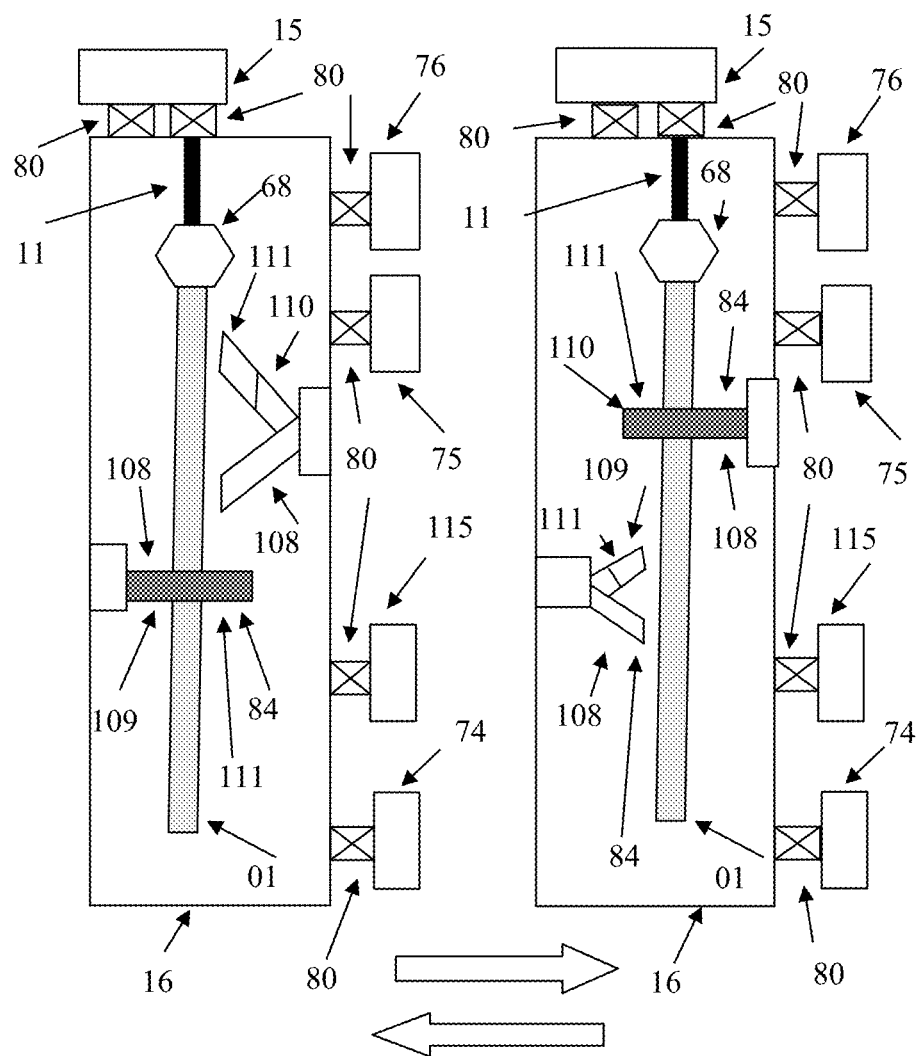
FIG. 37a is a schematic diagram of a primary grip retaining an object in an enclosed chamber and an open secondary grip.
FIG. 37b is a schematic diagram of a secondary grip retaining an object in an enclosed chamber with an open primary grip.
Figure 38:
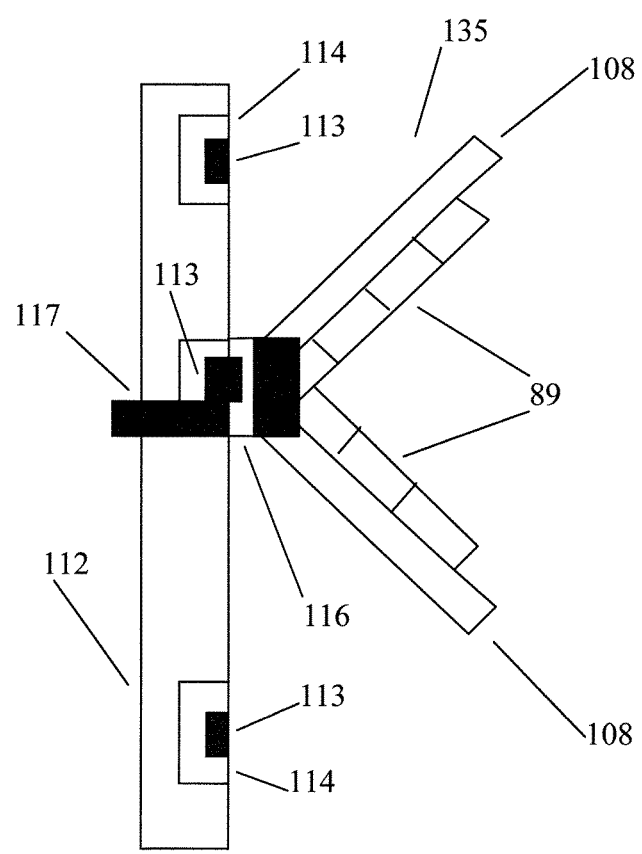
FIG. 38 is a schematic diagram of a grip retained on a linear positioning device.

With reference to FIGS. 36-37, the use of any heated air/gas may, without limitation, be used as processing activity(s) within the sterilization chamber(s) (16) as well as within the object(s) or endoscope(s) (01). Without being limited, heating the air or gas inside of the sterilization chamber(s) (16) may be accomplished with any air or gas heating device or means (115) known to those skilled in the art. It is preferred, without limitation, that the air or gas that is heated inside of the sterilization chamber (16) is any air or gas that is present inside of the sealed sterilization chamber(s) (16). The air or gas within the sterilization chamber(s) (16) and/or object(s) or endoscope(s) (01) can be heated, without limitation, at any time, and for any duration, and any temperature. The heated air or gas within the sterilization chamber(s) (16) may be utilized, without limitation, one or more times during any processing activities, for any duration, with any amount, and can be used in any order or with any combination of processing activities needed.

With reference to FIG. 37, and according to an embodiment, the sterilization chamber(s) (16) can also, without limitation, include one or more of any drain(s) (128). The drain(s) (128) can be located anywhere within the sterilization chamber(s) (16) and can be any size and construction known to those skilled in the art. It is preferred, without limitation, that at least one drain (128) is located in, or approximate to, the bottom of the sterilization chamber(s) (16), and the bottom of the sterilization chamber(s) (16), is designed and built to channel any liquid(s) present in the bottom of the sterilization chamber(s) (16) into the drain(s) (128). The flow of any gas(s) or liquid(s) through the drain(s) (128) can be, without limitation, controlled with one or more of any door, valve, cap, or other separating device or valve (Herein called "drain valve(s)") (130) known to those skilled in the art. It is also preferred, without limitation, that the drain valve(s) (130) can be controlled by one or more of any electronic, analog, or digital controller(s), or PLC(s). It is preferred, without limitation, that the drain valve(s) (130) can effectively seal. The one or more drain(s)

(128) can be, without limitation, plumbed or connected to one or more reservoir(s) (129) of any size and construction to hold any liquid(s) that are drained or removed from the sterilization chamber(s) (16). However, it is preferred, without limitation, that the sterilization chamber(s) (16), as well as any collection reservoir(s) (129) if they are utilized, are either directly or indirectly plumbed or connected to any sanitary waste system or sewer system. The reservoir(s) (129) can also be designed and construed so that they can be, without limitation, easily removed from the rest of the apparatus for removal of any liquids or cleaning. The drain(s) (128), valve(s) (130), reservoir(s) (129) or any other plumbing, or other related part(s) or component(s) can all be constructed from any material that is compatible, and suitable for use with the applied agent(s) (20).

Figure 44:
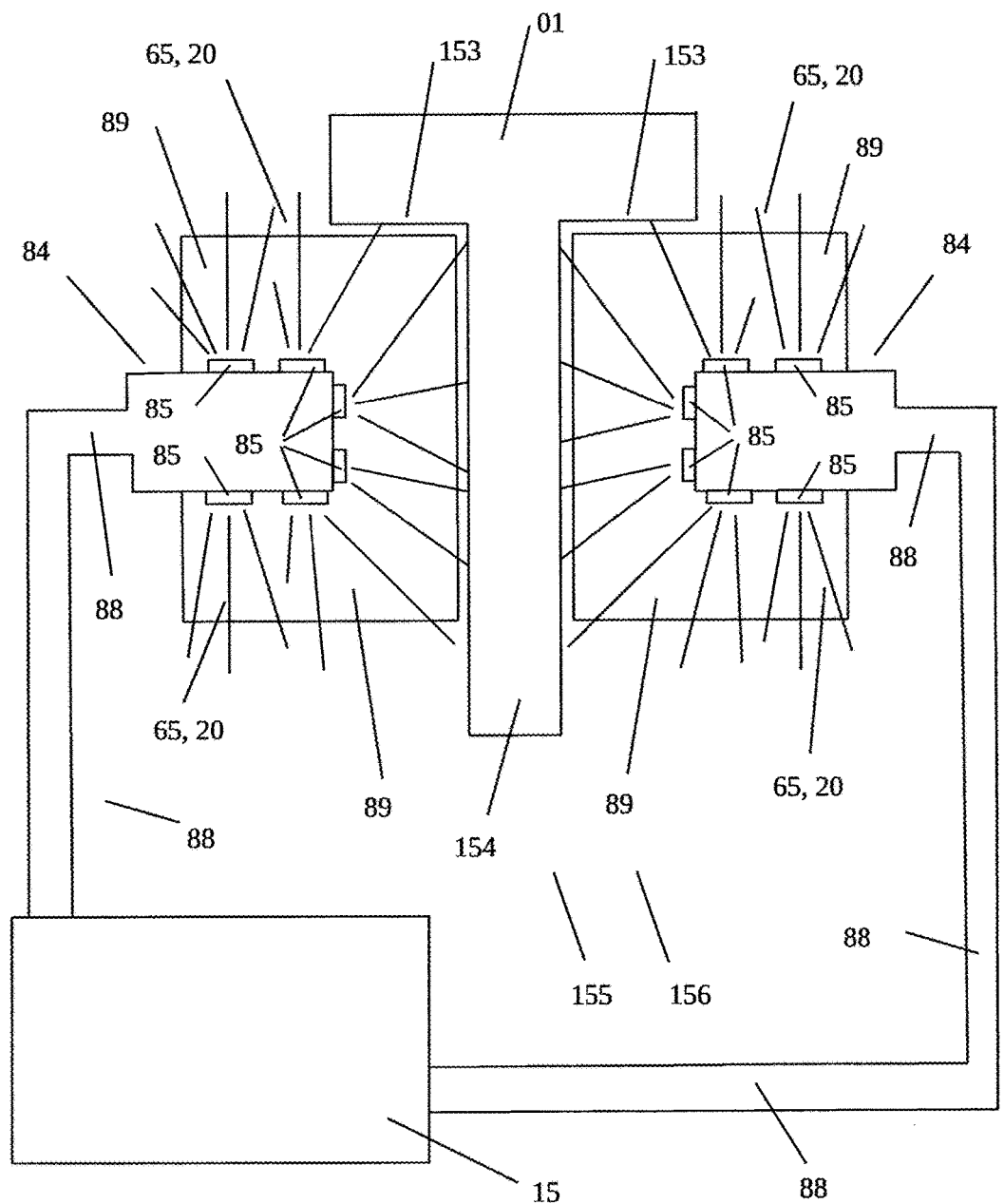
FIG. 44 is a side view of an object held by two enhanced object holders and agent flowing through the one or more openings of each enhanced object holders.
Figure 112:
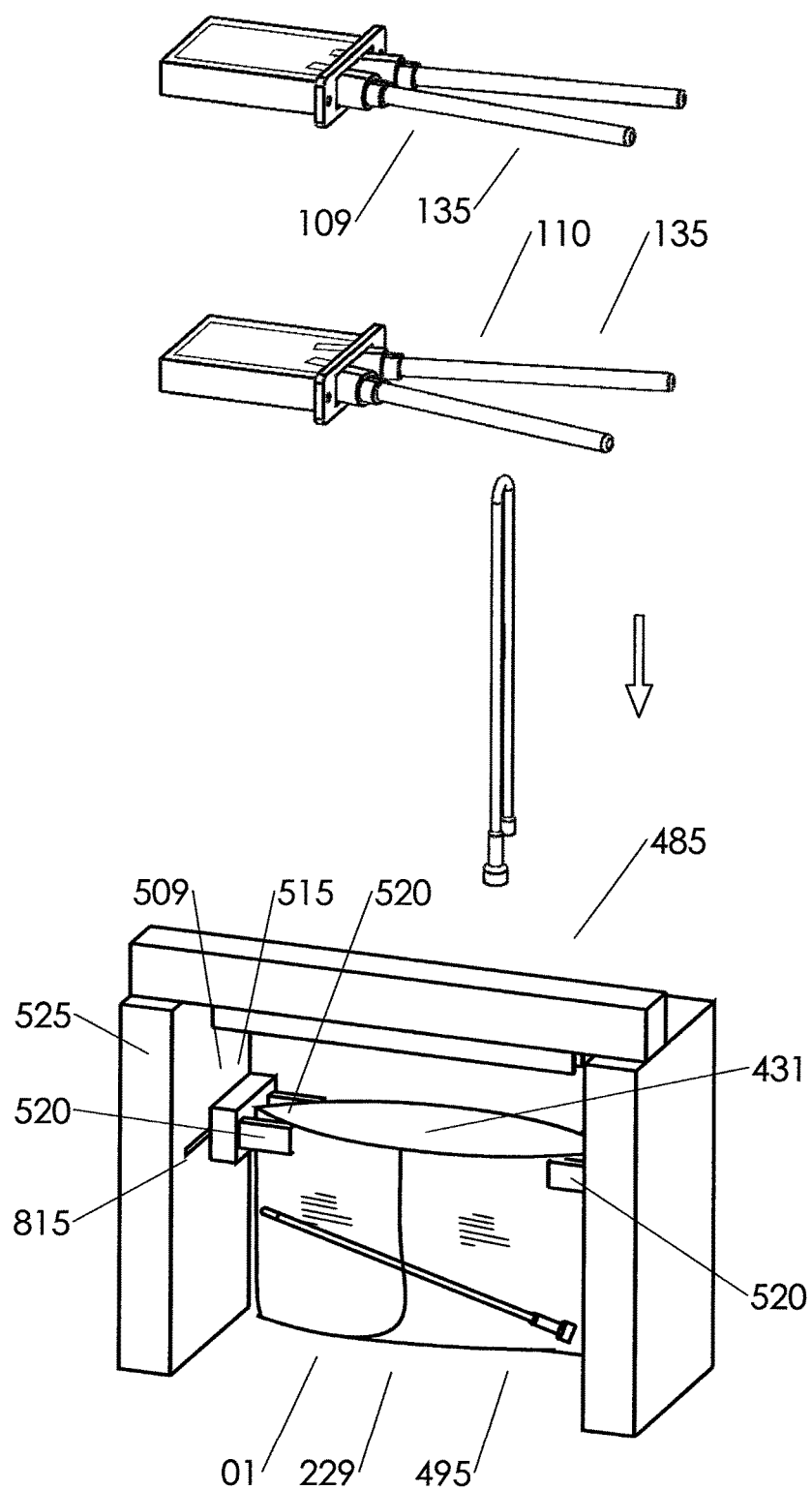
FIG. 112 is a schematic type view of, a plurality of gripping mechanism(s) (135) dropping object(s) into the open removable package(s) (229) and/or packaging and open packaging material(s) (495).

Referring to FIGS. 44-112, and without being limited, incomplete surface treatments and processing, for the sanitization, disinfection, high-level disinfection, sterilization, and/or decontamination, of various surface(s) of object(s), continues to be a problem in the current art, and therefore an important need still exists in the current art for the full, complete, and effective, sanitization, disinfection, high-level disinfection, sterilization, and/or decontamination, of various object(s) surfaces, such as, but not limited to any and/or all, external surfaces, and/or also including in certain instances but not limited to any and/or all targeted, internal surface(s), of one or more of any object(s) (01) such as, but not limited to any, endoscope(s), medical related apparatus(s) and tooling, scientific apparatus(s) and tooling, laboratory apparatus(s) and tooling, medical related sensor(s), medical instrumentation, data and/or communication cable(s), power wire(s) and cable(s), communication wire(s) and cable(s), fiber optic cable(s) and conduit(s), fiber optic line(s), ultrasonic probe(s), and/or including one or more of any attached and/or unattached object(s) such as, but not limited to any, tube(s), pipe(s), conduit(s), cable(s), wire(s), fiber optic line(s), plug(s), lid(s), support member(s), socket(s), interface(s), connector(s), and/or wire(s) (Herein called "Object(s)") (01).

This need especially presents itself when effectively, positioning, locating, supporting, holding, hanging, and/or suspending, the various object(s) (01) to be treated and processed, within one or more of any types of suitable and effective, treatment area(s), treatment space(s), and/or treatment enclosure(s). It is preferred, without limitation, that the various treated and processed surfaces belonging to area(s), locations(s), and object(s) such as, but not limited to any, object(s) (01), removable treatment enclosure(s) (230), open removable package(s) (229), open package(s) and/or packaging material(s) (495), and/or container holding chamber(s) (265), do not touch or contact, at least until after all of the various treatment and processing steps are completed, and preferably until all of the mentioned surface(s) are effectively, disinfected, high-level disinfected, and/or sterilized.

In one aspect, and without limitation, the one or more of any treatment enclosure(s) can be any suitable and effective chamber(s) (Herein called "Container Holding Chamber(s)") (265), that is preferably, and without limitation, accessed through one or more of any suitable opening(s) (Herein called "Access Opening(s)") (not shown) that can preferably, and without limitation, be suitably and effectively, covered, closed, and/or sealed, with one or more of any suitable and effective reopenable door(s) and/or resealable cover(s) at any effective time(s), but preferably can be closed and/or effectively sealed closed during any treatment and processing activities within the container holding chamber(s) (265). Without being limited, the access opening(s) can also be opened for various activities such as, but not limited to, placing, locating, installing, and/or removing, any open and/or closed enclosure(s) such as, but not limited to any, open removable package(s) (229), and/or sealed and/or closed package(s) (720), as well as, locating one or more object(s), removable treatment enclosure(s) (230), open removable package(s) (229), and/or open package(s) and/or packaging material(s) (495), effectively inside of the container holding chamber(s) (265). Without being limited, the container holding chamber(s) (265) and any of its access opening(s), can be any suitable and effective, size, length, width, height, depth, design, shape, and/or geometry. The container holding chamber(s) (265) can be, without limitation, effectively connected to one or more of any effective means to treat and process any, surface(s), contents, and/or object(s) (01) within the container holding chamber(s) (265). The various space(s) and surfaces within the container holding chamber(s) (265) can be suitably and effectively treated and processed at any time(s) as described later in the present invention.

Without limitation, the one or more of any object(s) (01) can be effectively located, treated, processed, and/or packaged, within the one or more of any container holding chamber(s) (265), in various ways including, but not limited to: (a) effectively locating the at least one object(s) (01) suitably above, semi-within, and/or within, at least one or more suitable open removable package(s) (229), and/or open package(s) and/or packaging material(s) (495), that is effectively open and effectively sized at or near its top or top area, and also preferably and without limitation effectively closed at or near its bottom area, and is effectively located inside of the container holding chamber(s) (265), and effectively dropping the one or more object(s) (01) effectively into the open removable package(s) (229) after the surface(s) of the object(s) (01), and also preferably and without limitation any packaging material(s), are effectively treated, dried, degassed, and/or processed, and then effectively sealing and/or closing the object(s) (01) within their open removable package(s) (229) to form one or more effectively closed package(s) (720) that is preferably, and without limitation, hermetically sealed, (b) effectively locating the at least one object(s) (01) suitably below, semi-below, and/or within, at least one of any suitable open removable package(s) (229), and/or open package(s) and/or packaging material(s) (495), that is effectively open and effectively sized at or near its bottom or bottom area, and also preferably and without limitation effectively closed at or near its top area, and is effectively located inside the container holding chamber(s) (265), effectively treating, drying, degassing, and/or processing, the surface(s) of the object(s) (01), and also preferably and without limitation any packaging material(s), then effectively moving and/or locating the one or more open removable package(s) (229) around the one or more object(s) (01) if needed, but preferably and without limitation, at least after the object(s) (01) and any other surfaces, are effectively treated, dried, and processed, and then effectively sealing and/or closing the object(s) (01) within their open removable package(s) (229) to form one or more effectively closed package(s) (720) that is preferably, and without limitation, hermetically sealed, and/or (c) effectively treating and processing the at least one object(s) (01) within the container holding chamber(s) (265), moving and/or locating one or more of any suitable open removable package(s) (229) and/or open package(s) and/or packaging material(s) (495) into any effective, proximity to, and/or location under, the object(s) (01) before and/or after the object(s) (01) are effectively treated, dried, degassed, and/or processed, where the object(s) (01) are then effectively dropped and/or moved into the one or more effective open removable package(s) (229) and/or any suitable open package (229) that is formed in a manner known to those skilled in the art within the container holding chamber(s) (265) using the supplied packaging material(s) (495), and then effectively sealing and/or closing the object(s) (01) within their open removable package(s) (229) to form one or more effectively closed package(s) (720) that is preferably, and without limitation, hermetically sealed. Without being limited, the open removable package(s) (229) can also include, but is not limited to, any suitable and effective, open package(s) and/or packaging material(s) (495). Also, without being limited, the "packaging material(s)" (495) can include, but is not limited to any, one or more of any suitable and effective material(s) used to form any, package(s), open package(s), open removable package(s) (229), partially created open package(s), and/or any partially created open packaging materials (Herein called "Open Package(s) And/or Packaging Material(s)") (495).

In another aspect, and without limitation, the one or more of any treatment enclosure(s) can also be any suitable and effective removable enclosure(s) (Herein called "Removable Treatment Enclosures") (230), that is effectively closed and/or sealed during the treatment and processing of the one or more of any object(s) located inside. The removable treatment enclosure(s) (230) can be, without limitation, effectively connected to one or more of any means to treat and process any contents and/or object(s) (01) within the removable treatment enclosure(s) (230). The various space(s) and surfaces within the removable treatment enclosure(s) (230) can be suitably and effectively treated and processed at any time(s) as described later in the present invention. The one or more removable treatment enclosure(s) (230) can be located at or within any suitable and effective location(s), however it is preferred, without limitation, that the removable treatment enclosure(s) (230) are suitably and effectively located at any suitable and effective location(s) inside of any suitable and effective container holding chamber(s) (265).

With reference to FIGS. 44-52, 53, 57, 64, 66, 68, 69-70, 73, 75, 82, 84, 86, 88, 91, and 98-101, and according to an embodiment, and without limitation, surfaces of object(s) (01) that are interfaced with any other surfaces, and are covered or otherwise "shadowed", can prevent effective and/or efficacious treatment of these covered or shadowed surfaces by the applied agents (20) such as, but not limited to any, aerosol(s) (65), gas(s), and/or vapor(s), presenting contamination and infection risks, especially in the health care environment. Also, and without being limited, the following embodiments address the need in the current art to effectively, treat, process, decontaminate, sanitize, high-level disinfect, and/or sterilize, various medical tooling, devices, equipment, and/or any other various attached and/or detached associated component(s).

Also with reference to FIGS. 44-52, 53, 57, 64, 66, 68, 69-70, 73, 75, 82, 84, 86, 88, 91, and 98-101, and without limitation, an apparatus and method of another embodiment of the present invention comprises an enhanced means to support and/or hold (155)(156)(160) one or more of any object(s) (01) such as, but not limited to any, endoscope(s), medical related sensor(s), medical instrumentation, medical tooling, data and/or communication cable(s), fiber optic cable(s), ultrasonic probe(s), and/or including one or more of any attached and/or unattached object(s) (01) such as, but not limited to any, tube(s), pipe(s), cable(s), fiber optic line(s), cable(s), plug(s), connector(s), and/or wire(s), that can be effectively located and/or positioned within one or more of any location(s) and/or area(s) such as, but not limited to any suitable and effective, removable treatment enclosure(s) (230), open removable package(s) (229), open package(s), and/or packaging material(s) (495), container holding chamber(s) (265), package(s), and/or enclosure(s), and to effectively, treat, sanitize, disinfect, high-level disinfect, sterilize, process, and/or decontaminate, the one or more of any surfaces of any of the supported and/or held object(s) (01), including any surfaces of any object(s) (01) that are interfaced or connected with the one or more means to support or hold the various object(s) (01). It is preferred, without being limited, that any other surfaces within the one or more of any suitable and effective area(s) and space(s) such as, but not limited to any, removable treatment enclosure(s) (230), open removable package(s) (229), open package(s), and/or packaging material(s) (495), container holding chamber(s) (265), package(s), and/or enclosure(s), are also treated, processed, and decontaminated, with the same and/or effectively similar treatment and processing step(s) or process(s) that takes place to treat and process the various surface(s) within any container holding chamber(s) (265).

Without being limited, the present invention provides for the effective support and holding of these various one or more object(s) (01), while treating the various object(s) (01) surfaces that can be present and interfaced, in one or more of any, angles, direction(s), geometries, size(s), dimension(s), aspect(s), and/or perspectives, as well as any other surface(s) that are not interfaced with any other surfaces or are otherwise "not shadowed".

Referring to FIGS. 44-52, and without being limited, even more detailed descriptions of FIGS. 44-52 can be described as follows. The one or more of any object(s) (01) can be effectively, and without limitation, supported, suspended, held, and or located, by one or more of any effective, enhanced object(s) holder(s) (155) such as, but not limited to any, (a) enhanced multiple member object holder(s) (156), (b) enhanced round object holder(s) (160), (c) enhanced forked extension(s) object holder(s) (165), and/or (d) enhanced cable and hose holder(s) (195), in one or more of any suitable and effective and location(s) within the one or more of any suitable and effective area(s) and/or enclosure(s) such as, but not limited to any, removable treatment enclosure(s) (230), open removable package(s) (229), open package(s), and/or packaging material(s) (495), and/or container holding chamber(s) (265).

Without being limited, the enhanced object(s) holder(s) (155) can include at least one effective layer(s) of any suitable and effective object interface material(s) (89) that are effectively, located on, connect with, and/or interface with, one more of any effective side(s) and/or axis(s) of the at least one object supports (84). The one or more object support(s) (84) can have, without limitation, one or more of any suitable and effective opening(s) (85) that can have any suitable and effective attribute(s) such as, but not limited to any, size, position, location, number, shape, density, and/or geometry. Without being limited, any effective number and density of opening(s) (85) can be located at one or more of any effective location(s) and effectively located on or more of any side(s) of the object supports (84), preferably and without limitation, on any sides of the object supports (84) that can have any chance of contact with any surface(s) of the object(s) and where these area(s) of surface contact(s) can be effectively treated and processed. It is preferred, without limitation, that at least an effective number of opening(s) (85) are present, and at least an effective quantity of deployed applied agent(s) (20), aerosol(s) (65), and/or vapor(s), are effectively moved out of and/or deployed from and/or through the various opening(s) (85). Without being limited, the object interface material(s) (89) can also have any suitable and effective, length, width, height, depth, design, interface, holding and/or mounting mechanism(s), shape, thickness, density, pore size, and/or geometry.

Without being limited, the various part(s), piece(s), and/or member(s) of any object support(s) (84), can be positioned at any effective angle(s) and/or orientation(s), and have any effective, length(s), width(s), height(s), depth(s), geometry(s), angle(s), shape(s), and/or design(s), so that the treated object(s) (01) can effectively fit onto and/or into the one or more enhanced object holder(s) (155), and also cannot move slide, and/or roll, off of the various object support(s) (84) once the object(s) (01) are effectively interfaced with the object support(s) (84) and/or any object interface material(s) (89).

Without being limited, the object interface material(s) (89) can also be suitably and effectively pre-treated and/or packaged with one or more of any effective, agent(s), treatment agent(s), decontamination agent(s) or substance(s), such as, but not limited to any effective, sanitizer(s), disinfectant(s), and/or sterilant(s), and packaged in any effective package(s) and manner, known to those skilled in the art. The object interface material(s) (89) can be removed from the package(s) (not shown) and installed and/or replaced at any suitable and effective time(s) by any employee(s) and/or technician(s).

It is preferred, without limitation, that the object interface material(s) (89) can be pre-treated with the same applied agent(s) (20) that are deployed in any airborne manner and/or modality. However, and without being limited, the object interface material(s) (89) can be used in any suitable condition(s) such as, but not limited to, untreated, treated, dry and untreated, wet and treated. It is preferred, without limitation, that the various object interface material(s) are supplied in any suitable dry and untreated state and/or wet and treated state, depending on the various situations of use and/or intended use and any level of, performance, effectiveness, and/or efficacy, that is needed.

Without being limited, one or more of any suitable and effective, protrusion(s), extension(s), member(s), and/or any other extending part(s), of the object(s) (01), (Herein called Object Extension(s)) (153) can rest on and/or be supported by, various part(s) of the enhanced object holder(s) (155) such as, but not limited to any, object support(s) (84), and object interface material(s) (89). It is preferred, without limitation that any part of the object(s) (01) such as, but not limited to any object extension(s) (153) and/or any other suitable and effective part(s) and/or surface(s) of the object(s) (01) can rest on and/or be supported by the various object interface material(s) (89) and at least an effective, volume, concentration, and flow rate, of the deployed applied agent(s) (20), aerosol(s) (65), and/or vapor(s) is able to flow through the various opening(s) (85) and object interface material(s) (89), and at least have an effective contact and efficacious interaction with the various surface(s) of the various object(s) (01).

Without limitation, the one or more of any object support(s) can connect with one or more of any suitable and effective supply(s) of and/or means of generation for, any effective, deployed applied agent(s) (20), aerosol(s) (65), and/or vapor(s), such as, but not limited to, one or more of any suitable generation chamber(s) (15). It is preferred, without limitation, that the generation chamber(s) (15) also includes one or more of any suitable and effective means to effectively move the deployed applied agent(s) (20), aerosol(s) (65), and/or vapor(s), to location(s) where they are needed, such as, but not limited to any, fan(s), blower(s), air pump(s), and/or any other suitable source(s) of pressurized air/gas(s) known to those skilled in the art (not shown). Without being limited, the generation chamber(s) (15) can effectively connect and communicate with various part(s) and location(s) such as, but not limited to any, container holding chamber(s) (265), object support(s) (84), opening(s) (85), and/or object interface material(s) (89), via one or more of any suitable, tube(s), hose(s) ducting(s), conduit(s), channel(s), tunnel(s) (Herein called pipe(s) (18) and/or process hose(s) (88). Without being limited, any enhanced object(s) holder(s) (155), and more preferably and without limitation, any object support(s) (84) of any enhanced object(s) holder(s) (155), can connect with one or more of any suitable process hose(s) (88) in one or more of any suitable and effective location(s). It is preferred, without limitation, that the process hose(s) (88) connect with the object support(s) (84) using one or more of any suitable releasable connections such as, but not limited to any process hose connection(s) (185) as shown in FIG. 47, and known to those skilled in the art.

Without being limited, one or more of any other suitable and effective substance(s) can also flow through the various object support(s) (84), opening(s) (85), and/or object interface material(s) (89), at one or more of any effective time(s), such as, but not limited to any, dehumidified air/gas(s), heated air/gas(s), cooled and/or refrigerated air/gas(s), air/gas(s) that have been removed of any vapor(s), filtered air/gas(s), and/or flows of air/gas(s) under with any effective positive and/or negative pressure(s). Also, without limitation, the said various substance(s) and any deployed applied agent(s) (20), aerosol(s) (65), and/or vapor(s), can be supplied to various area(s) and location(s) such as, but not limited to any, object support(s) (84), opening(s) (85), and/or object interface material(s) (89), with any suitable and effective attributes such as but not limited to any, flow rate(s), concentration(s) of applied agent(s), aerosol(s), and/or vapor(s), flow volume(s), and/or flow speed(s).

Without being limited, one or more, but preferably many, opening(s) (85) are effectively, sized, located, and positioned, with any effective, angles, density, number, direction(s), geometries, size(s), dimension(s), aspect(s), and/or perspectives, to allow the applied agent(s) (65)(20) that is supplied to the various object support(s) (84) and/or opening(s) (85), to interact with the various surface(s) of any, endoscope(s), ultrasonic probe(s), and/or object(s) (01), to effectively, sanitize, disinfect, high-level disinfect, sterilize, decontaminate, and/or treat, the various, object(s) (01), endoscope(s), and/or ultrasonic probe(s). Without being limited, these various opening(s) (85) can also be located at any location(s) including, but not limited to, any effective location(s) where an interface or even any potential interface, with any object interface material(s) (89) and/or object support(s) (84), and the various object(s) (01), shall, might, might possibly, might possibly not, and/or may not, occur.

Without limitation, the applied agent(s) (20)(65) that is generated and/or supplied by one or more of any suitable applied agent source(s) and/or generation chamber(s) (15), and preferably and without limitation, any suitable and effective means for creating any effective aerosol (65), can also flow through one or more of any suitable process hose(s) (88) that can effectively connect the generation chamber(s) (15) to any effective location(s) such as, but not limited to any, enhanced object(s) holder(s) (155), enhanced multiple member object holder(s) (156), enhanced round object holder(s) (160), enhanced forked extension(s) object holder(s) (165), enhanced cable and hose holder(s) (195), object supports(s) (84), and/or opening(s) (85). More specifically, and without limitation, the applied agent(s) (20) (65), aerosol(s), and/or vapor(s), can flow through any object supports(s) (84), then through the one or more of any effective opening(s) (85) in the object support(s) (84), and then preferably through one or more of any effective object interface material(s) (89) that is effectively located between the object support(s) (84) and the various, endoscope(s), ultrasonic probe(s), and/or object(s) (01), before it treats the various surface(s) of the interfacing object(s) (01). Without limitation, the interface material(s) (89) can also function as the object support(s) (84) and/or process hose(s) (88).

Without being limited, the at least one of any suitable object support(s) (84) and/or object interface material(s) (89), can be effectively located and positioned within any enclosure(s) in any effective and suitable manner known to those skilled in the art. For example, and without limitation, the one or more object support(s) (84) and/or process hose(s) (88) can be directly and/or indirectly, attached, hung, suspended, connected, and/or interfaced, to and or from, one or more of any suitable, positioning and/or support member(s) (not shown), and/or container hanging member(s) (450). Without being limited, one or more of any suitable and effective hose(s) (88) can also be used to position and/or locate one or more of any, object(s) (01) and object support(s) (84), within any area(s) or enclosure(s) such as, but not limited to any, container holding chamber(s) (265), if they have suitable attribute(s) such as, but not limited to, being effectively, thick, rigid, and/or possessing the necessary and effective material, design, and structural properties, known to those skilled in the art.

Figure 45:
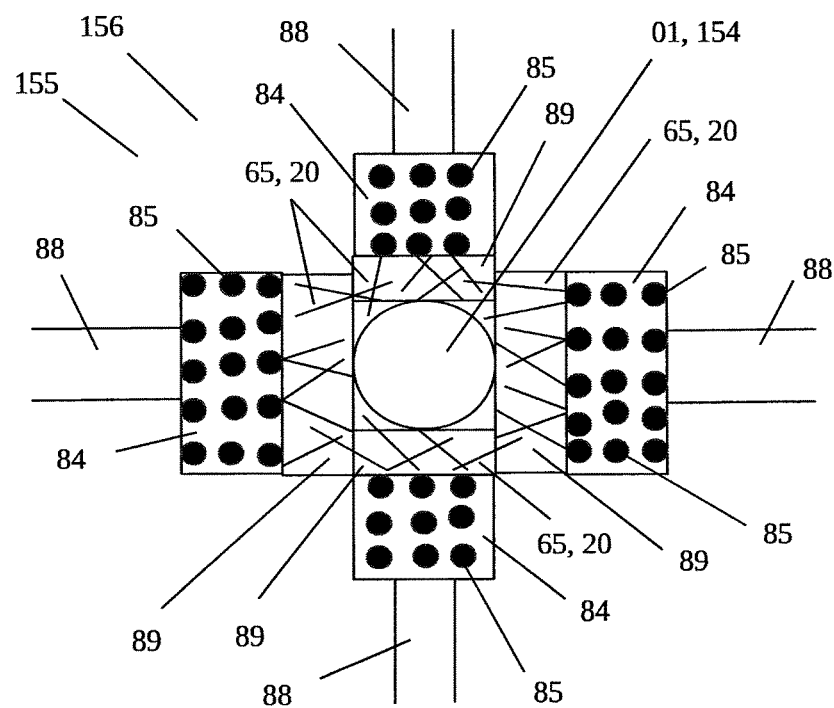
FIG. 45 is a top view of an enhanced multiple member object holder, for supporting, holding, and treating, the interfaced object(s). Agent is flowing through the one or more openings of each enhanced object holders, treating the object located in the middle of the multiple object supports (84).

In one aspect, and with reference to FIG. 44-45 without limitation, the one or more of any endoscope(s), patient sensor cable(s), ultrasonic probe(s), or otherwise "object(s)" (01) can be held and/or supported in any effective, orientation(s), vertical, upright, horizontal, semi-upright, and/or any other suitably angled, position(s), by the at least one, but preferably and without limitation, at least two, of any suitable object support(s) (84) and/or object interface material(s) (89), where the object(s) (01) are preferably and without limitation, interfaced with at least two object supports (84), and also without limitation, one or more of any effective object interface material(s) (89) that is effectively positioned between the two or more object supports (84) and the one or more treated object(s) (01) (Herein called "Enhanced Multiple Member Object Holder(s)") (156). Without being limited, one or more of any part(s) of the object(s) (01) can extend in any direction past the at least one of any suitable object support(s) (84) and/or object interface material(s) (89), but preferably and without limitation, in any vertical direction(s) past the at least one of any suitable object support(s) (84) and/or object interface material(s) (89) (Herein called "Object Vertical Extension(s)") (154). Without being limited, a plurality of effective opening(s) are located in any effective location(s) where the object(s) may contact the object support(s) (84), and/or object interface material(s) (89).

Figure 46:
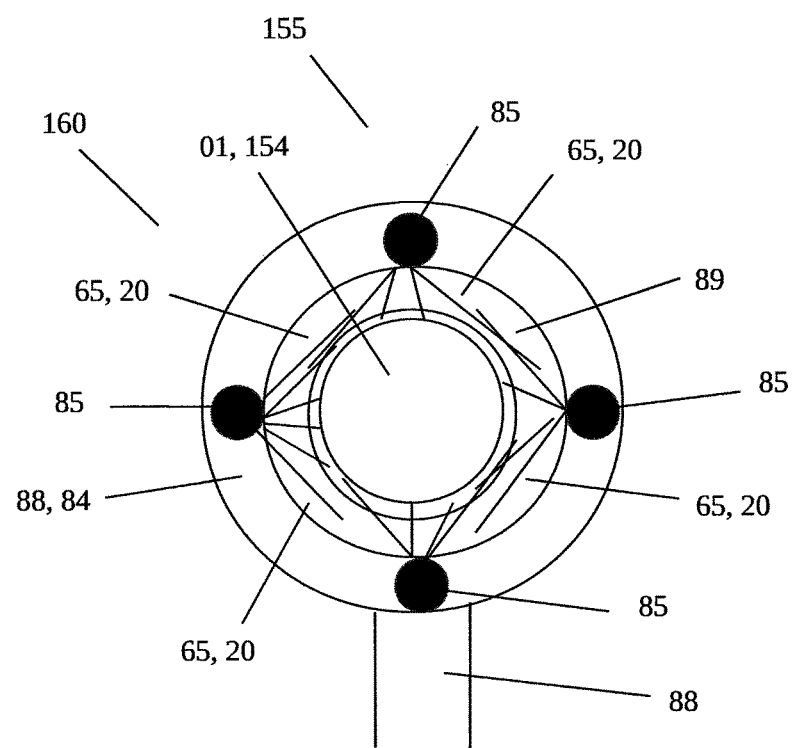
FIG. 46 is a top view of a round enhanced object holder, for supporting, holding, and treating, the interfaced object(s). Agent is flowing through the one or more openings in the object holder and directed towards the middle of the holder, treating the object located in the middle of the multiple object supports (84).

In another aspect, and with reference to FIG. 46, and without limitation, the one or more of any endoscope(s), patient sensor cable(s), ultrasonic probe(s), or otherwise "object(s)" (01) can be held and/or supported in any effective, orientation(s), vertical, upright, horizontal, semi-upright, and/or any other suitably angled, position(s), by the at least one, of any effective, encompassing, semi-encompassing, encircling, and/or semi-encircling, object support(s) (Herein called "Round Enhanced Object Holder(s)") (160) (84) where the treated object(s) (01) can be effectively interfaced with at least one round enhanced object holder(s) (160)(84), and also preferably, and without limitation, with one or more of any effective object interface material(s) (89) effectively positioned between the one or more object support(s) (84) and/or process hose(s) (88), and the object(s) (01). Without being limited, a plurality of any effective opening(s) can be located in any effective location(s) where the object(s) may contact the, object support(s) (84), and/or object interface material(s) (89). The round enhanced object holder(s) (160)(84) can effectively connect with and/or communicate with one or more of any suitable process hose(s) in one or more of any effective location(s).

Figure 47:
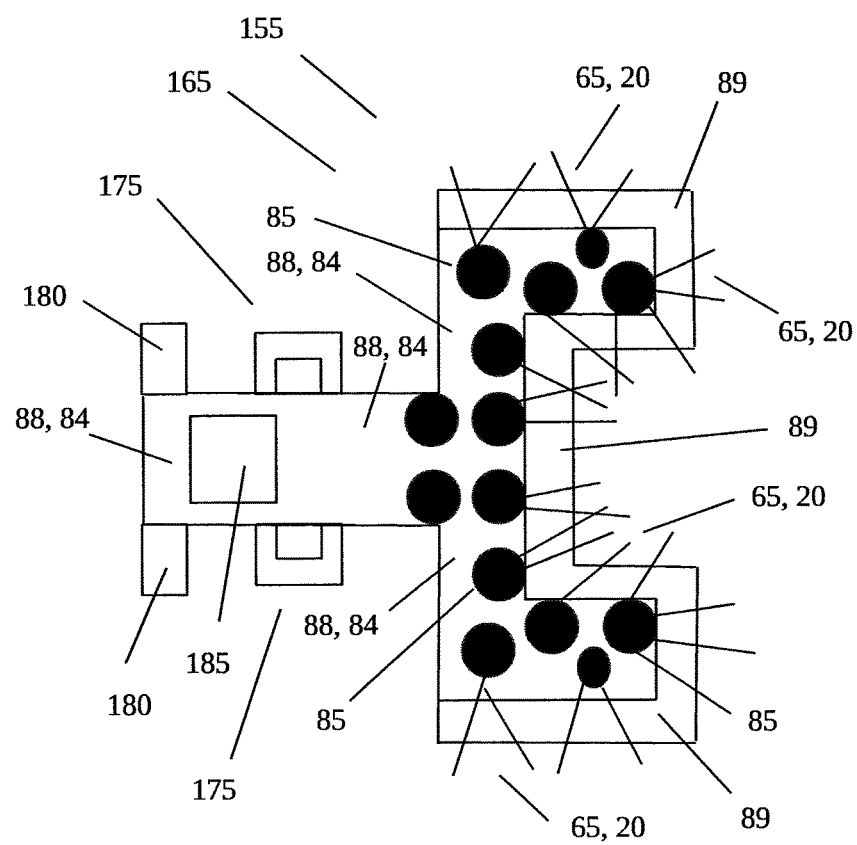
FIG. 47 is a top view of an enhanced forked extension object holder, for supporting, holding, and treating, the interfaced object(s). Agent is flowing through the one or more openings of the enhanced object holders.
Figure 48:
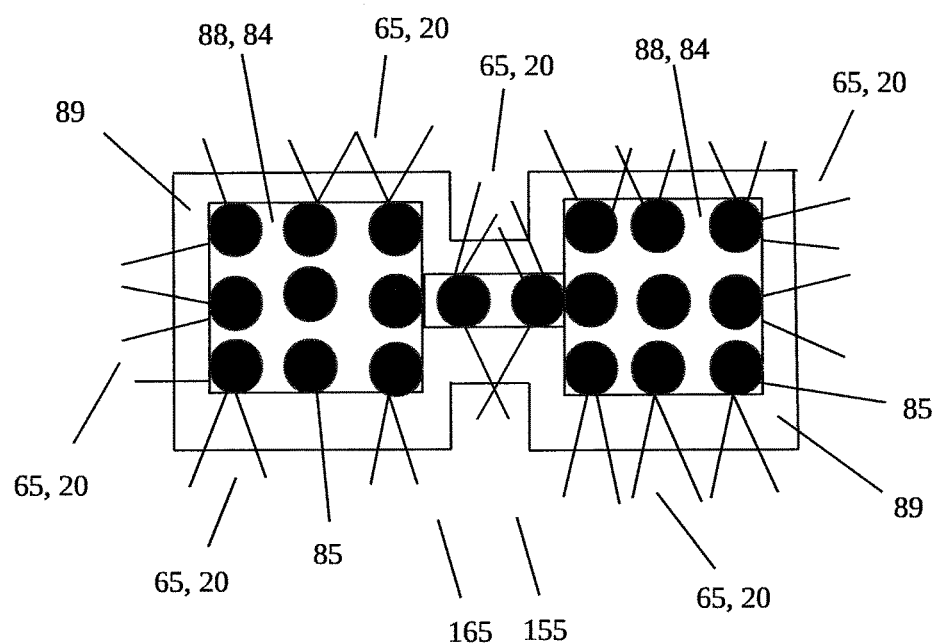
FIG. 48 is a front view of an of an enhanced forked extension object holder, for supporting, holding, and treating, the interfaced object(s). Agent is flowing through the one or more openings of the enhanced object holders.
Figure 49:
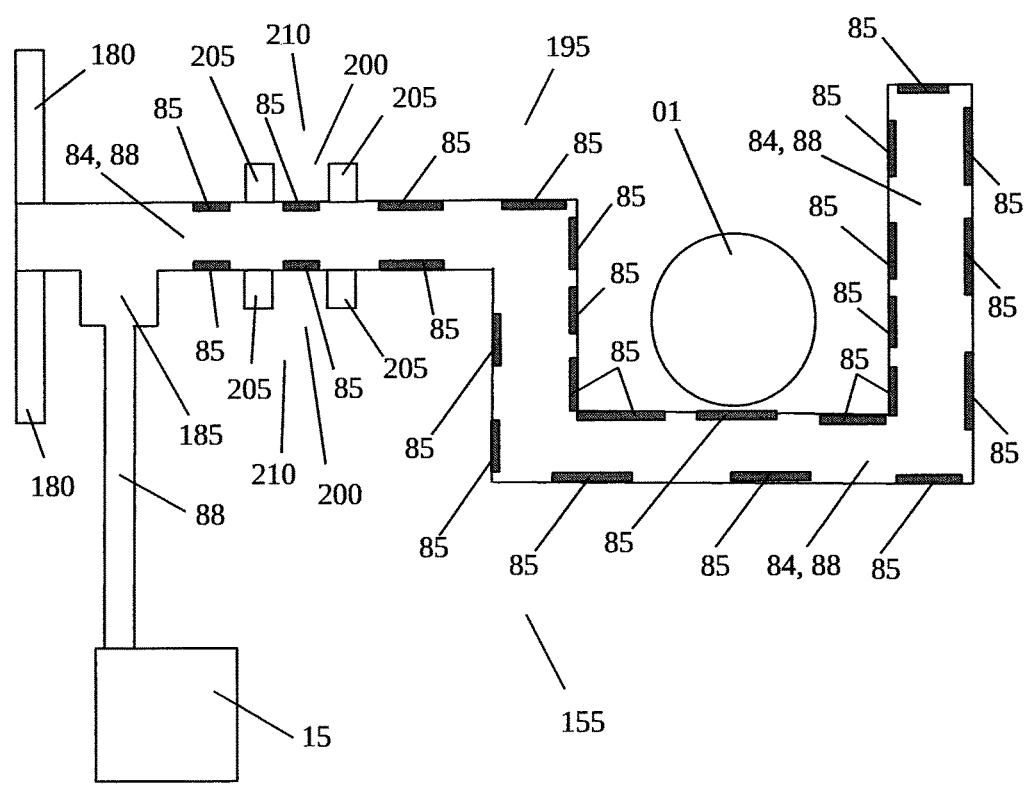
FIG. 49 is a side view of an enhanced cable and hose holder(s) (195), for supporting, holding, and treating, the interfaced object(s), where the objects can be located in the "u" shaped section so they can't roll off. Agent can flow through the hole(s) in various location(s) to treat various surface(s). Side view of round object is shown being held.
Figure 50:
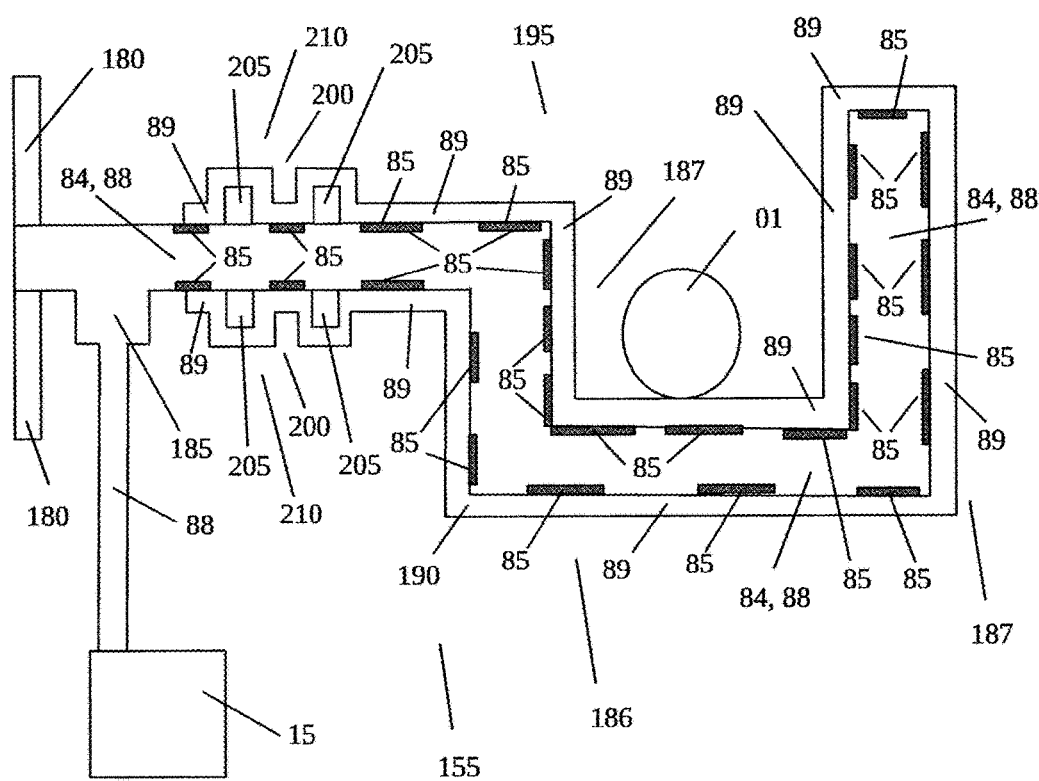
FIG. 50 is a side view of an enhanced cable and hose holder(s) (195), for supporting, holding, and treating, the interfaced object(s), where an object interface sock (190) is interfaced with the enhanced cable and hose holder(s) (195). Also retainer guide indentation(s) are shown and formed between at least two or more of any suitably and effectively sized and located protrusion(s) or retainer guide protrusion(s). Side view of round object is shown also being held.
Figure 51:
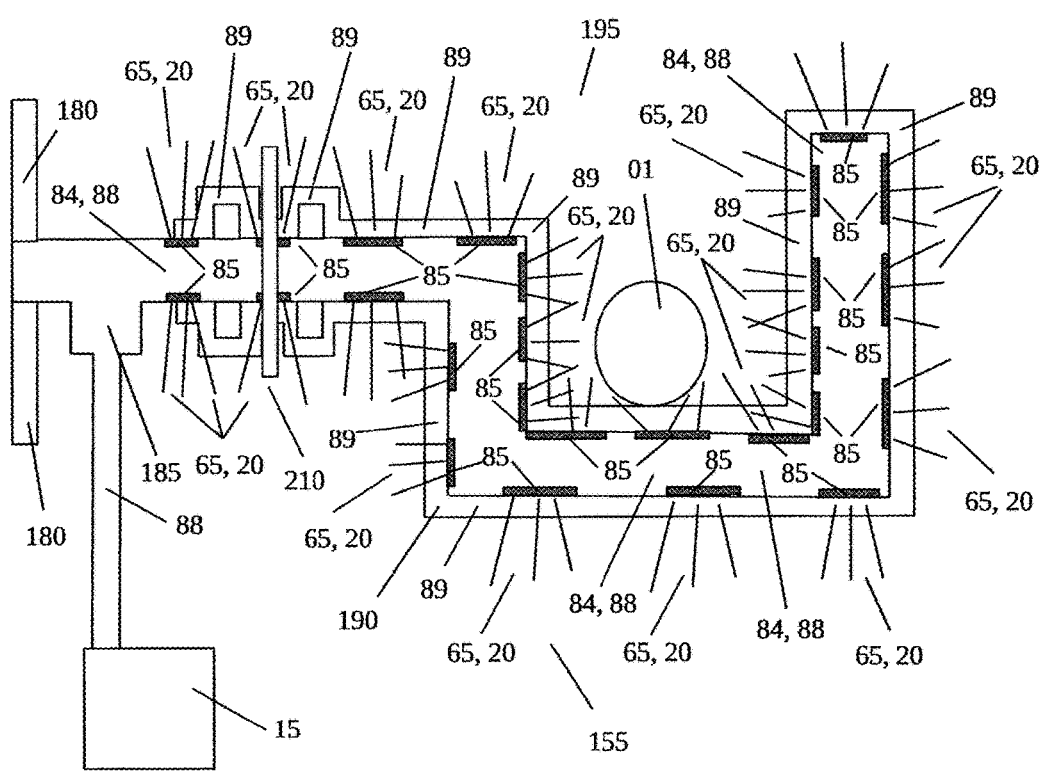
FIG. 51 is a side view of an enhanced cable and hose holder(s) (195), for supporting, holding, and treating, the interfaced object(s), where an object interface sock (190) is interfaced with the enhanced cable and hose holder(s) (195). Also retainer guide indentation(s) are shown and formed between at least two or more of any suitably and effectively sized and located protrusion(s) or retainer guide protrusion(s). Side view of round object is shown also being held. Agent (65)(20) is flowing through the one or more openings of the enhanced object holder (155).

In still another aspect, and with reference to FIGS. 47-48, and without limitation, the one or more of any endoscope(s), patient sensor cable(s), ultrasonic probe(s), or otherwise "object(s)" (01) can be held and/or supported in any effective, orientation(s), vertical, upright, horizontal, semi-upright, and/or any other suitably angled, position(s), by the at least one, effective fork shaped, object supports (Herein called "Enhanced Forked Extension Object Holder(s)") (165) where the treated object(s) (01) is interfaced with at least one object support(s) (84), with preferably, and without limitation, one or more of any effective object interface material(s) (89) effectively positioned between the one or more object support(s) (84) and the treated object(s) (01).

Also, without being limited, one or more of any enhanced object(s) holder(s) (155) can also be effectively interfaced within the container holding chamber(s) (265) to one or more of any mounting rail(s) (not shown) that is known to those skilled in the art, and located in the container holding chamber(s) (265). Referring to FIG. 47, and without being limited, the one or more enhanced object(s) holder(s) (155) can be interfaced at one or more of any suitable location(s) with one or more of any suitable track slide mechanism(s) (175) that can effectively interface and work with the said mounting rail(s) so that the enhanced object(s) holder(s) (155) can be moved to any suitable location(s) inside of the container holding chamber(s) (265). Without being limited, any enhanced object(s) holder(s) (155) can also have one or more of any suitable wall mount hardware (180) known to those skilled in the art, so that the enhanced object(s) holder(s) (155) can be effectively located at any suitable location(s) inside of any suitable enclosure(s) and/or container holding chamber(s) (265), all in a manner known to those skilled in the art.

In still another aspect, and with reference to FIGS. 49-52, and without limitation, the one or more of any endoscope(s), patient sensor cable(s), ultrasonic probe(s), or otherwise "object(s)" (01) can be held and/or supported in any effective, orientation(s), vertical, upright, horizontal, semi-upright, and/or any other suitably angled, position(s), by the at least one, of any hook shaped object support(s) (Herein called "Enhanced Cable and Hose Holder(s)") (195), where the treated object(s) (01) is interfaced with the enhanced cable and hose holder(s) (195), with preferably, and without limitation, one or more of any effective object interface material(s) (89) effectively positioned between the one or more object support(s) (84) and the treated object(s) (01).

It is preferred, without limitation, that the one or more member(s) of the enhanced cable and hose holder(s) (195), and more specifically and without limitation, any suitable and effective object support(s) (84), used to hold, removable interface with, and/or support, the object(s) (01), have any suitable and effective, shape(s), geometry(s), cavity(s), half circle(s), "u"-shaped indentation(s), "u"-shape(s), length(s), width(s), height(s), and/or depth(s), so that the various object(s) (01) are effectively held and supported. It is preferred, without limitation, that the one or more object(s) cannot move off of the object support(s) (84), unless it is needed and/or desired to do so.

It is also preferred, without limitation, that the at least one of any horizontal area(s), part(s), and/or member(s) (Herein called "Horizontal Member Part(s)") (186) of the object support(s) (84) that are connected to the at least one of any vertical member(s) (187), and the at least one of any vertical area(s), part(s), and/or member(s) (Herein called "Vertical Member Part(s)") (187) of the object support(s) (84) that are connected to and/or are perpendicular to, the at least one of any horizontal member(s) (186) of the object support(s) (84), can form the object support(s) (84) of the enhanced cable and hose holder(s) (195) into, and/or cause the object support(s) (84) to form, any effective shape(s) and/or geometry(s) such as, but not limited to any effective, hook(s), and/or half circle(s), shaped object support(s) (84).

Referring to FIGS. 49-51 and 52, and without being limited, the various object interface material(s) (89) can be removably, and/or permanently, interfaced with any suitable object support(s) (84) and/or process hose(s) (88), at any locations. It is preferred, without limitation, that one or more of any suitable and effective object interface material(s) (89) are effectively, removably interfaced with, one or more of any suitable and effective object support(s) (84) at any effective location(s). It is also preferred, without limitation, that the object interface material(s) (89) are designed and constructed in the form of any suitable and effective cover(s) and/or sock(s) (Herein called "Object Interface Sock(s)") (190), that is preferably, and without limitation, effectively designed and sized, in a manner known in the art, to fit over and effectively, preferably and without limitation, removably cover and/or interface with, the one or more of any object support(s) (84).

Without being limited, the object interface material(s) (89) can be kept in place while they are in contact with any suitable object support(s) (84) and/or process hose(s) (88), using one or more of any suitable and effective means, such as, but not limited to locating any, adhesive(s), and/or material(s) that have an effective level of "tack" and/or stickiness to them, suitably and effectively between the object support(s) (84) and the object interface material(s) (89). However, it is preferred, without limitation, that one or more of any suitable mechanical retaining apparatus(s) known to those skilled in the art (Herein called "Interface Material Retaining Apparatus(s)) (215) can be used to keep the one or more of any object interface material(s) (89) effectively interfaced with the object support(s) (84) and/or process hose(s) (88).

Without being limited, the interface material retaining apparatus (215) can include, but is not limited to, one or more of any suitable and effective, clip(s), clamp(s), pinch apparatus(s), and/or band(s) (Herein called "Interface Material Retainer(s)) (210), that is preferably, and without limitation, removable. Without being limited, one or more of any suitable interface material retainer(s) (210) can also effectively fit into, with, and/or interface between, one or more of any suitably and effectively sized and located indentation(s) (Herein called "Retainer Guide Indentation(s)") (200), that can be, without limitation, formed between at least two or more of any suitably and effectively sized and located protrusion(s) (Herein called "Retainer Guide Protrusion(s)") (205).

Figure 52:
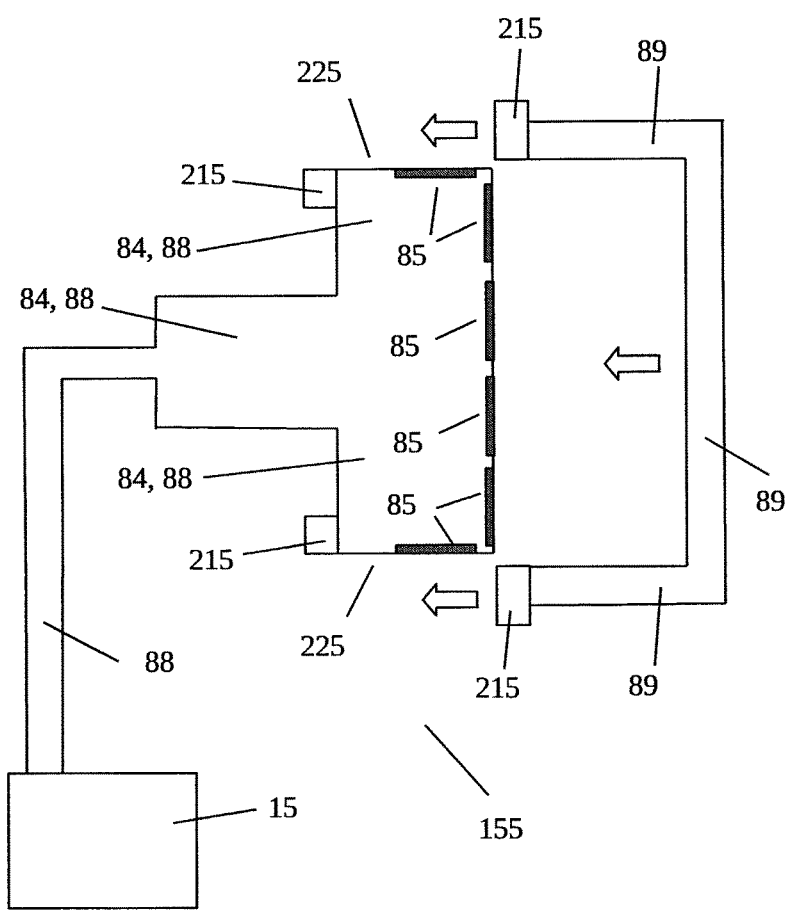
FIG. 52 is a side view of an object support(s) (84) that can have or be interfaced with one or more of any effective interface material retaining apparatus(s) (215) known to those skilled in the art, at one or more of any effective locations, to effectively maintain the location(s) and/or position(s) of the one or more of any suitable object interface material(s) (89) on and/or to location(s), part(s), and/or structure(s) such as, but not limited to any, object support(s) (84).

Referring to FIG. 52, and without being limited, the one or more object support(s) (84) can have or be interfaced with one or more of any effective interface material retaining apparatus(s) (215) known to those skilled in the art, at one or more of any effective locations, to effectively maintain the location(s) and/or position(s) of the one or more of any suitable object interface material(s) (89) on and/or to location(s), part(s), and/or structure(s) such as, but not limited to any, object support(s) (84) and/or process hose(s) (88).

Without being limited, the one or more interface material retaining apparatus(s) (215) can include, but is not limited to any, snap lock(s), removable snap lock(s), band(s), removable band(s), push lock(s), and/or removable push lock(s). In still another part of this aspect, and without limitation, the object interface material(s) (89) can be pre-treated with one or more of any effective, agent(s), applied agent(s) (20), treatment agent(s), decontamination agent(s) or substance(s), such as, but not limited to any effective, sanitizer(s), disinfectant(s), and/or sterilant(s), and packaged in any effective package(s), known to those skilled in the art, until it is time for their use and installation by any authorized technician and/or employee.

Without being limited, when interfacing the object interface material(s) (89), one or more of any effective part(s) and/or surface(s) of the object interface material(s) (89) can be interfaced with and/or cover one or more of any effective part(s) and/or surface(s) of the object support(s) (84) and/or process hose(s) (88), and the object interface material(s) can be kept in any effective position(s) relative to the object support(s) (84) and/or process hose(s) (88), by one or more of any interface material retaining apparatus(s) (215). Without being limited, the one or more of any interface material retaining apparatus(s) (215) can be suitably and effectively located in one or more of any suitable and effective location(s) of various part(s) such as, but not limited to any, object support(s) (84), process hose(s) (88), object interface material(s) (89), and/or any other suitable and effective part(s). It is preferred, without limitation, that the interface material retaining apparatus(s) (215) can also release the object interface material(s) (89) at any suitable and effective time(s) for the removal of the one or more object interface material(s) (89) for various purposes. It is preferred, without limitation, that the object interface material(s) (89) are manually installed, interfaced, and removed.

Figure 53:
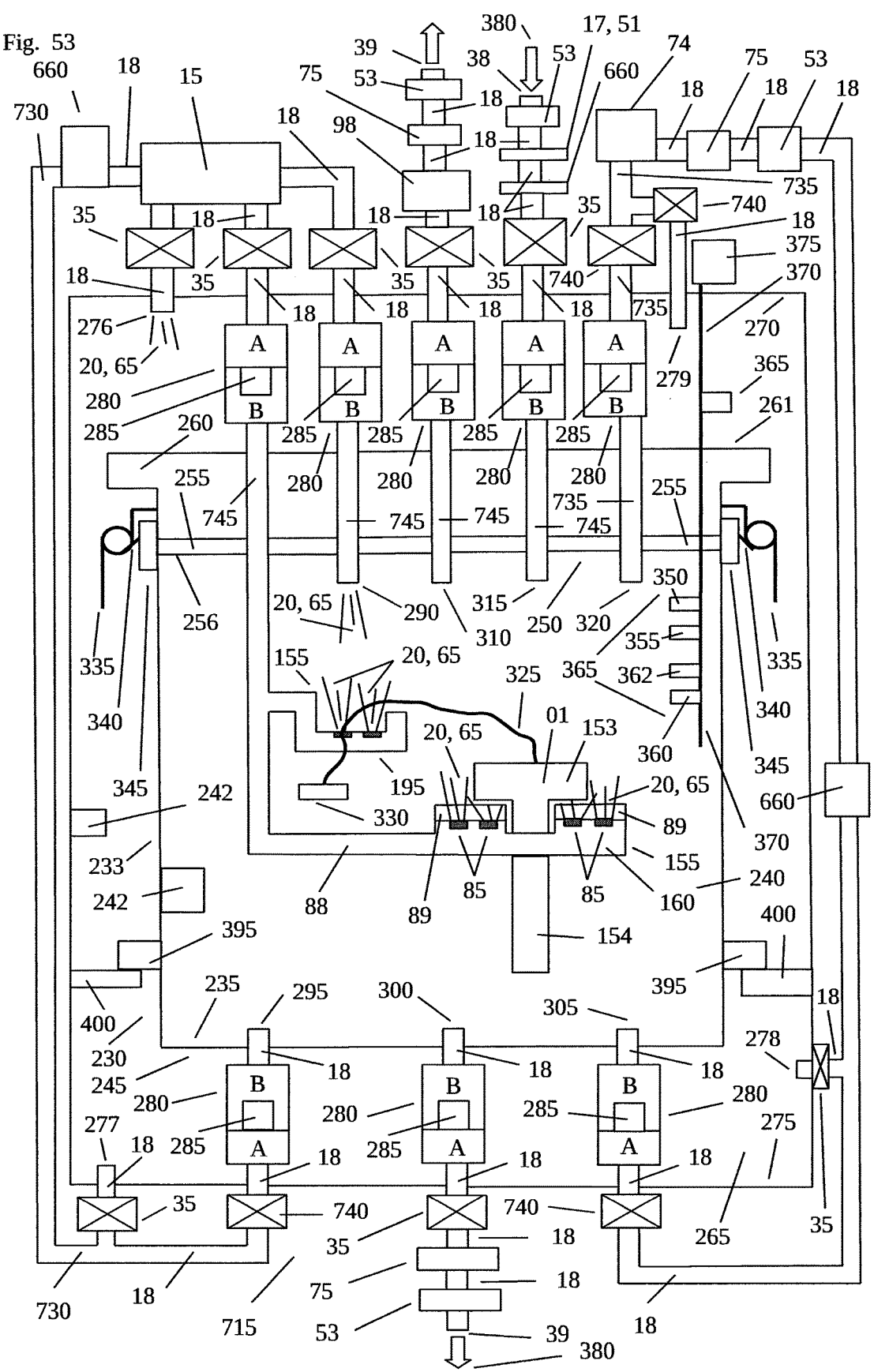
FIG. 53 is a side view schematic type view, that comprises an enhanced decontamination enclosure apparatus (715), and even more specifically and with reference to FIGS. 53-66, an enhanced decontamination enclosure apparatus (715) and enhanced removable treatment enclosure (230) that is removable. An object and its cable is held inside the removable treatment enclosure (230) with an enhanced object holder (155) that is used for supporting, holding, and treating, the interfaced object(s). The agents and various gas(s) can flow through the enhanced removable treatment enclosure (230). Quick disconnect valves connect the enhanced removable treatment enclosure (230) to the main treatment apparatus, for feeding and evacuation of the various substance(s), so the enhanced removable treatment enclosure (230 is removable. The enhanced removable treatment enclosure (230) is placed in a chamber to also treat its exterior surfaces. The agents and gas(s) flow THROUGH the removable treatment enclosure. Also different is that the treatment gas(s) can be filtered and heated to treat all the different surfaces. Lid of removable treatment enclosure (230) is also removable FIG. 54 is a side schematic type view that is the same as #52, except that the object inside of the enhanced removable treatment enclosure (230) is interfaced with a pressure interface assembly(s) (68) and the object hangs inside its removable enclosure (230) from this pressure interface assembly(s) (68).
Figure 54:
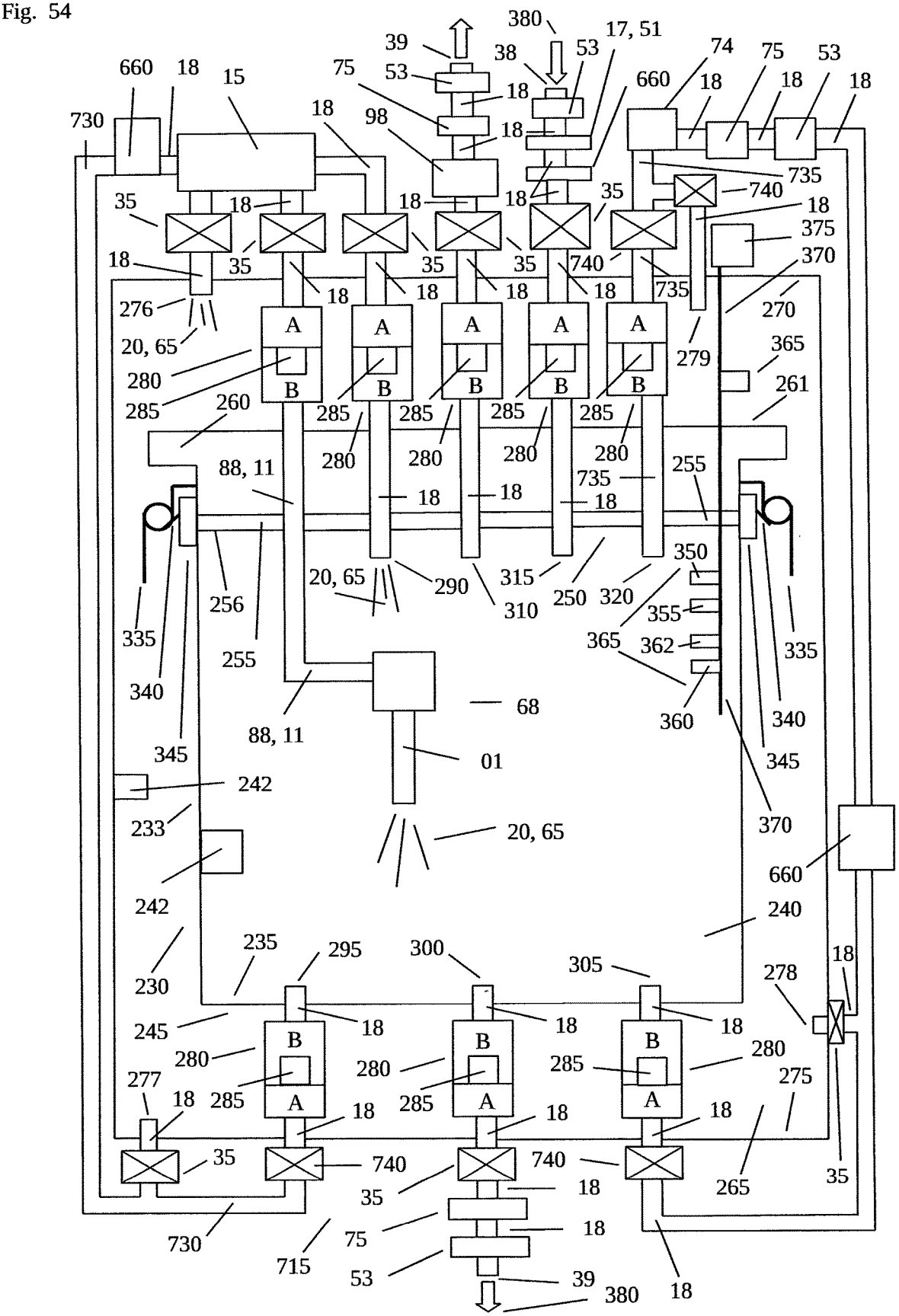
Figure 55:
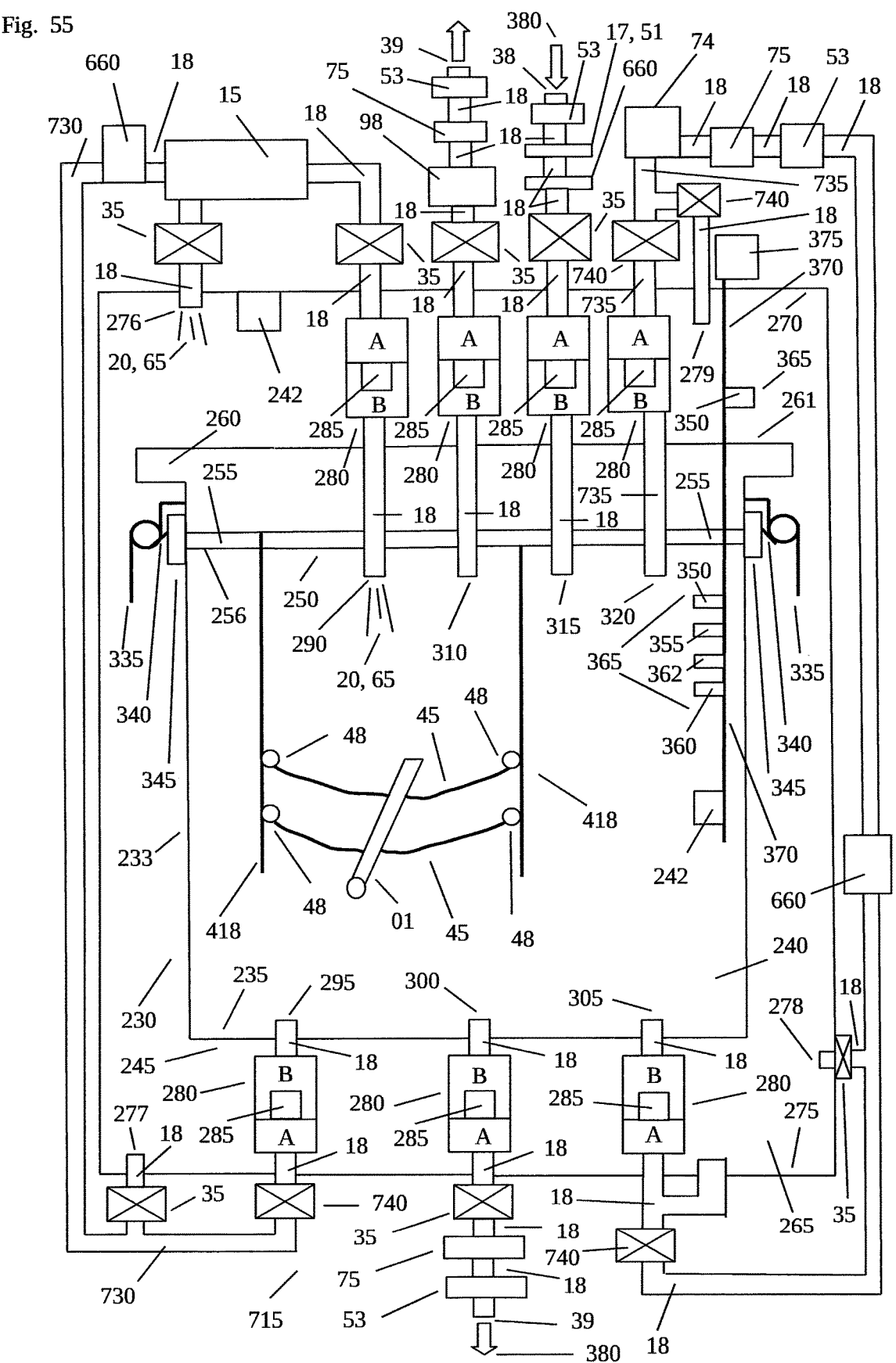
FIG. 55 is a side schematic type view that is the same as #52, except that the object inside of the enhanced removable treatment enclosure (230) is held or suspended in the removable enclosure (230), by a plurality of cradles (45).
Figure 56:
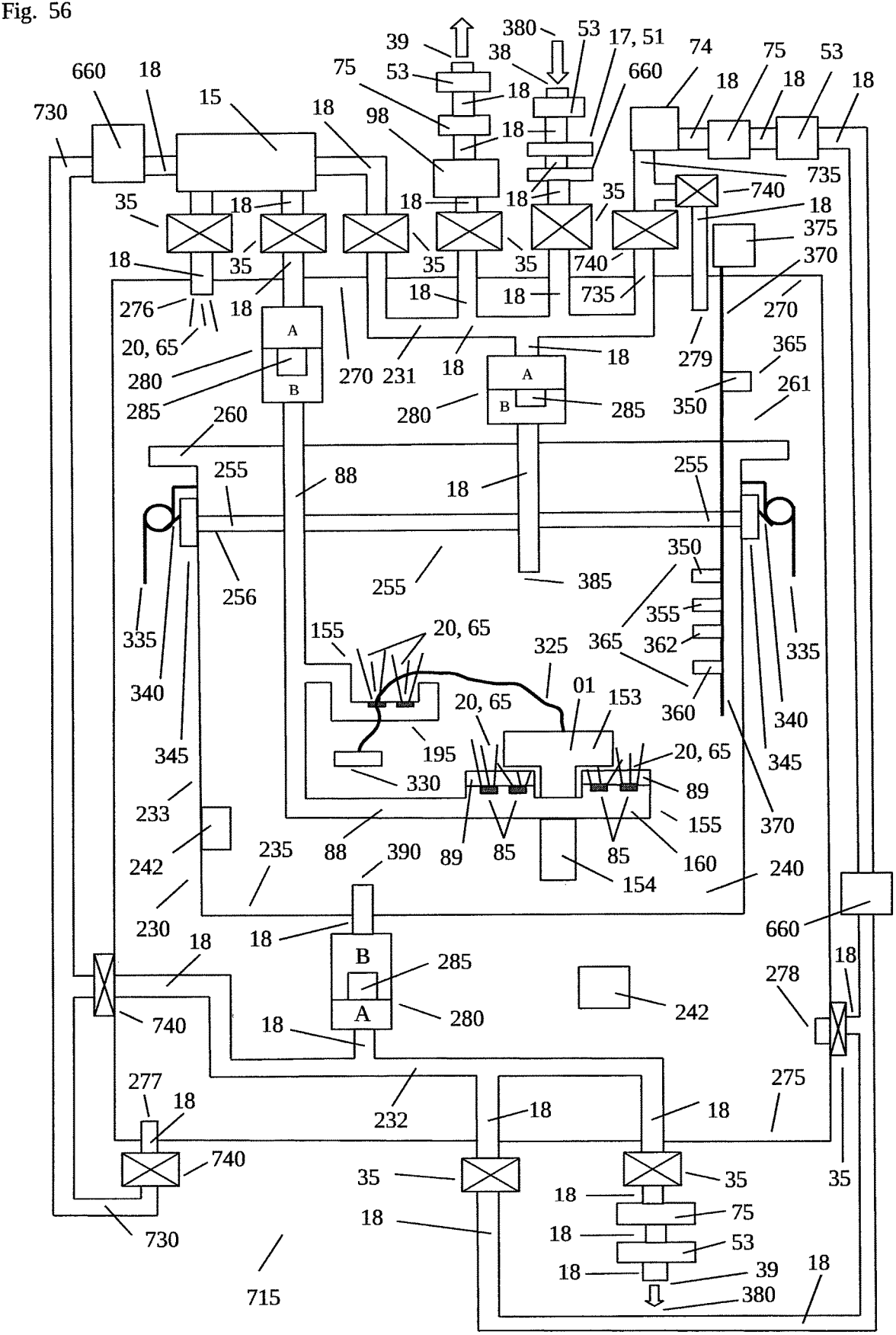
FIG. 56 is a side schematic type view that is the same as #52, except the various treatment plumbing/airflow paths is different, and the airflows are controlled by various different valves.
Figure 57:
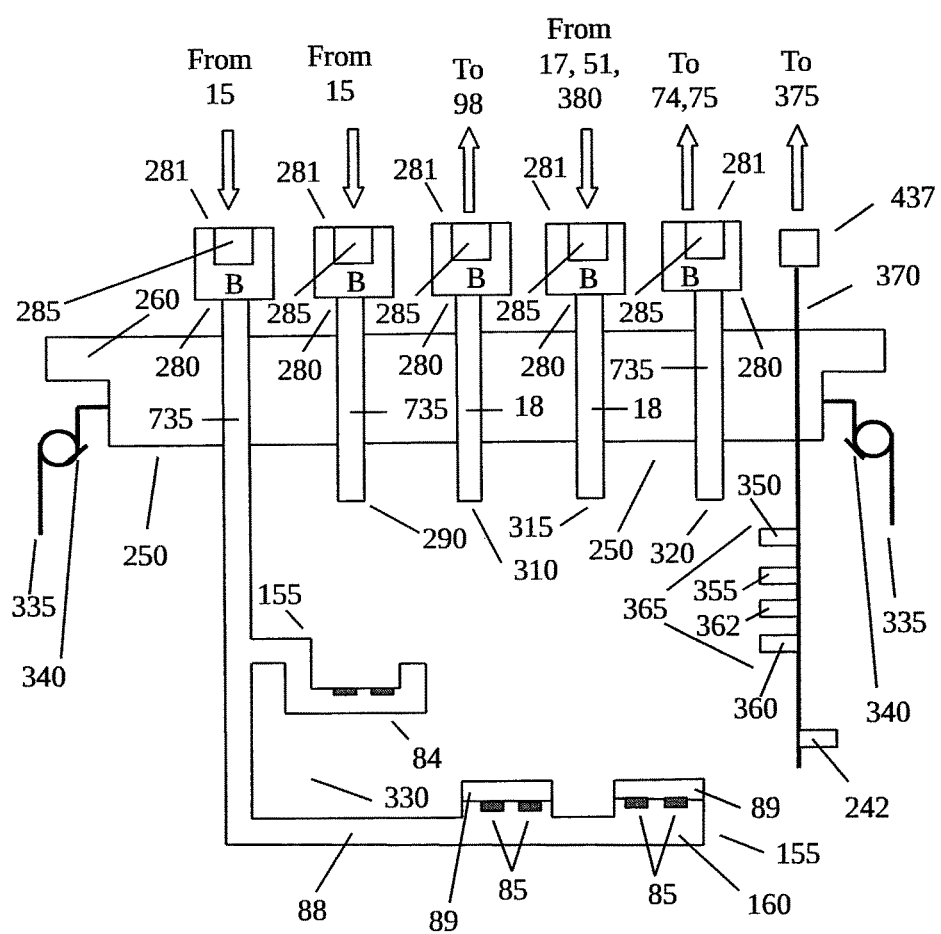
FIG. 57 is a side schematic type view of a lid for the removable enclosure (230). The lid incorporates an enhanced object holder (155), to hold, suspend, treat, and/or process the various surface(s) of the supported object(s). It also incorporates environment sensor(s) (365), to sense, record and send data. The lid can be affixed to the removable enclosure (230) via at least one clasp. The lid connects to the various supplies of the various agent(s) and air/gas(s) via the various connector valve(s) (280). External data connection(s) also present on exterior.
Figure 58:
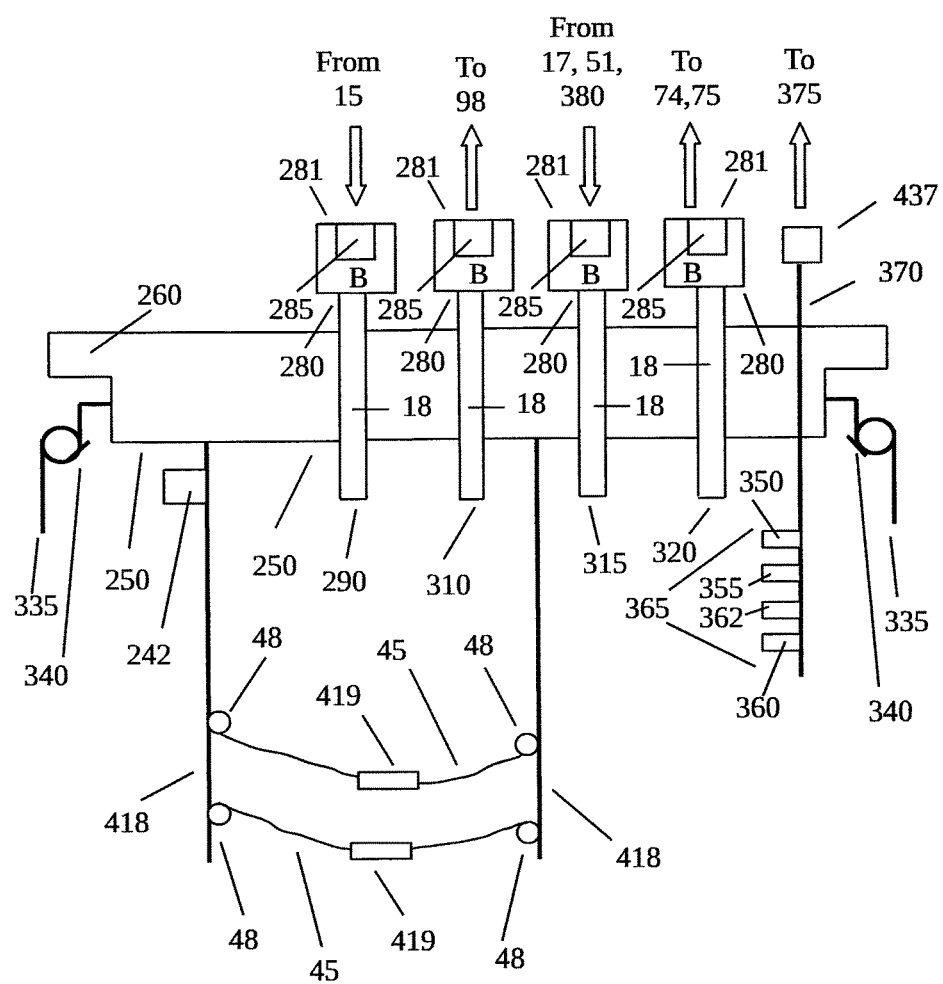
FIG. 58 is a side schematic type view of a lid for the removable enclosure (230). The lid incorporates a cradle (45) type means to hold, suspend, treat, and process the various surface(s) of the supported object(s). It also incorporates environment sensor(s) (365), to sense, record and send data. The lid can be affixed to the removable enclosure (230) via at least one clasp. The lid connects to the various supplies of the various agent(s) and air/gas(s) via the various connector valve(s) (280). External data connection(s) also present on exterior.
Figure 59:
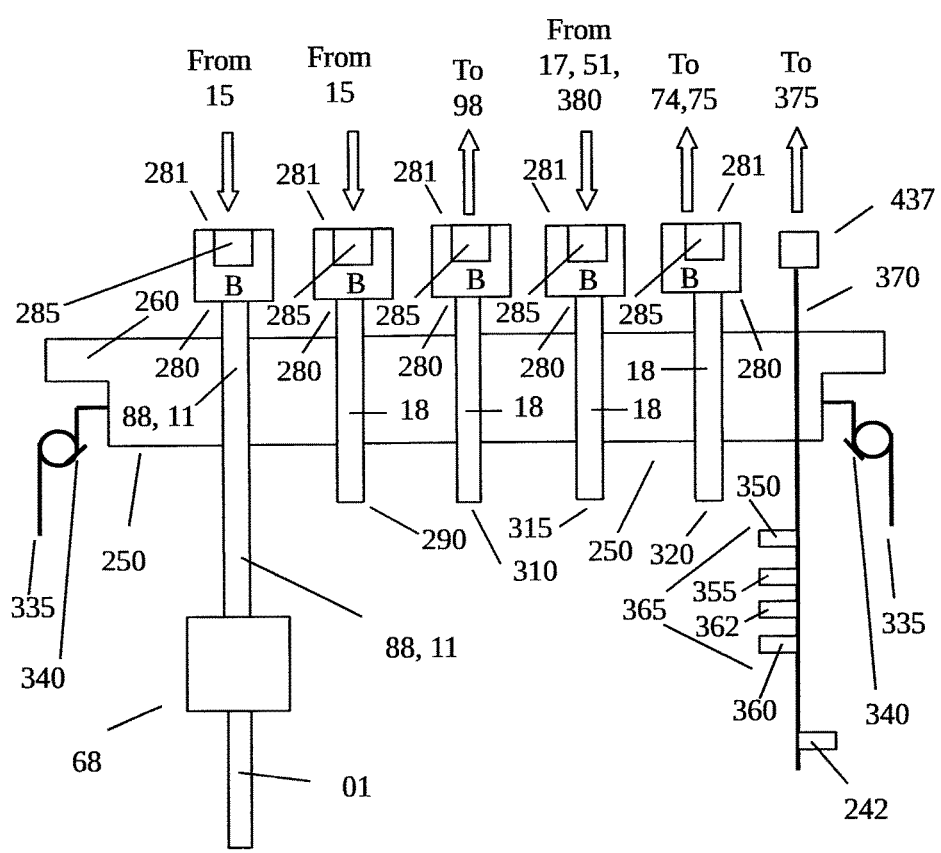
FIG. 59 is a side schematic type view of a lid for the removable enclosure (230). The lid incorporates a pressure interface assembly(s) (68) to hang and/or suspend, the object(s) and also treat, and process the various interfaced surface(s) of the supported object(s). It also incorporates environment sensor(s) (365), to sense, record and send data. The lid can be affixed to the removable enclosure (230) via at least one clasp. The lid connects to the various supplies of the various agent(s) and air/gas(s) via the various connector valve(s) (280). External data connection(s) also present on exterior.
Figure 60:
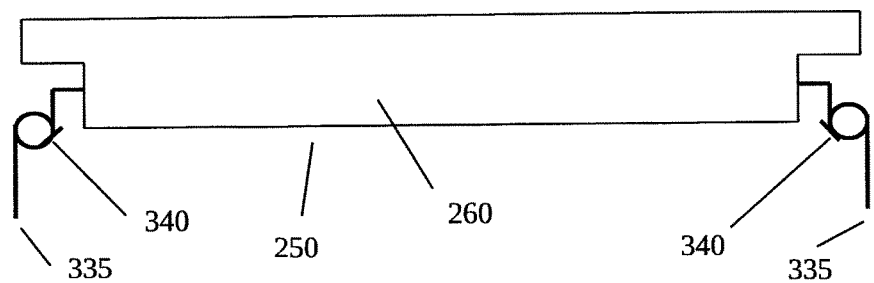
FIG. 60 is a side schematic type view of a plain lid for the removable enclosure (230). The sealing clasps are shown.

With reference to FIGS. 53-112, and more specifically FIGS. 24-25, 38-43, 53-56, 64-66, 68-71, 72-75, 80-91, and 98-112, an apparatus and method of another embodiment of the present invention comprises an enhanced decontamination enclosure apparatus (715), and even more specifically and with reference to FIGS. 53-66, an enhanced decontamination enclosure apparatus (715) and enhanced removable treatment enclosure (230). Without being limited, the one or more of any suitable and effective enhanced removable treatment enclosure(s) (Herein called "Removable Treatment Enclosure(s)") (230), can be suitably and effectively, treated, processed, located, and/or positioned, in one or more of any suitable and effective locations, preferably and without limitation, effectively positioned and located inside one or more of any suitable and effective treatment enclosure(s) such as, but not limited to one or more of any suitable and effective container holding chamber(s) (265), where any of the surfaces inside and/or outside of the removable treatment enclosure(s) (230), as well as inside of the container holding chamber(s) (265), can be effectively treated, dried, degassed, and/or processed. It is more preferred, without limitation, that both the interior and exterior surfaces of the removable treatment enclosure(s) (230) are effectively treated, dried, and processed, and the interior surfaces of the container holding chamber(s) (265) are also effectively treated, dried, and processed.

Without being limited the removable treatment enclosure(s) (230) and the container holding chamber(s) (265) can be effectively interfaced with one or more of any effective means to generate, create, and/or deliver, one or more of any effective airborne agent(s) and/or applied agent(s) (20) to effectively, sanitize, disinfect, high-level disinfect, sterilize, decontaminate, process, and/or treat, any surfaces and/or atmosphere(s) within and/or effectively connected to, any area(s) and space(s) such as, but not limited to any, container holding chamber(s) (265) and removable treatment enclosure(s) (230), including but not limited to any, object(s), part(s), component(s), medical device(s), cable(s), wire(s), tool(s), package(s), packaging material(s), equipment(s), component(s), instrument(s), sensor(s), power relay part(s), and/or communication relay part(s), such as, but not limited to any, endoscope(s), ultrasonic probe(s), medical related sensor(s), medical instrument(s), medical tool(s) or tooling(s), data and/or communication cable(s), data and/or communication wire(s), instrumentation cable(s), instrumentation wire(s), power relay cable(s), power relay wire(s), fiber optic line(s), fiber optic cable(s), and/or including one or more of any attached and/or unattached object(s) such as, but not limited to any, tube(s), pipe(s), plug(s), socket(s), cable(s), wire(s), and/or connector(s), as well as any, object support(s), object interface materials(s), support hardware, hanging hardware, object support(s) (84), moving support and dropping mechanism(s) (605), support and tilt mechanism(s) (655), gripping mechanism(s) (135), gripping finger(s) (108), movable holding and/or support apparatus(s) (606), open package(s), packaging film material(s), and/or pressure interface assembly(s) (68) (Herein also called "Object(s)") (01), that can be located in any of the said treated and processed area(s) and/or space(s).

Without being limited, the current art can be problematic because flowing any, airborne agent(s) (20), air/gas(s), heated air/gas(s), dehumidified air/gas(s), and/or applied agent(s) (20), such as, but not limited to any, vapor(s) and/or aerosol(s) (65), into one or more of any suitable and effective, enclosure(s), removable treatment enclosure(s) (230), and/or container holding chamber(s) (265), to effectively treat, process, and/or decontaminate, the various surfaces inside, from one entry port and without circulating any, air/gas(s), heated air/gas(s), dehumidified air/gas(s), vapor(s), and/or air/gas that is carrying any deployed agent(s) (20) or applied agent(s) (20), back to and thus returning through the various source(s) for the dehumidified air/gas(s) (74), heated air/gas(s) (660), and/or the source(s) or means for generating and/or applying (15) the various, vapor(s), aerosol(s) (65), and/or applied agent(s) (20), for any effective recirculation, thus forming a complete circuit and returning flow of any air/gas(s) flow(s) through any treated and/or processed enclosure(s) (265)(230), can present various problems, and without limitation, such as, but not limited to, (a) not filling the treated enclosure(s) (265) (230) with things such as, but not limited to, an effective amount of vapor(s) and/or aerosol(s) (65)(20) and/or heated air/gas(s), (b) causing an over pressurization of the inside area of the treated enclosure(s) (265)(230), which can pose various problems and hazards such as, but not limited to: back flow of any deployed aerosol (65), air/gas(s), vapor(s), and/or heated air/gas(s), burst enclosure(s) (265)(230), not filling the treated enclosure(s) (265)(230) with an effective amount or concentration of vapor(s), aerosol(s) (65)(20) and/or heated air/gas(s), and/or not exposing the targeted surfaces to the applied agent(s) or aerosol(s) (20)(65) for an effective amount of time before the over pressurization of the enclosure(s) (265)(230) occurs and, (c) the creation of turbulent air/gas flow and/or air/gas vorticies within one or more of any location(s) or area(s) of the enclosure(s) (265) (230) preventing full and effective coverage of any and/or all of the treatable and/or targeted surface(s) within the treated and/or processed enclosure(s) (265)(230) and/or not providing adequate contact time of the targeted or treated surfaces with the applied agent(s) or aerosol(s) (20)(65).

Without being limited, the present invention addresses these problems and improves the art, by suitably and effectively connecting and/or interconnecting, the at least one of any suitable and effective, removable treatment enclosure(s) (230) and/or container holding chamber(s) (265), to the at least one of any effective source(s) for any, dehumidified air/gas(s) (74), heated air/gas(s) (660), and/or production source(s) or generator(s) (15) of the applied agent(s) (20), vapor(s) and/or aerosol(s) (65), at one or more of any effective location(s) of the various enclosure(s) (265)(230), with at least one of any suitable and effective connection(s) for any entry (276)(315)(290)(305)(278) of any, air, gas(s), dehumidified air/gas(s), refrigerated air/gas(s), heated air/gas(s), deployed agent(s) (20), vapor(s), aerosol(s) (65), and/or carrier gas(s) for the aerosol(s) (65), and providing another at least one of any effective connection(s) to the same removable treatment enclosure(s) (230) and/or container holding chamber(s) (265), at one or more different effective location(s), so that any, air, gas(s), refrigerated air/gas(s), heated air/gas(s), dehumidified air/gas(s), deployed agent(s) (20), vapor(s), aerosol(s) (65), and/or carrier gas(s) for the aerosol(s) (65), that are deployed into the removable treatment enclosure(s) (230) and/or container holding chamber(s) (265), can eventually flow out of the removable treatment enclosure(s) (230) and/or container holding chamber(s) (265), through the one or more of any suitable and effective connection(s) for any exit (300)(277) (295)(310)(320)(279) of any, air, gas(s), heated air/gas(s), refrigerated air/gas(s), dehumidified air/gas(s), deployed agent(s) (20), vapor(s), aerosol(s) (65), and/or carrier gas(s) for the aerosol(s) (65), and then recirculate back to, via one or more of any suitable conduit(s) (18), and then through, the at least one, air/gas heating apparatus(s) (660), dehumidification apparatus (74), and/or production source(s), source(s), and/or generator(s) (15) of the applied airborne agent(s), applied agent(s) (20), vapor(s), and/or aerosol(s) (65), where these heated air/gas(s), dehumidified air/gas(s), applied airborne agent(s), applied agent(s) (20), vapor(s), and/or aerosol(s) (65), including any newly dehumidified air/gas(s), heated air/gas(s), refrigerated air/gas(s), and/or newly generated airborne aerosol(s) (65) and/or applied agent(s) (20), can then be deployed, delivered, redeployed, and/or recirculated, into and/or back through, the removable treatment enclosure(s) (230) and/or container holding chamber(s) (265). Without limitation, this can continue any effective number of times until the one or more process(s) of deploying and administering the dehumidified air/gas(s), heated air/gas(s), refrigerated air/gas(s), applied airborne agent(s), applied agent(s) (20), vapor(s), and/or aerosol(s) (65), and/or heated air/gas(s), to or within, the removable treatment enclosure(s) and/or container holding chamber(s), is suitably and effectively complete. Without being limited, the generated and deployed dehumidified air/gas(s), heated air/gas(s), refrigerated air/gas(s), airborne agent(s), applied agent(s) (20), vapor(s), and/or aerosol(s) (65), can flow through the removable treatment enclosure(s) (230), container holding chamber(s) (265), and any other connected parts, with any effective attribute(s) such as, but not limited to any effective, flow rate(s), and flow speed(s). It is preferred, without limitation, that any suitable and effective air/gas pressure(s) is maintained in the removable treatment enclosure(s) (230) and/or container holding chamber(s) (265) as well as in any connected area(s) and space(s).

Without limitation, one or more of any suitable and effective means (not shown) that is known to those skilled in the art, can also be used to cool or refrigerate any air/gas(s) that can be moved through any part(s) and/or area(s) within any removable treatment enclosure(s) (230) and/or container holding chamber(s) (265) at any suitable and effective time(s), and for any suitable and effective time duration(s). It is preferred, without limitation that if any cooled or refrigerated air/gas(s) is used, it is deployed or moved through any effective part(s) and/or area(s) within any removable treatment enclosure(s) (230) and/or container holding chamber(s) (265) just before any airborne agent(s), applied agent(s) (20), vapor(s), and/or aerosol(s) (65), are administered, moved, or flowed, into these same locations (230)(265). Without being limited, the cooled or refrigerated air can be any suitable and effective temperature(s), but preferably and without limitation, at least any suitable and effective temperature(s) below 80 degree Fahrenheit, and more preferably and without limitation, any suitable and effective temperature(s) below 55 degree Fahrenheit. Without being limited, the cooled or refrigerated air/gas(s) can be used for various purposes including, but not limited to, cooling any treated parts or object(s) (01) to accelerate the movement of any airborne agent(s), applied agent(s) (20), vapor(s), and/or aerosol(s) (65) to any targeted surface(s) of the object(s) (01), and/or to cool any part(s) or surface(s) within these space(s) or areas, to any suitable and effective temperature(s), that may have been heated during any step(s) of their processing at any time(s).

It is also preferred, without limitation, that any air/gas(s) and/or atmosphere(s) within area(s) and location(s) such as, but not limited to any, removable treatment enclosure(s) (230) and/or container holding chamber(s) (265), that are intended and/or need to be dehumidified and/or removed of any vapor(s), at any suitable and effective time(s), are only recirculated to and through the one or more of any air/gas dehumidification apparatus(s) (74) via one or more of any suitable conduit(s) (735)(18) that are designated and/or reserved for this purpose. Without being limited, one or more of any suitable and effective air/gas(s) dehumidification apparatus(s) (74) known to those skilled in the art, can be suitably and effectively located at one or more of any suitable and effective location(s) to suitability and effectively connect and communicate with at least the removable treatment enclosure(s) (230) and/or container holding chamber(s) (265). The air/gas(s) can be dehumidified to any suitable and effective humidity(s). Without limitation, it is preferred that any air/gas(s) and/or atmosphere(s) in part(s), location(s), and/or space(s) such as, but not limited to any, removable treatment enclosure(s) (230) and/or container holding chamber(s) (265), are dehumidified to at least 70 percent relative humidity, and more preferred to a humidity level or data less than 55 percent relative humidity.

It is also preferred, without limitation, that during the deployment of any airborne agent(s), applied agent(s) (20), vapor(s), and/or aerosol(s) (65), the air/gas(s), atmosphere(s), and any applied agent(s) (20), aerosol(s) (65), and vapor(s), already inside of the various area(s) and location(s) such as, but not limited to any, removable treatment enclosure(s) (230) and/or container holding chamber(s) (265), are only recirculated to and through the one or more of any production source(s) and/or generator(s) (15) of the applied airborne agent(s), applied agent(s) (20), vapor(s), and/or aerosol(s) (65), via one or more of any suitable conduit(s) (730)(18) that are designated and/or reserved for this purpose.

It is preferred, without limitation, that any air/gas(s) and/or atmosphere(s) within area(s) and location(s) such as, but not limited to any, removable treatment enclosure(s) (230) and/or container holding chamber(s) (265), that are intended and/or need to be heated at any suitable and effective time(s), are only recirculated to and through the one or more of any air/gas heating apparatus(s) (660) via one or more of any suitable conduit(s) (18) that are designated and/or reserved for this purpose. Without being limited, one or more of any suitable and effective air/gas(s) heating apparatus(s) (660) known to those skilled in the art, can be suitably and effectively located at one or more of any suitable and effective location(s) to suitability and effectively connect and communicate with at least the removable treatment enclosure(s) (230) and/or container holding chamber(s) (265). The air/gas(s) can be heated to any suitable and effective temperature(s). Without limitation, it is preferred that any air/gas(s) and/or atmosphere(s) in part(s), location(s), and/or space(s) such as, but not limited to any, removable treatment enclosure(s) (230) and/or container holding chamber(s) (265), are heated to at least 50 degree Fahrenheit or more, and more preferred to a temperature between 90 to 120 degree Fahrenheit.

Furthermore, it preferred, without limitation, that any of the one or more deployed, dehumidified air/gas(s), agent(s), vapor(s), aerosol(s), and/or carrier gas(s) for the aerosol(s), is flowed into, through, and/or deployed, at least through, into, and/or at, one or more of any effective location(s) of any end(s) or side(s), and/or at least through, into, and more preferably and without limitation, at and/or through one or more of any effective end location(s), of the removable treatment enclosure(s) (230) and/or container holding chamber(s) (265), and the dehumidified air/gas(s), deployed agent(s) (20), vapor(s), aerosol(s) (65), and/or carrier gas(s) for the aerosol(s) (65), are then effectively moved or flowed through the removable treatment enclosure(s) (230) and/or container holding chamber(s) (265), and are then moved or flowed out of these space(s) and/or exit the removable treatment enclosure(s) (230) and/or container holding chamber(s) (265), at least at and/or through one or more other effective location(s), preferably and without limitation, at or near at least any effective opposing and/or opposite end(s) or side(s) of the removable treatment enclosure(s) (230) and/or container holding chamber(s) (265) to the said entry point(s), and is then returned back, via one or more of any suitable recirculation return path(s) (730) or (735), to and then through the at least one source(s) for any, heated air/gas(s) (660), dehumidified air/gas(s) (74), and/or production source(s) or generator(s) (15) of the applied agent(s) (20), vapor(s) and/or aerosol(s) (65), where the heated air/gas(s), dehumidified air/gas(s), deployed agent(s) (20), vapor(s), aerosol(s) (65), and/or carrier gas(s) for the aerosol(s) (65), as well as any, newly heated air/gas(s), dehumidified air/gas(s), and/or any newly generated and/or supplied applied agent(s) (20), aerosol(s) (65), and/or vapor(s), is then flowed and/or re-flowed or moved back to and though the removable treatment enclosure(s) (230) and/or container holding chamber(s) (265), until this step of the treatment(s) and/or processing process(s) is effectively complete.

Without being limited, any, source, generator, and/or generation chamber, that creates and/or is the source (15) of the one or more airborne agent(s) and/or applied agent(s) (20), can be connected, interconnected, and/or interfaced with, one or more of any suitable and effective valve(s) (35).

The valve(s) (35) can suitably and effectively control the flow or movement of any airborne agent(s) and/or applied agent(s) (20) into one or more of any space(s) or location(s) such as, but not limited to any, removable treatment enclosure(s) (230), container holding chamber(s) (265), object support(s) (84), moving support and dropping mechanism(s) (605), support and tilt mechanism(s) (655), gripping mechanism(s) (135), gripping finger(s) (108), movable forks or beams (49)(50), movable holding and/or support apparatus(s) (606). Without being limited, the valve(s) (35) can be controlled by one or more of any suitable and effective, programmable logic controller(s), PLC, microcomputer(s), micro-controller(s), computer(s), and/or any other programmable device(s) (Herein called "Programmable Controller(s)/PLC") (375), and the valve(s) (35) can be opened and closed for any purposes, at any effective time(s) and for any effective duration of time(s). It is preferred, without limitation, that at least one separate valve(s) (35) is assigned to and controls the flow or movement of any airborne agent(s) and/or applied agent(s) (20), into and/or to, any suitable and effective location(s) such as, but not limited to any, (a) removable treatment enclosure(s) (230), (b) container holding chamber(s) (265), (c) object support(s) (84), moving support and dropping mechanism(s) (605), support and tilt mechanism(s) (655), gripping mechanism(s) (135), gripping finger(s) (108), movable forks or beams (49)(50), movable holding and/or support apparatus(s) (606), and/or (d) any other suitable and effective means for holding, supporting, and/or hanging, any object(s) (01), removable treatment enclosure(s) (230), and/or enclosure(s).

Without limitation, at least one valve(s) (35) can also control the flow or movement of any, gas(s), vapor(s), applied agent(s) (20), aerosol(s) (65), carrier gas(s) for the aerosol(s) (65), that is moved, intended to be returned, is any intended recirculation flow(s), or is the return flow(s), back to the one or more of any effective means to produce, create, generate, and/or deploy, the at least one airborne agent(s) and/or applied agent(s) (20), aerosol(s) (65), and/or generation chamber(s) (15), from any location(s) and/or enclosure(s) such as, but not limited to any, container holding chamber(s) (265), removable treatment enclosure(s) (230), and/or any other suitable and effective location(s), to provide one or more of any suitable and effective re-circulation path(s) back to (Herein called "Aerosol Recirculation Return Path(s)") (730) the one or more of any effective means to produce, create, generate, and/or deploy, the at least one airborne agent(s) and/or applied agent(s) (20), aerosol(s) (65), and/or generation chamber(s) (15).

Without being limited, one or more of any suitable and effective, fan(s), blower(s), forced air apparatus(s), air/gas pump(s), and/or any other source(s) of pressurized air/gas(s) (Herein called "Blower(s)") (not shown) located at one or more of any effective locations, may be effectively connected to and operated to move or flow any, air, gas(s), deployed applied agent(s) (20), vapor(s), aerosol(s) (65), and/or carrier gas(s) for the aerosol(s) (65), through various location(s) such as, but not limited to any, production source(s) or generator(s) (15) of the applied agent(s) (20), vapor(s) and/or aerosol(s) (65), generation chamber(s) (15), container holding chamber(s) (265), removable treatment enclosure(s) (230), object support(s) (84), moving support and dropping mechanism(s) (605), movable forks or beams (49)(50), support and tilt mechanism(s) (655), gripping mechanism(s) (135), gripping finger(s) (108), movable holding and/or support apparatus(s) (606), and/or any other suitably connected area(s), location(s), and part(s). It is preferred, without limitation, that the at least one production source(s) or generator(s) (15) of the applied agent(s) (20), vapor(s) and/or aerosol(s) (65), and/or generation chamber(s) (15), includes and is effectively connected to one or more of any effective said blower(s). Without being limited, the applied agent(s) (20)(65) and any accompanying air/gas(s) may be deployed and/o moved into the one or more of any suitable treated area(s) and enclosure(s) at any effective, flow rate(s), quantity(s), and speed(s), all in a manner known in the art.

Without being limited, the generated and deployed applied agent(s) (20), vapor(s), aerosol(s) (65), and/or air/gas(s), can also flow through various location(s) such as, but not limited to any, production source(s) or generator(s) (15) of the applied agent(s) (20), vapor(s) and/or aerosol(s) (65), generation chamber(s) (15), container holding chamber(s) (265), removable treatment enclosure(s) (230), object support(s) (84), moving support and dropping mechanism(s) (605), movable forks or beams (49)(50), support and tilt mechanism(s) (655), gripping mechanism(s) (135), gripping finger(s) (108), movable holding and/or support apparatus(s) (606), and/or any other suitably connected area(s), location(s), and part(s), for one or more of any effective time period(s), and any effective number of revolution(s) or travel circuit(s). It is preferred, without limitation, that any effective vapor(s) and/or aerosol (65) is produced in at least one of any suitable aerosol generation chamber(s) and/or generation chamber(s) (15), that is connected to any suitable location(s) such as, but not limited to any, removable treatment enclosure(s) (230), container holding chamber(s) (265), object support(s) (84), movable forks or beams (49)(50), moving support and dropping mechanism(s) (605), support and tilt mechanism(s) (655), gripping mechanism(s) (135), gripping finger(s) (108), and/or movable holding and/or support apparatus(s) (606), and it is more preferred, without limitation, that the aerosol (65) is ultrasonically produced, and it is even more preferred, without limitation, that the aerosol is produced using at least one ultrasonic aerosol generating apparatus(s) (15) as described in U.S. Pat. No. 9,551,996.

Without being limited, one or more of any suitable, area(s), space(s), and/or part(s) such as, but not limited to any, removable treatment enclosure(s) (230), container holding chamber(s) (265), object support(s) (84), movable forks or beams (49)(50), moving support and dropping mechanism(s) (605), support and tilt mechanism(s) (655), gripping mechanism(s) (135), gripping finger(s) (108), and/or movable holding and/or support apparatus(s) (606), can also be effectively connected and/or interconnected, at one or more of any effective location(s), with one or more of any effective means to dehumidify and/or remove any vapor(s) (Herein called "Dehumidification System(s)") (74), and/or heat (660), any air/gas(s) and/or atmosphere(s) within any removable treatment enclosure(s) (230) and/or container holding chamber(s) (265), and/or any other connected space(s), conduit(s), pipe(s), and/or any other part(s) and component(s). Without being limited, the dehumidification system(s) (74) can include one or more of any effective means for vapor(s) removal and/or to dehumidify, any air/gas(s) found in any air/gas(s) stream(s) and/or atmosphere(s) in any enclosure(s), and can include, but is not limited to any effective, (a) absorbent media dehumidification and/or vapor removal system known to those skilled in the art, (b) dehumidification and/or airborne vapor removal system that uses any effective, refrigerated, chilled, and/or cooled, surface(s) design(s) known to those skilled in the art, and/or (c) any other suitable and effective dehumidification system known to those skilled in the art.

It is preferred, without limitation, that the one or more of any effective means to dehumidify and/or remove any vapor(s) (74), and/or heat, any gas(s) and/or atmosphere within or at any location(s) such as, but not limited to any, air/gas flow path(s), removable treatment enclosure(s) (230), container holding chamber(s) (265), open removable package(s) (229), open package(s), and/or packaging material(s) (495), object support(s) (84), movable forks or beams (49)(50), moving support and dropping mechanism(s) (605), support and tilt mechanism(s) (655), gripping mechanism(s) (135), gripping finger(s) (108), and/or movable holding and/or support apparatus(s) (606), are at least effectively connected and/or interconnected, to at least one of any, removable treatment enclosure(s) (230) and/or container holding chamber(s) (265), at one or more of any effective location(s), and providing another at least one effective connection(s) to the same removable treatment enclosure(s) (230) and/or container holding chamber(s) (265), at one or more different effective location(s), so that any, air, gas(s), vapor(s), water vapor(s), humidity, aerosol(s) (65), carrier gas(s) for the aerosol(s) (65), and/or air/gas(s) that is heated (660), and/or dehumidified removed of vapor(s) (74), and/or filtered (75)(53), that is present in, deployed into, and/or moved into, the removable treatment enclosure(s) (230) and/or container holding chamber(s) (265), can eventually flow out of the removable treatment enclosure(s) (230) and/or container holding chamber(s) (265), and back to, via one or more of any suitable and effective re-circulation path(s) (Herein called "Recirculation Return Path(s)") (735), and then through the at least one effective means to heat (660), and/or dehumidify (74) and/or remove any vapor(s) (74)(75) from, the atmosphere and/or air/gas(s) within the removable treatment enclosure(s) (230) and/or container holding chamber(s) (265), where the heated, processed, dehumidified, and/or filtered, air/gas(s) and/or atmosphere, can then recirculate and flow back through various space(s) and area(s) such as, but not limited to any, removable treatment enclosure(s) (230) and/or container holding chamber(s) (265), and/or any other part(s) and components including, but not limited to any, object support(s) (84), movable forks or beams (49)(50), moving support and dropping mechanism(s) (605), support and tilt mechanism(s) (655), gripping mechanism(s) (135), gripping finger(s) (108), and/or movable holding and/or support apparatus(s) (606). Without limitation, this can continue any effective number of times until the process of heating, heating and drying, dehumidifying, and/or removing any, humidity, water vapor(s), and/or targeted gas(s) and/or vapor(s), from the air/gas(s) and/or atmosphere within the various space(s) and area(s) such as, but not limited to any, removable treatment enclosure(s) (230) and/or container holding chamber(s) (265), and/or any other part(s) and components including, but not limited to any, object support(s) (84), movable forks or beams (49)(50), moving support and dropping mechanism(s) (605), support and tilt mechanism(s) (655), gripping mechanism(s) (135), gripping finger(s) (108), and/or movable holding and/or support apparatus(s) (606), is effectively complete. Without being limited, any, vapor(s), air/gas(s), and/or atmosphere(s), can flow through any location(s), area(s), and part(s) such as, but not limited to any, removable treatment enclosure(s) (230), container holding chamber(s) (265), heating apparatus(s) (660), and dehumidification apparatus(s) (74), at any effective flow rate(s), flow quantity(s), and/or flow speed(s), at any effective time(s).

It is preferred, without limitation, that any air/gas(s) that is heated, dehumidified, removed of vapor(s), and/or filtered, is flowed into, through, and/or deployed, at least through, into, and/or at, one or more of any effective location(s) of or at any effective end(s) or side(s), and/or at least through, into, and more preferably and without limitation, at one or more of any effective end location(s), of the removable treatment enclosure(s) (230) and/or container holding chamber(s) (265), and the air/gas(s) that is heated, dehumidified, removed of vapor(s), and/or filtered, is then effectively moved or flowed into, via one or more of any suitable and effective entry point(s) or orifice(s) (305), and/or through the removable treatment enclosure(s) (230) and/or container holding chamber(s) (265), and is then moved or flowed out of these space(s) and/or exit, via one or more of any suitable and effective exit point(s) or orifice(s)(320), the removable treatment enclosure(s) (230) and/or container holding chamber(s) (265), at least at or near one or more other effective location(s), preferably and without limitation, at or near at least any effective opposite end(s) or side(s) of the removable treatment enclosure(s) (230) and/or container holding chamber(s) (265) to the said entry point(s) or orifice(s) (305), and is then returned back to and then through the one or more heating apparatus(s) (660) and/or dehumidification apparatus(s) (74), where the air/gas(s) flows are effectively, heated, dehumidified, removed of any vapor(s), treated, and/or processed, and then re-flowed or moved back to and through the removable treatment enclosure(s) (230) and/or container holding chamber(s) (265), until this step of the treatment(s) and/or processing process(s) is effectively complete.

Without being limited, the sources of any, and/or any flow(s) or movement(s) of any air/gas(s) that is, heated, dehumidified, removed of vapor(s), and/or filtered, can be effectively, connected, interconnected, and/or interfaced with, one or more of any suitable and effective valve(s) (740)(35). The valve(s) (35) can control the flow or movement of any air/gas(s) such as, but not limited to any, air/gas(s) that is, heated, dehumidified, removed of vapor(s), and/or filtered, into one or more of any space(s) or location(s) such as, but not limited to any, removable treatment enclosure(s) (230), container holding chamber(s) (265), movable forks or beams (49)(50), object support(s) (84), moving support and dropping mechanism(s) (605), support and tilt mechanism(s) (655), gripping mechanism(s) (135), gripping finger(s) (108), and/or movable holding and/or support apparatus(s) (606). Without being limited, the valve(s) (740)(35) can be controlled by one or more of any suitable and effective, programmable controller(s)/PLC(s) (375), and the one or more valve(s) (740)(35) can be opened and closed for any purposes, at any effective time(s), before, during, and/or after, any processing step(s), and for any effective duration of time(s).

It is preferred, without limitation, that at least one separate valve(s) (35) is assigned to and controls the flow or movement of any air/gas(s), that is heated, dehumidified, removed of vapor(s), and/or filtered, into, to, and/or out of, part(s) and location(s) such as, but not limited to any, (a) removable treatment enclosure(s) (230), (b) container holding chamber(s) (265), (c) object support(s) (84), moving support and dropping mechanism(s) (605), movable forks or beams (49)(50), support and tilt mechanism(s) (655), gripping mechanism(s) (135), gripping finger(s) (108), movable holding and/or support apparatus(s) (606), and/or (d) any other suitable and effective means for holding, supporting, and/or hanging, any object(s) (01), removable treatment enclosure(s) (230), and/or enclosure(s), at any effective time(s), and for any effective duration(s) of time(s).

Without limitation, at least one valve(s) (35)(740) can also control the flow or movement of any, gas(s), vapor(s), applied agent(s), humidity, aerosol(s), carrier gas(s) for the aerosol(s), and/or air/gas(s) that is heated, dehumidified, removed of vapor(s), and/or filtered, that is moved, intended to be returned, is any intended recirculation flow(s), or is the return flow(s), back to any part(s), component(s), and/or apparatus(s) such as, but not limited to any, means to heat, dehumidify, and/or remove any vapor(s) from any air/gas flow(s), and/or any means to filter any air/gas(s) flows and remove substance(s) such as, but not limited to any, particle(s), vapor(s), and/or applied agent(s), from any location(s) and/or enclosure(s) such as, but not limited to any, container holding chamber(s) (265), removable treatment enclosure(s) (230), and/or any other suitable and effective location(s), to provide one or more of any suitable and effective re-circulation path(s) (735) back to the one or more of any effective heating (660) and/or dehumidification system(s) (74).

Without being limited, the one or more of any, air filters (74)(75)(53), heating apparatus(s) (660), and/or dehumidification apparatus(s) (74), can effectively include in its design and/or use, all in a manner known in the art, one or more of any suitable and effective fan(s), blower(s), forced air apparatus(s), air/gas pump(s), and/or any other source(s) of pressurized air/gas(s) (not shown), to effectively move or flow any air/gas(s) into and/or through any area(s) and/or location(s) such as, but not limited to any, removable treatment enclosure(s) (230), container holding chamber(s) (265), object support(s) (84), moving support and dropping mechanism(s) (605), support and tilt mechanism(s) (655), movable forks or beams (49)(50), gripping mechanism(s) (135), gripping finger(s) (108), and/or movable holding and/or support apparatus(s) (606), as well as any means to heat (660), dehumidify and/or remove any aerosol(s), humidity, and/or vapor(s) (74).

It is preferred, without limitation, that at least one of any effective dehumidification system(s) (74) that uses at least one of any effective, refrigerated, chilled, and/or cooled, surface(s) design(s) known to those skilled in the art, chill coil(s), condenser coil(s), condensate forming, apparatus(s) known in the art, and/or any other suitable and effective dehumidification system(s) known to those skilled in the art (not shown), can be used in the present invention, and it can also include one or more of any effective blower(s) (not shown). Also, and without being limited, any vapor(s), air/gas(s), and/or atmosphere, can also flow through the one or more of any, heater system(s) (660), dehumidification system(s) (74), removable treatment enclosure(s) (230), and/or container holding chamber(s) (265), at any time(s), for any effective time period(s), and any effective number of revolutions or travel circuits that any, air/gas(s), vapor(s), and/or atmosphere, can make through the various component(s), area(s), and location(s) such as, but not limited to any, heating system(s) (660) dehumidification system(s) (74), removable treatment enclosure(s) (230), and/or container holding chamber(s) (265).

Without being limited, any air/gas(s), and/or atmosphere, that is moved or flowed through any parts, area(s), and/or components, used to treat and/or process any surfaces within any removable treatment enclosure(s) (230) and/or the container holding chamber(s) (265), can be effectively heated to one or more of any effective and suitable temperature(s), at any suitable and effective location(s), and at any suitable and effective time(s) and/or step(s) in any processing of any surface(s) within the removable treatment enclosure(s) (230) and/or the container holding chamber(s) (265), but preferably at least a temperature that is suitable and effective. The heated air/gas and/or atmosphere, can, without being limited, dry, aid in drying, and/or decrease the drying time for, any surface(s) such as, but not limited to, those within and/or on any, removable treatment enclosure(s) (230), container holding chamber(s) (265), object support(s) (84), movable forks or beams (49)(50), moving support and dropping mechanism(s) (605), support and tilt mechanism(s) (655), gripping mechanism(s) (135), gripping finger(s) (108), and/or movable holding and/or support apparatus(s) (606), connected space(s), air/gas flow path(s), and/or any other connected part(s), components, and/or apparatus(s) used to treat and/or process any surface(s) within the removable treatment enclosure(s) (230) and/or the container holding chamber(s) 265).

Without limitation, one or more of any effective means to heat (Herein called "Air/Gas Stream Heater(s)") (660) the various air/gas(s) and/or any atmosphere(s) that is found within and/or flowed to and/or through various location(s) such as, but not limited to any, removable treatment enclosure(s) (230), and/or the container holding chamber(s) (265), can be connected to the same one or more air/gas flow path(s), as the dehumidification system(s) (74). Also, and without limitation, the one or more of any air/gas stream heater(s) (660) can be suitably and effectively located along the one or more air/gas(s) flow path(s) after the dehumidification system(s) (74), but before the one or more removable treatment enclosure(s) (230) and/or container holding chamber(s) (265).

Without being limited, any, vapor(s), air/gas(s), and/or atmosphere, that is moved or flowed through any parts or components used to treat and/or process any surfaces within area(s) and location(s) such as, but not limited to any, removable treatment enclosure(s) (230), and/or the container holding chamber(s) (265), can also be effectively filtered with one or more of any suitable and effective filter(s) (75)(53), at one or more of any effective location(s), at any time(s) or at any part of any one or more of any process(s) to treat and/or process any surface(s) within the removable treatment enclosure(s) and/or the container holding chamber(s). Without being limited, the filtering of any of the air/gas and/or vapor(s) flow(s) can remove things such as, but not limited to any, airborne foreign object debris, airborne particles, vapor(s), and/or gas(s). Without being limited, any suitable and effective filter(s) (75)(53) known to those skilled in the art can be used. It is preferred, without limitation, that the filter(s) is one or more of any effective charcoal filter(s) (75) that can also be combined with one or more of any effective HEPA filter(s) (53), all in a manner known to those skilled in the art.

Without being limited, one or more of any effective means for air/gas(s) filtering (53), known to those skilled in the art, can be also used for any effective and suitable air/gas(s) filtration at one or more of any location(s) along any air/gas(s) flow path to and/or from the one or more of any removable treatment enclosure(s) (230) and/or the container holding chamber(s) (265), at any suitable and effective time(s), to filter any airborne substance(s) such as, but not limited to any, particle(s), foreign object debris, and/or dust(s). It is preferred, without limitation, that these filter(s) (53) are any effective HEPA filter(s) known to those skilled in the art. It is also preferred, without limitation, that at least one of any effective HEPA filter(s) (53) is effectively located in any air/gas stream(s) after any part(s) and apparatus(s) such as, but not limited to any, dehumidification system(s) (74), and/or air/gas stream heater(s) (660), and more preferably and without limitation, at least in any air/gas stream(s) after any air/gas stream heater(s) (660) that is located in the same air/gas stream(s) after any dehumidification system(s) (74).

Without being limited, any air and/or gas(s) that is free of any, chemical(s), vapor(s), particle(s), biohazard(s), bacteria(s), virus(s), aerosol(s), and/or applied agent(s) (20), from any suitable location(s) outside of, and preferably and without limitation, from outside of the enhanced decontamination enclosure apparatus (715) via one or more of any suitable fresh air/gas(s) inlet(s) (38), and/or separate from, any removable treatment enclosure(s) (230), container holding chamber(s) (265), and/or the enhanced decontamination enclosure apparatus (715) (Herein called "fresh air/gas(s)") (380), can also be moved or flowed into and through the removable treatment enclosure(s) (230), container holding chamber(s) (265), any connected air/gas(s) flow path(s), and/or any other suitable connected parts and component(s), at one or more of any suitable and effective time(s), to any suitable and effective location(s) such as, but not limited to any, suitable and effective location(s) outside of the: (a) removable treatment enclosure(s) (230), and/or (b) container holding chamber(s) (265), preferably and without limitation, via one or more of any suitable exhaust air/gas(s) outlet(s) (39), for purposes including, but not limited to, flushing and/or removing any, chemical(s), particle(s), heated air/gas(s), applied agent(s) (20), humidity, vapor(s), gas(s), water vapor, and/or aerosol(s) (65), from any of these one or more area(s) and space(s). Without being limited, the fresh air/gas(s) (380) can be effectively filtered before it is moved or flowed through any, removable treatment enclosure(s) (230), container holding chamber(s) (265), and/or any other connected parts and component(s). One or more of any suitable and effective filter(s) (75)(53) known to those skilled in the art can be used. It is preferred, without limitation, that these filter(s) are any effective HEPA filter(s) (53) all known to those skilled in the art.

Without being limited, one or more of any suitable and effective fan(s), blower(s), forced air apparatus(s), air/gas pump(s), and/or any other source(s) of pressurized air/gas(s) (17)(51), located at one or more of any effective locations known to those skilled in the art, can be effectively connected to and operated to move or flow any fresh air/gas(s) (380), into and through one or more of any space(s), area(s), part(s), component(s) and/or location(s) such as, but not limited to any, removable treatment enclosure(s) (230), container holding chamber(s) (265), object support(s) (84), moving support and dropping mechanism(s) (605), support and tilt mechanism(s) (655), gripping mechanism(s) (135), gripping finger(s) (108), movable holding and/or support apparatus(s) (606), and/or any other suitably connected parts.

It is preferred, without limitation, that any effective amount, and/or any effective rate of supply of, fresh air/gas(s) (380) is flowed into, through, and/or deployed, at least through, into, and/or at, one or more of any effective location(s) of any end(s) or side(s), and/or at least through, into, and more preferably and without limitation, at one or more of any effective end location(s), of the removable treatment enclosure(s) (230) and/or container holding chamber(s) (265), and the fresh air/gas(s) (380), that is preferably and without limitation, filtered, is then effectively moved or flowed into and through the removable treatment enclosure(s) (230) and/or container holding chamber(s) (265), and is then moved or flowed out of these space(s) and/or exit the removable treatment enclosure(s) (230) and/or container holding chamber(s) (265), at least at or near one or more other effective location(s), preferably and without limitation, at or near at least any effective opposite end(s) or side(s) to the said entry point(s) for the fresh air/gas(s) (380), of the removable treatment enclosure(s) (230) and/or container holding chamber(s) (265), and is then moved or flowed to any suitable and effective location(s) such as, but not limited to any, suitable and effective location(s) outside of the: (a) removable treatment enclosure(s) (230), (b) container holding chamber(s) (265), and/or preferably and without limitation, (c) enhanced decontamination enclosure apparatus(s) (715), through and out of one or more of any suitable exhaust air/gas(s) outlet(s) (39), until this step of the various treatment(s) and/or processing process(s) is complete.

Without being limited, the sources of any, and/or any flow(s) or movement(s) of any fresh air/gas(s) (380), can be connected, interconnected, and/or interfaced with, one or more of any suitable and effective valve(s) (35). The valve(s) (35) can control the flow or movement of any fresh air/gas(s) (380), into and/or through one or more of any space(s), area(s), part(s), component(s), and/or location(s) such as, but not limited to any, removable treatment enclosure(s) (230), container holding chamber(s) (265), object support(s) (84), movable forks or beams (49)(50), moving support and dropping mechanism(s) (605), support and tilt mechanism(s) (655), gripping mechanism(s) (135), gripping finger(s) (108), movable holding and/or support apparatus(s) (606), and/or any other suitably connected parts. Without being limited, any valve(s) (35) can be controlled by one or more of any suitable and effective, programmable controller(s)/PLC(s) (375), and the valve(s) (35) can be opened and closed for any purposes, at any effective time(s) and for any effective duration of time(s). It is preferred, without limitation, that at least one separate valve(s) (35) is assigned to and controls the flow or movement of any fresh air/gas(s) (380), into at least the following of each location: (a) removable treatment enclosure(s) (230), (b) container holding chamber(s) (265), and/or (c) object support(s) (84), moving support and dropping mechanism(s) (605), support and tilt mechanism(s) (655), movable forks or beams (49)(50), gripping mechanism(s) (135), gripping finger(s) (108), movable holding and/or support apparatus(s) (606), and/or any other suitably connected parts.

Without limitation, at least one of any suitable valve(s) (35) can also control the flow or movement of any fresh air/gas(s) (380), applied agent(s) (20), aerosol(s) (65), and/or vapor(s), that is moved or flowed out of, the removable treatment enclosure(s) (230), container holding chamber(s) (265), and/or any other suitably connected parts, to any suitable and effective location(s) such as, but not limited to any, suitable and effective location(s) outside of the: (a) removable treatment enclosure(s) (230), (2) container holding chamber(s) (265), and/or (3) enhanced decontamination enclosure apparatus(s) (715). Without being limited, the valve(s) (35) can be controlled by one or more of any suitable and effective, programmable controller(s)/PLC(s) (375), and the valve(s) (35) can be opened and closed for any purposes, at any effective time(s), during one or more of any processing step(s), and for any effective duration of time(s).

Without limitation, before any flow(s) of fresh air/gas(s) (380) and/or air/gas(s) flow(s), and any accompanying substance(s) such as, but not limited to any, aerosol(s) (65), vapor(s), applied agent(s) (20), heated air/gas(s), particle(s), and/or vapor(s), are permanently moved or flowed out of location(s) such as, but not limited to, the removable treatment enclosure(s) (230), container holding chamber(s) (265), and/or the enhanced decontamination enclosure apparatus (715), they can be suitably and effectively filtered (75)(53). Without being limited, the filtering (75)(53) of any of these air/gas(s) and/or vapor(s) flow(s) can remove things such as, but not limited to any, vapor(s), aerosol(s) (65), applied agent(s) (20), particle(s), and/or gas(s). Without being limited, any suitable and effective filter(s) (75)(53) known to those skilled in the art may be used. It is preferred, without limitation, that the filter(s) is one or more of any effective charcoal filter(s) (75), and can also be combined with one or more of any effective HEPA filter(s) (53) preferably, and without limitation, later in the air/gas(s) stream(s), all in a manner known to those skilled in the art.

Without being limited, one or more of any suitable and effective, vacuum pump(s), air/gas pump(s), vacuum apparatus(s), and/or any other suitable and effective apparatus(s) that can create any effective, vacuum, negative pressure, and/or cause any liquid to shift from a liquid to a gas phase (Herein called "Negative Pressure Device(s)") (98), can be suitably and effectively connected, interconnected, and/or interfaced with or to one or more locations such as, but not limited to, the removable treatment enclosure(s) (230), container holding chamber(s) (265), and/or any other effectively connected spaces, all in a manner known to those skilled in art, and can be used for purposes such as, but not limited to, (a) removing or evacuating any, gas(s), vapor(s), humidity, heated air/gas(s), applied agent(s) (20), aerosol(s) (65), and/or carrier gas(s) for the aerosol(s) (65), from any location(s) such as, but not limited to, the removable treatment enclosure(s) (230), container holding chamber(s) (265), and/or any other connected spaces, and/or (b) effectively drying any surface(s) within the removable treatment enclosure(s) (230), container holding chamber(s) (265) and/or any other connected spaces with any effective, vacuum, pressure, and/or negative pressure, all in a manner known to those skilled in the art. It is preferred, without limitation, that when any effective, vacuum, negative pressure, atmospheric pressure, pressure, and/or pressure measurement, is operated, drawn, maintained, and/or created, within any location(s) such as, but not limited to any, removable treatment enclosure(s) (230), container holding chamber(s) (265), and/or any other connected spaces, to effectively and suitably dry any surface(s) and/or object(s) (01) within, that at least any effective, vacuum, negative pressure, atmospheric pressure, pressure, and/or pressure measurement, is operated, drawn, maintained, and/or created, in the removable treatment enclosure(s) (230), container holding chamber(s) (265), and/or any other connected spaces, and it is more preferred, without limitation, that any effective, negative pressure, pressure, and/or vacuum, that is measured below 1 atmosphere is used and/or created in the removable treatment enclosure(s) (229), container holding chamber(s) (265), and/or any other connected spaces, and it is even more preferred, without limitation, that any effective, vacuum, negative pressure, atmospheric pressure, pressure, and/or pressure measurement, is operated, drawn, maintained, and/or created, for any effective length and time, and/or for any effective number of processing cycle(s), that can cause any liquid(s) and/or applied agent(s) (20) present in any area(s) and/or location(s) such as, but not limited to any, removable treatment enclosure(s) (230), container holding chamber(s) (265), object support(s) (84), moving support and dropping mechanism(s) (605), support and tilt mechanism(s) (655), movable forks or beams (49)(50), gripping mechanism(s) (135), gripping finger(s) (108), movable holding and/or support apparatus(s) (606), and/or any other suitably connected parts, to shift, transform, and/or transfer, into any effective vapor(s) and/or gas(s) phase(s), or otherwise turn into a gas(s), that is able to be removed from these various space(s) by any effective means such as, but not limited to, one or more of any suitable and effective, vacuum pump(s), air/gas pump(s), vacuum apparatus(s), blower(s), fan(s), fresh air/gas(s) (380) flushing (98) as discussed earlier, and/or any other source(s) of pressurized air/gas(s) (98), that can operate at any suitable and effective time(s), and for any duration of time(s).

Without limitation, at least one of any suitable valve(s) (35) can be located at any suitable and effective locations, including, but not limited to, before and/or after any, negative pressure device(s) (98), where the valve(s) (35) can control the flow or movement of any, air/gas(s), fresh air/gas(s) (380), heated air/gas(s), applied agent(s) (20), aerosol(s) (65), gas(s), particle(s), and/or vapor(s), that is moved or flowed into, and/or moved or flowed through and/or out of any area(s) and location(s) such as, but not limited to any, removable treatment enclosure(s) (230), container holding chamber(s) (265), and/or any other suitably connected parts, to any effective location(s) such as, but not limited to any one or more location(s) outside of the: (a) removable treatment enclosure(s) (230), (b) container holding chamber(s) (265), and/or (3) enhanced decontamination enclosure apparatus(s) (715), through one or more of any suitable exhaust air/gas(s) outlet(s) (39).

Without being limited, any valve(s) (35) used in the present invention, can be controlled and/or monitored, by one or more of any suitable and effective, programmable controller(s)/PLC(s) (375), and the one or more valve(s) (35) can be opened and closed for any purposes, at any effective time(s) and for any effective duration of time(s), all in a manner known to those skilled in the art.

Without limitation, before any air/gas(s) flow(s), and any accompanying substance(s) such as, but not limited to any, aerosol(s) (65), and/or vapor(s), are permanently moved or flowed out of location(s) such as, but not limited to, the removable treatment enclosure(s) (230), container holding chamber(s) (265), and/or the enhanced decontamination enclosure apparatus (715), by any component(s) or apparatus(s) such as, but not limited to any, negative pressure device(s) (98), they can be suitably and effectively filtered (75)(53). Without being limited, any flow(s) or movement(s) of any substance(s) such as, but not limited to any, air/gas(s), aerosol(s) (65), applied agent(s) (20), and/or vapor(s), can be effectively and suitably filtered before and/or after, they pass through one or more of any negative pressure device(s) (98), to remove any substance(s) such as, but not limited to any, vapor(s), applied agent(s) (20), aerosol(s) (65), particle(s), and/or gas(s). Without being limited, one or more of any suitable and effective filter(s) (75)(53) known to those skilled in the art may be used. It is preferred, without limitation, that the filter(s) is one or more of any effective charcoal filter(s) (75), and can also be combined with one or more of any effective HEPA filter(s) (53) preferably, and without limitation, later in the air/gas(s) stream(s), all in a manner known to those skilled in the art.

Without being limited, after any suitable and effective, negative pressure device(s) (98), vacuum, negative pressure, atmospheric pressure, pressure, and/or pressure measurement, is operated, drawn, maintained, and/or created, at any effective time(s) and for one or more of any effective duration of time(s), within any location(s) such as, but not limited to any, removable treatment enclosure(s) (230), container holding chamber(s) (265), and/or any other suitably connected part(s) and/or area(s), the pressure or atmospheric pressure within these one or more area(s) and space(s) can be, without limitation, adjusted, refreshed, returned, and/or reestablished, preferably and without limitation, with any air/gas(s), preferably and without limitation, any fresh air/gas(s) (380) to any effective pressure(s) or atmospheric pressure(s) that is preferably, and without limitation, suitably and effectively close to and/or at any ambient condition(s), and/or more preferably, and without limitation, suitably close to or equal to any pressure(s) or atmospheric pressure(s) outside of the enhanced decontamination enclosure apparatus (715). Without being limited, the fresh air/gas(s) (380) used for these purposes can be effectively filtered (75)(53) before it is moved or flowed into and/or through any, removable treatment enclosure(s) (230), container holding chamber(s) (265), and/or any other connected parts and component(s). One or more of any suitable and effective filter(s) (75)(53) known to those skilled in the art can be used. It is preferred, without limitation, that these filter(s) are at least any effective HEPA filter(s) (53), all in a manner known to those skilled in the art.

Without being limited, the fresh air/gas(s) (380) that fills or refills any evacuated and/or partially evacuated location(s) such as, but not limited to the, removable treatment enclosure(s) (230), container holding chamber(s) (265), and/or any other suitably connected part(s) and area(s), can be sourced from one or more of any suitable and effective location(s) and/or source(s), such as, but not limited to, the same effectively filtered supply of fresh air/gas(s) (380) that was described earlier, that can be used to flow into and through any location(s) such as, but not limited to any, removable treatment enclosure(s) (230), container holding chamber(s) (265), and/or any other suitably connected part(s), for purposes including, but not limited to, flushing and/or removing any, chemical(s), particle(s), applied agent(s) (20), humidity, vapor(s), gas(s), water vapor, and/or aerosol(s) (65), from these one or more area(s) and space(s).

Without being limited, one or more of any suitable and effective sensing means or sensor(s) can be used for purposes including, but not limited to any, detecting, recording, monitoring, and/or reporting, of various data, situation(s), and/or condition(s), such as, but not limited to any, temperature(s) (355), humidity(s) (350), dew point(s) (not shown), pressure(s) (not shown), atmospheric pressure(s) (not shown), liquid and/or moisture deposition(s) (not shown), airborne particle sensor(s) (not shown), airborne particle(s) and/or aerosol(s) (65) number(s) (not shown), airborne particle(s) and/or aerosol(s) (65) concentration(s) (not shown), presence and/or absence of any aerosol(s), and/or the presence or absence of any light(s) from one or more of any light source(s) (362) via one or more of any light detector(s) (362), within one or more of any effective area(s) and location(s) such as, but not limited to any, removable treatment enclosure(s) (230), container holding chamber(s) (265), and/or any other suitably connected part(s) and area(s), all in a manner known to those skilled in the art (Herein called "Environment Sensor(s)") (365). The one or more of any environment sensor(s) (365) can be suitably and effectively interfaced with and/or located in one or more of any suitable and effective, location(s), treated area(s), and/or space(s) such as, but not limited to any, removable treatment enclosure(s) (230), container holding chamber(s) (265), and/or any other suitably connected part(s) and/or area(s). Without being limited, the one or more of any environment sensor(s) (365) can be effectively positioned and/or located in any area(s), location(s), space(s), and/or enclosure(s), using one or more of any suitable and effective means, such as, but not limited to any suitable and effective sensor attachment member(s) (370), all in a manner known to those skilled in the art.

Without being limited, the various environment sensor(s) (365) used in the present invention, can be controlled by (ie: any light source(s) (362) for the light detector(s) (360), monitored by, and/or communicated with, one or more of any suitable and effective, programmable controller(s)/PLC(s) (375), all in a manner known to those skilled in the art. It is preferred, without limitation, that the various environment sensor(s) (365) report their data to any programmable controller(s)/PLC(s) (375), and the programmable controller(s)/PLC(s) (375) can use this data for purposes including, but not limited to, determining and/or controlling one or more of any step(s), activity(s), and/or action(s), to treat and process any, object(s) (01), atmosphere(s), and/or surface(s), in any location(s) such as, but not limited to any, removable treatment enclosure(s) (230), container holding chamber(s) (265), and/or any other suitably connected part(s) and area(s), all in a manner known to those skilled in the art.

Without being limited, the one or more of any environment sensor(s) (365) located in location(s) such as, but not limited to any, removable treatment enclosure(s) (230) and/or container holding chamber(s) (265), can also be connected and/or disconnected from one or more of any suitable and effective direct and/or indirect connection(s) made with the one or more of any suitable programmable controller(s)/PLC(s) (375) and/or any suitable power source(s) (not shown), at one or more of any suitable and effective location(s), all in a manner known to those skilled in the art.

It is preferred, without limitation, that the one or more of any suitable power and/or communication wire(s) and/or cable(s) (not shown) and/or any of their connector(s) or connection(s) (not shown) known to those skilled in the art, that connect directly and/or indirectly with the one or more of any environment sensor(s) (365), suitable and effectively connect with the one or more of any suitable and effective, power and/or communication cable(s) and wire(s) (not shown), and/or cable and/or wire(s) connection(s) or connector(s) (not shown), outside of the removable treatment enclosure(s) (230), and more preferably, and without limitation, the one or more connection(s) is made suitably and effectively close to the removable treatment enclosure(s) (230) at one or more of any suitable and effective location(s) within the container holding chamber(s) (265).

In another part of this embodiment, and without limitation, the one or more of any suitable, area(s), space(s), part(s), component(s), and/or enclosure(s), such as, but not limited to, the one or more of any, container holding chamber(s) (265), removable treatment enclosure(s) (230), and/or one or more of any suitable means or apparatus(s) to suitably and effectively, position, support, hold, interface, hang, suspend, and/or locate, any, object(s) (01), such as, but not limited to any, object support(s) (84), moving support and dropping mechanism(s) (605), support and tilt mechanism(s) (655), movable forks or beams (49)(50), gripping mechanism(s) (135), gripping finger(s) (108), movable holding and/or support apparatus(s) (606), and/or any other suitable part(s) and apparatus(s), within the removable treatment enclosure(s) (230) and/or container holding chamber(s) (265), can be suitably and effectively, and directly and/or indirectly, preferably and without limitation, removably connected to or with, one or more of any, treatment and processing equipment(s), apparatus(s), and/or component(s) such as, but not limited to any suitable and effective, (a) means and conduits (18) for generating, creating, administering, and/or delivering (otherwise called the "generation chamber(s)") (15), one or more of any, applied agent(s) (20), aerosol(s) (65), and/or vapor(s), into and/or through any location(s) such as, but not limited to any, container holding chamber(s) (265) and/or removable treatment enclosure(s) (230), (b) means and conduits (18) for dehumidification and/or means for removing one or more of any vapor(s), water vapor(s) (ie: humidity), (otherwise called the "dehumidification system(s)") (74), from within and/or through any location(s) such as, but not limited to any, container holding chamber(s) (265) and/or removable treatment enclosure(s) (230), (c) means and conduits (18) for moving or flowing fresh air/gas(s) (380) into and/or through any location(s) such as, but not limited to any, container holding chamber(s) (265) and/or removable treatment enclosure(s) (230), (d) means and conduits (18) for creating any effective negative pressure(s) and/or vacuum (otherwise called the "negative pressure device(s)") (98), within any, area(s) and location(s) such as, but not limited to any, container holding chamber(s) (265) and/or removable treatment enclosure(s) (230), (e) means and conduits (18) for any effective filtration (53) of any air/gas(s) and/or atmosphere(s) that is moved or flowed into and/or through any location(s) such as, but not limited to any, container holding chamber(s) (265) and/or removable treatment enclosure(s) (230), (f) means and conduits (18) for heating (otherwise called the "air/gas stream heater(s)" (660), any air/gas(s) or atmosphere(s) that is moved or flowed into and/or through any location(s) such as, but not limited to any, container holding chamber(s) (265) and/or removable treatment enclosure(s) (230), (g) means and conduits (18) for exhausting, and preferably and without limitation, also effectively filtering (75) (53) any substance(s) such as, but not limited to any, air/gas(s), vapor(s), aerosol(s) (65), and/or applied agent(s) (20), from any location(s) within and/or effectively connected to, any space(s), area(s) and enclosure(s) such as, but not limited to any, container holding chamber(s) (265), and/or removable treatment enclosure(s) (230), including but not limited to any attached or connected, part(s), space(s), and apparatus(s), to one or more of any suitable and effective location(s) outside of location(s) such as, but not limited to any, removable treatment enclosure(s) (230), container holding chamber(s) (265), and/or the enhanced decontamination enclosure apparatus(s) (715), (h) means and conduits (18) to recirculate and/or assist with any recirculation, of any substance(s) such as, but not limited to any, air/gas(s), applied agent(s) (20), aerosol(s) (65), vapor(s), from, to, and/or through, any locations such as, but not limited to any, container holding chamber(s) (265) and/or removable treatment enclosure(s) (230), and back to and through one or more of any suitable and effective, production source(s) or generator(s) (15) of the applied agent(s) (20), vapor(s) and/or aerosol(s) (65) and/or otherwise any suitable generation chamber(s) (15), and/or (i) means and conduits (18) to recirculate and/or assist with any recirculation, of any substance(s) such as, but not limited to any, air/gas(s), fresh air/gas(s) (380), vapor(s), applied agent(s) (20), atmosphere(s), dehumidified air/gas(s), heated air/gas(s), from, to, and/or through, any locations such as, but not limited to any, container holding chamber(s) (265) and/or removable treatment enclosure(s) (230), and back to and through one or more of any suitable and effective, dehumidification system(s) (74).

Without being limited, one or more of any suitable and effective connection(s), and more preferably and without limitation, any suitable and effective, removable connection(s), can be made between one or more of any of the said treatment and processing equipment(s), apparatus(s), and/or component(s), and the one or more of any suitable and effective enclosure(s) and/or chamber(s) such as, but not limited to any, removable treatment enclosure(s) (230) and/or container holding chamber(s) (265), and more preferably, and without limitation, at least any removable treatment enclosure(s) (230), object support(s) (84), moving support and dropping mechanism(s) (605), support and tilt mechanism(s) (655), movable forks or beams (49) (50), gripping mechanism(s) (135), gripping finger(s) (108), movable holding and/or support apparatus(s) (606), and/or any other suitably connected parts, space(s) apparatus(s), and/or component(s), located within any of these various location(s), enclosure(s), and/or area(s), and the said connection(s) can be made with one or more of any suitable and effective, connector(s), sealable split connector(s), sealable split connection valve(s), connection valve(s), and/or valve(s) (Herein called "Connector Valve(s)") (280), known to those skilled in the art.

Without being limited, the preferred connector valve(s) (280) design is known to those skilled in the art, and is constructed with at least two separate releasable halves that effectively seal together when combined to form an effective free flowing path for any liquid and/or gas(s). Also, without being limited, the two separate releasable halves used in the preferred connector valve(s) (280) design, preferably and without limitation, effectively seal or self-seal, when they are disconnected and/or removed from each other. It is preferred, without limitation, that one half of the said one or more of any effective connector valve(s) (280), effectively connects directly and/or indirectly with one or more of any of the said treatment and processing equipment(s), apparatus(s), and/or component(s), and the other half of the said one or more of any connector valve(s) (280), effectively connects directly and/or indirectly with one or more of any removable treatment enclosure(s) (230). It is also preferred, without limitation, that the said connector valve(s) (280) have at least one suitable actuator apparatus(s) and/or button(s) (285) included in their design, so that when actuated the two halves of the connector valve(s) (280) are effectively released, all in a manner known to those skilled in the art.

Without limitation, the said connector valve(s) (280) can be suitably and effectively connected at one or more of any suitable and effective location(s), however, it is preferred, without limitation, that the said connector valve(s) (280) are located suitably and effectively close to the removable treatment enclosure(s) (230) inside of the container holding chamber(s) (265).

Without being limited, the removable treatment enclosure(s) (230) can be connected to or with one or more of any connector valve(s) (280) at one or more of any suitable and effective location(s), and at any suitable and effective time(s), and they can connect to or with one or more of any suitable, part(s), component(s), apparatus(s), hose(s), tube(s), conduit(s), that connect directly and/or indirectly with one or more of any suitable connection(s) and/or interface location(s) that are located on, adjacent to, and/or in effective proximity to one or more of any, removable treatment enclosure(s) (230), and/or treatment and processing equipment(s), apparatus(s), and/or component(s), that are used at any suitable and effective time(s), for the effective treatment and/or processing of any object(s) (01) and/or surface(s) within the removable treatment enclosure(s) (230) and/or container holding chamber(s) (265).

Without being limited, one or more of any means to indicate and/or report the effectiveness and/or efficacy of one or more of any treatment(s) and/or processing step(s) of any, surface(s), object(s), space(s), and/or atmosphere(s), can be suitably and effectively located inside of, in effective proximity to, outside of, and/or on, one or more of any effective and suitable location(s), object(s), part(s), and/or material(s), such as, but not limited to any, removable treatment enclosure(s) (230), container holding chamber(s) (265), open package(s), packaging material(s) (495), and/or any other suitably connected part(s), and can include but is not limited to any suitable and effective, chemical exposure indicator(s) (244), and/or biological challenge(s) (243) (Herein called "Treatment Efficacy Indicator(s)") (242), all in a manner known to those skilled in the art. It is preferred, without limitation, that the chemical contact indicator(s) are any suitable and effective material that shows or visually indicates the presence of hydrogen peroxide and/or peroxyacetic acid, and the biological challenge(s) can include any suitable and effective bacteria(s) and/or bacterial spore(s) challenge(s), all in a manner known to those skilled in the art.

According to another embodiment of the present invention, and without limitation, one or more of any object(s) (01), such as, but not limited to any, endoscope(s), sensor instrument(s), sensor(s), sensor wire(s), sensor cable(s), and/or ultrasonic probe(s), including one or more of any attached and/or detached object(s) such as, but not limited to any, tube(s), pipe(s), cable(s), fiber optic line(s), cable(s), plug(s), connector(s), and/or wire(s), can be effectively located inside any removable treatment enclosure(s) (230), so that any of their treatable and/or processable surface(s) such as, but not limited to, all of their external and/or internal surfaces, and/or at least one or more of any targeted surface(s), and/or at least all of the various surface(s) that need to be effectively treated and processed, are effectively and/or efficaciously treated and processed, within any suitable and effective location(s), space(s), and/or enclosure(s), such as, but not limited to any, container holding chamber(s) (265) and/or removable treatment enclosure(s) (230). It is preferred, without limitation, that the treated and processed object(s) (01) are located in any effective, removable treatment enclosure(s) (230) in a manner so that their various surface(s) are not shadowed, covered, and/or interfaced with any other surface(s) in a manner that would disrupt, impede, and/or prevent, their effective and efficacious treatment and/or processing. It is even more preferred, without limitation, that the one or more treated object(s) (01) are effectively located in the middle, and/or effectively close to the middle, of the container holding chamber(s) (265) and/or removable treatment enclosure(s) (230), and are held, supported, interfaced, suspended, and or hung, in a manner so that all of the targeted surface(s) for treatment and/or processing of the object(s) (01), are effectively treated and processed.

In a first part of this embodiment, and without limitation, the one or more of any object(s) (01) can be effectively, held, supported, suspended, hung, and/or interfaced with, one or more of any effective and suitable object support(s) (84), enhanced object support(s) (155), and/or any effective and suitable enhanced means to support and/or hold the one or more of any object(s) (01), inside of the removable treatment enclosure(s) (230), where the one or more of any object(s) (01) are effectively treated and/or processed within the removable treatment enclosure(s) (230), including any surface(s) of the object(s) (01) that interface with the one or more of any object support(s) (84), enhanced object support(s) (155), and/or any effective and suitable enhanced means to support and/or hold the one or more of any object(s) (01).

In a second part of this embodiment, and without limitation, the one or more of any object(s) (01) can be effectively, held, supported, suspended, hung, and/or interfaced with, one or more of any pressure interface assembly(s) (68), inside of the removable treatment enclosure(s) (230), where the one or more of any object(s) (01) are effectively treated and/or processed within the removable treatment enclosure(s) (230), including any surface(s) of the object(s) (01) that interface with the one or more of any pressure interface assembly(s) (68).

In a third part of this embodiment, and without limitation, the one or more of any object(s) (01) can be effectively, held, supported, suspended, hung, and/or interfaced with, one or more of any cradle(s) and/or treated object rest(s) (Herein called "Cradle(s)") (45), inside of the removable treatment enclosure(s), where the one or more of any object(s) are effectively treated and/or processed within the removable treatment enclosure(s), including and without limitation, any surface(s) of the object(s) that interface with the one or more of any cradle(s) and/or treated object rest(s). Without being limited, the cradle(s) (45) can also be constructed from one or more of any object support(s) (84), and it is preferred, without limitation, that the object support(s) (84) are suitably and effectively flexible and have an effectively minimum sized width and/or radius measurement(s). Without being limited, the one or more cradle(s) (45) can suspend from at least one, but preferably an effective number of any suitable and effective cradle hanging member(s) (418). Also, without being limited, one or more, but preferably and without limitation, an effective plurality of cradle hanging member(s) (418), can be located in any suitable and effective location(s) such as, but not limited to any, removable treatment enclosure(s) (230).

In a fourth part of this embodiment, and without limitation, the one or more of any object(s) (01) can also be effectively, held, supported, suspended, hung, and/or interfaced at one or more of any suitable and effective location(s) within the removable treatment enclosure(s) (230) and/or container holding chamber(s) (265), via one or more of any other suitable and effective means such as, but not limited to any, removable plug(s) and/or socket(s) connection(s), plug decoupling apparatus(s) (536), tube disconnect apparatus(s) (462), removable tube(s) and/or hose(s) connection interface(s), where the one or more of any object(s) (01) and any connected part(s) and component(s) are effectively treated and/or processed within the removable treatment enclosure(s) (230) and/or container holding chamber(s) (265).

Figure 66:
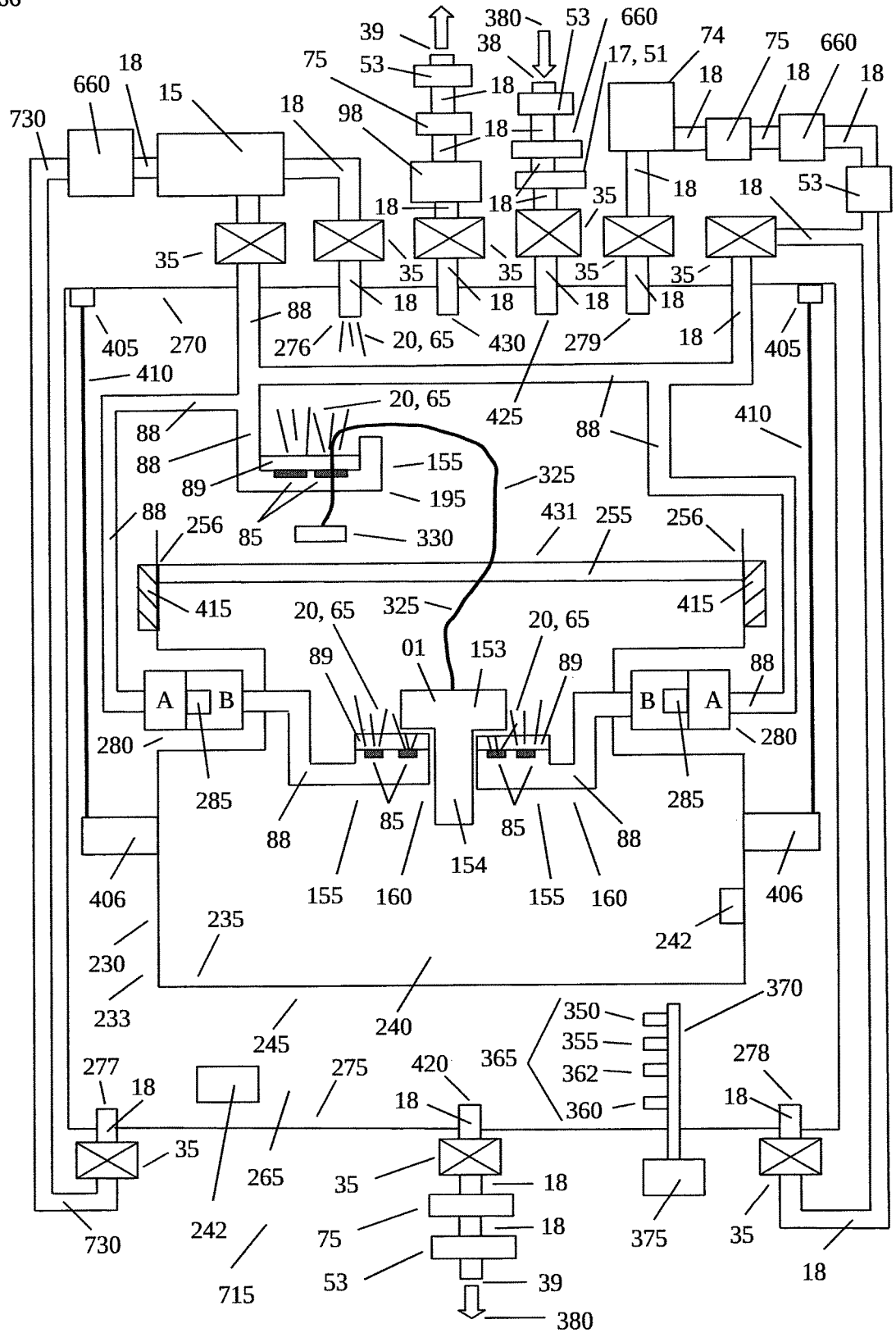
FIG. 66 is a side schematic type view that comprises an enhanced decontamination enclosure apparatus (715), and an open removable treatment enclosure (230) that is suspended inside of the container holding chamber(s) (265). An object and its cable is held inside the open removable treatment enclosure (230) with an enhanced object holder (155) that is used for supporting, holding, and treating, the interfaced object(s). The enhanced object holder (155) is plumbed or connected to various agent and air/gas sources controlled by various valve(s) (35).
Figure 67:
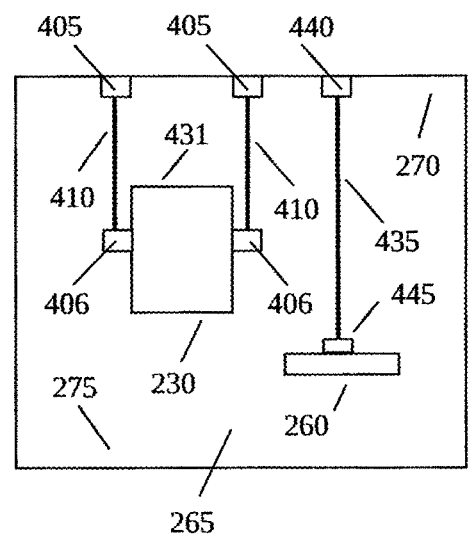
FIG. 67 is a side schematic type view that comprises an open removable treatment enclosure (230) and lid that are both suspended in a container holding chamber(s) (265) of an enhanced decontamination enclosure apparatus (715).
Figure 68:
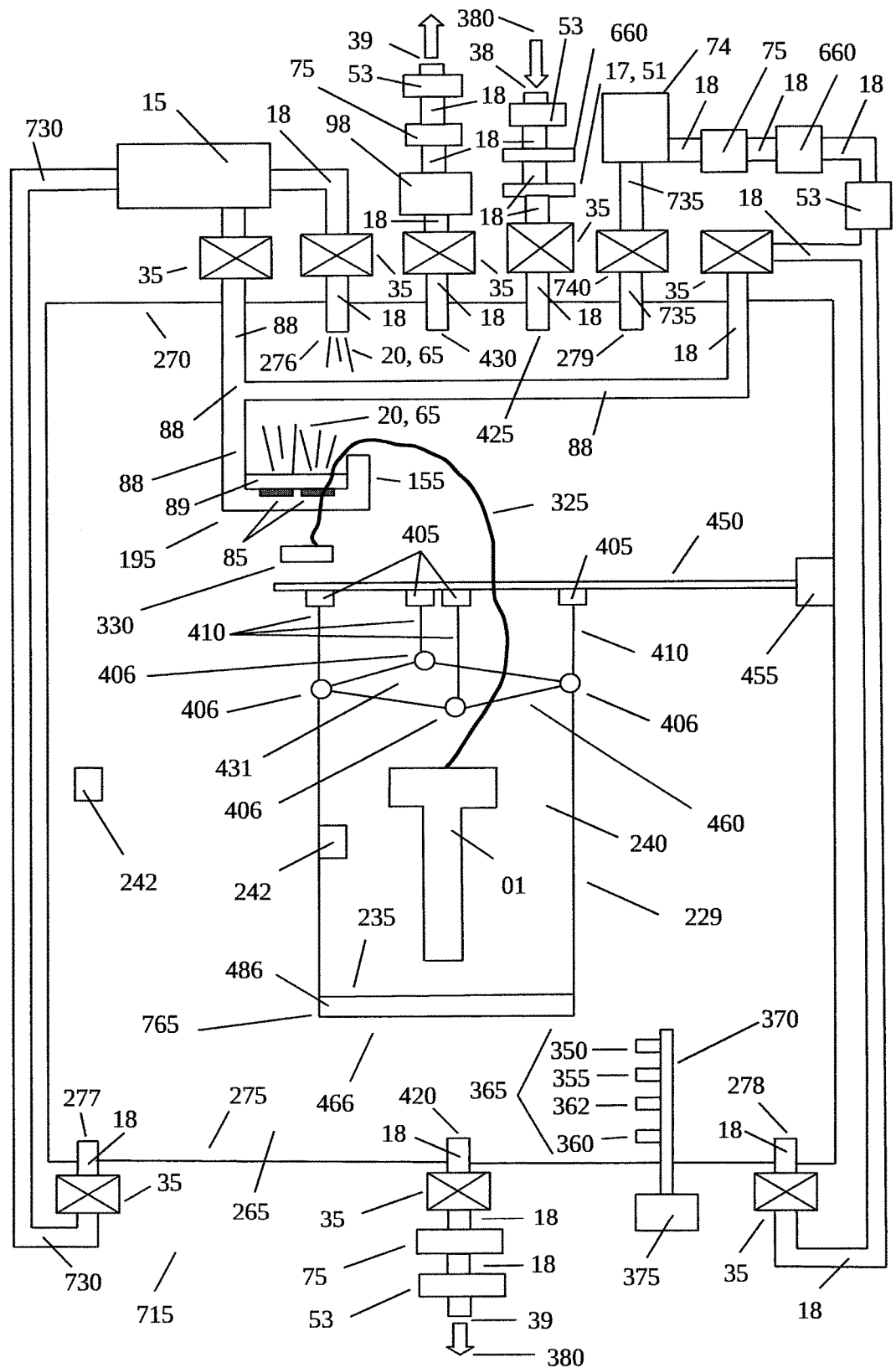
FIG. 68 is a side schematic type view of an enhanced decontamination enclosure apparatus (715), where an object cable is supported and an object is suspended inside and/or above a suspended open removable package(s) (229) with a sealed bottom, and the cable is held with an enhanced object holder (155) that is used for supporting, holding, and treating, the interfaced object(s). The top of the open removable package(s) (229) is open.
Figure 69:
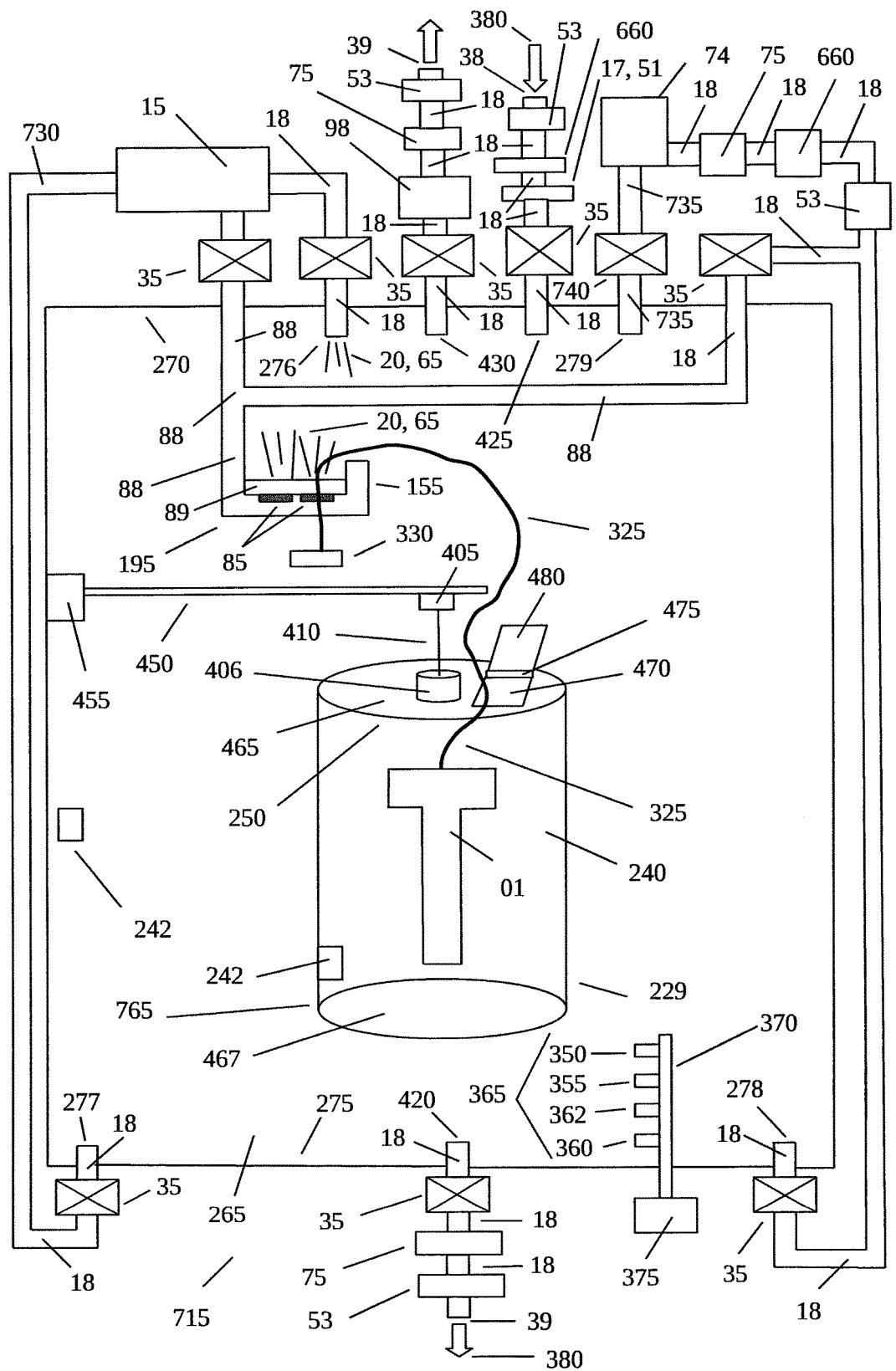
FIG. 69 is a side schematic type view of an enhanced decontamination enclosure apparatus (715), where object cable is supported and an object is suspended inside a suspended open removable package(s) (229) with an open bottom, and the cable is held with an enhanced object holder (155) that is used for supporting, holding, and treating, the interfaced object(s). The top of the open removable package(s) (229) is sealed, and the cable leaves through an open door (470) located at the top of the open removable package(s) (229). The object and the open removable package(s) (229) is located in the container holding chamber(s) (265).

With reference to FIGS. 66-67, and without limitation, the one or more of any part(s) such as, but not limited to any, lid(s) (260), removable treatment enclosure(s) (230), open removable treatment enclosure(s) (230), and/or open removable package(s) (229), can be suitably and effectively, treated, processed, and/or suspended, in any suitable and effective enclosures such as, but not limited to any, container holding chamber(s) (265). Without limitation, the one or more lid(s) (260), can be suitably and effectively, hung, held, and/or suspended, via one or more of any suitable and effective, removable lid suspension member(s) (435) that removably connects to one or more of any suitable and effective removable lid suspension attachment(s) (445) and removable lid suspension member roof attachment point(s) (440), all in a manner known to those skilled in the art.

Without limitation, the one or more of any suitable removable treatment enclosure(s) (230), open removable treatment enclosure(s) (230), and/or open removable package(s) (229), can be suitably and effectively, hung, held, and/or suspended, via one or more of any suitable and effective, suspension member(s) and/or removable container suspension member(s) (410) that removably connects to, (a) one or more of any suitable and effective container suspension member attachment point(s) (405), and (b) one or more of any suitable and effective attachment point(s) located on the one or more removable treatment enclosure(s) (230), open removable treatment enclosure(s), and/or open removable package(s) (229), such as, but not limited to any container suspension attachment(s) (406) point(s), all in a manner known to those skilled in the art. Without being limited, the one or more removable treatment enclosure(s) (230) can also be suitable and effectively open, at any time(s), when it is held and/or suspended in the one or more container holding chamber(s) (265). Without being limited, the removable lid suspension member roof attachment point(s) (440) and container suspension member attachment point(s) (405) can suitably and effectively connect to any suitable and effective, ceiling area(s), surface(s), and/or location(s) (Herein called "Container Holding Chamber Interior Roof Area(s)") (270), within any suitable enclosure(s) such as, but not limited to any container holding chamber(s) (265), all in a manner known to those skilled in the art.

With reference to FIGS. 53-66 and according to an embodiment, and without being limited, the removable treatment enclosure(s) (230) can have one or more of any suitable and effective, lid(s), cover(s), covering structure(s), and/or closure(s) (Herein called "Lid(s)") (260). It is preferred, without limitation, that the lid(s) (260) are effectively removable and resealable, all in a manner known to those skilled in the art. It is also preferred, without limitation, that the lid(s) (260) are suitably and effectively interfaced and/or directly and/or indirectly connected, with one or more of any means to treat and/or process any, atmosphere(s), location(s), area(s), surface(s), and/or object support(s) (84), moving support and dropping mechanism(s) (605), movable forks or beams (49)(50), support and tilt mechanism(s) (655), gripping mechanism(s) (135), gripping finger(s) (108), movable holding and/or support apparatus(s) (606), and/or any other suitably connected parts, located within the removable treatment enclosure(s) (230), with one or more of, but not limited to any of the said treatment and processing equipment(s), apparatus(s), and/or component(s), where any substance(s) such as, but not limited to any, air/gas(s), vapor(s), aerosol(s) (65), filtered(s) air/gas(s), heated air/gas(s), dehumidified air/gas(s), vacuum flow(s) of any air/gas(s), flow(s) of fresh air/gas(s) (380), and/or applied agent(s) (20), can effectively flow and/or move through one or more of any suitable lid(s), in any effective manner known to those skilled in the art, in either or any direction(s), either into and/or out of the removable treatment enclosure(s), through one or more, but at least an effective number, of any suitable and effective, passage(s), pipe(s), hole(s), tunnel(s), hose(s), conduit(s), connector(s), and/or connector valve(s) (280), (Herein called "Lid Pipe(s)") (745) and/or pipe(s) and/or conduits (18), that effectively connect directly and/or indirectly, with one or more of any, space(s), object(s), apparatus(s), and/or location(s), located within the removable treatment enclosure(s) (230).

Without being limited, the lid(s) (260) can also effectively, support, provide one or more mounting point(s), mounting surface(s), and/or interface(s), with or for, one or more of any, hose(s), conduit(s), pipe(s) (18), and/or process hose(s) (88), that connect with and/or support one or more of any structure(s) and/or apparatus(s) such as, but not limited to any, object support(s) (84), moving support and dropping mechanism(s) (605), support and tilt mechanism(s) (655), movable forks or beams (49)(50), gripping mechanism(s) (135), gripping finger(s) (108), movable holding and/or support apparatus(s) (606), any other suitably connected parts, and/or pressure interface assembly(s) (68). Also, and without being limited, the lid(s) (260) can effectively, support, provide one or more mounting point(s) and/or mounting surface(s), and/or interface with, one or more of any means or apparatus(s) to suitably and effectively position, support, hold, interface, hang, suspend, and/or locate, any, object(s) (01), hose(s), object support(s) (84), moving support and dropping mechanism(s) (605), support and tilt mechanism(s) (655), gripping mechanism(s) (135), movable forks or beams (49)(50), gripping finger(s) (108), movable holding and/or support apparatus(s) (606), any other suitably connected parts, within the removable treatment enclosure(s) (230).

Without being limited, one or more of any, connector(s), plug(s), sockets, cable(s) plug interface(s), removable plug(s) and/or socket(s) connection(s), plug decoupling apparatus(s) (536), tube disconnect apparatus(s) (462), removable tube(s) and/or hose(s) connection interface(s), can also be suitably and effectively, directly and/or indirectly, connected to, the lid(s) (260) and/or to any effective location(s) and/or area(s) of the underside of any lid(s) (Herein called "Lid Roof Area(s)") (250), in any suitable manner(s) so that they can be suitably and effectively located and positioned within any removable treatment enclosure(s) (230). It is preferred, without limitation, that one or more of any object(s) (01) such as, but not limited to any, medical device(s), sensor(s), ultrasonic probe(s), cable(s), and/or endoscope(s), are effectively connected and/or interfaced with one or more of any suitable and effective connection(s) such as, but not limited to any, connector(s), plug(s), sockets, cable(s) plug interface(s), removable plug(s) and/or socket(s) connection(s), plug decoupling apparatus(s) (536), tube disconnect apparatus(s) (462), removable tube(s) and/or hose(s) connection interface(s), and they can effectively hang and/or suspend within the removable treatment enclosure(s) (230), in any effective manner, and in any suitable and effective location(s) and/or position(s), so that all of the targeted surfaces within the removable treatment enclosure(s) (230) are effectively treated and processed.

It is also preferred, without limitation, that the one or more environmental sensor(s) are suitably and effectively located and positioned at one or more of any suitable and effective location(s) under the lid(s) (260) and/or within the removable treatment enclosure(s) (230), Without being limited, one or more of any suitable and effective environment sensor(s) (365) can also be suitably, directly and/or indirectly connected to, the lid(s) (260) in any effective manner so that they can be effectively located inside of the removable treatment enclosure(s) (230). It is preferred, without limitation, that the one or more of any environment sensor(s) (365) are effectively connected to one or more of any suitable and effective sensor attachment member(s) (370). It is also preferred, without limitation, that the one or more environment sensor(s) (365) are effectively located at one or more of any effective location(s) under the lid(s) (260), and are directly and/or indirectly attached to the lid(s) (260) and/or attachment member(s) (370), in any suitable and effective manner so that the one or more and/or various environment sensor(s) (365) are located at any effective, distance(s), height(s), position(s), spacing, and/or location(s), within the removable treatment enclosure(s) (230), when the lid(s) (260) is effectively interfaced with the removable treatment enclosure(s) (230).

Without being limited, the lid(s) (260) can effectively attach to, seal with, and/or interface with, the removable treatment enclosure(s) (230), all in any manner known to those skilled in the art. Without being limited, any effective, interface force, clamping force, and/or sealing force, can be applied between and/or to one or more of any effective part(s) and component(s) such as, but not limited to any, lid(s) (260), cap(s), seal material(s) (255), closure(s), means to apply any sealing force(s) and/or pressure(s) (340), material(s), and/or removable treatment enclosure(s) (230), in any suitable and effective manner and/or one or more of any location(s) that effectively and/or hermetically seals the lid(s) (260) to the removable treatment enclosure(s) (230), all in a manner known to those skilled in the art.

Without being limited, one or more of any effective seal(s) (255) can be effectively located at one or more of any effective location(s) between the removable treatment enclosure(s) (230) and the lid(s) (260). It is preferred, without limitation, that any suitable lid(s) (260), and any effective seal material(s) (Herein called "Seal(s)") (255), are effectively interfaced with any suitable removable treatment enclosure(s) (230), and at least one effective seal(s) (255) is formed between these various parts and components, with the use of at least one treatment container lid retainer mechanism(s) (340), resulting in a removable treatment enclosure(s) (230) that is hermetically sealed, all in a manner known to those skilled in the art. Without being limited, the lid(s) (260) can also be suitably attached to any removable treatment enclosure(s) (230) with one or more of any effective, hinge(s), articulation point(s), and/or pivot point(s) (Herein called "Hinge(s)") (436), all in a manner known to those skilled in the art.

Without being limited, the lid(s) (260) can also include parts and components for basic sealing such as, but not limited to one or more of any, seal material(s) (255), lid(s) (260), closure(s), closure apparatus(s), and any apparatus(s) or design(s) known to those skilled in the art for applying any effective sealing force(s) (340) to effectively and/or hermetically seal any suitable and effective lid(s) (260) to any suitable and effective removable treatment enclosure(s) (230).

Figure 64:
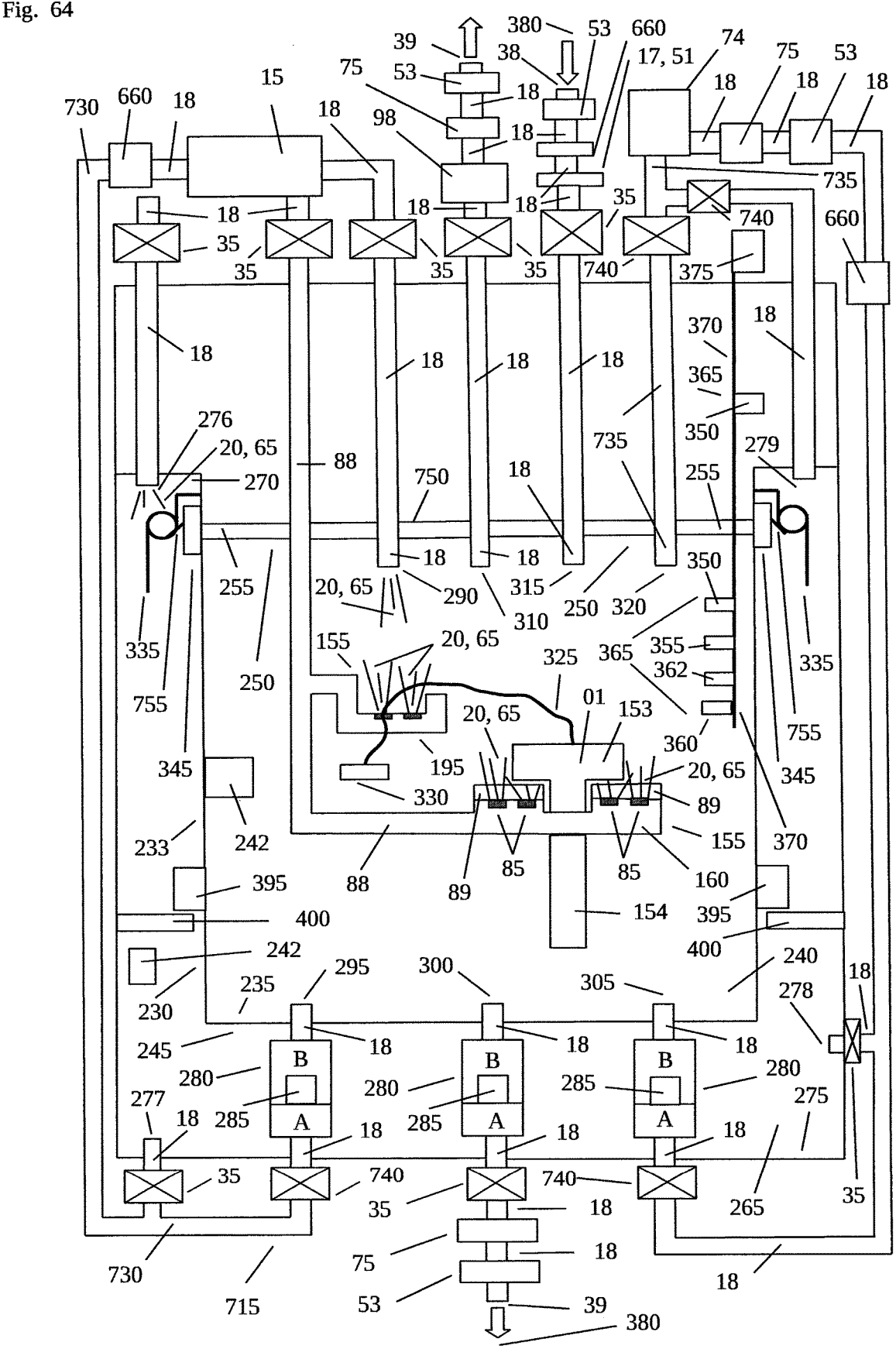
FIG. 64 is a side schematic type view that comprises an enhanced decontamination enclosure apparatus (715), and even more specifically an enhanced decontamination enclosure apparatus (715) and enhanced removable treatment enclosure (230) that is removable, where the removable treatment enclosure(s) (230) can also be suitably and effectively, removably attached to, removably interfaced with, and/or temporarily sealed to, any suitable and effective, area(s), mount point(s), mounting surface(s), interface area(s), interface location(s), docking port(s), docking ring(s), receiver(s), and or surface(s), (Herein called "Docking Receiver(s)") (750), within any container holding chamber(s) (265). The removable treatment enclosure(s) (230) in this case interfaces with the ceiling area inside of the container holding chamber. An object and its cable is held inside the removable treatment enclosure (230) with an enhanced object holder (155) that used for supporting, holding, and treating, the interfaced object(s). The removable treatment enclosure(s) (230) is also supported and/or positioned with the help of one or more container suspension point(s) (395) on its exterior walls, for support and/or placement, of the object in the container holding chamber(s) (265), and chamber container support(s) (400) located in the container holding chamber(s) (265).
Figure 65:
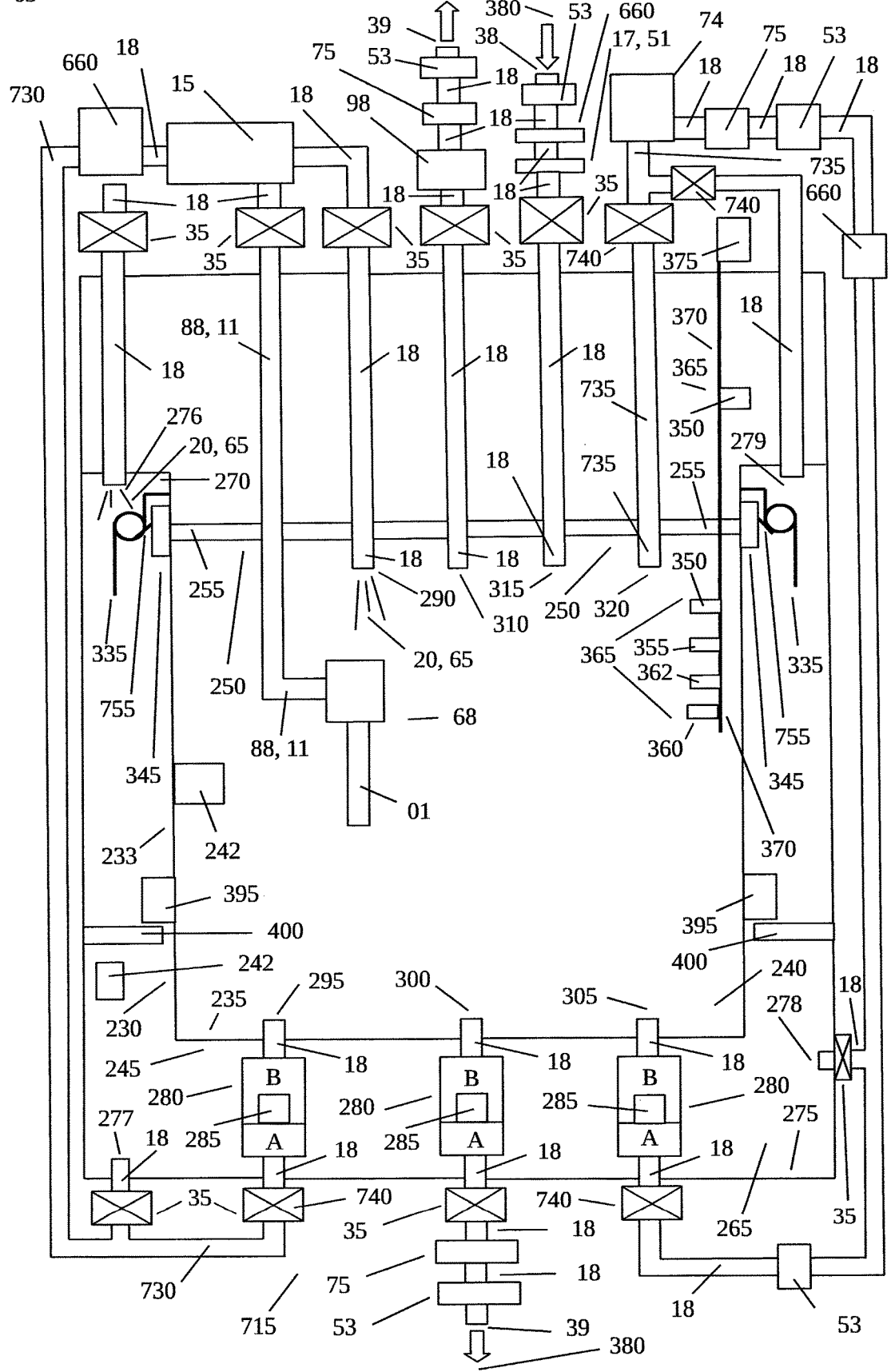
FIG. 65 is a side schematic type view that is the same as #64, except an object and its cable is held inside the removable treatment enclosure (230) with a pressure interface assembly(s) (68). Both the interior and exterior surfaces of the removable treatment enclosure(s) (230) can be treated and dried. The removable treatment enclosure(s) (230) is also supported and/or positioned with the help of one or more container suspension point(s) (395) on its exterior walls, for support and/or placement, of the object in the container holding chamber(s) (265), and chamber container support(s) (400) located in the container holding chamber(s) (265).

With reference to FIGS. 64-65, and according to another embodiment, and without being limited, the removable treatment enclosure(s) (230) can also be suitably and effectively, removably attached to, removably interfaced with, and/or temporarily sealed to, any suitable and effective, area(s), mount point(s), mounting surface(s), interface area(s), interface location(s), docking port(s), docking ring(s), receiver(s), and or surface(s), (Herein called "Docking Receiver(s)") (750), within any container holding chamber(s) (265), preferably and without limitation effectively at or near one or more of any top location(s) such as, but not limited to, near and/or at the interior roof area(s) and/or ceiling(s) (270) of the container holding chamber(s) (265), and/or near and/or at the interior bottom area(s) and/or floor(s) (275) of the container holding chamber(s) (265), but at least at any effective location(s) within the container holding chamber(s) (265).

Without being limited, the said various, docking receiver(s) (750), that are suitably and effectively located in any container holding chamber(s) (265), and that suitably and effectively, removably attach to, removably interface with, and/or are temporarily sealed to, any removable treatment enclosure(s) (230), can suitable and effectively connect with, interface with, communicate with, and/or act as any suitable and effective pass-through for, and directly and/or indirectly connect with, one or more of any, treatment and processing equipment(s), apparatus(s), and/or component(s) such as, but not limited to any suitable and effective, (a) any effective means, pipe(s), and conduits (18) for generating, creating, administering, and/or delivering (otherwise called the "generation chamber(s)") (15), one or more of any, applied agent(s) (20), aerosol(s) (65), and/or vapor(s), into and/or through any location(s) such as, but not limited to any, container holding chamber(s) (265) and/or removable treatment enclosure(s) (230), (b) any effective means, pipe(s), and conduits (18) for dehumidification and/or means for removing one or more of any vapor(s), water vapor(s) (ie: humidity), (otherwise called the "dehumidification system(s)") (74), from within and/or through any location(s) such as, but not limited to any, container holding chamber(s) (265) and/or removable treatment enclosure(s) (230), (c) any effective means, pipe(s), and conduits (18) for moving or flowing fresh air/gas(s) (380) into and/or through any location(s) such as, but not limited to any, container holding chamber(s) (265) and/or removable treatment enclosure(s) (230), (d) any effective means, pipe(s), and conduits (18) for creating any effective negative pressure(s) and/or vacuum (otherwise called the "negative pressure device(s)") (98), within any, area(s) and location(s) such as, but not limited to any, container holding chamber(s) (265) and/or removable treatment enclosure(s) (230), (e) any effective means, pipe(s), and conduits (18) for any effective filtration (53) of any air/gas(s) and/or atmosphere(s) that is moved or flowed into and/or through any location(s) such as, but not limited to any, container holding chamber(s) (265) and/or removable treatment enclosure(s) (230), (f) any effective means, pipe(s), and conduits (18) for heating (otherwise called the "air/gas stream heater(s)" (660), any air/gas(s) or atmosphere(s) that is moved or flowed into and/or through any location(s) such as, but not limited to any, container holding chamber(s) (265) and/or removable treatment enclosure(s) (230), (g) any effective means, pipe(s), and conduits (18) for exhausting, and preferably and without limitation, also effectively filtering (75)(53) any substance(s) such as, but not limited to any, air/gas(s), vapor(s), aerosol(s) (65), and/or applied agent(s) (20), from any location(s) within and/or effectively connected to, any space(s), area(s) and enclosure(s) such as, but not limited to any, container holding chamber(s) (265), and/or removable treatment enclosure(s) (230), including but not limited to any attached or connected, part(s), space(s), and apparatus(s), to one or more of any suitable and effective location(s) outside of location(s) such as, but not limited to any, removable treatment enclosure(s) (230), container holding chamber(s) (265), and/or the enhanced decontamination enclosure apparatus(s) (715), (h) any effective means, pipe(s), and conduits (18) to recirculate and/or assist with any recirculation, of any substance(s) such as, but not limited to any, air/gas(s), applied agent(s) (20), aerosol(s) (65), vapor(s), from, to, and/or through, any locations such as, but not limited to any, container holding chamber(s) (265) and/or removable treatment enclosure(s) (230), and back to and through one or more of any suitable and effective, production source(s) or generator(s) (15) of the applied agent(s) (20), vapor(s) and/or aerosol(s) (65) and/or otherwise any suitable generation chamber(s) (15), and/or (i) any effective means, pipe(s), and conduits (18) to recirculate and/or assist with any recirculation, of any substance(s) such as, but not limited to any, air/gas(s), fresh air/gas(s) (380), vapor(s), applied agent(s) (20), atmosphere(s), dehumidified air/gas(s), heated air/gas(s), from, to, and/or through, any locations such as, but not limited to any, container holding chamber(s) (265) and/or removable treatment enclosure(s) (230), and back to and through one or more of any suitable and effective, dehumidification system(s) (74).

Also, referring to FIGS. 53-67, and without being limited, the one or more of any suitable and effective opening(s) (431) of the one or more of any removable treatment enclosure(s) (230), and preferably and without limitation, any opening(s) (431) and/or top located opening(s) (431) of the of the removable treatment enclosure(s) (230), can be suitably and effectively, sealed to and/or with, interfaced to and/or with, and/or held to and/or with, one or more of any suitable and effective, area(s), mount point(s), mounting surface(s), interface location(s), docking port(s), docking ring(s), receiver(s), surface(s), and/or docking receiver(s) (750), that can be, without limitation, suitably and effectively located within any container holding chamber(s) (265), and these various surface(s) and seal(s) can all be effectively, interfaced, held, and/or sealed, all in a manner known to those skilled in the art. Without being limited, one or more of any suitable seal(s) (255) can be located in one or more of any suitable and effective location(s), and used to seal the removable treatment enclosure(s) (230) to the one or more of any suitable and effective surface(s) it is removably interfaced with, preferably and without limitation, within the container holding chamber(s) (265). It is preferred, without limitation, that the removable treatment enclosure(s) (230) effectively retains and/or is effectively interfaced with, one or more of any suitable and effective seal(s) (255), that can seal to the one or more of any suitable and effective, area(s), mount point(s), mounting surface(s), interface location(s), interface surface(s), docking port(s), docking ring(s), receiver(s), surface(s), and/or docking receiver(s) (750), that is preferably, and without limitation, located within any container holding chamber(s) (265).

Also referring to FIGS. 53-67, and according to another part of this embodiment, and without being limited, one or more of any suitable and effective, interface force(s), clamping force(s), and/or sealing force(s), can be applied with one or more of any suitable and effective apparatus(s), design, and manner, known to those skilled in the art, to create one or more of any effective and suitable seal(s) and/or hermetic seal(s) between the one or more of any suitable and effective part(s) and components such as, but not limited to any, removable treatment enclosure(s) (230), seal(s) (255), and/or docking receiver(s) (750), which are preferably, but not limited to, all located in one or more of any suitable and effective location(s) within one or more of any suitable and effective container holding chamber(s) (265). It is preferred, without limitation, that one or more, but preferably and without limitation, at least two, of any effective means (Herein called "Receiver Clamp(s)") (755) are used to apply any effective force(s) to suitably and effectively, hold, support, interface and/or seal, the various parts together such as, but not limited to any, removable treatment enclosure(s) (230), seal(s) (255), and/or docking receiver(s) (750), all in a manner known to those skilled in the art.

Referring to FIGS. 53-67, and according to an embodiment, and without being limited, after the one or more of any removable treatment enclosure(s) (230), and one or more of any, surface(s), object(s) (01), and/or any other connected part(s) and component(s), area(s), and/or space(s), located within any removable treatment enclosure(s) (230), are finished being treated and/or processed, the removable treatment enclosure(s) (230) can be removed and/or disconnected, either automatically in any manner known to those skilled in the art, and/or manually, from any part(s) and component(s) such as, but not limited to any, connector valve(s) (280), cable(s) and/or wire(s) connection(s), connector(s) plug(s), power and/or communication cable(s), tube(s) and/or pipe(s) (18), conduit(s), process hose(s) (88), connection(s), tube disconnect apparatus(s) (462), and/or plug decoupling apparatus(s) (536), and can then be removed from any container holding chamber(s) (265) if the removable treatment enclosure(s) (230) is placed within any container holding chamber(s), all at any suitable and effective time(s).

Without being limited, the various part(s) and component(s) used in the construction of the enhanced decontamination enclosure apparatus(s) (715) are at least constructed from any materials that are suitable and effective. For example, and without being limited, various parts of the enhanced decontamination enclosure apparatus(s) (715) such as, but not limited to any, container holding chamber(s) (265), removable treatment enclosure(s) (230), lid(s) (260), lid pipe(s) (745), conduit(s), pipe(s) (18), process hose(s) (88), seal(s) (255), docking receiver(s) (750), dehumidification apparatus(s) (74), air/gas(s) heating apparatus(s) 660), fan(s), blower(s), air pump(s), and/or valve(s) (35)(740), can be constructed from any suitable and effective material(s) known to those skilled in the art, such as, but not limited to any suitable and effective, stainless steel(s), and/or polymer(s). It is preferred, without limitation, that the various part(s) and component(s) are at least chemically and/or thermally compatible with any of the applied agent(s) (20) and/or any operating temperature(s), that are used to treat and process the various, object(s) (01), targeted surface(s), enclosure(s), and/or area(s).

Figure 61:
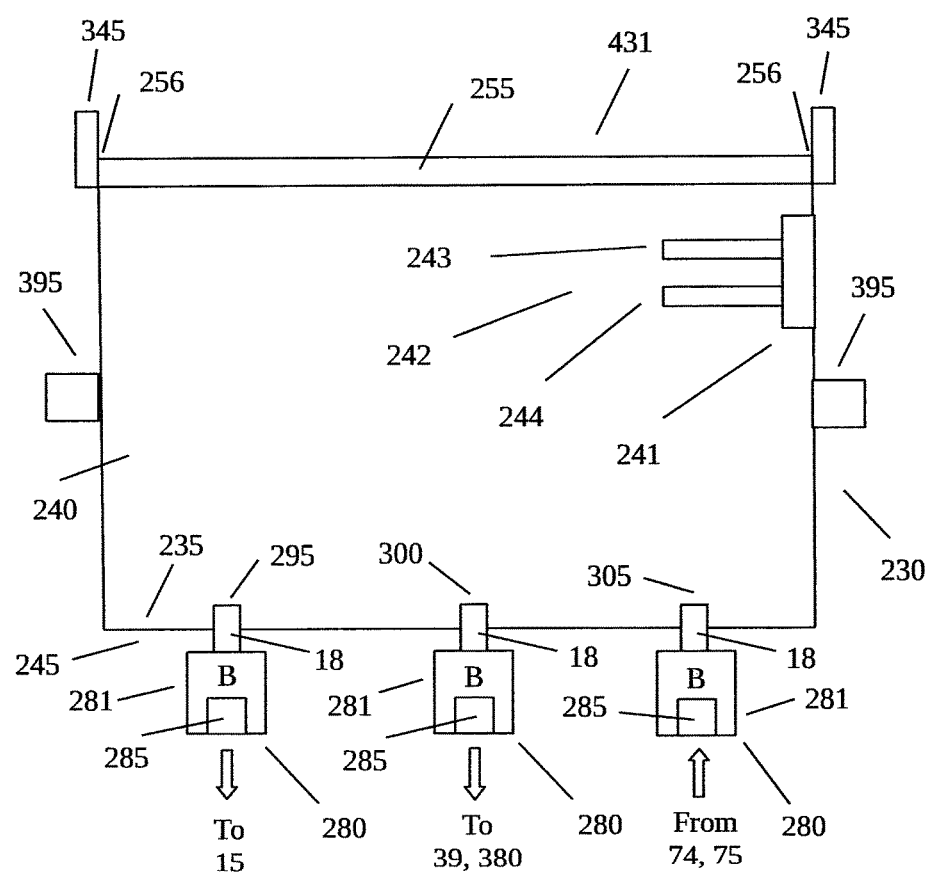
FIG. 61 is a side schematic type view of an open removable enclosure (230). The various connector valve(s) (280) are shown where the various air/gas(s) flow out of the removable enclosure (230). Chemical exposure indicator(s) (244), and/or biological challenge(s) (243) (Herein called "Treatment Efficacy Indicator(s)") (242), are shown located in the removable enclosure (230).
Figure 62:
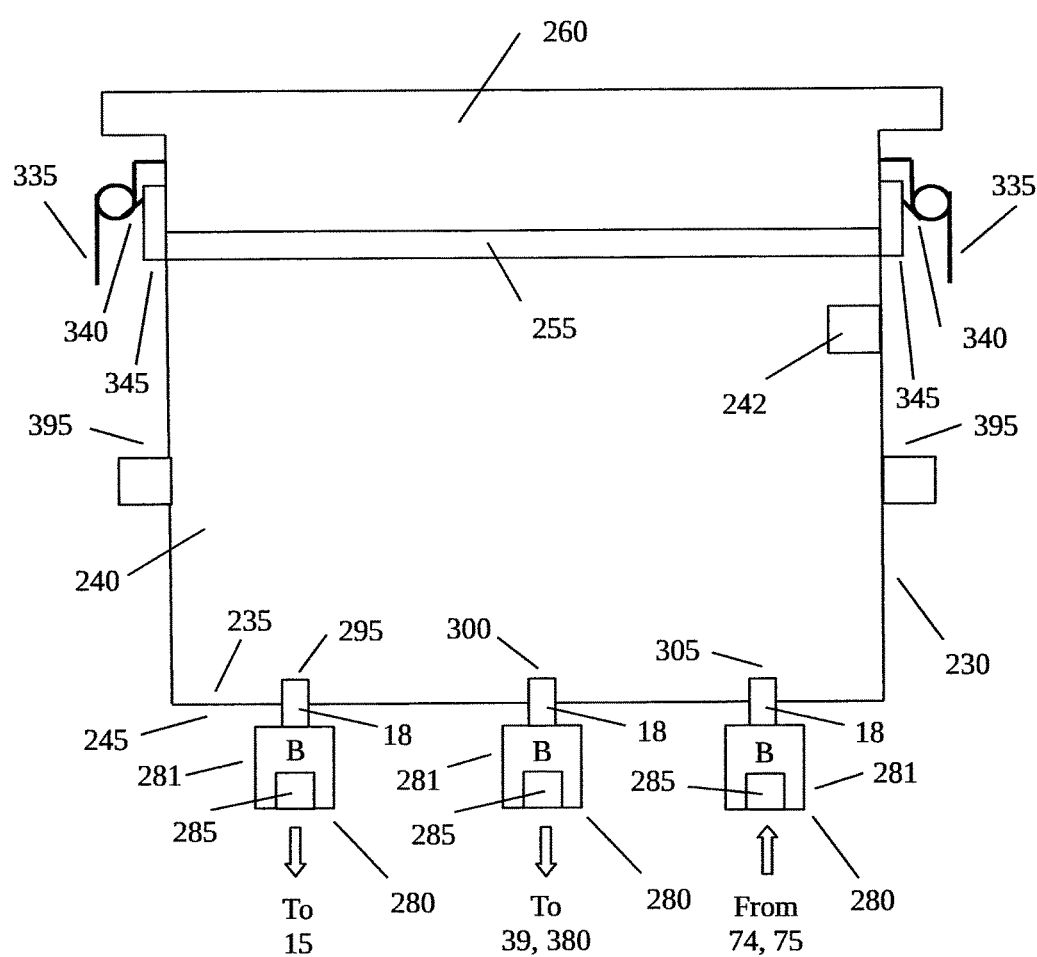
FIG. 62 is a side schematic type view of a closed and sealed removable enclosure (230) using a simple lid. The various connector valve(s) (280) are shown where the various air/gas(s) and agent(s) flows into and out of the removable enclosure (230).
Figure 63:
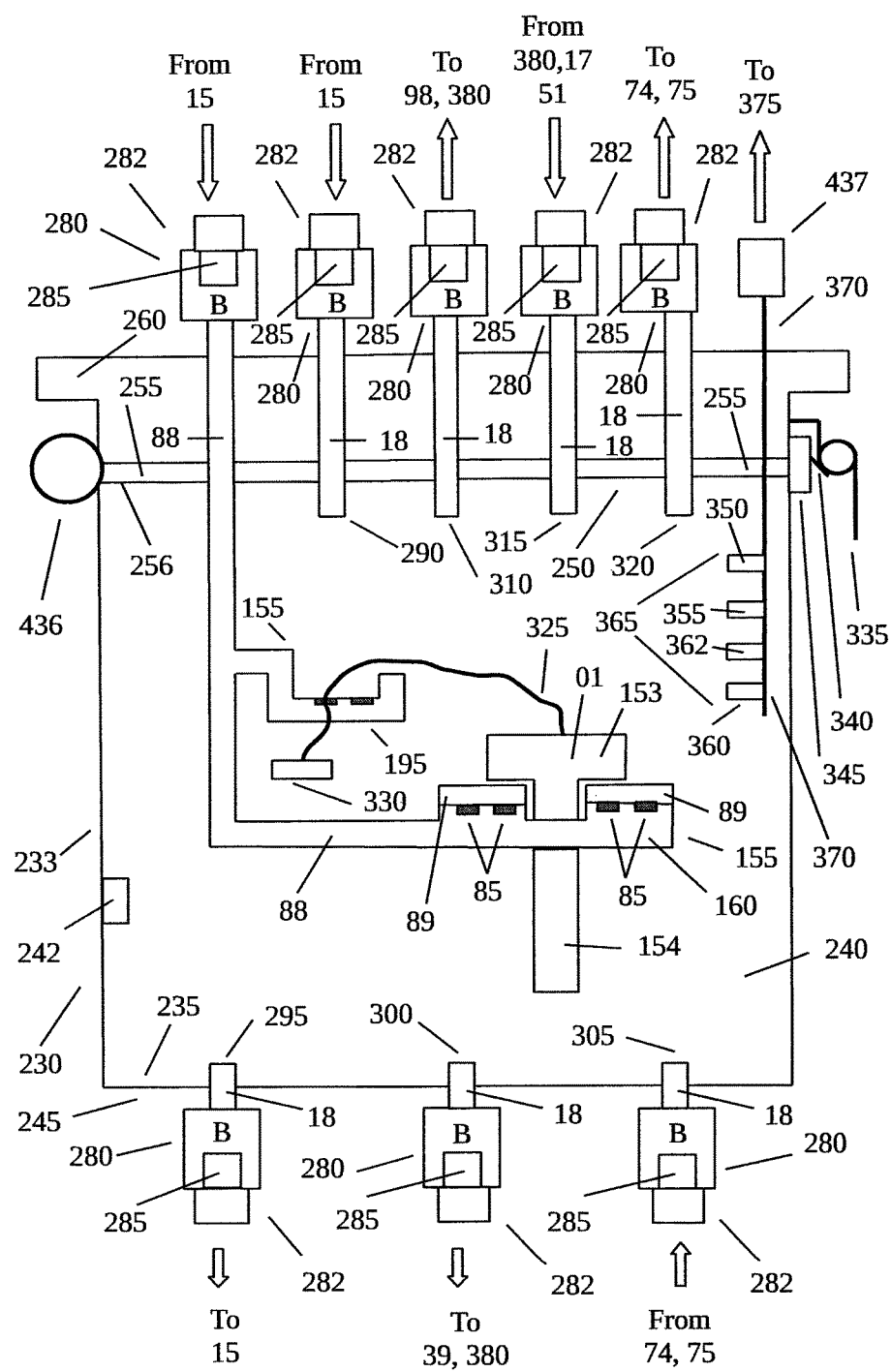
FIG. 63 is a side schematic type view of an closed removable enclosure (230). The various inbound and outbound air/gas(s) and agent(s), connector valve(s) (280) are shown where the various air/gas(s) flow into and out of the removable enclosure (230). The lid is attached and sealed to the enclosure with a hinge and clasp. An object and its cable is held inside the removable treatment enclosure (230) with an enhanced object holder (155) that is used for supporting, holding, and treating, the interfaced object(s).

Referring to FIGS. 53, 61, and 64, and without limitation, the removable treatment enclosure(s) (230) can also be, without limitation, effectively, interfaced with, located on, removably connected with, one or more of any suitable and effective means to effectively, rest, locate, and/or support, the one or more of any removable treatment enclosure(s) (230) at one or more of any suitable and effective location(s) within the container holding chamber(s) (265) (Herein called "Chamber Container Support(s)") (400), all in a manner known to those skilled in the art. The chamber container support(s) (400) can be, without limitation, any effective, size, shape, geometry, length, depth, width, and/or height, and be constructed from one or more of any suitable and effective material(s) such as, but not limited to any, stainless steel and/or polymer. Without being limited, the chamber container support(s) (400) can include, but is not limited to, one or more of any suitable and effective, object support(s) (84), support member(s), interface apparatus(s), and/or interface member(s), such as, but not limited to any suitably sized, shaped, and/or designed, shelf(s) and/or peg extensions, that can be interfaced with one or more of any interior wall(s) and/or protruding member(s) of and/or from the container holding chamber(s) (265), all in a manner known to those skilled in the art. It is preferred, without limitation, that the removable treatment enclosure(s) (230) is suitably and effectively removably located and/or interfaced on and/or with, at least one or more of any suitable and effective, chamber container support(s) (400).

Also referring to FIGS. 53, 61, 62, 64, and 65, and without being limited, one or more removable treatment enclosure(s) (230) can also have one or more of any suitable and effective, protrusion(s), support protrusion(s), support interface(s), support member extension(s), and/or suspension point(s) (Herein called "Container Suspension Point(s)") (395), which can effectively interface with one or more of any suitable and effective chamber container support(s) (400), to effectively support and/or locate the removable treatment enclosure(s) (230) within the container holding chamber(s) (265). The one or more container suspension point(s) (395) can be located at one or more of any suitable and effective location(s). It is preferred, without limitation, that the container suspension point(s) (395) are at least located at any suitable and effective location(s), and more preferably and without limitation, on any one or more suitable and effective location(s) on and/or interfacing with the exterior of the removable treatment enclosure(s) (230). For example, and without limitation, the removable treatment enclosure(s) (230) can be effectively located within the container holding chamber(s) (265), where the removable treatment enclosure(s) (230) and/or its one or more effective container suspension point(s) (395) are effectively interfaced with, and/or placed upon, at least one, but preferably at least two effective, chamber container support(s) (400) that can be used to effectively, hold, support, and/or locate, the one or more removable treatment enclosure(s) (230) within the container holding chamber(s) 265). It is also preferred, without limitation, that the one or more of any, chamber container support(s) (400) and container suspension point(s) (395), are suitability and effectively located close to and/or on, the same horizontal plane.

Without being limited, the container suspension point(s) (395) can also include, but is not limited to, one or more of any suitable and effective, object support(s) (84), support member(s), interface apparatus(s), and/or interface member(s), such as, but not limited to any suitably sized, shaped, and/or designed, shelf(s) and/or peg extensions, that can be interfaced with one or more wall(s) of and/or protruding member(s) of and/or from the removable treatment enclosure(s) (230), all in a manner known to those skilled in the art. The container suspension point(s) (395) can be, without limitation, any effective, size, shape, geometry, length, depth, width, and/or height, and be constructed from one or more of any suitable and effective material(s) such as, but not limited to any, stainless steel and/or polymer.

Without being limited, and as another part of this embodiment, one or more of any suitable and effective location(s) of the removable treatment enclosure(s) (230), such as, but not limited to, the top and/or bottom side(s) of the removable treatment enclosure(s) (230), having one or more of any area(s), mount point(s), mounting surface(s), interface location(s), interface surface(s), docking port(s), docking ring(s), receiver(s), surface(s), and/or docking receiver(s) (750), can be suitably and effectively sealed to one or more of any suitable and effective location(s) within any container holding chamber(s) (265), such as, but not limited to one or more of any suitable and effective, area(s), mount point(s), mounting surface(s), interface location(s), interface surface(s), docking port(s), docking ring(s), receiver(s), surface(s), and/or docking receiver(s) (750), located at and/or near any suitable and effective, top area(s) and/or ceiling location(s), and/or located at or near any suitable and effective, bottom area(s) and/or floor location(s). Without being limited, the removable treatment enclosure(s) (230) can be positioned and located in the container holding chamber(s) (265) at any suitable and effective orientation(s) and/or angle(s) at any suitable and effective time(s).

It is preferred, without limitation, that in this particular part of this embodiment, one or more of any suitable and effective, area(s), mount point(s), mounting surface(s), interface location(s), interface surface(s), docking port(s), docking ring(s), receiver(s), surface(s), and/or docking receiver(s) (750), belonging to, or intended to interface with, any suitable removable treatment enclosure(s) (230), but preferably and without limitation, located at and/or effectively near any suitable and effective top located opening(s) (431) of the removable treatment enclosure(s) (203), is suitably and effectively interfaced and/or removably connected to, one or more of any suitable and effective, area(s), mount point(s), mounting surface(s), interface location(s), interface surface(s), docking port(s), docking ring(s), receiver(s), surface(s), and/or docking receiver(s) (750), located at one or more of any suitable and effective, top area(s) and/or ceiling location(s), within any container holding chamber(s) (265), and once the removable treatment enclosure(s) (230) is effectively, interfaced, and/or removably locked and/or sealed into position, one or more of any suitable and effective, output(s), input(s), orifice(s) and/or opening(s), for one or more of any suitable, part(s), component(s), apparatus(s), treatment and processing equipment(s), apparatus(s), and/or component(s), and/or any hose(s) (88), tube(s) and pipe(s) (18), and/or conduit(s) that effectively connect with one or more of any treatment and processing equipment(s), apparatus(s), and/or component(s), can open into and/or effectively connect with, any one or more of any, part(s), component(s), object support(s) (84), moving support and dropping mechanism(s) (605), support and tilt mechanism(s) (655), gripping mechanism(s) (135), movable forks or beams (49)(50), gripping finger(s) (108), movable holding and/or support apparatus(s) (606), processing apparatus(s), area(s), and/or location(s), within the removable treatment enclosure(s) (230), or at least in any shared area(s) and/or space(s).

With reference to FIGS. 53-56, 61-65, and without being limited, one or more of any suitable and effective removable connection(s) can be made at or near the bottom of the removable treatment enclosure(s) (230), preferably and without limitation, with one or more of any suitable connector valve(s) (280), and can connect directly and/or indirectly with one or more of any suitable and effective treatment and processing equipment(s), apparatus(s), and/or component(s) such as but not limited to any suitable and effective, (a) means and conduits (18) for generating, creating, administering, and/or delivering (otherwise called the "generation chamber(s)") (15), one or more of any, applied agent(s) (20), aerosol(s) (65), and/or vapor(s), into and/or through any location(s) such as, but not limited to any, container holding chamber(s) (265) and/or removable treatment enclosure(s) (230), (b) means and conduits (18) for dehumidification and/or means for removing one or more of any vapor(s), water vapor(s) (ie: humidity), (otherwise called the "dehumidification system(s)") (74), from within and/or through any location(s) such as, but not limited to any, container holding chamber(s) (265) and/or removable treatment enclosure(s) (230), (c) means and conduits (18) for moving or flowing fresh air/gas(s) (380) into and/or through any location(s) such as, but not limited to any, container holding chamber(s) (265) and/or removable treatment enclosure(s) (230), (d) means and conduits (18) for creating any effective negative pressure(s) and/or vacuum (otherwise called the "negative pressure device(s)") (98), within any, area(s) and location(s) such as, but not limited to any, container holding chamber(s) (265) and/or removable treatment enclosure(s) (230), (e) means and conduits (18) for any effective filtration (53) of any air/gas(s) and/or atmosphere(s) that is moved or flowed into and/or through any location(s) such as, but not limited to any, container holding chamber(s) (265) and/or removable treatment enclosure(s) (230), (f) means and conduits (18) for heating (otherwise called the "air/gas stream heater(s)" (660), any air/gas(s) or atmosphere(s) that is moved or flowed into and/or through any location(s) such as, but not limited to any, container holding chamber(s) (265) and/or removable treatment enclosure(s) (230), (g) means and conduits (18) for exhausting, and preferably and without limitation, also effectively filtering (75) (53) any substance(s) such as, but not limited to any, air/gas(s), vapor(s), aerosol(s) (65), and/or applied agent(s) (20), from any location(s) within and/or effectively connected to, any space(s), area(s) and enclosure(s) such as, but not limited to any, container holding chamber(s) (265), and/or removable treatment enclosure(s) (230), including but not limited to any attached or connected, part(s), space(s), and apparatus(s), to one or more of any suitable and effective location(s) outside of location(s) such as, but not limited to any, removable treatment enclosure(s) (230), container holding chamber(s) (265), and/or the enhanced decontamination enclosure apparatus(s) (715), (h) means and conduits (18) to recirculate and/or assist with any recirculation, of any substance(s) such as, but not limited to any, air/gas(s), applied agent(s) (20), aerosol(s) (65), vapor(s), from, to, and/or through, any locations such as, but not limited to any, container holding chamber(s) (265) and/or removable treatment enclosure(s) (230), and back to and through one or more of any suitable and effective, production source(s) or generator(s) (15) of the applied agent(s) (20), vapor(s) and/or aerosol(s) (65) and/or otherwise any suitable generation chamber(s) (15), and/or (i) means and conduits (18) to recirculate and/or assist with any recirculation, of any substance(s) such as, but not limited to any, air/gas(s), fresh air/gas(s) (380), vapor(s), applied agent(s) (20), atmosphere(s), dehumidified air/gas(s), heated air/gas(s), from, to, and/or through, any locations such as, but not limited to any, container holding chamber(s) (265) and/or removable treatment enclosure(s) (230), and back to and through one or more of any suitable and effective, dehumidification system(s) (74).

Referring to FIGS. 66-102, and without limitation, an apparatus and method of another embodiment of the present invention comprises effectively, suspending, positioning, hanging, holding, and/or locating, one or more of any object(s) (01) such as, but not limited to any, endoscope(s), medical related sensor(s), medical tooling, ultrasonic probe(s), and/or including one or more of any attached and/or unattached object(s) (01) such as, but not limited to any, tube(s), pipe(s), cable(s), fiber optic line(s), cable(s), plug(s), connector(s), and/or wire(s), within, and/or in any effective proximity to and/or from, one or more of any suitable and effective, container holding chamber(s) (265), open removable package(s) (229), open package(s), packaging material(s) (495), removable treatment enclosure(s) (230), treatment enclosure(s), open treatment enclosure(s), open removable treatment enclosure(s) (230), package(s), removable package(s), and/or open packaging material(s), at one or more of any suitable and effective angle(s) and/or orientation(s), and effectively, treating, sanitizing, disinfecting, high-level disinfecting, sterilizing, decontaminating, and/or processing, the one or more of any, area(s), atmosphere(s), and/or surface(s), of and/or within these various, space(s), area(s), enclosure(s), and/or object(s) (01), with one or more of any effective substance(s) such as, but not limited to any, applied agent(s) (20), vapor(s), air/gas(s), heated air/gas(s), and/or aerosol(s) (65), at one or more of any effective time(s), effectively drying and/or removing any substance(s) such as, but not limited to any, applied agent(s) (20), rinsing fluid(s), alcohol liquid rinse(s), humidity, aerosol(s) (65), and/or vapor(s), from any surface(s) of and/or within the said various, space(s), area(s), enclosure(s), and/or object(s) (01), at one or more of any effective time(s), and for any effective duration(s) of time(s), and then suitably and effectively, dropping, releasing, and/or locating, the one or more object(s) (01) and any attached part(s) into one or more of any suitable and effective, open removable package(s) (229), open package(s), and/or packaging material(s) (495), and then effectively packaging the one or more object(s) (01) and any connected part(s), in one or more of, but not limited to, any suitable and effective, open treatment enclosure(s), open removable treatment enclosure(s), open package(s), open removable package(s), packaging material(s), semi-constructed package(s), partially created package(s), and/or open packaging material(s), (Herein called "Open Removable Package(s)" (229), with one or more of any suitable and effective method(s) and apparatus(s) known to those skilled in the art, to form one or more of any suitable and effective, closed, sealed and/or hermetically sealed, package(s) (Herein called "Closed Package(s)" (720), and then preferably, and without limitation, removing the one or more closed package(s) (720) from the one or more container holding chamber(s) (265) at any suitable or effective time(s).

Without being limited, the one or more of any treated and/or processed object(s) (01) can also be effectively treated and/or processed, at one or more of any suitable and effective location(s) such as, but not limited to, within, partially within, centered partially within, centered within, over, partially over, centered partially over, centered over, outside of, partially outside of, centered partially outside of, centered outside of, above, partially above, centered partially above, centered above, below, partially below, centered partially below, centered below, underneath, partially underneath, centered partially underneath, and/or centered underneath, any suitable and effective, open removable package(s) (229), open package(s), packaging material(s) (495), removable treatment enclosure(s) (230), treatment enclosure(s), open treatment enclosure(s), open removable treatment enclosure(s) (230), package(s), removable package(s), and/or open packaging material(s), at one or more of any suitable and effective angle(s) and/or orientation(s), that have at least one suitable and effective opening(s) (431), and are preferably, and without limitation, suitably and effectually located in one or more of any suitable and effective container holding chamber(s) (265).

Without being limited, the one or more of any treated and/or processed object(s) (01) can also be released, located, positioned, and/or dropped, into and/or within, the one or more of any suitable and effective, open removable package(s) (229), open package(s), packaging material(s) (495), removable treatment enclosure(s) (230), treatment enclosure(s), open treatment enclosure(s), open removable treatment enclosure(s) (230), package(s), removable package(s), and/or open packaging material(s), at one or more of any suitable and effective angle(s) and/or orientation(s), located suitably and effectively, near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, covering, partially covering, fully covering, and/or multi-axial covering, the said object(s) (01), after they are finished being effectively, treated, dried, and/or processed, and the said, open removable package(s) (229), open package(s), packaging material(s) (495), removable treatment enclosure(s) (230), treatment enclosure(s), open treatment enclosure(s), open removable treatment enclosure(s) (230), package(s), removable package(s), and/or open packaging material(s), at one or more of any suitable and effective angle(s) and/or orientation(s), can then be effectively, sealed, closed, packaged, and/or hermetically sealed, forming one or more of any suitable and effective closed package(s) (720), and then removed from the treatment area(s), preferably and without limitation, any suitable and effective, container holding chamber(s) (265), at any suitable and effective time(s).

Without being limited, the one or more of any object(s) (01) and/or any connected part(s), can be suspended, hung, held, positioned, and/or located, in one or more of any effective, angle(s), geometry(s), orientation(s), and/or position(s), preferably and without limitation, in any suitable and effective, vertical and/or horizontal position(s), near or close to any vertical and/or horizontal orientation(s), and/or in any effective horizontal and/or vertical manner, within any suitable and effective treatment area(s) such as, but not limited to any, container holding chamber(s) (265), open removable package(s) (229), removable treatment enclosure(s) (230), removable package(s), package(s), open removable treatment enclosure(s), open treatment enclosure(s), open package(s), container holding chamber(s), and/or treatment enclosure(s), preferably and without limitation, suitably and effectively, within, partially within, centered partially within, centered within, over, partially over, centered partially over, centered over, outside of, partially outside of, centered partially outside of, centered outside of, above, partially above, centered partially above, centered above, below, partially below, centered partially below, centered below, underneath, partially underneath, centered partially underneath, and/or centered underneath, at least any suitable and effective, open package(s), removable treatment enclosure(s) (230), open removable package(s) (229), packaging material(s) (495), and/or package(s), that are also preferably, and without limitation, suitably and effectively located within any suitable and effective, container holding chamber(s) (265) and/or treatment enclosure(s).

Also, and without being limited, there are various ways to effectively, suspend, hang, hold, position, and/or locate, one or more of any object(s) (01) within any suitable and effective, treatment enclosure(s), open treatment enclosure(s), removable treatment enclosure(s) (230), open removable treatment enclosure(s), package(s), removable package(s), open package(s), open removable package(s) (229), packaging material(s) (495), open packaging material(s), and/or container holding chamber(s) (265), during the treatment and/or processing of their various surface(s), and then to effectively, drop, release, position, and/or locate, these various object(s) (01) and/or any connected part(s), into and/or within, the one or more of any suitable and effective, removable treatment enclosure(s) (230), open package(s), packaging material(s) (495), open packaging material(s) (495), and/or open removable package(s) (229), after any and/or all of the various and/or any treatment and/or processing steps are completed to effectively treat, dry, and/or process any, part(s), surface(s), component(s), location(s), and/or area(s) such as, but not limited to any, object(s) (01), object interface material(s) (89), object support(s) (84), object(s) (01) surface(s), pressure interface assembly(s) (68), container holding chamber(s) (265), open package(s), open removable package(s) (229), tube(s), hose(s), conduit(s), moving support and dropping mechanism(s) (605), support and tilt mechanism(s) (655), gripping mechanism(s) (135), movable forks or beams (49)(50), gripping finger(s) (108), movable holding and/or support apparatus(s) (606), processing apparatus(s), area(s), and/or location(s), open package(s), packaging material(s) (495), and/or open removable package(s) (229), and/or any other connected and/or indirectly connected, surface(s), space(s), location(s), apparatuses(s), and/or part(s).

In one aspect, and according to FIGS. 59, 70, 73, 75, 82, 84, 86, 88, 91-97, 102, and FIGS. 103-112, and without limitation, the various object(s) (01) can be suitably and effectively, suspended, hung, held, temporarily held, temporarily supported, and/or located, at any suitable and effective position(s), such as, but not limited to, above, below, near, partially within, and/or within, one or more of any suitable and effective location(s) such as, but not limited to any, container holding chamber(s) (265), removable treatment enclosure(s) (230), packaging and open packaging material(s) (495), treatment enclosure(s), open treatment enclosure(s), open removable treatment enclosure(s), package(s), removable package(s), open package(s), open removable package(s) (229), and/or open packaging material(s), but preferably, and without limitation, any suitable, container holding chamber(s) (265), and/or treatment enclosure(s), via one or more of any suitable and effective, pressure interface assembly(s) (68) and/or any other suitable object(s) and/or apparatus(s), that has one or more of any suitable and effective, hose(s) conduit(s), tube(s), and/or pipe(s), that can effectively directly and/or indirectly connect to or with one or more of any suitable and effective, tube connector(s) (461), that can suitably and effectively connect with one or more of any suitable and effective tube disconnect apparatus(s) (462), that is located preferably, and without limitation, within the container holding chamber(s) (265). It is preferred, without limitation, that at least one end, of the at least one of any connecting part(s) and component(s) such as, but not limited to any, hose(s), tube(s), conduit(s), connector(s), supply tube(s) (11), and/or any other suitable connection(s), that connect with one or more of any object(s) (01), such as, but not limited to any, pressure interface assembly(s) (68), can be connected with one or more of any suitable and effective tube connector(s) (461), and the one or more tube connector(s) (461) can be suitably and effectively connected with one or more of any suitable and effective tube disconnect apparatus(s) (462), that can be located at any suitable and effective locations, but preferably and without limitation, at any suitable and effective location(s) within the container holding chamber(s) (265), and more preferably and without limitation, effectively at or near one or more of any top location(s) such as, but not limited to, near and/or at the interior roof area(s) and/or ceiling(s) (270) of the container holding chamber(s) (265), and/or any removable treatment enclosure(s) (230) that can be suitably and effectively open and/or closed. Without being limited, the pressure interface assembly(s) (68), tube connector(s) (461), and tube disconnect apparatus(s) (462), can be located in or at any suitable and effective location(s) in the container holding chamber(s) (265), as well as any suitable and effective height(s) above the enclosure floor(s) (265) and/or any packaging materials, at any suitable and effective time(s).

Without being limited, the tube disconnect apparatus(s) (462) can release the tube connector(s) (461) and any other connected part(s) and component(s) such as, but not limited to any connected, object(s) (01), pressure interface assembly(s) (68), hose(s), tube(s), conduit(s), supply tube(s) (11), and part(s), at any time, but preferably at least at any needed, suitable, and/or effective time(s), and more preferably once the effective treatment, drying, and/or processing of the various surface(s) of various, part(s), location(s), area(s), and/or component(s) such as, but not limited to any, object(s) (01), object interface material(s) (89), object support(s) (84), object(s) (01) surface(s), pressure interface assembly(s) (68), container holding chamber(s) (265), open package(s), open removable package(s) (229), tube(s), hose(s), conduit(s), moving support and dropping mechanism(s) (605), support and tilt mechanism(s) (655), gripping mechanism(s) (135), movable forks or beams (49)(50), gripping finger(s) (108), movable holding and/or support apparatus(s) (606), processing apparatus(s), area(s), and/or location(s), open package(s), packaging material(s) (495), and/or open removable package(s) (229), and/or any other connected and/or indirectly connected, surface(s), space(s), location(s), apparatuses(s), and/or part(s), and/or any other surface(s) and/or atmosphere within any container holding chamber(s) (265), and/or any other suitable and effective location(s) such as, but not limited to any, removable treatment enclosure(s) (230), packaging and open packaging material(s) (495), treatment enclosure(s), open treatment enclosure(s), open removable treatment enclosure(s), package(s), removable package(s), open packaging material(s), and/or any treatment enclosure(s), is complete. It is also preferred, without limitation, that the pressure interface assembly(s) (68), tube connector(s) (461), and tube disconnect apparatus(s) (462), are suitably and effectively located anywhere within the container holding chamber(s) (265), and/or any other suitable and effective location(s) such as, but not limited to any, container holding chamber(s) (265), removable treatment enclosure(s) (230), packaging and open packaging material(s) (495), treatment enclosure(s), open treatment enclosure(s), open removable treatment enclosure(s), package(s), removable package(s), open package(s), open removable package(s) (229), open packaging material(s), and/or any treatment enclosure(s).

Without being limited, once released, the object(s) (01), pressure interface assembly(s) (68), and/or any other part(s) and component(s) that can be suitably connected to any object(s) (01) and/or pressure interface assembly(s) (68) such as, but not limited to any, tube connector(s) (461), plug(s), socket(s), connector(s), hose(s), tube(s), conduit(s), wire(s), and/or cable(s), can be effectively, located, positioned, released, dropped, and/or fall, into one or more of any suitable and effective location(s), receptacle(s), and/or container(s), such as, but not limited to any, removable treatment enclosure(s) (230), packaging and open packaging material(s) (495), treatment enclosure(s), open treatment enclosure(s), open removable treatment enclosure(s), package(s), removable package(s), open package(s), open removable package(s) (229), open packaging material(s), and/or any treatment enclosure(s), that is suitably and effectively located, in one or more of any effective location(s) such as, but not limited to, below, partially below, centered partially below, centered below, underneath, partially underneath, centered partially underneath, centered underneath, around, centered around, partially around, completely around, encompassing, centered and encompassing, partially encompassing, completely encompassing, encompassing around, partially encompassing around, completely encompassing around, and/or centered around and encompassing, the object(s) (01) and/or any other connected part(s) and/or component(s).

Without being limited, the one or more of any, tube disconnect apparatus(s) (462), can effectively connect with one or more of any suitable and effective, supply(s), and/or source(s), of any suitable and effective, air, gas(s), treatment agent(s), and/or substance(s), used for any treatments, drying, and/or processing steps mentioned in the present invention such as, but not limited to any, air/gas(s), fresh air/gas(s) flow(s), heated air/gas(s), dehumidified air/gas(s), vapor(s), aerosol(s) (65), negative pressure air flow(s), and/or applied agent(s) (20), used for any treatment, drying, and/or processing of any, surface(s) and/or atmosphere(s) within any, suitable and effective area(s) and location(s) such as, but not limited to any, container holding chamber(s) (265). Without being limited, the one or more tube disconnect apparatus(s) (462) can also have, be integrated with, and/or interface with, one or more of any effective means, such as, but not limited to any plug decoupling apparatus(s) (536), to effectively connect with one or more of any suitable and effective, electrical connection(s), communication connection(s), and/or fiber optic connection(s), that can communicate with one or more of any suitable and effective programmable controller(s)/PLC(s) (375), and/or any other programmable device(s), at any location(s), for any suitable and effective purposes, such as, but not limited to those disclosed in U.S. Patent Application No. 62/483,486.

Figure 96:
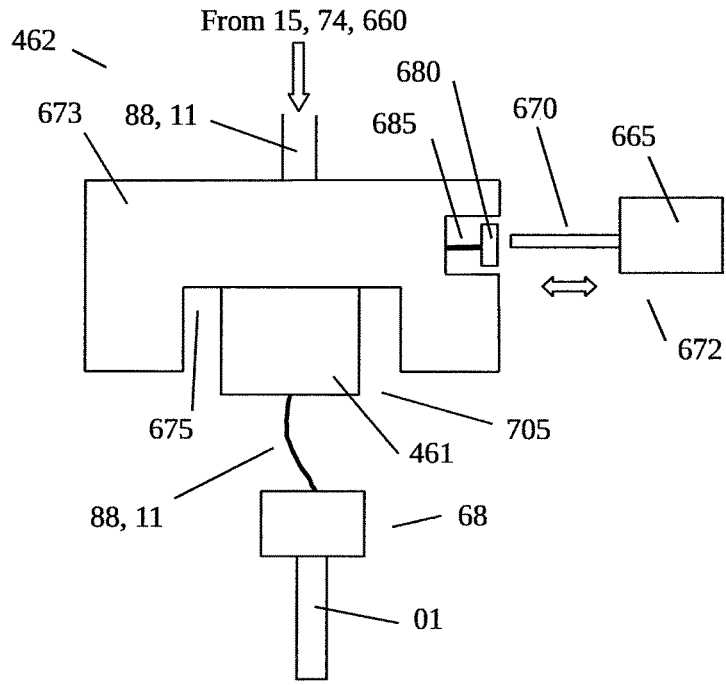
FIG. 96 is a schematic type side view showing a tube disconnect apparatus(s) (462), that can connect with various air/gas(s), heated air/gas(s), and/or agent(s). The object(s) connect to any tube connector(s) (461), and the said tube connector(s) (461) can releasably connect to any pipe interface block(s) (673), which can communicate with any flow(s) of any, air, gas(s), heated air gas(s), and/or agent(s). The tube connector(s) (461) can be released using one or more suitable and effective automated actuation means (672).
Figure 97:
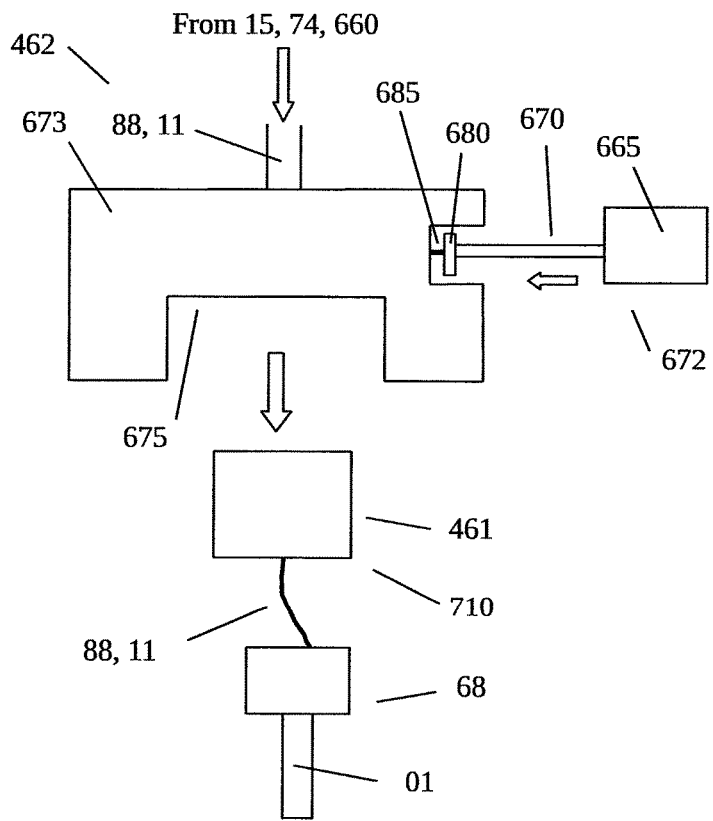
FIG. 97 is a schematic type side view showing a tube disconnect apparatus(s) (462), where the automated actuation means (672) is activated causing the release and disconnection of the tube connector(s) (461) and object(s), from the pipe interface block(s) (673).

Referring FIGS. 96-97, and without limitation, the one or more tube disconnect apparatus(s) (462) includes one or more pipe interface block(s) (673), where one or more pipe(s), tube(s), hose(s), and/or conduit(s) (Herein called "Internal Pipe(s)") (not shown), are preferably and without limitation, located suitably and effectively inside, and are also preferably and without limitation, suitably connected to at least one valve(s) or internal valve(s) (not shown), that is also preferably suitably located in the pipe interface block(s) (673), and the internal pipe(s) directly and/or indirectly, effectively connect, preferably and without limitation, releasably connect, via any other suitable pipe(s) and/or tube(s) (18), with one or more of any suitable and effective treatment and processing equipment(s), apparatus(s), and/or component(s), such as, but not limited to any suitable and effective source(s) of any, air/gas(s), fresh air/gas(s) flow(s), heated air/gas(s), dehumidified air/gas(s), vapor(s), aerosol(s) (65), negative pressure air flow(s), vacuum, and/or applied agent(s) (20). The pipe interface block(s) (673) can have one or more of any suitable tube connector socket(s) (675) that removably interfaces with one or more effective tube connector(s) (461). In FIGS. 96-97, and without limitation, the tube connector(s) (461) can be effectively interfaced (705) with the tube connector socket(s) (675), all in a manner known to those skilled in the art. In FIGS. 96-97, and without limitation, the tube connector(s) (461) can be effectively removed and/or released (710) from the tube connector socket(s) (675), also in a manner known to those skilled in the art. Without being limited, the tube connector(s) (461) can also be suitably connected to one or more of any suitable and effective pipe(s), tube(s), hose(s), and/or conduit(s) (88)(11). Without being limited, when the tube connector(s) (461) are suitably interfaced with the pipe interface block(s) (673), any suitable and effective flow(s) of one or more of any suitable and effective, air, gas(s), treatment agent(s), and/or substance(s), can effectively flow from any treatment and processing equipment(s), apparatus(s), and/or component(s), such as, but not limited to any suitable and effective source(s) of any, air/gas(s), fresh air/gas(s) flow(s), heated air/gas(s), dehumidified air/gas(s), vapor(s), aerosol(s) (65), negative pressure air flow(s), vacuum, and/or applied agent(s) (20), through various part(s) and location(s) such as, but not limited to any, pipe(s), tube(s), hose(s), and/or conduit(s) (88)(11), pipe interface block(s) (673), internal pipe(s) (not shown), internal valve(s) (not shown), tube connector(s) (461), and any suitable object(s) (01).

Without being limited, the pipe interface block(s) (673) can incorporate any suitable means known in the art to effectively interface with, hold, and release, any one or more tube connector(s) (461). It is preferred, without limitation, that the tube connector(s) (461) are released using one or more suitable and effective automated actuation means (672). Referring to FIG. 97, and without being limited, the tube connector(s) (461) can be released when the at least one actuation motor(s) (665) is actuated and/or effectively moves at least one actuation member(s) (670) that effectually connects with, and/or can move and then effectively connects with, at least one actuator connection (680), that is connected with one or more internal actuation member(s) (685). It is preferred, without limitation, that the actuation member(s) (670) can travel or move in one or more of any suitable shaft(s) (not shown). Without being limited, the movement, and preferably and without limitation, any effective inward movement, of the actuator connection (680) and/or preferably and without limitation, at least the connected internal actuation member(s) (685), causes the effective release of the tube connector(s) (461), all in a manner known to those skilled in the art. It is preferred, without limitation, that the tube disconnect apparatus(s) (462) is powered and/or controlled by any suitable and effective programmable controller(s)/PLC(s) (375), and the tube connector(s) (461) can be released at any suitable and effective time(s).

Without being limited, the one or more pressure interface assembly(s) (68), tube connector(s) (461), and/or tube disconnect apparatus(s) (462), can be located, positioned, and/or oriented, in one or more of any suitable and effective angle(s), direction(s), and/or orientation(s). It is preferred, without limitation, that the pressure interface assembly(s) (68), tube connector(s) (461), and/or tube disconnect apparatus(s) (462), are located in or at any suitable and effective location(s) in the container holding chamber(s) (265), and they are oriented and positioned so that any disconnected objects (01) and any directly and/or indirectly connected part(s) and component(s) such as, but not limited to any, attached or accompanying, cord(s), cable(s), plug(s), connector(s), socket(s), and/or hose(s), can fall downward towards the floor(s) (275) of the container holding chamber(s) (265) after being released. It is also preferred, without limitation, that the said released object(s) (01) and any associated part(s) and component(s), fall into or are otherwise effectively positioned and/or located into one or more of any, removable treatment enclosure(s) (230), packaging and open packaging material(s) (495), treatment enclosure(s), open treatment enclosure(s), open removable treatment enclosure(s), package(s), removable package(s), open package(s), open removable package(s) (229), and/or open packaging material(s).

In another aspect, and according to FIGS. 68, 70, 71, 72, 74, 76, 78, 79, 80, 81, 83, 85, 87, 89, 90, and 92-95, and without limitation, the various object(s) (01) can be suitably and effectively, suspended, hung, held, and/or located, at any suitable and effective position(s), such as, but not limited to, above, below, near, partially within, and/or within, one or more of any suitable and effective location(s) such as, but not limited to any, container holding chamber(s) (265), removable treatment enclosure(s) (230), packaging and open packaging material(s) (495), treatment enclosure(s), open treatment enclosure(s), open removable treatment enclosure(s), package(s), removable package(s), open package(s), open removable package(s) (229), and/or open packaging material(s), but preferably, and without limitation, any suitable, container holding chamber(s) (265), and/or treatment enclosure(s), via one or more of any suitable and effective, interface plug(s) (330), that can, and without limitation, suitably and effectively connect directly and/or indirectly with, one or more of any effective part(s) and component(s) such as, but not limited to any, cable(s), wire(s), cord(s), rope(s), tube(s), flexible member(s), conduit(s), fiber optic cable(s), and/or data cable(s), that can effectively connect with one or more of any object(s) (01), and where the interface plug(s) (330) can suitably and effectively, directly and/or indirectly, connect to or with, one or more of any suitable and effective, plug decoupling apparatus(s) (536), that is suitability and effectively located preferably, and without limitation, at any suitable and effective location(s) within the container holding chamber(s) (265). Without being limited, the interface plug(s) (330), can be located in or at any suitable and effective location(s) in the container holding chamber(s) (265), as well as any suitable and effective height(s) above the enclosure floor(s) (265) and/or any packaging materials, at any suitable and effective time(s).

It is preferred, without limitation, that at least one end, of the at least one of any connecting, cable(s), wire(s), cord(s), rope(s), tube(s), flexible member(s), conduit(s), fiber optic cable(s), and/or data cable(s), and/or any other suitable connection(s), that connect with the object(s) (01), can be directly and/or indirectly connected to one or more of any suitable and effective connector(s), electrical connector(s), electrical plug(s), communication connector(s), data plug(s), and any other connection(s) and/or connector(s) known to those skilled in the art (Herein called "Interface Plug(s) (330)"), and the one or more of any suitable and effective interface plug(s) (330) can be suitably and effectively connected with one or more of any suitable and effective means to suspend, hang, hold, grip, temporarily locate, temporarily hold, and/or temporarily position, the interface plug(s) (330) in one or more of any location(s) such as, but not limited to any, container holding chamber(s) (265), and then preferably and without limitation, automatically release the interface plug(s) (330) and any directly and/or indirectly connected object(s) (01), at any suitable and effective time(s), so they can fall into or are otherwise effectively positioned and/or located into one or more of any, removable treatment enclosure(s) (230), packaging and open packaging material(s) (495), treatment enclosure(s), open treatment enclosure(s), open removable treatment enclosure(s), package(s), removable package(s), open package(s), and/or open removable package(s) (229), after the effective treatment, drying, and/or processing of the various surface(s) of various, part(s), location(s), area(s), and/or component(s) such as, but not limited to any, object(s) (01), plug decoupling apparatus(s) (536), interface plug(s) (330), plug interface(s) (490), female plug shaft(s) (545), object interface material(s) (89), object support(s) (84), object(s) (01) surface(s), pressure interface assembly(s) (68), container holding chamber(s) (265), open removable package(s) (229), tube(s), hose(s), conduit(s), moving support and dropping mechanism(s) (605), support and tilt mechanism(s) (655), gripping mechanism(s) (135), movable forks or beams (49) (50), gripping finger(s) (108), movable holding and/or support apparatus(s) (606), processing apparatus(s), area(s), and/or location(s), open package(s), packaging material(s) (495), and/or open removable package(s) (229), and/or any other surface(s), space(s), location(s), apparatuses(s), and/or part(s), and/or any other surface(s) and/or atmosphere within any container holding chamber(s) (265), is complete.

It is preferred, without limitation, that the one or more of any suitable and effective interface plug(s) (330) can be suitably and effectively connected with one or more of any suitable and effective female plug shaft(s) (545) and/or plug decoupling apparatus(s) (536) that can be located at any suitable and effective locations, but preferably and without limitation, at any suitable and effective location(s) within the container holding chamber(s) (265), and more preferably and without limitation, effectively at or near one or more of any top location(s) such as, but not limited to, near and/or at the interior roof area(s) and/or ceiling(s) (270) of the container holding chamber(s) (265), and/or at or near the interior roof area(s), lid roof area(s) (250), and/or ceiling(s), of the removable treatment enclosure(s) (230) that can be suitably and effectively open and/or closed at any suitable and effective time(s).

Without being limited, the plug decoupling apparatus(s) (536) can release the interface plug(s) (330) and any connected, object(s) (01), hose(s), tube(s), conduit(s), and/or any other suitable connection(s), at any time, but preferably at least at any needed, suitable, and/or effective time(s), and more preferably once the effective treatment, drying, and/or processing, of the various surface(s) such as, but not limited to any, surface(s) of any object(s) (01), and/or any other connected and/or indirectly connected, surface(s), space(s), location(s), apparatuses(s), and/or part(s), and/or any other surface(s) and/or atmosphere within any container holding chamber(s) (265), and/or any other suitable and effective location(s) such as, but not limited to any, removable treatment enclosure(s) (230), packaging and open packaging material(s) (495), open treatment enclosure(s), open removable treatment enclosure(s), package(s), removable package(s), open packaging material(s), and/or any treatment enclosure(s), is complete.

It is also preferred, without limitation, that the interface plug(s) (330) and the plug shaft(s) (545) and/or plug decoupling apparatus(s) (536), are suitably and effectively, designed, sized, and located, for and/or within location(s) such as, but not limited to any, container holding chamber(s) (265), removable treatment enclosure(s) (230), packaging and open packaging material(s) (495), open treatment enclosure(s), open removable treatment enclosure(s), package(s), removable package(s), open packaging material(s), and/or any treatment enclosure(s).

Once released, the object(s) (01), and/or any other part(s) and component(s) that may be suitably connected to any object(s) (01) such as, but not limited to any, interface plug(s) (330), connector(s), hose(s), tube(s), conduit(s), wire(s), plug(s), and/or cable(s), can effectively, be located, positioned, released, dropped, and/or fall, into one or more of any suitable and effective, location(s), receptacle(s), and/or container(s), such as, but not limited to any, removable treatment enclosure(s) (230), packaging and open packaging material(s) (495), treatment enclosure(s), open treatment enclosure(s), open removable treatment enclosure(s), package(s), removable package(s), open package(s), open removable package(s) (229), open packaging material(s), and/or any treatment enclosure(s), that is suitably and effectively located, in one or more of any effective location(s) such as, but not limited to, below, partially below, centered partially below, centered below, underneath, partially underneath, centered partially underneath, centered underneath, around, centered around, partially around, completely around, encompassing, centered and encompassing, partially encompassing, completely encompassing, encompassing around, partially encompassing around, completely encompassing around, and/or centered around and encompassing, the object(s) (01) and/or any other connected part(s) and/or component(s).

Referring more specifically to FIGS. 92-95, and without limitation, the one or more plug decoupling apparatus(s) (536) includes at least one suitable plug interface(s) (490) that can have one or more of any suitable male (560) and/or female (550) configuration(s) known in the art, and can interface with one or more of any suitable interface plug(s) (330) that can also have one or more of any suitable male and/or female configuration(s) known in the art. It is preferred, without limitation, that the at least one suitable plug interface(s) (490) at least has any suitable female configuration(s) (550) known in the art, and the at least one interface plug(s) (330) at least has any suitable male configuration(s) known in the art.

Without being limited, the interface plug(s) (330) can have one or more suitable and effective communication connection(s) (535) with any male and/or female connection configuration(s) and design(s), all in a manner known to those skilled in the art. It is preferred, without limitation, that the communication connection(s) (535) are any suitable and effective fiber optic connection(s) and/or electrical conductor(s) configuration(s) known to those skilled in the art. It is also preferred, without limitation, that the fiber optic connection(s) and/or electrical conductor connection(s) for the communication connection(s) (535), are present in or with any suitable and effective male and/or female design(s) and configuration(s). The one or more interface plug(s) (330) can suitably connect with one or more of any suitable and effective, wire(s), cable(s), and/or fiber optic line(s) (Herein called "Data and Power Cable(s)") (325) that can suitably connect with one or more of any object(s) (01).

Without being limited, the at least one plug interface(s) (490), can have at least one suitable and effective plug shaft (545) that is preferably, and without limitation, a female connection. Without being limited, the plug interface(s) (490) can also have one or more of any suitable and effective communication connection(s) (535), and the communication connection(s) (535) can have any suitable and effective male and/or female fiber optic connection(s) and/or electrical conductor design(s) and/or configuration(s) (not shown) known to those skilled in the art. It is preferred, without limitation, that these fiber optic connection(s) and/or electrical conductor(s) (not shown) are present in or with any suitable and effective female design(s) and configuration(s). The one or more communication connection(s) (535) can suitably and effectively connect with one or more of any suitable and effective, data and power cable(s) (325) that can suitably connect with one or more of any suitable and effective programmable controller(s)/PLC(s) (375).

Without being limited, at least one interface plug(s) (330) can suitably and effectively interface with at least one suitable plug interface(s) (490), where the one or more communication connection(s) (535) of the interface plug(s) (330) can effectively interface with one or more suitable and effective communication connection(s) (535) of the at least one suitable and effective plug interface(s) (490). It is also preferred, without limitation, that the interface plug(s) (330) are effectively interfaced and/or held within and/or to the plug interface(s) (490), all in a manner known to those skilled in the art, until the interface plug(s) (330) is forced out, dropped out, and/or removed, preferably and without limitation, via any suitable and effective automatic mechanical means.

Without being limited, the interface plug(s) (330) can be mechanically detached from the plug interface(s) (490) with the assistance of at least one suitable and effective mechanical apparatus(s) that forces and/or causes the interface plug(s) (330) to be removed from the plug interface(s) (490). Referring to FIGS. 92-95, and without being limited, the interface plug(s) (330) can be released from the plug interface(s) (490), when the at least one suitable push protrusion movement apparatus(s) (570) is actuated and/or effectively moves at least one suitable push protrusion member(s) (555) for any suitable and effective distance(s) into the one or more plug interface(s) (490) and/or female plug shaft(s) (545) to cause the interface plug(s) (330) to completely back out of the plug interface(s) (490) and/or plug shaft(s) (545), and/or to cause the effective release and/or effective disconnection of the interface plug(s) (330) from the plug interface(s) (490), plug shaft(s) (545), and/or plug decoupling apparatus(s) (536), so that the interface plug(s) (330) preferably, and without limitation, completely drop away from the plug interface(s) (490), plug shaft(s) (545), and/or plug decoupling apparatus(s) (536) at any suitable and effective time(s).

Without being limited, the push protrusion member(s) (555) can be any suitable and effective, length, width, height, geometry, design, object, shape, configuration, and/or size. Also, without being limited, various other parts of the plug decoupling apparatus(s) (536) such as, but not limited to any, communication and/or power connection(s) (535), can also function as the push protrusion member(s) (555) (not shown). It is preferred, without limitation, that the push protrusion member(s) (555) can travel or move in one or more of any suitable shaft(s) (565). It is also preferred, without limitation, that only one push protrusion member(s) (555) moves in one shaft(s) (565). It is preferred, without limitation, that the plug decoupling apparatus(s) (536) is powered and/or controlled by any suitable and effective programmable controller(s)/PLC(s) (375), and the interface plug(s) (330) can be released at any suitable and effective time(s).

Without being limited, any part of the one or more of any, plug decoupling apparatus(s) (536) can also effectively connect with and/or communicate with, one or more of any suitable and effective, electrical connection(s), communication connections, and/or fiber optic connection(s), that can communicate with one or more of any suitable and effective, programmable controller(s)/PLC(s) (375), at any location(s), for any suitable and effective purposes, such as, but not limited to those disclosed in U.S. Patent Application No. 62/483,486, and/or for automation, operation, control, and/or automatic control, purposes.

Without being limited, the one or more interface plug(s) (330) and/or plug decoupling apparatus(s) (536), can be located, positioned, and/or oriented, in one or more of any suitable and effective angle(s), direction(s), and/or orientation(s). It is preferred, without limitation, that the interface plug(s) (330) and/or plug decoupling apparatus(s) (536) are located in or at any suitable and effective location(s) in the container holding chamber(s) (265), as well as any suitable and effective height(s) above the enclosure floor(s) (265) and/or any packaging materials, at any suitable and effective time(s), and they are oriented and positioned so that any released and/or disconnected objects (01) and any directly and/or indirectly connected part(s) and component(s) such as, but not limited to any, attached or accompanying, cord(s), cable(s), plug(s), connector(s), socket(s), and/or hose(s), can fall downward towards the floor(s) (275) of the container holding chamber(s) (265) after being released. It is also preferred, without limitation, that the said released object(s) (01) and any associated part(s) and component(s), fall into or are otherwise positioned and/or located into one or more of any, removable treatment enclosure(s) (230), packaging and open packaging material(s) (495), treatment enclosure(s), open treatment enclosure(s), open removable treatment enclosure(s), package(s), removable package(s), open package(s), open removable package(s) (229).

Also, without being limited, the one or more of any substance(s) that are used to treat and/or process any, object(s) (01), atmosphere(s), and/or surface(s), within any suitable and effective, treatment enclosure(s), removable treatment enclosure(s) (230), and/or container holding chamber(s) (265), such as, but not limited to any, air/gas(s), heated air/gas(s), dehumidified air/gas(s), vapor(s), aerosol(s) (65), and/or applied agent(s) (20), can also effectively flow through and out of, and/or be effectively applied via, any suitable and effective part(s) of the plug decoupling apparatus(s) (536) and/or interface plug(s) (330), and more preferably and without limitation, effectively flow through and out of any suitable and effective surface(s) and/or interfacing surface(s) of part(s) and location(s) such as, but not limited to any, interface plug(s) (330), plug interface(s) (490), plug shaft(s) (545), and/or object interface material(s) (89), via one or more of any suitable and effective opening(s) (85) in the said part(s), surface(s), and/or area(s), that are suitably and effectively connected to any source(s) of any substance(s) such as, but not limited to any, air/gas(s), heated air/gas(s), dehumidified air/gas(s), vapor(s), aerosol(s) (65), and/or applied agent(s) (20), that can be used to treat, dry, and/or process, these various area(s) surface(s), and/or material(s).

Referring to FIGS. 38-43 and 112, and in still another aspect, and without limitation, the various object(s) (01) can be suitably and effectively, suspended, hung, held, temporarily held, temporarily supported, and/or located, at any suitable and effective position(s), such as, but not limited to, above, below, near, partially within, and/or within, one or more of any suitable and effective location(s) such as, but not limited to any, container holding chamber(s) (265), removable treatment enclosure(s) (230), packaging and open packaging material(s) (495), treatment enclosure(s), open treatment enclosure(s), open removable treatment enclosure(s), package(s), removable package(s), open package(s), and/or open removable package(s) (229), but preferably, and without limitation, any suitable, container holding chamber(s) (265), and/or treatment enclosure(s), via one or more of any suitable and effective gripping mechanism(s) (135) and/or gripping finger(s) (108).

Without being limited, the gripping mechanism(s) (135) and/or gripping finger(s) (108) can be located or positioned in or at any suitable and effective location(s). It is preferred, without limitation, that the one or more gripping mechanism(s) (135) and/or gripping finger(s) (108) are suitably and effectively located within the container holding chamber(s) (265) and/or treatment enclosure(s), and also effectively located and centered above the one or more of any suitable and effective, open packaging and/or open packaging material(s) (495), open treatment enclosure(s), open removable treatment enclosure(s), open package(s), open removable package(s) (229). It is preferred, without limitation, that the gripping mechanism(s) (135) are located in or at any suitable and effective location(s) in the container holding chamber(s) (265).

Without being limited, the one or more gripping mechanism(s) (135) can be located, positioned, and/or oriented, in one or more of any suitable and effective angle(s), direction(s), and/or orientation(s). It is preferred, without limitation, that the gripping mechanism(s) (135) are located in or at any suitable and effective location(s) in the container holding chamber(s) (265), as well as any suitable and effective height(s) above the enclosure floor(s) (265) and/or any packaging materials, at any suitable and effective time(s), and they are oriented and positioned so that any released and/or disconnected objects (01) and any directly and/or indirectly connected part(s) and component(s) such as, but not limited to any, attached or accompanying, cord(s), cable(s), plug(s), connector(s), socket(s), and/or hose(s), can fall downward towards the floor(s) (275) of the container holding chamber(s) (265) after being released. It is also preferred, without limitation, that the said released object(s) (01) and any associated part(s) and component(s), fall into or are otherwise positioned and/or located into one or more of any, removable treatment enclosure(s) (230), packaging and open packaging material(s) (495), treatment enclosure(s), open treatment enclosure(s), open removable treatment enclosure(s), package(s), removable package(s), open package(s), open removable package(s) (229), and/or open packaging material(s).

It is also preferred, without limitation, that the gripping mechanism(s) (135) and/or gripping finger(s) (108) take turns using different gripping mechanism(s) (135) and/or gripping finger(s) (108), in any suitable and effective manner, to effectively, pinch, hold, interface with, and/or grip, one or more of any different and effective part(s) and/or location(s) of any, object(s) (01), pressure interface assembly(s) (68), and/or any other part(s) and component(s) that may be suitably and effectively connected to any object(s) (01) and/or pressure interface assembly(s) (68) such as, but not limited to any, hose(s), tube(s), conduit(s), wire(s), plug(s), connector(s), and/or cable(s), in an effective and/or efficacious manner so that all of the various surfaces are suitably and effectively treated, dried, and/or processed, at any time(s), with any suitable and effective, air/gas(s), heated air/gas(s), dehumidified air/gas(s), vapor(s), aerosol(s) (65), and/or applied agent(s) (20), at any suitable and effective time(s).

Without being limited, all of the gripping mechanism(s) (135) and/or gripping finger(s) (108) can release the object(s) (01), pressure interface assembly(s) (68), and/or any other part(s) and component(s) that may be suitably connected to any object(s) (01), and/or pressure interface assembly(s) (68), such as, but not limited to any, hose(s), tube(s), conduit(s), wire(s), and/or cable(s), at any time(s), but preferably at least at any needed, suitable, and/or effective time(s), and more preferably once the effective treatment, drying, and/or processing, of the various surface(s) of the various, part(s), location(s), area(s), and/or component(s), such as, but not limited to any, object(s) (01), object interface material(s) (89), part(s), apparatus(s), object support(s) (84), and/or any other surface(s) and/or atmosphere(s) within any container holding chamber(s) (265) and/or treatment enclosure(s), is complete.

Once fully released from all of the gripping mechanism(s) (135) and/or gripping finger(s) (108), the object(s) (01), and/or any other part(s) and component(s) that may be connected to any object(s) (01) such as, but not limited to any, pressure interface assembly(s) (68), hose(s), tube(s), conduit(s), wire(s), and/or cable(s), can be effectively, located, positioned, released, dropped, and/or fall, into one or more of any suitable and effective, open removable package(s) (229), open package(s), and/or packaging material(s) (495), that is suitably and effectively located, at any suitable and effective location(s) such as, but limited to, below, partially below, centered partially below, centered below, underneath, partially underneath, centered partially underneath, centered underneath, around, centered around, partially around, completely around, encompassing, centered and encompassing, partially encompassing, completely encompassing, encompassing around, partially encompassing around, completely encompassing around, and/or centered around and encompassing, any one or more object(s) (01) and/or any other connected part(s) and/or component(s).

Also, without being limited, the one or more of any substance(s) that are used to treat and/or process any, object(s) (01), atmosphere(s), and/or surface(s), within any suitable and effective, treatment enclosure(s), removable treatment enclosure(s) (230), and/or container holding chamber(s) (265), such as, but not limited to any, air/gas(s), heated air/gas(s), dehumidified air/gas(s), vapor(s), aerosol(s) (65), and/or applied agent(s) (20), can also effectively flow through and out of, and/or be effectively applied via, any gripping mechanism(s) (135) and/or gripping finger(s) (108), and more preferably effectively flow through and out of any suitable and effective surface(s) of any, gripping finger(s) (108), object support(s) (84), and/or object interface material(s) (89), to treat, dry, and/or process various area(s) and/or surface(s) such as, but not limited to any, object(s) (01) surface(s) that interface with any, gripping mechanism(s) (135) and/or gripping finger(s) (108), object support(s) (84), and/or object interface material(s) (89), preferably and without limitation using and/or via one or more of any suitably and effectively located opening(s) (85) that effectively communicate with the various source(s) of the said substance(s).

In still another aspect, and according to FIGS. 98-101, and without limitation, the various object(s) (01) can be suitably and effectively, suspended, hung, held, temporarily held, temporarily supported, and/or located, at any suitable and effective position(s), such as, but not limited to, above, below, near, partially within, and/or within, one or more of any suitable and effective location(s) such as, but not limited to any, container holding chamber(s) (265), removable treatment enclosure(s) (230), packaging and open packaging material(s) (495), treatment enclosure(s), open treatment enclosure(s), open removable treatment enclosure(s), package(s), removable package(s), open package(s), and/or open removable package(s) (229), but preferably, and without limitation, any suitable, container holding chamber(s) (265), and/or treatment enclosure(s), via one or more of any suitable and effective support and release apparatus(s) (606), movable support member(s) (620) and/or hold and tilt apparatus(s) (655). Without being limited, the support and release apparatus(s) (606), hold and tilt apparatus(s) (655), and/or movable support member(s) (620), can suitably and effectively, support, hold, and/or locate, one or more of any, object(s) (01), wire(s), hose(s), cable(s), suitable part(s) and/or location(s) of any, object(s) (01), pressure interface assembly(s) (68), and/or any other part(s) and component(s) that may be suitably connected to any object(s) (01) and/or pressure interface assembly(s) (68) such as, but not limited to any, hose(s), tube(s), conduit(s), wire(s), plug(s), connector(s), and/or cable(s), within any suitable and effective locations, preferably and without limitation, any suitable and effective location(s) within any container holding chamber(s) (265) and/or treatment enclosure(s).

Without being limited, the support and release apparatus(s) (606), hold and tilt apparatus(s) (655), and/or movable support member(s) (620), can be located or positioned in or at any suitable and effective location(s). It is preferred, without limitation, that the one or more support and release apparatus(s) (606), hold and tilt apparatus(s) (655), and/or movable support member(s) (620) are suitably and effectively located within the container holding chamber(s) (265) and/or treatment enclosure(s), and also effectively located and centered above the one or more of any suitable and effective, open packaging and/or open packaging material(s) (495), open treatment enclosure(s), open removable treatment enclosure(s), open package(s), open removable package(s) (229). Without limitation, it is also preferred that the support and release apparatus(s) (606), hold and tilt apparatus(s) (655), and/or movable support member(s) (620) are located in or at any suitable and effective location(s) in the container holding chamber(s) (265), as well as any suitable and effective height(s) above the enclosure floor(s) (265) and/or any packaging materials, at any suitable and effective time(s).

Without being limited, the one or more support and release apparatus(s) (606), hold and tilt apparatus(s) (655), and/or movable support member(s) (620) can be located, positioned, and/or oriented, in one or more of any suitable and effective angle(s), direction(s), and/or orientation(s). It is preferred, without limitation, that the support and release apparatus(s) (606), hold and tilt apparatus(s) (655), and/or movable support member(s) (620) are located in or at any suitable and effective location(s) in the container holding chamber(s) (265), and they are oriented and positioned so that any released and/or disconnected objects (01) and any directly and/or indirectly connected part(s) and component(s) such as, but not limited to any, attached or accompanying, cord(s), cable(s), plug(s), connector(s), socket(s), and/or hose(s), can fall downward towards the floor(s) (275) of the container holding chamber(s) (265) after being released and/or dropped. It is also preferred, without limitation, that the said released object(s) (01) and any associated part(s) and component(s), fall into or are otherwise positioned and/or located into one or more of any, removable treatment enclosure(s) (230), packaging and open packaging material(s) (495), treatment enclosure(s), open treatment enclosure(s), open removable treatment enclosure(s), package(s), removable package(s), open package(s), open removable package(s) (229), and/or open packaging material(s).

Also, without being limited, the support and release apparatus(s) (606) can include one or more, but preferably and without limitation, at least two, movable support and dropping mechanism(s) (605). Without being limited, each movable support and dropping mechanism(s) (605) can include at least one suitable and effective means to move (Herein called "Support Member Movement Means") (625) the at least one suitable and effective movable support member(s) (620), that can be suitably and effectively connected to the support member movement means (625).

Without limitation, the support member movement means (625) can include one or more of any suitable and effective apparatus(s) to cause the movable support member(s) (620) to effectively move to one or more of any suitable and effective location(s) and/or position(s), preferably and without limitation, to be moved effectively close to one another, and even more preferably and without limitation, to be effectively pinched together, and very preferred without limitation, almost or close to being pinched together but not actually where the movable support member(s) (620) are touching, all to cause the one or more object(s) and/or any attached part(s) to be held by the one or more of any suitable and effective support and release apparatus(s) (606), at one or more of any effective time(s).

Also, without limitation, the support member movement means (625) can include one or more of any suitable and effective apparatus(s) to cause the movable support member(s) (620) to effectively move to one or more of any suitable and effective location(s) and/or position(s), to cause the one or more object(s) and/or any attached part(s) to effectively, fall, drop, and/or be disconnected from, the support and release apparatus(s) (606), at one or more of any effective time(s), all in a manner known to those skilled in the art.

Figure 98:
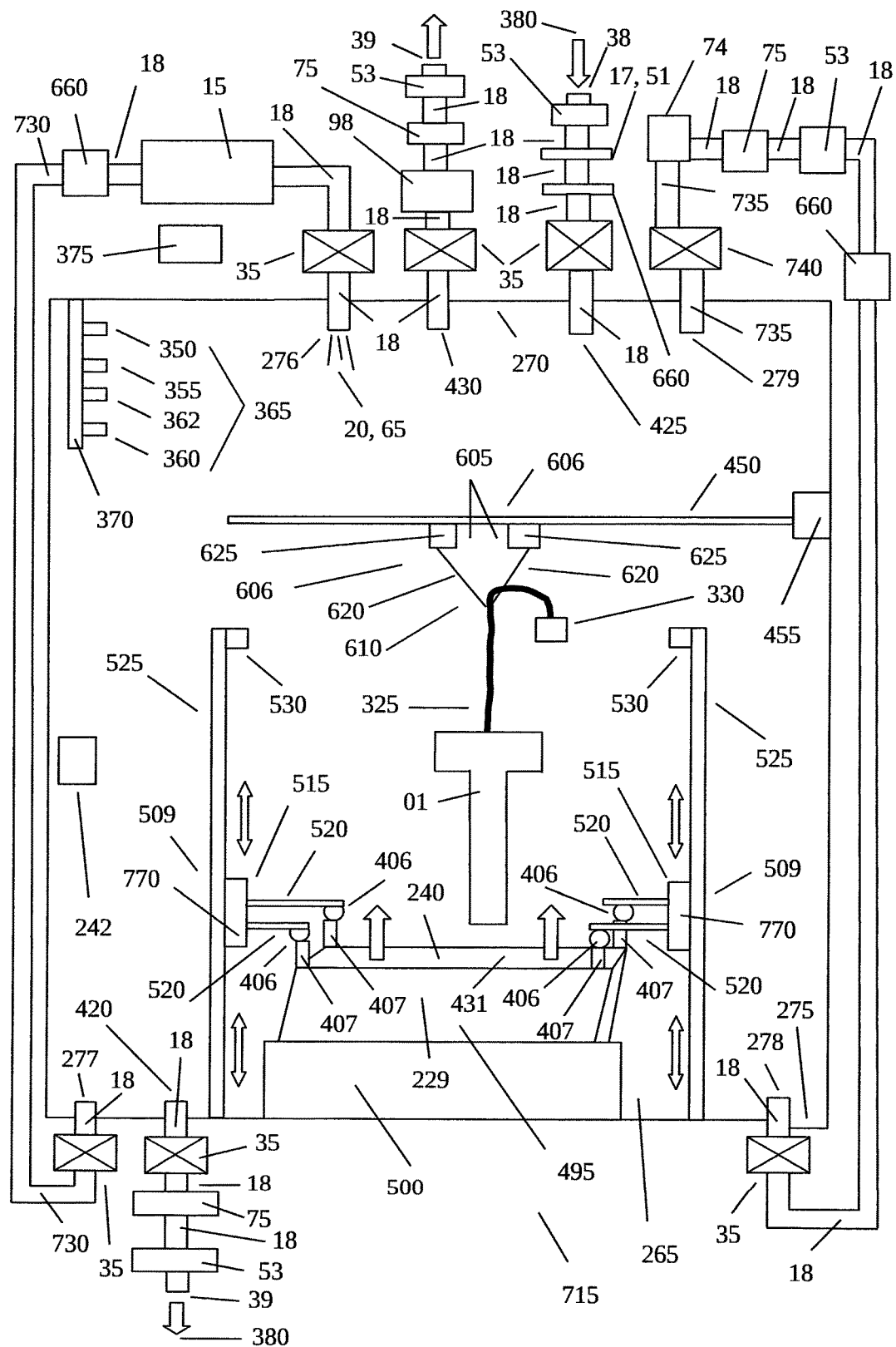
FIG. 98 is a side schematic type view of an enhanced decontamination enclosure apparatus (715), where an object and its cable is suspended inside a container holding chamber(s) (265) with a movable holding and/or support apparatus(s) (606), that is NOT plumbed in this instance, but is used for supporting, and holding, the interfaced object(s). At least one packaging guided lift apparatus(s) (515) is located in the container holding chamber(s) (265), with the open removable package(s) (229) and/or packaging and open packaging material(s) (495), ready for use.
Figure 99:
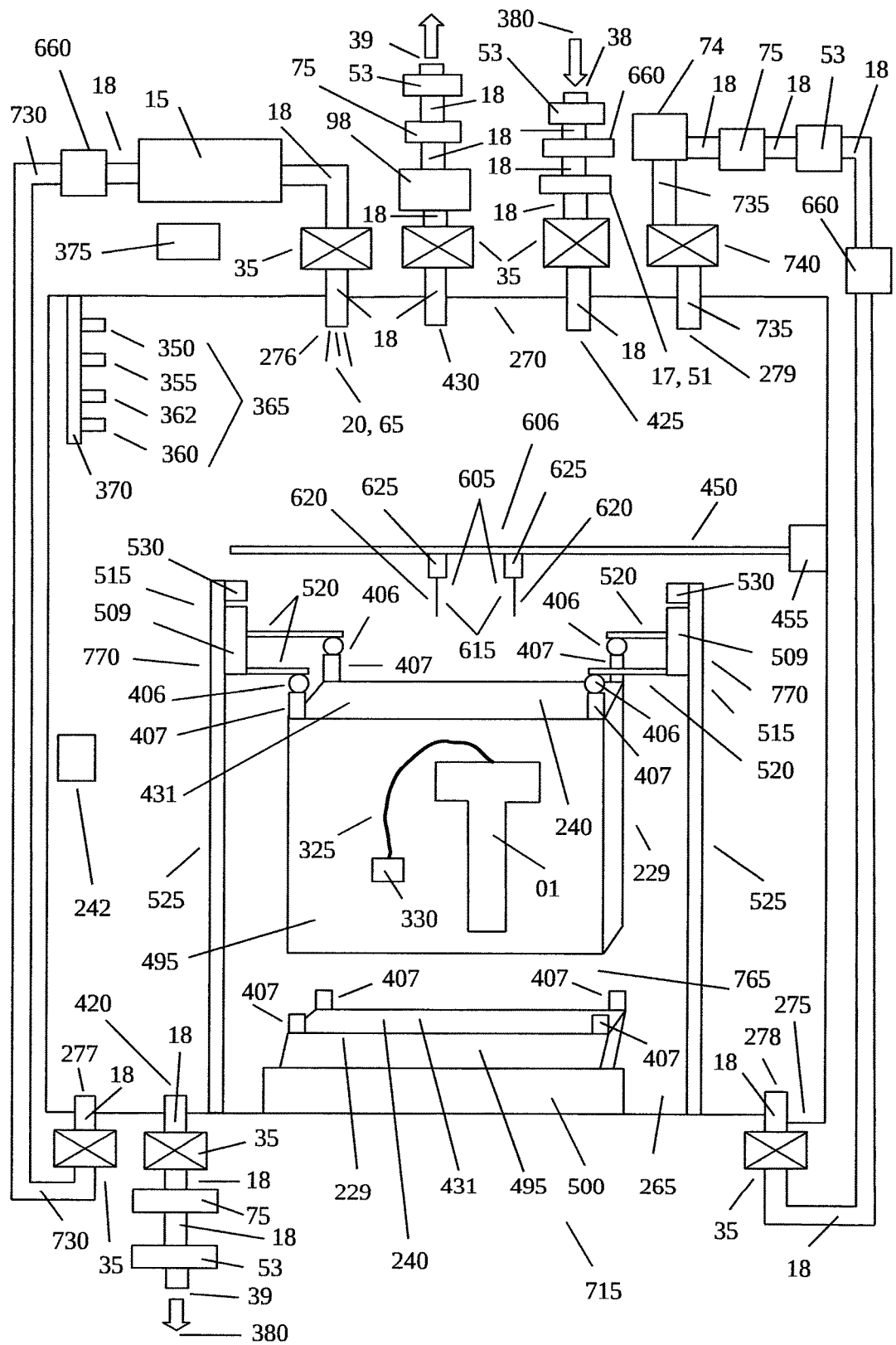
FIG. 99 is a side schematic type view of an enhanced decontamination enclosure apparatus (715), where at least one packaging guided lift apparatus(s) (515) is located in the container holding chamber(s) (265), and has moved the open removable package(s) (229) and/or packaging and open packaging material(s) (495), effectively under the object(s) and/or to effectively surround the object(s). After being treated, processed, and/or dried, the object(s) was released by the one or more movable holding and/or support apparatus(s) (606) and then dropped and/or positioned into the open removable package(s) (229) and/or packaging and open packaging material(s) (495).

With reference to FIG. 98-99, it is preferred, without limitation, that at least two movable support and dropping mechanism(s) (605), that are each suitably and effectively connected to at least one or more of any suitable and effective support member movement means (625), and also to at least one or more suitable and effective movable support member(s) (620), are effectively located and positioned so that the two or more movable support member(s) (620) can be moved into one or more of any suitable and effective, location(s), proximity(s), and/or position(s), so that: (a) the two or more movable support member(s) (620) are at least in any effective proximity to one another to effectively support and/or hold the one or more of any, object(s) (01), cable(s), wire(s), and/or hose(s), and/or (b) the two or more movable support member(s) (620) can be effectively and releaseably contacted, close to being contacted, interfaced, and/or close to being interfaced, in any suitable and effective manner to effectively support and/or hold the one or more of any object(s) (01), cable(s), wire(s), and/or hose(s). Without being limited, FIG. 98-99 shows the at least two movable support member(s) (620) in or at any effective proximity(s) to each other, and/or in or at any effective "closed" position(s) (610), to effectively support and/or hold the one or more of any object(s) (01), cable(s), wire(s), and/or hose(s).

Without being limited, the one or more movable support member(s) (620) can be effectively positioned so that any suitable, object(s) (01), cable(s), wire(s), and/or hose(s), can rest on or at any suitable and effective location(s) and/or position(s) over and/or on top of, the interfaced, and/or releasably connected, and/or contacting, movable support member(s) (620). Without being limited, the support member movement means (625) and movable support member(s) (620) can be suitably and effectively designed and constructed to support and/or hold the various object(s) (01), cable(s), wire(s), and/or hose(s). Also, and without being limited, the movable support member(s) (620) can be designed and function as object support(s) (84) and with all the previously described attributes and functionality, except the movable support member(s) (620) can be moved at any suitable and effective time(s). Without being limited, the movable support member(s) (620) can interface with one or more of any suitable and effective object interface material(s) (89).

Without being limited, when needed and/or desired, the support member movement means (625), can be located, positioned, and/or effectually move the movable support member(s) (620), in any suitable and effective manner, direction(s), angle(s), and/or orientation(s), to cause the one or more object(s) (01) to fall, drop, and/or be effectively released from, the support and dropping mechanism(s) (605), and preferably and without limitation, into any suitable location(s) such as, but not limited to any, open removable package(s) (229) and/or packaging and open packaging material(s) (495).

Also, without being limited, the support and dropping mechanism(s) (605) and/or movable support member(s) (620) can release the, object(s) (01), pressure interface assembly(s) (68), and/or any other part(s) and component(s) that may be suitably connected to any object(s) (01), and/or pressure interface assembly(s) (68), such as, but not limited to any, hose(s), tube(s), conduit(s), wire(s), and/or cable(s), at any time(s), but preferably at least at any needed, suitable, and/or effective time(s), and more preferably once the effective treatment, drying, and/or processing, of the various surface(s) of various, part(s), location(s), area(s), and/or component(s), such as, but not limited to any, object(s) (01), object interface material(s) (89), part(s), apparatus(s), object support(s) (84), and/or any other surface(s) and/or atmosphere(s) within any container holding chamber(s) (265), and/or treatment enclosure(s), is complete. Without being limited, FIG. 98-99 shows the at least two movable support member(s) (620) at any effective distance(s) from each other, and/or in or at any effective "open" position(s) (615), so that the one or more of any object(s) (01), cable(s), wire(s), and/or hose(s), can effectively, fall from, drop from, and/or be removed from, the one or more support and dropping mechanism(s) (605) and/or movable support member(s) (620).

Once released, the object(s) (01), and/or any other part(s) and component(s) that may be connected to any object(s) (01) such as, but not limited to any, pressure interface assembly(s) (68), hose(s), tube(s), conduit(s), wire(s), and/or cable(s), can be effectively, located, positioned, released, dropped, and/or fall, into one or more of any suitable and effective, open removable package(s) (229), open package(s), and/or packaging material(s) (495), that is suitably and effectively located, at any suitable and effective location(s) such as, but limited to, below, partially below, centered partially below, centered below, underneath, partially underneath, centered partially underneath, centered underneath, around, centered around, partially around, completely around, encompassing, centered and encompassing, partially encompassing, completely encompassing, encompassing around, partially encompassing around, completely encompassing around, and/or centered around and encompassing, any one or more object(s) (01) and/or any other connected part(s) and/or component(s).

Also, without being limited, the one or more of any substance(s) that are used to treat, dry, and/or process any, object(s) (01), atmosphere(s), and/or surface(s), within any suitable and effective, treatment enclosure(s), removable treatment enclosure(s) (230), and/or container holding chamber(s) (265), such as, but not limited to any, air/gas(s), heated air/gas(s), dehumidified air/gas(s), vapor(s), aerosol(s) (65), and/or applied agent(s) (20), can also effectively flow through and out of, and/or be effectively applied via, any support and dropping mechanism(s) (605) and/or movable support member(s) (620), and more preferably effectively flow through and out of any suitable and effective surface(s) of any, movable support member(s) (620), object support(s) (84), and/or object interface material(s) (89), preferably and without limitation, using and/or via one or more of any suitably and effectively located opening(s) (85) that effectively communicate with the various source(s) of the said substance(s), to treat, dry, and/or process various area(s) and/or surface(s) such as, but not limited to any, object(s) (01) surface(s) that interface with any, support and dropping mechanism(s) (605) and/or movable support member(s) (620), object support(s) (84), and/or object interface material(s) (89).

Figure 100:
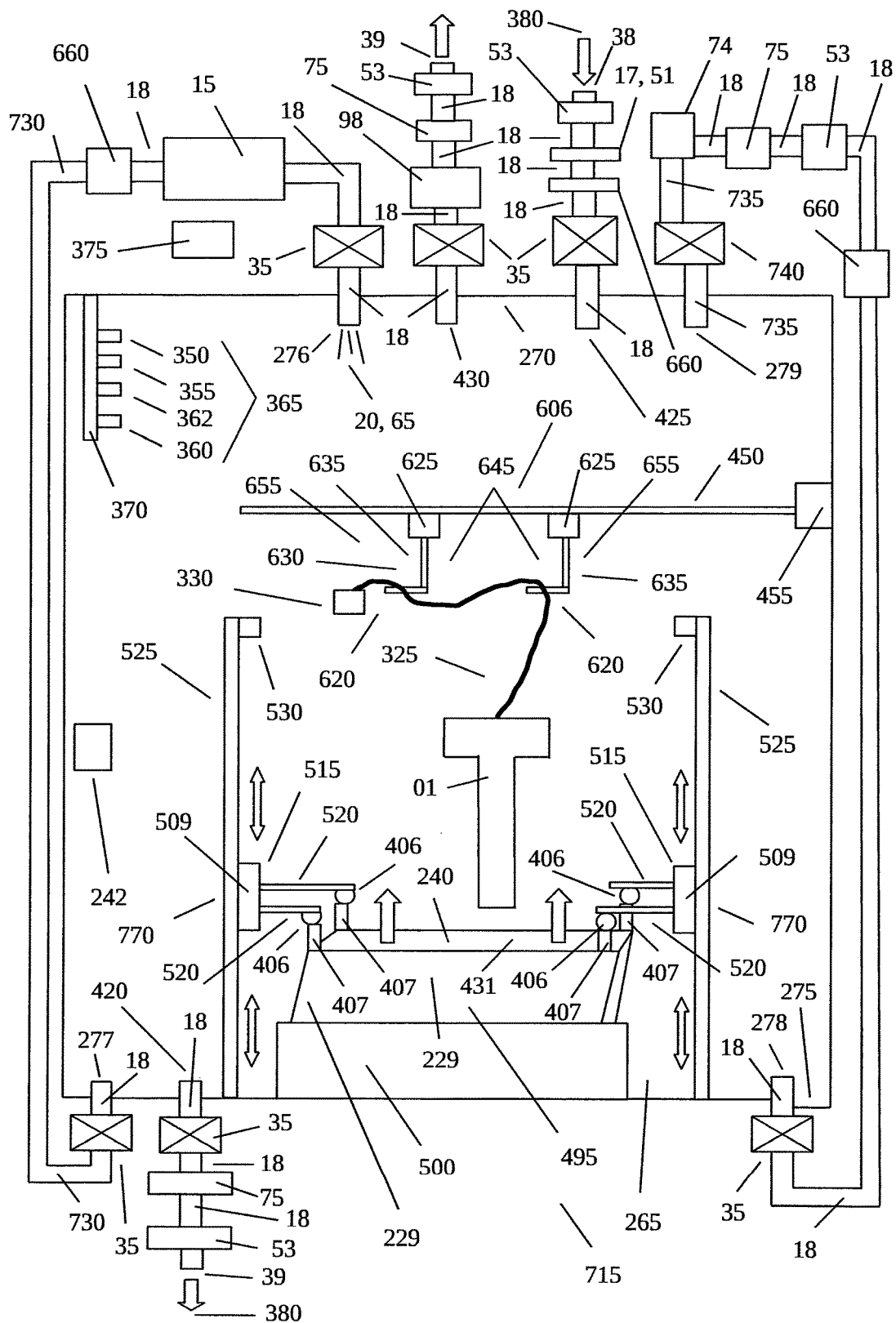
FIG. 100 is a side schematic type view of an enhanced decontamination enclosure apparatus (715), where an object(s) and its cable(s) is supported and/or suspended in the container holding chamber(s) (265) with a movable holding and/or support apparatus(s) (606) that is NOT plumbed in this instance, but is used for supporting, and holding the interfaced object(s). The open removable package(s) (229) and/or packaging and open packaging material(s) (495), can be moved up under and/or around the suspended object(s) via one or more packaging guided lift apparatus(s) (515). The top of the open removable package(s) (229) and/or packaging and open packaging material(s) (495) that is lifted up and into position around the objects is open.
Figure 101:
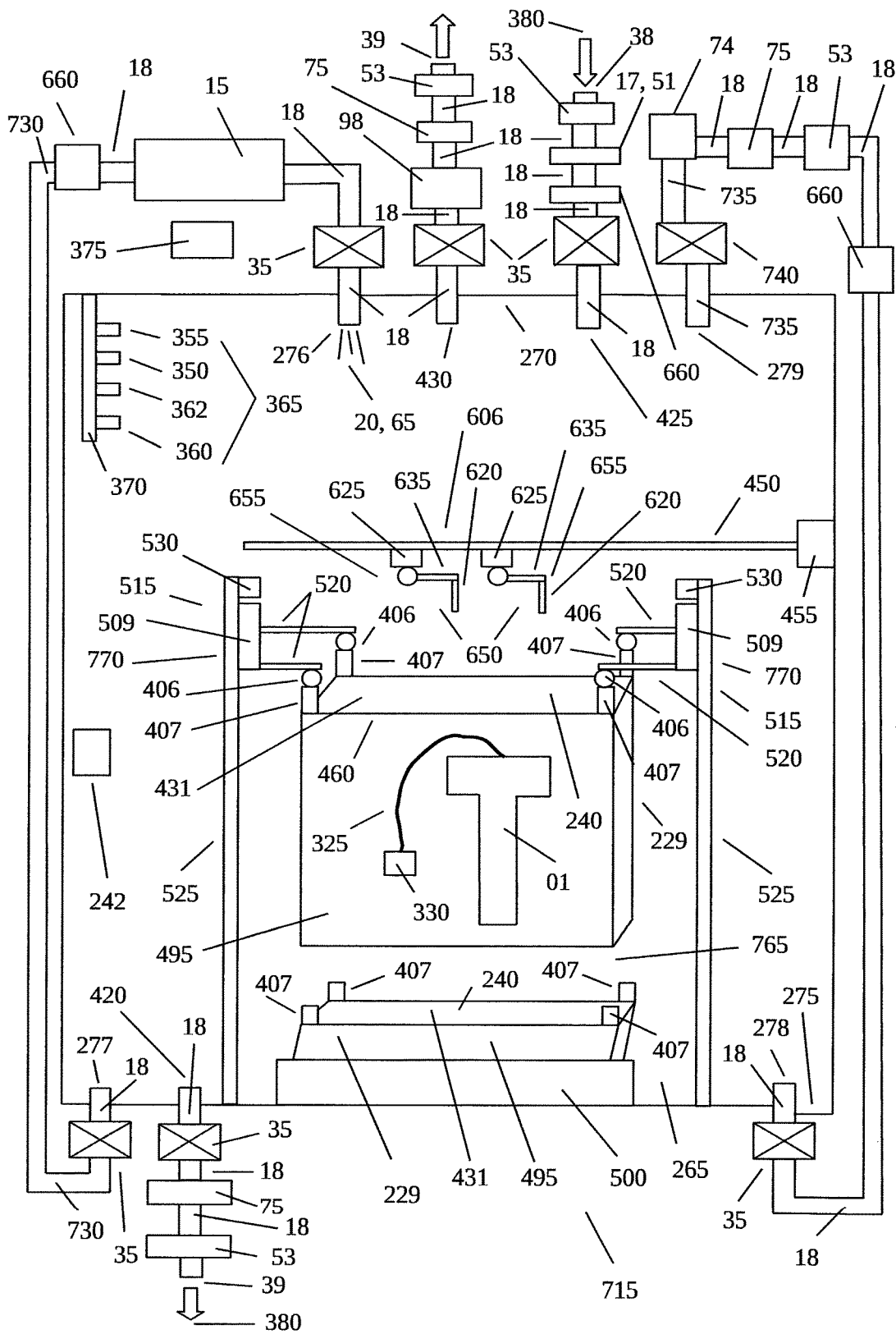
FIG. 101 is a side schematic type view of an enhanced decontamination enclosure apparatus (715), where at least one packaging guided lift apparatus(s) (515) is located in the container holding chamber(s) (265), and has moved the open removable package(s) (229) and/or packaging and open packaging material(s) (495), effectively under the object(s) and/or to effectively surround the object(s). After being treated, processed, and/or dried, the object(s) was released by the one or more movable holding and/or support apparatus(s) (606) and then dropped and/or positioned into the open removable package(s) (229) and/or packaging and open packaging material(s) (495).
Figure 102:
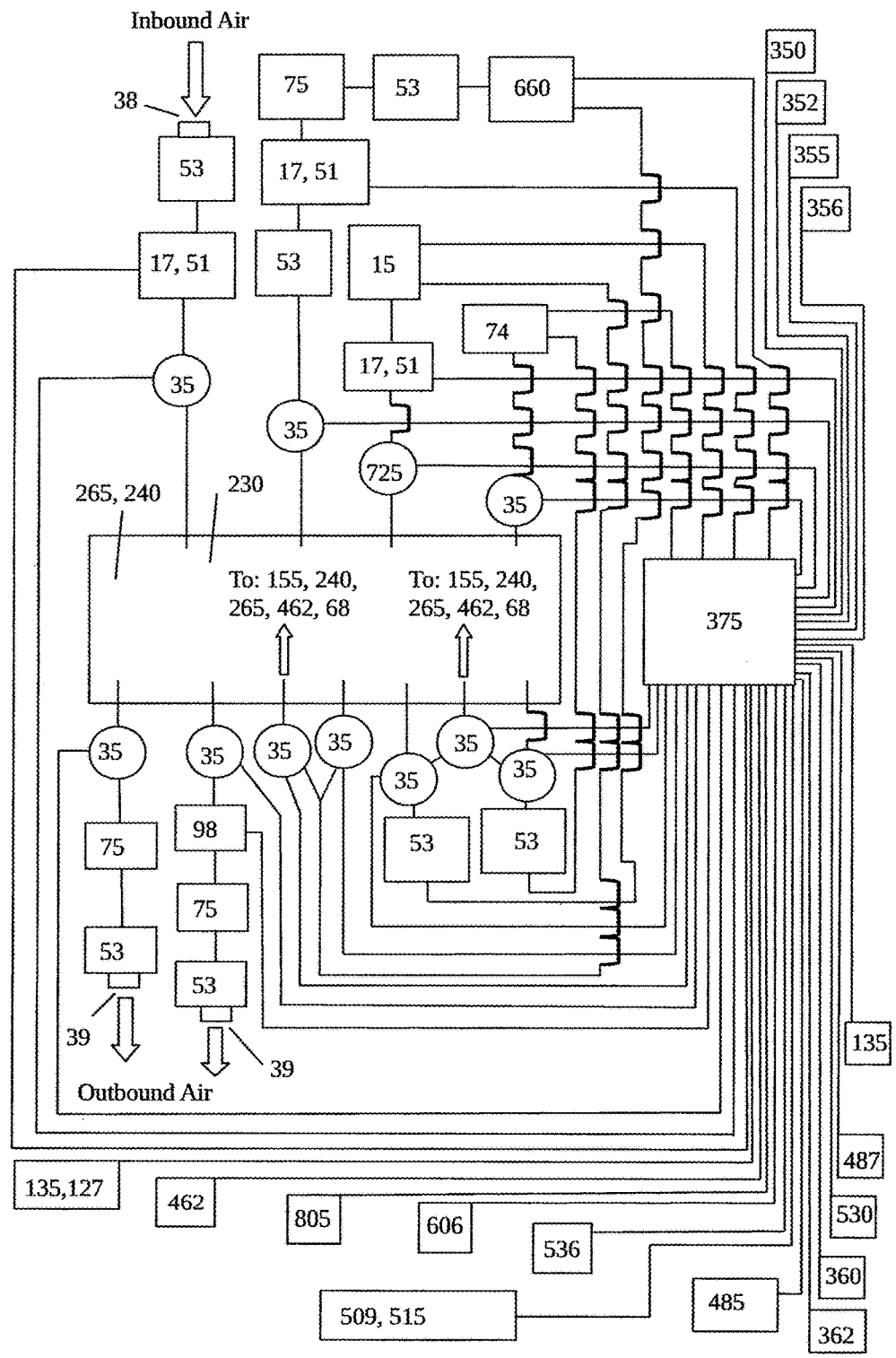
FIG. 102 is a schematic type view of, without limitation, the various parts of the enhanced decontamination enclosure apparatus (715), that can be controlled by and/or communicate with any programmable controller(s)/PLC(s) (375).
Figure 103:
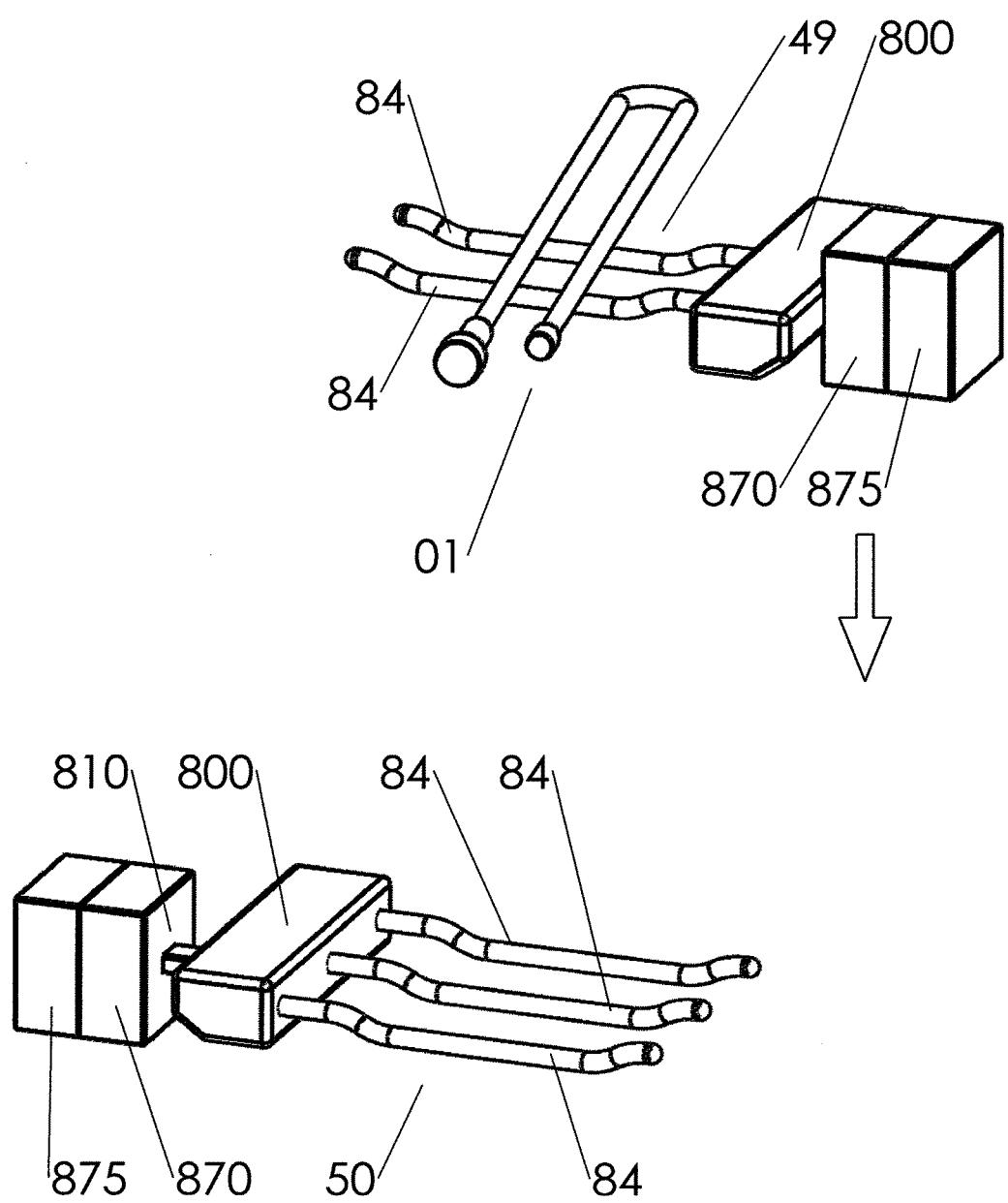
FIG. 103 is a schematic type view of, an apparatus used to transfer the object(s) and/or any treated, dried, and/or processed object(s), back and forth between any start beam(s) (84)(49) and any secondary beam(s) (84)(50), during any, treatment, drying, and/or processing step(s), so all of the targeted object surface(s) are treated and dried. When all of the treatment, drying, and/or processing step(s) are complete, the object support(s) (84), and more particularly the start beam(s) (84)(49) and/or the secondary beam(s) (84)(50) are tilted or pivoted downward or at least out of the way of any falling object(s) (01), when the object(s) (01) are released, with the intention for the object(s) to fall down and into any, open removable package(s) (229) and/or packaging and open packaging material(s) (495). It is intended without limitation for the start beam(s) (84)(49) to move up and down to transfer the object(s). The object(s) is initially removably interfaced with the start beam(s) (84)(49), and the start beam(s) (84)(49) are moved down to transfer the object(s) to the secondary beam(s) (84)(50).
Figure 104:
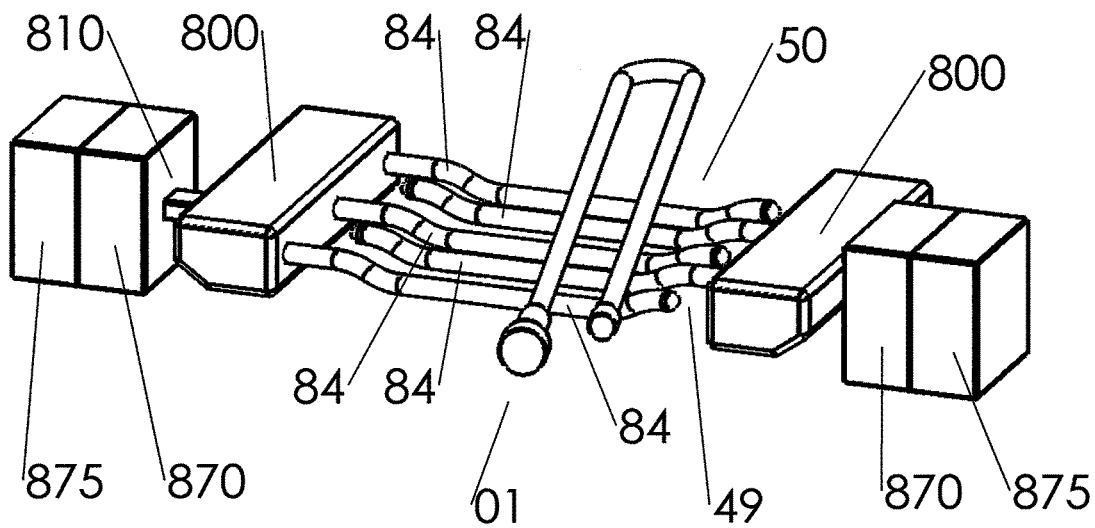
FIG. 104 is a schematic type view of, the start beam(s) (84)(49) moving down through and past the secondary beam(s) (84), and handing the one or more object(s) off to the secondary beam(s) (84)(50).
Figure 105:
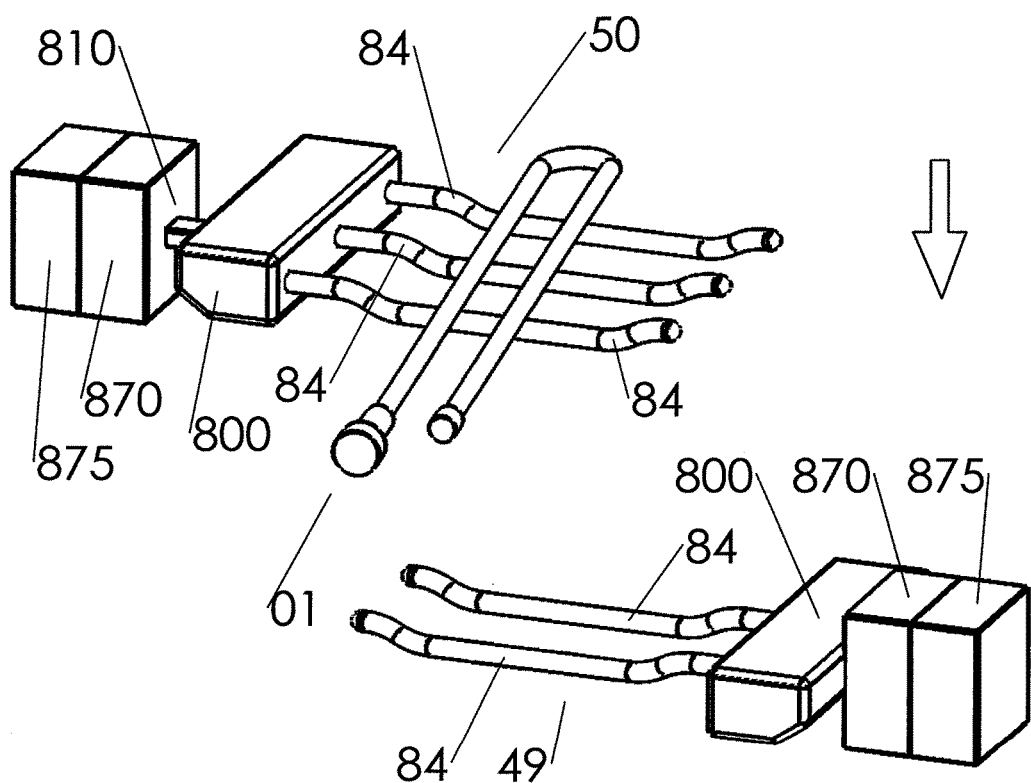
FIG. 105 is a schematic type view of, the start beam(s) (84)(49) that have moved down past the secondary beam(s) (84)(50), and have passed the object(s) off to the secondary beam(s) (84)(50).
Figure 106:
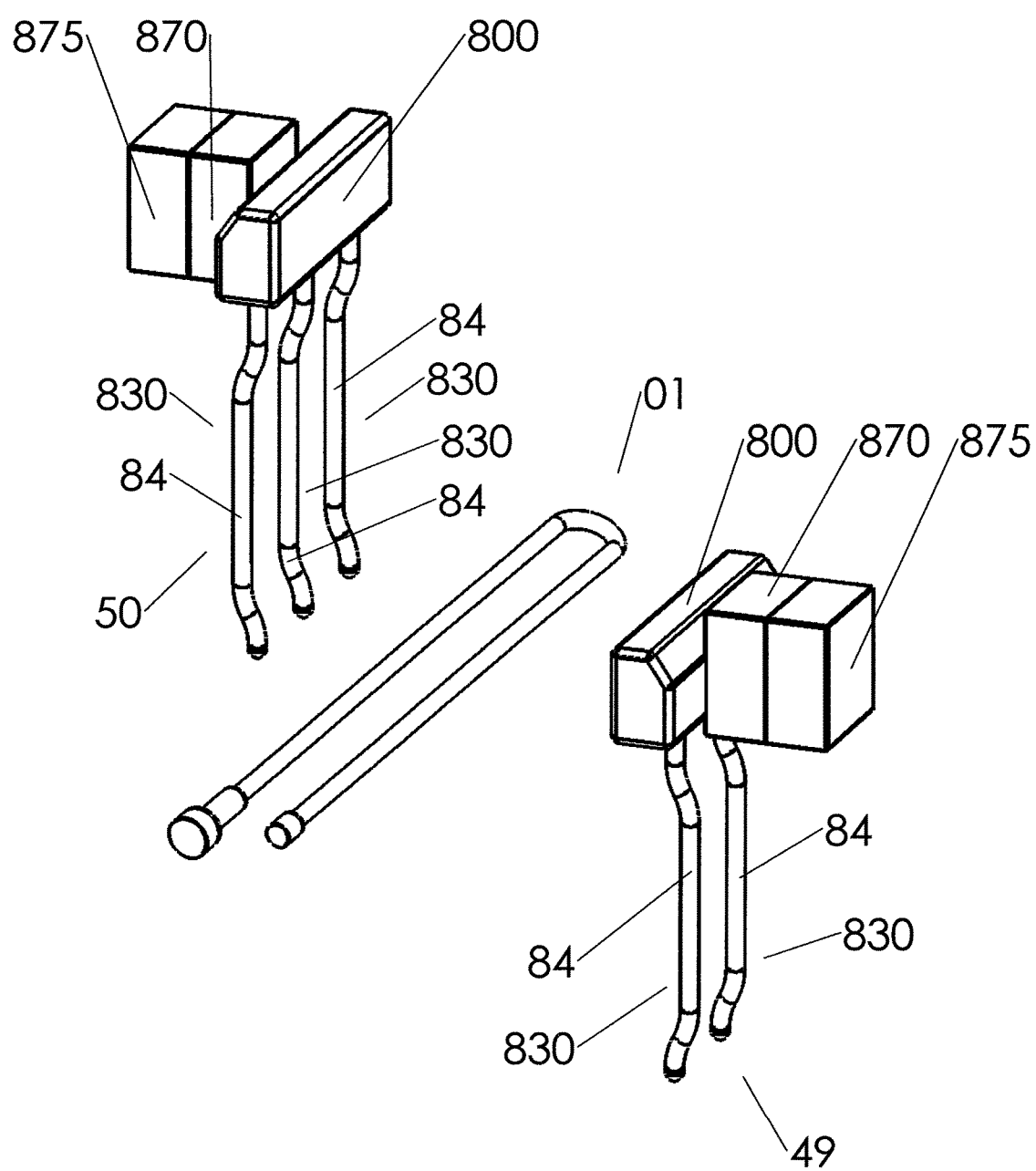
FIG. 106 is a schematic type view of, the start beam(s) (84)(49) and the secondary beam(s) (84)(50) pivoting and/or tilting effectively downward to cause the object(s) to fall down and into any open removable package(s) (229) and/or packaging and open packaging material(s) (495), located below the object(s).
Figure 107:
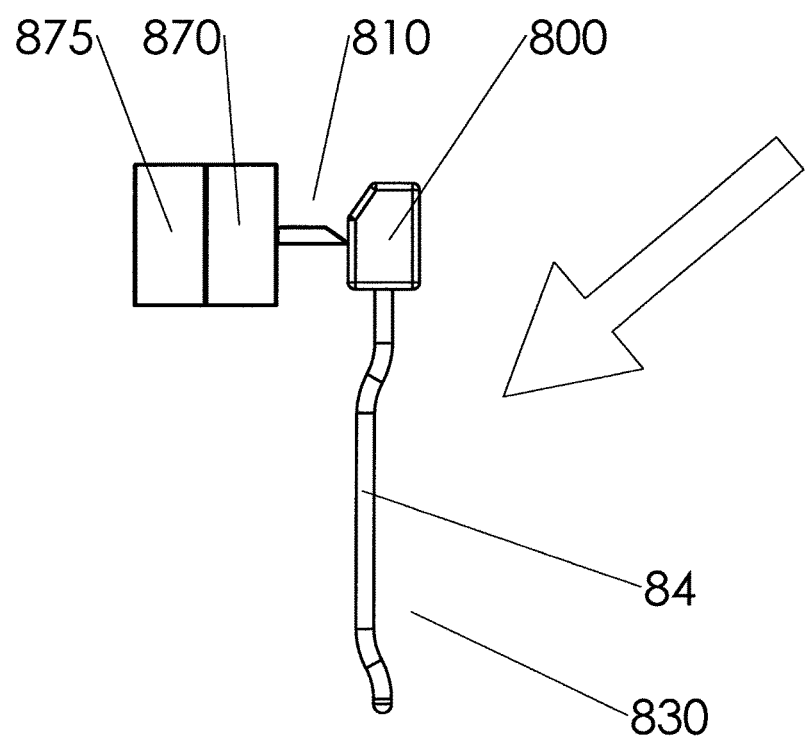
FIG. 107 is a schematic type view of, the start beam(s) (84)(49) and the secondary beam(s) (84)(50) pivoting and/or tilting effectively downward about one or more of any joint(s) (810). One or more positioning apparatus(s) (870) can be used to help move, tilt, and or pivot, the various beams.
Figure 109:
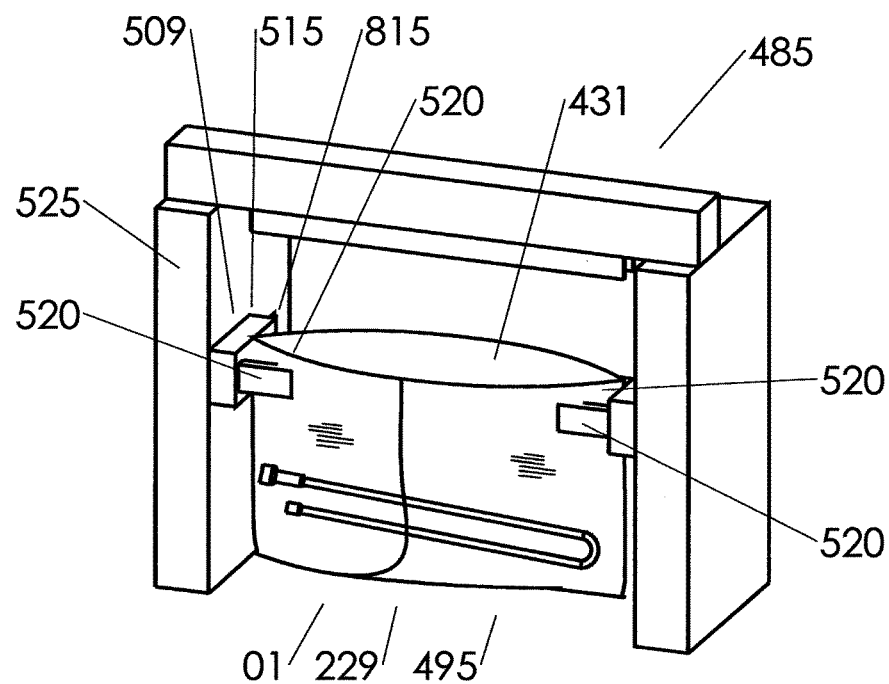
FIG. 109 is a schematic type view of, the open removable package(s) (229) and/or packaging and open packaging material(s) (495) repositioned under the package sealer(s) (485) after catching the falling object(s) and before any sealing activities.
Figure 110:
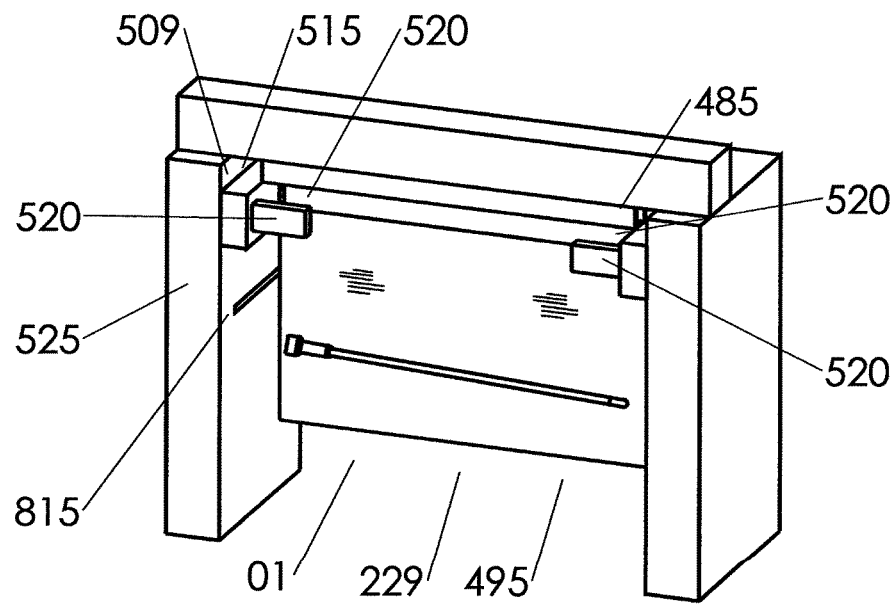
FIG. 110 is a schematic type view of, the open removable package(s) (229) and/or packaging and open packaging material(s) (495) being sealed by the package sealer(s) (485).
Figure 111:
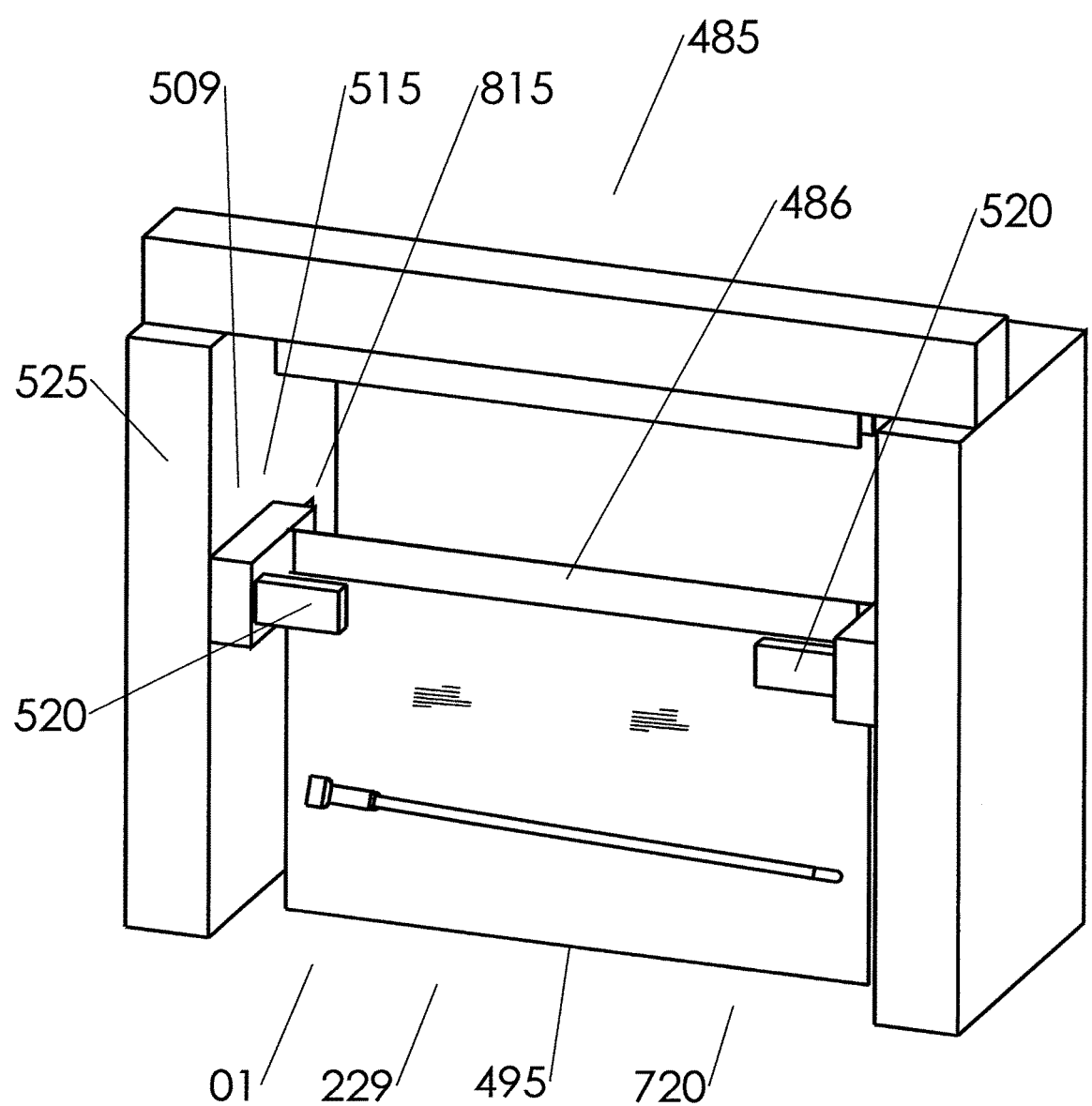
FIG. 111 is a schematic type view of, a sealed package (720) after being sealed by the package sealer(s) (485).

In still even another aspect, and according to FIGS. 100-101, and without limitation, the support and release apparatus(s) (606) can also include one or more of any hold and tilt apparatus(s) (655). Without being limited, the various object(s) (01) can be suitably and effectively, supported, suspended, hung, held, and/or located, within and/or at one or more of any suitable and effective location(s) within one or more of any suitable and effective, container holding chamber(s) (265), removable treatment enclosure(s) (230), packaging material(s) (495), treatment enclosure(s), open treatment enclosure(s), open removable treatment enclosure(s), package(s), removable package(s), open package(s), open removable package(s), and/or open packaging material(s), by one or more of any suitable and effective hold and tilt apparatus(s) (655).

Without being limited, the one or more, but preferably and without limitation at least two, hold and tilt apparatus(s) (655) can be located or positioned in or at any suitable and effective location(s). It is preferred, without limitation, that the hold and tilt apparatus(s) (655) are suitably and effectively located at any suitable and effective location(s) within the container holding chamber(s) (265) and/or treatment enclosure(s), and can suitably and effectively, hold, support, and/or interface with, one or more of any, suitable part(s), surface(s), and/or location(s), of any, object(s) (01), pressure interface assembly(s) (68), and/or any other part(s) and component(s) that may be suitably connected to any object(s) (01) and/or pressure interface assembly(s) (68), such as, but not limited to any, hose(s), tube(s), conduit(s), wire(s), and/or cable(s).

Without being limited, FIG. 100-101 shows the at least one, but preferably and without limitation, two, movable support member(s) (620) at any effective distance(s) and angle(s) from each other, and in or at any effective "object holding and/or object support" position(s) (645), so that the one or more of any, hold and tilt apparatus(s) (655) and/or movable support member(s) (620), can effectively, hold and/or support the one or more object(s) (01), cable(s), wire(s), and/or hose(s), Without being limited, the support and release apparatus(s) (606) can also include at least one, but preferably and without limitation, at least two hold and tilt apparatus(s) (655). Without being limited, each hold and tilt apparatus(s) (655) can include at least one suitable and effective means to move (Herein called "Support Member Movement Means") (625) the at least one suitable and effective movable support member(s) (620), that is suitably and effectively connected to the support member movement means (625). Without being limited, the movable support member(s) (620) can be any suitable and effective size, shape, length, width, height, geometry, and/or diameter. It is preferred, without limitation, that the movable support member(s) (620) in this aspect has at least has one suitable and effective horizontal aspect and/or horizontal member part(s) (Herein called "Horizontal Support Member Part(s)") (630), and also has at least one suitable and effective vertical aspect and/or vertical member part(s) (Herein called "Vertical Extension Member Part(s)") (635) that can suitably and effectively connect with the one or more support member movement means (625).

Without limitation, the support member movement means (625) can include one or more of any suitable and effective part(s) and/or apparatus(s) to cause the movable support member(s) (620) to effectively move to one or more of any suitable and effective location(s), angle(s), and/or position(s), to cause the one or more object(s) (01) and/or any attached part(s) to effectively, fall, drop, and/or be disconnected from, the hold and tilt apparatus(s) (655) and/or any part(s) of the hold and tilt apparatus(s) (655), at one or more of any effective time(s). It is preferred, without limitation, that the one or more of any movable support member(s) (620), support member movement means (625), and/or any other directly and/or indirectly connected part(s), can be constructed and/or designed, so the one or more hold and tilt apparatus(s) (655) and/or any of its movable support member(s) (620), can effectively tilt, move, angle, and/or be repositioned, at one or more of any effective angle(s), position(s) and/or orientation(s) to release, stop holding, stop supporting, and/or drop, the one or more of any object(s) (01), and/or to effectively move the hold and tilt apparatus(s) (655) and/or any part(s) of the move the hold and tilt apparatus(s) (655), that is in directly and/or indirectly in contact with and/or releasably interfaced with the object(s) (01), so that the one or more object(s) (01) and any connected part(s), can be effectively, located, positioned, released, dropped, and/or fall, into one or more of any suitable and effective, open package(s), and/or open removable package(s) (229).

Without being limited, FIG. 101 shows the at least one, but preferably and without limitation, two, movable support member(s) (620) at any effective distance(s) from each other, and in or at any effective "object releasing and/or object removal" position(s) (650), so that the one or more of any object(s) (01), cable(s), wire(s), and/or hose(s), can effectively, fall from, drop from, and/or be removed from, the one or more hold and tilt apparatus(s) (655) and/or movable support member(s) (620).

Also, without being limited, the hold and tilt apparatus(s) (655) and/or the movable support member(s) (620) can release the, object(s) (01), pressure interface assembly(s) (68), and/or any other part(s) and component(s) that may be suitably connected to any object(s) (01), and/or pressure interface assembly(s) (68), such as, but not limited to any, hose(s), tube(s), conduit(s), wire(s), and/or cable(s), at any time(s), but preferably, and without limitation, at least at any needed, suitable, and/or effective time(s), and more preferably, and without limitation, once the effective treatment, drying, and/or processing of the various surface(s) of various, part(s), location(s), area(s), and/or component(s), such as, but not limited to any, object(s) (01), object interface material(s) (89), part(s), apparatus(s), object support(s) (84), and/or any other surface(s) and/or atmosphere(s) within any container holding chamber(s) (265), and/or treatment enclosure(s), is complete.

Once released, the object(s) (01), and/or any other part(s) and component(s) that may be connected to any object(s) (01) such as, but not limited to any, pressure interface assembly(s) (68), hose(s), tube(s), conduit(s), wire(s), and/or cable(s), can be effectively, located, positioned, released, dropped, and/or fall, into one or more of any suitable and effective, open removable package(s) (229), open package(s), and/or packaging material(s) (495), that is suitably and effectively located, at any suitable and effective location(s) such as, but limited to, below, partially below, centered partially below, centered below, underneath, partially underneath, centered partially underneath, centered underneath, around, centered around, partially around, completely around, encompassing, centered and encompassing, partially encompassing, completely encompassing, encompassing around, partially encompassing around, completely encompassing around, and/or centered around and encompassing, any one or more object(s) (01) and/or any other connected part(s) and/or component(s).

Also, without being limited, the one or more of any substance(s) that are used to treat and/or process any, object(s) (01), atmosphere(s), and/or surface(s), within any suitable and effective, treatment enclosure(s), removable treatment enclosure(s) (230), and/or container holding chamber(s) (265), such as, but not limited to any, air/gas(s), heated air/gas(s), dehumidified air/gas(s), vapor(s), aerosol(s) (65), and/or applied agent(s) (20), can also effectively flow through and out of, and/or be effectively applied via, any hold and tilt apparatus(s) (655) and/or the movable support member(s) (620), and more preferably, and without limitation, effectively flow through and out of any suitable and effective surface(s) of any, movable support member(s) (620), object support(s) (84), and/or object interface material(s) (89), to treat and/or process various area(s) and/or surface(s) such as, but not limited to any, object(s) (01) surface(s) that interface with any, hold and tilt apparatus(s) (655) and/or the movable support member(s) (620), object support(s) (84), and/or object interface material(s) (89), preferably and without limitation, using and/or via one or more of any suitably and effectively located opening(s) (85) that effectively communicate with the various source(s) of the said substance(s), to treat, dry, and/or process, various area(s) and/or surface(s) such as, but not limited to any, object(s) (01) surface(s) that interface with any, support and dropping mechanism(s) (605), hold and tilt apparatus(s) (655), and/or movable support member(s) (620), object support(s) (84), and/or object interface material(s) (89).

Without being limited, the one or more of any, support and release apparatus(s) (606), hold and tilt apparatus(s) (655), and/or movable support member(s) (620), and/or any other related part(s) and component(s), can be located and positioned at any suitable and effective height(s) above any, floor(s) (275) of the container holding chamber(s) (265), removable treatment enclosure(s) (230), packaging and open packaging material(s) (495), treatment enclosure(s), open treatment enclosure(s), open removable treatment enclosure(s), package(s), removable package(s), open package(s), open removable package(s) (229), and/or open packaging material(s).

In another aspect, and according to FIGS. 68-91, 98-101, 108-112, and without limitation, after the one or more of any treated and/or processed object(s) (01) have been effectively, located, positioned, dropped, and/or released, into and/or effectively, located, encircled, inserted, and/or encompassed, within one or more of any suitable and effective, packaging and open packaging material(s) (495), open package(s), and/or open removable package(s) (229), that can be, without limitation, open on one or more of any effective side(s), the said open package(s), packaging and open packaging material(s) (495), and/or open removable package(s) (229), can be effectively sealed, closed, and/or hermetically sealed, with one or more of any effective sealing and/or closing means or manner (Herein called "package sealer(s)") (485) known to those skilled in the art such as, but not limited to any, heat sealing, impulse sealing, adhesive sealing, pressure sealing, snap actuated seal(s), contact sealing, pressure adhesive sealing, ultrasonic sealing, zip locking, and/or pull cord closure(s), on one or more of any side(s), opening(s), and or sealing surface(s) of any suitable open package(s), packaging and open packaging material(s) (495), and/or open removable package(s) (229), all in manner known to those skilled in the art.

Without being limited, the one or more of any effective, pull cord closure(s) (Herein called "Cinched Package Closed Interface(s)") (497) can include pulling one or more of any effective, cord(s), string(s), rope(s), wire(s), cable(s), member(s), and/or flexible member(s) (Herein called "Pull Cord(s)") (492), at one or more of any effective open end(s) and/or opening(s) (431)(467) of the open removable package(s) (229) and/or packaging and open packaging material(s) (495), that when effectively pulled it can effectively gather any effective quantity of one or more of any, wall(s) of any open removable package(s) (229), and/or material(s) and/or packaging material(s) (495), at one or more of any opening(s) (431) of the open package(s), and/or open removable package(s) (229), and effectively close and/or seal any of the said opening(s) (431)(467), all in a manner known to those skilled in the art. Without being limited, the one or more pull cord(s) (492) and/or any attached members, can also effectively, loop through, pass through, and/or exit the various packaging material(s) and/or material(s) that are used to construct the open removable package(s) (229) and/or closed package(s) (720) at one more effective location(s) and/or opening(s) (Herein called "Pull Cord Opening(s)") (498). Without being limited, the one or more of any suitable and effective pull cinch package closure assembly (494) can include, but is not limited to the following one or more part(s) such as, but not limited to any, pull cord handle(s) (493), pull cord(s) (492), and/or pull cord opening(s) (498).

Without being limited, the various cord(s) (492) can also be attached to one or more of any suitable grip(s) and/or handle(s) (Herein called "Pull Cord Handle(s)") (493) that can be located at one or more of any effective location(s), and preferably and without limitation, at any end(s) of any cord(s) (492). It is preferred, without limitation, that after any, open package(s), open removable package(s) (229), removable treatment enclosure(s) (230), packaging and open packaging material(s) (495), treatment enclosure(s), open treatment enclosure(s), open removable treatment enclosure(s), package(s), removable package(s), packaging and open packaging material(s) (495), and/or any treatment enclosure(s), holding any object(s) (01) and/or any part(s) and component(s) connected to any object(s) (01), is effectively sealed and/or closed, they can be removed from the container holding chamber(s) 265) and/or treatment enclosure(s) at any suitable time(s). Without being limited, the various closed package(s) (720), can also include any package(s) and/or enclosures that are effectively sealed, closed, and/or hermetically sealed, with one or more of any effective sealing and/or closing means such as, but not limited to any "Cinched Package Closed Interface(s)") (497).

According to FIGS. 71, 76-79, 89, and 111 and without limitation, various closed, sealed, and/or hermetically sealed, package(s), enclosure(s), and/or closed package(s) (720) are shown. Without limitation, the various material(s), package(s), enclosure(s), and/or treatment enclosure(s), such as, but not limited to any, open package(s), open removable package(s) (229), removable treatment enclosure(s) (230), packaging and open packaging material(s) (495), treatment enclosure(s), open treatment enclosure(s), open removable treatment enclosure(s), package(s), removable package(s), and/or any treatment enclosure(s), can have one or more of any suitable and effective, structure(s), part(s), member(s), attachment point(s), attachment apparatus(s), attachment part(s), such as, but not limited to any, container suspension member attachment point(s) (405), container suspension attachment(s) (406), and/or container suspension interface member(s) (407), that can fulfill various purpose(s), such as, but not limited to, assisting with the hanging, holding, moving, and/or locating, of one or more of any of these various, material(s), package(s), enclosure(s), and/or treatment enclosure(s), such as, but not limited to any, open package(s), open removable package(s) (229), removable treatment enclosure(s) (230), packaging and open packaging material(s) (495), treatment enclosure(s), open treatment enclosure(s), open removable treatment enclosure(s), package(s), removable package(s), and/or any treatment enclosure(s), within any area(s) and enclosure(s) such as, but not limited to any, container holding chamber(s) (265).

Referring to FIGS. 71, 76-79, 89, and 111, and without limitation, the various package(s), open removable package(s) (229), packaging material(s) (495), and/or closed package(s) (720), can have one or more of any effective sealed and/or closed interface(s) (Herein called "Container Sealed Material Interface(s)") (486) formed by one or more of any suitable and effective means known to those skilled in the art such as, but not limited to any, heat sealing, impulse sealing, adhesive sealing, pressure sealing, snap actuated seal(s), contact sealing, pressure adhesive sealing, ultrasonic sealing, zip locking, and/or pull cord closure(s), at any suitable and effective time(s). Without limitation, one or more of any suitable and effective closed package(s) (720) can also have one or more of any suitable and effective container sealed material interface(s) (486) such as, but not limited to any, snap closure(s) and/or zip locking apparatus(s) (Herein called "Sealing Component(s)") (491), all in a manner known to those skilled in the art. Without limitation, one or more of any suitable and effective closed package(s) (720) can also have at least one end effectively sealed and closed by one or more of any suitable and effective container sealed material interface(s) (486), and at least one other end(s) effectively sealed and closed by one or more of any suitable and effective pull cinch package closure assembly (494). Without limitation, one or more of any suitable and effective closed package(s) (720) can also be effectively sealed and closed on all open ends by one or more of any suitable and effective pull cinch package closure assembly (494).

With reference to FIGS. 71, 89 and 108-112, and without limitation, one example of at least one package sealing apparatus(s) is shown. In this figure, and without limitation, at least one closed and/or sealed package(s) (720) is shown after at least one package(s) (720) was effectively closed and/or sealed by one or more suitable package sealer(s) (485) known to those skilled in the art, such as, but not limited to any, thermal sealer(s), ultrasonic sealer(s), and/or impulse sealer(s). Also in this figure, and without limitation, at least one thermal sealer(s) is used that comprises at least two thermal sealing element(s) and/or thermal sealing member element(s) (487), where the package(s) are effectively clamped and sealed, between the sealing member element(s) (487), all in a manner known to those skilled in the art.

In another aspect, and without limitation, the one or more of any suitable, hole(s), port(s), door(s), and/or opening(s) (Herein called "Opening(s)") (431), that are, a part of, integrated into the design of, and/or are effectively located in and/or formed by one or more of any wall(s) and/or side(s) of, one or more of any suitable, enclosure(s), open package(s), and/or open removable package(s) (229), can be any suitable and effective, size(s), angle(s), orientation(s), shape(s), geometry(s), dimension(s), design(s), length(s), width(s), depth(s), and/or height(s), all in a manner known to those skilled in the art, and can be positioned or located in or at, one or more of any suitable and effective location(s) of any, enclosure(s), open package(s), open removable package(s) (229), removable treatment enclosure(s) (230), packaging and open packaging material(s) (495), treatment enclosure(s), open treatment enclosure(s), open removable treatment enclosure(s), package(s), removable package(s), and/or any treatment enclosure(s).

It is preferred, without limitation, that at least one suitable and effective opening(s) (431) is effectively located at the top(s), top surface(s), top area(s), and/or top panel(s), of any, enclosure(s), removable treatment enclosure(s) (230), treatment enclosure(s), open treatment enclosure(s), open removable treatment enclosure(s), package(s), removable package(s), and/or any treatment enclosure(s), and even more preferably, and without limitation, any suitable and effective, packaging and open packaging material(s) (495), open package(s), and/or open removable package(s) (229), and the opening(s) (431) is designed and constructed in a manner so that one or more of any object(s) (01) as well as one or more of any connected and/or associated part(s)

and/or component(s), can be effectively, dropped, released, positioned, and/or located, into and/or within, the enclosure(s), removable treatment enclosure(s) (230), treatment enclosure(s), open treatment enclosure(s), open removable treatment enclosure(s), package(s), removable package(s), and/or any treatment enclosure(s), open package(s), packaging and open packaging material(s) (495), and/or open removable package(s) (229). However, alternatively, and without limitation, at least one opening(s) (431) can be effectively located at one or more of any, side(s), bottom(s), bottom surface(s), bottom area(s) (765), and/or bottom panel(s), of the open package(s), and/or open removable package(s) (229), and the opening(s) (431) is designed and constructed in a manner so that one or more of any object(s) (01) as well as one or more of any connected and/or associated part(s) and/or component(s), can be effectively, dropped into, inserted, positioned, and/or located, into and/or within, the enclosure(s), removable treatment enclosure(s) (230), treatment enclosure(s), open treatment enclosure(s), open removable treatment enclosure(s), package(s), removable package(s), and/or any treatment enclosure(s), open package(s), packaging and open packaging material(s) (495), and/or open removable package(s) (229), and preferably, and without limitation, then suitably, effectively, and/or efficaciously, sealed within.

Without being limited, any of the enclosure(s), removable treatment enclosure(s) (230), treatment enclosure(s), open treatment enclosure(s), open removable treatment enclosure(s), package(s), removable package(s), and/or any treatment enclosure(s), open package(s), packaging and open packaging material(s) (495), and/or open removable package(s) (229), can be constructed from one or more of any suitable and effective material(s) and/or packaging material(s) (495) know to those skilled in the art. It is preferred, without limitation, that any, enclosure(s), removable treatment enclosure(s) (230), treatment enclosure(s), open treatment enclosure(s), open removable treatment enclosure(s), package(s), removable package(s), and/or any treatment enclosure(s), open package(s), packaging and open packaging material(s) (495), and/or open removable package(s) (229), are constructed from one or more of any suitable and effective material(s) such as, but not limited to any, stainless steel, polymer(s), flexible polymer(s), and/or rigid polymer(s), all in a manner known to those skilled in the art. It is also preferred, without limitation, that any, package(s), and/or open removable package(s) (229), are constructed from one or more of any suitable and effective material(s) such as, but not limited to any, polymer(s), polymer film(s), flexible polymer(s), polymer laminate(s), and/or foil, material(s), all in a manner known to those skilled in the art.

In still another aspect, it is preferred, without limitation, that the various one or more object(s) (01) and any other connected part(s), shall not touch, contact, and/or interface with, anything except any suitable and effective, part(s), component(s), and/or means, to effectively, locate, hold, hang, suspend, and/or position, the one or more object(s) (01) within any suitable location(s) such as, but not limited to any, open package(s), and/or open removable package(s) (229), container holding chamber(s) (265), removable treatment enclosure(s) (230) and/or treatment enclosure(s). It is also preferred, without limitation, that the one or more of any, open package(s), and/or open removable package(s) (229), do not touch anything except suitably and effectively, touch, contact, and/or interface with, the one or more of any suitable and effective, part(s), component(s), and/or means, to effectively, locate, hold, suspend, and/or position, the one or more open package(s), and/or removable package(s) (229) within any suitable location(s) such as, but not limited to any, container holding chamber(s) (265), and/or treatment enclosure(s).

In the first part of this embodiment, and without limitation, the one or more of any object(s) (01) can be effectively, positioned, suspended, hung, held, and/or located, at any effective location(s) such as but limited to, below, partially below, centered partially below, centered below, within, partially within, centered partially within, centered within, underneath, partially underneath, centered partially underneath, and/or centered underneath, one or more of any suitable opening(s) (431) of the one or more of any suitable, open package(s), packaging and open packaging material(s) (495), and/or open removable package(s) (229), at any suitable and effective time(s), that is suitably and effectively located within the one or more of any suitable container holding chamber(s) (265) and/or treatment enclosure(s), using one or more of any suitable and effective method(s) and/or apparatus(s).

Alternatively, and without limitation, using one or more of any suitable and effective method(s) and/or apparatus(s), the one or more of any object(s) (01) and any connected part(s), can be effectively, positioned, hung, suspended, held, and/or located, at any effective location(s) such as but limited to, above, partially above, centered partially above, centered above, outside of, partially outside of, centered partially outside of, centered outside of, over, partially over, centered partially over, centered over, within, partially within, centered partially within, and/or centered within, one or more of any suitable opening(s) (431) of the one or more of any suitable, open package(s), packaging and open packaging material(s) (495), and/or open removable package(s) (229), that is suitably and effectively located within the one or more of any suitable container holding chamber(s) (265) and/or treatment enclosure(s), at any suitable and effective time(s). It is preferred, without limitation, that the various object(s) (01) and any connected part(s) and/or hardware is effectively located and centered, in any vertical or close to vertical orientation(s), at any effective location(s) such as but limited to, above, partially above, centered partially above, centered above, outside of, partially outside of, centered partially outside of, centered outside of, over, partially over, centered partially over, centered over, within, partially within, centered partially within, and/or centered within, any, open package(s), packaging and open packaging material(s) (495), and/or open removable package(s) (229), at any suitable and effective time(s).

Without being limited, the one or more of any, enclosure(s), removable treatment enclosure(s) (230), treatment enclosure(s), open treatment enclosure(s), open removable treatment enclosure(s), package(s), removable package(s), and/or any treatment enclosure(s), and/or packaging and open packaging material(s) (495), and more preferably and without limitation, any, open package(s), and/or open removable package(s) (229), can be suitably and effectively, suspended, held, and/or located, in one or more of any effective location(s) within the container holding chamber(s) (265) and/or treatment enclosure(s), using one or more of any suitable and effective method(s) and/or apparatus(s). It is preferred, without limitation, that one or more of any, top(s), top surface(s), top area(s), and/or top panel(s), of any, open package(s), packaging and open packaging material(s) (495), and/or open removable package(s) (229), is suitably and effectively open (431), and any, bottom(s), bottom surface(s), bottom area(s) (765), and/or bottom panel(s), is effectively closed and sealed. It is also preferred, without limitation, that the object(s) (01) and any, open package(s), packaging and open packaging material(s) (495), and/or open removable package(s) (229), do not touch anything except the one or more of any suitable and effective, part(s), component(s), and/or means, to suitably and effectively, locate and/or position any, open package(s), packaging and open packaging material(s) (495), and/or open removable package(s) (229), in location(s) such as, but not limited to any, container holding chamber(s) (265) and/or treatment enclosure(s), until they are being sealed if that process step is taken or needed.

Referring to FIG. 67, and without being limited, one or more of any suitable lid(s) (260) can be also be effectively, suspended, hung, held, and/or located, at or in one or more of any suitable and effective location(s) within the one or more container holding chamber(s) (265) and/or treatment enclosure(s), using one or more of any suitable and effective method(s) and/or apparatus(s). It is preferred, without limitation, that the lid(s) (260), also do not touch anything except for the one or more of any suitable and effective, part(s), component(s), and/or means, to effectively, locate, hold, suspend, and/or position, the lid(s) (260) within any suitable location(s) such as, but not limited to any, container holding chamber(s) and/or treatment enclosure(s).

According to an embodiment, and without being limited, the following examples, parts, and aspects, refer to FIGS. 66-112, and describe various improvements to the art for the effective, treatment(s), drying(s), and/or processing(s), and then packaging(s), of the one or more of any object(s) in any suitable and effective enclosure(s).

Without being limited, the one or more of any object(s) (01), can be effectively, located, positioned, dropped, and/or released, into one or more of any suitable and open, open removable package(s) (229), open package(s), and/or packaging material(s) (495), that is located at any one or more of any effective location(s) such as, but not limited to, below, partially below, centered partially below, centered below, underneath, partially underneath, centered partially underneath, centered underneath, around, centered around, partially around, completely around, encompassing, centered and encompassing, partially encompassing, completely encompassing, encompassing around, partially encompassing around, completely encompassing around, and/or centered around and encompassing, the object(s) (01) and/or any other connected part(s) and/or component(s), after they are finished being, treated, dried, and/or processed. It is preferred, without limitation, that after the treatment and processing step(s) and/or regimen(s) such as, but not limited to being, treated, dried, and/or processed, are finished for one or more of any, object(s) (01), location(s), and/or area(s), such as, but not limited to any, object(s) (01), lid(s) (260), any connected part(s) and/or component(s) to the object(s) (01), open removable package(s) (229), open package(s), and/or packaging material(s) (495), and/or container holding chamber(s) (265) and/or treatment enclosure(s), the various object(s) (01) and any connected part(s) and component(s), and/or lid(s) (260), can be effectively, dropped, released, positioned, and/or located, into and/or within any, open removable package(s) (229), open package(s), and/or packaging material(s) (495). It is also preferred, without limitation, that any treated and processed lid(s) (260), if they are used or needed, are effectively interfaced and/or hermetically sealed with or to any, open package(s), and/or packaging material(s) (495), open enclosure(s), and/or open removable package(s) (229), either manually and/or with any automated means known to those skilled in the art, before the object(s) (01) and lid(s) (260) are dropped, released, positioned, and/or located, into any, open enclosure(s), open removable package(s) (229), open package(s), and/or packaging material(s) (495), and packaged either manually and/or with any automated means known to those skilled in the art.

In the second part of this embodiment, and without limitation, the one or more of any object(s) (01) can be effectively, suspended, hung, held, and/or located, at any effective location(s) such as but limited to, below, partially below, centered partially below, centered below, within, partially within, centered partially within, centered within, underneath, partially underneath, centered partially underneath, and/or centered underneath, one or more of any suitable opening(s) (431) of the one or more of any suitable and effective, open enclosure(s), open removable package(s) (229), open package(s), and/or packaging material(s) (495), that is suitably and effectively located within the one or more of any suitable and effective, container holding chamber(s) (265) and/or treatment enclosure(s), using one or more of any suitable and effective method(s) and/or apparatus(s).

Alternatively, and without limitation, using one or more of any suitable and effective method(s) and/or apparatus(s), the one or more of any object(s) (01) can be effectively, suspended, held, and/or located, at any effective location(s) such as but limited to, above, partially above, centered partially above, centered above, outside of, partially outside of, centered partially outside of, centered outside of, over, partially over, centered partially over, centered over, within, partially within, centered partially within, and/or centered within, one or more of any suitable and effective opening(s) (431) of the one or more of any, open enclosure(s), open removable package(s) (229), open package(s), and/or packaging material(s) (495), that is suitably and effectively located within any suitable location(s) such as, but not limited to any, container holding chamber(s) (265) and/or treatment enclosure(s).

Without being limited, any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, open enclosure(s), open removable package(s) (229), and/or open package(s) and/or packaging material(s) (495), can preferably have one or more of any suitable and effective, top(s), top surface(s), top area(s), and/or top panel(s), that is effectively open and/or has one or more of any effective opening(s) (431), and also have one or more of any suitable and effective bottom area(s) (765) that is effectively closed and/or sealed (Herein called "Treatment Container Closed Bottom(s)") (466).

Alternatively, and without limitation, any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, open enclosure(s), open removable package(s) (229), and/or open package(s) and/or packaging material(s) (495), can have one or more of any suitable and effective, top(s), top surface(s), top area(s), and/or top panel(s) that is effectively open (431), and also have one or more of any suitable and effective, bottom(s), bottom surface(s), bottom area(s) (765), and or bottom panel(s), that is also effectively open (Herein called "Treatment Container Open Bottom(s)") (467). It is also preferred, without limitation, that the object(s) (01), as well as any open, enclosure(s), removable treatment enclosure(s) (230), treatment enclosure(s), open treatment enclosure(s), open removable treatment enclosure(s), package(s), removable package(s), treatment enclosure(s), open enclosure(s), open removable package(s) (229), and/or open package(s) and/or packaging material(s) (495), do not contact anything except the one or more of any suitable and effective, part(s), component(s), and/or means, to effectively, locate and/or position, them within the container holding chamber(s) (265) and/or treatment enclosure(s).

Without being limited, the one or more of any open, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, open enclosure(s), open removable package(s) (229), and/or open package(s) and/or packaging material(s) (495), can also be suitably and effectively, suspended, hung, held, and/or located, in one or more of any effective location(s) within the container holding chamber(s) (265) and/or treatment enclosure(s), using one or more of any suitable and effective method(s) and/or apparatus(s). It is preferred, without limitation, that any, top(s), top surface(s), top area(s), and/or top panel(s), of the open package(s), and/or removable package(s), is suitably and effectively open (431), and any, bottom(s), bottom surface(s), bottom area(s) (765), and/or bottom panel(s), is effectively closed and/or sealed (466).

In a first example, and without being limited, the one or more of any object(s) (01) can be effectively, suspended, hung, held, and/or located, at or within one or more of any effective location(s) such as, but not limited to, within any, container holding chamber(s) (265), enclosure(s), removable treatment enclosure(s) (230), treatment enclosure(s), open treatment enclosure(s), open removable treatment enclosure(s), package(s), removable package(s), treatment enclosure(s), open enclosure(s), open removable package(s) (229), and/or open package(s) and/or packaging material(s) (495), by removably, interfacing, connecting, and/or resting, in any effective manner, the one or more of any, cord(s), rope(s), fiber optic line(s), tube(s), pipe(s), wire(s), cable(s), conduit(s), member(s), and/or object(s), to, on, and/or with, the one or more of any suitable and effective, object support(s) (84), hook(s) and/or enhanced object(s) holder(s) (155), and more particularly, and without limitation, the object support(s) (84) and their object interface material(s) (89), that is located in one or more of any suitable and effective location(s) within any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, container holding chamber(s) (265), open enclosure(s), open removable package(s) (229), and/or open package(s) and/or packaging material(s) (495).

It is preferred, without limitation, that the any suitable and effective part(s) and apparatus(s) such as, but not limited to any, object support(s) (84), hook(s) and/or enhanced object(s) holder(s) (155), are at least located at one or more of any suitable and effective location(s), such as, but not limited to, above, partially above, centered partially above, centered above, outside of, partially outside of, centered partially outside of, centered outside of, over, partially over, centered partially over, centered over, within, partially within, centered partially within, and/or centered within, any, open enclosure(s), open removable package(s) (229), and/or open package(s) and/or packaging material(s) (495), that are preferably, and without limitation, effectively located within any suitable and effective container holding chamber(s) (265). Without being limited, the various part(s) such as, but not limited to any, object support(s) (84), and/or enhanced object(s) holder(s) (155), can be located in any suitable and effective location(s), and more preferably and without limitation, located in any effective manner, so that the object(s) (01) can be effectively located and/or positioned, and preferably and without limitation, effectively located and/or positioned in or at any angle(s) and/or orientation(s), but preferably, and without limitation, vertical or about vertical orientation(s), such as, but not limited to, above, partially above, centered partially above, centered above, outside of, partially outside of, centered partially outside of, centered outside of, over, partially over, centered partially over, centered over, within, partially within, centered partially within, and/or centered within, the open removable package(s) (229), open enclosure(s), open package(s) and/or packaging material(s) (495) and/or the container holding chamber(s) (265) and/or treatment enclosure(s). It is also preferred, without limitation, that the said object(s) (01) and any connected part(s) and/or component(s), do not touch anything except any suitable and effective part(s) such as, but not limited to any, object support(s) (84), enhanced object(s) holder(s) (155), and/or movable holding and/or support apparatus(s) (606), and even more preferably, and without limitation, any object interface material(s) (89), until activities such as but not limited to any, packaging, and/or removal by an employee, take place.

In a second example, and without being limited, the one or more of any object(s) (01) can be effectively, suspended, hung, held, and/or located, at or within one or more of any effective location(s) such as, but not limited to, within any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, container holding chamber(s) (265), open enclosure(s), open removable package(s) (229), and/or open package(s) and/or packaging material(s) (495), by suitably and effectively connecting and/or interfacing the one or more of any object(s) (01) to one or more of any suitable and effective part(s) and component(s) such as, but not limited to any, cable(s), wire(s), hose(s), cord(s), rope(s), tube(s), flexible member(s), conduit(s), connector(s), object(s) (01), and/or any other suitable connection(s), that can be suitably and effectively connected and/or interfaced to one or more of any suitable and effective, interface plug(s) (330) and/or tube connector(s) (461), which can be suitably and effectively connected to one or more of any suitable and effective, female plug shaft(s) (545), plug decoupling apparatus(s) (536), tube connector(s) (461), and/or tube disconnect apparatus(s) (462), that is preferably, and without limitation, effectively located within the container holding chamber(s) (265) and/or treatment enclosure(s). However, one or more of any other suitable and effective method(s) and/or apparatus(s) can also be used to effectively, suspend, hang, hold, and/or locate, the various object(s) (01) and any connected part(s) and component(s) within any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, container holding chamber(s) (265), open enclosure(s), open removable package(s) (229), and/or open package(s) and/or packaging material(s) (495).

In a third example, and without being limited, the one or more of any object(s) (01) can be effectively, suspended, hung, held, and/or located, at or within one or more of any effective location(s) such as, but not limited to, within any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, container holding chamber(s) (265), open enclosure(s), open removable package(s) (229), and/or open package(s) and/or packaging material(s) (495), by suitably and effectively connecting and/or interfacing the one or more of any object(s) (01) and/or any connected part(s) and/or component(s), directly and/or indirectly, to one or more of any suitable and effective, pressure interface assembly(s) (68), gripping mechanism(s) (135) and/or gripping finger(s) (108), tube connector(s) (461), and/or tube disconnect apparatus(s) (462), as described in the present invention, and these various part(s) and component(s) can be, without limitation, suitably and effectively located within any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, container holding chamber(s) (265), open enclosure(s), open removable package(s) (229), and/or open package(s) and/or packaging material(s) (495).

The various suitable and effective part(s) and component(s) used in the present invention, to effectively locate and position, the one or more object(s) (01) and/or any connected part(s) and/or component(s), at one or more of any effective location(s) within the container holding chamber(s) (265) and/or any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, open enclosure(s), open removable package(s) (229), and/or open package(s) and/or packaging material(s) (495), such as, but not limited to any, interface plug(s) (330), female plug shaft(s) (545), various other object(s) (01), plug decoupling apparatus(s) (536), pressure interface assembly(s) (68), gripping mechanism(s) (135) and/or gripping finger(s) (108), tube connector(s) (461), tube disconnect apparatus(s) (462), object support(s) (84), movable support member(s) (620), horizontal support member part(s) (630), vertical extension member part(s) (635), support and release apparatus(s) (606), enhanced object(s) holder(s) (155), object interface material(s) (89), and/or one or more of any other suitable and effective method(s), apparatus(s), and/or part(s) and component(s) (Herein called "Object Positioning & Connection Hardware"), can be located in or at one or more of any effective location(s) such as, but not limited to any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, container holding chamber(s) (265), open enclosure(s), open removable package(s) (229), and/or open package(s) and/or packaging material(s) (495).

It is preferred, without limitation, that any of the various object (01) positioning & connection hardware, used in the present invention, is located and/or positioned in any effective location(s) and/or in any effective manner, so that the various object(s) (01) and any connected part(s) and/or hardware, can be effectively located and/or positioned, and preferably and without limitation, effectively located and/or positioned in any effective orientation(s), such as but limited to, above, partially above, centered partially above, centered above, outside of, partially outside of, centered partially outside of, centered outside of, over, partially over, centered partially over, centered over, within, partially within, centered partially within, and/or centered within, any, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, container holding chamber(s) (265), open enclosure(s), open removable package(s) (229), and/or open package(s) and/or packaging material(s) (495). It is more preferred, without limitation, that the object(s) (01) and any connected part(s) and/or hardware is effectively located at least about centered above any, open package(s), and/or open package(s) and/or packaging material(s) (495), and/or open removable package(s) (229), within the container holding chamber(s) (265). It is even more preferred, without limitation, that the object(s) (01) and any connected part(s) and/or hardware is effectively located and centered, in any vertical or close to vertical orientation, above, partially above, centered partially above, centered above, outside of, partially outside of, centered partially outside of, centered outside of, over, partially over, centered partially over, centered over, within, partially within, centered partially within, and/or centered within, any open package(s), and/or open removable enclosure(s) (229).

In the third part of this embodiment, and without limitation, the one or more of any object(s) (01) can be effectively, suspended, hung, held, and/or positioned, at any effective location(s) such as but limited to, below, partially below, centered partially below, centered below, within, partially within, centered partially within, centered within, underneath, partially underneath, centered partially underneath, centered underneath, and/or centered within and underneath, one or more of any suitable and effective, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, open enclosure(s), open removable package(s) (229), and/or open package(s) and/or packaging material(s) (495), that is suitably and effectively located within the one or more of any suitable container holding chamber(s) (265) and/or treatment enclosure(s), using one or more of any suitable and effective method(s) and/or apparatus(s). It is preferred, without limitation, that the object(s) (01) and any connected part(s) and/or hardware can be effectively located and centered, under, and/or within and underneath, the one or more of any suitable and effective, enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, open enclosure(s), open removable package(s) (229), and/or open package(s) and/or packaging material(s) (495). It is even more preferred, without limitation, that the object(s) (01) and any connected part(s) and/or hardware is effectively, suspended, hung, held, and/or positioned, in any vertical and/or close to vertical orientation(s), at any effective location(s) such as but limited to, below, partially below, centered partially below, centered below, within, partially within, centered partially within, centered within, underneath, partially underneath, centered partially underneath, centered underneath, and/or centered within and underneath, at least any, open enclosure(s), open removable package(s) (229), and/or open package(s) and/or packaging material(s) (495).

Without being limited, and in one aspect, the one or more of any suitable, effective, and removable, open enclosure(s), open removable package(s) (229), and/or open package(s) and/or packaging material(s) (495), can have at least one suitable and effective opening(s) (431), where the at least one of any suitable and effective opening(s) (431) is located at or near one or more of any, bottom(s), bottom surface(s), bottom area(s), bottom panel(s), and/or without limitation, any open bottom(s) (765)(467), of the open package(s), and/or open removable package(s) (229). It is also preferred, without limitation, that the one or more of any suitable and effective, top(s), top surface(s), top area(s), and/or top panel(s), of the enclosure(s), removable treatment enclosure(s) (230), treatment enclosure(s), open treatment enclosure(s), open removable treatment enclosure(s), package(s), removable package(s), and/or any treatment enclosure(s), and preferably and without limitation, at least any, open enclosure(s), open removable package(s) (229), and/or open package(s) and/or packaging material(s) (495) is effectively closed and/or sealed.

In one part of this example, and without being limited, the one or more of any object(s) (01) and/or any connected part(s) and/or component(s), can be effectively, suspended, held, and/or located, by removably, interfacing, connecting, and/or resting, in any effective manner, any object(s) (01) and/or the one or more of any, cord(s), rope(s), wire(s), cable(s), any other object(s), tube(s), conduit(s), member(s), and/or flexible member(s), that is suitably and effectively connected to the said object(s) (01), to, on, and/or with, the one or more of any suitable and effective, object support(s) (84), enhanced object(s) holder(s) (155), and/or movable holding and/or support apparatus(s) (606), and even more preferably, and without limitation, any object interface material(s) (89), that can be located in one or more of any suitable and effective location(s) within at least any suitable and effective, open enclosure(s), open removable package(s) (229), and/or open package(s) and/or packaging material(s) (495) and/or container holding chamber(s) (265).

Without limitation, any of the, removable treatment enclosure(s) (230), open enclosure(s), open removable package(s) (229), and/or open package(s) and/or packaging material(s) (495), used in the present invention, can also be designed so that any suitable object(s) (01), pipe(s), conduit(s), and/or hose(s), that can supply any applied agent(s) (20) and/or substance(s) to treat and/or process any object(s) (01) and/or any connected part(s), can effectively pass through any part(s) and/or location(s) of any, removable treatment enclosure(s) (230), open enclosure(s), open removable package(s) (229), and/or open package(s) and/or packaging material(s) (495), at one or more of any effective location(s), to transport any substance(s) such as, but not limited to any, air/gas(s), vapor(s) and/or applied agent(s) (20), to any location(s) such as, but not limited to any, effective means to hold, interface with, treat, and/or process, any object(s) (01), surface(s) of object(s) (01), and/or any connected part(s) and component(s).

In another part of this example, and without being limited, any object(s) (01) and/or any connected part(s) and/or component(s), can be suitably and effectively removably interfaced, directly and/or indirectly, on, to, with, from, and/or or near, any effective location(s) such as, but not limited to any, ceiling surface(s), top surface(s), and/or roof surface(s), inside of any, removable treatment enclosure(s) (230), open enclosure(s), open removable package(s) (229), and/or open package(s) and/or packaging material(s) (495), with one or more of any suitable and effective means, method(s), and/or apparatus(s), such as, but not limited to any, interface plug(s) (330), female plug shaft(s) (545), plug decoupling apparatus(s) (536), pressure interface assembly(s) (68), gripping mechanism(s) (135) and/or gripping finger(s) (108), tube connector(s) (461), tube disconnect apparatus(s) (462), object support(s) (84), movable support member(s) (620), horizontal support member part(s) (630), vertical extension member part(s) (635), support and release apparatus(s) (606), enhanced object(s) holder(s) (155), object interface material(s) (89), and/or one or more of any other suitable and effective method(s), apparatus(s), and/or part(s) and component(s) known to those skilled in the art.

In the fourth part of this embodiment, and without limitation, the one or more of any object(s) (01) and any connected part(s), can be effectively, suspended, hung, held, positioned, and/or located, within the one or more of any suitable container holding chamber(s) (265) and/or treatment enclosure(s), and one or more of any suitable and effective, open package(s), open removable package(s) (229), and/or one or more of any effectively open packaging material(s) (495), can be effectively located, below, partially below, centered partially below, centered below, underneath, partially underneath, centered partially underneath, centered underneath, around, centered around, partially around, completely around, encompassing, centered and encompassing, partially encompassing, completely encompassing, encompassing around, partially encompassing around, completely encompassing around, covering, fully covering, multi-axial covering, and/or centered around and encompassing, the object(s) (01), and/or any other part(s) that connect with any object(s) (01), at one or more of any effective time(s) and/or during one or more of any effective step(s) in the treatment(s), drying(s), and/or processing(s), of various object(s) (01), surface(s), and/or area(s) within the container holding chamber(s) (265) and/or treatment enclosure(s).

Without limitation, the one or more of any effective, open package(s), open removable package(s) (229), and/or one or more of any effectively open packaging material(s) (495), can be effectively positioned within the container holding chamber(s) (265) and/or treatment enclosure(s), at any effective time(s), and for one or more of any purposes such as, but not limited to, the preparation for any packaging activities for the various object(s) (01), either before and/or after the treatment(s), drying, and/or processing, of the various surface(s) and area(s) within the container holding chamber(s) (265) and/or treatment enclosure(s), such as, but not limited to any, atmosphere(s), object(s) (01) surface(s), object support(s) (84), object interface material(s) (89), and/or pressure interface assembly(s) (68).

It is preferred, without limitation, that the open package(s), open removable package(s) (229), and/or one or more of any effectively open packaging material(s) (495) are suitably and effectively located and positioned at one or more of any suitable and effective location(s) within the container holding chamber(s) (265) and/or treatment enclosure(s), for the effective packaging of one or more of any object(s) (01), before any surface(s) and/or area(s) within the container holding chamber(s) (265) and/or treatment enclosure(s) are treated, dried, and/or processed.

In this example, and without limitation, the one or more of any object(s) (01) are effectively, suspended, hung, held, and/or located, by one or more of any suitable and effective means, within the one or more of any suitable container holding chamber(s) (265) and/or treatment enclosure(s), and preferably, and without limitation, before any treatment(s), drying(s), and/or processing(s), of the various surface(s)

and/or area(s) within the container holding chamber(s) (265) and/or treatment enclosure(s), has started, one or more of any suitable and effective, open package(s), open removable package(s) (229), and/or one or more of any effectively open packaging material(s) (495) to create any suitable and effective, package(s), open package(s), and/or open removable package(s) (229), can be effectively moved from one or more of any effective location(s), but preferably and without limitation, from one or more of any effective location(s) below the one or more of any object(s) (01) and/or any connecting part(s), within the container holding chamber(s) (265) and/or treatment enclosure(s), and then suitably and effectively, surround, encompass, encircle, and/or be positioned around, the one or more of any object(s) (01) and/or any connecting part(s). After any effective treatment(s), drying(s), and/or processing(s), of the various surface(s) and area(s) within the container holding chamber(s) (265) and/or treatment enclosure(s), including any targeted object (01) surface(s), is effectively complete, the one or more object(s) (01) can then be effectively released by whatever suitable means that is effectively, holding, suspending, hanging, and/or otherwise positioning, the one or more object(s) (01) and/or any connecting part(s), within the container holding chamber(s) (265) and/or treatment enclosure(s), where the object(s) (01) and any connected part(s), can then, fall, drop, and/or otherwise be effectively located into, one or more of any suitable and effective, open package(s), open removable package(s) (229), and/or one or more of any effectively open packaging material(s) (495), where the open package(s), open removable package(s) (229), and/or one or more of any effectively open packaging material(s) (495), are then effectively, closed, sealed, completely sealed, and/or hermetically sealed, using any effective, manual means, and/or automated means, in any suitable manner(s), all known to those skilled in the art, to form any effective, closed, hermetically sealed, and/or sealed, package(s), and/or closed package(s) (720).

In another example, and without limitation, the open package(s), open removable package(s) (229), and/or one or more of any effectively open packaging material(s) (495), are suitably and effectively located and positioned at one or more of any suitable and effective location(s) within the container holding chamber(s) (265) and/or treatment enclosure(s), for the effective packaging of one or more of any object(s) (01), after any surface(s) and/or area(s) within the container holding chamber(s) (265) and/or treatment enclosure(s) are treated and processed. In this example, and without limitation, the one or more of any object(s) (01) can be effectively, suspended, hung, held, and/or located, within the one or more of any suitable container holding chamber(s) (265) and/or treatment enclosure(s), and preferably, and without limitation, after any treatment(s), drying(s), and/or processing(s), of the various surface(s) and/or area(s) within the container holding chamber(s) (265) and/or treatment enclosure(s), is effectively finished, one or more of any suitable and effective, open package(s), and/or open removable package(s) (229), and/or one or more of any suitable and effective material(s) to create any suitable and effective, package(s), open package(s), and/or open removable package(s) (229), that is preferably and without limitation, effectively sterile, disinfected, high-level disinfected, clean enough to meet all United States FDA standard(s), and/or at least effectively clean, all in a manner known to those skilled in the art, can be effectively moved from one or more of any effective location(s), but preferably and without limitation, from one or more effective location(s) below the one or more of any object(s) (01) and/or any connecting part(s), within the container holding chamber(s) (265) and/or treatment enclosure(s), and then suitably and effectively, surround, encompass, encircle, and/or be positioned around and/or under, the one or more of any object(s) (01) and/or any connecting part(s), before and/or after any effective treatment(s), drying, and/or processing, step(s) and/or activities for the surface(s) of the various object(s) (01), and the said object(s) (01) can then be effectively released by whatever suitable means that is effectively, holding, suspending, hanging, and/or otherwise positioning, the one or more object(s) (01) and/or any connecting part(s), within the container holding chamber(s) (265) and/or treatment enclosure(s), where the said object(s) (01) and any connected part(s), can then, fall, drop, and/or otherwise be effectively located into, one or more of any suitable and effective, open package(s), open removable package(s) (229), and/or one or more of any effectively open packaging material(s) (495), where the open package(s), open removable package(s) (229), and/or one or more of any effectively open packaging material(s) (495), are then effectively, closed, sealed, completely sealed, and/or hermetically sealed, using any effective, manual means, and/or automated means, in any suitable manner(s) known to those skilled in the art, to form any effective, closed, hermetically sealed, and/or sealed, package(s), and/or closed package(s) (720).

Without limitation, if the one or more of any open, package(s), semi-constructed package(s), open package(s), open removable package(s) (229), and/or one or more of any suitable and effective packaging material(s) (495), are moved from one or more of any suitable location(s) below any object(s) (01) and/or connected part(s), the one or more of any open bottom(s) (765)(467) of any, package(s), semi-constructed package(s), open package(s), open removable package(s) (229), and/or one or more of any suitable and effective packaging material(s) (495), can be suitably and effectively sealed and/or closed, at one or more of any suitable and effective time(s), before, during, and/or after, any treatment(s), drying, and/or processing, of any object(s) (01) and any connected part(s).

It is preferred, without limitation, that the one or more of any bottom(s) and/or bottom area(s) (765) of any package(s), semi-constructed package(s), open package(s), open removable package(s) (229), and/or one or more of any suitable and effective packaging material(s) (495), are effectively sealed and/or closed, in any suitable manner known to those skilled in the art, before the open package(s), open removable package(s) (229), and/or one or more of any effectively open packaging material(s) (495), are moved from any suitable, feeding, resting, and/or storage, location(s), and into any effective location(s) and position(s) below the object(s) (01), before the object(s) (01) are treated, but at least before the object(s) are released, positioned into, and/or fall into any, open package(s), open removable package(s) (229), and/or one or more of any effectively open packaging material(s) (495).

It is more preferred, without limitation, that the one or more of any, sealed and/or closed bottom(s), bottom area(s) (765), and/or side(s) of the one or more of any, package(s), semi-constructed package(s), open package(s), open removable package(s) (229), and/or one or more of any suitable and effective packaging material(s) (495), are effectively created before the one or more of any, package(s), semi-constructed package(s), open package(s), open removable package(s) (229), and/or one or more of any suitable and effective packaging material(s) (495), are located, and/or used, within any one or more part(s) and enclosure(s) of the enhanced decontamination enclosure apparatus(s) (715).

Without limitation, if the one or more of any open, package(s), semi-constructed package(s), open package(s), open removable package(s) (229), and/or one or more of any suitable and effective packaging material(s) (495), are moved from one or more of any suitable location(s) above any object(s) (01) and/or connected part(s), to package the one or more object(s) (01) and/or any connected part(s) and component(s), at any suitable and effective time(s), the one or more of any open top(s) (431) and/or open bottom(s) (467)) of any, package(s), semi-constructed package(s), open package(s), open removable package(s) (229), and/or one or more of any suitable and effective packaging material(s) (495), can be suitably and effectively sealed at one or more of any suitable and effective time(s), before, during, and/or after, any treatment(s), drying, and/or processing of any object(s) (01) and any connected part(s).

It is preferred, without limitation, that in this top-fed example, the one or more of any top(s) of any package(s), semi-constructed package(s), open package(s), open removable package(s) (229), and/or one or more of any suitable and effective packaging material(s) (495), are effectively sealed and/or closed, before these said material(s), are moved from any suitable, feeding, resting, and/or storage, location(s), and into any effective location(s) and position(s) such as, but not limited to suitably and effectively, surrounding, encompassing, encircling, and/or be positioned around, over, and/or under, the various object(s) (01), and also preferably, and without limitation, before the object(s) (01) are treated, but at least before the object(s) (01) are effectively, positioned, released, positioned into, sealed into, and/or fall, into, the open package(s), open removable package(s) (229), and/or one or more of any effectively open packaging material(s) (495).

In addition, and without limitation, the one or more of any bottom(s) (765) of any package(s), semi-constructed package(s), open package(s), open removable package(s) (229), and/or one or more of any suitable and effective packaging material(s) (495), can also be effectively sealed and/or closed, at any effective time(s), but preferably and without limitation, before the object(s) (01) are treated, but at least before any object(s) (01) are released, positioned into, and/or fall into, the open package(s), and/or open removable package(s) (229).

Also, and without being limited, the one or more object(s) (01) and/or any connecting part(s), can be effectively, suspended, hung, held, and/or located, at one or more of any suitable and effective location(s) within the one or more of any suitable and effective treatment area(s) such as, but not limited to any, container holding chamber(s) (265), treatment enclosure(s), open package(s), open removable package(s) (229), and/or one or more of any effectively open packaging material(s) (495), using one or more of any suitable and effective means, method(s), and/or apparatus(s), such as, but not limited to any, interface plug(s) (330), female plug shaft(s) (545), plug decoupling apparatus(s) (536), pressure interface assembly(s) (68), gripping mechanism(s) (135) and/or gripping finger(s) (108), tube connector(s) (461), tube disconnect apparatus(s) (462), object support(s) (84), movable support member(s) (620), horizontal support member part(s) (630), vertical extension member part(s) (635), support and release apparatus(s) (606), enhanced object(s) holder(s) (155), object interface material(s) (89), and/or one or more of any other suitable and effective method(s), apparatus(s), and/or part(s) and component(s) known to those skilled in the art.

Also, and without limitation, one or more of any object(s) (01) and/or any connected part(s) and/or component(s), can be suitably and effectively, positioned, located, gripped, supported, suspended, hung, held, and/or located, effectively, directly and/or indirectly, on, to, with, from, and/or or near, one or more of any effective location(s) such as, but not limited to any, ceiling surface(s), top surface(s), and/or roof surface(s) and/or area(s) (270), located inside (240) of any suitable and effective location(s) such as, but not limited to any, container holding chamber(s) (265), treatment enclosure(s), open package(s), open removable package(s) (229), and/or one or more of any effectively open packaging material(s) (495).

In addition, and without being limited, one or more of any object(s) (01) and/or any connected part(s) and/or component(s), can also be suitably and effectively, positioned, located, gripped, supported, suspended, hung, held, and/or located, directly and/or indirectly, on, to, with, from, and/or or near, any effective structure(s) and/or location(s) such as, but not limited to one or more of any, container hanging member(s) (450) that can be suitably and effectively located inside (240) of any suitable and effective location(s) and/or area(s) such as, but not limited to any, container holding chamber(s) (265), treatment enclosure(s), open package(s), and/or open removable package(s) (229). Without being limited, the one or more suitable container hanging member(s) (450) can suitably connect with one or more suitable hanging member mount point(s) (455) that can be located at and/or connected to, any suitable and effective location(s) such as, but not limited to any suitable, side wall(s) of any, container holding chamber(s) (265), treatment enclosure(s), open package(s), and/or open removable package(s) (229).

Without being limited, the one or more of any suitable and effective, open package(s), open removable package(s) (229), package(s), and/or packaging material(s) (495), can also be located and/or moved into one or more of any suitable and effective location(s) and position(s) either manually and/or automatically, such as, but not limited to, near, around, centered around, partially around, completely around, encompassing, centered and encompassing, partially encompassing, completely encompassing, encompassing around, partially encompassing around, completely encompassing around, below, partially below, centered around and encompassing, below, partially below, centered partially below, centered below, underneath, partially underneath, centered partially underneath, centered underneath, around, covering, fully covering, and/or multi-axial covering, the one or more of any object(s) (01) and any connecting part(s), either before and/or after the object(s) (01) and any connecting part(s), as well as any other surfaces and atmosphere(s) in any other location(s) such as, but not limited to any, container holding chamber(s) (265) and/or treatment enclosure(s), have been effectively treated, dried, and/or processed. Without being limited, this can happen at any suitable and effective time(s), and/or before, during, and/or after, any suitable and effective, treatment(s), drying(s), and/or processing step(s) for any object(s) (01) and/or area(s) within any container holding chamber(s) (265) and/or treatment enclosure(s).

It is preferred, without limitation, that any suitable and effective, open package(s), open removable package(s) (229), package(s) and/or packaging material(s) (495), are effectively located and/or positioned at one or more of any effective location(s) and position(s) such as, but not limited to, near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, covering, fully covering, and/or multi-axial covering, the one or more object(s) (01) and any connecting part(s), within the container holding chamber(s) (265) and/or treatment enclosure(s), and then effectively sealed and/or closed, after the object(s) (01) and any targeted surface(s) and area(s) within the container holding chamber(s) (265) and/or treatment enclosure(s), have all been effectively treated, dried, and/or processed, and the object(s) (01) and any connected part(s), have been effectively, dropped, released, located and positioned, into, within, and/or at, the any effective, open package(s), open removable package(s) (229), and/or one or more of any suitable and effective open packaging material(s) (495).

Without being limited, any suitable and effective, open package(s), open removable package(s) (229), package(s), and/or packaging material(s) (495), can be effectively, manually and/or automatically moved into one or more of any effective position(s), at one or more of any effective time(s) and/or during one or more of any suitable and effective treatment(s), drying(s), and/or processing step(s), from one or more of any suitable and effective location(s) such as, but not limited to, above, from any side(s), and/or below, any object(s) (01) and/or any connecting part(s), that are targeted and/or intended for any treatment(s), drying(s), processing(s), and/or packaging.

It is preferred, without limitation, that any suitable and effective, open package(s), open removable package(s) (229), package(s), and/or packaging material(s) (495), are at least effectively open (431) to allow any object(s) (01) and any connecting part(s), to be effectively, dropped, released, located and positioned, into, within, and/or at any effective proximity to, any effective, open package(s), open removable package(s) (229), and/or one or more of any suitable and effective open packaging material(s) that would be used to form any effective closed and/or sealed package(s) (720).

Without being limited, the one or more of any suitable and effective, open package(s), open removable package(s) (229), package(s), and/or packaging material(s) (495), can be effectively stored in, maintained, fed from, and/or supplied from, one or more of any suitable and effective location(s) and/or means, all in a manner known to those skilled in the art. It is preferred, without limitation, that the one or more of any suitable and effective, open package(s), open removable package(s) (229), package(s), and/or packaging material(s) (495), are effectively stored in, maintained, fed from, and/or supplied from, one or more of any suitable location(s) and/or means, within the one or more of any suitable container holding chamber(s) (265) and/or treatment enclosure(s).

Also, and without being limited, the one or more of any suitable and effective, open package(s), open removable package(s) (229), package(s), and/or packaging material(s) (495), can be effectively, stored, housed, fed from, and/or supplied from, any suitable and effective, packaging equipment, and/or equipment and apparatus(s), (Herein called "Packaging Dispenser(s)") (500) to effectively, position, locate, raise, and/or lower, any, open package(s), open removable package(s) (229), package(s), and/or packaging material(s) (495), into any effective, location(s) and/or position(s), to effectively package the one or more of any object(s) (01) and any connected part(s), all in a manner known to those skilled in the art. It is also preferred, without limitation, that any suitable and effective, open package(s), open removable package(s) (229), package(s), and/or packaging material(s) (495), are constructed from at least one layer of any suitable and effective material(s) such as, but not limited to any, cloth(s), fabric(s), polymer(s), and/or foil(s), that can be effectively, closed, sealed, and/or hermetically sealed. It is preferred, without limitation, that at least one of any suitable and effective moisture and/or chemically compatible packaging material(s) (495) are used, all in a manner known to those skilled in the art.

It is also preferred, without limitation, that the one or more of any suitable and effective, open package(s), open removable package(s) (229), package(s), and/or packaging material(s) (495), that are used in this embodiment, at least have one suitable and effective top opening(s) (431), and are effectively moved from one or more of any effective location(s) from under or underneath the said object(s) (01) and any connecting part(s), and are then moved effectively up and effectively past the object(s) (01) and any connecting part(s), where the packaging material(s) (495) are then effectively located and/or positioned at one or more of any suitable and effective location(s) such as, but not limited to, near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, covering, fully covering, and/or multi-axial covering, the said object(s) (01) and any connecting part(s) and component(s). Without limitation, the object(s) (01) and any connecting part(s), can be effectively sealed and/or closed in or into, the one or more of any suitable and effective, open package(s), open removable package(s) (229), and/or package(s) constructed from any suitable and effective packaging material(s) (495), at any effective time(s) after the object(s) (01) and any connecting part(s), container holding chamber(s) (265), and/or treatment enclosure(s), have been effectively treated, dried, and/or processed, and the object(s) (01) and any connected part(s), have been effectively, dropped, released, located and positioned, into, within, and/or at, the said, open package(s), open removable package(s) (229), and/or one or more of any suitable and effective open packaging material(s) (495).

With reference to FIGS. 81-84, and FIG. 89, and in one aspect, and without limitation, one or more of any effective automated lifting means, known to those skilled in the art, can also be effectively located at one or more of any effective location(s) and/or distance(s), preferably and without limitation, above the object(s) (01) and any connecting part(s), and can be used to effectively pull and/or move one or more of any effectively attached, open package(s), open removable package(s) (229), package(s), and/or packaging material(s) (495), effectively, up and into any suitable and effective location(s) and position(s) such as, but not limited to, near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, covering, fully covering, and/or multi-axial covering, and/or past, the object(s) (01) and any connecting part(s), until the open package(s), open removable package(s) (229), package(s), and/or packaging material(s) (495), are in any suitable and effective, location(s) and/or position(s), to effectively package the object(s) (01) and/or any connecting part(s) (Herein called "Packaging Lift Apparatus(s)") (509). Without being limited, the one or more packaging lift apparatus(s) (509) can include, but is not limited to, one or more of any suitable and effective, motorized lifting means known to those skilled in the art. Also, and without limitation, one or more of any suitable and effective means to start and/or stop the lifting, movement, and/or pulling of the, open package(s), open removable package(s) (229), package(s), and/or packaging material(s) (495), into and/or past any one or more of any suitable and effective, direction(s), location(s), and/or position(s), such as, but not limited to, up and/or down, by the packaging lift apparatus(s) (509), can be used, and is known to those skilled in the art.

Without being limited, the one or more of any suitable and effective packaging lift apparatus(s) (509) can suitably connect with one or more of any suitable and effective container suspension member(s) (410), that can suitably connect with one or more of any suitable and effective container suspension attachment(s) (406), that can suitably connect with one or more of any suitable and effective container suspension interface member(s) (407), that can suitably connect with one or more of any suitable and effective, open package(s), open removable package(s) (229), package(s), and/or packaging material(s) (495), at any suitable and effective location(s), and with any suitable method(s) known to those skilled in the art. It is preferred, without limitation, that at least each corner and/or one or more of any other suitable and effective location(s) near the one or more of any suitable opening(s) (431), and/or any other suitable and effective part(s) of the, open package(s), open removable package(s) (229), package(s), and/or packaging material(s) (495), is suitably and effectively connected directly and/or indirectly, to the at least one container suspension member(s) (410).

Without being limited, any of these packaging and/or automated system(s) can also be reversed (not shown) and the various, equipment(s), component(s), apparatus(s), package(s), open package(s), open removable package(s) (229), and/or one or more of any effectively open packaging material(s) (495), for effectively packaging the object(s) (01), can be suitably and effectively located in this alternative arrangement, so the package(s), open removable package(s) (229), and/or packaging material(s) (495), can be instead effectively, pulled and/or moved down, to one or more of any suitable and effective location(s), near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, covering, fully covering, and/or multi-axial covering, and/or past the object(s) (01) and/or any connecting part(s).

Without being limited, once the one or more of any suitable and effective, open package(s), open removable package(s) (229), package(s), and/or packaging material(s) (495), are in any suitable and effective location(s) and position(s) relative to the object(s) (01), the object(s) (01) and any connected part(s), can be effectively, dropped, released, located and positioned, into, within, and/or at, any effective, open package(s), open removable package(s) (229), and/or one or more of any suitable and effective open packaging material(s) (495), where the one or more of any object(s) (01) and any connected part(s), can then be effectively sealed and/or closed inside (240) the open package(s), open removable package(s) (229), package(s), and/or packaging material(s) (495), creating any suitable and effective closed and/or sealed package(s) (720), all in a manner known to those skilled in the art. Without being limited, the packaging lift apparatus(s) (509) can be operated either manually and/or automatically. It is preferred, without limitation, that the packaging lift apparatus(s) (509) is operated automatically and is controlled by one or more of any suitable programmable controller(s)/PLC(s) (375).

With reference to FIGS. 85-88, FIGS. 98-101, FIG. 108, and FIGS. 110-112, and in another aspect, and without limitation, one or more of any effective lifting means, and/or any means to lift, move, move up, and/or move down, position up, and/or position down, any, package(s), open package(s), open removable package(s) (229), and/or one or more of any effectively open packaging material(s) (495), known to those skilled in the art, can also be located at one or more of any suitable and effective location(s), position(s), angle(s), and/or geometry(s), but preferably and without limitation, positioned at least effectively parallel to and/or alongside of, the one or more object(s) (01) and any connecting part(s), at any effective distance(s) and/or angle(s) from the said object(s) (01) and any connecting part(s) and component(s). Without being limited, the said lifting means can travel in any effective direction(s) and/or orientation(s), but preferably and without limitation, at least vertically, along any suitable and effective guided path(s) (Herein called "Lift Travel Member(s)" (525), and pull and/or move any effectively removably attached, open package(s), open removable package(s) (229), package(s), and/or packaging material(s) (495), effectively, up and/or down, but at least in any effective direction(s), at any suitable and effective time(s), to any suitable and effective location(s) such as, but not limited to, near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, fully covering, and/or multi-axial covering, and/or past, the object(s) (01) and any connecting part(s), until the open package(s), open removable package(s) (229), package(s), and/or packaging material(s) (495), are in any suitable and effective location(s) and/or position(s) to effectually package the object(s) (01) and any connecting part(s) (Herein called "Packaging Guided Lift Apparatus(s)") (515).

Without being limited, the one or more of any suitable and effective packaging guided lift apparatus(s) (515) comprises one or more of any suitable and effective parts and component(s) such as, but not limited to any, movable lift apparatus(s) (770), lifting member(s) (520), container suspension attachment(s) (406), lift travel member(s) (525), and/or lift travel sensor(s) (530). Without being limited, the movable lift apparatus(s) (770) can be any suitable and effective, automated, mechanical, gear driven, and/or motorized, means to move or travel, along, up, and/or down, one or more of any means, such as, but not limited to any, suitable and effective lift travel member(s) (525), all in a manner known to those skilled in the art. Without being limited, the one or more movable lift apparatus(s) (770) can be controlled by one or more of any suitable and effective programmable controller(s)/PLC(s) (375). Also, without being limited, the one or more of any suitable and effective movable lift apparatus(s) (770) can effectively interface with the one or more of any suitable and effective lift travel member(s) (525), and the lift travel member(s) (525) can include, but is not limited to, one or more of any suitable and effective, rail(s), rod(s), threaded material(s), track(s), and/or any other effective guide(s) and/or movement means known to those skilled in the art, that the movable lift apparatus(s) (770) can use to effectively travel and/or move, and/or travel and/or move into one or more of any suitable and effective location(s) and/or position(s). Without being limited, the movable lift apparatus(s) (770) can directly and/or indirectly interface with and/or connect to, one or more of any open package(s), open removable package(s) (229), package(s), and/or packaging material(s) (495), in any suitable and effective manner known to those skilled in the art.

Without being limited, one or more of any suitable and effective lifting member(s) (520) can interface with and/or be effectively connected to, the one or more of any movable lift apparatus(s) (770), and the one or more lifting member(s) (520) can effectively directly and/or indirectly connect to or with one or more of any suitable and effective, open package(s), open removable package(s) (229), package(s), and/or packaging material(s) (495), but preferably and without limitation, with one or more of any suitable and effective container suspension attachment(s) (406), that can suitably connect with one or more of any suitable and effective container suspension interface member(s) (407), that can also preferably and without limitation, suitably connect with one or more of any suitable and effective, open package(s), open removable package(s) (229), package(s), and/or packaging material(s) (495), at one or more of any suitable and effective location(s). Without being limited, it is preferred, that at least one, but more preferably at least a plurality, and even more preferably each corner and/or one or more of any other suitable and effective location(s), near the one or more of any suitable opening(s) (431), and/or one or more of any other suitable and effective part(s) and/or location(s) of the, open package(s), open removable package(s) (229), package(s), and/or packaging material(s) (495), is suitably and effectively connected directly and/or indirectly to the at least one lifting member(s) (520) and/or packaging guided lift apparatus(s) (515). Without being limited, the one or more of any container suspension attachment(s) (406) can include any means and/or method(s) known to those skilled in the art to effectively releasably connect to one or more of an parts and/or any directly and/or indirectly connected part(s) of any open package(s), open removable package(s) (229), package(s), and/or packaging material(s) (495), such as, but not limited to any suitable and effective, loop(s), tab(s), attachment point(s), hole(s), and/or ring(s), using any suitable and effective means known in the art such as, but not limited to any, carabiner(s), clamp(s), grip(s), gripping mechanism(s) (135), gripping finger(s) (108), releasable grips(s), releasable attachment hardware, releasable clip(s), and/or any other connectable and/or releasable part(s).

With reference to FIGS. 72-75 (not shown), FIGS. 81-84 and FIGS. 89-91 (not shown), FIGS. 85-88, FIGS. 98-102, and FIGS. 108-112 (not shown), and without limitation, one or more of any means known to those skilled in the art, such as, but not limited to any effective ("Lift Travel Sensor(s))" (530), can be used to detect, and/or report to one or more of any suitable programmable controller(s)/PLC(s) (375), the location(s) and position(s) of any part(s) and/or component(s) at any time(s), and/or when the one or more of any part(s) and component(s) such as, but not limited to any, open package(s), open removable package(s) (229), package(s), and/or packaging material(s) (495), and/or any one or more of any means to move and/or position the open package(s), open removable package(s) (229), package(s), and/or packaging material(s) (495), such as, but not limited to any, movable lift apparatus(s) (770), is at one or more of any effective location(s) and/or position(s).

Without being limited, the one or more movable lift apparatus(s) (770) can move the one or more open package(s), open removable package(s) (229), package(s), and/or packaging material(s) (495), and the one or more lift travel sensor(s) (530) can alert and/or communicate with and/or report to, the one or more of any programmable controller(s)/PLC(s) (375) at any suitable and effective time(s) such as, but not limited to, when the movable lift apparatus(s) (770) and/or the open package(s), open removable package(s) (229), package(s), and/or packaging material(s) (495) is in or at one or more of any desirable, suitable, and/or effective, location(s) and/or position(s), where the programmable controller(s)/PLC(s) (375) can then stop the movement and/or positioning of the various part(s) and component(s) such as, but not limited to any, movable lift apparatus(s) (770) and/or open package(s), open removable package(s) (229), package(s), and/or packaging material(s) (495), so that the one or more object(s) (01) can be effectively packaged. Without being limited, the lift travel sensor(s) (530) can be located and/or positioned in or at one or more of any locations, and preferably, and without limitation at least any one or more of any suitable and effective location(s), and more preferably at any suitable and effective location(s) and/or distance(s) from and/or above any floor(s) (275) of the container holding chamber(s) (265), so any packaging activities can be effectively performed at any suitable and effective distance(s) above any floor(s) (275) of the container holding chamber(s) (265).

Without being limited, the various automated system(s) that are described in the present invention, to move any, open package(s), open removable package(s) (229), package(s), and/or packaging material(s) (495), into any effective position(s) and/or location(s), can also be reversed (not shown) so the one or more of any suitable and effective, open package(s), open removable package(s) (229), package(s), and/or packaging material(s) (495), can be instead effectively, pulled and/or moved down to one or more of any suitable and effective location(s) such as, but not limited to, near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, fully covering, and/or multi-axial covering, and/or past, the object(s) (01) and any connecting part(s) and component(s).

Without being limited, once the one or more of any suitable and effective, open package(s), open removable package(s) (229), package(s), and/or packaging material(s) (495), are in any suitable and effective location(s) and position(s) relative to the object(s) (01), the object(s) (01) and any connected part(s), can be effectively, dropped, released, located and positioned, into, within, and/or at, any effective, open package(s), open removable package(s) (229), and/or one or more of any suitable and effective open packaging material(s) (495), where the one or more of any object(s) (01) and any connected part(s), can then be effectively sealed and/or closed inside the open package(s), open removable package(s) (229), package(s), and/or packaging material(s) (495), all in a manner known to those skilled in the art. Without being limited, the packaging guided lift apparatus(s) (515) can be operated either manually and/or automatically. It is preferred, without limitation, that the packaging guided lift apparatus(s) (515) is operated automatically and is controlled by one or more of any suitable programmable controller(s)/PLC(s) (375).

With reference to FIGS. 68-75, FIG. 80, and FIGS. 90-91, and in still another aspect, and without limitation, one or more of any suitable and effective, open package(s), open removable package(s) (229), package(s), and/or packaging material(s) (495), can be manually, located, positioned, pulled, and/or moved, at any suitable and effective time(s), by any person or authorized staff member, into any suitable and effective position(s) and location(s) such as, but not limited to, near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, fully covering, and/or multi-axial covering, the object(s) (01) and/or any connecting part(s) and component(s), and be suitably and effectively, positioned, located, gripped, supported, suspended, hung, held, and/or located, in any container holding chamber(s) (265) and/or treatment enclosure(s), using one or more of any suitable and effective, part(s), apparatus(s), and/or means, known to those skilled in the art. It is preferred, without limitation, that one or more of any suitable attachment apparatus(s) such as, but not limited to any, one or more effective releasable clip(s) and/or container suspension attachment(s) (406), are effectively attached to one or more or any effective container suspension member(s) (410), which are connected to one or more of any effective container suspension member attachment point(s) (405), which can be, without limitation, connected to one or more of any suitable and effective, container hanging member(s) (450), and/or any suitable and effective, wall(s), ceiling(s), and/or roof location(s) and/or area(s) (270), also located preferably and without limitation, within any container holding chamber(s) (265).

Without being limited, the open package(s), open removable package(s) (229), package(s), and/or packaging material(s) (495), can be effectively located into one or more of any effective location(s) within any container holding chamber(s) (265) and/or treatment enclosure(s), at any time(s), but at least preferably, and without limitation, any effective time(s). Also, and without being limited, the object(s) (01) and any connected part(s), can be effectively, dropped, released, located and positioned, into, within, and/or at, any effective, open package(s), open removable package(s) (229), and/or one or more of any suitable and effective open packaging material(s) (495), at any time(s), but at least preferably and without limitation, any effective time(s). Without limitation, the one or more of any, open package(s), open removable package(s) (229), and/or one or more of any suitable and effective open packaging material(s) (495), can be effectively closed and/or sealed at any time(s), but at least preferably, and without limitation, any effective time(s).

It is preferred, without limitation, that in this particular aspect, the one or more of any suitable and effective, open package(s), open removable package(s) (229), package(s), and/or packaging material(s) (495), are manually pulled and/or moved effectively, up to one or more of any suitable and effective location(s), near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, fully covering, and/or multi-axial covering, and/or past, the object(s) (01) and any connecting part(s) and component(s), until the open package(s), open removable package(s) (229), package(s), and/or packaging material(s) (495), are in any suitable and effective location(s) and/or position(s) to effectually package the object(s) (01) and any connecting part(s), and then manually attached to the one or more of any suitable means known in the art, to effectively hold the one or more of any suitable and effective, open package(s), open removable package(s) (229), package(s), and/or packaging material(s) (495), effectively in place at any effective location(s).

Without being limited, once the one or more of any suitable and effective, open package(s), open removable package(s) (229), package(s), and/or packaging material(s) (495), are in any suitable and effective location(s) and position(s) relative to the object(s) (01), the object(s) (01) and any connected part(s), can be effectively, dropped, released, located and positioned, into, within, and/or at, any effective, open package(s), open removable package(s) (229), and/or one or more of any suitable and effective open packaging material(s) (495), at any effective time(s), but preferably, and without limitation, after the various surface(s) within the container holding chamber(s) (265) and/or treatment enclosure(s) such as, but not limited to those of any, treatment enclosure(s), open removable package(s) (229), and object(s) (01), have been effectively treated, dried, and/or processed. Once the object(s) (01) and any connected part(s) are effectively located within any open package(s), open removable package(s) (229), and/or one or more of any suitable and effective open packaging material(s) (495), the said open package(s), open removable package(s) (229), and/or one or more of any suitable and effective open packaging material(s) (495), can be effectively sealed and/or closed, all in a manner known to those skilled in the art.

Without being limited, the manually operated system described in this aspect, can also be reversed (not shown) so the said, open package(s), open removable package(s) (229), and/or one or more of any suitable and effective open packaging material(s) (495), can instead be effectively, pulled down to one or more of any suitable and effective location(s), near, around, centered around, partially around, completely around, encompassing, centered and encompassing, partially encompassing, completely encompassing, encompassing around, partially encompassing around, completely encompassing around, below, partially below, centered around and encompassing, centered partially below, centered below, underneath, partially underneath, centered partially underneath, centered underneath, fully covering, and/or multi-axial covering, and/or past the object(s) (01) and any connecting part(s).

Also, without being limited, the one or more of any suitable and effective, package(s), open removable package(s) (229), package(s), and/or packaging material(s) (495), that are used to package the various object(s) (01) and any connecting part(s), can be effectively attached either manually and/or automatically, to any means used to effectively locate, position, and/or move, the various, package(s), open removable package(s) (229), and/or packaging material(s) (495), into one or more of any effective location(s), position(s), and/or place(s), at any effective time(s), within the one or more of any suitable container holding chamber(s) (265) and/or treatment enclosure(s), all in a manner known to those skilled in the art.

Broadly speaking, and according to another embodiment and without limitation, any one or more of any object(s) (01) and/or any connected part(s), can be suitably and effectively, positioned, located, gripped, supported, suspended, hung, held, and/or located, directly and/or indirectly, and centered, about centered, and/or not centered, in any effective location(s) and/or position(s) such as, but not limited to, within, partially within, centered partially within, centered within, over, partially over, centered partially over, centered over, outside of, partially outside of, centered partially outside of, centered outside of, above, partially above, centered partially above, centered above, below, partially below, centered partially below, centered below, underneath, partially underneath, centered partially underneath, centered underneath, within and/or inside, any suitable and effective location(s) such as, but not limited to any, removable treatment enclosure(s), removable package(s), treatment enclosure(s), package(s), open removable treatment enclosure(s), open removable package(s), open treatment enclosure(s), open package(s), open packaging material(s), and/or container holding chamber(s), and/or treatment enclosure(s), using one or more of any suitable and effective means, method(s), and/or apparatus(s), such as, but not limited to any, interface plug(s) (330), female plug shaft(s) (545), plug decoupling apparatus(s) (536), pressure interface assembly(s) (68), gripping mechanism(s) (135) and/or gripping finger(s) (108), tube connector(s) (461), tube disconnect apparatus(s) (462), object support(s) (84), movable support member(s) (620), horizontal support member part(s) (630), vertical extension member part(s) (635), support and release apparatus(s) (606), enhanced object(s) holder(s) (155), object interface material(s) (89), cradle(s) (45), gripping mechanism(s) (135) and/or gripping finger(s) (108), object support(s) (84), and/or one or more of any other suitable and effective method(s), apparatus(s), and/or part(s) and component(s) known to those skilled in the art. Without being limited, at any suitable time(s), but preferably and without limitation, after the completion of all treatment and processing steps, the various treated object(s) (01), can be suitably and effectively, dropped, released into, and/or positioned in, one or more of any suitable, package(s), open package(s), open removable package(s) (229), and/or one or more of any effectively open packaging material(s) (495), when any suitable and effective, package(s), open package(s), open removable package(s) (229), and/or one or more of any effectively open packaging material(s) (495), are located in any suitable location(s), proximity(s), and/or position(s), relative to the various treated object(s) (01), and then the one or more object(s) (01) can be effectively, closed within and/or sealed into. the said, package(s), open package(s), open removable package(s) (229), and/or one or more of any effectively open packaging material(s) (495), if needed or desired, before the various, package(s), open package(s), open removable package(s) (229), and/or one or more of any effectively open packaging material(s) (495), and/or closed package(s) (720), are removed from the container holding chamber(s) (265) and/or enhanced decontamination apparatus(s) (715).

It is preferred, without limitation, that the object(s) (01) and any connected part(s) and component(s), are suitably and effectively located and/or positioned in the various area(s) and/or space(s), such as, but not limited to any, container holding chamber(s) (265), and/or package(s), open package(s), open removable package(s) (229), and/or one or more of any effectively open packaging material(s) (495), in a manner so that they do not have contact with any surfaces except the one or more of any effective and suitable surface(s) of any, part(s), component(s) and/or hardware, that is used to suitably and effectively, position, locate, grip, support, suspend, hang, hold, and/or locate, any object(s) (01) and/or any connected part(s) and/or component(s), in, at, and/or within, these suitable and effective location(s), space(s), and/or enclosure(s).

Also, and without being limited, one or more of any, object(s) (01) and/or any connected part(s), can be suitably and effectively, positioned, located, gripped, supported, suspended, hung, held, and/or located, directly and/or indirectly, on, to, with, from, and/or or near, one or more of any effective location(s) such as, but not limited to any, ceiling surface(s), top surface(s), and/or roof surface(s), located inside of any suitable and effective, removable treatment enclosure(s) (230), open removable package(s) (229), treatment enclosure(s), package(s), open removable treatment enclosure(s) (230), open removable package(s), open treatment enclosure(s), open package(s), and/or container holding chamber(s) (265), and/or treatment enclosure(s).

In addition, and without being limited, one or more of any object(s) (01) and/or any connected part(s) and/or component(s), can also be suitably and effectively, positioned, located, gripped, supported, suspended, hung, held, and/or located, directly and/or indirectly, on, to, with, from, and/or or near, any effective structure(s) and/or location(s) such as, but not limited to one or more of any, support member(s), support beam(s), extension member(s), and/or any other suitable and effective means to position, locate, support, suspend, hang, hold, and/or locate, directly and/or indirectly, one or more of any object(s) (01) and/or any other connected part(s) and component(s) (Herein called "Container Hanging Member(s)") (450), where the one or more of any container hanging member(s) (450) can be suitably and effectively located and/or positioned within one or more of any suitable and effective location(s) such as, but not limited to any, removable treatment enclosure(s) (230), treatment enclosure(s), open removable treatment enclosure(s) (229), container holding chamber(s) (265), treatment enclosure(s), package(s), open package(s), and/or one or more of any effectively open packaging material(s) (495).

Without being limited, the hose(s) (18) can be rigid and can form any suitable and effective weight bearing structure(s), all in a manner known to those skilled in the art. Also, without being limited, one or more of any suitable and effective structural support(s) and/or support structure(s) (not shown) can be used to support any, structure(s), apparatus(s), and/or part(s), such as, but not limited to any, hose(s) 18), object(s) (01), object support(s) (84), moving support and dropping mechanism(s) (605), support and tilt mechanism(s) (655), gripping mechanism(s) (135), movable holding and/or support apparatus(s) (606), and/or any other suitably connected parts, within any space(s), area(s), and/or enclosure(s) such as, but not limited to any, removable treatment enclosure(s) (230), and/or container holding chamber(s) (265).

According to an embodiment, and without being limited, any, removable treatment enclosure(s) (230), treatment enclosure(s), open removable treatment enclosure(s) (229), container holding chamber(s) (265), treatment enclosure(s), package(s), open package(s), and/or one or more of any effectively open packaging material(s) (495), can also include one or more of any suitable and effective means to effectively, hold, cradle, support, and/or hang, the one or more object(s) (01) and any associated component(s), within, such as, but not limited to any, plug decoupling apparatus(s) (536), support and release apparatus(s) (606), and/or enhanced object(s) holder(s) (155), interface plug(s) (330), female plug shaft(s) (545), plug decoupling apparatus(s) (536), pressure interface assembly(s) (68), gripping mechanism(s) (135) and/or gripping finger(s) (108), tube connector(s) (461), tube disconnect apparatus(s) (462), object support(s) (84), movable support member(s) (620), horizontal support member part(s) (630), vertical extension member part(s) (635), support and release apparatus(s) (606), enhanced object(s) holder(s) (155), object interface material(s) (89), cradle(s) (45), gripping mechanism(s) (135) and/or gripping finger(s) (108), object support(s) (84), and/or one or more of any other suitable and effective method(s), apparatus(s), part(s), component(s), and/or any other supporting and/or associated part(s) and component(s), known to those skilled in the art.

According to another embodiment, and without being limited, any air/gas(s) flow(s) from and/or supplied to location(s) such as, but not limited to any, removable treatment enclosure(s) (230), treatment enclosure(s), open removable treatment enclosure(s) (229), container holding chamber(s) (265), treatment enclosure(s), package(s), open package(s), and/or one or more of any effectively open packaging material(s) (495), can be filtered via one or more of any suitable and effective filter(s) (75)(53) and/or any charcoal-type filter(s) (75), at any suitable and effective time(s), and for any suitable and effective duration of time(s), and can be connected separately from any air/gas(s) flow(s) from and/or supplied to the one or more of any dehumidified air/gas(s) supply(s) (74), and the various air/gas(s) flow(s), that can also contain any, vapor(s), aerosol(s), and/or applied agent(s), can be controlled by one or more of any suitable and effective valve(s) at any suitable and effective time(s).

According to an embodiment, and without being limited, the one or more of any dehumidification apparatus(s) (74) can also be effectively, decontaminated, sanitized, disinfected, high-level disinfected, and/or sterilized (Hereinafter called "disinfected"), at any suitable and effective times, but preferably, and without limitation, after its various parts used for removing any, vapor(s), water vapor(s), and/or humidity, from the air/gas(s) that is flowed through the dehumidification apparatus(s) (74), such as, but not limited to any, condenser coils, cooling surface(s), chill coil(s), chill surface(s), catch plate(s), and/or catch basin(s), and all known to those skilled in the art, (Herein called "condenser coil(s)) (not shown), have been effectively dried and/or about dried, and more preferably, before the one or more object(s) (01) are treated within the container holding chamber(s) (265) and/or removable treatment enclosure(s) (230), with any applied agent(s) (20), aerosol(s), and/or vapor(s).

It is preferred, without limitation, that disinfecting the various internal part(s) and/or condenser coil(s) of the dehumidification apparatus(s) (74) includes, without limitation, the following processing activities and/or steps: (i) effectively drying the various internal part(s) and/or condenser coil(s) of the dehumidification apparatus(s) (74), and (ii) effectively exposing the various internal part(s) and/or condenser coil(s) of the dehumidification apparatus(s) (74) to any effective quantity, of any suitable and effective, vapor(s), applied agent(s) (20), and/or aerosol(s) (65), for any effective amount of time.

Without being limited, the various internal part(s) and/or condenser coil(s) of the dehumidification apparatus(s) (74) can be dried in various ways including, but not limited to, (i) flowing any effective quantity of heated air/gas(s), that is heated to any suitable and effective temperature(s) using one or more of any suitable and effective means to heat any related air/gas(s) flow(s) that is suitably and effectively located, through the dehumidification apparatus(s) (74) in any effective manner so that the heated air/gas(s) can dry the various internal part(s) and/or condenser coil(s) of the dehumidification apparatus(s) (74), and/or (ii) exposing the various internal part(s) and/or condenser coil(s) of the dehumidification apparatus(s) (74) to any effective vacuum and/or negative pressure(s), in any effective manner, and for any suitable and effective duration of time(s), and using one or more of any suitable and effective vacuum and/or negative pressure apparatus(s) known to those skilled in the art, that is suitably and effectively located, to cause any liquid(s) present on the various internal part(s) and/or condenser coil(s) to transfer into a gas(s) form or phase, that can then be removed by the vacuum and/or negative pressure process and/or later flushed out of the container holding chamber(s) (265) and/or removable treatment enclosure(s) (230) with any effective quantity of fresh air/gas(s).

Without limitation, the various internal part(s) and/or condenser coil(s) can be exposed to any heated air/gas(s) flow(s) in any effective way(s) and manner(s). However, it is preferred, without limitation, that the various internal part(s) and/or condenser coil(s) of the dehumidification apparatus(s) (74) can be exposed to the heated air/gas(s) by closing the various valves (35) to the container holding chamber(s) (265) except for the ones that would allow heated air/gas(s) to flow into the container holding chamber(s) (265) from any heated air/gas(s) supply(s) (660), and then from the container holding chamber(s) (265) into and through the dehumidification apparatus(s) (74), and back into the container holding chamber(s) (265) from the dehumidification apparatus(s) (74), and applying the heated air/gas(s) to the various internal part(s) and/or condenser coil(s) of the dehumidification apparatus(s) (74), for any effective amount of time. Alternatively, and without limitation, the various valve(s) can also be closed to isolate the various internal part(s) and/or condenser coil(s) of the dehumidification apparatus(s) (74), and at least one heated air/gas(s) source(s) can be suitably and effectively located so that it can apply any effective heated air/gas(s) only to the various targeted internal part(s) and/or condenser coil(s) of the dehumidification apparatus(s) (74).

Without limitation, the various internal part(s) and/or condenser coil(s) can be exposed to any vacuum and/or negative air/gas pressure(s) in any effective way(s) and manner(s). However, it is more preferred, without limitation, that the various internal part(s) and/or condenser coil(s) of the dehumidification apparatus(s) (74) can be exposed to any effective negative pressure(s) and/or vacuum by closing the various valves (35) to the container holding chamber(s) (265) except for the ones that would be open for the inflow(s) and outflow(s) for the dehumidification apparatus(s) (74), as well as the source(s) of the vacuum and/or negative pressure(s) (98), and applying the vacuum and/or negative air/gas(s) pressure(s) for any effective amount of time. It is also preferred, without limitation, that when operating the source(s) of the vacuum and/or negative pressure(s) (98) within the present invention, the various valve(s) that connect to or communicate with the aerosol(s), vapor(s), and/or applied agent(s) supply(s) (15, 20, 65), are effectively closed. Alternatively, and without limitation, the various valve(s) can also be closed to isolate the various internal part(s) and/or condenser coil(s) of the dehumidification apparatus(s) (74), and at least one vacuum and/or air/gas(s) negative pressure source(s) can be suitably and effectively located so that it can apply any effective vacuum and/or air/gas(s) negative pressure only to the various targeted internal part(s) and/or condenser coil(s) of the dehumidification apparatus(s) (74).

Once dry, and without being limited, the various internal part(s) and/or condenser coil(s) of the dehumidification apparatus(s) (74) can be effectively treated and/or disinfected, by closing the various valves to the container holding chamber(s) (265) except for the ones that would be open for the inflow(s) and outflow(s), or the flow(s) of air/gas(s), to and from the dehumidification apparatus(s) (74), as well as keeping open the inflow(s) and outflow(s) to and from the source(s) of the aerosol(s), applied agent(s), and/or vapor(s) (20, 65), and/or the flow(s) to and from the generation chamber(s) (15), and then applying any effective quantity of the aerosol(s), applied agent(s), and/or vapor(s) (15, 20, 65), for any effective amount of time into the container holding chamber(s) (265) where it can then be effectively circulated and/or recirculated through the dehumidification apparatus(s) (74) for any effective duration of time(s). It is preferred, without limitation, that any, source(s) of the aerosol(s), applied agent(s), and/or vapor(s) (20, 65), and/or the dehumidification apparatus(s) (74), has one or more of any of its own effective, blower(s), fan(s), and/or air pump(s), to circulate any, vapor(s), air/gas(s), applied agent(s) (20), and/or aerosol(s) (65), and/or heated air/gas(s), through the various internal part(s) and/or condenser coil(s) of the dehumidification apparatus(s) (74), and or any removable treatment enclosure(s) (230), treatment enclosure(s), open removable treatment enclosure(s) (229), container holding chamber(s) (265), treatment enclosure(s), package(s), open package(s), and/or one or more of any effectively open packaging material(s) (495), at any suitable and effective time(s), and for any suitable and effective duration of time(s).

Without being limited, one or more of any, removable treatment enclosure(s) (230), treatment enclosure(s), open removable treatment enclosure(s) (229), container holding chamber(s) (265), treatment enclosure(s), package(s), open package(s), and/or one or more of any effectively open packaging material(s) (495), and/or effectively sealed and/or closed package(s) (720), can also be removed from the container holding chamber(s) (265) and/or the enhanced decontamination enclosure apparatus (715), at any suitable and effective time(s), but preferably and without limitation after any and/or all, targeted surface(s) of any treated object(s) (01) and/or any targeted surfaces within any container holding chamber(s) (265), have been effectively treated by any, applied agent(s) (20), vapor(s), and/or aerosol(s) (65), and even more preferably and without limitation, after all of the targeted and effectively treated surface(s) have been dried, and even more preferably and without limitation, after all of the targeted and effectively treated surface(s) have been dried, and any concentration(s) of any chemical gas(s) and/or vapor(s), and/or any humidity, in the atmosphere that is contained within one or more of any, removable treatment enclosure(s) (230), treatment enclosure(s), open removable treatment enclosure(s) (229), container holding chamber(s) (265), treatment enclosure(s), package(s), open package(s), and/or one or more of any effectively open packaging material(s) (495), and/or effectively sealed and/or closed package(s) (720), has been removed, processed, conditioned, and/or brought to any suitable and effective level(s) and/or any established target point(s), using any equipment(s), method(s), and/or step(s) disclosed in the present invention and/or are known to those skilled in the art.

In one part, and without limitation, the design and construction of any, removable treatment enclosure(s) (230) and/or effectively sealed and/or closed package(s) (720), includes one or more of any suitable and effective self-sealing valve(s) and/or split connector valve(s) (280), where the valve(s) (280) are preferably, and without limitation, effectively open while they are effectively connected in any suitable and effective way, and then effectively closed, preferably and without limitation, automatically closed, when the valve(s) (280) are disconnected, all in a manner known to those skilled in the art.

Without limitation, any of the removable treatment enclosure(s) (230) and/or effectively sealed and/or closed package(s) (720), can be removed from the container holding chamber(s) (265), at any suitable and effective time(s), and the one or more of any of their effectively connected self-sealing valves (280) can also be suitably and effectively interfaced with, at any suitable, effective, and/or desired time(s), in a manner known in the art, with one or more of any suitable and effective, apparatus(s) (not shown), that can subject and/or treat the exterior and/or interior of the said removable treatment enclosure(s) (230) and/or effectively sealed and/or closed package(s) (720), with any suitable and effective, negative pressure atmosphere(s), negative pressure air/gas(s), heated air/gas(s), filtered air/gas(s), and/or dehumidified air/gas(s), that is preferably, and without limitation, separate from any enhanced decontamination enclosure apparatus(s) (715). Also, without being limited, the removable treatment enclosure(s) (230) and/or effectively sealed and/or closed package(s) (720), can be both effectively located within, effectively treated within, as well as effectively connected with any self-sealing valve(s) and/or split connector valve(s) (280) to any, effective apparatus (not shown), that is preferably, and without limitation, separate from any enhanced decontamination enclosure apparatus(s) (715), that can create, treat with, and/or deliver any effective, vacuum(s), negative pressure(s), dehumidified air/gas(s), heated air/gas(s), filtered air/gas(s), and/or charcoal filtered air/gas(s), at any suitable and effective time(s), and for any suitable and effective duration(s) of time(s), for purposes including but not limited to, processing and drying both the internal and/or external surface(s) and/or atmosphere(s), of the removable treatment enclosure(s) (230) and/or effectively sealed and/or closed package(s) (720).

Without limitation, any effective, vacuum(s), negative pressure(s), dehumidified air/gas(s), heated air/gas(s), filtered air/gas(s), and/or charcoal filtered air/gas(s), can be, applied to, surround, and/or flowed through, the removable treatment enclosure(s) (230) and/or effectively sealed and/or closed package(s) (720), and/or any internal area(s) and/or space(s) of the removable treatment enclosure(s) (230) and/or effectively sealed and/or closed package(s) (720), for any effective amount of time(s), and preferably, and without limitation, at least any effective duration of time(s) to cause any liquid(s) present on any surface(s), and/or in the internal area(s) or space(s) of the removable treatment enclosure(s) (230) and/or effectively sealed and/or closed package(s) (720), to turn into any gas(s), that can also be removed by ways including, but not limited to any, vacuum device(s), negative pressure(s) device(s) (98), and/or any flow(s) of any air/gas(s) that is preferably, and without limitation, filtered before it is exhausted from the said apparatus (not shown). Without being limited, after the various processing step(s) is complete, one or more of any effective flow(s) of any effectively filtered air/gas(s) can also be flowed into and/or through, the internal area(s) and space(s) of the removable treatment enclosure(s) (230) and/or effectively sealed and/or closed package(s) (720), at any suitable and effective pressure(s) and/or flow rate(s), and this can also help to remove any unwanted gas(s) from within these area(s) and/or space(s).

In another part, and without limitation, the design and construction of the removable treatment enclosure(s) (230) and/or effectively sealed and/or closed package(s) (720), can include one or more of any suitable and effective, porous, permeable, and/or breathable, material(s) (Herein called "Breathable Panel(s)")(not shown) of any suitable and effective size(s) and/or construction(s), all in a manner known to those skilled in the art. Without limitation, the removable treatment enclosure(s) (230) and/or effectively sealed and/or closed package(s) (720) can be removed from the container holding chamber(s) (265), at any suitable and effective time(s), and they can later be suitably and effectively located, at any suitable and/or desired time(s), within one or more of any suitable and effective separate chamber(s) (not shown) of any suitable and effective apparatus(s) (not shown) all known to those skilled in the art, that is suitably and effectively connected to one or more of any suitable and effective vacuum device(s) and/or negative pressure(s) device(s) (not shown), also in a manner known to those skilled in the art. Any effective vacuum and/or effective negative pressure(s) can be, without limitation, applied to the internal area(s) and/or space(s) of any of the said, separate chamber(s), removable treatment enclosure(s) (230), and/or effectively sealed and/or closed package(s) (720), for any effective amount of time(s), and preferably, and without limitation, at least any effective duration of time(s), to cause any liquid(s) present in any, area(s), internal area(s), or space(s), to turn into any gas(s), that can then pass through the breathable panel(s), all in a manner known to those skilled in the art, and be removed by means such as, but not limited to any, vacuum device(s) and/or negative pressure(s) device(s) (not shown). Without being limited, after the processing step of applying the vacuum and/or negative pressure(s) is complete, one or more of any effective flow(s) of filtered air/gas(s) can also be flowed into and/or through, the said separate chamber(s) in which the removable treatment enclosure(s) (230) and/or effectively sealed and/or closed package(s) (720) are located, as well as any of the internal area(s) and space(s) of the removable treatment enclosure(s) (230) and/or effectively sealed and/or closed package(s) (720), via the one or more of any self-sealing valve(s) and/or split connector valve(s) (280), at any suitable and effective pressure(s) and speed(s), all in a manner known to those skilled in the art.

Referring to FIGS. 53-56, FIGS. 63-65, and according to an embodiment, and without limitation, any treatment(s), drying(s), and/or processing(s), activities and/or steps for any, surface(s), space(s), area(s), and/or compartment(s), such as, but not limited to any area(s) and/or surface(s) outside of and/or within, one or more of any, open enclosure(s), open removable package(s) (229), open package(s) and/or packaging material(s) (495), enclosure(s), treatment enclosure(s), open treatment enclosure(s), open removable treatment enclosure(s), package(s), and/or removable package(s), and preferably and without limitation, at least any, container holding chamber(s) (265), and/or removable treatment enclosure(s) (230), as well as one or more of any surfaces and/or area(s) of any, object(s) (01), and/or one or more of any suitable and effective means to effectively, hold, cradle, support, and/or hang, the one or more object(s) (01) and any associated component(s), such as, but not limited to any, plug decoupling apparatus(s) (536), support and release apparatus(s) (606), and/or enhanced object(s) holder(s) (155), interface plug(s) (330), female plug shaft(s) (545), plug decoupling apparatus(s) (536), pressure interface assembly(s) (68), gripping mechanism(s) (135) and/or gripping finger(s) (108), tube connector(s) (461), tube disconnect apparatus(s) (462), object support(s) (84), movable support member(s) (620), horizontal support member part(s) (630), vertical extension member part(s) (635), support and release apparatus(s) (606), enhanced object(s) holder(s) (155), object interface material(s) (89), cradle(s) (45), gripping mechanism(s) (135) and/or gripping finger(s) (108), object support(s) (84), and/or one or more of any other suitable and effective method(s), apparatus(s), part(s), component(s), and/or any other supporting and/or associated part(s) and component(s), known to those skilled in the art, that can be located within these space(s) and/or area(s), can include, but is not limited to:

(a) locating one or more of any object(s) (01) within one or more of any suitable and effective removable treatment enclosure(s) (230), and preferably, and without limitation, effectively locating the one or more removable treatment enclosure(s) (230) within one or more of any suitable and effective container holding chamber(s) (265). Without being limited, the removable treatment enclosure(s) (230) can also be effectively open in one or more effective location(s) and in any suitable and effective manner(s), and have any effective opening size(s), when present inside the container holding chamber(s) (265), and then be effectively sealed, in any suitable and effective manner(s) known to those skilled in the art, after all of the various surface(s) within the removable treatment enclosure(s) (230) and/or the container holding chamber(s) (265), are effectively treated, dried, and/or processed.

Without limitation, the interior of the container holding chamber(s) (265) effectively connects and/or interfaces with one or more of any apparatus(s) and/or supplies such as, but not limited to any, aerosol(s), vapor(s), and/or applied agent(s) supply(s) (15, 20, 65), vacuum and/or negative pressure(s) (98), fresh air/gas (380) supply(s) (17, 51, 38), heated (660) fresh air/gas(s) supply(s) (380), dehumidified air/gas(s) supply(s) (74), heated air/gas(s) supply(s) (660), and/or filtered air/gas(s) supply(s) (75)(53). Without limitation, the flows of any, applied agent(s), aerosol(s) and/or vapor(s) (20, 65), fresh air/gas(s) (380), dehumidified air/gas(s), heated air/gas(s), and/or filtered air/gas(s), can be preferably and without limitation, supplied to, and/or more preferably and without limitation, supplied to and flowed through, and/or supplied to and recirculated through, location(s) such as, but not limited to any: (i) container holding chamber(s) (265), (ii) various apparatus(s) such as, but not limited to any, generation chamber(s) (15), means to dehumidify any air/gas(s) (74), means to heat any air/gas(s) (660), and/or means to filter any air/gas(s) (75, 53), at any suitable and effective time(s) and for any suitable and effective duration(s) of time(s).

Also, and without being limited, any suitable and effective valve(s) (35) (740) can be opened and closed at one or more of any suitable and effective time(s), for any suitable and effective purpose(s), and for any effective duration of time(s), to control any entry and/or exit of any flow(s) of any air/gas(s) and/or substance(s) such as, but not limited to any, air, fresh air, gas(s), vapor(s), aerosol(s), dehumidified air/gas(s), heated air/gas(s), vacuum or negative pressure atmosphere, and/or filtered air/gas(s), into, out of, and/or through, the various area(s), space(s), and/or location(s), such as, but not limited to any, container holding chamber(s) (265), removable treatment enclosure(s) (230), and/or any means to hold, support, and/or treat, any object(s) (01) and/or any connected parts(s) and component(s), such as, but not limited to any, plug decoupling apparatus(s) (536), support and release apparatus(s) (606), and/or enhanced object(s) holder(s) (155), interface plug(s) (330), female plug shaft(s) (545), plug decoupling apparatus(s) (536), pressure interface assembly(s) (68), gripping mechanism(s) (135) and/or gripping finger(s) (108), tube connector(s) (461), tube disconnect apparatus(s) (462), object support(s) (84), movable support member(s) (620), horizontal support member part(s) (630), vertical extension member part(s) (635), support and release apparatus(s) (606), enhanced object(s) holder(s) (155), object interface material(s) (89), cradle(s) (45), gripping mechanism(s) (135) and/or gripping finger(s) (108), object support(s) (84), and/or one or more of any other suitable and effective method(s), apparatus(s), part(s), component(s), and/or any other supporting and/or associated part(s) and component(s), known to those skilled in the art, that can be located within the container holding chamber(s) (265). It is preferred, without limitation, that the one or more object(s) (01) are removably interfaced, inside the removable treatment enclosure(s) (230), with one or more of any of the said suitable and effective means to hold, support, and/or treat, any object(s) (01), that are preferably, and without limitation, located within the one or more removable treatment enclosure(s) (230).

(b) releasably connecting and/or interfacing the one or more removable treatment enclosure(s) (230), preferably and without limitation, within any suitable and effective container holding chamber(s) (265), to one or more of any suitable and effective connection(s), and more preferably, and without limitation, with one or more of any suitable and effective self-sealing valve(s) and/or split connector valve(s) (280), that can connect to various apparatus(s) and/or supplies such as, but not limited to any: aerosol(s), applied agent(s), and/or vapor(s) supply(s) (15, 20, 65), vacuum and/or negative pressure(s) (98), fresh air/gas (380) supply(s) (17, 51, 38), heated (660) fresh air/gas(s) supply(s) (380), dehumidified air/gas(s) supply(s) (74), heated air/gas(s) supply(s) (660), and/or filtered air/gas(s) supply(s) (75, 53). Without limitation, the flows of any, applied agent(s), aerosol(s) and/or vapor(s) (20, 65), fresh air/gas, heated (660) fresh air/gas(s), dehumidified air/gas(s), heated air/gas(s), and/or filtered air/gas(s), can be preferably and without limitation, supplied to, flowed through, and/or more preferably and without limitation, supplied to and recirculated through, location(s) such as, but not limited to any: (i) removable treatment enclosure(s) (230), (ii) container holding chamber(s) (265), (iii) means to hold, cradle, and/or support any object(s) (01), and/or (iii) various apparatus(s) such as, but not limited to any, generation chamber(s) (15), means to dehumidify any air/gas(s) (74), means to heat any air/gas(s) (660), and/or means to filter any air/gas(s) (75, 53), at any suitable and effective time(s) and for any suitable and effective duration(s) of time(s).

Without being limited, any suitable and effective valve(s) (35)(740) can be opened and closed at one or more of any suitable and effective time(s), for any suitable and effective purpose(s), and for any effective duration of time(s), to control any entry and/or exit of any flow(s) of any air/gas(s) and/or substance(s) such as, but not limited to any, air, fresh air/gas(s), heated fresh air/gas(s), gas(s), vapor(s), aerosol(s), dehumidified air/gas(s), heated air/gas(s), vacuum or negative pressure atmosphere, and/or filtered air/gas(s), into, out of, and/or through, the various area(s), space(s), and/or location(s), such as, but not limited to any, removable treatment enclosure(s) (230), and/or any means to hold, support, and/or treat, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), that can be, without limitation, located within the removable treatment enclosure(s) (230).

(c) effectively drying any targeted surface(s) such as, but not limited to, those found in any, space(s), area(s), and/or compartment(s), such as, but not limited to any, container holding chamber(s) (265), and/or removable treatment enclosure(s) (230), as well as any object(s) (01), and/or gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), that can be located within these space(s) and/or area(s). The drying of any of these area(s) and/or surface(s) can be accomplished with the use of one or more of any effective, (i) heater(s) (660) to heat any air/gas flow(s) that can be moved through these various location(s), (ii) dehumidification apparatus(s) (74) to dry or dehumidify any air/gas flow(s) that can be moved through these various location(s), (iii) vacuum apparatus(s) or negative pressure device(s) (98) to evacuate the air/gas(s) and drop the air/gas pressure within these location(s) causing any liquid(s) present in these area(s) to transfer into gas(s) that can be removed by any negative pressure device(s) (98) and/or as any fresh air/gas(s) is later flowed through these area(s) and/or location(s), and/or (iv) flowing fresh air/gas(s), that is preferably and without limitation, effectively filtered and/or heated, through these area(s) and/or location(s).

It is preferred, without limitation, that at least one or more of the following drying steps can be followed, if needed, before the applied agent(s) are effectively deployed:

(i) dehumidified air/gas(s) can be effectively flowed into and through, and/or effectively recirculated through, the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, then (ii) more preferably, and without limitation, effectively heated (660) fresh air/gas(s) (380), that is also preferably and without limitation, effectively filtered, is flowed into and through, and/or effectively recirculated through the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, then (iii) optionally, and without limitation, effectively filtered fresh air (380)(17, 51, 38) can also be effectively flowed into and through, and/or effectively recirculated through, the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, However, it is more preferred, without limitation, that at least the following drying steps can be followed, if needed, before the applied agent(s) are fully and efficaciously deployed:

(i) any effective vacuum, negative pressure, and/or effective atmospheric pressure, that can cause all liquid(s) within any location(s) such as, but not limited to any, removable treatment enclosure(s) (230) and/or container holding chamber(s) (265), to change into a gaseous state, is established by one or more of any effective negative pressure device(s) (98) in location(s) such as, but not limited to any, removable treatment enclosure(s) (230) and/or container holding chamber(s) (265), for any effective amount of time, then, (ii) effectively filtered fresh air and/or gas(s) (380) is flowed into and/or through, and/or effectively circulated through, the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time(s), to at least fill location(s) such as, but not limited to any, removable treatment enclosure(s) (230) and/or container holding chamber(s) (265) with any effective quantity of fresh air/gas(s).

(d) effectively treating the various area(s), location(s), and/or surface(s), such as, but not limited to, those found in any, space(s), area(s), and/or compartment(s), such as, but not limited to any, container holding chamber(s) (265), and/or removable treatment enclosure(s) (230), as well as any, object(s) (01), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), with any aerosol(s) (65), applied agent(s) (20), gas(s), and/or vapor(s), that is preferably, but without limitation, generated within and deployed from, one or more of any generation chamber(s) (15), and circulated and/or recirculated through the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time(s).

(e) effectively drying any targeted area(s) and/or surface(s) such as, but not limited to, those found in any, space(s), area(s), and/or compartment(s), such as, but not limited to any, container holding chamber(s) (265), and/or removable treatment enclosure(s) (230), as well as any object(s) (01), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time(s), that can be located within these space(s) and/or area(s). The drying of any of these area(s) and/or surface(s) can be accomplished by using, for any effective amount of time(s), and at any suitable and effective time(s), of one or more of any effective, (i) heater(s) (660) to heat any air/gas flow(s) that can be moved through these various location(s), (ii) dehumidification apparatus(s) (74) to dry or dehumidify any air/gas flow(s) that can be moved through these various location(s), (iii) vacuum apparatus(s) or negative pressure device(s) (98) to evacuate the air/gas(s) and drop the air/gas pressure within these location(s) thus causing any liquid(s) present in these area(s) to transfer into a gas(s) that can then be removed by any effective negative pressure device(s) (98) and/or as fresh air/gas(s) can be later flowed through these area(s) and/or location(s), and/or (iv) flowing fresh air/gas, that is preferably and without limitation, effectively filtered and/or heated, through these area(s) and/or location(s).

It is preferred, without limitation, that at least the following drying steps are followed after the applied agent(s) are fully and efficaciously deployed:

(i) effectively dehumidified air/gas(s) can be flowed into and recirculated through the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, then (ii) effectively filtered air/gas(s) that is preferably, and without limitation, filtered with one or more of any suitable and effective charcoal-type filter(s), can also be flowed into and recirculated through the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time(s), for any effective duration of time, then (iii) more preferably, and without limitation, effectively heated (660) air/gas(s), that is also preferably and without limitation, effectively filtered fresh air/gas(s) (380), is effectively, flowed into, through, and/or recirculated through, the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, then (iv) optionally, and without limitation, effectively filtered fresh (380) air/gas(s) (17, 51, 38) and/or effectively filtered air/gas(s), is effectively flowed through and/or recirculated through, the removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective amount of time, for various purposes including, but not limited to, to cool and/or dry any targeted area(s), space(s), and/or surface(s), and/or to effectively remove any unwanted gas(s)/vapor(s), and/or to drop the concentration of any unwanted gas(s)/vapor(s) within the removable treatment enclosure(s) (230) and/or container holding chamber(s) (265), to, within, and/or under, any acceptable limits and/or government agency standards.

However, it is more preferred, without limitation, that at least the following drying steps are followed after the applied agent(s) are fully and efficaciously deployed:

(i) any effective vacuum and/or effective atmospheric pressure that can cause all liquid(s) within any location(s) such as, but not limited to any, removable treatment enclosure(s) (230) and/or container holding chamber(s) (265), to change into a gaseous state, is established by one or more of any effective negative pressure device(s) (98) in location(s) such as, but not limited to any, removable treatment enclosure(s) (230) and/or container holding chamber(s) (265), for any effective amount of time, then, (ii) effectively filtered fresh air and/or gas(s), that is preferably and without limitation, heated to any effective temperature(s), is flowed into and recirculated through location(s) such as, but not limited to any, removable treatment enclosure(s) (230), container holding chamber(s) (265), and/or any, gripping mechanism(s) (135), object support(s) (84), support and release apparatus(s) (606), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, for various purposes including, but not limited to, to dry any targeted area(s), space(s), and/or surface(s), and/or effectively removing any unwanted gas(s)/vapor(s), to at least fill the removable treatment enclosure(s) (230) and/or container holding chamber(s) (265) with any effective quantity of air/gas(s), and/or to drop the concentration of any unwanted gas(s)/vapor(s) within the removable treatment enclosure(s) (230) and/or container holding chamber(s) (265) to, within, and/or under, any acceptable limits and/or government agency standards.

(f) disconnecting, removing, and/or deinterfacing, the one or more removable treatment enclosure(s) (230), from the one or more of any effective connection(s) to various supplies such as, but not limited to any: aerosol(s) and/or vapor(s) (15, 20, 65), vacuum and/or negative pressure(s) (98), fresh air/gas and/or heated fresh air/gas(s) supply(s) (17, 51, 38), dehumidified air/gas(s) (74), heated air/gas(s) (660), and/or filtered air/gas(s) (75, 53), and it is preferred, without limitation, that these one or more connection(s) are effectively self-sealing at least on the side of the removable treatment enclosure(s) (230), so that the surface(s) and/or atmosphere(s) within the removable treatment enclosure(s) (230) cannot become contaminated and/or the internal area(s) and space(s) of the removable treatment enclosure(s) (230) can remain hermetically sealed, all in a manner known to those skilled in the art.

(g) removing the removable treatment enclosure(s) (230) from the container holding chamber(s) (265) at any effective and/or desired time(s).

Referring to FIGS. 67-75, and FIGS. 80-91, and FIGS. 98-112, and according to an embodiment, and without limitation, any treatment(s), drying(s), and/or processing(s), activities and/or steps for any, surface(s), space(s), area(s), and/or compartment(s), such as, but not limited to any area(s) and/or surface(s) within, one or more of any, container holding chamber(s) (265), and/or within and/or outside of any, open enclosure(s), open removable package(s) (229), open package(s) and/or packaging material(s) (495), enclosure(s), treatment enclosure(s), open treatment enclosure(s), open removable treatment enclosure(s), package(s), removable package(s), and/or removable treatment enclosure(s) (230), that can be preferably and without limitation, located within the container holding chamber(s) (265), as well as one or more of any surfaces and/or area(s) of any, object(s) (01), and/or any means to hold, treat, dry, process, and/or support, any object(s) (01) within the container holding chamber(s) (265) such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), that can be located within these space(s) and/or area(s), can include, but is not limited to:

(a) locating one or more of any object(s) (01) within one or more of any suitable and effective container holding chamber(s) (265). It is preferred, without limitation, that the one or more object(s) (01) are removably interfaced with one or more of any suitable and effective means to hold, support, treat, dry, and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), that are preferably, and without limitation, located within the one or more container holding chamber(s) (265).

Without limitation, the interior of the container holding chamber(s) (265) effectively, connects, communicates, and/or interfaces, with one or more of any apparatus(s) and/or supplies such as, but not limited to any, aerosol(s) and/or vapor(s) supply(s) (15, 20, 65), vacuum and/or negative pressure(s) (98), fresh air/gas supply(s) (17, 51, 38), dehumidified air/gas(s) supply(s) (74), heated air/gas(s) supply(s) (660), and/or filtered air/gas(s) supply(s) (75)(53). Without limitation, the flows of any, applied agent(s), aerosol(s), gas(s), and/or vapor(s) (20, 65), fresh air/gas(s), dehumidified air/gas(s), heated air/gas(s), and/or filtered air/gas(s), can be preferably and without limitation, supplied to, flowed through, and/or more preferably and without limitation, supplied to and recirculated through at any effective time(s) and duration of time(s), location(s) such as, but not limited to any: (i) container holding chamber(s) (265), (ii) means to hold and/or support (135)(606) (155) any object(s) (01), and/or (iii) various apparatus(s) such as, but not limited to any, aerosol(s) and/or gas(s) generation and/or deployment chamber(s) (15), means to dehumidify any air/gas(s) (74), means to heat any air/gas(s) (660), and/or means to filter any air/gas(s) (75, 53), at any suitable and effective time(s) and for any suitable and effective duration(s) of time(s). Also, and without being limited, any suitable and effective valve(s) (35) can be opened and closed at one or more of any suitable and effective time(s), for any suitable and effective purpose(s), and for any effective duration of time(s), to control any entry and/or exit of any flow(s) of any air/gas(s) and/or substance(s) such as, but not limited to any, air, fresh air, gas(s), applied agent(s), vapor(s), aerosol(s), dehumidified air/gas(s), heated air/gas(s), vacuum or negative pressure atmosphere, and/or filtered air/gas(s), into, out of, and/or through, the various area(s), space(s), and/or location(s), such as, but not limited to any, container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), that can be located within the container holding chamber(s) (265).

(b) effectively drying any targeted surface(s) such as, but not limited to, those found in any, space(s), area(s), and/or compartment(s), such as, but not limited to any, container holding chamber(s) (265), as well as any object(s) (01), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), that can be located within these space(s) and/or area(s). The drying of any of these area(s) and/or surface(s) can be accomplished with the use of one or more of any effective, (i) heater(s) (660) to heat any air/gas flow(s) that can be moved through these various location(s), (ii) dehumidification apparatus(s) (74) to dry or dehumidify any air/gas flow(s) that can be moved through these various location(s), (iii) vacuum apparatus(s) and/or negative pressure device(s) (98), to evacuate the air/gas(s) and drop the air/gas pressure within these location(s) causing any liquid(s) present in these area(s) to transfer into gas(s) that can then be removed by the vacuum or negative pressure device(s) (98), and/or as fresh air/gas(s), that is preferably and without limitation, effectively filtered, can later be flowed through these area(s) and/or location(s), and/or (iv) preferably, flowing fresh air/gas(s), that is preferably and without limitation, effectively filtered, and even more preferably, and without limitation, that is also effectively heated to any effective temperature(s), through these area(s) and/or location(s).

It is preferred, without limitation, that at least the following drying steps can be followed, if needed, before the applied agent(s) is deployed:

(i) dehumidified air/gas(s) can be flowed into and effectively recirculated through one or more location(s) and/or areas such as, but not limited to any, container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, (ii) more preferably, and without limitation, effectively heated fresh air/gas(s) (380), that is also preferably and without limitation, effectively filtered, is effectively flowed into and/or through, and/or also effectively recirculated through, the container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, then (iii) optionally, and without limitation, effectively filtered fresh air (380) can also be flowed into and through the container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration(s) of time(s) and at any suitable and effective time(s), However, it is even more preferred, without limitation, that at least the following drying steps can be followed, if needed, before the applied agent(s) are fully and efficaciously deployed:

(i) any effective vacuum and/or effective atmospheric pressure that can cause all liquid(s) within location(s) such as, but not limited to any, container holding chamber(s) (265), to change into a gaseous state, is established by one or more of any effective negative pressure device(s) (98) in location(s) such as, but not limited to any, container holding chamber(s) (265), for any effective amount of time, then, (ii) effectively filtered fresh air and/or gas(s), that can also be, without limitation, heated at any suitable and effective time(s), is flowed into and through the container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time(s) and at any effective time(s), to at least fill the container holding chamber(s) (265) with any effective quantity of air/gas(s), then, (c) if applicable, desired, and/or if it hasn't already been completed before the previous step(s) have already taken place which is, without limitation, preferred, effectively moving and/or positioning one or more of any suitable, open package(s), open removable package(s) (229), and/or one or more of any effectively open packaging material(s) (495), into any effective location(s) within the container holding chamber(s) (265), so the object(s) (01) can be located and/or dropped later, into the open package(s), open removable package(s) (229), and/or one or more of any effectively open packaging material(s) (495), after being effectively, treated with any applied agent(s) (20)(65), dried, and/or any other processing step(s).

(d) effectively treating the various area(s), location(s), and/or surface(s), such as, but not limited to, those found in any, space(s), area(s), and/or compartment(s), such as, but not limited to any, container holding chamber(s) (265), as well as any object(s) (01), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s)

and/or apparatus(es) meant to effectively hold, cradle, treat, process, dry, and/or support, any object(s) (01) and/or any connected part(s) and component(s), that can be located within these space(s) and/or area(s), with any aerosol(s) (65), applied agent(s) (20), gas(s), and/or vapor(s), that is preferably, and without limitation, created and/or generated within and deployed from, one or more of any generation chamber(s) (15), and recirculated through the container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time(s) and/or for any effective number of time(s).

(e) effectively drying any targeted and treated surface(s) such as, but not limited to, those found in any, space(s), area(s), and/or compartment(s), such as, but not limited to any, container holding chamber(s) (265), as well as any object(s) (01), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), that can be located within these space(s) and/or area(s). The drying of any of these area(s) and/or surface(s) can be accomplished by using, for any effective amount of time, one or more of any effective, (i) heater(s) (660) to heat any air/gas flow(s) that can move through these various location(s), (ii) dehumidification apparatus(s) (74) to dry or dehumidify any air/gas flow(s) that can move through these various location(s), (iii) vacuum apparatus(s) or negative pressure device(s) (98) to evacuate the air/gas(s) and drop the air/gas pressure within these location(s) thus causing any liquid(s) present in these area(s) to transfer into gas(s) that can be removed by the vacuum or negative pressure device(s) (98) and/or as any filtered fresh air/gas(s) (380) can later be flowed through these area(s) and/or location(s), and/or (iv) preferably, flowing fresh air/gas(s), that is preferably and without limitation, effectively filtered, and even more preferably, and without limitation, that is also effectively heated to any effective temperature(s), through these area(s) and/or location(s).

It is preferred, without limitation, that at least one or more of the following drying steps can be followed after the applied agent(s) are fully and efficaciously deployed:

(i) dehumidified air/gas(s) can be effectively flowed into and through, and/or effectively recirculated through, the container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time, then (ii) more preferably, and without limitation, effectively heated fresh air/gas(s) (380), that is also preferably and without limitation, effectively filtered, is effectively flowed into and through, and/or effectively recirculated through, the container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), for any effective amount of time(s), for various purposes including, but not limited to, to dry any targeted area(s), space(s), and/or surface(s), and/or to effectively remove any unwanted gas(s)/vapor(s), and/or to drop the concentration of any unwanted gas(s)/vapor(s) within the container holding chamber(s) (265), to, within, and/or under, any acceptable limits and/or government agency standards, then (iii) optionally, and without limitation, effectively filtered fresh air/gas(s) can be effectively flowed through, and/or effectively recirculated through, the container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), also for any effective amount of time(s), for various purposes including, but not limited to, to cool and/or dry, any targeted area(s), space(s), and/or surface(s), and/or to effectively remove any unwanted gas(s)/vapor(s), and/or to drop the concentration of any unwanted gas(s)/vapor(s) within location(s) such as, but not limited to any, container holding chamber(s) (265), to, within, and/or under, any acceptable limits and/or government agency standards.

However, it is more preferred, without limitation, that at least one or more of the following drying steps can follow after the applied agent(s) are fully and efficaciously deployed:

(i) any effective vacuum and/or effective atmospheric pressure that can cause all liquid(s) within location(s) such as, but not limited to any, container holding chamber(s) (265), to change into a gaseous state, is established by one or more of any effective negative pressure device(s) (98) in location(s) such as, but not limited to any, container holding chamber(s) (265), for any effective amount of time, then, (ii) effectively filtered fresh air and/or gas(s) (380) is effectively flowed into and through the container holding chamber(s) (265), and/or any means to hold, support, treat, dry and/or process, any object(s) (01), such as, but not limited to any, gripping mechanism(s) (135), object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), for any effective duration of time(s), for various purposes including, but not limited to, to dry any targeted area(s), space(s), and/or surface(s), and/or effectively removing any unwanted gas(s)/vapor(s), to at least fill the container holding chamber(s) (265) with any effective quantity of air/gas(s), and/or to drop the concentration of any unwanted gas(s)/vapor(s) within location(s) such as, but not limited to any, container holding chamber(s) (265) to, within, and/or under, any acceptable limits and/or government agency standards.

(f) if applicable and not already completed: effectively moving and/or positioning one or more of any suitable, open package(s), open removable package(s) (229), and/or one or more of any effectively open packaging material(s) (495), into any effective location(s) within the container holding chamber(s) (265), so the one or more object(s) (01) can be located and/or dropped into the open package(s), open removable package(s) (229), and/or one or more of any effectively open packaging material(s) (495).

(g) effectively locating, but preferably and without limitation, dropping the treated, and also preferably and without limitation, dried, object(s) (01) into the open package(s), open removable package(s) (229), and/or one or more of any effectively open packaging material(s) (495).

(h) effectively sealing and/or closing the open package(s), open removable package(s) (229), and/or one or more of any effectively open packaging material(s) (495), in any effective manner and/or with any effective means, known to those skilled in the art, if applicable, needed, and/or desired.

(i) removing the package(s), open removable package(s) (229), and/or effectively sealed and/or closed package(s) (720) from the container holding chamber(s) (265) at any effective and/or desired time(s).

Referring to FIGS. 38-43, and FIGS. 109-110, and FIG. 112, and according to an embodiment, and without limitation, a more detailed description of the use of the one or more gripping mechanism(s) (135) is given, for any treatment(s), drying(s), processing(s), and/or packaging(s), activities and/or steps for any, surface(s), space(s), area(s), and/or compartment(s), such as, but not limited to any area(s) and/or surface(s) within, one or more of any, container holding chamber(s) (265), removable treatment enclosure(s) (230), and/or within and/or outside of any, open enclosure(s), open removable package(s) (229), open package(s) and/or packaging material(s) (495), enclosure(s), treatment enclosure(s), open treatment enclosure(s), open removable treatment enclosure(s), package(s), removable package(s), and/or removable treatment enclosure(s) (230), that can be preferably and without limitation, located within the container holding chamber(s) (265) and/or removable treatment enclosure(s) (230), as well as one or more of any surfaces and/or area(s) of any, object(s) (01), and/or any means to hold, treat, dry, process, and/or support, any object(s) (01) within the container holding chamber(s) (265) and/or removable treatment enclosure(s) (230), such as, but not limited to any, object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), but more particularly, and without limitation, any one or more of any suitable and effective gripping mechanism(s) (135), that can be located within these space(s) and/or area(s), can include, but is not limited to:

(a) locating one or more of any object(s) (01) within one or more of any suitable and effective container holding chamber(s) (265) and/or removable treatment enclosure(s) (230). It is preferred, without limitation, that the one or more object(s) (01) are removably interfaced with one or more, but preferably and without limitation, at least an effective number, of any suitable and effective gripping mechanism(s) (135), that are preferably, and without limitation, located within the one or more container holding chamber(s) (265).

Without limitation, the interior of the container holding chamber(s) (265) and/or removable treatment enclosure(s) (230), effectively, connects, communicates, and/or interfaces, with one or more of any apparatus(s) and/or supplies such as, but not limited to any, aerosol(s) and/or vapor(s) supply(s) (15, 20, 65), vacuum and/or negative pressure(s) (98), fresh air/gas supply(s) (17, 51, 38), dehumidified air/gas(s) supply(s) (74), heated air/gas(s) supply(s) (660), and/or filtered air/gas(s) supply(s) (75)(53). Without limitation, the flows of any, applied agent(s), aerosol(s), gas(s), and/or vapor(s) (20, 65), fresh air/gas(s), dehumidified air/gas(s), heated air/gas(s), and/or filtered air/gas(s), can be preferably and without limitation, supplied to, flowed through, and/or more preferably and without limitation, supplied to and recirculated through at any effective time(s) and duration of time(s), location(s) such as, but not limited to any: (i) container holding chamber(s) (265), (ii) gripping mechanism(s) (135), (iii) removable treatment enclosure(s) (230), and/or (iv) various apparatus(s) such as, but not limited to any, aerosol(s) and/or gas(s) generation and/or deployment chamber(s) (15), means to dehumidify any air/gas(s) (74), means to heat any air/gas(s) (660), and/or means to filter any air/gas(s) (75, 53), at any suitable and effective time(s) and for any suitable and effective duration(s) of time(s). Also, and without being limited, any suitable and effective valve(s) (35) can be opened and closed at one or more of any suitable and effective time(s), for any suitable and effective purpose(s), and for any effective duration of time(s), to control any entry and/or exit of any flow(s) of any air/gas(s) and/or substance(s) such as, but not limited to any, air, fresh air, gas(s), applied agent(s), vapor(s), aerosol(s), dehumidified air/gas(s), heated air/gas(s), vacuum or negative pressure atmosphere, and/or filtered air/gas(s), into, out of, and/or through, the various area(s), space(s), and/or location(s), such as, but not limited to any, container holding chamber(s) (265), and/or removable treatment enclosure(s) (230), and/or any means to hold, support, treat, dry and/or process, any object(s) (01), such as, but not limited to any, gripping mechanism(s) (135), that can be located within the container holding chamber(s) (265).

(b) effectively drying any targeted surface(s) such as, but not limited to, those found in any, space(s), area(s), and/or compartment(s), such as, but not limited to any, container holding chamber(s) (265) and/or removable treatment enclosure(s) (230), as well as any object(s) (01), and/or any means to hold, support, treat, dry and/or process, any object(s) (01), such as, but not limited to any, gripping mechanism(s) (135), that can be located within these space(s) and/or area(s). The drying of any of these area(s) and/or surface(s) can be accomplished with the use of one or more of any effective, (i) heater(s) (660) to heat any air/gas flow(s) that can be moved through these various location(s), (ii) dehumidification apparatus(s) (74) to dry or dehumidify any air/gas flow(s) that can be moved through these various location(s), (iii) vacuum apparatus(s) and/or negative pressure device(s) (98), to evacuate the air/gas(s) and drop the air/gas pressure within these location(s) causing any liquid(s) present in these area(s) to transfer into gas(s) that can then be removed by the vacuum or negative pressure device(s) (98), and/or as fresh air/gas(s), that is preferably and without limitation, effectively filtered, can later be flowed through these area(s) and/or location(s), and/or (iv) preferably, flowing fresh air/gas(s), that is preferably and without limitation, effectively filtered, and even more preferably, and without limitation, that is also effectively heated to any effective temperature(s), through these area(s) and/or location(s).

It is preferred, without limitation, that at least one or more of the following drying steps can be followed, if needed, before the applied agent(s) is deployed:

(i) dehumidified air/gas(s) can be flowed into and effectively recirculated through one or more location(s) and/or areas such as, but not limited to any, container holding chamber(s) (265), removable treatment enclosure(s) (230), and/or any gripping mechanism(s) (135), for any effective duration of time(s), then (ii) more preferably, and without limitation, effectively heated (660) fresh air/gas(s) (380), that is also preferably and without limitation, effectively filtered, is effectively flowed into and through, and/or also effectively recirculated through, various location(s) and area(s) such as, but not limited to any, container holding chamber(s) (265), removable treatment enclosure(s) (230), and/or any gripping mechanism(s) (135), for any effective duration of time(s), then (iii) optionally, and without limitation, effectively filtered fresh air (380) can also be effectively flowed into and through, and/or also effectively recirculated through, various location(s) and area(s) such as, but not limited to any, container holding chamber(s) (265), removable treatment enclosure(s) (230), and/or any gripping mechanism(s) (135), for any effective duration(s) of time(s) and at any suitable and effective time(s) then, However, it is even more preferred, without limitation, that at least the following drying steps can be followed, if needed, before the applied agent(s) is effectively deployed:

(i) any effective vacuum and/or effective atmospheric pressure that can cause all liquid(s) within location(s) such as, but not limited to any, container holding chamber(s) (265) and/or removable treatment enclosure(s) (230), to change into a gaseous state, is established by one or more of any effective negative pressure device(s) (98) in location(s) such as, but not limited to any, container holding chamber(s) (265) and/or removable treatment enclosure(s) (230), for any effective amount of time(s), then, (ii) effectively filtered fresh air and/or gas(s), that can also be, without limitation, effectively heated at any suitable and effective time(s), is flowed into and through the container holding chamber(s) (265), removable treatment enclosure(s) (230), and/or any gripping mechanism(s) (135), for any effective duration of time(s) and at any effective time(s), to at least fill the container holding chamber(s) (265) and/or removable treatment enclosure(s) (230), with any effective quantity of air/gas(s), then, (c) if applicable, desired, and/or if it hasn't already been completed before the previous step(s) have already taken place which is, without limitation, preferred, effectively moving and/or positioning one or more of any suitable, open package(s), open removable package(s) (229), and/or one or more of any effectively open packaging material(s) (495), into any effective location(s) within the container holding chamber(s) (265), so the object(s) (01) can be located and/or dropped later, into the open package(s), open removable package(s) (229), and/or one or more of any effectively open packaging material(s) (495), after being effectively, treated with any applied agent(s) (20)(65), dried, and/or any other processing step(s).

(d) effectively treating the various area(s), location(s), and/or surface(s), such as, but not limited to, those found in any, space(s), area(s), and/or compartment(s), such as, but not limited to any, container holding chamber(s) (265) and/or removable treatment enclosure(s) (230), as well as any object(s) (01), and/or any gripping mechanism(s) (135), that can be located within these space(s) and/or area(s), with any aerosol(s) (65), applied agent(s) (20), gas(s), and/or vapor(s), that is preferably, and without limitation, created and/or generated within and deployed from, one or more of any generation chamber(s) (15), and recirculated through the container holding chamber(s) (265), and/or any gripping mechanism(s) (135), for any effective duration of time(s) and/or for any effective number of time(s).

(e) effectively drying any targeted and treated surface(s) such as, but not limited to, those found in any, space(s), area(s), and/or compartment(s), such as, but not limited to any, container holding chamber(s) (265), removable treatment enclosure(s) (230), as well as any object(s) (01), and/or any gripping mechanism(s) (135), that can be located within these space(s) and/or area(s). The drying of any of these area(s) and/or surface(s) can be accomplished by using, for any effective amount of time, one or more of any effective, (i) heater(s) (660) to heat any air/gas flow(s) that can move through these various location(s), (ii) dehumidification apparatus(s) (74) to dry or dehumidify any air/gas flow(s) that can move through these various location(s), (iii) vacuum apparatus(s) or negative pressure device(s) (98) to evacuate the air/gas(s) and drop the air/gas pressure within these location(s) thus causing any liquid(s) present in these area(s) to transfer into gas(s) that can be removed by the vacuum or negative pressure device(s) (98) and/or as any filtered fresh air/gas(s) (380) can later be flowed through these area(s) and/or location(s), and/or (iv) preferably, flowing fresh air/gas(s), that is preferably and without limitation, effectively filtered, and even more preferably, and without limitation, that is also effectively heated to any effective temperature(s), through these area(s) and/or location(s).

It is preferred, without limitation, that at least one or more of the following drying steps can follow after the applied agent(s) are fully and efficaciously deployed:

(i) dehumidified air/gas(s) can be effectively flowed into and through, and/or effectively recirculated through, the container holding chamber(s) (265), removable treatment enclosure(s) (230), and/or any gripping mechanism(s) (135), for any effective duration of time(s), and any effective number of time(s), (ii) more preferably, and without limitation, effectively heated fresh air/gas(s) (380), that is also preferably and without limitation, effectively filtered, is effectively flowed into and through, and/or effectively recirculated through, the container holding chamber(s) (265), removable treatment enclosure(s) (230), and/or any gripping mechanism(s) (135), for any effective amount of time(s) and any effective number of time(s), for various purposes including, but not limited to, to dry any targeted area(s), space(s), and/or surface(s), and/or to effectively remove any unwanted gas(s)/vapor(s), and/or to drop the concentration of any unwanted gas(s)/vapor(s) within the container holding chamber(s) (265) and/or removable treatment enclosure(s) (230), to, within, and/or under, any acceptable limits and/or government agency standards, then (iii) optionally, and without limitation, effectively filtered fresh air/gas(s) can be effectively flowed through, and/or effectively recirculated through, the container holding chamber(s) (265), removable treatment enclosure(s) (230), and/or any gripping mechanism(s) (135), also for any effective amount of time(s) and any effective number of time(s), for various purposes including, but not limited to, to cool and/or dry any targeted area(s), space(s), and/or surface(s), and/or to effectively remove any unwanted gas(s)/vapor(s), and/or to drop the concentration of any unwanted gas(s)/vapor(s) within location(s) such as, but not limited to any, container holding chamber(s) (265) and/or removable treatment enclosure(s) (230), to, within, and/or under, any acceptable limits and/or government agency standards.

However, it is more preferred, without limitation, that at least one or more of the following drying steps can be followed after the applied agent(s) are fully and efficaciously deployed:

(i) any effective vacuum and/or effective atmospheric pressure that can cause all liquid(s) within location(s) such as, but not limited to any, container holding chamber(s) (265) and/or removable treatment enclosure(s) (230), to change into a gaseous state, is established by one or more of any effective negative pressure device(s) (98) in location(s) such as, but not limited to any, container holding chamber(s) (265) and/or removable treatment enclosure(s) (230), for any effective amount of time, then, (ii) effectively filtered fresh air and/or gas(s) (380) is effectively flowed into and through the container holding chamber(s) (265), removable treatment enclosure(s) (230), and/or any gripping mechanism(s) (135), for any effective duration and number of time(s), for various purposes including, but not limited to, to dry any targeted area(s), space(s), and/or surface(s), and/or effectively removing any unwanted gas(s)/vapor(s), to at least fill the container holding chamber(s) (265) and/or removable treatment enclosure(s) (230), with any effective quantity of air/gas(s), and/or to drop the concentration of any unwanted gas(s)/vapor(s) within location(s) such as, but not limited to any, container holding chamber(s) (265) and/or removable treatment enclosure(s) (230), to, within, and/or under, any acceptable limits and/or government agency standards.

(f) if applicable and not already completed: effectively moving and/or positioning one or more of any suitable, open package(s), open removable package(s) (229), and/or one or more of any effectively open packaging material(s) (495), into any effective location(s) within the container holding chamber(s) (265), so the one or more object(s) (01) can be located and/or dropped into the open package(s), open removable package(s) (229), and/or one or more of any effectively open packaging material(s) (495).

(g) effectively locating, but preferably and without limitation, dropping the treated, and also preferably and without limitation, dried, object(s) (01), and/or removable treatment enclosure(s) (230), into the open package(s), open removable package(s) (229), and/or one or more of any effectively open packaging material(s) (495).

(h) effectively sealing and/or closing the open package(s), open removable package(s) (229), and/or one or more of any effectively open packaging material(s) (495), in any effective manner and/or with any effective means, known to those skilled in the art, if applicable, needed, and/or desired.

(i) removing the package(s), open removable package(s) (229), and/or effectively sealed and/or closed package(s) (720) from the container holding chamber(s) (265) at any effective and/or desired time(s).

Without being limited, before, during, and/or after, each and/or any processing step(s) such as, but not limited to any, pre-drying of any object(s) (01) surface(s), pre-cooling of any object(s) (01) surface(s), treating the various surface(s) of any object(s) (01), with any gas(s), vapor(s), aerosol(s) and/or applied agent(s) (20), drying of any object(s) (01) surface(s), heating any of any object(s) (01) surface(s), cooling of any object(s) (01) surface(s), flowing any fresh air/gas(s), and/or purging any atmosphere(s) in any location(s), the object(s) (01) can be effectively moved, for one or more time(s), but preferably and without limitation, at least any effective number of time(s), and for any effective duration of time(s), between the one or more, and preferably, and without limitation, at least a plurality, of any suitable and effective gripping mechanism(s) (135), and more particularly between any suitable and effective "primary gripping mechanism(s)" (109)(135) and the one or more of any suitable and effective "secondary gripping mechanism(s)" (110)(135), and even more particularly, effectively moved back and forth between the one or more of any suitable and effective, first used, initially used, and/or initially interfaced with the various object(s) (01), gripping mechanism(s) (135) and/or "primary gripping mechanism(s)" (109)(135), and the one or more of any suitable and effective, secondary, following, subsequently used, and/or subsequently interfaced with the various object(s) (01), gripping mechanism(s) (135) and/or "secondary gripping mechanism(s)" (110) (135), at any effective time(s), and for any effective number and effective duration of time(s), so all of the various surfaces or targeted surface(s) of the object(s) (01) and/or any connected part(s) and component(s), are effectively, treated, processed, and/or effectively subjected to all of the same processing, processing step(s), and treatment activities. Without being limited, the various object(s) (01) can be passed back and forth between the various gripping mechanism(s) (135) during each step of any of the various, processing(s), treatment(s), and/or drying(s), step(s), for any effective number of time(s), and for any effective duration of time(s).

It is preferred, without limitation, that after each processing step(s) occurs such as, but not limited to any, pre-drying of any object(s) (01) surface(s), pre-cooling of any object(s) (01) surface(s), treating the various surface(s) of any object(s) (01), with any gas(s), vapor(s), aerosol(s) and/or applied agent(s) (20), drying of any object(s) (01) surface(s), heating any of any object(s) (01) surface(s), cooling of any object(s) (01) surface(s), flowing any fresh air/gas(s) in any location(s), and/or purging any atmosphere(s) in any location(s), the object(s) (01) are effectively moved and/or transferred back to the one or more "primary gripping mechanism(s)" (109)(135). However, and without limitation, the one or more object(s) (01) can also start any of the various processing step(s) interfaced with any suitable and effective, "primary gripping mechanism(s)" (109)(135) and/ or the "secondary gripping mechanism(s)" (110)(135). It is more preferred, without limitation, that the object(s) (01) start the first of the various processing step(s) by being removably interfaced with the "primary gripping mechanism(s)" (109)(135), and end the various processing step(s) removably interfaced with the "secondary gripping mechanism(s)" (110)(135).

Without being limited, the one or more object(s) (01) can be preferably, and without limitation, dropped into the one or more open package(s), open removable package(s) (229), and/or one or more of any effectively open packaging material(s) (495), when all of the, gripping mechanism(s) (135), "primary gripping mechanism(s)" (109) (135) and/or the "secondary gripping mechanism(s)" (110)(135), that is in contact with the object(s) (01), release the object(s) (01), at any suitable and effective time(s), but preferably, and without limitation, at about the same time(s).

It is preferred, without limitation, that all of the various means to hold and/or support the object(s) (01) such as, but not limited to any, gripping mechanism(s) (135), are effectively moved to any suitable and effective location(s) and/or positions, preferably and without limitation, for any suitable and effective temporary period(s) of time(s), in any suitable and effective manner known to those skilled in the art, so the one or more released object(s) (01) can be effectively and/or safely, released, dropped, and/or positioned, into any, open package(s), open removable package(s) (229), and/or one or more of any effectively open packaging material(s) (495), at any suitable and effective time(s), without any obstructions, and/or any blocking, hardware, apparatus(s), part(s) and/or gripping mechanism(s) (135) in the path of the falling object(s) (01). This can be accomplished in various ways (not shown) such as, but not limited to, using any automated means known to those skilled in the art, to swing, pivot, pivot up and/or down, locate, and/or temporarily position, any gripping mechanism(s) (135), so there are no collisions with any falling object(s) (01).

Alternatively, and without limitation, the various gripping mechanism(s) (135) can also be effectively timed, in any manner known to those skilled in the art, so the one or more lowest gripping mechanism(s) (135) is the only gripping mechanism(s) (135) that is in contact with the object(s) (01) when it is time to release the object(s) (01) into the one or more of any, open package(s), open removable package(s) (229), and/or one or more of any effectively open packaging material(s) (495). In another aspect, and without limitation, the one or more gripping mechanism(s) (135) can be suitably and effectively, mounted, positioned, and/or located, horizontally and facing downward (not shown), so any released object(s) (01) can fall effectively into the one or more of any, open package(s), open removable package(s) (229), and/or one or more of any effectively open packaging material(s) (495), without any gripping mechanism(s) (135), part(s), component(s), obstacle(s), and/or obstruction(s), in the path of any falling object(s) (01).

It is preferred, without limitation, that all of the various means to hold and/or support the object(s) (01) such as, but not limited to any, primary gripping mechanism(s) (109) and/or the secondary gripping mechanism(s) (110), are effectively moved to any suitable and effective location(s) and/or positions, preferably and without limitation, for any suitable and effective temporary period(s) of time(s), in any suitable and effective manner known to those skilled in the art, so the one or more released object(s) (01) can be effectively and/or safely, released, dropped, and/or positioned, into any, open package(s), open removable package(s) (229), and/or one or more of any effectively open packaging material(s) (495), at any suitable and effective time(s), without any obstructions, and/or any blocking, hardware, apparatus(s), part(s), primary gripping mechanism(s) (109) and/or the secondary gripping mechanism(s) (110), in the path of the falling object(s) (01). This can be accomplished in various ways such as, but not limited to, using any automated means known to those skilled in the art, to swing, move, tilt, angle, pivot, pivot up and/or down, locate, and/or temporarily position, any primary gripping mechanism(s) (109) and/or the secondary gripping mechanism(s) (110), so there are no collisions with any falling object(s) (01).

According to an embodiment, and referring to FIGS. 10-11, FIGS. 24-25, and FIGS. 103-108, and without limitation, the one or more of any suitable and effective, start beam(s) (49) and opposing beam(s) (50) can also, and preferably and without limitation, include any of the various, function(s), feature(s), attribute(s), and/or component(s), of any of the object support(s) (84) and/or any movable object support(s) (84), including, but not limited to any, opening(s) (85). Alternatively, and without limitation, any of the object support(s) (84) and/or any movable object support(s) (84), can also include any of the various, function(s), feature(s), attribute(s), and/or component(s), of any start beam(s) (49) and opposing beam(s) (50). Without being limited, any, start beam(s) (49), opposing beam(s) (50), object support(s) (84), and/or movable object support(s) (84), can be used interchangeably, and without limitation, also have any equal, meaning(s), function(s), functionality(s), attribute(s), use(s), application(s), and/or operating characteristic(s).

Referring to FIGS. 24-25, and FIGS. 103-111, and according to an embodiment, and without limitation, a more detailed description of the use of the one or more movable object support(s) (84)(49)(50) is given, for any treatment(s), drying(s), processing(s), and/or packaging(s), activities and/or steps for any, surface(s), space(s), area(s), and/or compartment(s), such as, but not limited to any area(s) and/or surface(s) within, one or more of any, container holding chamber(s) (265), and/or within and/or outside of any, open enclosure(s), open removable package(s) (229), open package(s) and/or packaging material(s) (495), enclosure(s), treatment enclosure(s), open treatment enclosure(s), open removable treatment enclosure(s), package(s), removable package(s), and/or removable treatment enclosure(s) (230), that can be preferably and without limitation, located within the container holding chamber(s) (265), as well as one or more of any surfaces and/or area(s) of any, object(s) (01), and/or any means to hold, treat, dry, process, and/or support, any object(s) (01) within the container holding chamber(s) (265) such as, but not limited to any, object support(s) (84), tube disconnect apparatus(s) (462), plug decoupling apparatus(s) (536), support and release apparatus(s) (606), pressure interface assembly (68), enhanced object(s) holder(s) (155), and/or any other part(s) and/or apparatus(s) meant to effectively hold, cradle, treat, process, dry, and/or support, any object(s) (01) and/or any connected part(s) and component(s), but more particularly, and without limitation, any one or more of any suitable and effective movable object support(s) (84)(49)(50), that can be located within these space(s) and/or area(s), can include, but is not limited to:

(a) locating one or more of any object(s) (01) within one or more of any suitable and effective container holding chamber(s) (265). It is preferred, without limitation, that the one or more object(s) (01) are removably interfaced with one or more, but preferably and without limitation, at least an effective number, of any suitable and effective movable object support(s) (84)(49)(50), that are preferably, and without limitation, located within the one or more container holding chamber(s) (265) and/or removable treatment enclosure(s) (230).

Without limitation, the interior of the container holding chamber(s) (265) and/or removable treatment enclosure(s) (230), effectively, connects, communicates, and/or interfaces, with one or more of any suitable and effective, apparatus(s), substance(s), and/or supplies of any, air, gas(s), agent(s), and/or substance(s), such as, but not limited to any, aerosol(s) and/or vapor(s) supply(s) (15, 20, 65), vacuum and/or negative pressure(s) (98), fresh air/gas supply(s) (17, 51, 38), dehumidified air/gas(s) supply(s) (74), heated air/gas(s) supply(s) (660), heated and filtered air/gas(s), filtered air/gas(s) supply(s) (75)(53), heated and filtered fresh air/gas(s) supply(s). Without limitation, the flows of any, applied agent(s), aerosol(s), gas(s), and/or vapor(s) (20, 65), fresh air/gas(s), dehumidified air/gas(s), heated air/gas(s), and/or filtered air/gas(s), can be preferably and without limitation, supplied to, flowed through, and/or more preferably and without limitation, supplied to and recirculated through at any effective time(s) and duration of time(s), location(s) such as, but not limited to any: (i) container holding chamber(s) (265), (ii) movable object support(s) (84)(49)(50), (iii) removable treatment enclosure(s) (230), and/or (iv) various apparatus(s) such as, but not limited to any, aerosol(s) and/or gas(s) generation and/or deployment chamber(s) (15), means to dehumidify any air/gas(s) (74), means to heat any air/gas(s) (660), and/or means to filter any air/gas(s) (75, 53), at any suitable and effective time(s) and for any suitable and effective duration(s) of time(s). Also, and without being limited, any suitable and effective valve(s) (35) can be opened and closed at one or more of any suitable and effective time(s), for any suitable and effective purpose(s), and for any effective duration of time(s), to control any entry and/or exit of any flow(s) of any air/gas(s) and/or substance(s) such as, but not limited to any, air, fresh air, gas(s), applied agent(s), vapor(s), aerosol(s), dehumidified air/gas(s), heated air/gas(s), vacuum or negative pressure atmosphere, and/or filtered air/gas(s), into, out of, and/or through, the various area(s), space(s), and/or location(s), such as, but not limited to any, container holding chamber(s) (265), removable treatment enclosure(s) (230), and/or any means to hold, support, treat, dry and/or process, any object(s) (01), such as, but not limited to any, movable object support(s) (84)(49)(50), that can be effectively located within the container holding chamber(s) (265) and/or removable treatment enclosure(s) (230).

(b) effectively drying any targeted surface(s) such as, but not limited to, those found in any, space(s), area(s), and/or compartment(s), such as, but not limited to any, container holding chamber(s) (265) and/or removable treatment enclosure(s) (230), as well as any object(s) (01), and/or any means to hold, support, treat, dry and/or process, any object(s) (01), such as, but not limited to any, movable object support(s) (84)(49)(50), that can be located within these space(s) and/or area(s). The drying of any of these area(s) and/or surface(s) can be accomplished with the use of one or more of any effective, (i) heater(s) (660) to heat any air/gas flow(s) that can be moved through these various location(s), (ii) dehumidification apparatus(s) (74) to dry or dehumidify any air/gas flow(s) that can be moved through these various location(s), (iii) vacuum apparatus(s) and/or negative pressure device(s) (98), to evacuate the air/gas(s) and drop the air/gas pressure within these location(s) causing any liquid(s) present in these area(s) to transfer into gas(s) that can then be removed by the vacuum or negative pressure device(s) (98), and/or as fresh air/gas(s), that is preferably and without limitation, effectively filtered, can later be flowed through these area(s) and/or location(s), and/or (iv) preferably, flowing fresh air/gas(s), that is preferably and without limitation, effectively filtered, and even more preferably, and without limitation, that is also effectively heated to any effective temperature(s), through these area(s) and/or location(s).

It is preferred, without limitation, that at least one or more of the following drying steps can be followed, if needed, before the applied agent(s) is deployed:

(i) dehumidified air/gas(s) can be flowed into and effectively recirculated through one or more location(s) and/or areas such as, but not limited to any, container holding chamber(s) (265), removable treatment enclosure(s) (230), and/or any movable object support(s) (84)(49)(50), for any effective duration of time(s), then (ii) more preferably, and without limitation, effectively heated (660) fresh air/gas(s) (380), that is also preferably and without limitation, effectively filtered, is effectively flowed into and through, and/or also effectively recirculated through, various location(s) and area(s) such as, but not limited to any, container holding chamber(s) (265), removable treatment enclosure(s) (230), and/or any movable object support(s) (84)(49) (50), for any effective duration of time(s), then (iii) optionally, and without limitation, effectively filtered fresh air (380) can also be effectively flowed into and through, and/or also effectively recirculated through, various location(s) and area(s) such as, but not limited to any, container holding chamber(s) (265), removable treatment enclosure(s) (230), and/or any movable object support(s) (84) (49)(50), for any effective duration(s) of time(s) and at any suitable and effective time(s) then, However, it is even more preferred, without limitation, that at least the following drying steps can be followed, if needed, before the applied agent(s) is effectively deployed:

(i) any effective vacuum and/or effective atmospheric pressure that can cause all liquid(s) within location(s) such as, but not limited to any, container holding chamber(s) (265) and/or removable treatment enclosure(s) (230), to change into a gaseous state, is established by one or more of any effective negative pressure device(s) (98) in location(s) such as, but not limited to any, container holding chamber(s) (265) and/or removable treatment enclosure(s) (230), for any effective amount of time(s), then, (ii) effectively filtered fresh air and/or gas(s), that can also be, without limitation, effectively heated at any suitable and effective time(s), is flowed into and through the container holding chamber(s) (265), removable treatment enclosure(s) (230), and/or any movable object support(s) (84)(49)(50), for any effective duration of time(s) and at any effective time(s), to at least fill the container holding chamber(s) (265) with any effective quantity of air/gas(s), then, (c) if applicable, desired, and/or if it hasn't already been completed before the previous step(s) have already taken place which is, without limitation, preferred, effectively moving and/or positioning one or more of any suitable, open package(s), open removable package(s) (229), and/or one or more of any effectively open packaging material(s) (495), into any effective location(s) within the container holding chamber(s) (265), so the object(s) (01) can be located and/or dropped later, into the open package(s), open removable package(s) (229), and/or one or more of any effectively open packaging material(s) (495), after being effectively, treated with any applied agent(s) (20)(65), dried, and/or any other processing step(s).

(d) effectively treating the various area(s), location(s), and/or surface(s), such as, but not limited to, those found in any, space(s), area(s), and/or compartment(s), such as, but not limited to any, container holding chamber(s) (265), removable treatment enclosure(s) (230), as well as any object(s) (01), and/or any movable object support(s) (84) (49)(50), that can be located within these space(s) and/or area(s), with any aerosol(s) (65), applied agent(s) (20), gas(s), and/or vapor(s), that is preferably, and without limitation, created and/or generated within and deployed from, one or more of any generation chamber(s) (15), and recirculated through the container holding chamber(s) (265), removable treatment enclosure(s) (230), and/or any movable object support(s) (84)(49) (50), for any effective duration of time(s) and/or for any effective number of time(s).

(e) effectively drying any targeted and treated surface(s) such as, but not limited to, those found in any, space(s), area(s), and/or compartment(s), such as, but not limited to any, container holding chamber(s) (265), removable treatment enclosure(s) (230), as well as any object(s) (01), and/or any movable object support(s) (84)(49)(50), that can be located within these space(s) and/or area(s). The drying of any of these area(s) and/or surface(s) can be accomplished by using, for any effective amount of time, one or more of any effective, (i) heater(s) (660) to heat any air/gas flow(s) that can move through these various location(s), (ii) dehumidification apparatus(s) (74) to dry or dehumidify any air/gas flow(s) that can move through these various location(s), (iii) vacuum apparatus(s) or negative pressure device(s) (98) to evacuate the air/gas(s) and drop the air/gas pressure within these location(s) thus causing any liquid(s) present in these area(s) to transfer into gas(s) that can be removed by the vacuum or negative pressure device(s) (98) and/or as any filtered fresh air/gas(s) (380) can later be flowed through these area(s) and/or location(s), and/or (iv) preferably, flowing fresh air/gas(s), that is preferably and without limitation, effectively filtered, and even more preferably, and without limitation, that is also effectively heated to any effective temperature(s), through these area(s) and/or location(s).

It is preferred, without limitation, that at least one or more of the following drying steps can follow after the applied agent(s) are fully and efficaciously deployed:

(i) dehumidified air/gas(s) can be effectively flowed into and through, and/or effectively recirculated through, the container holding chamber(s) (265) and/or removable treatment enclosure(s) (230), and/or any movable object support(s) (84)(49)(50), for any effective duration of time(s), and any effective number of time(s), (ii) more preferably, and without limitation, effectively heated fresh air/gas(s) (380), that is also preferably and without limitation, effectively filtered, is effectively flowed into and through, and/or effectively recirculated through, the container holding chamber(s) (265), and/or removable treatment enclosure(s) (230), and/or any movable object support(s) (84)(49)(50), for any effective amount of time(s) and any effective number of time(s), for various purposes including, but not limited to, to dry any targeted area(s), space(s), and/or surface(s), and/or to effectively remove any unwanted gas(s)/vapor(s), and/or to drop the concentration of any unwanted gas(s)/vapor(s) within the container holding chamber(s) (265) and/or removable treatment enclosure(s) (230), to, within, and/or under, any acceptable limits and/or government agency standards, then (iii) optionally, and without limitation, effectively filtered fresh air/gas(s) can be effectively flowed through, and/or effectively recirculated through, the container holding chamber(s) (265), and/or any movable object support(s) (84)(49)(50), also for any effective amount of time(s) and any effective number of time(s), for various purposes including, but not limited to, to cool and/or dry any targeted area(s), space(s), and/or surface(s), and/or to effectively remove any unwanted gas(s)/vapor(s), and/or to drop the concentration of any unwanted gas(s)/vapor(s) within location(s) such as, but not limited to any, container holding chamber(s) (265) and/or removable treatment enclosure(s) (230), to, within, and/or under, any acceptable limits and/or government agency standards.

However, it is more preferred, without limitation, that at least one or more of the following drying steps can be followed after the applied agent(s) are fully and efficaciously deployed:

(i) any effective vacuum and/or effective atmospheric pressure that can cause all liquid(s) within location(s) such as, but not limited to any, container holding chamber(s) (265) and/or removable treatment enclosure(s) (230), to change into a gaseous state, is established by one or more of any effective negative pressure device(s) (98) in location(s) such as, but not limited to any, container holding chamber(s) (265), and/or removable treatment enclosure(s) (230), for any effective amount of time, then, (ii) effectively filtered fresh air and/or gas(s) (380) is effectively flowed into and through the container holding chamber(s) (265) and/or removable treatment enclosure(s) (230), and/or any movable object support(s) (84)(49)(50), for any effective duration and number of time(s), for various purposes including, but not limited to, to dry any targeted area(s), space(s), and/or surface(s), and/or effectively removing any unwanted gas(s)/vapor(s), to at least fill the container holding chamber(s) (265) and/or removable treatment enclosure(s) (230), with any effective quantity of air/gas(s), and/or to drop the concentration of any unwanted gas(s)/vapor(s) within location(s) such as, but not limited to any, container holding chamber(s) (265) and/or removable treatment enclosure(s) (230), to, within, and/or under, any acceptable limits and/or government agency standards.

(f) if applicable and not already completed: effectively moving and/or positioning one or more of any suitable, open package(s), open removable package(s) (229), removable treatment enclosure(s) (230), and/or one or more of any effectively open packaging material(s) (495), into any effective location(s) within the container holding chamber(s) (265), so the one or more object(s) (01) and/or removable treatment enclosure(s) (230), can be located and/or dropped into the open package(s), open removable package(s) (229), and/or one or more of any effectively open packaging material(s) (495).

(g) effectively locating, but preferably and without limitation, dropping the treated, and also preferably and without limitation, dried, object(s) (01) into the open package(s), open removable package(s) (229), and/or one or more of any effectively open packaging material(s) (495).

(h) effectively sealing and/or closing the open package(s), open removable package(s) (229), and/or one or more of any effectively open packaging material(s) (495), in any effective manner and/or with any effective means, known to those skilled in the art, if applicable, needed, and/or desired.

(i) removing the package(s), open removable package(s) (229), and/or effectively sealed and/or closed package(s) (720) from the container holding chamber(s) (265) at any effective and/or desired time(s).

Without being limited, before, during, and/or after, each and/or any processing step(s) such as, but not limited to any, pre-drying of any object(s) (01) surface(s), pre-cooling of any object(s) (01) surface(s), treating the various surface(s) of any object(s) (01), with any gas(s), vapor(s), aerosol(s) and/or applied agent(s) (20), drying of any object(s) (01) surface(s), heating any of any object(s) (01) surface(s), cooling of any object(s) (01) surface(s), flowing any fresh air/gas(s), and/or purging any atmosphere(s) in any location(s), the object(s) (01) can be effectively moved, for one or more time(s), but preferably and without limitation, at least any effective number of time(s), and for any effective duration of time(s), between the one or more, and preferably, and without limitation, at least a plurality, of any suitable and effective movable object support(s) (84)(49)(50), and more particularly, effectively moved, back and forth between the one or more of any suitable and effective, first used, initially used, and/or initially interfaced with the various object(s) (01), movable object support(s) (84)(49), such as, but not limited to any, start beam(s), primary movable object support(s), initial object support(s), initial movable object support(s) (Herein called "start beam(s)" (84)(49)), and the one or more of any suitable and effective, secondary, following, subsequently used, and/or subsequently interfaced with the various object(s) (01), movable object support(s) (84)(50), such as, but not limited to any, opposing beam(s), secondary beam(s), subsequent beam(s), subsequent object support(s), secondary movable object support(s), secondary object support(s), secondary movable object support(s) (Herein called "secondary beam(s)" (84)(50)), at any effective time(s), and for any effective number and effective duration of time(s), so all of the various surfaces or targeted surface(s) of the object(s) (01) and/or any connected part(s) and component(s), are effectively, treated, processed, and/or effectively subjected to all of the same processing, processing step(s), and treatment activities.

It is preferred, without limitation, that after each processing step(s) occurs such as, but not limited to any, pre-drying of any object(s) (01) surface(s), pre-cooling of any object(s) (01) surface(s), treating the various surface(s) of any object(s) (01), with any gas(s), vapor(s), aerosol(s) and/or applied agent(s) (20), drying of any object(s) (01) surface(s), heating any of any object(s) (01) surface(s), cooling of any object(s) (01) surface(s), flowing any fresh air/gas(s) in any location(s), and/or purging any atmosphere(s) in any location(s), the object(s) (01) are effectively moved and/or transferred back to the one or more start beam(s) (84)(49). However, and without limitation, the one or more object(s) (01) can also start any of the various processing(s), drying(s), and/or treatment(s), step(s) interfaced with either the start beam(s) (84)(49) and/or the secondary beam(s) (84)(50). It is more preferred, without limitation, that the object(s) (01) start the various processing(s), treatment(s), and/or drying(s), step(s) by being interfaced with the start beam(s) (84)(49), and end the various processing(s), drying(s), and/or treatment(s), step(s) interfaced with the secondary beam(s) (84)(50).

Without being limited, the one or more object(s) (01) can be preferably, and without limitation, dropped into the one or more open package(s), open removable package(s) (229), and/or one or more of any effectively open packaging material(s) (495), when all of the, object support(s) (84), start beam(s) (84)(49), and/or the secondary beam(s) (84)(50), that is in contact with the object(s) (01), release the object(s) (01), at any suitable and effective time(s), but preferably, and without limitation, at about the same time(s).

It is preferred, without limitation, that all of the various means to hold and/or support the object(s) (01) such as, but not limited to any, object support(s) (84), start beam(s) (84)(49), and/or secondary beam(s) (84)(50), are effectively moved to any suitable and effective location(s) and/or positions, preferably and without limitation, for any suitable and effective temporary period(s) of time(s), in any suitable and effective manner known to those skilled in the art, so the one or more released object(s) (01) can be effectively and/or safely, released, dropped, and/or positioned, into any, open package(s), open removable package(s) (229), and/or one or more of any effectively open packaging material(s) (495), at any suitable and effective time(s), without any obstructions, and/or any blocking, hardware, apparatus(s), part(s), object support(s) (84), start beam(s) (84)(49), and/or secondary beam(s) (84)(50), in the path of the falling object(s) (01). This can be accomplished in various ways such as, but not limited to, using any automated means known to those skilled in the art, to swing, pivot, pivot up and/or down, locate, and/or temporarily position, any object support(s) (84), start beam(s) (84)(49), and/or secondary beam(s) (84)(50), so there are no collisions with any falling object(s) (01).

Referring to FIGS. 103-108, and without being limited, a more detailed description of the improved movable object support(s) (84) is given. Without being limited, one or more of any object(s) (01) is removably interfaced with and/or supported by, one or more start beam(s) (84)(49). Located effectively below the one or more start beam(s) (84)(49) is one or more secondary beam(s) (84)(50). Both the start beam(s) (84) (49) and the secondary beam(s) (84)(50), have one or more suitable and effective object support(s) (84) that effectively connect with one or more of any suitable and effective object support connector(s) (800). Without being limited, the various object support(s) (84) and any associated part(s), can be effectively located at any effective distance(s) above the floor(s) (265) within the container holding chamber(s) (265).

Without being limited, the one or more object support connector(s) (800) can suitably and effectively connect with the one or more of any suitable and effective hinge(s), articulation point(s), and/or pivot point(s) (Herein called "Joint(s)") (810), all in a manner known to those skilled in the art. Optionally, and without limitation, the one or more object support(s) (84) can directly connect with the one or more joint(s) (810), all in a manner known to those skilled in the art. Without being limited, the joint(s) (810) and any connected object support(s) (84), can pivot, tilt, and/or move, in one more or more of any suitable and effective direction(s) and/or angle(s), but at least, and without limitation, effectively downward, and more preferably, and without limitation, pivoted downward, or at any other effective location(s), so the object support(s) (84) are positioned at or near any effective orientation(s) and/or angle(s), but at least and without limitation, at any effective angle(s) an/or location(s), that would cause the one or more object(s) that is removably interfaced with the object support(s) (84), to effectively slide and/or fall off and/or be removed from the object support(s) (84), and be effectively, located, positioned, and/or fall, into one or more of any, open package(s), open removable package(s) (229), and/or one or more of any effectively open packaging material(s) (495), at any suitable and effective time(s). It is preferred, without limitation, that the object support(s) (84) can pivot, angle, move, and/or tilt, downward so that they are oriented, vertically, close to or at about a vertical angle, or at or close to any vertical orientation (830).

Without being limited, the one or more joint(s) (810) can suitability and effectively connect with one or more of any suitable and effective movement and positioning apparatus(s) (870) that can effectively, move, cause to move, and/or position, the object support(s) (84) at any suitable and effective time(s), all in a manner known to those skilled in the art. It is preferred, without limitation, that the object support(s) (84) can be pivoted at any suitable and effective speed(s) or rate(s) of travel, but at least fast enough so the object(s) (01) are not damaged, and they can be effectively located within and/or into any, open package(s), open removable package(s) (229), and/or one or more of any effectively open packaging material(s) (495), at any suitable and effective time(s).

Also without being limited, the said movement and positioning apparatus(s) (870) can be directly and/or indirectly connected to one or more of any suitable and effective, positioning apparatus(s) (875), known to those skilled in the art, that can effectively move and/or position the object support(s) (84) to any suitable and effective location(s), but more preferably and without limitation, so the object support(s) (84) can travel up and/or down in any suitable and effective angle(s) and/or orientation(s), but preferably and without limitation, at least vertically and/or about vertically.

Without being limited, the one or more of any suitable and effective positioning apparatus(s) (875) can effectively interface with the one or more of any suitable and effective travel guide(s) (880) (not shown), and the travel guide(s) (880) can include, but is not limited to, one or more of any suitable and effective, rail(s), rod(s), track(s), and/or any other effective track(s), rail(s), guide(s), or any other effective travel means known to those skilled in the art, and in any effective manner known to those skilled in the art, that the positioning apparatus(s) (875) can use to effectively travel and/or move, and/or travel and/or move into one or more of any suitable and effective location(s) and/or position(s), at any effective time(s).

Without being limited, the start beam(s) (84)(49) and/or the secondary beam(s) (84)(50), can move in various effective ways to cause the object(s) (01) to transfer from the start beam(s) (84)(49) to the secondary beam(s) (84)(50), and then from the secondary beam(s) (84)(50) back to the start beam(s) (84)(49). It is preferred, without limitation, that the secondary beam(s) (84)(50) remain static, and the start beam(s) (84)(49) move down after any processing(s), drying(s), and/or treatment, step(s) are completed for the object(s), and then effectively transfer the object(s) to the secondary beam(s) (84)(50) for any of the same processing(s), drying(s), and/or treatment(s), step(s), and then the start beam(s) (84)(49) move back up to pick up the object(s) once the said one or more processing(s), drying(s), and/or treatment(s), step(s) is complete. Without being limited, this can be repeated for any number of time(s), for any duration of time(s), and for any number of processing(s), treatment(s), and/or drying(s), step(s). Also without being limited, the various object(s) (01) can be passed back and forth between the various object support(s) (84) during each step of any of the various, processing(s), treatment(s), and/or drying(s), step(s), for any effective number of time(s), and for any effective duration of time(s).

Also without being limited, after the various processing(s), drying(s), and/or treatment(s), step(s) are complete, and all of the various object(s) (01) surface(s), but at least all of the various targeted surface(s), are effectively treated, processed, and/or dried, then the object support(s) (84) that are at least in contact with the object(s) (01), and more preferably, and without limitation, all of the object support(s) (84) in the container holding chamber(s) (265), can be without limitation, effectively pivoted, and even more preferably and without limitation, pivoted effectively downward, causing the one or more object(s) (01) to fall effectively into the one or more of any, open package(s), open removable package(s) (229), open enclosure(s), and/or one or more of any effectively open packaging material(s) (495).

Referring to FIGS. 108-111 and according to an embodiment, and without limitation, a means for packaging various object(s), preferably, and without limitation, where the one or more of the said means is located effectively inside (not shown) of any container holding chamber(s) (265), is shown and described, and includes an added improvement to the current art. In situation(s) where one or more of any suitable package sealer(s) (485) such as, but not limited to any, thermal sealer(s), and/or impulse sealer(s), is mounted at any effective location(s) above the one or more of any, open package(s), open removable package(s) (229), open enclosure(s), and/or one or more of any effectively open packaging material(s) (495), the package sealer(s) (485), can present one or more physical obstruction(s) and/or obstacle(s) for dropping any object(s) into the said open package(s), open removable package(s) (229), open enclosure(s), and/or one or more of any effectively open packaging material(s) (495).

Without being limited, the present invention improves the art, by providing an effective means for the one or more of any, open package(s), open removable package(s) (229), open enclosure(s), and/or one or more of any effective, open packaging material(s) (495), to be effectively and temporarily moved out from underneath the package sealer(s) (485) in any effective direction(s), orientation(s), and/or angle(s), and more preferably and without limitation, moved in one or more of any suitable and effective lateral direction(s), that is also preferably and without limitation, parallel to the package sealer(s) (485), to one or more of any effective location(s) so that the open package(s), open removable package(s) (229), open enclosure(s), and/or one or more of any effective, open packaging material(s) (495), is effectively located and positioned, to effectively catch any object(s) that have been released by any means to releasably, hold, grip, and/or support, any object(s) (01) within the container holding chamber(s) (265) such as, but not limited to any, object support(s) (84), gripping mechanism(s) (135), tube disconnect apparatus(s) (462), plug decoupling apparatus(s) (536), support and release apparatus(s) (606), pressure interface assembly (68), and/or any other part(s) and/or apparatus(s) meant to effectively and releasably, hold, cradle, grip, and/or support, any object(s) (01) and/or any connected part(s) and component(s).

It is preferred, without limitation, that once the object(s) are effectively located within the open package(s), open removable package(s) (229), open enclosure(s), and/or one or more of any effective, open packaging material(s) (495), the open package(s), open removable package(s) (229), open enclosure(s), and/or one or more of any effective, open packaging material(s) (495) is effectively repositioned back under the package sealer(s) (485). Once the open package(s), open removable package(s) (229), open enclosure(s), and/or one or more of any effective, open packaging material(s) (495) containing the object(s) (01) is under the package sealer(s) (485), the open package(s), open removable package(s) (229), open enclosure(s), and/or one or more of any effective, open packaging material(s) (495) can either be moved up to the one or more package sealer(s) (485) and effectively sealed, and/or the one or more package sealer(s) (485) can be brought down to any of the, open package(s), open removable package(s) (229), open enclosure(s), and/or one or more of any effective, open packaging material(s) (495), and effectively seal any of the, open package(s), open removable package(s) (229), open enclosure(s), and/or one or more of any effective, open packaging material(s) (495), all in a manner known to those skilled in the art.

More particularly, and without limitation, the various open package(s), open removable package(s) (229), open enclosure(s), and/or one or more of any effective, open packaging material(s) (495), can be effectively connected to at least one, but preferably and without limitation a plurality, of lifting member(s) (520), which can be suitability connected to one or more, but preferably and without limitation a plurality, of packaging lift apparatus(s) (509). Also without being limited, the packaging lift apparatus(s) (509) can not only move vertically as previously described in the present invention, but can also travel back and forth laterally for any suitable and effective distance(s), via one or more of any suitable and effective "lateral track(s)" (815), at any suitable and effective time(s). Any suitable and effective means known to those skilled in the art, can be used to control, as well as effectively locate and move, the one or more packaging lift apparatus(s) (509) and/or any of the said, open package(s), open removable package(s) (229), open enclosure(s), and/or one or more of any effective, open packaging material(s) (495), on and/or along, the one or more lateral track(s) (815).

Without being limited, alternatively, the various open package(s), open removable package(s) (229), open enclosure(s), and/or one or more of any effective, open packaging material(s) (495), can be kept in any effective static position(s), and filled with the one or more object(s) (01), and after the one or more, open package(s), open removable package(s) (229), open enclosure(s), and/or one or more of any effective, open packaging material(s) (495), is filled with the said object(s) (01), the one or more package sealer(s) (485) can be suitably and effectively moved into one more of any suitable and effective position(s) where it can then effectively seal the said, open package(s), open removable package(s) (229), open enclosure(s), and/or one or more of any effective, open packaging material(s) (495). After the said, open package(s), open removable package(s) (229), open enclosure(s), and/or one or more of any effective, open packaging material(s) (495), is effectively sealed, the package sealer(s) (485) can then be moved away from the package sealer(s) (485), into any suitable an effective location(s). The package sealer(s) (485) can be moved and travel in any suitable manner and with any suitable means known to those skilled in the art. Without being limited, any enclosure(s) and/or packaging material(s) such as, but not limited to any, open package(s), open removable package(s) (229), open enclosure(s), and/or one or more of any effective, open packaging material(s) (495), can be located at any suitable and effective, angle(s), direction(s), and/or orientation(s), within the container holding chamber(s) (265), at any suitable and effective time(s).

Figure 70:
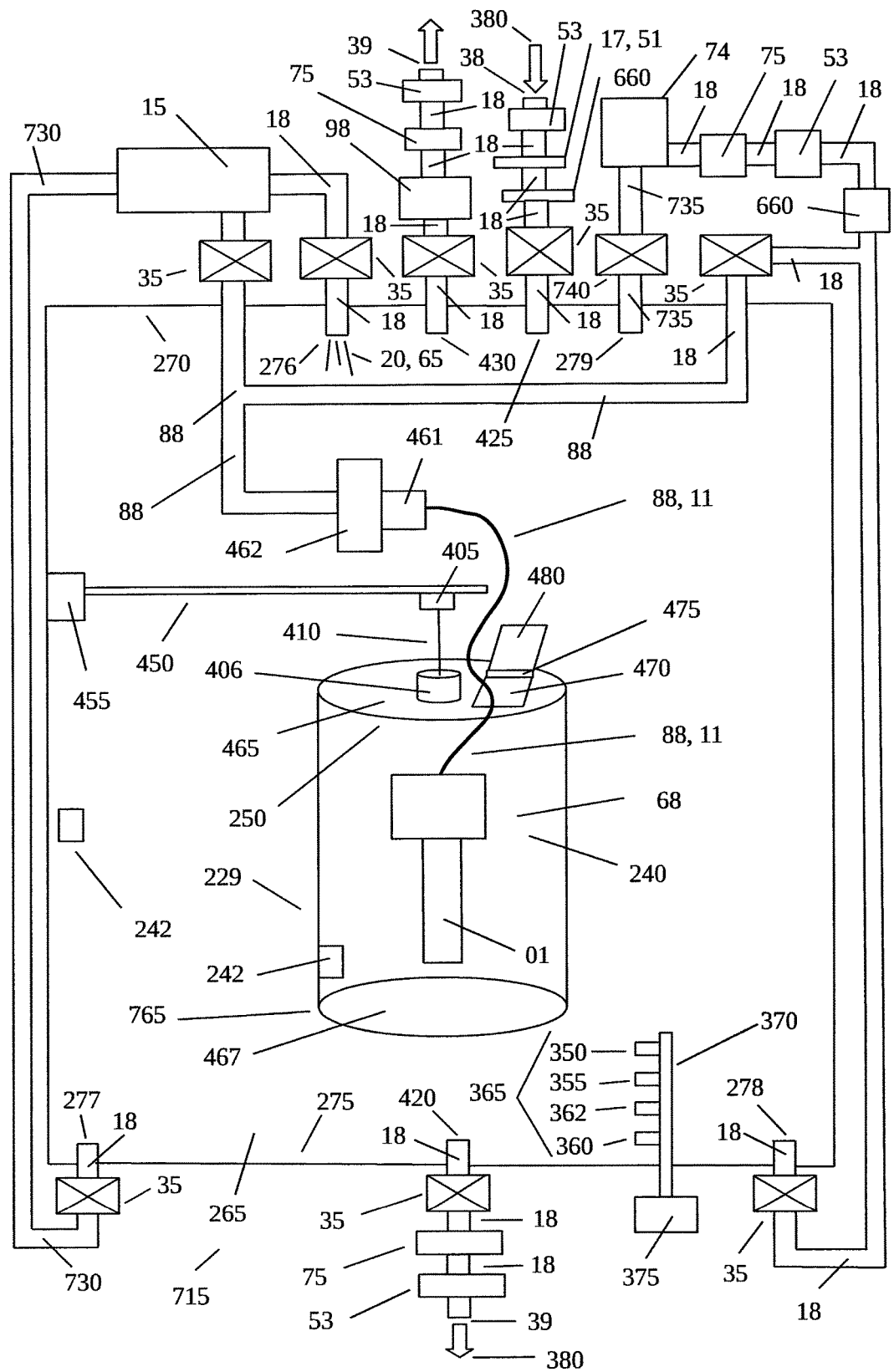
FIG. 70 is a side schematic type view of an enhanced decontamination enclosure apparatus (715), where an object and its cable is suspended inside a suspended open removable package(s) (229), with a tube connector(s) (461) and tube disconnect apparatus(s) (462) that is used for supporting, holding, and treating, the interfaced object(s), and the object(s) is suspended inside of an open removable package(s) (229), that is open on its bottom side, and an open door on its top side. The said cable leaving the open removable package(s) (229), through the said open top door (470). The object and the open removable package(s) (229) is located in the container holding chamber(s) (265).
Figure 71:
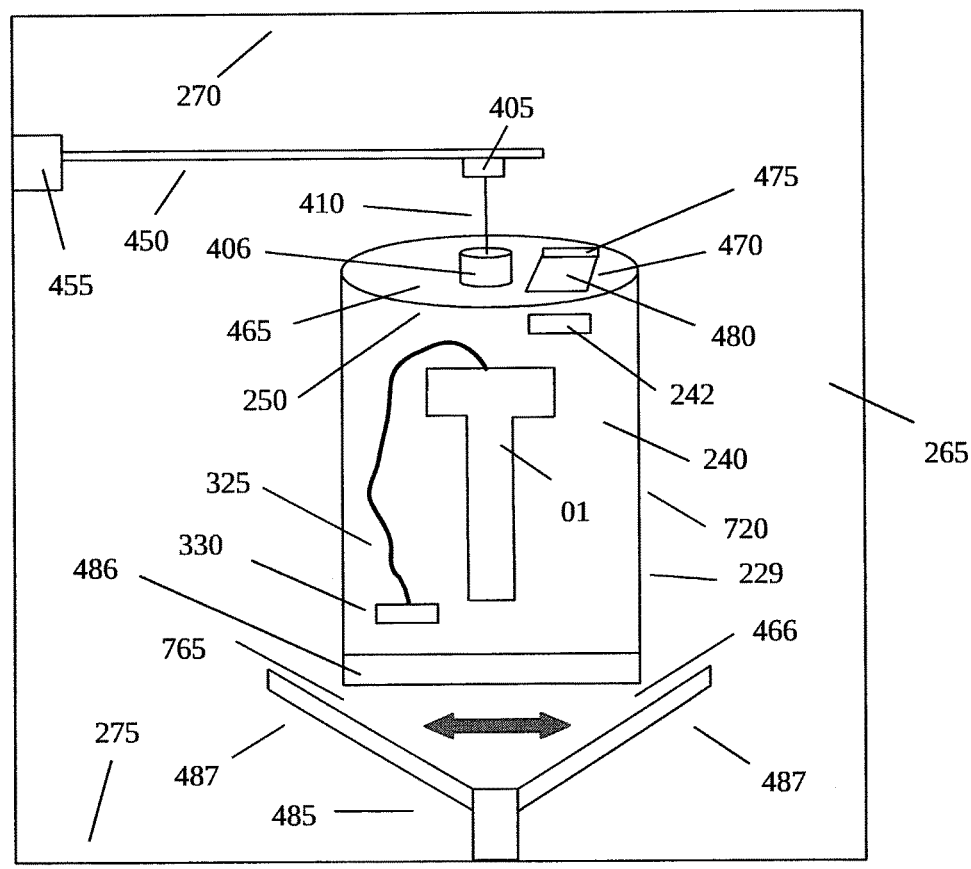
FIG. 71 is a side schematic type view of a sealed package(s) (720) with a treated and processed object inside. The top door of the sealed package(s) (720) is also effectively closed and/or sealed. The suspended open removable package(s) (229) being sealed by at least one package sealer(s) (485) inside a container holding chamber(s) (265). The sealed package(s) (720) suspended inside container holding chamber(s) (265).
Figure 72:
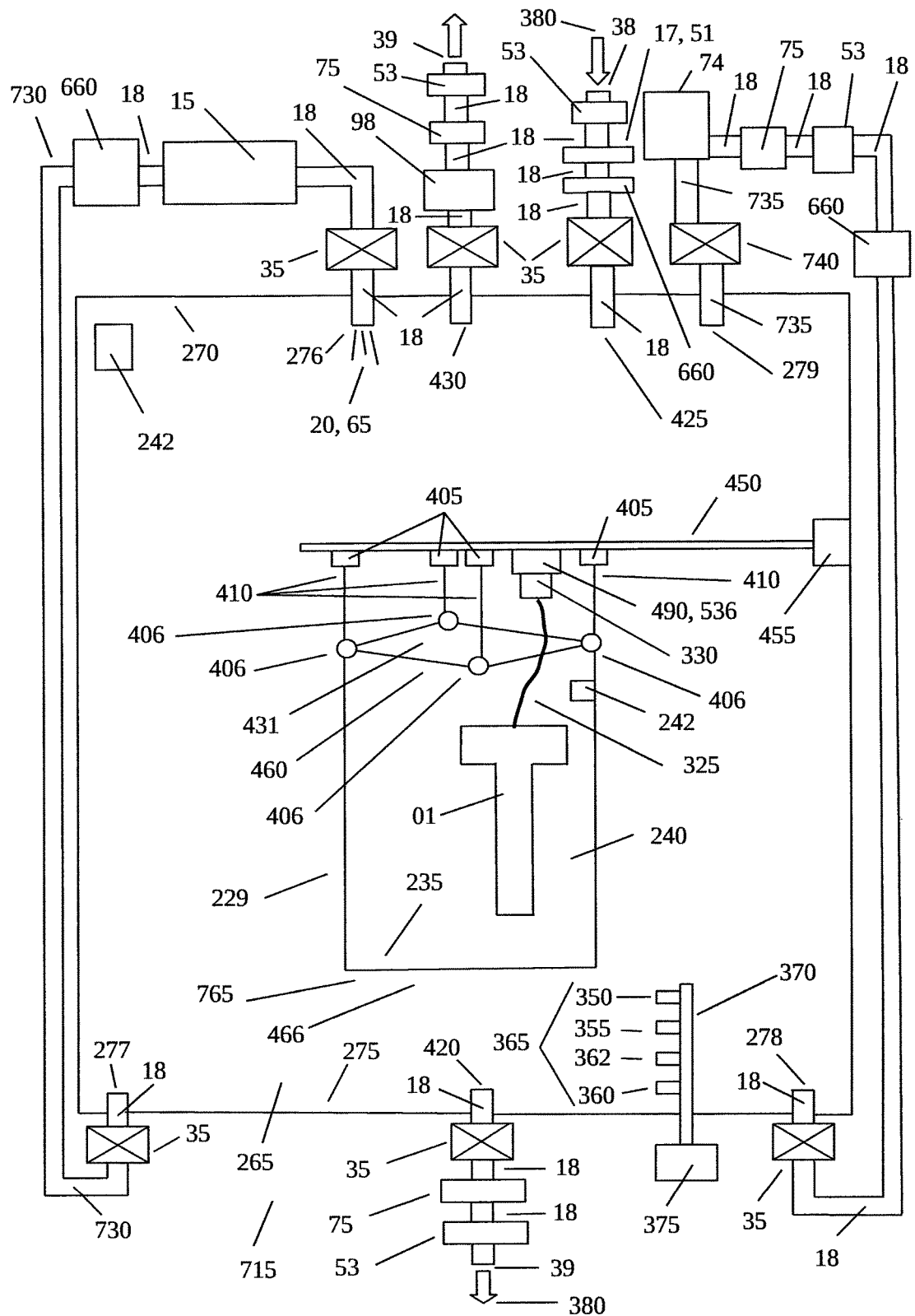
FIG. 72 is a side schematic type view of an enhanced decontamination enclosure apparatus (715), where an object and its cable is suspended inside an open removable package(s) (229) with a plug decoupling apparatus(s) (536) that is NOT plumbed in this instance, but is used for supporting, and holding, the interfaced object(s), and the object(s) is suspended inside of an open removable package(s) (229), that is open on its top side, and a closed bottom. The object and the open removable package(s) (229) is located in the container holding chamber(s) (265).
Figure 73:
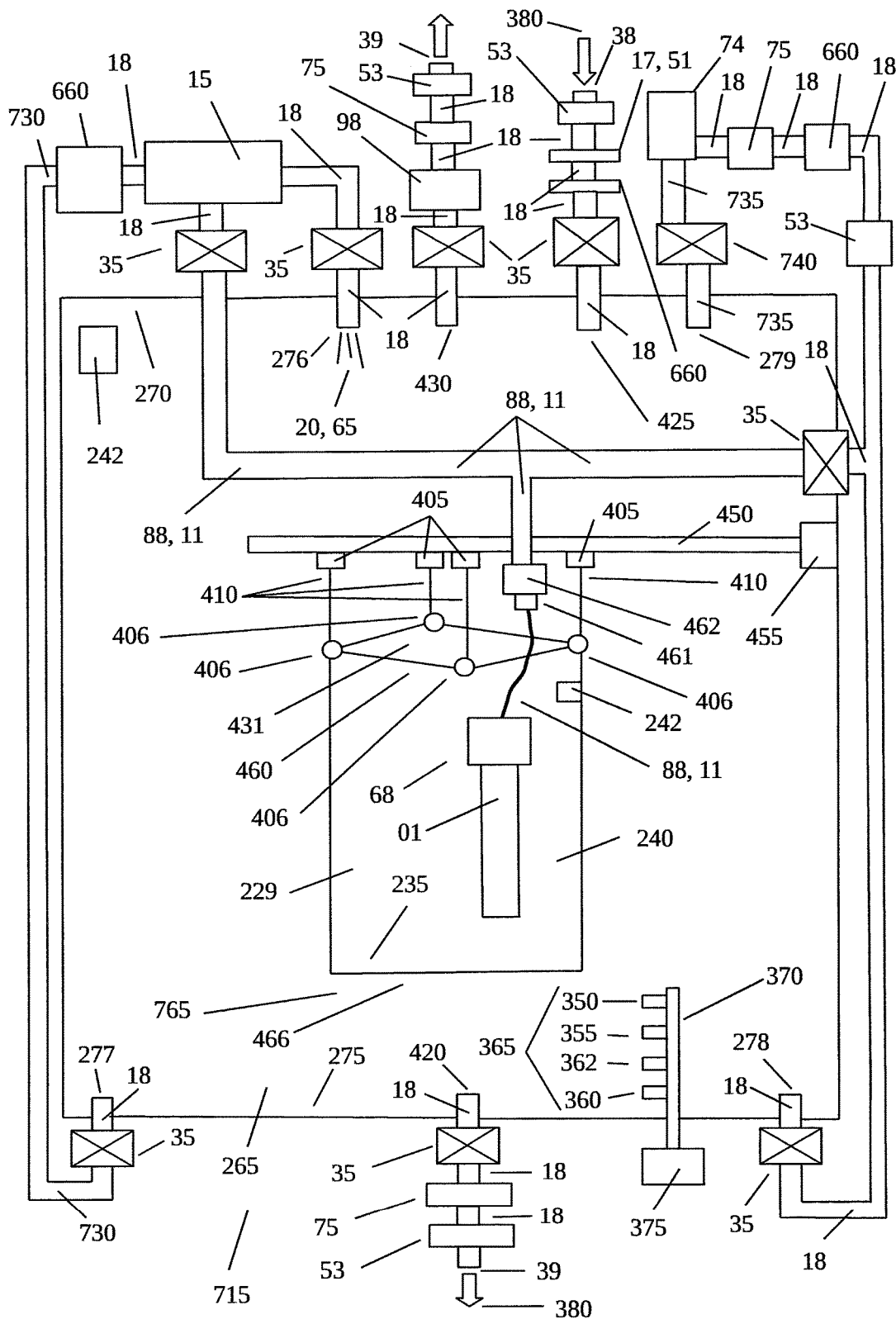
FIG. 73 is a side schematic type view of an enhanced decontamination enclosure apparatus (715), where an object and its cable is suspended inside an open removable package(s) (229) with a tube connector(s) (461) and tube disconnect apparatus(s) (462) that is used for supporting, holding, and treating, the interfaced object(s), and the object(s) is suspended inside of open removable package(s) (229), that is sealed on its bottom side, and open its top. The object and the open removable package(s) (229) is located in the container holding chamber(s) (265). The tube connector(s) (461) and tube disconnect apparatus(s) (462) are plumbed to dispense any air/gas(s) and/or agent(s).
Figure 74:
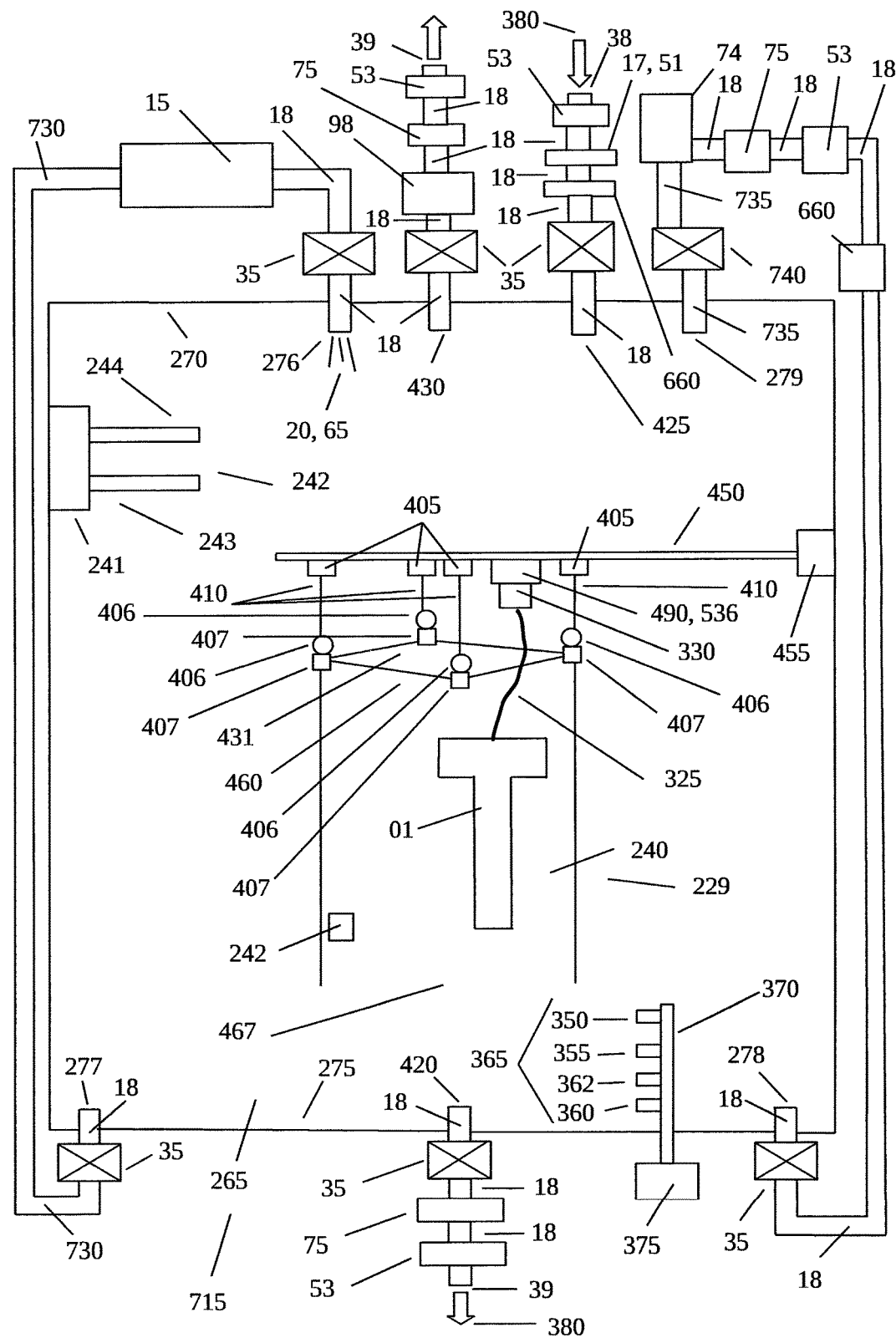
FIG. 74 is a side schematic type view of an enhanced decontamination enclosure apparatus (715), where an object and its cable is suspended inside an open removable package(s) (229) with a plug decoupling apparatus(s) (536) that is NOT plumbed in this instance, but is used for supporting, and holding, the interfaced object(s), and the object(s) is suspended inside of an open removable package(s) (229), that is open on its top side, and has an open bottom. The object and the open removable package(s) (229) is located in the container holding chamber(s) (265).
Figure 75:
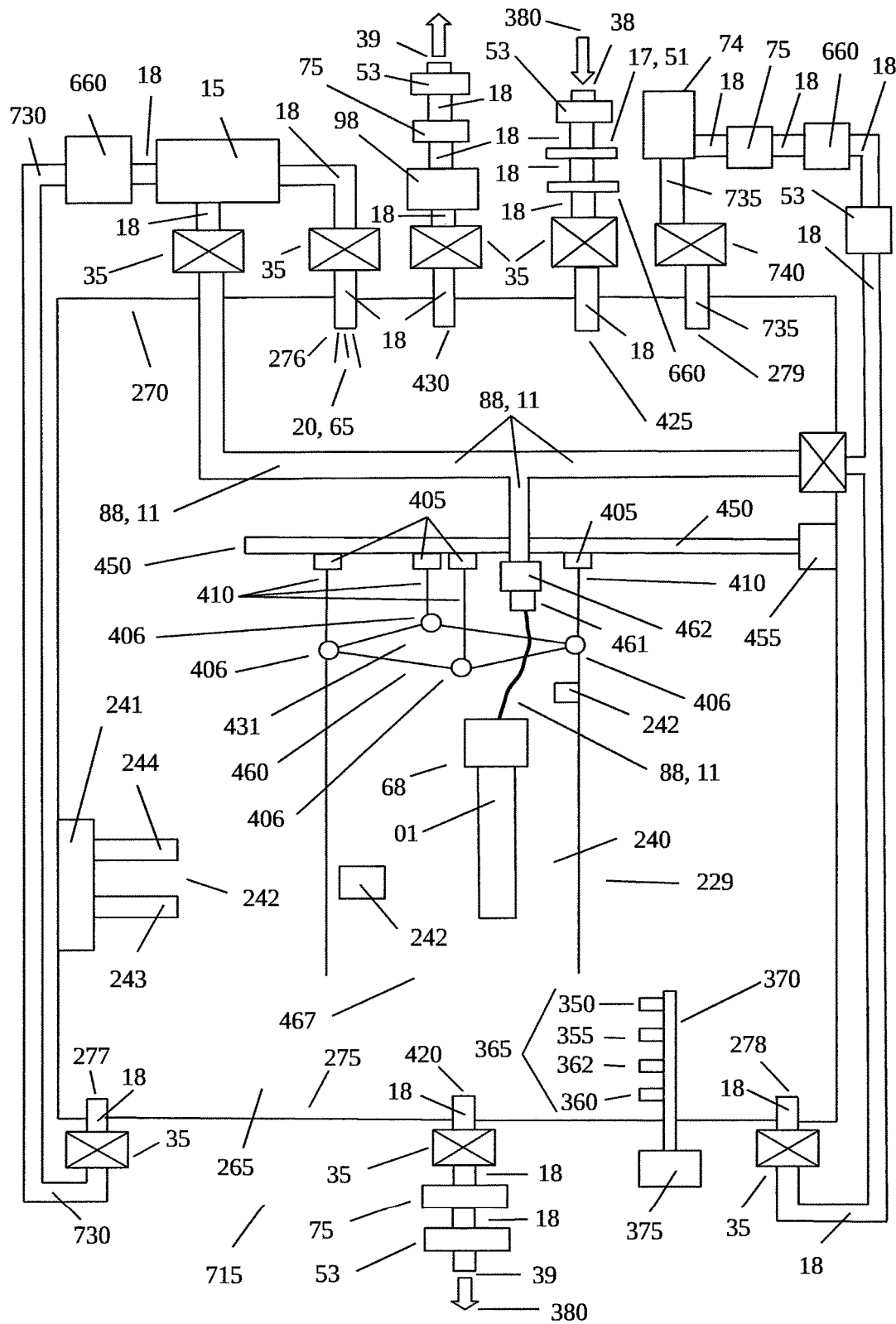
FIG. 75 is a side schematic type view of an enhanced decontamination enclosure apparatus (715), where an object and its cable is suspended inside an open removable package(s) (229) with a tube connector(s) (461) and tube disconnect apparatus(s) (462) that is used for supporting, holding, and treating, the interfaced object(s), and the object(s) is suspended inside of open removable package(s) (229), that has an open bottom and an open top. The object and the open removable package(s) (229) is located in the container holding chamber(s) (265). The tube connector(s) (461) and tube disconnect apparatus(s) (462) are plumbed to dispense any air/gas(s) and/or agent(s).
Figure 76:
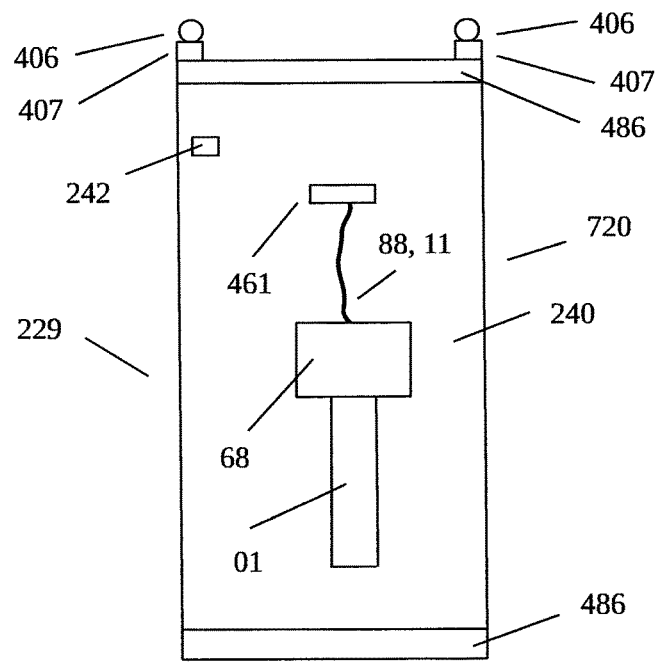
FIG. 76 is a side schematic type view of a closed package(s) (720), that is effectively sealed and/or has effective container sealed material interface(s) (486) on both ends.
Figure 77:
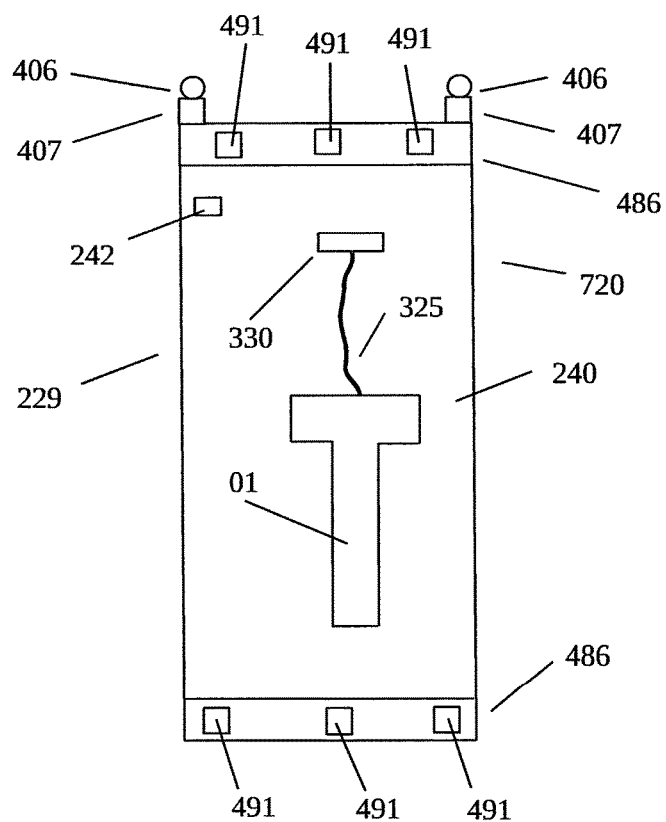
FIG. 77 is a side schematic type view of an effectively closed package(s) (720) that has effective container sealed material interface(s) (486) on both ends such as, but not limited to any, snap closure(s) and/or zip locking apparatus(s) (Herein called "Sealing Component(s)") (491).
Figure 78:
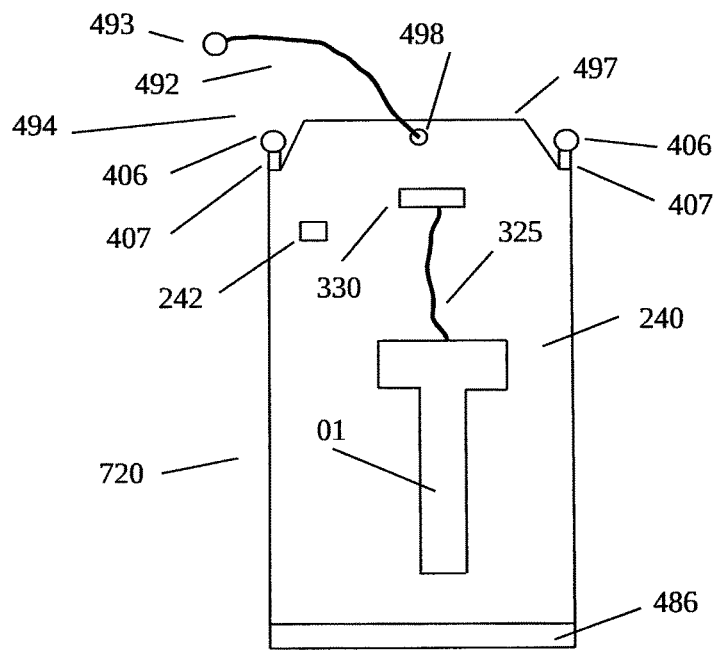
FIG. 78 is a side schematic type view of a closed package(s) (720), that is effectively sealed and/or has effective container sealed material interface(s) (486) on one end, and one or more of any suitable and effective pull cinch package closure assembly (494) one the other end.
Figure 79:
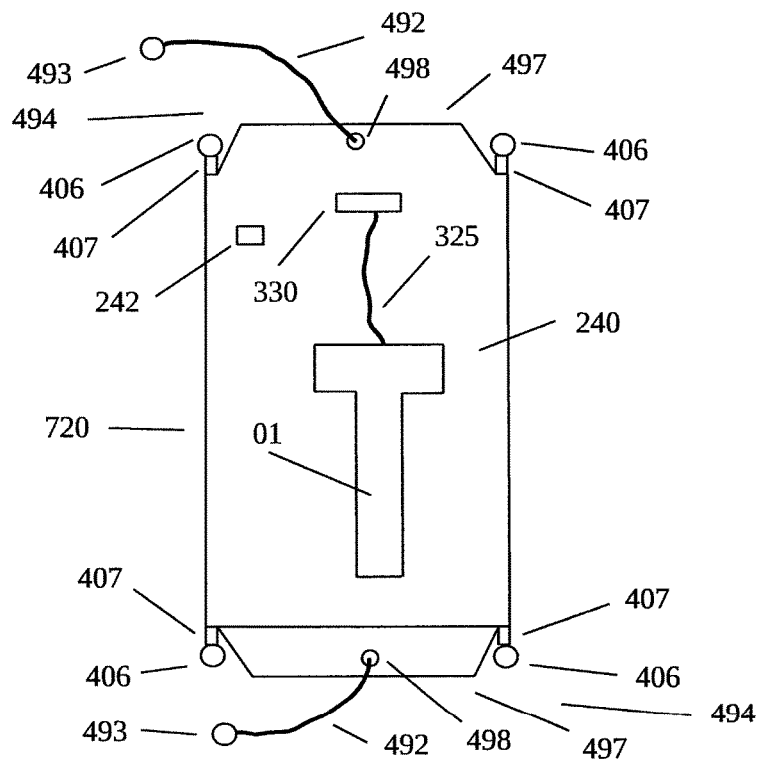
FIG. 79 is a side schematic type view of a closed package(s) (720), that has one or more of any suitable and effective pull cinch package closure assembly(s) (494) on both ends.
Figure 80:
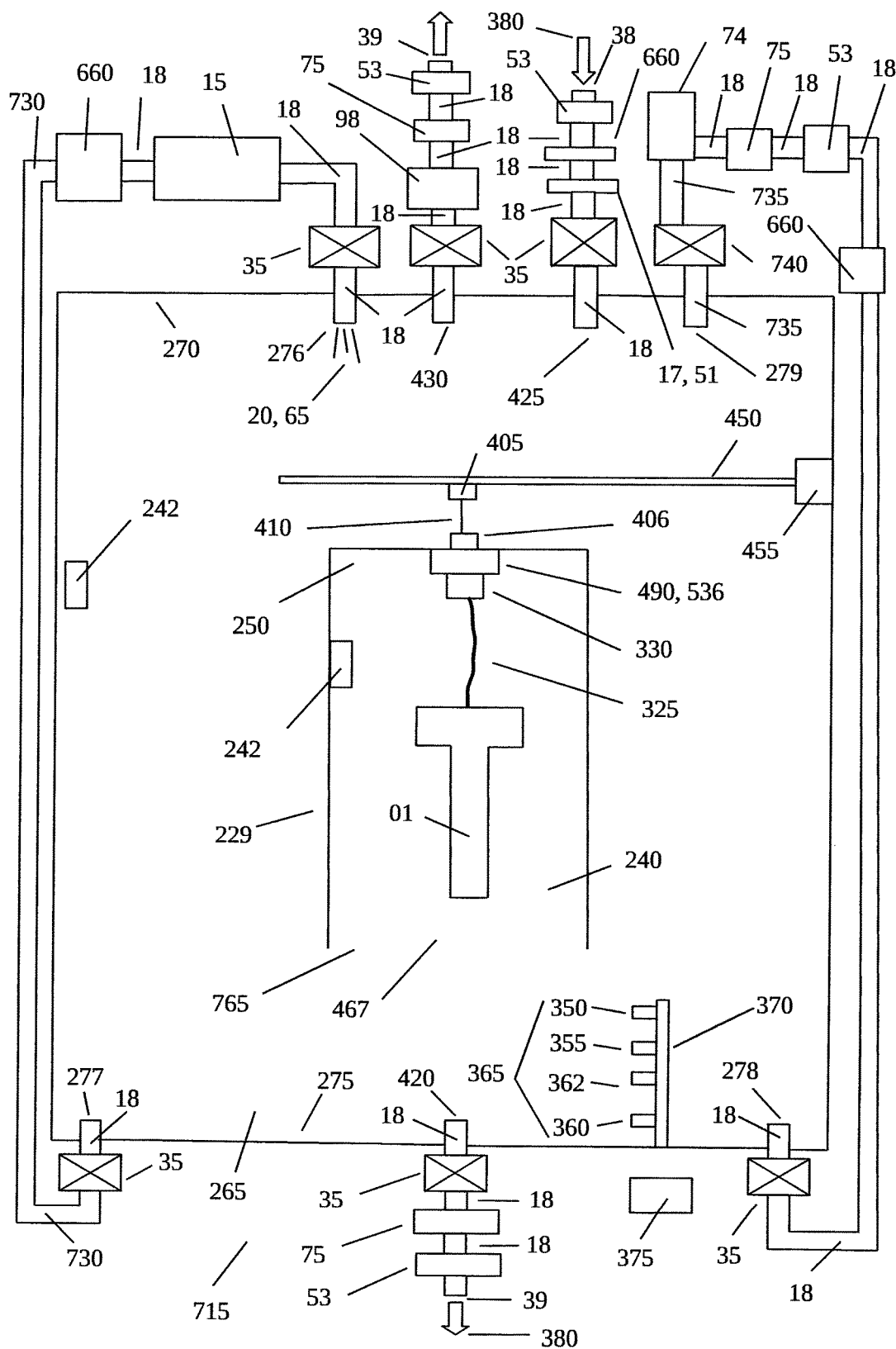
FIG. 80 is a side schematic type view of an enhanced decontamination enclosure apparatus (715), where an object and its cable is suspended inside an open removable package(s) (229) with a plug decoupling apparatus(s) (536) that is NOT plumbed in this instance, but is used for supporting, and holding, the interfaced object(s), and the object(s) is suspended inside of an open removable package(s) (229), that is open on its bottom side, and has closed top. The object and the open removable package(s) (229) is located in the container holding chamber(s) (265).
Figure 81:
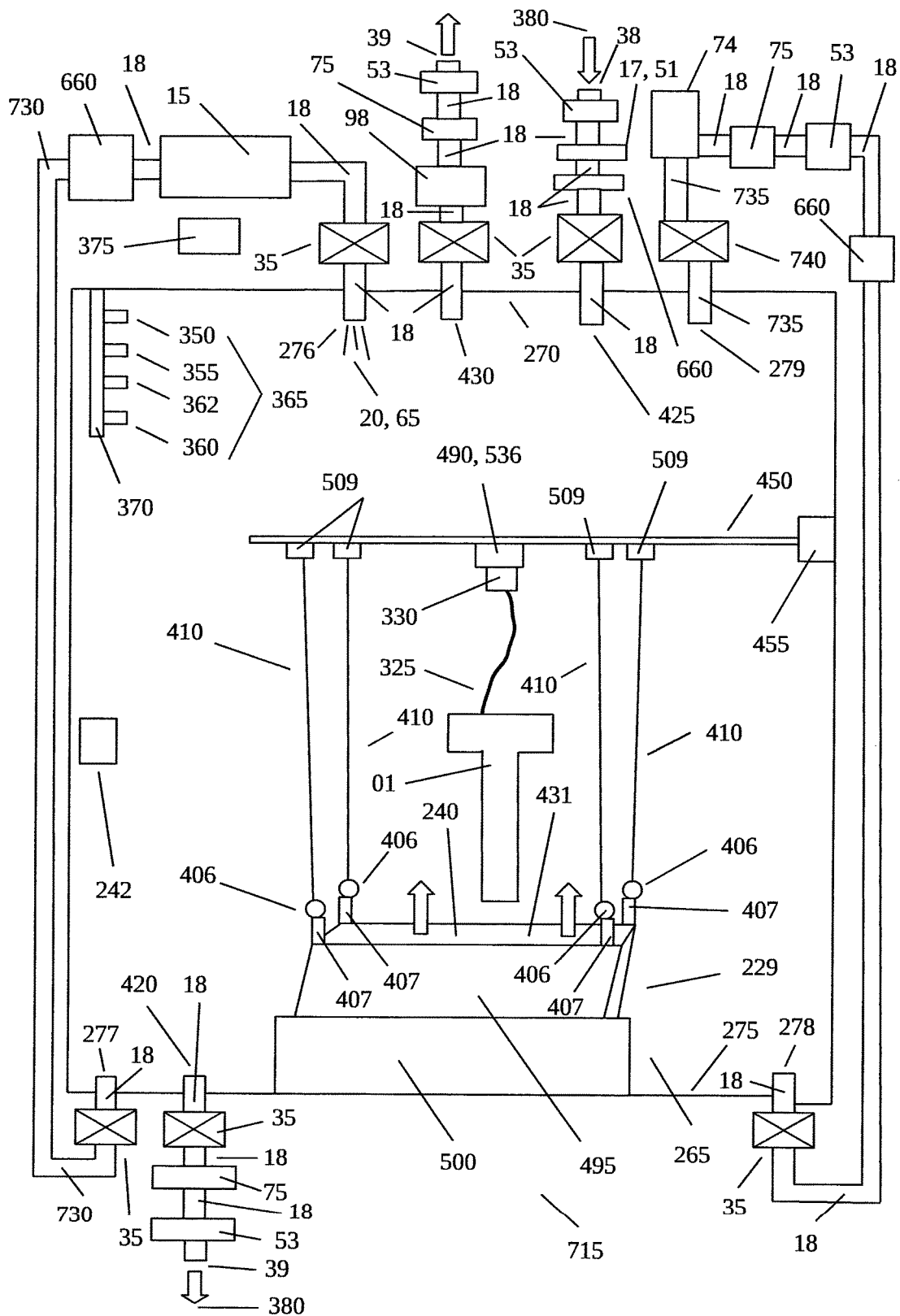
FIG. 81 is a side schematic type view of an enhanced decontamination enclosure apparatus (715), where an object(s) and its cable(s) is suspended in the container holding chamber(s) (265) with a plug decoupling apparatus(s) (536) that is NOT plumbed in this instance, but is used for supporting, and holding, the interfaced object(s). The open removable package(s) (229) and/or packaging and open packaging material(s) (495) can be moved up under and/or around the suspended object(s) via one or more packaging lift apparatus(s) (509). The top of the open removable package(s) (229) and/or packaging and open packaging material(s) (495) that is lifted up and into position around the objects is open.
Figure 82:
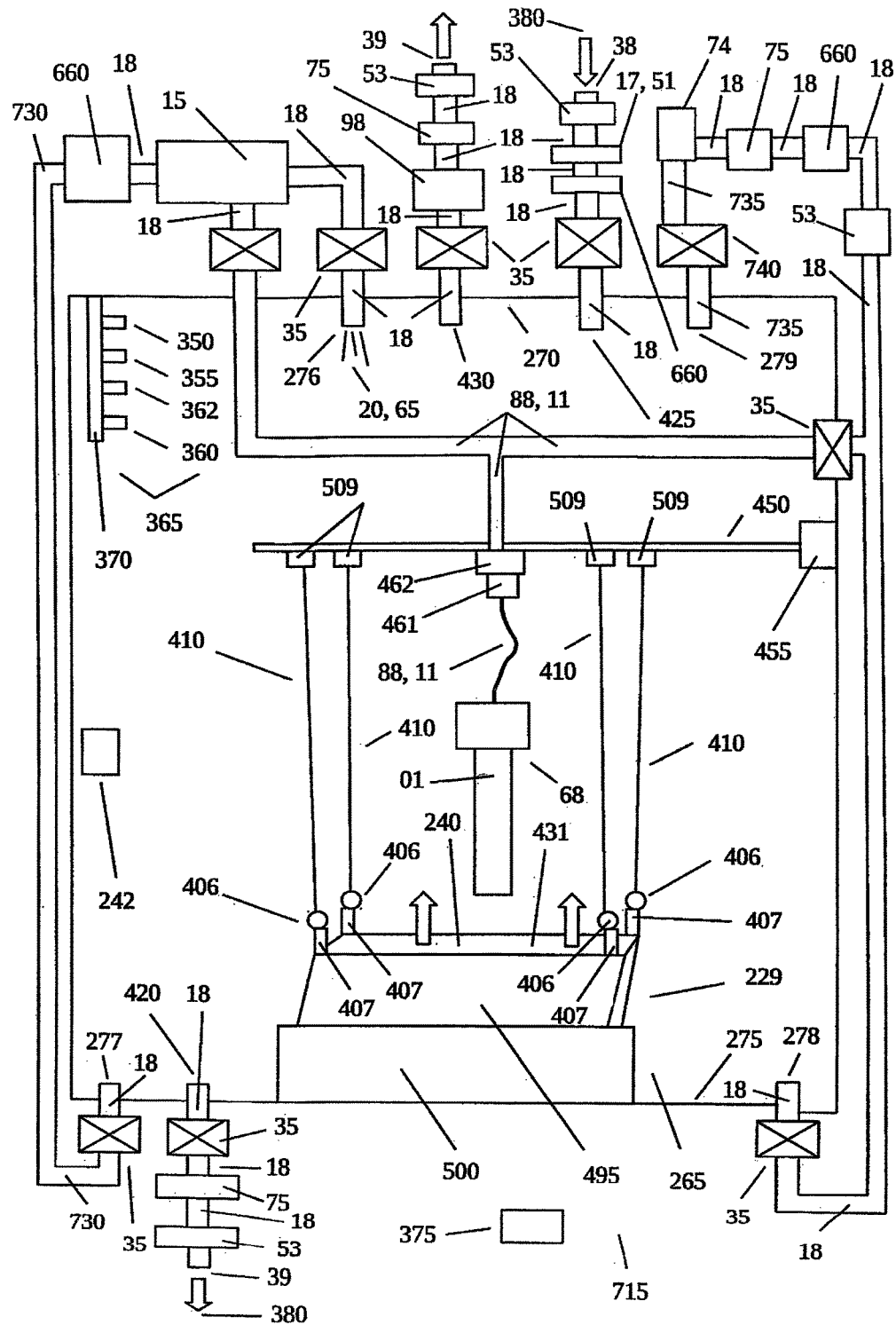
FIG. 82 is a side schematic type view of an enhanced decontamination enclosure apparatus (715), where an object(s) and its cable(s) is suspended in the container holding chamber(s) (265) with a tube connector(s) (461) and tube disconnect apparatus(s) (462) that is used for supporting, holding, and treating, the interfaced object(s). The open removable package(s) (229) and/or packaging and open packaging material(s) (495) can be moved up under and/or around the suspended object(s) via one or more packaging lift apparatus(s) (509). At least the top of the open removable package(s) (229) and/or packaging and open packaging material(s) (495) that is lifted up and into position around the objects is open.
Figure 83:
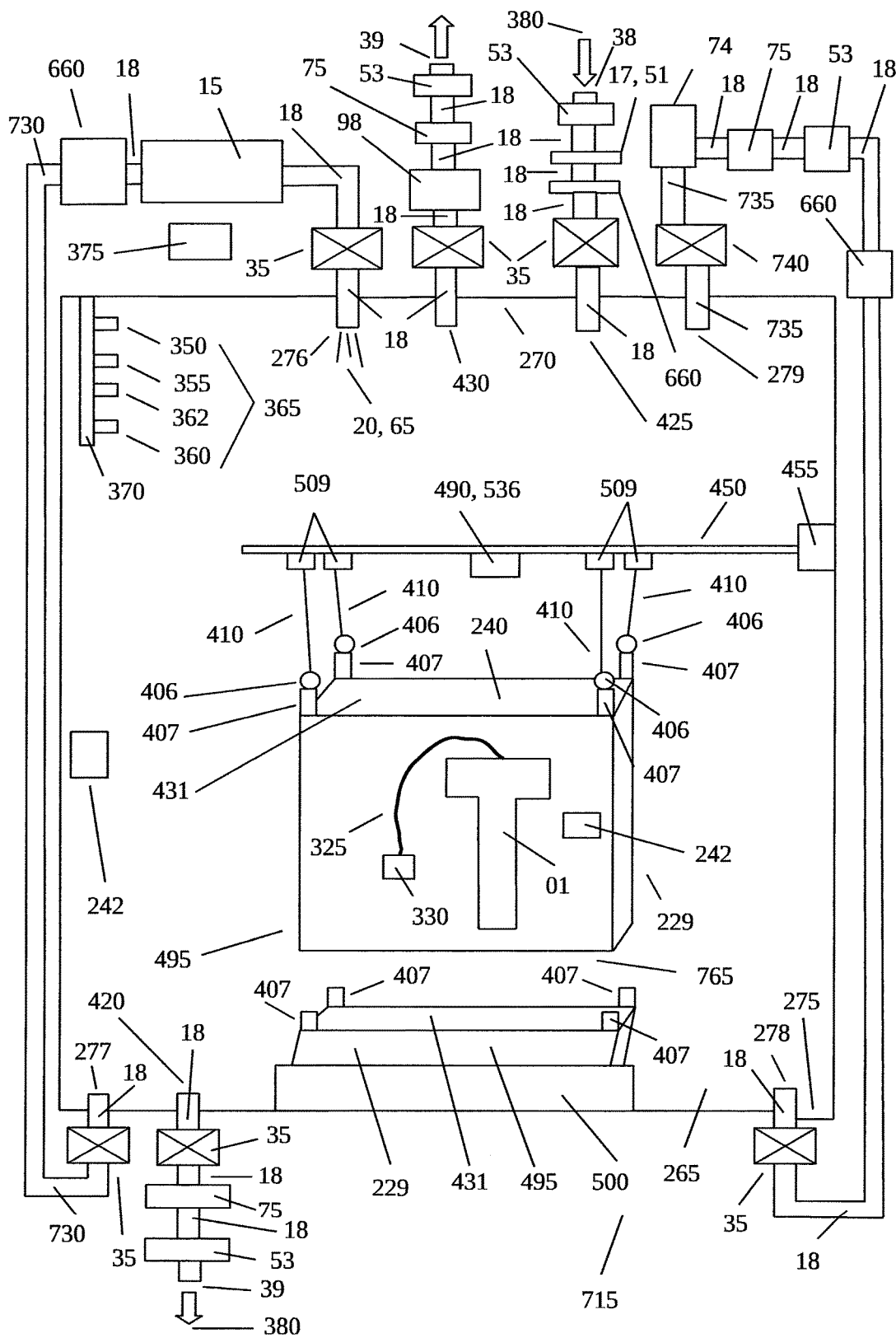
FIG. 83 is a side schematic type view of an enhanced decontamination enclosure apparatus (715), where a suspended object(s) and its cable(s) is released from a plug decoupling apparatus(s) (536), and the object(s) falls and/or is located into the open removable package(s) (229) and/or packaging and open packaging material(s) (495), that was moved up and under and/or around the suspended object(s) via one or more packaging lift apparatus(s) (509), before the object was located inside. The top of the open removable package(s) (229) and/or packaging and open packaging material(s) (495) that is lifted up and into position around the objects is open, and its bottom is closed.
Figure 84:
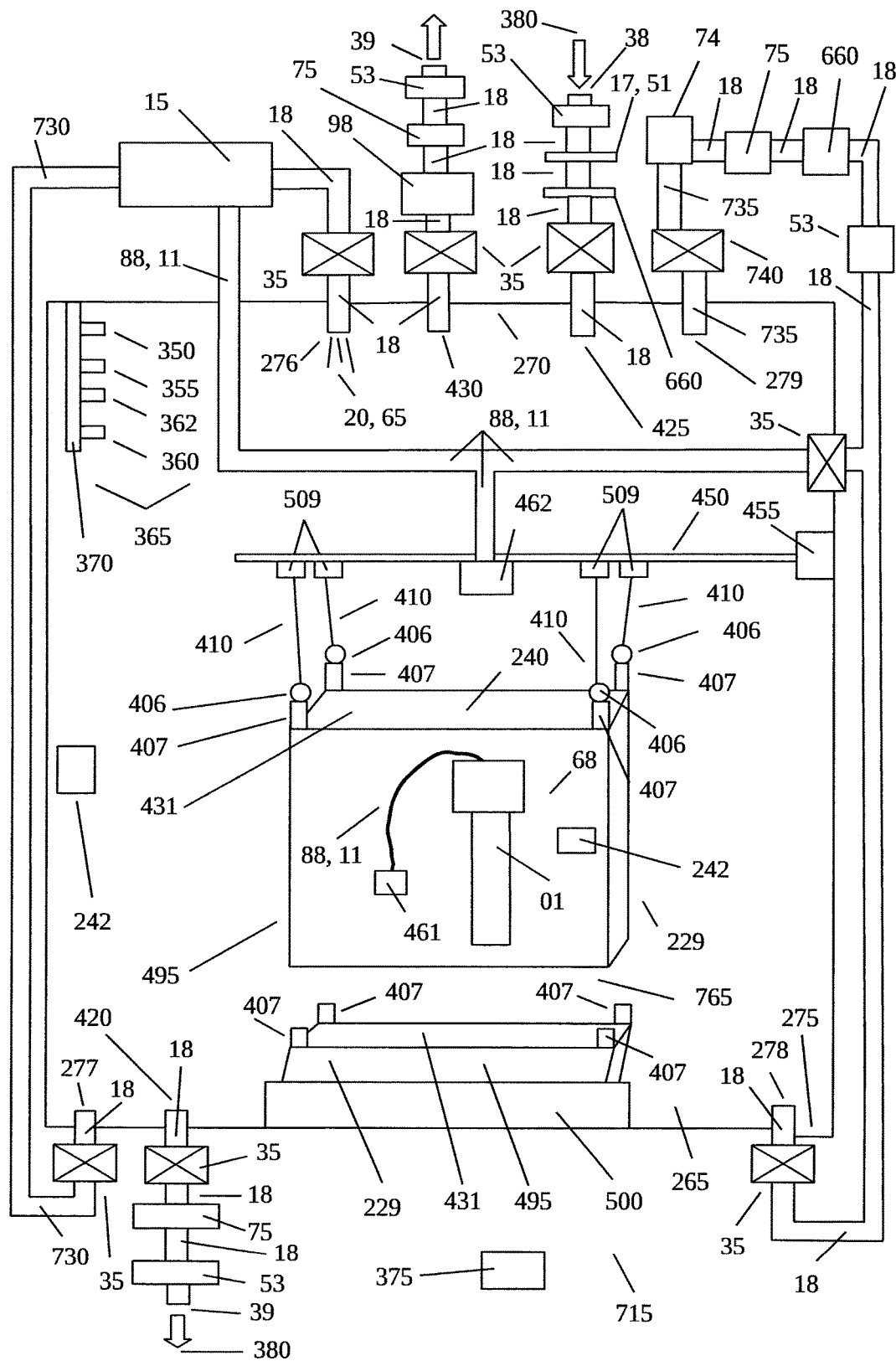
FIG. 84 is a side schematic type view of an enhanced decontamination enclosure apparatus (715), where a suspended object(s) and its cable(s) is released from a a tube connector(s) (461) and tube disconnect apparatus(s) (462), and the object(s) falls and/or is located into the open removable package(s) (229) and/or packaging and open packaging material(s) (495), that was moved up and under and/or effectively around the suspended object(s) via one or more packaging lift apparatus(s) (509), before the object was located inside. The top of the open removable package(s) (229) and/or packaging and open packaging material(s) (495) that is lifted up and into position around the objects is open, and its bottom is closed.
Figure 85:
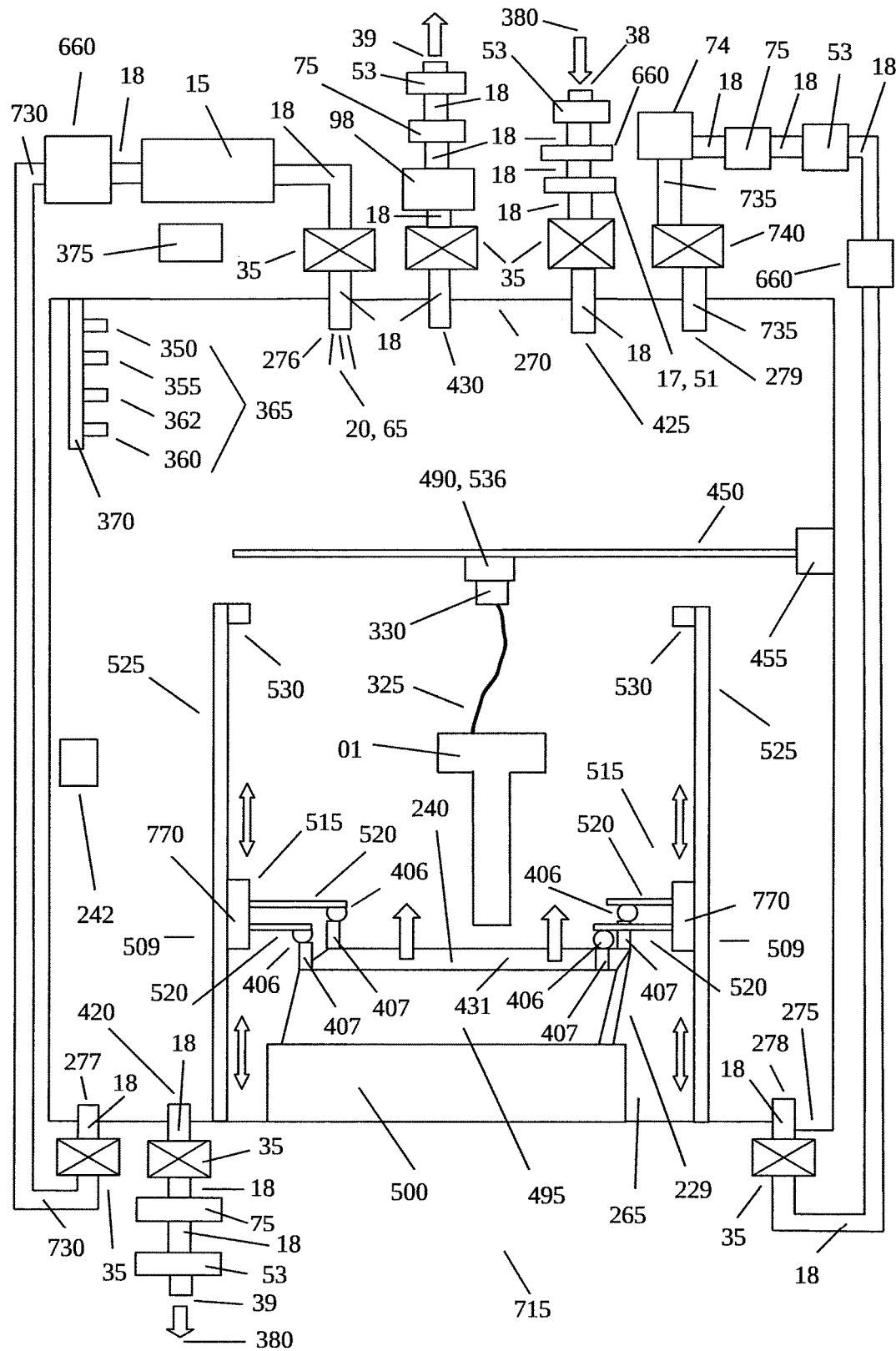
FIG. 85 is a side schematic type view of an enhanced decontamination enclosure apparatus (715), where an object and its cable is suspended inside a container holding chamber(s) (265) with a plug decoupling apparatus(s) (536) that is NOT plumbed in this instance, but is used for supporting, and holding, the interfaced object(s), and the object(s). At least one packaging guided lift apparatus(s) (515) is located in the container holding chamber(s) (265), with the open removable package(s) (229) and/or packaging and open packaging material(s) (495), ready for use.
Figure 86:
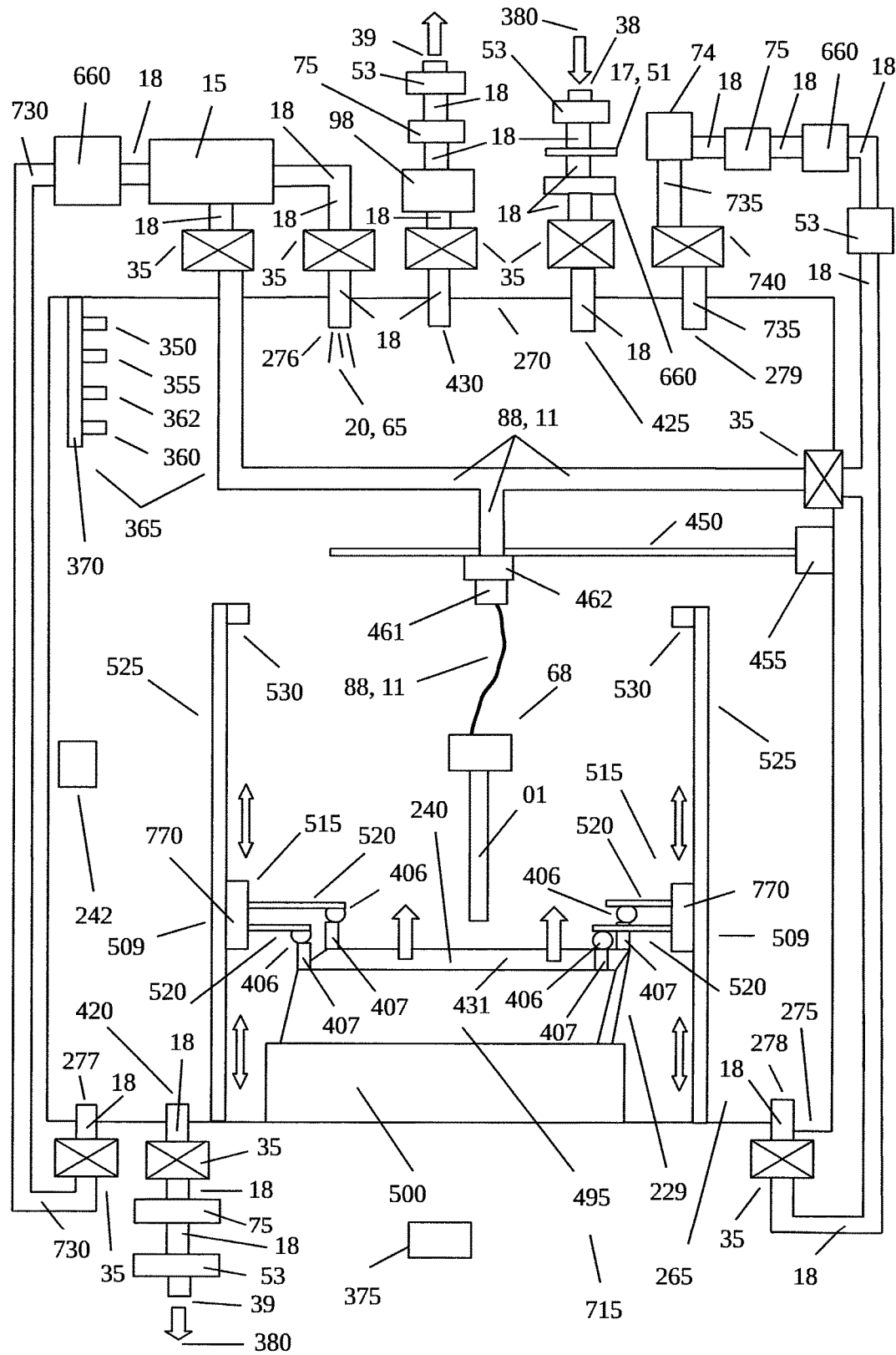
FIG. 86 is a side schematic type view of an enhanced decontamination enclosure apparatus (715), where an object and its cable is suspended inside a container holding chamber(s) (265) with a tube connector(s) (461) and tube disconnect apparatus(s) (462). At least one packaging guided lift apparatus(s) (515) is located in the container holding chamber(s) (265), with the open removable package(s) (229) and/or packaging and open packaging material(s) (495), ready for use.
Figure 87:
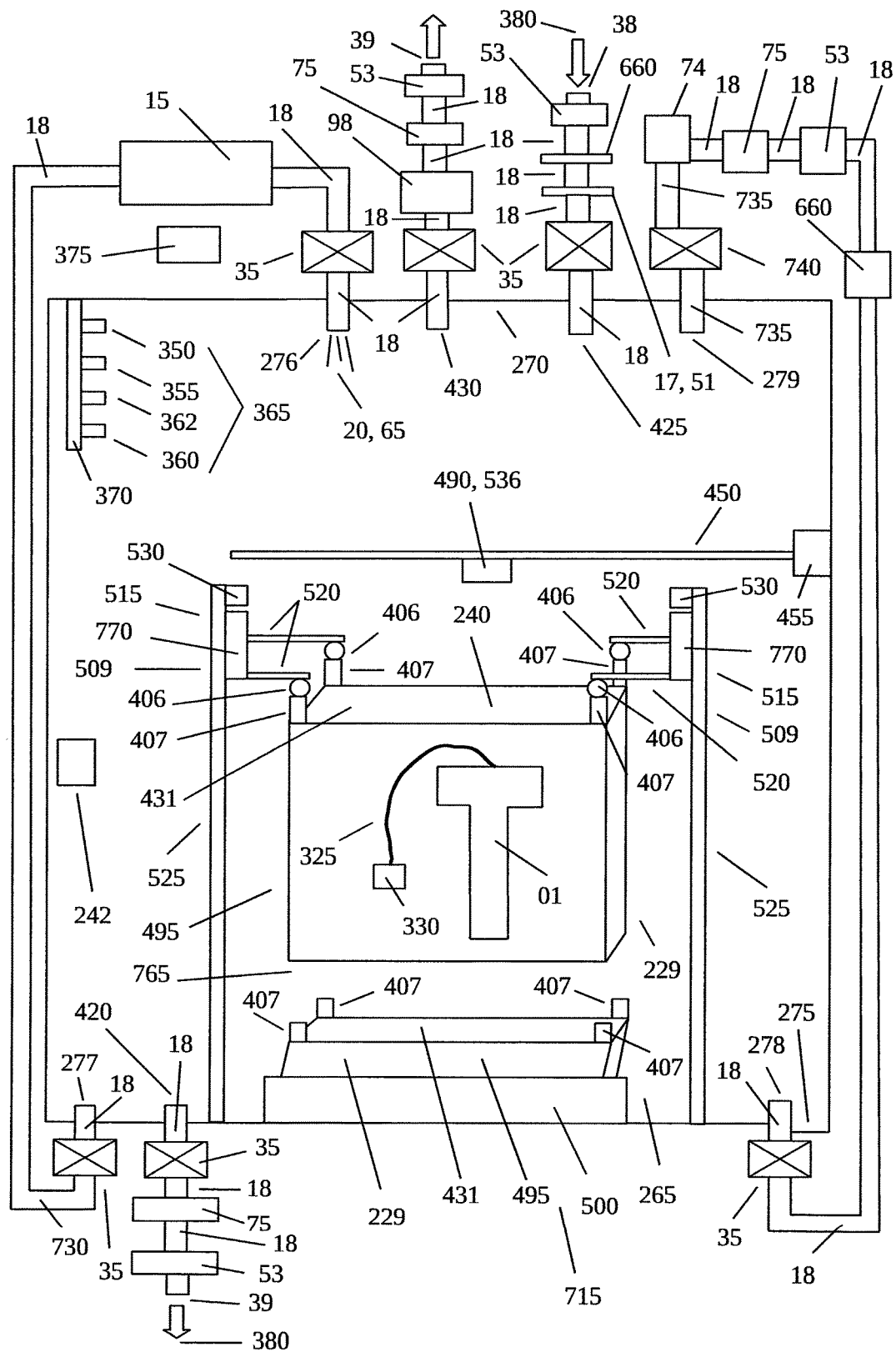
FIG. 87 is a side schematic type view of an enhanced decontamination enclosure apparatus (715), where at least one packaging guided lift apparatus(s) (515) is located in the container holding chamber(s) (265), and has moved the open removable package(s) (229) and/or packaging and open packaging material(s) (495) effectively under the object(s) and/or to effectively surround the object(s), and the object was then removed and/or disconnected, and/or preferably automatically removed, from the plug decoupling apparatus(s) (536), and then dropped and/or positioned into the open removable package(s) (229) and/or packaging and open packaging material(s) (495).
Figure 88:
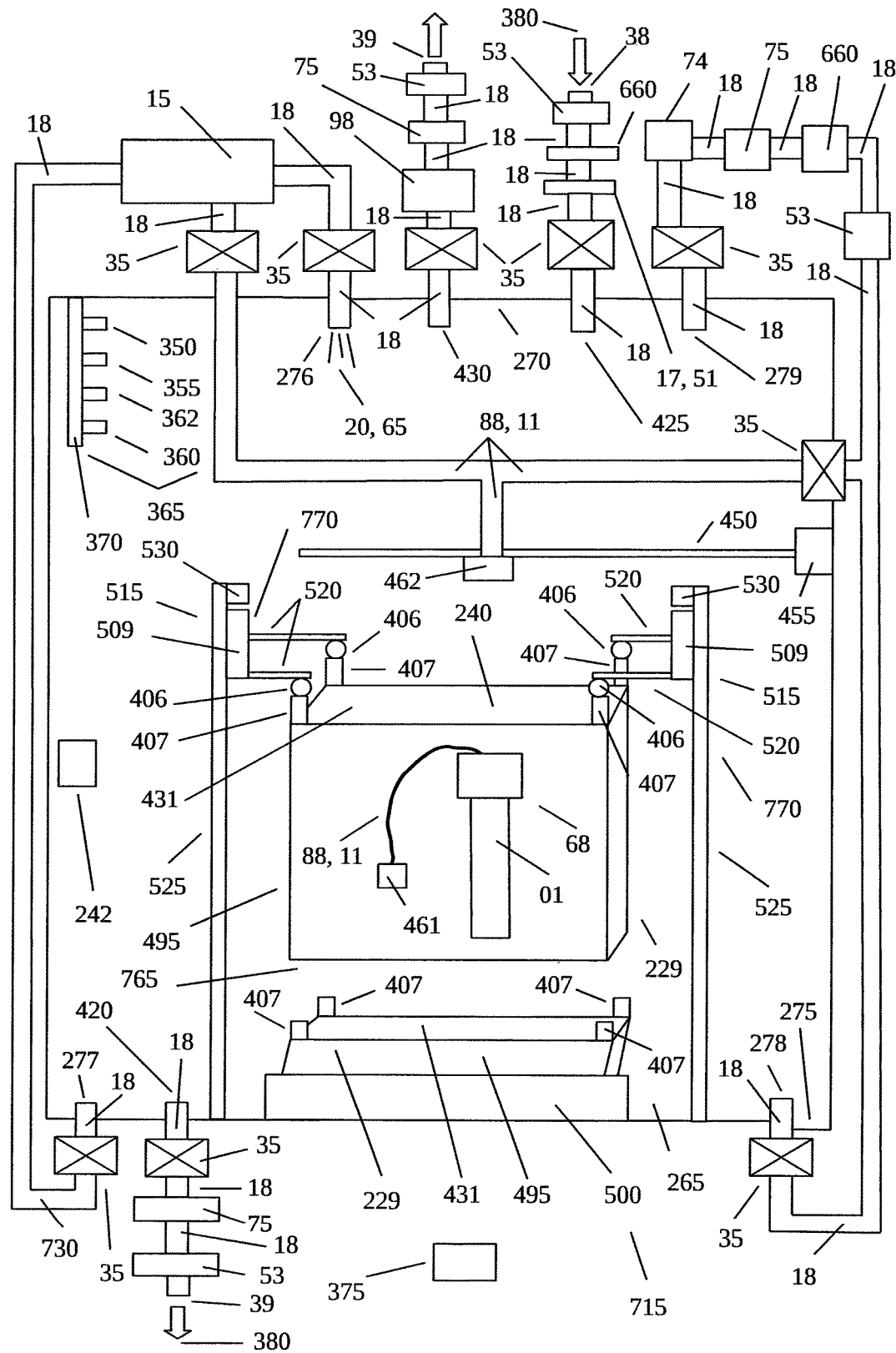
FIG. 88 is a side schematic type view of an enhanced decontamination enclosure apparatus (715), where at least one packaging guided lift apparatus(s) (515) is located in the container holding chamber(s) (265), and has moved the open removable package(s) (229) and/or packaging and open packaging material(s) (495) effectively under and/or to effectively surround the object(s), and the object was then removed, and/or preferably automatically removed, from the tube disconnect apparatus(s) (462), and then dropped and/or positioned into the open removable package(s) (229) and/or packaging and open packaging material(s) (495).
Figure 89:
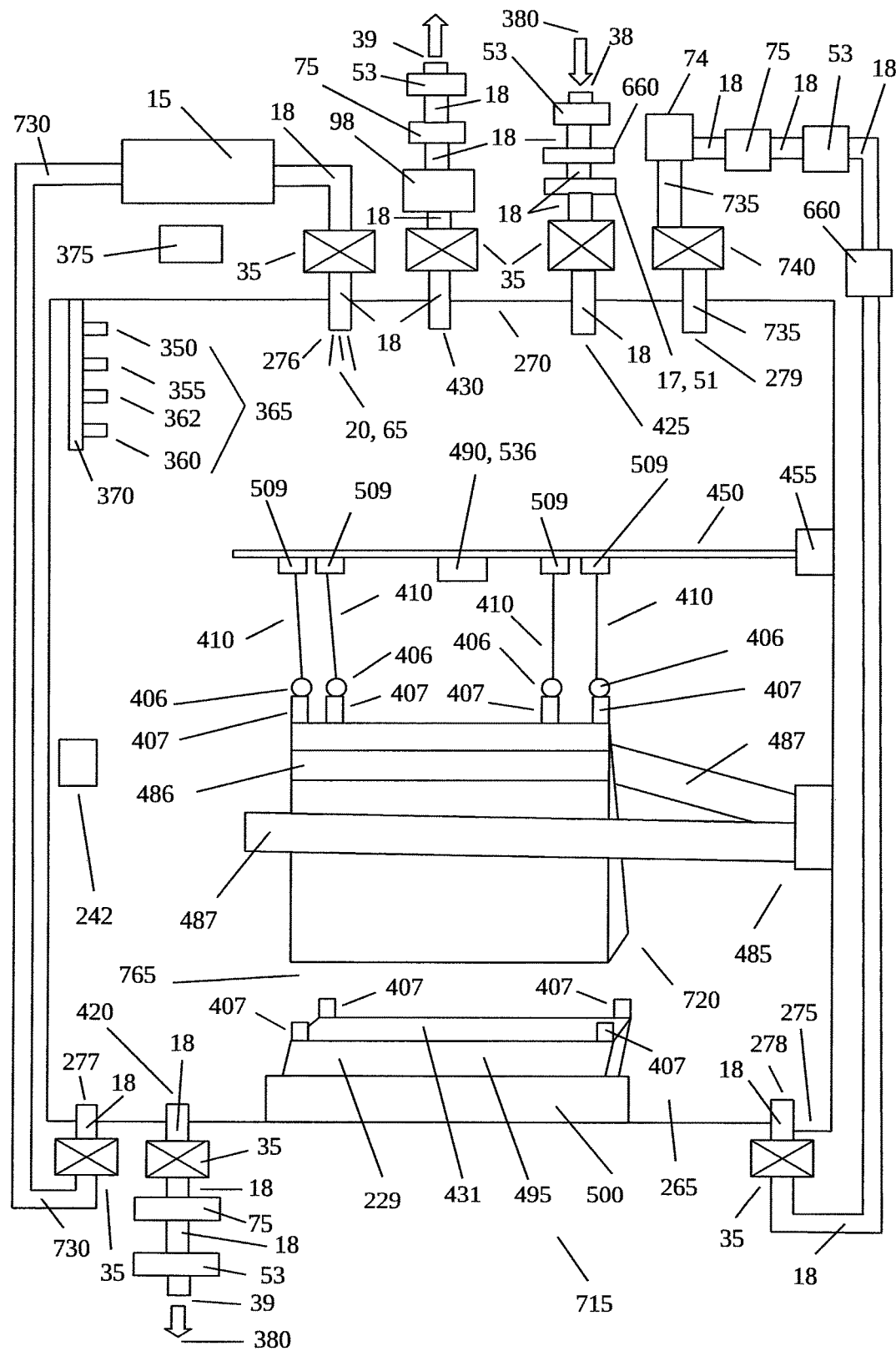
FIG. 89 is a side schematic type view of an enhanced decontamination enclosure apparatus (715), where at least one packaging guided lift apparatus(s) (515) is located in the container holding chamber(s) (265), and has moved the open removable package(s) (229) and/or packaging and open packaging material(s) (495) effectively under the object(s) and/or to effectively surround the object(s), and the object was then removed, and/or preferably automatically removed, from the plug decoupling apparatus(s) (536), and then dropped and/or positioned into the open removable package(s) (229) and/or packaging and open packaging material(s) (495). The package is then sealed by one or more package sealer(s) (485) forming a sealed package.
Figure 90:
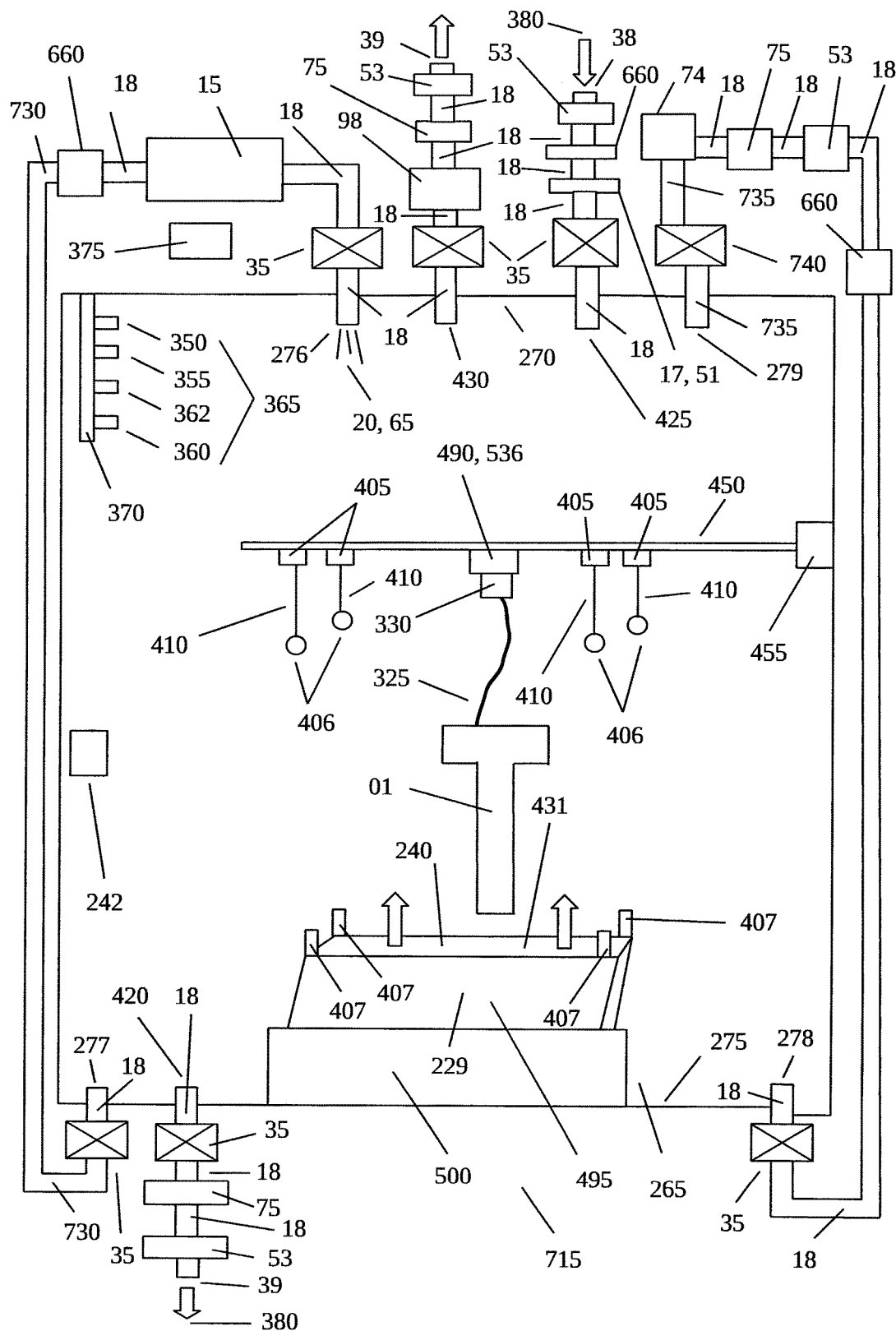
FIG. 90 is a side schematic type view of an enhanced decontamination enclosure apparatus (715), where an object and its cable is suspended inside a container holding chamber(s) (265) with a plug decoupling apparatus(s) (536) that is NOT plumbed in this instance, but is used for supporting, and holding, the interfaced object(s), and the object(s). The open removable package(s) (229) and/or packaging and open packaging material(s) (495), is located in the container holding chamber(s) (265) and can be manually raised up under and/or to effectively surround the object(s) at any time(s), and then the object(s) can be released from the plug decoupling apparatus(s) (536) either automatically and/or manually so they can fall or be positioned into the various, open removable package(s) (229) and/or packaging and open packaging material(s) (495).
Figure 91:
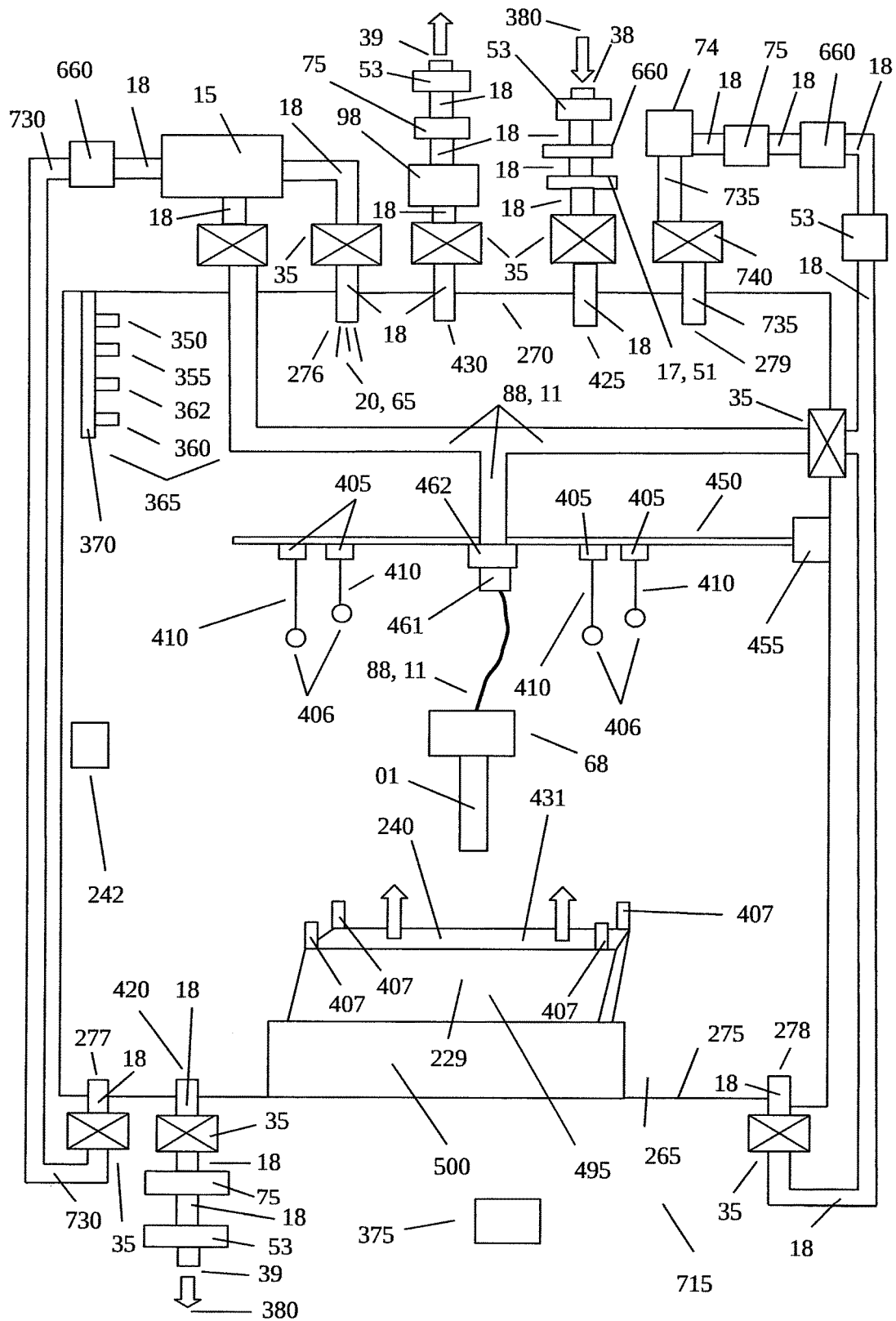
FIG. 91 is a side schematic type view of an enhanced decontamination enclosure apparatus (715), where an object and its cable is suspended inside a container holding chamber(s) (265) with a tube connector(s) (461) and tube disconnect apparatus(s) (462). The open removable package(s) (229) and/or packaging and open packaging material(s) (495), is located in the container holding chamber(s) (265) and can be manually raised up under and/or to effectively surround the object(s) at any time(s), and then the object(s) can be released from the tube connector(s) (461) and tube disconnect apparatus(s) (462) either automatically and/or manually so they can fall or be positioned into the various, open removable package(s) (229) and/or packaging and open packaging material(s) (495).
Figure 92:
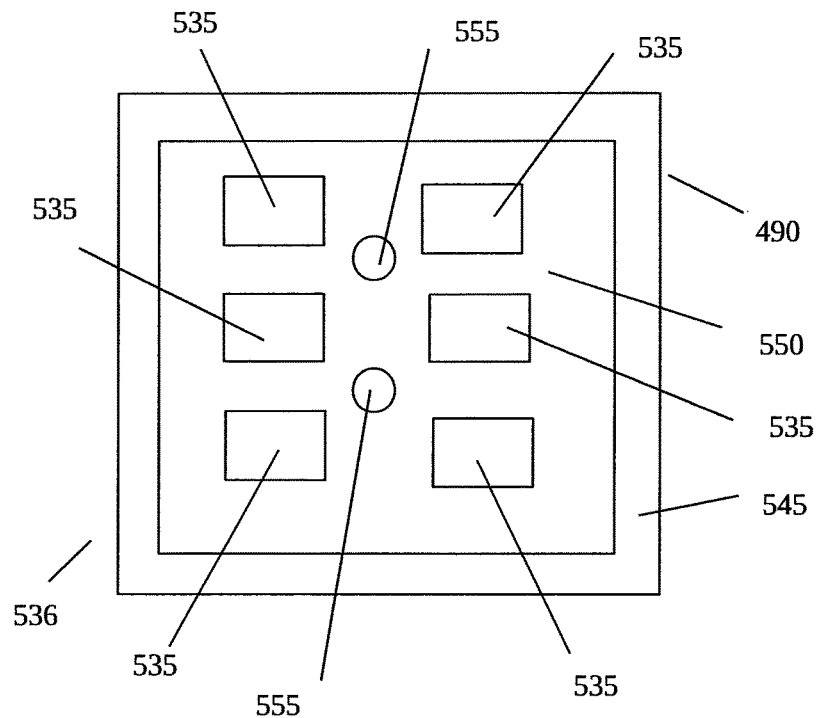
FIG. 92 is a schematic type view of a plug decoupling apparatus(s) (536) that has a plug interface (490) configured as a female plug type interface (550) with a plug shaft (545), and one or more communication connection(s) (535). One or more push protrusion member(s) (555) are also present that can push any suitable plug (330) out of the female plug shaft (545), and generally from the female plug interface (550) (490).
Figure 93:
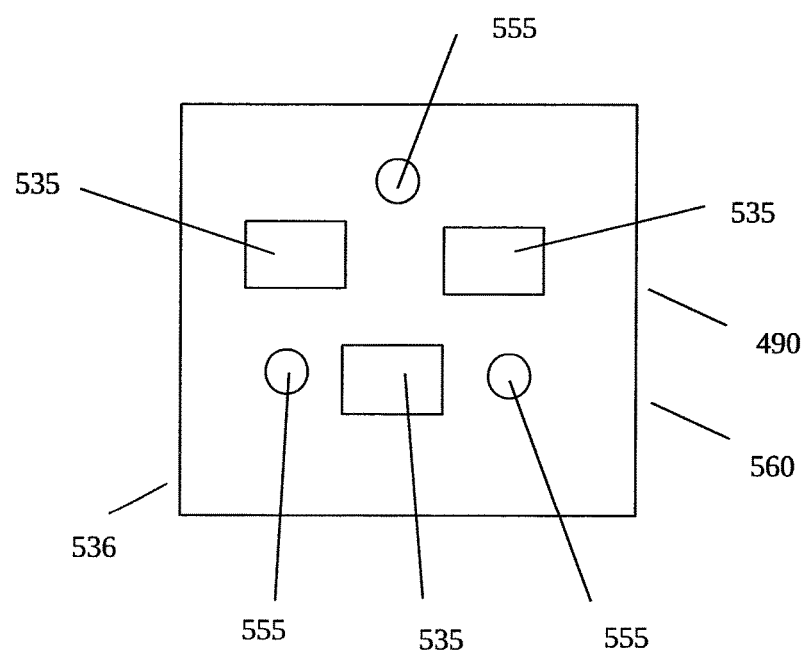
FIG. 93 is a schematic type view of a plug decoupling apparatus(s) (536) that has a plug interface (490) configured as a male plug type interface (560) with one or more communication connection(s) (535). One or more push protrusion member(s) (555) are also present that can push any suitable plug (330) away, and generally from the plug interface (490).
Figure 94:
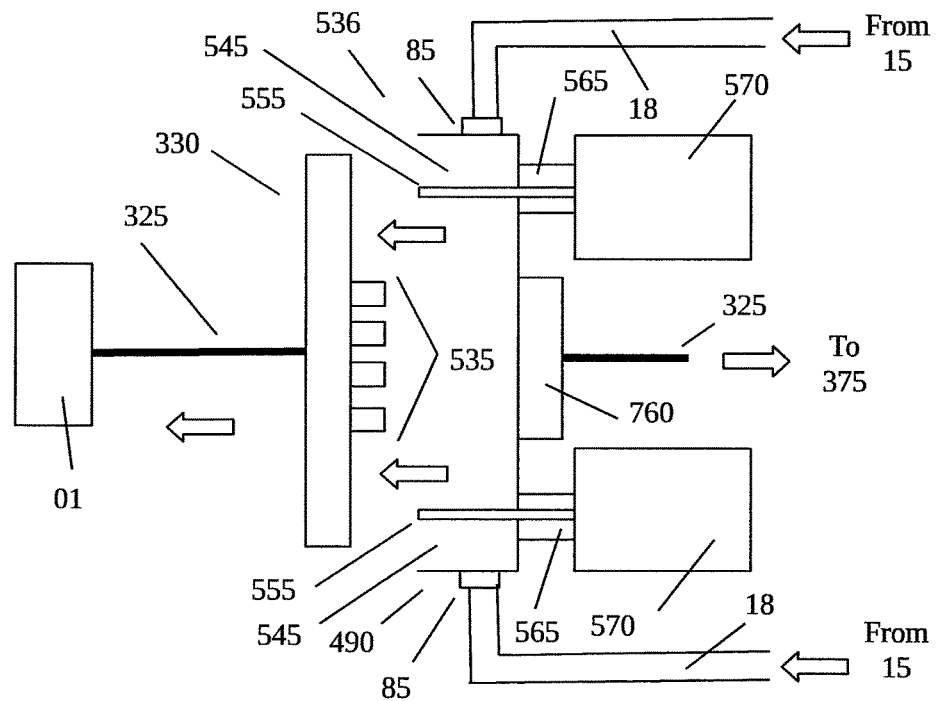
FIG. 94 is a schematic type view showing a plug decoupling apparatus(s) (536) and a plug (330) that has been pushed away from the plug decoupling apparatus(s) (536). When the at least one suitable push protrusion movement apparatus(s) (570) is actuated and/or effectively moves at least one suitable push protrusion member(s) (555) for any suitable and effective distance(s) into the one or more plug interface(s) (490) and/or female plug shaft(s) (545) to preferably, and without limitation, contact the interface plug(s) (330), it causes the interface plug(s) (330) to completely back out of the plug interface(s) (490) and/or plug shaft(s) (545), and/or it causes the effective release and/or effective disconnection of the interface plug(s) (330) from the plug interface(s) (490), plug shaft(s) (545), and/or plug decoupling apparatus(s) (536). Also, the plug decoupling apparatus(s) (536) can also, treat, dry, and/or process any surface(s), such as, but not limited to any, plug(s) (330), plug interface(s) (490), plug shaft(s) (545), and/or object interface material(s), via one or more vent(s) (85).
Figure 95:
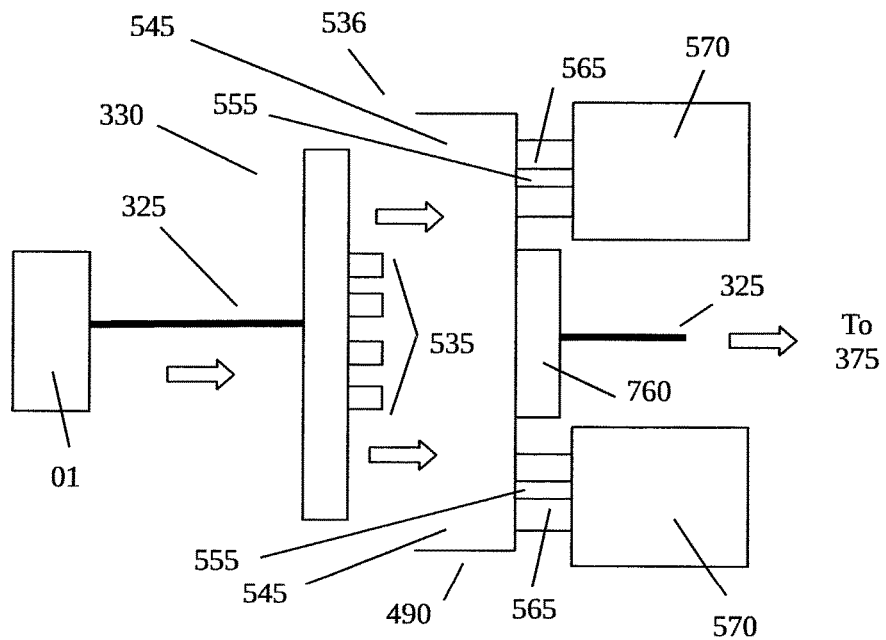
FIG. 95 is a schematic type view showing a plug decoupling apparatus(s) (536) and a plug (330) that is about to be interfaced with the plug decoupling apparatus(s) (536). The push protrusion movement apparatus(s) (570) is not actuated, and the push protrusion member(s) (555) are not protruding into the more plug interface(s) (490) and/or plug shaft(s) (545).

Referring to FIGS. 70-71 and according to an embodiment, and without limitation, at least one of any, open package(s), open removable package(s) (229), open enclosure(s), and/or one or more of any effective, open packaging material(s) (495), is shown that can include at least one of any suitable, top pass through hole(s) (470), hinge(s), and top pass through hole(s) cover(s) (480), that is preferably, but without limitation, located on any effective top area(s) (465) of the said, open package(s), open removable package(s) (229), open enclosure(s), and/or one or more of any effective, open packaging material(s) (495). The said top pass through hole(s) (470) can be effectively open (480) during one or more of any suitable and effective treatment, processing, and/or drying, step(s), and they can be suitably sized for any object(s) (01). Without being limited, FIG. 70 shows the open package(s), open removable package(s) (229), open enclosure(s), and/or one or more of any effective, open packaging material(s) (495), open and unsealed, and FIG. 71 shows the object(s) effectively sealed within the previously, open package(s), open removable package(s) (229), open enclosure(s), and/or one or more of any effective, open packaging material(s) (495), and the said top pass through hole(s) (470) in any effective closed position.

Without being limited, any heated air/gas(s) and/or any heated fresh (380) air/gas(s), that is flowed into any area(s) and/or location(s) such as, but not limited to any, open enclosure(s), open removable package(s) (229), open package(s) and/or packaging material(s) (495), enclosure(s), treatment enclosure(s), open treatment enclosure(s), open removable treatment enclosure(s), package(s), and/or removable package(s), and preferably and without limitation, at least any, container holding chamber(s) (265), and/or removable treatment enclosure(s) (230), as well as one or more of any surfaces and/or area(s) of any, object(s) (01), and/or one or more of any suitable and effective means to effectively, hold, cradle, support, and/or hang, the one or more object(s) (01) and any associated component(s), such as, but not limited to any, plug decoupling apparatus(s) (536), support and release apparatus(s) (606), and/or enhanced object(s) holder(s) (155), interface plug(s) (330), female plug shaft(s) (545), plug decoupling apparatus(s) (536), pressure interface assembly(s) (68), gripping mechanism(s) (135) and/or gripping finger(s) (108), tube connector(s) (461), tube disconnect apparatus(s) (462), object support(s) (84), movable support member(s) (620), horizontal support member part(s) (630), vertical extension member part(s) (635), support and release apparatus(s) (606), enhanced object(s) holder(s) (155), object interface material(s) (89), cradle(s) (45), gripping mechanism(s) (135) and/or gripping finger(s) (108), object support(s) (84), and/or one or more of any other suitable and effective method(s), apparatus(s), part(s), component(s), and/or any other supporting and/or associated part(s) and component(s), known to those skilled in the art, can be used for any purposes such as, but not limited to, effectively drying various surface(s), and/or to assist with turning any liquid treatment agent(s) from a liquid into any gas(s), and can be heated to any suitable and effective temperature(s), preferably and without limitation, any suitable and effective temperature(s) between 60 and 200 degree Fahrenheit, and more preferably any temperature between 70 and 130 degree Fahrenheit.

Also, without being limited, any, air, gas(s), and/or vapor(s), that are flowed through any of the various chamber(s), treatment area(s), part(s) and component(s), of the enhanced decontamination enclosure apparatus(s) (715), can be effectively filtered before they are exhausted from the container holding chamber(s) (265) and/or the enhanced decontamination enclosure apparatus(s) (715). It is preferred, without limitation, that any suitable and effective, air/gas(s) filtering apparatus(s), filter(s), and/or charcoal media filter(s), are used, all in a manner known to those skilled in the art.

According to another embodiment, and without being limited, the various start beam(s) (84)(49), secondary beam(s) (84)(50), primary gripping mechanism(s) (109) and/or the secondary gripping mechanism(s) (110), can be color coded in any suitable and effective manner and/or with any suitable and effective means, known to those skilled in the art. It is preferred, without limitation, that the start beam(s) (84)(49) and primary gripping mechanism(s) (109) are colored green, and the secondary beam(s) (84)(50) and the secondary gripping mechanism(s) (110), are colored red. It is also preferred, without limitation, that these part(s) are constructed from any suitable and effective colored material(s) such as, but not limited to any, suitable anodized and/or colored metal(s), and/or any suitable colored plastic(s). In addition, it is preferred, without limitation, that the start beam(s) (84)(49) and primary gripping mechanism(s) (109), are visually labeled "first, start, or primary", and the secondary beam(s) (84)(50) and the secondary gripping mechanism(s) (110) are visually labeled "second, or end".

According to another embodiment, and without being limited, one or more of any suitable and effective sensor(s), and/or any suitable and effective optical sensor(s), known to those skilled in the art, can be used to monitor and report, at any suitable and effective time(s), when any object(s) (01) have or have not been effectively located into one or more of any, open package(s), open removable package(s) (229), open enclosure(s), and/or one or more of any effective, open packaging material(s) (495). These sensor(s) and/or data, can be used for various purpose(s) such as, but not limited to, aiding in the control of any automated process(s), all in a manner known to those skilled in the art.

According to still another embodiment, and without being limited, any suitable and effective number of gripping mechanism(s) (135), start beam(s) (84)(49), secondary beam(s) (84)(50), primary gripping mechanism(s) (109) and/or the secondary gripping mechanism(s) (110), can be suitably and effectively located and/or designed into, any suitable and effective location(s), space(s), and/or enclosure(s) such as, but not limited to any, package(s), open package(s), enclosure(s), open removable package(s) (229), open enclosure(s), removable treatment enclosure(s) (230), and/or containers that can be opened. Without being limited, the various object(s) (01) can be treated, dried, and/or processed, using any suitable and effective step(s) known to those skilled in the art, and using the various gripping mechanism(s) (135), start beam(s) (84)(49), secondary beam(s) (84)(50), primary gripping mechanism(s) (109) and/or the secondary gripping mechanism(s) (110), in any suitable and effective, space(s), location(s), and/or enclosure(s), and at any suitable and effective, time(s), and duration of time(s). Without being limited, when the one or more object(s) are moved back and forth between any of the various location(s) such as, but not limited to one or more of any, gripping mechanism(s) (135), start beam(s) (84) (49), secondary beam(s) (84)(50), primary gripping mechanism(s) (109) and/or the secondary gripping mechanism(s) (110), for any treatment(s), processing(s), and/or drying(s), step(s), the object(s) (01) can spend any effective amount of time at these location(s) before being moved, and this can happen multiple time(s) for any of the various, treatment(s), processing(s), and/or drying(s), step(s). Without being limited, the various object(s) can be moved back and forth multiple times, and without being limited, at least an effective amount of time(s), between the various, gripping mechanism(s) (135), start beam(s) (84)(49), secondary beam(s) (84)(50), primary gripping mechanism(s) (109) and/or the secondary gripping mechanism(s) (110), during each step within any series of step(s) such as, but not limited to any, processing steps, treatment steps, and/or drying steps.

According to even another embodiment, and without being limited, the container holding chamber(s) (265) can also be designed to be removable, preferably and without limitation, easily and quickly, from the enhanced decontamination enclosure apparatus(s) (715), and function, and/or have, any and/or all of the various suitable and effective, feature(s), functionality(s), and attribute(s), as a removable enclosure(s) (230), that can be suitably and effectively opened to access the contents inside, at any suitable and effective time(s). Without being limited, various suitable valve(s) known to those skilled in the art, that are designed for quick disconnections and reconnections, can be used to removably and effectively connect the container holding chamber(s) (265), with the enhanced decontamination enclosure apparatus(s) (715) and/or any source(s) of any, air, gas(s), and/or substance(s), and more particularity, with one or more of any apparatus(s) and/or supplies such as, but not limited to any, aerosol(s), gas(s), agent(s) (20), and/or vapor(s) supply(s) (15, 20, 65), vacuum and/or negative pressure(s) (98), fresh air/gas supply(s) (17, 51, 38), dehumidified air/gas(s) supply(s) (74), heated air/gas(s) supply(s) (660), and/or filtered air/gas(s) supply(s) (75)(53).

According to another embodiment, and without being limited, the various valve(s) (35)(740) mentioned in these various embodiments can be opened and closed in a manner that is obvious to one skilled in the art, so that the various functions, steps, and procedures described in the present invention can operate effectively. It is preferred, without limitation, that the various valve(s) (35)(740) are effectively and suitably controlled by one or more of any suitable and effective programmable controller(s)/PLC(s) (375), and/or any other suitable programmable device(s), all in a manner known to those skilled in the art.

With reference to FIGS. 113-119, and without limitation, two variations of the current invention are described. Without being limited, the first variation is an improved cabinet mounted treatment chamber processing system (Herein also called "Treatment Cabinet") (2519), that includes, and without limitation, at least one suitable and effective treatment chamber(s) (2026), and where the said one or more treatment chamber(s) (2026) and the various, part(s), equipment(s), and/or device(s), used and/or associated with the function and/or operation of the present invention, are effectively housed within and/or effectively located in, to, and/or directly and/or indirectly connected to, any suitable and effective, cabinet(s), enclosure(s), bulkhead(s), mounting structure(s), mobile mounting structure(s), mobile cabinet(s), mobile surface(s), mobile wall(s), mobile bulkhead(s), mobile frame(s), mobile and/or wheeled apparatus(s), portable device(s), carriage(s), mobile structure(s), mobile mounting structure(s), mobile enclosure(s), mobile cabinet(s), and/or cart(s), (Herein called "Cabinet Outer Enclosure") (2865).

Without being limited, the improved cabinet mounted treatment chamber processing system or treatment cabinet (2519), also includes, and without limitation, at least one airflow system(s) (2521), that includes, and without limitation, at least one of any suitable and effective, filtered and heated inbound air/gas assembly(s) (2525), treatment chamber(s) (2026), and filtered exhaust assembly(s) (2530). Also, without being limited, any one or more parts of the one or more said airflow system(s) (2521) can include one or more of any suitable and effective pipe(s), conduit(s), shaft(s), connector(s), plenum(s), filter support(s), connector fitting(s), filter mounting and/or filter holding means(s), fitting(s), chamber(s), and/or enclosure(s), through which one or more of any, air/gas(s), fresh air/gas(s), heated air/gas(s), heated fresh air/gas(s), humidity(s), vapor(s), gas(s), aerosol(s), airborne chemical(s), and/or deployed agent(s) (2100), can travel through at one or more of any suitable and effective time(s) and for one or more of any suitable and effective length(s) of time(s). These various said pipe(s), conduit(s), shaft(s), connector(s), plenum(s), filter support(s), connector fitting(s), filter mounting and/or filter holding means(s), fitting(s), chamber(s), and/or enclosure(s), can be constructed from one or more of any compatible and suitable and effective, material(s), glass(s), metal(s), and/or plastic(s), known to those skilled in the art. It is preferred, without limitation, that the said pipe(s), conduit(s), shaft(s), connector(s), plenum(s), filter support(s), connector fitting(s), filter mounting and/or filter holding means(s), fitting(s), chamber(s), and/or enclosure(s), are at least constructed from any suitable 316 stainless steel and/or one or more of any suitable and effective plastic(s) such as, but not limited to any, PVC and/or Polypropylene. Also, and without being limited, the said any, pipe(s), conduit(s), shaft(s), connector(s), plenum(s), filter support(s), connector fitting(s), filter mounting and/or filter holding means(s), fitting(s), chamber(s), and/or enclosure(s), can also include one or more of any suitable and effective, measurement(s), dimension(s), size(s), length(s), width(s), height(s), diameter(s), shape(s), and/or geometry(s).

The second variation of the present invention is an improved chamber and/or enclosure mobile processing system which is also called a remote chamber treatment system (2730), that includes, and without limitation, at least one or more of any suitable treatment chamber(s) (2026), that is suitably and effectively located independently from, and/or located at one or more of any suitable and effective different location(s) from, the one or more of any suitable and effective, enclosure(s), cabinet(s), bulkhead(s), mounting structure(s), mobile mounting structure(s), mobile cabinet(s), mobile surface(s), mobile wall(s), mobile bulkhead(s), mobile frame(s), mobile and/or wheeled apparatus(s), portable device(s), carriage(s), mobile structure(s), mobile mounting structure(s), mobile enclosure(s), mobile cabinet(s), and/or cart(s), (Herein called "Processing System Outer Enclosure(s)") (2735), that the various associated and related, parts and components to effectively control, operate, and/or function, the said improved chamber and/or enclosure mobile processing system (2730) can be suitably and effectively, positioned, mounted, and/or located on, to, and/or within, such as, but not limited to one or more of any suitable and effective, modified airflow system(s) (2734), treatment and processing system(s) (2736), processing system outer enclosure(s) (2735), modified treatment agent deployment apparatus(s) (2780), modified filtered and heated inbound air/gas(s) assembly(s) (2790), modified filtered exhaust assembly(s) (2785), inbound air/gas(s) valve(s) control system(s) (2750), outbound air/gas(s) and agent(s) valve(s) valve control system(s) (2795), fan(s), air pump(s), and/or blower(s) (2550)(2660)(2715)(2640), valve(s) (2810)(2805)(2760)(2765), decontamination system(s) (2040) and any associated part(s) and component(s), air/gas(s) flow conduits and/or pipe(s) (2535)(2545)(2555)(2565)(2580)(2800)(2820)(2745)(2755) (2770)(2635)(2652)(2650), at least one of any suitable and effective system control part(s) and component(s) such as, but not limited to one or more of any suitable and effective, computer(s), controller(s), PLC(s), programmable logic circuit(s), programmable logic controller(s), and/or microcomputer(s), to effectively automate and/or control the various operations of the improved chamber and/or enclosure mobile processing system (2730) known to those skilled in the art (Herein called "Microcontroller(s)") (2920), heated air/gas(s) system(s) (2568) to effectively heat the air/gas(s) and/or fresh air/gas(s) before they enter the said treatment chamber(s) (2026), and/or a plurality of any various suitable and effective filter(s) (2540)(2560)(2615)(2620)(2625)(2630)(2645) located at any various suitable and effective location(s) within and/or along the one or more of any airflow system(s) and/or one or more various air/gas(s) flow(s) path(s) of the improved chamber and/or enclosure mobile processing system (2730) such as, but not limited to any, modified filtered and heated inbound air/gas(s) assembly(s) (2790), treatment and processing system(s) (2736), and/or modified filtered exhaust assembly(s) (2785).

Without being limited, the improved chamber and/or enclosure mobile processing system or remote chamber treatment system (2730), also includes, and without limitation, at least one of any suitable and effective, modified airflow system(s) (2734), that includes, and without limitation, at least one of any suitable and effective, modified filtered and heated inbound air/gas assembly(s) (2790), outbound air/gas(s) and agent(s) valve control system(s) (2795), treatment chamber(s) (2026), inbound air/gas valves control system(s) (2750), modified treatment agent deployment apparatus(s) (2780), and modified filtered exhaust assembly(s) (2785).

Without being limited, any object(s) (2300) such as, but not limited to any, equipment(s), device(s), accessory(s), tool(s), cord(s), tube(s), pipe(s), hose(s), tube(s), conduit(s), cable(s), wire(s), umbilical connection(s), scope(s), endoscope(s), ultrasonic probe(s), medical device(s), dental device(s) veterinary device(s), industrial device(s), tool(s) and device(s) for the life sciences industries, ultrasonic device(s), ultrasonic probe(s), imaging device(s), topical imaging device(s), temperature reading device(s), blood pressure monitoring and/or measuring device(s), oxygen monitoring and/or measuring device(s), cutting tool(s), irrigation device(s), suction and/or vacuum device(s), drilling device(s), scope(s), optical tool(s), magnifier(s), optical magnifier(s), light source(s), head lamp(s), helmet(s), head mounted shield(s), face shield(s), eye shield(s), glass(s), clamp(s), surgical tool(s), scope(s) used for ear nose and throat medicine, and/or patient monitoring equipment, including, but not limited to, any of their part(s), accessories, and/or component(s), can be suitably and effectively located and/or positioned within one or more of any suitable and effective, cabinet(s), enclosure(s), chamber(s), sealed chamber(s), sealed enclosure(s), resealable chamber(s), resealable treatment chamber(s), resealable treatment enclosure(s), sealed treatment chamber(s), and/or treatment enclosure(s) (Herein called "Treatment Chamber(s)") (2026), and be effectively, treated, decontaminated, sanitized, disinfected, high-level disinfected, sterilized, and/or dried. Without limitation, the said object(s) (2300) can be suitably and effectively, held, supported, placed, located, and/or hung, within the said treatment chamber(s) (2026) in any suitable and effective manner known to those skilled in the art and with any suitable and effective means such as, but not limited to, that which is described in US Patent #<DON-UP & DOWN FINGERS> Ricciardi, et al., US Patent #<DON-GRIPPERS> Ricciardi, et al., US Patent #<DON-PACKAGING PATENT APPLICATION> Ricciardi, et al., as well as one or more of any other suitable and effective manners and/or with any other suitable and effective means, known to those skilled in the art.

According to FIGS. 113-119, and without limitation, a detailed description of an apparatus and method for an improved cabinet mounted treatment chamber processing system (2519), and the treatment, decontamination, treatment, sanitization, disinfection, high-level disinfection, sterilization, drying, and/or processing, of any surfaces located within one or more of any associated treatment chamber(s) (2026) and/or one or more object(s) (2300) located within the said treatment chamber(s) (2026), is given. Without being limited, the treatment cabinet(s) (2519) can be used for purposes such as, but not limited to, the effective, decontamination, treatment, sanitization, disinfection, high-level disinfection, sterilization, and/or drying, of any surfaces and/or one or more of any surface(s) of one or more of any suitable objects (2300), located within one or more of any suitable and effective treatment chamber(s) (2026).

Figure 113:
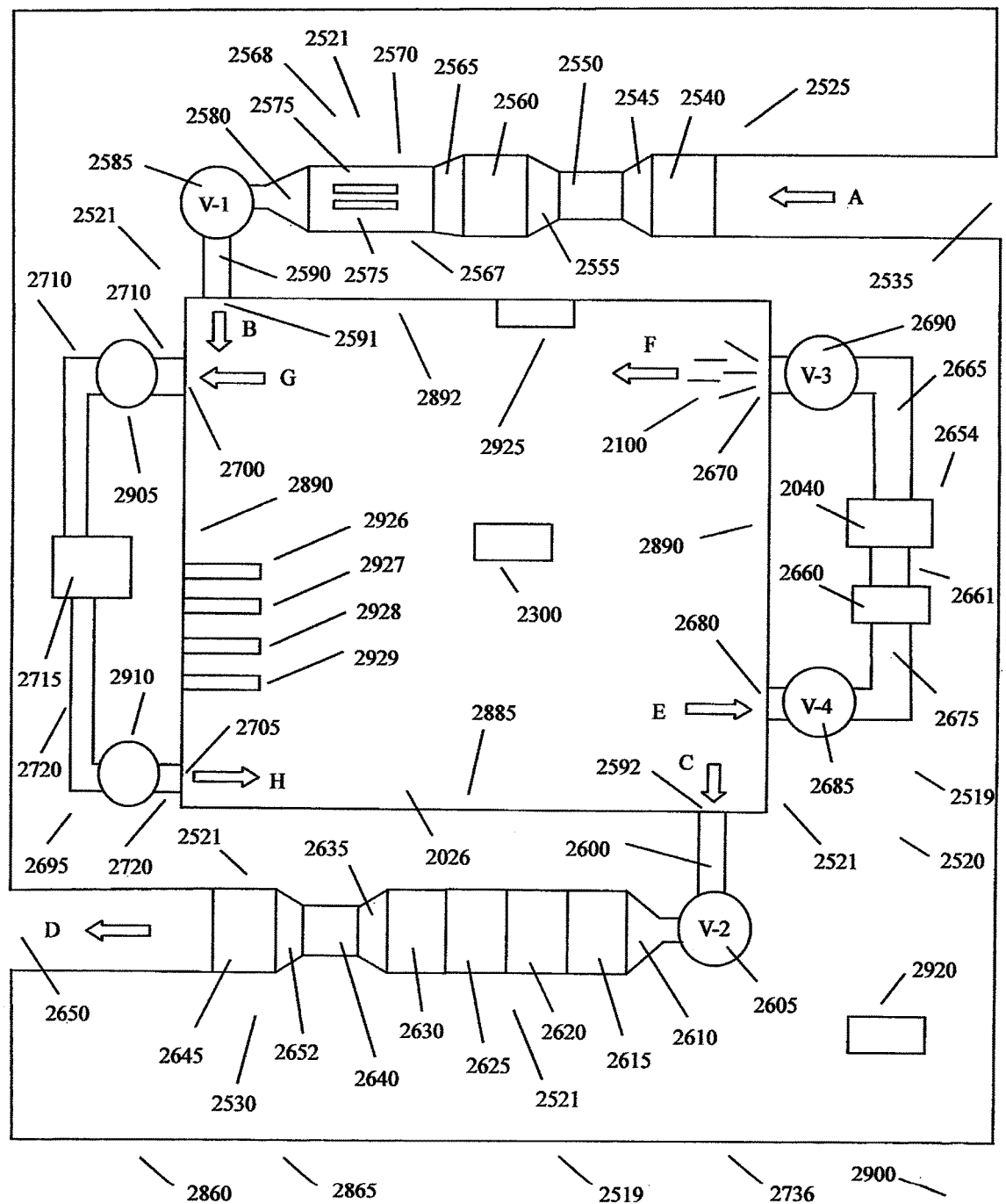
FIG. 113 is a schematic diagram of an improved cabinet mounted treatment chamber processing system where a treatment chamber that connects with an externally accessed resealable access door and supporting components for the treatment and processing system are located inside of a cabinet.
Figure 114:
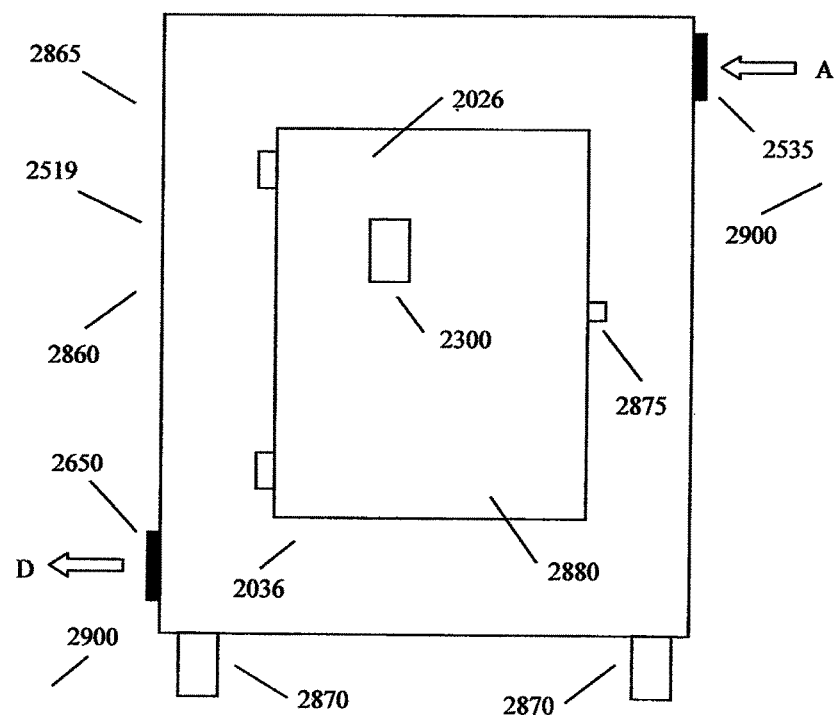
FIG. 114 is a front view of an improved cabinet mounted treatment chamber processing system where a treatment chamber that connects with an externally accessed resealable access door is shown. Also shown is the at least one external air/gas(s) inlet and the external system exhaust outlet.
Figure 115:
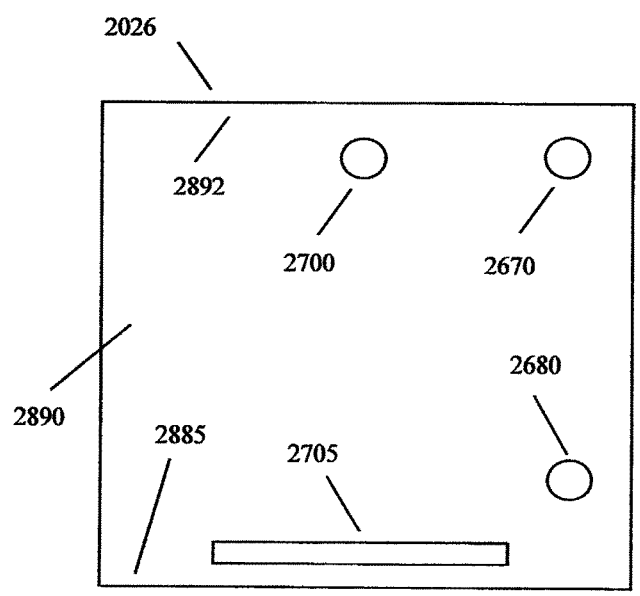
FIG. 115 is a view of the rear treatment chamber wall for the inside of the one or more treatment chambers of an improved cabinet mounted treatment chamber processing system, showing the inlets and outlets for the treatment agents deployment apparatus and the treatment chamber circulation apparatus.
Figure 116:
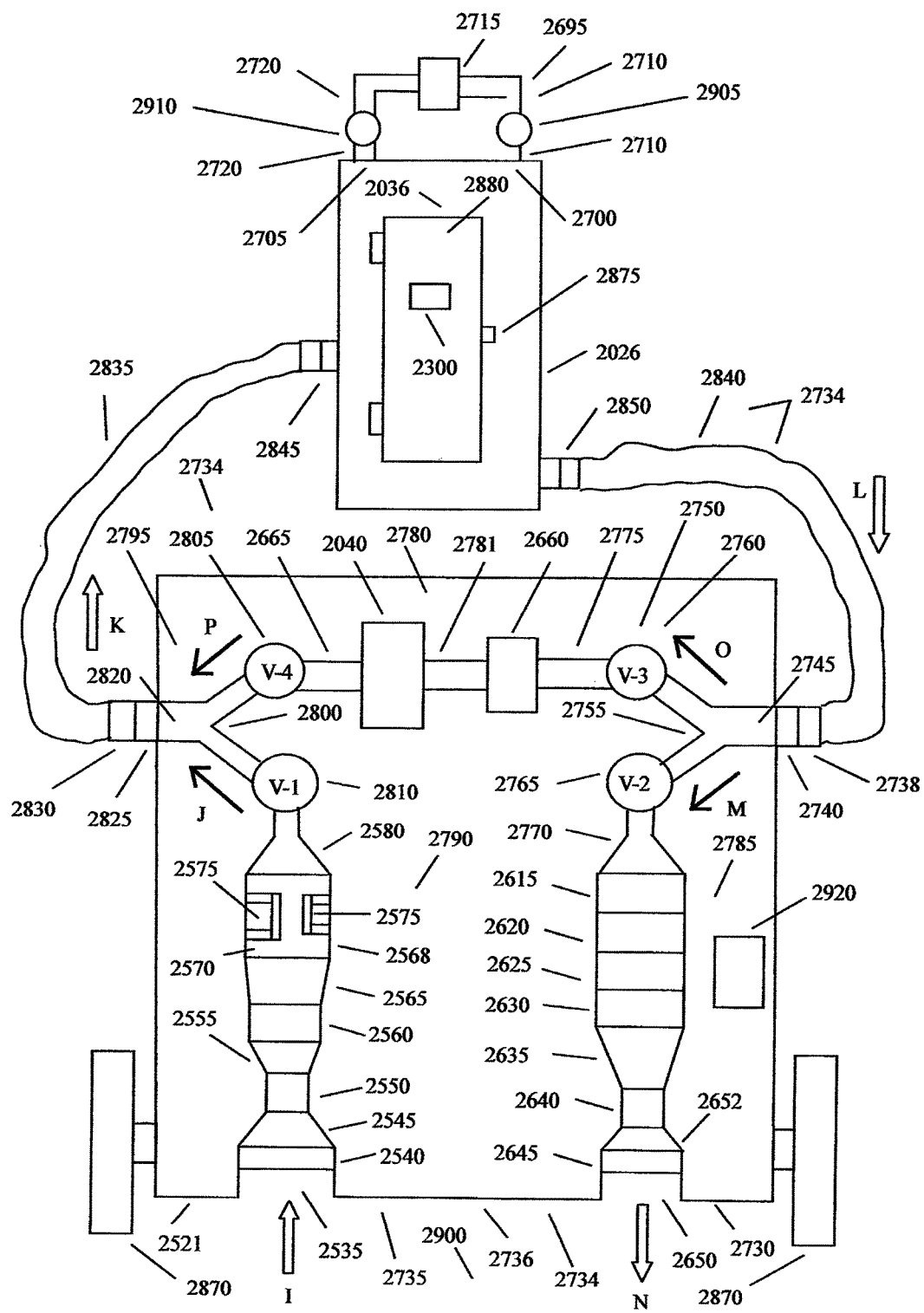
FIG. 116 is a schematic diagram of an improved chamber and/or enclosure mobile processing system where at least one treatment chamber is connected with various conduits to at least one treatment and processing system that is located in an effective housing.
Figure 117:
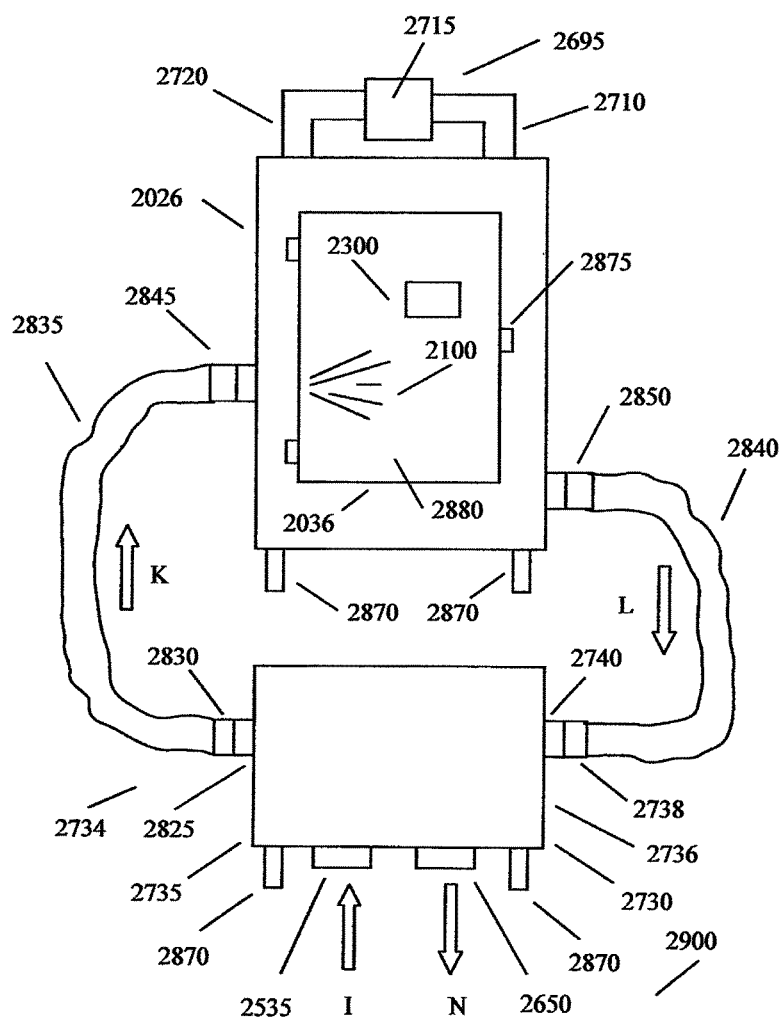
FIG. 117 is a view of an improved chamber and/or enclosure mobile processing system where at least one treatment chamber is connected with various conduits to at least one treatment and processing system that is located in an effective housing.

With reference to FIGS. 113-114, and without limitation, one or more object(s) (2300) are suitably and effectively located inside the treatment chamber(s) (2026). Without limitation, the one or more of any suitable access port(s) and/or door(s) (2036) that access and communicate with the said treatment chamber(s) (2026) can be opened to access the interior of the said treatment chamber(s) (2026) and then effectively closed and sealed, once the said one or more object(s) (2300) are effectively located inside of the said treatment chamber(s) (2026). It is preferred, without limitation, that the said treatment chamber(s) (2026) are hermetically sealed when the said door(s) (2036) are effectively closed. Also, and without limitation, the said door(s) (2036) can be reopened and the one or more treated and/or processed object(s) (2300) can be removed from the said treatment chamber(s) (2026) by any employee(s) after the said object(s) (2300) are effectively, treated, decontaminated, sanitized, disinfected, high-level disinfected, sterilized, and/or dried. Without being limited, the said access port(s) and/or door(s) (2036) can be any suitable and effective size(s) and shape(s), and they can also have one or more of any suitable and effective window(s) (Herein called "Chamber Door Window(s)") (2880) known to those skilled in the art. Also, without being limited, the said access port(s) and/or door(s) (2036) can be secured closed with one or more door holding and/or door securing apparatuses (Herein called "Door Latch(s)") (2875) all in a manner known to those skilled in the art. It is preferred, without limitation, that the said access port(s) and/or door(s) (2036) are effectively sealed and/or hermetically sealed when effectively closed, all in a manner known to those skilled in the art. Without being limited, the said treatment chamber(s) (2026) can be any suitable and effective, measurement(s), dimension(s), size(s), length(s), width(s), height(s), diameter(s), shape(s), and/or geometry(s). Without being limited, the interior of the said treatment chamber(s) (26) can have at least one suitable, chamber floor(s) (2885), ceiling(s) or roof(s) (2892), and chamber wall(s) (2890).

According to FIG. 114, and without being limited, the one or more treatment and processing cabinet(s) (2860) can include one or more of any suitable and effective cabinet outer enclosure(s) (2865) that can suitably and effectively, house, enclose, hold, directly interface with, indirectly interface with, one or more of any suitable and effective treatment chamber(s) (2026). In addition, and without limitation, the treatment and processing cabinet(s) (2860) can be connected to a plurality of more of any suitable and effective wheel(s) and/or any other suitable and effective means (2870) for providing effective movement of the treatment and processing cabinet(s) (2860) when needed, all in a manner known to those skilled in the art.

Without being limited, one or more of any suitable and effective air/gas(s) inlet(s) (2535) and air/gas(s) outlet(s) (2650) can be suitably and effectively located at one or more of any suitable and effective locations on, at, directly connect to, and/or indirectly connected to, the exterior of the treatment and processing cabinet(s) (2860) and/or the cabinet outer enclosure(s) (2865). Also, without being limited, the said air/gas(s) inlet(s) (2535) and air/gas(s) outlet(s) (2650) can be any suitable and effective, measurement(s), dimension(s), size(s), shape(s), geometry(s), diameter(s), length(s), width(s), and/or height(s). It is preferred, without limitation, that at least the one or more air/gas(s) inlet(s) (2535) is located effectively at and/or near the top of the treatment and processing cabinet(s) (2860) and/or the cabinet outer enclosure(s) (2865). However, and without limitation, it is more preferred, without limitation, that both the air/gas(s) inlet(s) (2535) and air/gas(s) outlet(s) (2650) are located effectively at and/or near the top of the treatment and processing cabinet(s) (2860) and/or the cabinet outer enclosure(s) (2865). According to FIGS. 113-114, and without limitation, the one or more air/gas(s) outlet(s) (2650) can also be located at and/or effectively near the bottom of the treatment and processing cabinet(s) (2860) and/or the cabinet outer enclosure(s) (2865).

Without being limited, air/gas(s) and/or fresh air/gas(s) from the environment and/or atmosphere that surrounds the outside of the treatment cabinet(s) (2519), treatment and processing cabinet(s) (2860), and/or the cabinet outer enclosure(s) (2865) (Herein called "Surrounding Environment") (2900), flows and/or is pulled into the air/gas(s) inlet(s) (2535), as shown by "Letter A", and into, through, and/or out of, the one or more airflow system(s) (2521) of the treatment cabinet(s) (2519), and where the air/gas(s), fresh air/gas(s), heated air/gas(s), heated fresh air/gas(s), as well as one or more of any substance(s) that may be present within the treatment chamber(s) such as, but not limited to any, humidity, vapor(s), gas(s), aerosol(s), chemical(s), and/or deployed agent(s) (2100), is flowed, exhausted, and/or pushed, out of the one or more air/gas(s) outlet(s) (2650) and into the environment and/or atmosphere that surrounds the outside of the treatment cabinet(s) (2519), treatment and processing cabinet(s) (2860), and/or the cabinet outer enclosure(s) (2865), as shown by "Letter D". Without being limited, the air/gas(s) and/or fresh air/gas(s) can flow into and through the air/gas(s) inlet(s) (2535) and airflow system(s) (2521) at any suitable and effective, speed(s), velocity(s), quantity(s) of air/gas(s), and/or cubic feet per minute (CFM), and exit the air/gas(s) outlet(s) (2650) at any suitable and effective, speed(s), velocity(s), quantity(s) of air/gas(s), and/or cubic feet per minute (CFM).

Referring again to FIGS. 113-115, and without limitation, after the one or more object(s) (2300) are suitably and effectively located inside of the one or more treatment chamber(s), and the access port(s) and/or door(s) (2036) to the treatment chamber(s) (2026) are effectively closed and sealed, it is preferred, without limitation, that the various valves that control the flow of any substances such as, but not limited to any, air/gas(s), fresh air/gas(s), heated air/gas(s), heated fresh air/gas(s), humidity, vapor(s), gas(s), aerosol(s), chemical(s), and/or deployed agent(s) (2100), into and/or out of the treatment chamber(s) (2026), such as but not limited to, one or more of any, chamber inlet valve(s) (2585) and chamber outlet valve(s) (2605), are effectively closed. Without being limited, the one or more chamber inlet valve(s) (2585) and chamber outlet valve(s) (2605) can prevent various substances such as, but not limited to any, vapor(s), gas(s), aerosol(s), chemical(s), humidity, and/or deployed agent(s) (2100), from leaving and/or flowing out of the treatment chamber(s) (2026) when they are effectively closed. It is preferred, without limitation, that both the various chamber inlet valve(s) (2585) and chamber outlet valve(s) (2605) can at least remain closed until the various surfaces and various surfaces of any object(s) (2300) present within the said treatment chamber(s) (2026) are effectively treated, decontaminated, sanitized, disinfected, high-level disinfected, and/or sterilized.

Without being limited, the various chamber inlet valve(s) (2585) and chamber outlet valve(s) (2605), that communicate with the treatment chamber(s) (2026), can be effectively opened and/or closed at one or more of any suitable and effective time(s) and for any suitable and effective duration of time(s). Also, without being limited, the various chamber inlet valve(s) (2585) and chamber outlet valve(s) (2605) are effectively closed after the one or more object(s) (2300) are effectively located within the treatment chamber(s) (2026), and before and/or about before the deployed agent(s) (2100) are moved, flowed, and/or deployed, into the said treatment chamber(s) (2026).

It is preferred, without limitation, that the various valves (2585)(2605)(2685) (2690) described in the present invention, are controlled and/or communicate with and/or by one or more of any suitable and effective means to effectively automate the treatment cabinet(s) (2519), such as, but not limited to, one or more of any suitable and effective programmable controller(s), programmable logic controller(s), and/or microcontoller(s) (2920), all in a manner known to those skilled in the art.

Without being limited, the one or more of any valve(s) that communicate with the treatment chamber(s) (2026) and the one or more of any, agent generator(s) and/or decontamination system(s) (2040), such as, but not limited to, one or more of any, deployed agent(s) inlet valve(s) (2685) and deployed agent(s) outlet valve(s) (2690), can be effectively opened and/or closed at one or more of any suitable and effective time(s) and for any suitable and effective duration of time(s). It is preferred, without limitation, that the deployed agent(s) inlet valve(s) (2685) and deployed agent(s) outlet valve(s) (2690) are at least effectively open when the deployed agent(s) (2100) are moved, flowed, and/or deployed, into the treatment chamber(s) (2026) from the one or more of any, agent generator(s) and/or decontamination system(s) (2040).

Without being limited, the said deployed agent(s) inlet valve(s) (2685) and deployed agent(s) outlet valve(s) (2690) can remain effectively open or be effectively closed after the various and/or all surfaces within the treatment chamber(s) (2026) and/or the various and/or all surfaces of the one or more object(s) (2300) are: (a) finished being treated by the deployed agent(s) (2100), (b) have been effectively exposed to the deployed agent(s) (2100), (c) the various targeted surfaces of the object(s) (2300) and/or any and/or all surfaces, located in the treatment chamber(s) (2026), have been effectively and/or successfully, treated, decontaminated, sanitized, disinfected, high-level disinfected, and/or sterilized.

Also, without being limited, the said deployed agent(s) inlet valve(s) (2685) and deployed agent(s) outlet valve(s) (2690) can remain effectively open after the entire operation cycle is complete and/or after any cycles such as, but not limited to any, treatment cycle(s), decontamination cycle(s), sanitization cycle(s), disinfection cycle(s), high-level disinfection cycle(s), sterilization cycle(s), drying cycle(s), object(s) (2300) surface(s) drying cycle(s), flushing or removing of the deployed agent(s) (2100) from the treatment chamber(s) (2026) cycle(s), and/or operation cycle(s), are complete, for purposes such as, but not limited to, allowing the one or more agent generator(s) and/or decontamination system(s) (2040) and any connecting conduit(s) to effectively dry in situations such as, but not limited to, after the agent generator(s) and/or decontamination system(s) (2040) has been effectively drained (if applicable).

However, and without being limited, the said deployed agent(s) inlet valve(s) (2685) and deployed agent(s) outlet valve(s) (2690) can also be effectively closed after the entire operation cycle is complete and/or after any cycles such as, but not limited to any, treatment cycle(s), decontamination cycle(s), sanitization cycle(s), disinfection cycle(s), high-level disinfection cycle(s), sterilization cycle(s), drying cycle(s), object(s) (2300) surface(s) drying cycle(s), flushing or removing of the deployed agent(s) (2100) from the treatment chamber(s) (2026) cycle(s), and/or operation cycle(s), are complete for purposes such as, but not limited to, sealing off the one or more agent generator(s) and/or decontamination system(s) (2040) and any connecting conduit(s) so they cannot communicate with the treatment chamber(s) (2026) and deployed agent(s) (2100) cannot continue to move or flow into the treatment chamber(s) (2026) when it is unwanted or not desired. Also, and without being limited, this can be helpful to control and/or prevent odor problems in the treatment chamber(s) (2026) when the chamber door(s) (2036) are closed for any effective period of time after an operation and/or treatment cycle and then later reopened by a machine operator for purposes including, but not limited to, locating new object(s) (2100) inside of the said treatment chamber(s) (2026) to start any new, operation, treatment, decontamination, sanitization, disinfection, high-level disinfection, sterilization, and/or drying, cycle(s).

Additionally, and without limitation, the said deployed agent(s) inlet valve(s) (2685) and deployed agent(s) outlet valve(s) (2690) can also be effectively closed after the various and/or all surfaces within the treatment chamber(s) (2026) and/or the various and/or all surfaces of the one or more object(s) (2300) are: (a) finished being treated by the deployed agent(s) (2100), (b) have been effectively exposed to the deployed agent(s) (2100), (c) have been effectively and/or successfully, treated, decontaminated, sanitized, disinfected, high-level disinfected, and/or sterilized. It is preferred, without limitation, that the deployed agent(s) inlet valve(s) (2685) and deployed agent(s) outlet valve(s) (2690) are effectively closed at least after the various and/or all surfaces within the treatment chamber(s) (2026) and/or the various and/or all surfaces of the one or more object(s) (2300) are: (a) finished being treated by the deployed agent(s) (2100), (b) have been effectively exposed to the deployed agent(s) (2100), (c) the various targeted surfaces of the object(s) (2300) and/or any and/or all surfaces, located in the treatment chamber(s) (2026), have been effectively and/or successfully, treated, decontaminated, sanitized, disinfected, high-level disinfected, and/or sterilized. It is more preferred, without limitation, that the deployed agent(s) inlet valve(s) (2685) and deployed agent(s) outlet valve(s) (2690) are effectively closed after the various, targeted, and/or all, surfaces and/or object surface(s) (2300) within the treatment chamber(s) (2026) have been effectively dried and/or any effective and/or required quantity of the deployed agent(s) (2100) have been effectively removed from the various, targeted, and/or all, surfaces within the treatment chamber(s) (2026). It is even more preferred, without limitation, that the deployed agent(s) inlet valve(s) (2685) and deployed agent(s) outlet valve(s) (2690) are effectively closed after the various, targeted, and/or all, surfaces and/or object surface(s) (2300) within the treatment chamber(s) (2026) have been effectively dried and/or any effective quantity of the deployed agent(s) (2100) have been effectively removed from all of the surfaces within the treatment chamber(s) (2026) and/or all of the surfaces of the treated object(s) (2300) within the treatment chamber(s) (2026).

Without being limited, after activities such as, but not limited to, the one or more object(s) (2300) are effectively located in the treatment chamber(s) (2026), the one or more door(s) (2036) or any effective means to access the inside of the treatment chamber(s) are suitably and effectively closed and sealed, the chamber inlet valve(s) (2585) and chamber outlet valve(s) (2605) are effectively closed and sealed, and both deployed agent(s) inlet valve(s) (2685) and deployed agent(s) outlet valve(s) (2690) are effectively opened, the one or more of any suitable and effective means to generate and/or deploy one or more of any suitable and effective deployed agent(s) (2100) into the treatment chamber(s) (2026), such as, but not limited to one or more of any, agent generator(s), gas(s) source(s), agent producing and/or deployment apparatus(s), hot plate(s), aerosol generator(s), ultrasonic aerosol generator(s), aerosol producing and/or deployment apparatus(s), gas(s) and/or vapor generator(s), gas(s) and/or vapor producing and/or deployment apparatus(s), plasma producing and/or deployment apparatus(s), into the treatment chamber(s), for purposes including, but not limited to any, treatment, decontamination, sanitization, disinfection, high-level disinfection, and/or sterilization, of the various surfaces within the treatment chamber(s)

(2026), are activated and deploy and/or move the said deployed agent(s) (2100) into the said treatment chamber(s) (2026).

Without being limited, the said deployed agent(s) (2100) can be deployed into the said treatment chamber(s) (2026) for any suitable and effective number of time(s) and for any suitable and effective duration of time(s), and any suitable and effective, quantity(s), amount(s), and/or concentration(s), of the deployed agent(s) (2100) can be moved, flowed, and/or deployed, into the said treatment chamber(s) (2026). Also, without being limited, the deployed agent(s) (2100) can remain in the said treatment chamber(s) (2026) for one or more of any suitable and effective duration(s) and/or amounts of time(s) (Herein called "Dwell Time(s)"), before being removed and/or exhausted from the said treatment chamber(s) (2026), all in a manner known to those skilled in the art.

Also, without being limited, at one or more suitable and effective time(s), the deployed agent(s) (2100) that are present in the treatment chamber(s) (2026) and/or present and airborne in the atmosphere(s) within the treatment chamber(s) (2026), can be suitably and effectively stirred, mixed, and/or homogenized. However, and without being limited, the deployed agent(s) (2100) can also be deployed into the said treatment chamber(s) (2026) and not be stirred, mixed, and/or homogenized, and/or be partially stirred, partially mixed, and/or partially homogenized, which in certain situations known to those skilled in the art, may result in any suitable, effective, and/or efficacious, outcome and/or result.

It is preferred, without limitation, that the deployed agent(s) (2100) that are deployed into and/or are present inside of the treatment chamber(s) (2026), are effectively, stirred, moved, homogenized, and/or mixed, one or more time(s), but at least for any effective number of time(s), and at least for any suitable and effective length of time(s), in or within the atmosphere, air, and/or gas(s), inside of the one or more treatment chamber(s) (2026), causing the deployed agent(s) (2100) to uniformly and effectively disperse within the said treatment chamber(s) (2026). It is more preferred, without limitation, that the deployed agent(s) (2100) present within the treatment chamber(s) (2026) are at least suitably and effectively, stirred, moved, homogenized, and/or mixed, one or more time(s) after the treatment chamber(s) (2026) are filled at and/or between about 0.5 percent to 100 percent of the total deployed quantity of the deployed agent(s) (2100) that is needed to completely and/or effectively fill the said treatment chamber(s) (2026). It is even more preferred, without limitation, that the deployed agent(s) (2100) are at least effectively, stirred, moved, homogenized, and/or mixed, one or more time(s), within the said treatment chamber(s) (2026), during and/or after the said treatment chamber(s) (2026) is filled to and/or at one or more of any suitable and effective percentage(s) of the space and/or area(s) within the treatment chamber(s) (2026) with the said deployed agent(s) (2100), but at least when the internal space of the treatment chamber (2026) is filled with the deployed agent(s) (2100) to any effective percentage of the possible total fillable and/or total internal space within the treatment chamber (2026). It is very preferred, without limitation, that the deployed agent(s) (2100) are at least effectively, stirred, moved, homogenized, and/or mixed, one or more time(s), within the said treatment chamber(s) (2026), when the said treatment chamber(s) (2026) is filled to and/or at any suitable and effective percentage of space with the said deployed agent(s) (2100), but at least one or more time(s) when the internal space of the treatment chamber (2026) is filled between about 0.5 percent to 100 percent of the total space within the treatment chamber(s) (2026) with the deployed agent(s) (2100) for a treatment cycle of the said one or more treated object(s) (2300), and then the deployed agent(s) (2100) is effectively, stirred, moved, homogenized, and/or mixed, again one or more time(s), and for any suitable and effective duration of time(s), within the said treatment chamber(s) (2026), any time after the completion of the flowing, moving, and/or deployment of the deployed agent(s) (2100) into the said treatment chamber(s) (2026) and/or during any suitable and effective dwell phase or time before the said deployed agent(s) (2100) are removed from the said treatment chamber(s) (2026). It is extremely preferred, without limitation, that the said deployed agent(s) (2100) are at least effectively, stirred, moved, homogenized, and/or mixed, within the treatment chamber(s) (2026), one or more time(s) after any effective, amount, quantity, and/or concentration, of the deployed agent(s) (2100) has been deployed into and/or is present within the treatment chamber(s) (2026).

Without being limited, the deployed agent(s) (2100) are at least uniformly and effectively mixed, homogenized, and/or dispersed, within the said treatment chamber(s) (2026) one or more time(s) before, during, after, and/or until: (a) the deployment of the deployed agent(s) (2100) into the treatment chamber(s) (2026), (b) the start of one or more of any suitable and effective process(s) to allow the deployed agent(s) (2100) to dwell within the treatment chamber(s) (2026) and provide one or more of any effective amount(s) and/or duration(s) of time(s) for the deployed agent(s) (2100) to be present within the treatment chamber(s) (2026) and interact with the various surfaces within the treatment chamber(s) (2026), and (c) any one or more time(s) the deployed agent(s) (2100) are dwelling or are present within the treatment chamber(s) (2026) so that they can interact with the various surfaces within the treatment chamber(s) (2026). It is also preferred, without limitation, that the deployed agent(s) (2100) are uniformly and effectively dispersed within the said treatment chamber(s) (2026) until the various chamber inlet valve(s) (2585) and chamber outlet valve(s) (2605), that communicate with the treatment chamber(s) (2026), are effectively opened and air/gas(s), heated air/gas(s), fresh air/gas(s), and/or heated fresh air/gas(s), are moved and/or flowed into, through, and out of, the said treatment chamber(s) (2026) for purposes including, but not limited to, removing the deployed agent(s) (2100).

Without being limited, the deployed agent(s) (2100) can be effectively, stirred, moved, and/or mixed, one or more time(s), but at least any effective number of time(s), in or within the atmosphere, air, and/or gas(s), inside of the one or more treatment chamber(s) (2026), using one or more of any effective treatment chamber circulation apparatuses (2695). The said treatment chamber circulation apparatuses (2695) can include, without limitation, one or more of any suitable and effective, circulation inlet(s) (2700), circulation outlet(s) (2705), circulation inlet conduit(s) (2710), circulation blower(s) (2715), and circulation outlet conduit(s) (2720).

Without being limited, any air/gas(s), fresh air/gas(s), heated air/gas(s), heated fresh air/gas(s), humidity, vapor(s), gas(s), aerosol(s), chemical(s), and/or deployed agent(s) (2100), within the treatment chamber(s) (2026) is flowed and/or moved from one or more of any suitable and effective location(s) at and/or within the said treatment chamber(s) (2026), and is pulled, moved, and/or flowed, into the one or more of any suitable and effective circulation inlet(s) (2700) as shown or denoted by "Letter "G". Also without being limited, the said air/gas(s), fresh air/gas(s), heated air/gas(s), heated fresh air/gas(s), humidity, vapor(s), gas(s), aerosol(s), chemical(s), and/or deployed agent(s) (2100) can be flowed, pulled, and/or moved, into the one or more of any suitable and effective treatment chamber circulation apparatuses (2695) at one or more of any suitable and effective, speed(s), velocity(s), cubic feet per minute (CFM), and/or quantity per minute.

Generally, and without being limited, the said air/gas(s), fresh air/gas(s), heated air/gas(s), heated fresh air/gas(s), humidity, vapor(s), gas(s), aerosol(s), chemical(s), and/or deployed agent(s) (2100) can be flowed and/or moved into and through the said circulation inlet(s) (2700) as shown or denoted by "Letter G", then into and through one or more of any suitable and effective circulation input valve(s) (2905), then through the one or more of any suitable and effective circulation inlet conduit(s) (2710), then into and/or through one or more of any suitable and effective circulation blower(s) (2715), then through one or more of any suitable and effective circulation outlet conduit(s) (2720), then into and through one or more of any suitable and effective circulation output valve(s) (2910), and then finally flowed and/or moved through and out of the one or more of any suitable and effective circulation outlet(s) (2705) as shown or denoted by "Letter H".

Without being limited, the said circulation inlet(s) (2700), circulation outlet(s) (2705), circulation inlet conduit(s) (2710), and circulation outlet conduit(s) (2720), can be any suitable and effective size(s), shape(s), length(s), diameter(s), width(s), design(s), and/or construction(s). Also, without being limited, the one or more circulation blower(s) (2715) can be any suitable and effective, size(s), type(s) of fan(s), blower(s), and/or air/gas(s) pump(s), and have any suitable and effective output(s) and airflow(s), and the air/gas(s) that flow out of the said circulation blower(s) (2715) can flow and/or move at any suitable and effective speed(s), velocity(s), quantity(s), flow rate(s), and/or cubic feet per minute(s) (CFM).

More specifically, and without being limited, the treatment chamber circulation apparatuses (2695) and any parts, components, and locations, such as, but not limited to one or more of any, circulation inlet(s) (2700) and circulation outlet(s) (2705), can be located at any suitable and effective location(s). Even more specifically, and without being limited, the one or more treatment chamber circulation apparatuses (2695) and any of its parts and components can be located at and/or communicate with, any suitable and effective locations within, near, approximate to, and/or to, the treatment chamber(s) (2026).

Also, and without being limited, the one or more circulation inlet(s) (2700) can be located and/or positioned at and communicate with, any suitable and effective locations within and/or to the treatment chamber(s) (2026). It is preferred, without limitation, that the one or more circulation inlet(s) (2700) are located at or on one or more of any suitable and effective location(s), near, adjacent to, approximate to, on, and/or at, the ceiling(s) of and/or the top(s) (2892) of the treatment chamber(s) (2026). It is more preferred, without limitation, that the one or more circulation inlet(s) (2700) are located at or on one or more of any suitable and effective location(s) of any suitable and effective wall(s) and/or interior wall(s) (2890) of the treatment chamber(s) (2026) and they are also located at one or more of any suitable and effective location(s), near, adjacent to, approximate to, on, and/or at, any ceiling(s) and/or top(s) (2892) of the treatment chamber(s) (2026).

In addition, and without being limited, the one or more circulation outlet(s) (2705) can be located and/or positioned at and communicate with, any suitable and effective locations within and/or to the treatment chamber(s) (2026). It is preferred, without limitation, that the one or more circulation outlet(s) (2705) are located at or on one or more of any suitable and effective location(s), near, adjacent to, approximate to, on, and/or at, the bottom(s) of and/or the floor(s) (2885) of the treatment chamber(s) (2026). It is more preferred, without limitation, that the one or more circulation outlet(s) (2705) are located at or on one or more of any suitable and effective location(s) of any suitable and effective wall(s) and/or interior wall(s) (2890) of the treatment chamber(s) (2026) and they are also located at one or more of any suitable and effective location(s), near, adjacent to, approximate to, on, and/or at, any bottom(s) of and/or floor(s) (2885) of the treatment chamber(s) (2026).

Without being limited, the circulation outlet(s) (2705) can have any suitable and effective, measurement(s), dimension(s), shape(s), size(s), length(s), geometry(s), width(s), and/or height(s). Also, and without limitation, the said circulation outlet(s) (2705) can have one or more of any suitable and effective orifices having any suitable and effective, measurement(s), dimension(s), shape(s), size(s), length(s), geometry(s), width(s), and/or height(s), through which air/gas(s) can pass through and into the said treatment chamber(s) (2026). Without being limited, the air/gas(s) that leave the said circulation outlet(s) (2705) can exit and/or be directed, at one or more of any suitable and effective angle(s) and/or directions. It is preferred, without limitation, that the one or more circulation outlet(s) (2705) have at least one orifice(s), and the air/gas(s) that leave the said circulation outlet(s) (2705) are directed downward, toward, and/or along, the one or more of any bottom(s) of and/or floor(s) (2885) of the treatment chamber(s) (2026) and/or any one or more of any suitable and effective location(s) and/or area(s), near, adjacent to, approximate to, on, and/or at, any bottom(s) of and/or floor(s) (2885) of the treatment chamber(s) (2026), at one or more of any suitable and effective, speed(s), velocity(s), quantity(s), flow rate(s), and/or cubic feet per minute(s) (CFM). It is even more preferred, without limitation, that the said circulation outlet(s) (2705) have one or more internal and/or external directors that can flow the air/gas(s) that are pushed, flowed, and circulated, by the the one or more circulation blower(s) (2715), outward onto and/or along the one or more of any bottom(s) of and/or floor(s) (2885) of the treatment chamber(s) (2026), in one or more of any effective arc(s) and/or airflow pattern(s). Without being limited, the air/gas(s) that are flowed out of the said circulation outlet(s) (2705) can also be used to effectively dry various surfaces within the treatment chamber(s) (2026) such as, but not limited to any bottom(s) of and/or floor(s) (2885) of the treatment chamber(s) (2026), when it is desired and/or needed to dry various surfaces within the treatment chamber(s) (2026).

Without being limited, one or more of any suitable and effective chamber circulation apparatus(s) (2695) can also dry and/or assist in any drying, the one or more of any surface(s) within the treatment chamber(s) (2026) at one or more of any suitable and effective time(s) and for any suitable and effective quantity of time(s). It is preferred, without limitation, that the said chamber circulation apparatus(s) (2695) is also used to circulate the air/gas(s) within the treatment chamber(s) (2026) to assist in drying the various surface(s) within the treatment chamber(s) (2026) at the beginning of any drying cycle(s) and/or exhaust cycle(s), that is used to remove the deployed agent(s) (2100) from and/or dry the one or more object(s) (2300) and any other targeted and/or desired surface(s), within the treatment chamber(s) (2026).

For example, it is preferred, without limitation, that the chamber circulation apparatus(s) (2695) is also activated and flows any suitable and effective amount(s) of air/gas(s) out of the said circulation outlet(s) (2705) at any suitable and effective, speed(s), velocity(s), quantity(s), flow rate(s), and/or cubic feet per minute(s) (CFM), when air/gas(s), fresh air/gas(s), heated air/gas(s), and/or heated fresh air/gas(s) are flowed into and through the said at least one treatment chamber(s) (2026) for purposes such as, but not limited to, removing the deployed agent(s) (2100) from the inside of the treatment chamber(s) (2026) and/or drying the one or more object(s) (2300) and any other targeted and/or desired surface(s), within the treatment chamber(s) (2026).

According to an embodiment, and FIG. 113, it is preferred, without limitation, that the one or more deployed agent(s) (2100) are created and/or deployed into the one or more treatment chamber(s) (2026) using one or more of any suitable and effective treatment agent deployment apparatus(s) (2654), and more particularly any suitable and effective decontamination system(s) (2040), as described in the present invention. However, and without limitation, any other suitable and effective means and/or apparatus(s) known to those skilled in the art, for generating, creating, deploying, controlling, and/or moving, any suitable and effective deployed agent(s) (2100) in, into, and/or through, the said treatment chamber(s) (2026), can also be used and/or included in the current invention.

Generally, and without being limited, the operation of the treatment agent deployment apparatus(s) (2654) can include, pulling and moving air, gas(s), vapor(s), and/or deployed agent(s) (2100) from within the one or more treatment chamber(s) (2026) as shown be "Letter E", through the at least one deployed agent(s) inlet(s) (2680), through the at least one deployed agent(s) inlet valve(s) (2685) and through the at least one deployed agent(s) air/gas(s) return conduit(s) (2675), where the said air, gas(s), vapor(s), and/or deployed agent(s) (2100) travels to and is then effectively pulled and/or suctioned through the at least one agent blower(s) (2660), and then travels under positive pressure and is effectively pushed through at least one agent generator blower connection conduit(s) (2661) to the at least one decontamination system(s) (2040). Also, without being limited, the said air, gas(s), vapor(s), and/or deployed agent(s) (2100) that are pushed and flow to and then through the said one or more decontamination system(s) (2040) effectively carry, interact with, mix with, and/or move, the one or more deployed agent(s) (2100) that are created, generated, and/or released, by the said decontamination system(s) (2040), and move and/or flow the newly created, generated, and/or released, deployed agent(s) (2100), out of the said decontamination system(s) (2040), through the deployed agent(s) outlet conduit(s) (2665), through the deployed agent(s) outlet valve(s) (2690), and then out of the deployed agent(s) outlet(s) (2670) and into the treatment chamber(s) (2026) as shown by "Letter F".

Alternatively, and without being limited, at least one agent blower(s) (2660), can also be suitably and effectively located at one or more of any suitable and effective location(s) after (not shown) the one or more decontamination system(s) (2040). In this alternative form, the operation of the treatment agent deployment apparatus(s) (2654) can include, pulling and moving air, gas(s), vapor(s), and/or deployed agent(s) (2100) from within the one or more treatment chamber(s) (2026) as shown be "Letter E", through the at least one deployed agent(s) inlet(s) (2680), through the at least one deployed agent(s) inlet valve(s) (2685) and through the at least one deployed agent(s) air/gas(s) return conduit(s) (2675), where the said air, gas(s), vapor(s), and/or deployed agent(s) (2100) travels to and is then effectively pulled and/or suctioned through the at least one agent generator blower connection conduit(s) (2661) and the at least one decontamination system(s) (2040). Also, without being limited, the said air, gas(s), vapor(s), and/or deployed agent(s) (2100) that are pulled and/or suctioned through the said one or more decontamination system(s) (2040) effectively carry, interact with, mix with, and/or move, the one or more deployed agent(s) (2100) that are created, generated, and/or released, by the said decontamination system(s) (2040), and move and/or flow the newly created, generated, and/or released, deployed agent(s) (2100), out of the said decontamination system(s) (2040), through a first deployed agent(s) outlet conduit(s) (not shown), where the said air, gas(s), vapor(s), and/or deployed agent(s) (2100), and newly created deployed agent(s) (2100) travels to and is then effectively pulled and/or suctioned through the at least one agent blower(s) (2660), and then travels under positive pressure and is effectively pushed through the deployed agent(s) outlet conduit(s) (2665), through the deployed agent(s) outlet valve(s) (2690), and then out of the deployed agent(s) outlet(s) (2670) and into the treatment chamber(s) (2026) as shown by "Letter F".

Without being limited, the at least one agent blower(s) (2660), can be any suitable and effective fan(s), air pump(s), and/or blower(s), known to those skilled in the art, and can be located at one or more of any suitable and effective location(s). It is preferred, without limitation, that the agent blower(s) (2660) is any suitable and effective blower(s) known to those skilled in the art. Without limitation, the agent blower(s) (2660) can move and/or flow the various air, gas(s), vapor(s), and/or deployed agent(s) (2100), into, through, within, and/or out of, the treatment agent deployment apparatus(s) (2654) at any suitable and effective, speed(s), velocity(s), quantity(s) per unit of time, and/or cubic feet per minute (CFM). Without being limited, the one or more conduits through which the various air, gas(s), vapor(s), and/or deployed agent(s) (2100) travel, can be any suitable and effective, size(s), diameter(s), shape(s), and length(s).

Without being limited, the one or more deployed agent(s) inlet(s) (2680) and deployed agent(s) outlet(s) (2670) can be located at and communicate with, any one or more of any suitable and effective locations within, inside of, and/or to the treatment chamber(s) (2026). It is preferred, without limitation, that the one or more deployed agent(s) inlet(s) (2680) are at least located at or on one or more of any suitable and effective location(s), near, adjacent to, approximate to, on, and/or at, the middle area of the inside of the treatment chamber(s) (2026). It is more preferred, without limitation, that the one or more deployed agent(s) inlet(s) (2680) are located at or on one or more of any suitable and effective location(s), near, adjacent to, approximate to, on, and/or at, the bottom(s) of and/or the floor(s) of the inside of the treatment chamber(s) (2026). It is even more preferred, without limitation, that the one or more deployed agent(s) inlet(s) (2680) are located at or on one or more of any suitable and effective location(s) of any suitable and effective wall(s) and/or interior wall(s) of the treatment chamber(s) (2026) and they are also located at one or more of any suitable and effective location(s), near, adjacent to, approximate to, on, and/or at, any bottom(s) of and/or floor(s) of the inside of the treatment chamber(s) (2026). It is also preferred, without limitation, that the one or more deployed agent(s) outlet(s) (2670) are located at or on one or more of any suitable and effective location(s), near, adjacent to, approximate to, on, and/or at, the top(s) of and/or the ceilings(s) of the treatment chamber(s) (2026). It is more preferred, without limitation, that the one or more deployed agent(s) outlet(s) (2670) are located at or on one or more of any suitable and effective location(s) of any suitable and effective wall(s) and/or interior wall(s) of the treatment chamber(s) (2026) and they are also located at one or more of any suitable and effective location(s), near, adjacent to, approximate to, on, and/or at, any top(s) of and/or ceilings(s) of the treatment chamber(s) (2026).

Without being limited, the deployed agent(s) inlet(s) (2680) and deployed agent(s) outlet(s) (2670), can have any suitable and effective, measurement(s), dimension(s), shape(s), size(s), length(s), geometry(s), width(s), outlet(s), and/or height(s). Also, and without limitation, the said deployed agent(s) outlet(s) (2670), can have one or more of any suitable and effective orifices having any suitable and effective, measurement(s), dimension(s), shape(s), size(s), length(s), geometry(s), width(s), and/or height(s), through which any deployed agent(s) (2100) and/or air/gas(s) can pass through and into the said treatment chamber(s) (2026). Without being limited, any deployed agent(s) (2100) and/or air/gas(s) that leave the said deployed agent(s) outlet(s) (2670) can exit and/or be directed, in one or more of any suitable and effective angle(s) and/or direction(s). It is preferred, without limitation, that the one or more deployed agent(s) outlet(s) (2670) can have at least one orifice(s), and the deployed agent(s) (2100) and/or air/gas(s) that leave the said deployed agent(s) outlet(s) (2670) are directed suitably and effectively, outward, downward, and/or upward, within and/or into the said treatment chamber(s) (2026).

Without being limited, once any suitable and effective, amount, quantity, ppm level, and/or concentration, of the deployed agent(s) (2100) is moved, flowed, and/or deployed into the treatment chamber(s) (2026), the flow of the said deployed agent(s) (2100) into the said treatment chamber(s) (2026) can stop, and one or more of any suitable and effective dwell cycle(s) can take place, for any suitable and effective duration(s) of time(s), so that the deployed agent(s) (2100) can remain airborne within the said treatment chamber(s) (2026), and have any suitable and effective amount of time(s) to suitably and effectively interact with, coat, and/or interface with, the various surface(s) within the said treatment chamber(s) (2026) such as, but not limited to any one or more surface(s) of the treated object(s) (2300).

More specifically, and without being limited, during one or more of any time(s) between when the deployed agent(s) (2100) have stopped being moved, flowed, and/or deployed into the treatment chamber(s) (2026), and the start of one or more of any process(s) to move the deployed agent(s) (2100) out of the said treatment chamber(s) (2026) and/or the start of one or more of any process(s) to dry any surface(s) within the treatment chamber(s) (2026) (Herein called "Dwell Cycle(s)), the deployed agent(s) (2100) can be given any suitable and effective amount of time to suitably and effectively interact with, coat, and/or interface with, the various surface(s) within the said treatment chamber(s) (2026) such as, but not limited to, any one or more surface(s) of the treated object(s) (2300). Also, and without being limited, the deployed agent(s) that are airborne and present within the said treatment chamber(s) (2026) during this time, can be suitably and effectively stirred, moved, homogenized, and/or mixed, within the treatment chamber(s) (2026), one or more time(s).

Without being limited, any one or more dwell time(s) and/or any one or more of any processes of using one or more of any dwell time(s) or lengthening the time that the deployed agent(s) (2100) can persist in the said treatment chamber(s) (2026), can also be bypassed and/or not used, and the one or more of any action(s) and/or process(s) to remove the deployed agent(s) (2100) from the treatment chamber(s) (2026) and/or dry the one or more of any various surface(s) and/or surface(s) of the treated object(s) (2300), can take place and/or is used instead. It is preferred, without limitation, that one or more of any suitable and effective dwell cycle(s) and/or dwell time(s) is used, transpires, and/or is undertaken.

Without being limited, when the one or more of any surface(s) and/or one or more of any surface(s) of the treated object(s) (2300) within the one or more treatment chamber(s) (2026) are suitably and effectively, treated, decontaminated, sanitized, disinfected, high-level disinfected, and/or sterilized, the following at least two options and/or actions can be, and without limitation, taken: (a) in the first option, the deployed agent(s) (2100) are removed from the said treatment chamber(s) (2026) before the said treated object(s) (2300) are removed from the said treatment chamber(s) (2026), and (b) in the second and preferred option, and without limitation, the deployed agent(s) (2100) are removed from the said treatment chamber(s) (2026) and the said treated object(s) (2300) are effectively dried and/or the deployed agent(s) (2100) are effectively removed from the various surfaces inside of the said treatment chamber(s) (2026) from various surfaces such as, but not limited to, the one or more surface(s) of the said one or more treated object(s) (2300), before the said treated object(s) (2300) are removed from the said treatment chamber(s) (2026).

Also, and without being limited, once the one or more of any surface(s) and/or one or more of any surface(s) of the treated object(s) (2300) within the one or more treatment chamber(s) (2026) are suitably and effectively, treated, decontaminated, sanitized, disinfected, high-level disinfected, and/or sterilized, the deployment, movement, and/or flow, of the deployed agent(s) (2100) into the said treatment chamber(s) (2026) from the one or more treatment agent deployment apparatus(s) (2654) or any other deployed agent(s) (2100) generator(s) and/or dispenser(s) is stopped, and the process for removing the said deployed agent(s) (2100) from the said treatment chamber(s) (2026) and/or drying the various surfaces within the said treatment chamber(s) (2026) can begin.

Without being limited, effectively and/or suitably removing the deployed agent(s) (2100) from the treatment chamber(s) (2026), chamber circulation apparatus(s) (2695), and/or treatment agent deployment apparatus(s) (2654), can include, and without limitation, flowing and/or moving, air/gas(s), fresh air/gas(s), heated air/gas(s), and/or heated fresh air/gas(s), into, through, and/or out of, the said treatment chamber(s) (2026), chamber circulation apparatus(s) (2695), and/or treatment agent deployment apparatus(s) (2654), at one or more of any suitable and effective time(s) and for one or more of any suitable and effective duration(s) of time(s), and at least until one or more of any, level(s), quantity(s), concentration(s), amount(s), and/or parts per million (PPM), of the deployed agent(s) (2100), within the treatment chamber(s) (2026), chamber circulation apparatus(s) (2695) and/or treatment agent deployment apparatus(s) (2654), are at any suitable, effective, legal, permissible, acceptable, targeted, safe, and/or desired, level(s), quantity(s), concentration(s), amount(s), and/or parts per million (PPM), and where the said air/gas(s), fresh air/gas(s), heated air/gas(s), and/or heated fresh air/gas(s), are moved and/or flowed at any suitable and effective, speed(s), velocity(s), quantity(s) per unit of time, and/or cubic feet per minute (CFM), into, through, and out of, the said treatment chamber(s) (2026), chamber circulation apparatus(s) (2695), and/or treatment agent deployment apparatus(s) (2654).

Also, and without limitation, suitably and effectively drying the one or more of any surface(s) within the treatment chamber(s) (2026), chamber circulation apparatus(s) (2695), and/or treatment agent deployment apparatus(s) (2654), can include, and without limitation, flowing and/or moving, air/gas(s), fresh air/gas(s), heated air/gas(s), and/or heated fresh air/gas(s), into, through, and out of, the said treatment chamber(s) (2026), chamber circulation apparatus(s) (2695), and/or treatment agent deployment apparatus(s) (2654), at one or more of any suitable and effective time(s) and for one or more of any suitable and effective duration(s) of time(s), and at least until the one or more of any surface(s) inside of the said treatment chamber(s) (2026), chamber circulation apparatus(s) (2695), and/or treatment agent deployment apparatus(s) (2654), including, but not limited to, the one or more of any surface(s) of the said treated object(s) (2300) and/or any other surfaces such as, but not limited to, any of those within the treatment chamber(s) (2026), chamber circulation apparatus(s) (2695), and/or treatment agent deployment apparatus(s) (2654), are suitably and/or effectively dry and/or the various surface(s) of the treated object(s) (2300) are at and/or meet any suitable, effective, legal, permissible, acceptable, targeted, safe, and/or desired, level(s), quantity(s), concentration(s), amount(s), and/or parts per million (PPM), of the deployed agent(s) (2100), and/or meet or exceed any standards established by the United States Food and Drug Administration (FDA).

Without being limited, once the deployment, movement, and/or flow, of the deployed agent(s) (2100) into the said treatment chamber(s) (2026) from the one or more treatment agent deployment apparatus(s) (2654) or any other deployed agent(s) (2100) generator(s) and/or dispenser(s) is stopped, and the one or more treated object(s) (2300) are suitably and effectively, treated, decontaminated, sanitized, disinfected, high-level disinfected, and/or sterilized, the one or more chamber inlet valve(s) (2585) and chamber outlet valve(s) (2605), that communicate with the treatment chamber(s) (2026), are effectively opened. It is preferred, without limitation, that once both the one or more chamber inlet valve(s) (2585) and chamber outlet valve(s) (2605) are suitably and effectively opened and/or open, the inbound blower(s) (2550) and exhaust blower(s) (2640) are activated and/or operated, so that a suitable and effective amount of air/gas(s), fresh air/gas(s), heated air/gas(s), and/or heated fresh air/gas(s), are flowed into, through, and out of, the one or more treatment chamber(s) (2026). It is preferred, without limitation, that the said air/gas(s) and/or fresh air/gas(s) are effectively heated, by one or more of any suitable and effective means to heat the said air/gas(s) and/or fresh air/gas(s) known to those skilled in the art, to one or more of any suitable and effective temperature(s), before being flowed into, through, and out of, the one or more treatment chamber(s) (2026).

Without being limited, air/gas(s) and/or more preferred, and without limitation, fresh air/gas(s), are sourced from the surrounding environment (2900) or from the environment and/or atmosphere that surrounds the outside of the treatment cabinet(s) (2519), treatment and processing cabinet(s) (2860), and/or the cabinet outer enclosure(s) (2865), are pulled and/or drawn in by the one or more of any suitable and effective inbound blower(s) (2550) into the filtered and heated inbound air/gas(s) assembly (2525).

Without being limited, the at least one filtered and heated inbound air/gas(s) assembly(s) (2525) can include, and without limitation, at least one of any various suitable and effective parts and components that suitably and effectively connect and communicate with each other, such as, but not limited to any, airflow inlet(s) (2535), where the airflow inlet(s) (2535) suitably and effectively connects to and communicates with any airflow inlet prefilter(s) (2540), where the at least one airflow inlet prefilter(s) (2540) connects and communicates with the at least one inlet conduit(s) (2545), and where the at least one inbound blower(s) (2550) connects and communicates with at least one inlet conduit(s) (2545) and at least one prefilter conduit(s) (2555), and where the inbound air filter(s) (2560) connects and communicates with at least one prefilter conduit(s) (2555) and at least one post filter conduit(s) (2565), and where the at least one post filter conduit(s) (2565) connects and communicates with the at least one heated air/gas(s) system(s) (2568), and where the heated air/gas(s) system(s) (2568) includes, and without limitation, at least one heated air/gas(s) conduit(s) (2570) and at least one heater element(s) (2575), and where any air/gas(s) and/or fresh air/gas(s) flow suitably and effectively through the heated air/gas(s) system(s) (2568) and heated air/gas(s) conduit(s) (2570), and also where the at least one heated air/gas(s) system(s) (2568) and heated air/gas(s) conduit(s) (2570) connects and communicates with at least one prevalve conduit(s) (2580), and where the at least one prevalve conduit(s) (2580) connects and communicates with the at least one chamber inlet valve(s) (2585), and where the at least one chamber inlet valve(s) (2585) connects and communicates with the at least one chamber inlet conduit(s) (2590), and where the at least one chamber inlet conduit(s) (2590) connects and communicates with the at least one chamber inlet(s) (2591), and where the at least one chamber inlet(s) (2591) connects and communicates with the one or more interior space(s) of the one or more treatment chamber(s) (2026). Without being limited, the one or more flows, streams, and/or movements of the one or more air/gas(s), fresh air/gas(s), heated air/gas(s), and/or heated fresh air/gas(s) out of the filtered and heated inbound air/gas(s) assembly (2525) and into the said treatment chamber(s) (2026), is shown or denoted by "Letter "B".

Without being limited, the various said parts and components of the filtered exhaust assembly(s) (2530) can be located at one or more of any suitable and effective location(s) and/or position(s), and can be located in one or more of any suitable and effective order(s) and/or one or more of any suitable and effective combination(s) of position(s) and/or order(s) of location(s) and/or position(s).

Without being limited, the said various parts and components of the said filtered and heated inbound air/gas(s) assembly(s) (2525) can effectively connect and communicate with each other so that air/gas(s), fresh air/gas(s), heated air/gas(s), and/or heated fresh air/gas(s), can flow into and through the said filtered and heated inbound air/gas(s) assembly(s) (2525) and into and through the said treatment chamber(s) (2026).

Without being limited, the inbound blower(s) (2550) can be any suitable and effective, fan(s), air pump(s), and/or blower(s), known to those skilled in the art, and can be located at one or more of any suitable and effective location(s). It is preferred, without limitation, that the one or more inbound blower(s) (2550) is any suitable and effective blower(s) known to those skilled in the art, and more preferred, without limitation, is any suitable and effective fan(s) known to those skilled in the art. Without being limited, the said inbound blower(s) (2550) can have any suitable and effective output, airflow, and/or cubic feet per minute (CFM) rating. It is preferred, without limitation, that the said inbound blower(s) (2550) has an output and/or is rated at least at about 1 cubic feet per minute or more. It is more preferred, without limitation, that the said inbound blower(s) (2550) has an output and/or is rated between about 5 and about 1,000 cubic feet per minute. It is even more preferred, without limitation, that the said inbound blower(s) (2550) has an output and/or is rated between about 200 and about 700 cubic feet per minute. Without being limited, the said inbound blower(s) (2550) can have any suitable and effective, length, width, height, and/or diameter, and preferably, and without limitation, a diameter between about 1 inch to about 24 inch, and even more preferably, and without limitation, a diameter between about 3 inch to about 8 inch.

Without being limited, the air/gas(s), fresh air/gas(s), heated air/gas(s), and/or heated fresh air/gas(s), can flow into and through the filtered and heated inbound air/gas(s) assembly (2525) and any of its various parts and components, at one or more of any suitable and effective, speed(s), velocity(s), quantity(s), flow rate(s), and/or cubic feet per minute(s) (CFM).

Without limitation, the inbound blower(s) (2550) can move and/or flow the air/gas(s), fresh air/gas(s), heated air/gas(s), heated fresh air/gas(s), humidity, vapor(s), gas(s), aerosol(s), chemical(s), and/or deployed agent(s) (2100), and/or assist with the movement and/or flow of, the air/gas(s), fresh air/gas(s), heated air/gas(s), heated fresh air/gas(s), humidity, vapor(s), gas(s), aerosol(s), chemical(s), and/or deployed agent(s) (2100), with the assistance of the one or more exhaust blower(s) (2640), into, through, within, and/or out of, various locations, parts, and components, such as, but not limited to, the filtered and heated inbound air/gas(s) assembly (2525), treatment chamber(s) (2026), and filtered exhaust assembly (2530), and any of their various parts and components, at any suitable and effective, speed(s), velocity(s), quantity(s) per unit of time, and/or cubic feet per minute (CFM).

It is preferred, without limitation, that the air/gas(s) and/or fresh air/gas(s) are flowed and/or moved into, through, within, and/or out of, various locations, parts, and components, such as, but not limited to, the one or more, filtered and heated inbound air/gas(s) assembly(s) (2525), treatment chamber(s) (2026), and filtered exhaust assembly (2530), with a cubic feet per minute value or measurement that is at least suitable and effective. It is more preferred, without limitation, that the air/gas(s) and/or fresh air/gas(s) are flowed and/or moved into, through, within, and/or out of, various locations, parts, and components, such as, but not limited to, the one or more, filtered and heated inbound air/gas(s) assembly(s) (2525), treatment chamber(s) (2026), and filtered exhaust assembly (2530), with a cubic feet per minute value or measurement of at least 2 or more cubic feet per minute (CFM). It is even more preferred, without limitation, that the air/gas(s) and/or fresh air/gas(s) are flowed and/or moved into, through, within, and/or out of, various locations, parts, and components, such as, but not limited to, the filtered and heated inbound air/gas(s) assembly (2525), treatment chamber(s) (2026), and filtered exhaust assembly (2530), with a cubic feet per minute value or measurement between at least 10 to 950 or more cubic feet per minute (CFM). It is very preferred, without limitation, that the air/gas(s) and/or fresh air/gas(s) are flowed and/or moved into, through, within, and/or out of, various locations, parts, and components, such as, but not limited to, the filtered and heated inbound air/gas(s) assembly (2525), treatment chamber(s) (2026), and filtered exhaust assembly (2530), with a cubic feet per minute value or measurement between at least about 10 to about 1,000 cubic feet per minute (CFM).

Without being limited, the air/gas(s), fresh air/gas(s), heated air/gas(s), heated fresh air/gas(s), humidity, vapor(s), gas(s), aerosol(s), chemical(s), and/or deployed agent(s) (2100), can flow into and through the filtered and heated inbound air/gas(s) assembly (2525) at one or more of any suitable and effective, speed(s), velocity(s), quantity(s), flow rate(s), and/or cubic feet per minute(s) (CFM).

Without being limited, the air/gas(s) and/or fresh air/gas(s) can first pass through one or more of any suitable and effective first air/gas(s) filter(s) or airflow inlet prefilter(s) (2540) before being pulled into and through the filtered exhaust assembly (2530) and/or the inbound blower(s) (2550). Without being limited, the airflow inlet prefilter(s) (2540) can have one or more of any suitable and effective, performance rating(s), filter rating(s), DOP filter rating(s), MERV filter rating(s), HEPA filter rating(s), and/or ULPA filter rating(s), all in a manner known to those skilled in the art for any given use and/or application. Without being limited, the one or more airflow inlet prefilter(s) (2540) can also include and/or be one or more of any suitable and effective, DOP, HEPA, and/or ULPA, rated filters, all in a manner known to those skilled in the art.

Also, and without being limited, the airflow inlet prefilter(s) (2540) can be used and/or provide one or more of any suitable and effective purposes, uses, and/or functions, such as, but not limited to, providing one or more easily replaceable and/or cheaper first filter(s) that can assist with keeping the inbound blower(s) (2550) effectively clean and/or extending the life of the inbound air filter(s) (2560). It is preferred, without limitation, that the airflow inlet prefilter(s) (2540) is at least one or more of any effective filter(s), sponge(s), and/or screen(s), material(s) that is commonly supplied with various muffin type fans in a manner known to those skilled in the art, and the said airflow inlet prefilter(s) (2540) has a MERV rating between about 0 MERV to about 20 MERV. It is more preferred, without limitation, that the airflow inlet prefilter(s) (2540) has at least a MERV 0.25 or higher rating. It is even more preferred, without limitation, that the airflow inlet prefilter(s) (2540) has any MERV rating between about 1 MERV to about 20 MERV. It is very preferred, without limitation, that the airflow inlet prefilter(s) (2540) is any suitable and effective filter that has a MERV rating between about 3 MERV to about 10 MERV Without being limited, the airflow inlet prefilter(s) (2540) can have any suitable and effective, flow resistance, airflow resistance, airflow filter resistance, and/or air resistance, at any suitable and effective airflow rate, airflow speed, and/or airflow measurement in cubic feet per minute (CFM), but it is preferred, without limitation, that the said airflow inlet prefilter(s) (2540) at least has as effectively low or minimal of flow resistance, airflow resistance, airflow filter resistance, and/or air resistance as possible. Also, without being limited, the said airflow inlet prefilter(s) (2540) can have any suitable and effective, length, width, height, and/or diameter, and preferably, and without limitation, a diameter and/or length, width and/or height, between about 1 inch to about 48 inch, and even more preferably, and without limitation, a diameter and/or length, width, and/or height, between about 3 inch to about 10 inch.

Without being limited, the said air/gas(s) and/or fresh air/gas(s) enters the said one or more inbound blower(s) (2550) and is then blown out of the said one or more inbound blower(s) (2550), in any effective manner known to those skilled in the art, towards the one or more treatment chamber(s) (2026) it connects and communicates with. Without being limited, the said air/gas(s) and/or fresh air/gas(s) is blown, pushed, forced, flowed, and/or moved, with any suitable and effective, and without limitation, force, pressure(s), and/or positive pressure(s) created by the said inbound blower(s) (2550), through one or more of any suitable and effective inbound air filter(s) (2560).

Without being limited, the air/gas(s) and/or fresh air/gas(s) can pass through one or more of any suitable and effective second air/gas(s) filter(s) or inbound air filter(s) (2560) before being pushed and/or flowed into and through the one or more heated air/gas(s) system(s) (2568), the chamber inlet valve(s) (2585), and the treatment chamber(s) (2026). Without being limited, the inbound air filter(s) (2560) can have one or more of any suitable and effective, performance rating(s), filter rating(s), DOP filter rating(s), MERV rating(s), HEPA rating(s), and/or ULPA rating(s), all in a manner known to those skilled in the art for any given use and/or application. Without being limited, the one or more inbound air filter(s) (2560) can also include one or more of any suitable and effective, DOP, HEPA, and/or ULPA, rated filters, all in a manner known to those skilled in the art. It is preferred, without limitation, that the inbound air filter(s) (2560) has at least a MERV 1 or higher rating. It is more preferred, without limitation, that the inbound air filter(s) (2560) has any MERV rating between about 0.25 MERV to at least 20 MERV. It is even more preferred, without limitation, that the one or more inbound air filter(s) (2560) is any suitable and/or effective HEPA filter(s) and/or ULPA filter(s).

Without being limited, the inbound air filter(s) (2560) can have any suitable and effective, flow resistance, airflow resistance, airflow filter resistance, and/or air resistance, at any suitable and effective airflow rate, airflow speed, and/or airflow measurement in cubic feet per minute (CFM), but it is preferred, without limitation, that the said inbound air filter(s) (2560) at least has as effectively low or minimal of flow resistance, airflow resistance, airflow filter resistance, and/or air resistance as possible. Also, without being limited, the said inbound air filter(s) (2560) can have any suitable and effective, length, width, height, and/or diameter, and preferably, and without limitation, a diameter and/or length, width and/or height, between about 1 inch to about 48 inch, and even more preferably, and without limitation, a diameter and/or length, width, and/or height, between about 3 inch to about 10 inch.

Also, and without being limited, after passing through the one or more inbound air filter(s) (2560) the air/gas(s) and/or fresh air/gas(s) can pass through one or more of any suitable and effective means to effectively and suitably heat the flow of the said moving air/gas(s) and/or fresh air/gas(s) to one or more of any suitable and effective temperature(s) (Herein called the "Heated Air/gas(s) System(s)") (2568), before passing through one or more of any suitable and effective chamber inlet valve(s) (2585) and then traveling into and through the said one or more treatment chamber(s) (2026).

Without being limited, the heated air/gas(s) system(s) (2568) includes, and without limitation, at least one of any suitable and effective heated air/gas(s) conduit (2570) that includes, without limitation, at least one of any suitable and effective heater element(s) (2575) that is suitably and effectively located inside of the said heated air/gas(s) conduit (2570). Without being limited, the heated air/gas(s) system(s) (2568), heated air/gas(s) conduit(s) (2570), and heater element(s) (2575), can be any suitable and effective design(s) and/or construction(s) known to those skilled in the art. Also, without being limited, the heated air/gas(s) system(s) (2568), heated air/gas(s) conduit(s) (2570), and heater element(s) (2575), can have any suitable and effective, measurement(s), dimension(s), length(s), width(s), height(s), dimension(s), geometry(s), and/or diameter(s). Without being limited, the said heater element(s) (2575) can also be suitably and effectively located at one or more of any suitable and effective location(s) between the said one or more airflow inlet(s) (2535) and the said one or more treatment chamber(s) (2026).

Without being limited, the said, one or more heater element(s) (2575), heated air/gas(s) conduit(s) (2570), and/or heated air/gas(s) system(s) (2568), can also be suitable and effectively located at any one or more location(s) between the said chamber inlet valve(s) (2585) and one or more of any interior space(s) of the said treatment chamber(s). Also, without being limited, the said, one or more heater element(s) (2575), heated air/gas(s) conduit(s) (2570), and/or heated air/gas(s) system(s) (2568), can also be suitably and effectively located at any suitable and effective location(s) at and/or near any one or more of any suitable and effective entrance(s) to the said treatment chamber(s) (2026) and/or at any suitable and effective location(s) inside of the said treatment chamber(s) (2026). It is preferred, without limitation that the said heater element(s) (2575) are suitably and effectively located inside of the one or more heated air/gas(s) conduit(s) (2570), all in a manner known to those skilled in the art. It is also preferred, without limitation, that the said one or more heater element(s) (2575), heated air/gas(s) conduit(s) (2570), and/or heated air/gas(s) system(s) (2568), are located at any suitable and effective location(s) after the said inbound air filter(s) (2560), but before the said chamber inlet valve(s) (2585).

Without being limited, at least one prevalve conduit(s) (2580) can be located between and communicate with, the at least one heated air/gas(s) system(s) (2568) and the at least one chamber inlet valve(s) (2585). Without being limited, the at least one prevalve conduit(s) (2580) can be any suitable and effective, measurement(s), dimension(s), size, shape, design, geometry, length, width, and/or height. It is preferred, without limitation, that the said prevalve conduit(s) (2580) is at least any suitable and effective length to prevent the at least one chamber inlet valve(s) (2585) from getting damaged from the heat or energy emitted or given off by any one or more parts of the heated air/gas(s) system(s) (2568), such as, but not limited to, the one or more heater element(s) (2575). Without being limited, one or more of any suitable and effective heat shields or infrared energy shields (not shown) using any suitable and effective, measurement(s), dimension(s), design(s), shape(s), material(s), geometry(s), length(s), width(s), and height(s), known to those skilled in the art, can be located between the said one or more heater element(s) (2575) and the chamber inlet valve(s) (2585), and can be designed so that any effective and suitable flow of air/gas(s) and/or fresh air/gas(s) can flow and move through the filtered and heated inbound air/gas(s) assembly (2525).

Without being limited, at least one post filter conduit(s) (2565) can be located between and communicate with, the at least one heated air/gas(s) system(s) (2568) and the at least one inbound air filter(s) (2560). Without being limited, the at least one post filter conduit(s) (2565) can be any suitable and effective, measurement(s), dimension(s), size, shape, design, geometry, length, width, and/or height. It is preferred, without limitation, that the said post filter conduit(s) (2565) is at least any suitable and effective length to prevent the at least one inbound air filter(s) (2560) from getting damaged from the heat or energy emitted or given off by any of the one or more parts of the heated air/gas(s) system(s) (2568), such as, but not limited to, the one or more heater element(s) (2575). Without being limited, one or more of any suitable and effective heat shields or infrared energy shields (not shown) using any suitable and effective, measurement(s), dimension(s), design(s), shape(s), material(s), geometry(s), length(s), width(s), and height(s), known to those skilled in the art, can be located between the said one or more heater element(s) (2575) and the inbound air filter(s) (2560), and be designed so that any effective and suitable flow of air/gas(s) and/or fresh air/gas(s) can flow through the filtered and heated inbound air/gas(s) assembly (2525).

Also, and without limitation, one or more of any suitable and effective heater element(s) (2575) can heat the flow of the said air/gas(s) and/or fresh air/gas(s) as it travels to, into, and/or inside of, the said treatment chamber(s) (2026). It is preferred, without limitation, that at least one of any suitable and effective heater element(s) (2575) is used and included in the design and construction of the said heated air/gas(s) system(s) (2568). It is also preferred, without limitation, that the various parts and components of the heated air/gas(s) system(s) (2568), heated air/gas(s) conduit(s) (2570), and heater element(s) (2575), are constructed from one or more of any suitable and effective materials that are and/or would be, approved by the United States Food and Drug Administration (FDA), and more specifically, and without limitation, approved by the FDA for use in any apparatuses that may be used to treat, decontaminate, sanitize, disinfect, high-level disinfect, sterilize, and/or process, any apparatuses, tooling, device(s), and/or equipment, that are used for any medical, pharmaceutical, and/or food related applications. It is even more preferred, without limitation, that the said heated air/gas(s) system(s) (2568), heated air/gas(s) conduit(s) (2570), and heater element(s) (2575), are constructed from any suitable and effective stainless steel such as, but not limited to any, suitable and effective 316 and/or 316-L stainless steel.

Also, and without being limited, the said, one or more heater element(s) (2575), heated air/gas(s) conduit(s) (2570), and/or heated air/gas(s) system(s) (2568), can be any suitable and effective design(s) and/or construction(s), all in a manner known to those skilled in the art. Without being limited, the heated air/gas(s) conduit(s) (2570) and heater element(s) (2575) can also have one or more of any suitable and effective length(s), width(s), height(s), and/or dimension(s), all in a manner known to those skilled in the art.

Without being limited, the heater element(s) (2575), and/or heated air/gas(s) system(s) (2568), can heat the flow and/or movement of any air/gas(s) and/or fresh air/gas(s) to one or more of any suitable and effective temperature(s). Also, and without being limited, the flow of air/gas(s) and/or fresh air/gas(s) can be suitably and effectively heated to one or more of any suitable and effective temperature(s) so that the said air/gas(s) and/or fresh air/gas(s) that flow into, through, and out of, the said treatment chamber(s) (2026), can suitably and effectively dry and/or remove the deployed agent(s) (2100) from the various surfaces within the treatment chamber(s) (2026) including, but not limited to any one or more surface(s) of the one or more treated object(s) (2300). Without being limited, the said heater element(s) (2575), and/or heated air/gas(s) system(s) (2568), can suitably and effectively heat the flow of the said air/gas(s) and/or fresh air/gas(s) to one or more of any suitable and effective temperature(s) before it enters the treatment chamber(s) (2026).

It is preferred, without limitation, that the said flow(s) of air/gas(s) and/or fresh air/gas(s) that flow through the filtered and heated inbound air/gas(s) assembly, are heated by the said one or more heater element(s) (2575) and/or heated air/gas(s) system(s) (2568), to one or more of any suitable and effective temperature(s), so that the flow of air/gas(s) and/or fresh air/gas(s) that flow into and through the said treatment chamber(s) is at least one or more of any suitable and effective temperature(s). It is more preferred, without limitation, that the said flow of air/gas(s) and/or fresh air/gas(s) that flow past and/or through the said one or more heater element(s) (2575) and/or heated air/gas(s) system(s) (2568), are heated to one or more of any suitable and effective temperature(s), so that the flow of air/gas(s) and/or fresh air/gas(s) that flow into and through the said treatment chamber(s) is maintained at one or more of any suitable and effective temperature(s). It is even more preferred, without limitation, that the said flow of air/gas(s) and/or fresh air/gas(s) are suitably and effectively heated by the one or more of any suitable and effective means known to those skilled in the art to suitably and effectively heat the said moving air/gas(s) and/or moving fresh air/gas(s), to one or more of any suitable and effective temperature(s), so that one or more of any flow(s) of air/gas(s) and/or fresh air/gas(s) that flow into the said treatment chamber(s) is maintained at one or more of any suitable and effective temperature(s) to suitably and effectively dry the various surface(s) and/or materials within the said treatment chamber(s) (2026). It is very preferred, without limitation, that the one or more flows and/or movements of air/gas(s) and/or fresh air/gas(s) that move and/or flow through and/or past the heater element(s) (2575) and/or heated air/gas(s) system(s) (2568) and into and through the said treatment chamber(s) (2026), are suitably and effectively heated by the one or more of any suitable and effective means known to those skilled in the art to suitably and effectively heat moving air/gas(s) and/or moving fresh air/gas(s), to one or more of any suitable and effective temperature(s), so that the flow of air/gas(s) and/or fresh air/gas(s) that flow into and through the said treatment chamber(s) is maintained at one or more of any suitable and effective temperature(s) such as, but not limited to, at least any suitable and effective temperature(s) between about 32 degrees Fahrenheit to about 300 degrees Fahrenheit, to suitably and effectively dry the various surface(s) and/or materials within the said treatment chamber(s) (2026). It is extremely preferred, without limitation, that the one or more flows and/or movements of air/gas(s) and/or fresh air/gas(s) that move and/or flow through and/or past the heater element(s) (2575) and/or heated air/gas(s) system(s) (2568) and into and through the said treatment chamber(s) (2026), are suitably and effectively heated to one or more of any suitable and effective temperature(s), so that the flow of air/gas(s) and/or fresh air/gas(s) that flow into and through the said treatment chamber(s) is maintained at one or more of any suitable and effective temperature(s) such as, but not limited to, at least any suitable and effective temperature(s) between about 40 degree Fahrenheit to about 250 degree Fahrenheit, but more preferably between about 80 degree Fahrenheit to about 180 degree Fahrenheit, and even more preferably between about 90 degree Fahrenheit to about 130 degree Fahrenheit, to suitably and effectively dry the various surface(s) and/or materials within the said treatment chamber(s) (2026) and/or remove the deployed agent(s) (2100) from the various surfaces within the treatment chamber(s) (2026) including, but not limited to any one or more surface(s) of the one or more treated object(s) (2300).

Without being limited, the one or more of any flows and/or movements of one or more of any, air/gas(s), fresh air/gas(s), heated air/gas(s), and/or heated fresh air/gas(s), into, through, and out of, the one or more treatment chamber(s) (2026), at one or more of any suitable and effective time(s) and for one or more of any suitable and effective duration(s) of time(s), can occur for one or more of any purposes and/or actions such as, but not limited to, (a) suitably and effectively removing and/or reducing the deployed agent(s) (2100) from the air/gas(s) and/or atmosphere(s) within the one or more treatment chamber(s) (2026) after the one or more object(s) (2300) surface(s) and/or any other surface(s) located within the treatment chamber(s) (2026) are treated with the deployed agent(s) (2100), (b) suitably and effectively removing and/or reducing the deployed agent(s) (2100) from one or more of any surface(s) and/or targeted surface(s) of any object(s) (2300) located within the one or more treatment chamber(s) (2026) after the one or more object(s) (2300) surface(s) and/or any other surface(s) located within the treatment chamber(s) (2026) are treated with the deployed agent(s) (2100), (c) suitably and effectively removing and/or reducing the deployed agent(s) (2100) from the various surface(s) located within and/or connected to the one or more treatment chamber(s) (2026) after the one or more object(s) (2300) surface(s) and/or any other surface(s) located within the treatment chamber(s) (2026) are treated with the deployed agent(s) (2100), (d) suitably and effectively drying the deployed agent(s) (2100) from the various surface(s) located within and/or connected to the one or more treatment chamber(s) (2026), after the one or more object(s) (2300) surface(s) and/or any other surface(s) located within the treatment chamber(s) (2026) are treated with the deployed agent(s) (2100), (e) suitably and effectively drying the deployed agent(s) (2100) from the one or more of any surfaces of the treated object(s) (2300) located within the one or more treatment chamber(s) (2026) after the one or more object(s) (2300) surface(s) and/or any other surface(s) located within the treatment chamber(s) (2026) are treated with the deployed agent(s) (2100), (f) suitably and effectively drying and/or removing one or more of any suitable and effective substance(s) and/or agent(s) such as, but not limited to, any, drying agent(s) and/or substance(s), rinsing agent(s) and/or substance(s), cleaning agent(s) and/or substance(s), surface preparation agent(s) and/or substance(s), sanitizer(s) agent(s) and/or substance(s), disinfectant(s) agent(s) and/or substance(s), high-level disinfectant(s) agent(s) and/or substance(s), sterilant(s) agent(s) and/or substance(s), sporicide(s) agent(s) and/or substance(s), and/or deployed agent(s) (2100) agent(s) and/or substance(s), and/or any other suitable and effective agent(s) and/or substance(s), such as, but not limited, to any, alcohol(s) in any solution(s), hydrogen peroxide(s) in any solution(s), enzymes in any solution(s), water(s), detergent(s), detergent(s) in in any solution(s), and/or peroxyacetic acid(s) in any solution(s), from the one or more of any surface(s) of the treated object(s) (2300) and/or any other surface(s) located within the one or more treatment chamber(s) (2026), before the one or more object(s) are treated with the deployed agent(s) (2100), (g) suitably and effectively cooling one or more of any treated object(s) (2300) surface(s) and/or any other surface(s) within the treatment chamber(s) (2026) to one or more of any suitable and effective temperature(s), after the said surface(s) are dried with any heated air/gas(s) and/or heated fresh air/gas(s), but before the one or more of any surface(s) of the treated object(s) (2300) and/or one or more of any other surface(s) located within the one or more treatment chamber(s) (2026) are treated with the deployed agent(s) (2100), and (h) cooling one or more of any treated object(s) (2300) surface(s) and/or any other surface(s) located within the treatment chamber(s) (2026) to one or more of any suitable and effective temperature(s), after the said surface(s) are suitably and effectively treated with the deployed agent(s) (2100) and then suitably and effectively dried and/or the deployed agent(s) (2100) are suitably and effectively removed from the said surface(s) with any heated air/gas(s) and/or heated fresh air/gas(s).

Without being limited, one or more of any suitable and effective, air/gas(s) temperature sensor(s) (2926), humidity sensor(s) (2927), surface temperature sensor(s) (2929), chemical and/or molecule sensor(s) (2928), known to those skilled in the art, can suitably and effectively, be located inside of, be mounted inside of, located at, be attached to, and/or communicate with, one or more of any suitable and effective location(s) such as, but not limited to, any locations of, communicating with, and/or inside of, the one or more treatment chamber(s) (2026). Also, and without being limited, the said air/gas(s) temperature sensor(s) (2926), surface temperature sensor(s) (2929), humidity sensor(s) (2927), and/or chemical and/or molecule sensor(s) (2928), can communicate with one or more of any suitable and effective microcontroller(s) (2920) also known to those skilled in the art. Also, without being limited, the one or more surface temperature sensor(s) (2929), can be any suitable and effective means to measure and report one or more of any surface temperature(s) inside of the treatment chamber(s) (2026), all in a manner known to those skilled in the art. It is preferred, without limitation, that the said surface temperature sensor(s) (2929), is any suitable and effective temperature sensing means that can be located outside of the treatment chamber(s) (2026), but still suitably and effectively measure one or more of any temperature(s) of one or more of any surface(s) inside of the treatment chamber(s) (2026), and also suitably and effectively communicate with the inside of the treatment chamber(s) (2026) through one or more of any suitable and effective, signal transparent window(s), infrared transparent glass(s), infrared transparent window(s), and/or infrared transparent plastic(s), and/or any other suitable and effective port(s) and/or window(s) that does not interfere with the ability and/or effectiveness of the surface temperature sensor(s) (2929) to measure and/or sense the one or more temperature(s) of one or more surface(s) located within the treatment chamber(s) (2026), and also suitably and effectively seal to and/or with the interior of the treatment chamber(s) (2026) and suitably and effectively communicates with the interior of the treatment chamber(s) (2026).

Without being limited, the various data and/or information sent from the said any suitable and effective, air/gas(s) temperature sensor(s) (2926), humidity sensor(s) (2927), chemical and/or molecule sensor(s) (2928), and/or surface temperature sensor(s) (2929), can represent, indicate, and/or report, various, condition(s), status(s), data(s), process(s), step(s), and/or situation(s), inside of the treatment chamber(s) (2026) such as, but not limited, to, (a) the one or more of any temperature(s) sensed by one or more of any suitable and effective air/gas(s) temperature sensor(s) (2926) at one or more of any suitable and effective time(s) and at one or more of any suitable and effective location(s) inside of the treatment chamber(s) (2026) and/or communicating with the said treatment chamber(s) (2026), (b) the one or more of any temperature(s) sensed by one or more of any suitable and effective surface temperature sensor(s) (2929) at one or more of any location(s) such as, but not limited to, one or more of any locations of and/or on one or more of any surface(s) of the treated object(s) (2300), and where these said one or more treated object(s) (2300) surface temperature(s) are sensed, reported, and processed, all in a manner known to those skilled in the art, (c) the one or more of any, relative humidity data(s), humidity data(s), and/or relative humidity reading(s) sensed by one or more of any suitable and effective humidity sensor(s) (2927) at one or more of any suitable and effective time(s) and at one or more of any suitable and effective location(s) inside of the treatment chamber(s) (2026) and/or communicating with the said treatment chamber(s) (2026), and (d) the one or more of any, chemical concentration data(s), molecule concentration data(s), presence of chemical(s) data(s), and presence of molecule(s) data(s),) sensed by one or more of any suitable and effective chemical and/or molecule sensor(s) (2928), at one or more of any suitable and effective time(s) and at one or more of any suitable and effective location(s) inside of the treatment chamber(s) (2026) and/or communicating with the said treatment chamber(s) (2026).

Also, and without being limited, the various said, condition(s), status(s), data(s), and/or situation(s), that are sensed inside of the treatment chamber(s) (2026) and reported to the said microcontroller(s) (2920), can be used for and/or during one or more of any suitable and effective operation(s) and/or process step(s) such as, but not limited to, in a first aspect, and without limitation, one or more of any object(s) (2300) may be located inside of the one or more treatment chamber(s) (2026) and it is sensed by the one or more of any suitable and effective surface temperature sensor(s) (2929) that one or more of any surface(s) of the said object(s) (2300) are too warm, hot, and/or excessive in temperature, and/or the one or more of the said object(s) (2300) has one or more of any surface(s) that are: (a) not at, about, and/or below, one or more of any maximum allowable operating temperature(s) and/or not at, about, and/or within, one or more of any suitable and/or effective temperature(s) range(s) and/or suitable and effective operating temperature(s) range(s) for one or more of any suitable and/or effective treatment cycle(s) and/or processing cycle(s) with the deployed agent(s) (2100).

It is preferred, without limitation, that before the said object(s) (2300) are treated and/or exposed to the deployed agent(s) (2100) the temperature of the one or more of any surface(s) of the said object(s) (2300) are at least within a temperature range that is suitable and effective. It is more preferred, without limitation, that before the said object(s) (2300) are treated and/or exposed to the deployed agent(s) (2100) the temperature of the one or more surface(s) of the said object(s) (2300) are at least within a temperature range that is between about 32 degree Fahrenheit and 190 degree Fahrenheit. It is very preferred, without limitation, that before the said object(s) (2300) are treated and/or exposed to the deployed agent(s) (2100) the temperature of the one or more surface(s) of the said object(s) (2300) are at least within a temperature range that is between about 50 degree Fahrenheit and 80 degree Fahrenheit. It is extremely preferred, without limitation, that before the said object(s) (2300) are treated and/or exposed to the deployed agent(s) (2100) the one or more surface(s) of the said object(s) (2300) are about standard room temperature.

Without being limited, if the temperature of the one or more of any surface(s) of the said object(s) (2300) and/or the atmosphere and/or air/gas(s) within the treatment chamber(s) (2026), exceeds one or more of any suitable and effective temperature(s) and/or any established temperature(s), before the said surface(s) of the said object(s) (2300) is treated with the deployed agent(s) (2100), the said atmosphere(s) and/or air/gas(s) and/or various surfaces within the treatment chamber(s) (2026) and/or the various surface(s) of the said object(s) (2300) located within the treatment chamber(s) (2026), can be suitably and effectively cooled to one or more of any suitable and effective temperature(s) by flowing and/or moving unheated air/gas(s) and/or unheated fresh air/gas(s) at one or more of any suitable and effective temperature(s) into, through, and out of, the treatment chamber(s) (2026) for one or more of any suitable and effective time(s) and for one or more of any suitable and effective duration(s) of time(s), to cool and/or suitably and effectively reduce the temperature(s) of the said atmosphere(s) and/or air/gas(s) and/or various surfaces within the treatment chamber(s) (2026) and/or the various surface(s) of the said object(s) (2300) located within the treatment chamber(s) (2026) to one or more of any suitable and effective temperature(s) and/or temperature range(s). Without being limited, the said treated object(s) (2300) located within the treatment chamber(s) (2026) can also be suitably and effectively, held, gripped, and/or supported, at one or more of any suitable and effective location(s), one or more of any suitable and effective time(s) and duration of time(s), during this cooling and/or temperature reducing process, all in a manner known to those skilled in the art. Without being limited, the temperature of the air/gas(s) and/or atmosphere(s) within the said treatment chamber(s) (2026) and/or any connected area(s) can be monitored by the one or more of any suitable and effective air/gas(s) temperature sensor(s) (2926), and any temperature(s) of the surface(s) of the said object(s) (2300) can also be monitored by the one or more of any suitable and effective surface temperature sensor(s) (2929).

Alternatively, and without being limited, if the temperature of the one or more surface(s) of the said object(s) (2300) and/or the atmosphere and/or air/gas(s) within the treatment chamber(s) (2026), is below one or more of any suitable and effective temperature(s) and/or any established temperature(s), before the said surface(s) of the said object(s) (2300) is treated with the deployed agent(s) (2100), the said atmosphere(s) and/or air/gas(s) and/or various surfaces within the treatment chamber(s) (2026) and/or the various surface(s) of the said object(s) (2300) located within the treatment chamber(s) (2026), can be suitably and effectively heated to one or more of any suitable and effective temperature(s) by flowing and/or moving heated air/gas(s) and/or heated fresh air/gas(s) at one or more of any suitable and effective temperature(s) into, through, and out of, the treatment chamber(s) (2026) for one or more of any suitable and effective time(s) and for one or more of any suitable and effective duration(s) of time(s), to heat and/or suitably and effectively increase the temperature(s) of the said atmosphere(s) and/or air/gas(s) and/or various surfaces within the treatment chamber(s) (2026) and/or the various surface(s) of the said object(s) (2300) located within the treatment chamber(s) (2026) to one or more of any suitable and effective temperature(s) and/or temperature range(s). Without being limited, the said treated object(s) (2300) located within the treatment chamber(s) (2026) can also be suitably and effectively, held, gripped, and/or supported, at one or more of any suitable and effective location(s), one or more of any suitable and effective time(s) and duration of time(s), during this heating and/or temperature increasing process, all in a manner known to those skilled in the art. Without being limited, the temperature of the air/gas(s) and/or atmosphere(s) within the said treatment chamber(s) (2026) and/or any connected area(s) can be monitored by the one or more of any suitable and effective air/gas(s) temperature sensor(s) (2926), and any temperature(s) of the surface(s) of the said object(s) (2300) can also be monitored by the one or more of any suitable and effective surface temperature sensor(s) (2929).

Without being limited, once various temperature(s) such as, but not limited to, the temperature(s) of the air/gas(s) and/or atmosphere(s) within the treatment chamber(s) (2026), and/or the temperature(s) of the various surface(s) are within, at, and/or about, any one or more suitable and effective temperature(s) and/or temperature range(s), the deployed agent(s) (2100) can be deployed and/or moved into the one or more treatment chamber(s) (2026) at any suitable and effective time(s).

In a second aspect, and without limitation, the process, completion, and/or effectiveness, of the one or more treatment(s) and/or exposure(s) of the various surface(s) within the treatment chamber(s) (2026) and/or one or more of any surface(s) of the treated object(s) (2300), with the one or more deployed agent(s) (2100), can be monitored, sensed, measured, and/or determined, by one or more of any suitable and effective sensor(s) such as, but not limited to any, surface temperature sensor(s) (2929), air/gas(s) temperature sensor(s) (2926), humidity sensor(s) (2927), chemical and/or molecule sensor(s) (2928), and/or one or more of any other suitable and effective sensor(s) known to those skilled in the art.

In one embodiment that serves as an example, and without limitation, the effective filling and/or treatment of the treatment chamber(s) (2026) with the deployed agent(s) (2100) can be sensed and/or indicated by the one or more of any suitable and effective, surface temperature sensor(s) (2929) and/or air/gas(s) temperature sensor(s) (2926), by sensing one or more of any suitable and effective, data(s) and/or signal(s) and/or change(s) in data(s) and/or signal(s), in any temperature(s) inside of the treatment chamber(s) (2026) such as, but not limited to any, (a) increase(s) of any temperature(s) within the treatment chamber(s) (2026), (b) decrease(s) of any temperature(s) within the treatment chamber(s) (2026), (c) increase(s) and then decrease(s) of any temperature(s) within the treatment chamber(s) (2026), (d) decrease(s) and then increase(s) of any temperature(s) within the treatment chamber(s) (2026), (e) increase(s) and then stabilization of any temperature(s) within the treatment chamber(s) (2026), (f) decrease(s) and then stabilization of any temperature(s) within the treatment chamber(s) (2026), (g) increase(s) and then decrease(s) of any temperature(s) within the treatment chamber(s) (2026), and then stabilization of any temperature(s) within the treatment chamber(s) (2026), (h) decrease(s) and then increase(s) of any temperature(s) within the treatment chamber(s) (2026), and then stabilization of any temperature(s) within the treatment chamber(s) (2026), (i) increase(s) of any temperature(s) within the treatment chamber(s) (2026) to one or more of any suitable and effective temperature(s) that can indicate any effective treatment(s) with the deployed agent(s) (2100) of the various surface(s) within the treatment chamber(s) (2026) and/or the one or more surface(s) of the treated object(s) (2300), and/or (j) increase(s) and then stabilization of any temperature(s) within the treatment chamber(s) (2026), to one or more of any suitable and effective temperature(s) that can indicate any effective treatment(s) with the deployed agent(s) (2100) of the various surface(s) within the treatment chamber(s) (2026) and/or the one or more surface(s) of the treated object(s) (2300), at any suitable and effective time(s), at any suitable and effective number of time(s), and for any suitable and effective duration(s) of time(s), for the air/gas(s) temperature(s) at one or more of any suitable and effective location(s) inside of the treatment chamber(s) (2026).

For example, and without limitation, the effective filling of the treatment chamber(s) with the deployed agent(s) (2100) can be sensed and/or indicated by conditions and/or progression of events, such as, but not limited to, a similar, about similar, and/or identical change, of any temperature(s) inside of the treatment chamber(s) (2026) and then a stabilization and/or leveling off of the temperature(s) inside of the treatment chamber(s) (2026) after the supply of the deployed agent(s) (2100) into the treatment chamber(s) (2026) is stopped, at one or more of any suitable and effective location(s) inside of the treatment chamber(s) (2026) such as, but not limited to, one or more of any suitable and effective location(s) near the bottom of the treatment chamber(s) (2026) and one or more of any suitable and effective location(s) near the top of the treatment chamber(s) (2026), all at and/or within any suitable and effective, moment(s) of time(s), duration(s) of time(s), and for any suitable and effective number(s) of time(s).

In another embodiment that serves as an example, and without limitation, the effective filling and/or treatment of the treatment chamber(s) (2026) with the deployed agent(s) (2100) can be sensed and/or indicated by the one or more humidity sensor(s) (2927), by sensing one or more of any suitable and effective, data(s) and/or change(s) in data(s), in any humidity level(s) inside of the treatment chamber(s) (2026) such as, but not limited to any, (a) increase(s) of the humidity level(s) and/or percentage(s) of humidity within the treatment chamber(s) (2026), (b) increase(s) and then stabilization of the humidity level(s) and/or percentage(s) of humidity within the treatment chamber(s) (2026), (c) increase(s) of the humidity level(s) and/or percentage(s) of humidity within the treatment chamber(s) (2026) to one or more of any suitable and effective humidity level(s) and/or percentage(s) of humidity that can indicate any effective treatment(s) with the deployed agent(s) (2100) of the various surface(s) within the treatment chamber(s) (2026) and/or the one or more surface(s) of the treated object(s) (2300), and/or (d) increase(s) and then stabilization of the humidity level(s) and/or percentage(s) of humidity within the treatment chamber(s) (2026), to one or more of any suitable and effective humidity level(s) and/or percentage(s) of humidity that can indicate any effective treatment(s) with the deployed agent(s) (2100) of the various surface(s) within the treatment chamber(s) (2026) and/or the one or more surface(s) of the treated object(s) (2300), at any suitable and effective time(s), at any suitable and effective number of time(s), and for any suitable and effective duration(s) of time(s), for the air/gas(s) humidity level(s) and/or atmosphere humidity level(s) at one or more of any suitable and effective location(s) inside of the treatment chamber(s) (2026).

For example, and without limitation, the effective filling of the treatment chamber(s) with the deployed agent(s) (2100) can be sensed and/or indicated by conditions and/or progression of events and/or conditions, such as, but not limited to, a similar, about similar, and/or identical change, of any one or more humidity level(s) and/or percentage(s) of humidity inside of the treatment chamber(s) (2026) and then a stabilization and/or leveling off of any one or more humidity level(s) and/or percentage(s) of humidity inside of the treatment chamber(s) (2026) after the supply of the deployed agent(s) (2100) into the treatment chamber(s) (2026) is stopped, at one or more of any suitable and effective location(s) inside of the treatment chamber(s) (2026) such as, but not limited to, one or more of any suitable and effective location(s) near the bottom of the treatment chamber(s) (2026) and one or more of any suitable and effective location(s) near the top of the treatment chamber(s) (2026), all at and/or within any suitable and effective, moment(s) of time(s), duration(s) of time(s), and for any suitable and effective number(s) of time(s).

In still another embodiment that serves as an example, and without limitation, the effective filling and/or treatment of the treatment chamber(s) (2026) with the deployed agent(s) (2100) can be sensed and/or indicated by one or more of any chemical and/or molecule sensor(s) (2928), by sensing one or more of any suitable and effective, data(s) and/or change(s) in data(s), in any one or more chemical concentration level(s) of the deployed agent(s) (2100) inside of the treatment chamber(s) (2026) such as, but not limited to any, (a) increase(s) in any chemical concentration level(s) of the deployed agent(s) (2100), (b) increase and then stabilization of any chemical concentration level(s) of the deployed agent(s) (2100), (c) increase(s) in any chemical concentration level(s) of the deployed agent(s) (2100) to one or more of any suitable and effective chemical concentration level(s) that can indicate any effective treatment(s) with the deployed agent(s) (2100) of the various surface(s) within the treatment chamber(s) (2026) and/or the one or more surface(s) of the treated object(s) (2300), and/or (d) and/or increase(s) and then stabilization in any chemical concentration level(s) of the deployed agent(s) (2100) to one or more of any suitable and effective chemical concentration level(s) that can indicate any effective treatment(s) with the deployed agent(s) (2100) of the various surface(s) within the treatment chamber(s) (2026) and/or the one or more surface(s) of the treated object(s) (2300), at any suitable and effective time(s), any suitable and effective number of time(s), and for any suitable and effective duration(s) of time(s), for the chemical concentration level(s) in the air/gas(s) at one or more of any suitable and effective location(s) inside of the treatment chamber(s) (2026).

For example, and without limitation, the effective filling of the treatment chamber(s) with the deployed agent(s) (2100) can be sensed and/or indicated by conditions and/or progression of events and/or conditions, such as, but not limited to, a similar, about similar, and/or identical change, of the chemical concentration level(s) of the deployed agent(s) (2100) inside of the treatment chamber(s) (2026) and then a stabilization and/or leveling off of the chemical concentration level(s) of the deployed agent(s) (2100) inside of the treatment chamber(s) (2026) after the supply of the deployed agent(s) (2100) into the treatment chamber(s) (2026) is stopped, at one or more of any suitable and effective location(s) inside of the treatment chamber(s) (2026) such as, but not limited to, one or more of any suitable and effective location(s) near any bottom(s) of the treatment chamber(s) (2026) and one or more of any suitable and effective location(s) near any top(s) of the treatment chamber(s) (2026), all at and/or within any suitable and effective, moment(s) of time(s), duration(s) of time(s), and for any suitable and effective number(s) of time(s).

In a third aspect, and without limitation, the process, completion, and/or effectiveness, of the one or more cycles to dry and/or remove the deployed agent(s) (2100) from various location(s) such as, but not limited to, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), can be monitored, measured, and/or determined, by one or more of any suitable and effective sensor(s) such as, but not limited to any, air/gas(s) temperature sensor(s) (2926), humidity sensor(s) (2927), chemical and/or molecule sensor(s) (2928), and/or one or more of any other suitable and effective sensor(s) known to those skilled in the art.

In one embodiment that serves as an example, and without limitation, the effective drying and/or removal of the one or more deployed agent(s) (2100) from various location(s) such as, but not limited to, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), can be monitored, sensed, measured, and/or determined, by one or more of any suitable and effective sensor(s) such as, but not limited to any, air/gas(s) temperature sensor(s) (2926) known to those skilled in the art, located at one or more of any suitable and effective location(s) inside of the said treatment chamber(s) (2026) and/or any suitable and effective area(s) and/or spaces connected to the treatment chamber(s) (2026).

Without limitation, the suitable and effective drying and/or removal of the deployed agent(s) (2100) from the air/gas(s) and/or atmosphere(s) inside of the treatment chamber(s) (2026) and/or various surfaces within the said treatment chamber(s) (2026) can be sensed and/or indicated by the one or more air/gas(s) temperature sensor(s) (2926) at one or more of any suitable and effective location(s) within the treatment chamber(s) (2026), by sensing one or more of any suitable and effective, data(s) and/or change(s) in data(s), in any temperature(s), at one or more of any suitable and effective location(s) inside of the treatment chamber(s), (2026) such as, but not limited to any, (a) increase(s) of the temperature(s) within the treatment chamber(s) (2026), (b) decrease(s) of the temperature(s) within the treatment chamber(s) (2026), (c) increase(s) and then decrease(s) of the temperature(s) within the treatment chamber(s) (2026), (d) decrease(s) and then increase(s) of the temperature(s) within the treatment chamber(s) (2026), (e) increase(s) and then stabilization of the temperature(s) within the treatment chamber(s) (2026), (f) decrease(s) and then stabilization of the temperature(s) within the treatment chamber(s) (2026), (g) increase(s) and then decrease(s) of the temperature(s) within the treatment chamber(s) (2026), and then stabilization of the temperature(s) within the treatment chamber(s) (2026), (h) decrease(s) and then increase(s) of the temperature(s) within the treatment chamber(s) (2026), and then stabilization of the temperature(s) within the treatment chamber(s) (2026), (i) increase(s) of the temperature(s) within the treatment chamber(s) (2026) to one or more of any suitable and effective temperature(s) that can indicate any effective flow(s) and/or movement(s) of the air/gas(s), fresh air/gas(s), heated air/gas(s), and/or heated fresh air/gas(s) into, through, and out of, the treatment chamber(s) (2026), (j) increase(s) and then stabilization of the temperature(s) within the treatment chamber(s) (2026), to one or more of any suitable and effective temperature(s) that can indicate any effective flow(s) and/or movement(s) of the air/gas(s), fresh air/gas(s), heated air/gas(s), and/or heated fresh air/gas(s), at one or more of any suitable and effective temperature(s), into, through, and out of, the treatment chamber(s) (2026) and/or any effective, removal, reduction, and/or drying, of the one or more deployed agent(s) (2100) from various location(s) such as, but not limited to, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), all at and/or within any suitable and effective, moment(s) of time(s), duration(s) of time(s), and for any suitable and effective number(s) of time(s).

In another embodiment that serves as an example, and without limitation, the effective drying and/or removal of the one or more deployed agent(s) (2100) from various location(s) such as, but not limited to, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), can be monitored, sensed, measured, and/or determined, by one or more of any suitable and effective sensor(s) such as, but not limited to any, humidity sensor(s) (2927) known to those skilled in the art, located at one or more of any suitable and effective location(s) inside of the said treatment chamber(s) (2026) and/or any suitable and effective area(s) and/or spaces connected to the treatment chamber(s) (2026).

Without limitation, the suitable and effective drying and/or removal of the deployed agent(s) (2100) from the air/gas(s) and/or atmosphere(s) inside of the treatment chamber(s) (2026) and/or various surfaces within the said treatment chamber(s) (2026) can be sensed and/or indicated by the one or more of any suitable and effective air/gas(s) humidity sensor(s) (2927) located at one or more of any suitable and effective location(s) within the treatment chamber(s) (2026), by sensing one or more of any suitable and effective, data(s) and/or change(s) in data(s), in any humidity level(s) and/or percentage(s) of humidity, at one or more of any suitable and effective location(s) inside of the treatment chamber(s), (2026) such as, but not limited to any, (a) decrease(s) of the humidity(s) within the treatment chamber(s) (2026), (b) decrease(s) and then stabilization of the humidity(s) within the treatment chamber(s) (2026), and/or (c) decrease(s) of the humidity(s) within the treatment chamber(s) (2026) to one or more of any suitable and effective humidity level(s) and/or percentage(s) of humidity that can indicate any effective flow(s) and/or movement(s) of the air/gas(s), fresh air/gas(s), heated air/gas(s), and/or heated fresh air/gas(s), at one or more of any suitable and effective temperature(s), into, through, and out of, the treatment chamber(s) (2026) and/or any effective, removal, reduction, and/or drying, of the one or more deployed agent(s) (2100) from various location(s) such as, but not limited to, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), all at and/or within any suitable and effective, moment(s) of time(s), duration(s) of time(s), and for any suitable and effective number(s) of time(s).

In still another embodiment that serves as an example, and without limitation, the effective drying and/or removal of the one or more deployed agent(s) (2100) from various location(s) such as, but not limited to, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), can be monitored, sensed, measured, and/or determined, by one or more of any suitable and effective sensor(s) such as, but not limited to any, chemical and/or molecule sensor(s) (2928) known to those skilled in the art, located at one or more of any suitable and effective location(s) inside of the said treatment chamber(s) (2026) and/or any suitable and effective area(s) and/or spaces connected to the treatment chamber(s) (2026).

Without limitation, the suitable and effective drying and/or removal of the deployed agent(s) (2100) from the air/gas(s) and/or atmosphere(s) inside of the treatment chamber(s) (2026) and/or various surfaces within the said treatment chamber(s) (2026) can be sensed and/or indicated by the one or more of any suitable and effective air/gas(s) chemical and/or molecule sensor(s) (2928) located at one or more of any suitable and effective location(s) within the treatment chamber(s) (2026), by sensing one or more of any suitable and effective, data(s) and/or change(s) in data(s), in any chemical concentration level(s) of the deployed agent(s) (2100) inside of the treatment chamber(s) (2026) such as, but not limited to any, (a) decrease(s) of the chemical concentration level(s) of the deployed agent(s) (2100) within the treatment chamber(s) (2026), (b) decrease(s) and then stabilization of the chemical concentration level(s) of the deployed agent(s) (2100) within the treatment chamber(s) (2026), and/or (c) decrease(s) of the chemical concentration level(s) of the deployed agent(s) (2100) within the treatment chamber(s) (2026) to one or more of any suitable and effective chemical concentration level(s) of the deployed agent(s) (2100) that can indicate any effective flow(s) and/or movement(s) of the air/gas(s), fresh air/gas(s), heated air/gas(s), and/or heated fresh air/gas(s), at one or more of any suitable and effective temperature(s), into, through, and out of, the treatment chamber(s) (2026) and/or any effective, removal, reduction, and/or drying, of the one or more deployed agent(s) (2100) from various location(s) such as, but not limited to, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), all at and/or within any suitable and effective, moment(s) of time(s), duration(s) of time(s), and for any suitable and effective number(s) of time(s).

In a fourth aspect, and without limitation, the process, completion, and/or effectiveness, of the one or more cycles to suitably and effectively cool and/or reduce any temperature(s) of the various surfaces inside of the treatment chamber(s) (2026), and/or the one or more surface(s) of the treated object(s) (2300) inside of the treatment chamber(s), can be monitored, measured, and/or determined, by one or more of any suitable and effective sensor(s) such as, but not limited to any, air/gas(s) temperature sensor(s) (2926), surface temperature sensor(s) (2929), and/or one or more of any other suitable and effective sensor(s) known to those skilled in the art.

In one embodiment that serves as an example, and without limitation, the suitable and effective cooling and/or reducing of any temperature(s), of various surfaces inside of the treatment chamber(s) (2026), the atmosphere(s) and/or gas(s) inside of the treatment chamber(s) (2026), and/or the one or more surface(s) of the treated object(s) (2300) inside of the treatment chamber(s), can be monitored, sensed, measured, and/or determined, by one or more of any suitable and effective sensor(s) such as, but not limited to any, air/gas(s) temperature sensor(s) (2926) known to those skilled in the art, located at one or more of any suitable and effective location(s) inside of the said treatment chamber(s) (2026) and/or any suitable and effective area(s) and/or spaces connected to the treatment chamber(s) (2026).

Without limitation, the suitable and effective cooling and/or reduction of any temperature(s), of the various surfaces inside of the treatment chamber(s) (2026), the atmosphere(s) and/or gas(s) inside of the treatment chamber(s) (2026), and/or the one or more of any surface(s) of the treated object(s) (2300) inside of the treatment chamber(s) (2026), can be sensed and/or indicated by the one or more air/gas(s) temperature sensor(s) (2926) at one or more of any suitable and effective location(s) within the treatment chamber(s) (2026), by sensing one or more of any suitable and effective, data(s) and/or change(s) in data(s), in any temperature(s), at one or more of any suitable and effective location(s) inside of the treatment chamber(s), (2026) such as, but not limited to any, (a) decrease(s) of any temperature(s) within the treatment chamber(s) (2026), (b) increase(s) and then decrease(s) of any temperature(s) within the treatment chamber(s) (2026), (c) decrease(s) and then stabilization of any temperature(s) within the treatment chamber(s) (2026), (d) decrease(s) of any temperature(s) within the treatment chamber(s) (2026) to one or more of any suitable and effective temperature(s) that can indicate any effective flow(s) and/or movement(s) of the air/gas(s), fresh air/gas(s), heated air/gas(s), and/or heated fresh air/gas(s), at one or more of any suitable and effective temperature(s), into, through, and out of, the treatment chamber(s) (2026), (e) decrease(s) and then stabilization of any temperature(s) within the treatment chamber(s) (2026), to one or more of any suitable and effective temperature(s) that can indicate any effective flow(s) and/or movement(s) of the air/gas(s), fresh air/gas(s), heated air/gas(s), and/or heated fresh air/gas(s) into, through, and out of, the treatment chamber(s) (2026) and/or any suitable and effective, cooling and/or reduction any temperature(s) of, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), all at and/or within any suitable and effective, moment(s) of time(s), duration(s) of time(s), and for any suitable and effective number(s) of time(s).

In another embodiment that serves as an example, and without limitation, the suitable and effective cooling and/or reducing of any temperature(s), of various surfaces inside of the treatment chamber(s) (2026), the atmosphere(s) and/or gas(s) inside of the treatment chamber(s) (2026), and/or the one or more surface(s) of the treated object(s) (2300) inside of the treatment chamber(s), can be monitored, sensed, measured, and/or determined, by one or more of any suitable and effective sensor(s) such as, but not limited to any, surface temperature sensor(s) (2929) known to those skilled in the art, located at one or more of any suitable and effective location(s) inside of and/or communicating with, the said treatment chamber(s) (2026) and/or any suitable and effective area(s) and/or spaces connected to the treatment chamber(s) (2026).

Without limitation, the suitable and effective cooling and/or reduction of any temperature(s), of the various surfaces inside of the treatment chamber(s) (2026), the atmosphere(s) and/or gas(s) inside of the treatment chamber(s) (2026), and/or the one or more of any surface(s) of the treated object(s) (2300) inside of the treatment chamber(s) (2026), can be sensed and/or indicated by the one or more surface temperature sensor(s) (2929) at one or more of any suitable and effective location(s) within the treatment chamber(s) (2026), by sensing one or more of any suitable and effective, data(s) and/or change(s) in data(s), in any temperature(s), at one or more of any suitable and effective location(s) inside of the treatment chamber(s), (2026) such as, but not limited to any, (a) decrease(s) of any temperature(s) within the treatment chamber(s) (2026), (b) increase(s) and then decrease(s) of any temperature(s) within the treatment chamber(s) (2026), (c) decrease(s) and then stabilization of any temperature(s) within the treatment chamber(s) (2026), (d) decrease(s) of any temperature(s) within the treatment chamber(s) (2026) to one or more of any suitable and effective temperature(s) that can indicate any effective flow(s) and/or movement(s) of the air/gas(s), fresh air/gas(s), heated air/gas(s), and/or heated fresh air/gas(s), at one or more of any suitable and effective temperature(s), into, through, and out of, the treatment chamber(s) (2026), (e) decrease(s) and then stabilization of any temperature(s) within the treatment chamber(s) (2026), to one or more of any suitable and effective temperature(s) that can indicate any effective flow(s) and/or movement(s) of the air/gas(s), fresh air/gas(s), heated air/gas(s), and/or heated fresh air/gas(s) into, through, and out of, the treatment chamber(s) (2026) and/or any suitable and effective, cooling and/or reduction any temperature(s) of, the air/gas(s) and/or atmosphere(s) inside of the treatment chamber(s) (2026), the various surfaces inside of the treatment chamber(s) (2026), and/or the one or more surface(s) of the treated object(s) (2300) inside of the treatment chamber(s), all at and/or within any suitable and effective, moment(s) of time(s), duration(s) of time(s), and for any suitable and effective number(s) of time(s).

Without being limited, the various surfaces inside of the treatment chamber(s) (2026) and/or the one or more surface(s) of the treated object(s) (2300) inside of the treatment chamber(s), can be suitably and effectively cooled and/or the temperatures of these various surfaces can be reduced, to one or more of any suitable and effective temperature(s) and/or to any suitable and effective temperature(s) known to those skilled in the art.

The one or more flows and/or movements of air/gas(s) and/or fresh air/gas(s), that are preferably and without limitation, unheated, that move and/or flow into and through the treatment chamber(s) (2026), for the purpose(s) of cooling and/or reducing the temperature(s) of the various surface(s) within the treatment chamber(s) (2026) to one or more of any suitable and effective temperature(s), can be maintained at one or more of any suitable and effective temperature(s).

It is preferred, without limitation, that the one or more flows and/or movements of air/gas(s), unheated air/gas(s), unheated fresh air/gas(s), and/or fresh air/gas(s), that move and/or flow into and through the treatment chamber(s) (2026), for the purpose(s) of cooling and/or reducing the temperature(s) of the various surface(s) within the said treatment chamber(s) (2026) and/or the one or more surface(s) of the one or more treated treated object(s) (2300), is maintained at one or more of any suitable and effective temperature(s) such as, but not limited to, at least any suitable and effective temperature(s) between about 28 degree Fahrenheit to about 250 degree Fahrenheit, but more preferably between about 48 degree Fahrenheit to about 80 degree Fahrenheit, and even more preferably between about 60 degree Fahrenheit to about 80 degree Fahrenheit.

Without being limited, the one or more filtered and heated inbound air/gas(s) assembly(s) (2525) can have one or more of any suitable and effective combinations, positions, locations, and/or orders, of the various means to: filter, heat, valve control, and/or move, flow, blow, and/or positive pressurize, the air/gas(s) and/or fresh air/gas(s) that enter and/or pass through the said heated inbound air/gas(s) assembly (2525), such as, but not limited to: In a first combination, and without being limited, air/gas(s) and/or fresh air/gas(s) is pulled from the surrounding environment(s) (2900) through one or more of any suitably and effectively sized, shaped, and/or constructed, airflow inlet(s) (2535), where the said air/gas(s) and/or fresh air/gas(s) then pass through one or more of any suitable and effective first filter(s) or airflow inlet prefilter(s) (2540), and where the air/gas(s) and/or fresh air/gas(s) then pass through one or more of any suitable and effective inbound blower(s) (2550), and then forced out of the said inbound blower(s) (2550) via positive pressure created by the said inbound blower(s) (2550) in a manner known to those skilled in the art, where the said air/gas(s) and/or fresh air/gas(s) then pass through one or more of any suitable and effective second filter(s) or inbound air filters(s) (2560), before the said air/gas(s) and/or fresh air/gas(s) passes by and/or through and can be effectively heated to one or more of any suitable and effective temperature(s), by one or more of any suitable and effective, heater(s), heater element(s) (2575), and/or heated air/gas(s) system(s) (2568), and then flowed and/or moved through one or more of any suitable and effective valve(s) or chamber inlet valve(s) (2585), before the said air/gas(s) and/or fresh air/gas(s) are suitably and effectively flowed into, through, and/or out of, the said treatment chamber(s) (2026).

In a second combination, and without being limited, air/gas(s) and/or fresh air/gas(s) is pulled from the surrounding environment(s) (2900) through one or more of any suitably and effectively sized, shaped, and/or constructed, airflow inlet(s) (2535), where the said air/gas(s) and/or fresh air/gas(s) then pass through and is effectively filtered by one or more of any suitable and effective first filter(s) or airflow inlet prefilter(s) (2540), where the air/gas(s) and/or fresh air/gas(s) then pass through and is effectively filtered by one or more of any suitable and effective second filter(s) or inbound air filters(s) (2560), before the said air/gas(s) and/or fresh air/gas(s) pass through one or more of any suitable and effective inbound blower(s) (2550), and then forced out of the said inbound blower(s) (2550) via positive pressure(s) created by the said inbound blower(s) (2550) in a manner known to those skilled in the art, where the said air/gas(s) and/or fresh air/gas(s) then passes by and/or through and can be effectively heated to one or more of any suitable and effective temperature(s), by one or more of any suitable and effective, heater(s), heater element(s) (2575), and/or heated air/gas(s) system(s) (2568), and then flowed and/or moved through one or more of any suitable and effective valve(s) or chamber inlet valve(s) (2585), before the said air/gas(s) and/or fresh air/gas(s) are suitably and effectively flowed into, through, and/or out of, the said treatment chamber(s) (2026).

In a third combination, and without being limited, air/gas(s) and/or fresh air/gas(s) is pulled from the surrounding environment(s) (2900) through one or more of any suitably and effectively sized, shaped, and/or constructed, airflow inlet(s) (2535), where the said air/gas(s) and/or fresh air/gas(s) then pass through and is effectively filtered by one or more of any suitable and effective first filter(s) or airflow inlet prefilter(s) (2540), where the air/gas(s) and/or fresh air/gas(s) then pass through and is effectively filtered by one or more of any suitable and effective second filter(s) or inbound air filters(s) (2560), where the said air/gas(s) and/or fresh air/gas(s) then passes by and/or through and can be effectively heated to one or more of any suitable and effective temperature(s), by one or more of any suitable and effective, heater(s), heater element(s) (2575), and/or heated air/gas(s) system(s) (2568), where the said air/gas(s) and/or fresh air/gas(s) then pass through one or more of any suitable and effective inbound blower(s) (2550), and is then forced out of the said inbound blower(s) (2550) via positive pressure(s) created by the said inbound blower(s) (2550) in a manner known to those skilled in the art, and where the said air/gas(s) and/or fresh air/gas(s) is then flowed and/or moved through one or more of any suitable and effective valve(s) or chamber inlet valve(s) (2585), before the said air/gas(s) and/or fresh air/gas(s) are suitably and effectively flowed into, through, and/or out of, the said treatment chamber(s) (2026).

In a fourth combination, and without being limited, air/gas(s) and/or fresh air/gas(s) is pulled from the surrounding environment(s) (2900) through one or more of any suitably and effectively sized, shaped, and/or constructed, airflow inlet(s) (2535), where the said air/gas(s) and/or fresh air/gas(s) then pass through and is effectively filtered by one or more of any suitable and effective first filter(s) or airflow inlet prefilter(s) (2540), where the said air/gas(s) and/or fresh air/gas(s) then pass through one or more of any suitable and effective inbound blower(s) (2550), and is then forced out of the said inbound blower(s) (2550) via positive pressure(s) created by the said inbound blower(s) (2550) in a manner known to those skilled in the art, where the said air/gas(s) and/or fresh air/gas(s) then passes by and/or through and can be effectively heated to one or more of any suitable and effective temperature(s), by one or more of any suitable and effective, heater(s), heater element(s) (2575), and/or heated air/gas(s) system(s) (2568), where the air/gas(s) and/or fresh air/gas(s) then pass through and is effectively filtered by one or more of any suitable and effective second filter(s) or inbound air filters(s) (2560), and where the said air/gas(s) and/or fresh air/gas(s) is then flowed and/or moved through one or more of any suitable and effective valve(s) or chamber inlet valve(s) (2585), before the said air/gas(s) and/or fresh air/gas(s) are suitably and effectively flowed into, through, and/or out of, the said treatment chamber(s) (2026).

In a fifth combination, and without being limited, air/gas(s) and/or fresh air/gas(s) is pulled from the surrounding environment(s) (2900) through one or more of any suitably and effectively sized, shaped, and/or constructed, airflow inlet(s) (2535), where the said air/gas(s) and/or fresh air/gas(s) then pass through and is effectively filtered by one or more of any suitable and effective first filter(s) or airflow inlet prefilter(s) (2540), and where the said air/gas(s) and/or fresh air/gas(s) then passes by and/or through and can be effectively heated to one or more of any suitable and effective temperature(s), by one or more of any suitable and effective, heater(s), heater element(s) (2575), and/or heated air/gas(s) system(s) (2568), where the said air/gas(s) and/or fresh air/gas(s) then pass through one or more of any suitable and effective inbound blower(s) (2550), and is then forced out of the said inbound blower(s) (2550) via positive pressure(s) created by the said inbound blower(s) (2550) in a manner known to those skilled in the art, where the air/gas(s) and/or fresh air/gas(s) then pass through and is effectively filtered by one or more of any suitable and effective second filter(s) or inbound air filters(s) (2560), and where the said air/gas(s) and/or fresh air/gas(s) is then flowed and/or moved through one or more of any suitable and effective valve(s) or chamber inlet valve(s) (2585), before the said air/gas(s) and/or fresh air/gas(s) are suitably and effectively flowed into, through, and/or out of, the said treatment chamber(s) (2026).

In a sixth combination, and without being limited, air/gas(s) and/or fresh air/gas(s) is pulled from the surrounding environment(s) (2900) through one or more of any suitably and effectively sized, shaped, and/or constructed, airflow inlet(s) (2535), where the said air/gas(s) and/or fresh air/gas(s) then pass through one or more of any suitable and effective inbound blower(s) (2550), and is then forced out of the said inbound blower(s) (2550) via positive pressure(s) created by the said inbound blower(s) (2550) in a manner known to those skilled in the art, and where the said air/gas(s) and/or fresh air/gas(s) then pass through and is effectively filtered by one or more of any suitable and effective first filter(s) or airflow inlet prefilter(s) (2540), where the air/gas(s) and/or fresh air/gas(s) then pass through and is effectively filtered by one or more of any suitable and effective second filter(s) or inbound air filters(s) (2560), where the said air/gas(s) and/or fresh air/gas(s) then passes by and/or through and can be effectively heated to one or more of any suitable and effective temperature(s), by one or more of any suitable and effective, heater(s), heater element(s) (2575), and/or heated air/gas(s) system(s) (2568), and where the said air/gas(s) and/or fresh air/gas(s) is then flowed and/or moved through one or more of any suitable and effective valve(s) or chamber inlet valve(s) (2585), before the said air/gas(s) and/or fresh air/gas(s) are suitably and effectively flowed into, through, and/or out of, the said treatment chamber(s) (2026).

In a seventh combination, and without being limited, air/gas(s) and/or fresh air/gas(s) is pulled from the surrounding environment(s) (2900) through one or more of any suitably and effectively sized, shaped, and/or constructed, airflow inlet(s) (2535), where the said air/gas(s) and/or fresh air/gas(s) then pass through and is effectively filtered by one or more of any suitable and effective first HEPA or ULPA rated filter(s) or airflow inlet prefilter(s) (2540), and where the said air/gas(s) and/or fresh air/gas(s) then pass through one or more of any suitable and effective inbound blower(s) (2550), and is then forced out of the said inbound blower(s) (2550) via positive pressure(s) created by the said inbound blower(s) (2550) in a manner known to those skilled in the art, where the said air/gas(s) and/or fresh air/gas(s) then passes by and/or through and can be effectively heated to one or more of any suitable and effective temperature(s), by one or more of any suitable and effective, heater(s), heater element(s) (2575), and/or heated air/gas(s) system(s) (2568), and where the said air/gas(s) and/or fresh air/gas(s) is then flowed and/or moved through one or more of any suitable and effective valve(s) or chamber inlet valve(s) (2585), before the said air/gas(s) and/or fresh air/gas(s) are suitably and effectively flowed into, through, and/or out of, the said treatment chamber(s) (2026).

In an eighth combination, and without being limited, air/gas(s) and/or fresh air/gas(s) is pulled from the surrounding environment(s) (2900) through one or more of any suitably and effectively sized, shaped, and/or constructed, airflow inlet(s) (2535), where the said air/gas(s) and/or fresh air/gas(s) then pass through one or more of any suitable and effective inbound blower(s) (2550), and is then forced out of the said inbound blower(s) (2550) via positive pressure(s) created by the said inbound blower(s) (2550) in a manner known to those skilled in the art, and where the said air/gas(s) and/or fresh air/gas(s) then passes by and/or through and can be effectively heated to one or more of any suitable and effective temperature(s), by one or more of any suitable and effective, heater(s), heater element(s) (2575), and/or heated air/gas(s) system(s) (2568), where the said air/gas(s) and/or fresh air/gas(s) then pass through and is effectively filtered by one or more of any suitable and effective HEPA or ULPA rated first filter(s) or airflow inlet prefilter(s) (2540), and where the said air/gas(s) and/or fresh air/gas(s) is then flowed and/or moved through one or more of any suitable and effective valve(s) or chamber inlet valve(s) (2585), before the said air/gas(s) and/or fresh air/gas(s) are suitably and effectively flowed into, through, and/or out of, the said treatment chamber(s) (2026).

Without being limited, both the one or more chamber inlet valve(s) (2585) and chamber outlet valve(s) (2605) can remain open for any suitable and effective number of time(s) and for any suitable and effective duration(s) of time(s). It is preferred, without limitation, that they are at least suitably and effectively open for any number of time(s) and duration(s) of time(s) so that the air/gas(s), fresh air/gas(s), heated air/gas(s) and/or heated fresh air/gas(s) can flow and/or move through the one or more chamber inlet valve(s) (2585) and suitably and effectively into and through the one or more treatment chamber(s) (2026), and where any air/gas(s), fresh air/gas(s), heated air/gas(s), heated fresh air/gas(s), humidity(s), vapor(s), gas(s), aerosol(s), chemical(s), and/or deployed agent(s) (2100) present within the said treatment chamber(s) (2026) can then flow and/or move into, through, and out of, the one or more chamber outlet valve(s) (2605) and into, through, and out of, the one or more filtered exhaust assembly(s) (2530), where it is eventually exhausted into the environment and/or atmosphere that surrounds the outside of the treatment cabinet(s) (2519), treatment and processing cabinet(s) (2860), and/or the cabinet outer enclosure(s) (2865), for various purposes such as, but not limited to, (a) effectively removing one or more substance(s), humidity, vapor(s), gas(s), aerosol(s), chemical(s), and/or deployed agent(s) (2100) from anywhere inside of the one or more treatment chamber(s) (2026) and/or one or more of any connecting and/or targeted space(s), (b) effectively drying the one or more of any surface(s) of the one or more of any object(s) (2300) and/or surface(s) located inside of the said treatment chamber(s) (2026), and (c) effectively cooling the one or more of any surface(s) of the one or more of any object(s) (2300) and/or surface(s) located inside of the said treatment chamber(s) (2026).

Without being limited, air/gas(s) and/or fresh air/gas(s), can be sourced from the surrounding environment (2900) or from the environment and/or atmosphere that surrounds the outside of the treatment cabinet(s) (2519), treatment and processing cabinet(s) (2860), and/or the cabinet outer enclosure(s) (2865), and pulled and/or drawn into and through the filtered and heated inbound air/gas(s) assembly (2525), by one or more of any suitable and effective inbound blower(s) (2550). Generally, and without limitation, the filtered and heated inbound air/gas(s) assembly (2525) includes, without limitation, at least one, inbound air/gas airflow inlet(s) (2535), first filter(s) or airflow inlet prefilter(s) (2540), inbound blower(s) (2550), inbound air filters(s) (2560), heated air/gas(s) system(s) (2568) that can include one or more of any, and without limitation, heater(s), heater element(s) (2575), conduit(s), heated air/gas(s) conduit(s) (2570), that can effectively heat the inbound said air/gas(s) and/or fresh air/gas(s), and chamber inlet valve(s) (2585). Also, without being limited, the said various parts and components of the filtered and heated inbound air/gas(s) assembly (2525) can suitably and effectively connect to and with each other with various suitable and effective conduits, pipes, and connectors, known to those skilled in the art, so that these various parts and components can suitably and effectively communicate with the said one or more treatment chamber(s) (2026).

Without being limited, air/gas(s), fresh air/gas(s), heated air/gas(s), and/or heated fresh air/gas(s), can pass through the one or more of any chamber inlet valve(s) (2585) and then pass into the one or more of any chamber(s), enclosure(s), and/or interior space(s), of the one or more treatment chamber(s) (2026) through one or more of any suitable and effective chamber inlet(s) (2591) located at one or more of any suitable and effective location(s) of and/or for the said treatment chamber(s) (2026).

Without being limited, the one or more chamber inlet(s) (2591) can be located at and/or communicate with, one or more of any suitable and effective locations, within, inside, inside of, to, of, and/or at, the treatment chamber(s) (2026). It is preferred, without limitation, that the one or more chamber inlet(s) (2591) are at least located at, to, and/or on, one or more of any suitable and effective location(s), near, adjacent to, approximate to, on, and/or at, any upper and/or top area(s) of the treatment chamber(s) (2026) and/or inside of the treatment chamber(s) (2026). It is more preferred, without limitation, that the one or more chamber inlet(s) (2591) are located at, to, and/or on, one or more of any suitable and effective location(s), near, adjacent to, approximate to, on, and/or at, the ceiling(s) of the treatment chamber(s) and/or inside of the treatment chamber(s) (2026). It is even more preferred, without limitation, that the one or more chamber inlet(s) (2591) are located at, to, near, and/or on, one or more of any suitable and effective location(s) of any suitable and effective wall(s) and/or interior wall(s) of the treatment chamber(s) (2026) and they are also located at one or more of any suitable and effective location(s), near, adjacent to, approximate to, on, and/or at, any ceiling(s) of and/or top area(s) of the treatment chamber(s) and/or inside of the treatment chamber(s) (2026).

Without being limited, the chamber inlet(s) (2591) can have any suitable and effective, measurement(s), dimension(s), shape(s), size(s), length(s), geometry(s), diameter(s), width(s), outlet(s), and/or height(s). Also, and without limitation, the said chamber inlet(s) (2591), can have one or more of any suitable and effective orifice(s) and or opening(s) having any suitable and effective, measurement(s), dimension(s), shape(s), size(s), length(s), geometry(s), width(s), and/or height(s), through which any air/gas(s), fresh air/gas(s), heated air/gas(s), and/or heated fresh air/gas(s) can pass through and into the said treatment chamber(s) (2026). Without being limited, any air/gas(s), fresh air/gas(s), heated air/gas(s), and/or heated fresh air/gas(s) that leave the said chamber inlet(s) (2591) can exit and/or be directed, in one or more of any suitable and effective angle(s) and/or direction(s), and in one or more of any suitable and effective, dimension(s), geometry(s), and/or shape(s). It is preferred, without limitation, that the one or more chamber inlet(s) (2591) can have at least one suitable and effective orifice(s), and the air/gas(s), fresh air/gas(s), heated air/gas(s), and/or heated fresh air/gas(s) that leave the said chamber inlet(s) (2591) are directed suitably and effectively, outward, angled, and/or downward, within and/or into the said treatment chamber(s) (2026). Without being limited, the air/gas(s), fresh air/gas(s), heated air/gas(s), and/or heated fresh air/gas(s), can be, and without limitation, flowed, moved, dispensed, directed, and/or dispersed, to one or more and/or all area(s) within the treatment chamber(s) (2026). The air/gas(s), fresh air/gas(s), heated air/gas(s), and/or heated fresh air/gas(s), can also be, and without limitation, flowed, moved, dispensed, directed, and/or dispersed, so that it can contact and/or interact with one or more and/or all surface(s) within the treatment chamber(s) (2026). It is preferred, without limitation, that the air/gas(s), fresh air/gas(s), heated air/gas(s), and/or heated fresh air/gas(s) is at least effectively dispersed and it is effectively flowed into and through the treatment chamber(s) (2026).

Without being limited, the air/gas(s), fresh air/gas(s), heated air/gas(s), and/or heated fresh air/gas(s) can leave the said chamber inlet(s) (2591) and flow into the treatment chamber(s) (2026) at one or more of any suitable and effective, speed(s), velocity(s), quantity(s), flow rate(s), and/or cubic feet per minute(s) (CFM). Also, and without limitation, the said chamber inlet(s) (2591) can have one or more of any suitable and effective internal and/or external director(s) that can flow, move, and/or direct, the air/gas(s), fresh air/gas(s), heated air/gas(s), and/or heated fresh air/gas(s) into the treatment chamber(s) (2026), in one or more of any effective, arc(s), direction(s), and/or airflow pattern(s). Also, without being limited, the air/gas(s), fresh air/gas(s), heated air/gas(s), and/or heated fresh air/gas(s) that are flowed out of the said chamber inlet(s) (2591) and into the said treatment chamber(s) (2026) can be used for various purposes such as, but not limited to, the recycling, refreshing, and/or removing, of any suitable and effective quantity(s) and/or concentration(s) of one or more of any air/gas(s), fresh air/gas(s), heated air/gas(s), and/or heated fresh air/gas(s), substance(s), humidity(s), vapor(s), gas(s), aerosol(s), chemical(s), and/or deployed agent(s) (2100) from one or more of any location(s) and/or surface(s) inside of the treatment chamber(s) (2026) and/or to effectively dry the various surfaces within the treatment chamber(s) (2026) such as, but not limited to, one or more of any surface(s) of any object(s) (2300) at any suitable and effective time(s) and for any suitable and effective duration(s) of time(s).

Without being limited, the said air/gas(s) and/or fresh air/gas(s) that enter the filtered and heated inbound air/gas(s) assembly (2525) and the treatment chamber(s) (2026) can also not be heated and/or the said air/gas(s) and/or fresh air/gas(s) can also be suitably and effectively cooled in any manner known to those skilled in the art, and flowed out of the said chamber inlet(s) (2591) and into the said treatment chamber(s) (2026) for purposes including, but not limited to, effectively cooling the various surfaces within the treatment chamber(s) (2026) such as, but not limited to, one or more of any surface(s) of any object(s) (2300) at any suitable and effective time(s) and for any suitable and effective duration(s) of time(s). It is preferred, without limitation, that the various surface(s) inside of the treatment chamber(s) (2026) such as, but not limited to any, one or more surface(s) of any object(s) (2300), can be effectively cooled to one or more of any suitable and effective temperature(s), at least after they are suitably and effectively treated, dried, and/or the various substance(s) and/or deployed agent(s) (2100) is suitably and/or effectively removed from one or more of any location(s) and/or surface(s) inside of the treatment chamber(s) (2026).

Without being limited, any suitable and effective quantity(s) of air/gas(s), fresh air/gas(s), heated air/gas(s), and/or heated fresh air/gas(s), can be flowed from the filtered and heated inbound air/gas(s) assembly (2525) and into and through the treatment chamber(s) for one or more of any suitable and effective duration of time(s) after the deployment and/or movement of the deployed agent(s) (2100) into the treatment chamber(s) (2026) is finished, terminated, and/or is terminated for any reasons known to those skilled in the art, and the one or more of any chamber inlet valve(s) (2585) and chamber outlet valve(s) (2605) are effectively open. It is preferred, without limitation, that the inbound blower(s) (2550) and the exhaust blower(s) (2640) are not operated until the said chamber inlet valve(s) (2585) and chamber outlet valve(s) (2605) are effectively open.

Without being limited, the air/gas(s), fresh air/gas(s), heated air/gas(s), and/or heated fresh air/gas(s), can be flowed into and through the treatment chamber(s) (2026) for one or more of any suitable and effective duration(s) of any suitable and effective length(s) of time(s) after the deployment and/or movement of the deployed agent(s) (2100) into the treatment chamber(s) (2026) is finished and/or is terminated, and where various combinations of unheated and/or heated air/gas(s) and/or fresh air/gas(s) can be flowed into and through the said treatment chamber(s) (2026) at one or more of any time(s) for purposes such as, but not limited to, removing the deployed agent(s) (2100) from inside and/or within the treatment chamber(s) (2026) and/or drying the various surfaces inside of the said treatment chamber(s) (2026) and/or drying the various one or more surfaces of the treated object(s) (2300) located inside of the treatment chamber(s) (2026).

In one example, and without limitation, the flow of the deployed agent(s) (2100) into the treatment chamber(s) (2026) is stopped and terminated, the said chamber inlet valve(s) (2585) and chamber outlet valve(s) (2605) are effectively opened, the inbound blower(s) (2550) and exhaust blower(s) (2640) are then turned on or effectively operated and flow air/gas(s) into and through the treatment chamber(s) (2026), and any effective quantity of unheated air/gas(s) and/or fresh air/gas(s) is first flowed or moved into and through the treatment chamber(s) (2026) for any suitable and effective duration of time, followed by flowing or moving any effective quantity of heated air/gas(s) and/or heated fresh air/gas(s), that is heated to any suitable and effective temperature(s), into and through the treatment chamber(s) (2026) for any suitable and effective duration of time and/or until the treated object(s) (2300) are effectively dry, and is then followed with the flow or movement of any effective quantity of unheated air/gas(s) and/or fresh air/gas(s) flowed from the filtered and heated inbound air/gas(s) assembly (2525) and into and through the treatment chamber(s) (2026), for any suitable and effective duration of time and/or until the treated object(s) (2300) are effectively cool, for purposes such as, but not limited to, effectively cooling the various surfaces and/or treated object(s) (2300) surface(s) within the said treatment chamber(s) (2026), before the treated object(s) (2300) are removed from the treatment chamber(s) (2026). It is preferred, without limitation, that the flow or movement of the said unheated air/gas(s) and/or fresh air/gas(s) through the treatment chamber(s) (2026) at the end of the said process is stopped or terminated before the treated object(s) (2300) are removed from the treatment chamber(s) (2026). However, and without limitation, in some circumstances in this example known to those skilled in the art, the flow or movement of the said unheated air/gas(s) and/or fresh air/gas(s) at the end of this said process, through the treatment chamber(s) (2026), may not be stopped or terminated until any suitable and effective time after the treated object(s) (2300) are removed from the treatment chamber(s) (2026).

In another example, and without limitation, the flow of the deployed agent(s) (2100) into the treatment chamber(s) (2026) to treat the one or more treated object(s) (2300) is stopped and/or terminated, the said chamber inlet valve(s) (2585) and chamber outlet valve(s) (2605) are effectively opened, the inbound blower(s) (2550) and exhaust blower(s) (2640) are turned on or effectively operated and flow air/gas(s) into and through the treatment chamber(s) (2026), and any effective quantity of heated air/gas(s) and/or heated fresh air/gas(s), that is heated to any suitable and effective temperature(s), is first flowed into and through the treatment chamber(s) (2026) for any suitable and effective duration of time and/or until the treated object(s) (2300) are effectively dry, and is then followed with the flow or movement of any effective quantity of unheated air/gas(s) and/or fresh air/gas(s) into and through the treatment chamber(s) (2026), for any suitable and effective duration of time and/or until the treated object(s) (2300) are effectively cool, for purposes such as, but not limited to, effectively cooling the various surfaces and/or treated object(s) (2300) surface(s) within the said treatment chamber(s) (2026), before the treated object(s) (2300) are removed from the treatment chamber(s) (2026). It is preferred, without limitation, that the flow or movement of the said unheated air/gas(s) and/or fresh air/gas(s) into and through the treatment chamber(s) (2026) in this example, is stopped or terminated before the treated object(s) (2300) are removed from the treatment chamber(s) (2026). However, and without limitation, in some circumstances in this example known to those skilled in the art, the flow and/or movement of the said unheated air/gas(s) and/or fresh air/gas(s) into and through the treatment chamber(s) (2026) may not be stopped and/or terminated until any suitable and effective time after the treated object(s) (2300) are removed from the treatment chamber(s) (2026).

In yet another and preferred example, and without limitation, the flow of the deployed agent(s) (2100) into the treatment chamber(s) (2026) to treat the one or more treated object(s) (2300) is stopped and/or terminated, the said chamber inlet valve(s) (2585) and chamber outlet valve(s) (2605) are effectively opened, the inbound blower(s) (2550) and exhaust blower(s) (2640) are turned on or effectively operated and flow air/gas(s) into and through the treatment chamber(s) (2026), and any effective quantity of heated air/gas(s) and/or fresh air/gas(s), that is heated to any suitable and effective temperature, is flowed into and through the treatment chamber(s) (2026) for any suitable and effective duration of time, and the flow of the said heated air/gas(s) and/or fresh air/gas(s) is stopped and/or terminated at any suitable and effective time and/or after the treated object(s) (2300) are effectively dry, and the treated object(s) (2300) can be removed from the treatment chamber(s) (2026) at any suitable, convenient, and/or effective, time(s). It is preferred, without limitation, that the flow or movement of the said heated air/gas(s) and/or fresh air/gas(s) into and through the treatment chamber(s) (2026) is stopped or terminated before the treated object(s) (2300) are removed from the treatment chamber(s) (2026). However, and without limitation, in some circumstances in this example known to those skilled in the art, the flow or movement of the said heated air/gas(s) and/or fresh air/gas(s) through the treatment chamber(s) (2026) may not be stopped and/or terminated until any suitable and effective time after the treated object(s) (2300) are removed from the treatment chamber(s) (2026).

Without being limited, the air/gas(s), fresh air/gas(s), heated air/gas(s), and/or heated fresh air/gas(s), can also be flowed into and through the treatment chamber(s) (2026) for one or more of any suitable and effective duration(s) of any suitable and effective length(s) of time(s) before the deployment and/or movement of the deployed agent(s) (2100) into the treatment chamber(s) (2026), and where various combinations of unheated and/or heated air/gas(s) and/or fresh air/gas(s) can also be flowed into and through the said treatment chamber(s) (2026) at one or more of any time(s) before any deployed agent(s) (2100) are moved and/or flowed into the treatment chamber(s) (2026), for purposes such as, but not limited to, drying and/or cooling the various surfaces inside of the said treatment chamber(s) (2026) and/or drying and/or cooling the various one or more surfaces of the treated object(s) (2300) located inside of the treatment chamber(s) (2026).

In one example, and without limitation, the one or more treated object(s) (2300) are effectively placed and/or located within the treatment chamber(s) (2026) all in a manner known to those skilled in the art, the chamber door(s) (2036) is effectively closed, the chamber inlet valve(s) (2585) and chamber outlet valve(s) (2605) are effectively opened, the inbound blower(s) (2550) and exhaust blower(s) (2640) are turned on or effectively operated and flow air/gas(s) into and through the treatment chamber(s) (2026), and any effective quantity of air/gas(s) and/or fresh air/gas(s) that is preferably, and without limitation, unheated and is at any suitable and effective temperature(s), is flowed into and through the treatment chamber(s) (2026) for any suitable and effective duration(s) of time, and the flow of the said unheated air/gas(s) and/or unheated fresh air/gas(s) is stopped and/or terminated at any suitable and effective time and/or after the treated object(s) (2300) are effectively dry and/or the one or more surface(s) of the treated object(s) (2300) are are cooled to any suitable and effective temperature(s), before the treated object(s) (2300) are exposed to and/or treated with the deployed agent(s) (2100), the said exhaust blower(s) (2640) are then turned off, the chamber inlet valve(s) (2585) and chamber outlet valve(s) (2605) are effectively closed, and the said treated object(s) (2300) are exposed to and/or treated with any suitable and effective amount, quantity, and/or concentration, of deployed agent(s) (2100).

In another example, and without limitation, the one or more treated object(s) (2300) are effectively placed and/or located within the treatment chamber(s) (2026) all in a manner known to those skilled in the art, the chamber door(s) (2036) is effectively closed, the chamber inlet valve(s) (2585) and chamber outlet valve(s) (2605) are effectively opened, the inbound blower(s) (2550) and exhaust blower(s) (2640) are turned on or effectively operated and flow air/gas(s) into and through the treatment chamber(s) (2026), and any effective quantity of air/gas(s) and/or fresh air/gas(s) that is preferably, and without limitation, heated to any suitable and effective temperature, is flowed into and through the treatment chamber(s) (2026) for any suitable and effective duration(s) of time(s), and the flow of the said heated air/gas(s) and/or heated fresh air/gas(s) is stopped and/or terminated at any suitable and effective time and/or after the treated object(s) (2300) are effectively dry and/or heated, and the said exhaust blower(s) (2640) are then turned off, the chamber inlet valve(s) (2585) and chamber outlet valve(s) (2605) are effectively closed, and the said treated object(s) (2300) are exposed to and/or treated with any suitable and effective amount, quantity, and/or concentration, of deployed agent(s) (2100).

In still another and preferred example, and without limitation, the one or more treated object(s) (2300) are effectively placed and/or located within the treatment chamber(s) (2026) all in a manner known to those skilled in the art, the chamber door(s) (2036) is effectively closed, the chamber inlet valve(s) (2585) and chamber outlet valve(s) (2605) are effectively opened, the inbound blower(s) (2550) and exhaust blower(s) (2640) are turned on or effectively operated and flow air/gas(s) into and through the treatment chamber(s) (2026), and any effective quantity of air/gas(s) and/or fresh air/gas(s) that is preferably, and without limitation, heated to any suitable and effective temperature, is flowed into and through the treatment chamber(s) (2026) for any suitable and effective duration(s) of time(s), and the flow of the said heated air/gas(s) and/or heated fresh air/gas(s) is stopped and/or terminated at any suitable and effective time and/or after the treated object(s) (2300) are effectively dry, and then any effective quantity(s) and/or amount(s) of unheated air/gas(s) and/or unheated fresh air/gas(s) is flowed and/or moved into and through the treatment chamber(s) (2026), for any suitable and effective duration of time and/or until the treated object(s) (2300) are effectively cooled, for purposes such as, but not limited to, effectively cooling the various surfaces and/or treated object(s) (2300) surface(s) within the said treatment chamber(s) (2026) to any suitable and effective temperature(s), before the treated object(s) (2300) are exposed to and/or treated with the deployed agent(s) (2100), the said exhaust blower(s) (2640) are then turned off, the chamber inlet valve(s) (2585) and chamber outlet valve(s) (2605) are effectively closed, and the said treated object(s) (2300) are exposed to and/or treated with any suitable and effective amount, quantity, and/or concentration, of deployed agent(s) (2100).

Without being limited, the one or more of any, air/gas(s), fresh air/gas(s), heated air/gas(s), and/or heated fresh air/gas(s), substance(s), humidity(s), vapor(s), gas(s), aerosol(s), chemical(s), and/or deployed agent(s) (2100) that is flowed into and through the said treatment chamber(s) (2026) and/or is present within the said treatment chamber(s) (2026), can travel out of the one or more treatment chamber(s) (2026) by passing through the one or more of any chamber outlet(s) (2592) and into, through, and out of, the one or more filtered exhaust assembly(s) (2530) and then out of the treatment cabinet(s) (2519), treatment and processing cabinet(s) (2860), and/or the cabinet outer enclosure(s) (2865), and into the surrounding environment (2900). More specifically, and without limitation, the air/gas(s), fresh air/gas(s), heated air/gas(s), and/or heated fresh air/gas(s), substance(s), humidity(s), vapor(s), gas(s), aerosol(s), chemical(s), and/or deployed agent(s) (2100) that is flowed into and through the said treatment chamber(s) (2026) and/or is present within the said treatment chamber(s) (2026), can travel out of the one or more treatment chamber(s) (2026) by passing through the one or more of any chamber outlet(s) (2592) and into, through, and out of, the one or more chamber outlet valve(s) (2605) and filtered exhaust assembly(s) (2530).

Without being limited, the one or more chamber outlet(s) (2592) can be located at and/or communicate with, any one or more of any suitable and effective locations, within, inside, inside of, to, of, and/or at, the treatment chamber(s) (2026). It is preferred, without limitation, that the one or more chamber outlet(s) (2592) are at least located at or on one or more of any suitable and effective location(s), near, adjacent to, approximate to, on, and/or at, any bottom(s) and/or lower area(s) of the inside of the treatment chamber(s) (2026). It is more preferred, without limitation, that the one or more chamber outlet(s) (2592) are located at or on one or more of any suitable and effective location(s), near, adjacent to, approximate to, on, and/or at, the floor(s) of the inside of the treatment chamber(s) (2026). It is even more preferred, without limitation, that the one or more chamber outlet(s) (2592) are located at or on one or more of any suitable and effective location(s) of any suitable and effective wall(s) and/or interior wall(s) of the treatment chamber(s) (2026) and they are also located at one or more of any suitable and effective location(s), near, adjacent to, approximate to, on, and/or at, any floor(s) of and/or bottom area(s) of the inside of the treatment chamber(s) (2026).

Without being limited, the chamber outlet(s) (2592) can have any suitable and effective, measurement(s), dimension(s), shape(s), size(s), length(s), geometry(s), width(s), inlet(s), and/or height(s). Also, and without limitation, the said chamber outlet(s) (2592), can have one or more of any suitable and effective orifices and or openings having any suitable and effective, measurement(s), dimension(s), shape(s), size(s), length(s), geometry(s), width(s), and/or height(s), through which any air/gas(s), fresh air/gas(s), heated air/gas(s), and/or heated fresh air/gas(s), substance(s), humidity(s), vapor(s), gas(s), aerosol(s), chemical(s), and/or deployed agent(s) (2100) can pass through and out of the said treatment chamber(s) (2026).

Without being limited, the air/gas(s), fresh air/gas(s), heated air/gas(s), and/or heated fresh air/gas(s), substance(s), humidity(s), vapor(s), gas(s), aerosol(s), chemical(s), and/or deployed agent(s) (2100) can enter the said chamber outlet(s) (2592) and flow out of the treatment chamber(s) (2026) at one or more of any suitable and effective, speed(s), velocity(s), quantity(s), flow rate(s), and/or cubic feet per minute(s) (CFM). Also, without limitation, the said chamber outlet(s) (2592) can also have one or more of any suitable and effective internal and/or external director(s) that can flow the air/gas(s), fresh air/gas(s), heated air/gas(s), and/or heated fresh air/gas(s), substance(s), humidity(s), vapor(s), gas(s), aerosol(s), chemical(s), and/or deployed agent(s) (2100) out of the treatment chamber(s) (2026), in one or more of any airflow pattern(s).

Without being limited, during, at the same time as, and/or at the same time during the one or more of any suitable and effective step(s), method(s), and/or process(es) of, flowing and/or moving the one or more of any, air/gas(s), fresh air/gas(s), heated air/gas(s), and/or heated fresh air/gas(s), into, through, and out of, the treatment chamber(s) (2026), the one or more of any valve(s) that connect with and/or communicate with the one or more space(s) and/or atmosphere(s) inside of the treatment chamber(s) (2026) and the one or more of any treatment agent deployment apparatus(s) (2654) and/or any other deployed agent(s) (2100) dispenser(s) and/or generator(s), such as, but not limited to the one or more of any, deployed agent(s) inlet valve(s) (2685) and deployed agent(s) outlet valve(s) (2690), can also be effectively open in addition to both the one or more chamber inlet valve(s) (2585) and chamber outlet valve(s) (2605) also being effectively open.

In addition, and without being limited, while the one or more deployed agent(s) inlet valve(s) (2685), deployed agent(s) outlet valve(s) (2690), chamber inlet valve(s) (2585), and chamber outlet valve(s) (2605), are effectively open, and air/gas(s), fresh air/gas(s), heated air/gas(s), and/or heated fresh air/gas(s), are suitably and effectively flowed and moved into, through, and out of, the treatment chamber(s) (2026), various one or more of any, air/gas(s), fresh air/gas(s), heated air/gas(s), heated fresh air/gas(s), atmosphere(s), and any other substance(s) that may be present, within the treatment chamber(s) (2026) and at any one or more time(s), can be circulated through the one or more of any, agent blower(s) (2660), treatment agent deployment apparatus(s) (2654), decontamination system(s) (2040), and/or any other deployed agent(s) (2100) dispenser(s) and/or generator(s), by one or more of any agent blower(s) (2660) and/or any other suitable means for moving air/gas(s) that is a part of any treatment agent deployment apparatus(s) (2654), for any suitable and effective number of time(s) and for any suitable and effective duration(s) of time(s).

It is preferred, without limitation, that air/gas(s), fresh air/gas(s), heated air/gas(s), and/or heated fresh air/gas(s), are circulated through the treatment agent deployment apparatus(s) (2654) until at least the various conduit(s) and pipe(s) that connect the said treatment agent deployment apparatus(s) (2654) to the treatment chamber(s) (2026) are suitably and effectively, dry and/or clear and/or free of the deployed agent(s) (2100). Alternatively, and without limitation, the one or more deployed agent(s) inlet valve(s) (2685) and deployed agent(s) outlet valve(s) (2690) can also be effectively closed before, during, and/or effectively about after, the chamber inlet valve(s) (2585) and chamber outlet valve(s) (2605), are effectively opened.

Without limitation, the one or more deployed agent(s) inlet valve(s) (2685) and deployed agent(s) outlet valve(s) (2690) can also be effectively closed after the deployment of the deployed agent(s) (2100) into the treatment chamber(s) (2026) is effectively finished and complete, and before, during, and/or effectively after, the chamber inlet valve(s) (2585) and chamber outlet valve(s) (2605), are effectively opened and/or when the said air/gas(s), fresh air/gas(s), heated air/gas(s), and/or heated fresh air/gas(s), are suitably and effectively flowed and/or moved into, the treatment chamber(s) (2026). It is more preferred, without limitation, that the one or more deployed agent(s) inlet valve(s) (2685) and deployed agent(s) outlet valve(s) (2690), are at least not closed until the effective deployment of the deployed agent(s) (2100) into the treatment chamber(s) (2026) is effectively finished and complete, and an effective flow of air/gas(s), fresh air/gas(s), heated air/gas(s), and/or heated fresh air/gas(s), is flowed and/or moved into, through, and out of, the treatment agent deployment apparatus(s) (2654), using any suitable and effective means to move the said air/gas(s), fresh air/gas(s), heated air/gas(s), and/or heated fresh air/gas(s), such as, but not limited to, one or more of any, agent blower(s) (2660), and at least the various deployed agent(s) (2100), humidity, and/or any other unwanted substance(s), are suitably and effectively removed from one or more part(s) and component(s) of the agent blower(s) (2660), treatment agent deployment apparatus(s) (2654), decontamination system(s) (2040), and/or any other deployed agent(s) (2100) dispenser(s) and/or generator(s), and/or any pipe(s) and conduit(s) that connect to these said part(s) and component(s).

However, it is also preferred, without limitation, that at least the deployed agent(s) inlet valve(s) (2685) and deployed agent(s) outlet valve(s) (2690), are suitably and effectively closed after the various one or more, processing step(s), treatment cycle(s), deployment(s) of the deployed agent(s) (2100), surface drying and/or deployed agent(s) (2100) removal cycle(s) and/or step(s), processing cycle(s), and/or packaging step(s), is finished and the one or more treated object(s) (2300) are ready to be removed from the treatment chamber(s) (2026), preferably, and without limitation, by the machine operator.

For example, and without being limited, closing the deployed agent(s) inlet valve(s) (2685) and deployed agent(s) outlet valve(s) (2690), after the various one or more, processing step(s), treatment cycle(s), deployment(s) of the deployed agent(s) (2100), surface drying and/or deployed agent(s) (2100) removal cycle(s) and/or step(s), processing cycle(s), and/or packaging step(s), is finished, can prevent any deployed agent(s) (2100) in any gas, aerosol, and/or vapor form(s), from migrating and/or moving from one or more area(s) and/or part(s) such as, but not limited to any, one or more of any part(s) of the treatment agent deployment apparatus(s) (2654), agent blower(s) (2660), and/or decontamination system(s) (2040), into the treatment chamber(s) (2026), and any deployed agent(s) (2100) in any gas, aerosol, and/or vapor form(s), that are present in the treatment chamber(s) (2026) and/or any area(s) that communicate with the said treatment chamber(s) (2026), can, and without limitation, escape and/or flow out of these said space(s) (2026) through either and/or both the chamber inlet valve(s) (2585) and/or the chamber outlet valve(s) (2605) into and through either and/or both the filtered and heated Inbound air/gas(s) assembly (2525) and/or the filtered exhaust assembly (2530), and ventilate, escape, and/or move, out of the improved cabinet mounted treatment chamber processing system (2519).

It is also more preferred, without limitation, that the various valve(s) that access and/or communicate with the treatment chamber(s) (2026) such as, but not limited to any, deployed agent(s) inlet valve(s) (2685), deployed agent(s) outlet valve(s) (2690), chamber inlet valve(s) (2585), and chamber outlet valve(s) (2605), are suitably and effectively closed after the various one or more, processing step(s), treatment cycle(s), deployment(s) of the deployed agent(s) (2100), surface drying and/or deployed agent(s) (2100) removal cycle(s) and/or step(s), processing cycle(s), and/or packaging step(s), is finished and the one or more treated object(s) (2300) are ready to be removed from the treatment chamber(s) (2026), preferably, and without limitation, by the machine operator.

For example, and without being limited, closing the various valves that communicate with the treatment chamber(s) such as, but not limited to any, the deployed agent(s) inlet valve(s) (2685), deployed agent(s) outlet valve(s) (2690), chamber inlet valve(s) (2585), chamber outlet valve(s) (2605), circulation input valve(s) (2905), and circulation output valve(s) (2910), after all of the various step(s) and/or process(s) is completed such as, but not limited to any, processing step(s), treatment cycle(s), deployment(s) of the deployed agent(s) (2100), circulation, mixing, and/or homogenization of the deployed agent(s) (2100) inside of the treatment chamber(s) (2026), surface drying and/or effective removal of the deployed agent(s) (2100) from various surface(s) inside of the treatment chamber(s) (2026) cycle(s) and/or step(s), processing cycle(s), and/or packaging step(s), is finished, can prevent any deployed agent(s) (2100) in any gas, aerosol, and/or vapor form(s), from migrating and/or moving from one or more area(s) and/or part(s) such as, but not limited to any, one or more of any part(s) of the chamber circulation apparatus(s) (2695), treatment agent deployment apparatus(s) (2654), agent blower(s) (2660), and/or decontamination system(s) (2040), into the treatment chamber(s) (2026), and another benefit, and without limitation, is that this can also keep the treatment chamber(s) (2026) suitably and effectively clean and/or free of any unwanted foreign object debris.

Without being limited, the one or more chamber circulation apparatus(s) (2695) can be suitably and effectively operated for various purposes such as, but not limited to, suitably and effectively, drying any floor(s) within the treatment chamber(s) (2026), circulating, moving, flowing, stirring, and/or mixing, the one or more of any, atmosphere(s), substance(s), deployed agent(s) (2100), humidity(s), air/gas(s), fresh air/gas(s), heated air/gas(s), and/or heated fresh air/gas(s), within the treatment chamber(s) (2026), and the chamber circulation apparatus(s) (2695) can be operated at one or more of any suitable and effective time(s) and for one or more of any suitable and effective duration(s) of time(s).

Without being limited, the flow of air/gas(s) and one or more of any other substance(s) into and out of the said chamber circulation apparatus(s) (2695) can also be controlled by one or more of any suitable and effective air/gas(s) flow control valve(s), all in a manner known to those skilled in the art. If these valves are used, and without being limited, at least one of any suitable and effective valve(s) or circulation input valve(s) (2905), can be suitably and effectively located near and effectively communicate with the one or more circulation inlet(s) (2700) and/or circulation inlet conduit(s) (2710), and can control the flow of any air/gas(s) and/or substance(s) into and/or through the circulation inlet conduit(s) (2710) and circulation blower(s) (2715), and at least one of any suitable and effective valve(s) or circulation output valve(s) (2910) can also be suitably and effectively located near and effectively communicate with the circulation outlet(s) (2705) and/or circulation outlet conduit(s) (2720), and can control the flow of any air/gas(s) and/or substance(s) through and/or out of the circulation outlet conduit(s) (2720) and circulation blower(s) (2715). Without being limited, the said air/gas(s) flow control valve(s) can be located at any suitable and effective location(s). Without limitation, the said air/gas(s) flow control valve(s) can be opened and closed at any suitable and effective time(s). It is preferred, without limitation, that the said valves are at least effectively open before the operation of the said chamber circulation apparatus(s) (2695), and they are effectively closed after any termination, stoppage, and/or shut down, of the said chamber circulation apparatus(s) (2695).

Without being limited, the operation of the chamber circulation apparatus(s) (2695) can be terminated, stopped, and/or shut down, at any suitable and effective time(s) but preferably, and without limitation, at least after the various one or more, processing step(s), treatment chamber(s) (2026) floor drying step(s), various surface drying and/or deployed agent(s) (2100) removal cycle(s) and/or step(s) for various surface(s) and/or area(s) inside of the said treatment chamber(s) (2026), is finished.

Without limitation, the various valves in the present invention can be opened and closed at any suitable and effective time(s) and remain open and/or closed for one or more of any suitable and effective duration of time(s). Also, and without being limited, before the various, blowers, air/gas(s) pumps, and/or fans, in the present invention, are turned on, powered, actuated, and/or operated, it is preferred, without limitation, that the various valves that they communicate with are effectively open, and/or at least the said valves are in a state of opening and are effectively open while the said various, blowers, air/gas(s) pumps, and/or fans, are being effectively turned on, powered, actuated, and/or operated, and/or are in any start-up mode, start up condition, and/or operating state.

For example, and without limitation, it is preferred, without limitation, that the chamber inlet valve(s) (2585) and chamber outlet valve(s) (2605) are effectively open, when the inbound blower(s) (2550) and exhaust blower(s) (2640) are turned on and/or are effectively operated. It is also preferred, without limitation, that the chamber inlet valve(s) (2585) and chamber outlet valve(s) (2605) are effectively closed, when the inbound blower(s) (2550) and exhaust blower(s) (2640) are turned off and/or are not powered. In another example, and without limitation, it is also preferred, without limitation, that the deployed agent(s) inlet valve(s) (2685) and the deployed agent(s) outlet valve(s) (2690) are effectively open, when the decontamination system(s) (2040) and/or agent blower(s) (2660) are turned on and/or are operated. In still another example, and without limitation, it is also preferred, without limitation, that the circulation input valve(s) (2905) and the circulation output valve(s) (2910) are effectively open, when the circulation blower(s) (2715) are turned on and/or are operated.

Without being limited, when the chamber inlet valve(s) (2585) and chamber outlet valve(s) (2605), are effectively open and both the inbound blower(s) (2550) and exhaust blower(s) (2640) are turned on, powered, actuated, and/or operating, the air/gas(s), fresh air/gas(s), heated air/gas(s), heated fresh air/gas(s), humidity, vapor(s), gas(s), aerosol(s), chemical(s), and/or deployed agent(s) (2100), can flow out of the treatment chamber(s) (2026) through one or more of any suitable and effective chamber outlet(s) (2592) and into and through one or more of any suitable and effective filtered exhaust assembly(s) (2530).

Without being limited, the said air/gas(s), fresh air/gas(s), heated air/gas(s), heated fresh air/gas(s), humidity, vapor(s), gas(s), aerosol(s), chemical(s), and/or deployed agent(s) (2100), are both effectively pushed and moved through and out of the treatment chamber(s) (2026) with any suitable and effective pressure(s) and force(s) created by the one or more inbound blower(s) (2550) and also at the same time effectively pulled through and out of the said treatment chamber(s) (2026) with any suitable and effective pressure(s), negative pressure(s), vacuum(s), force(s), and/or pulling and pushing force(s), created by the one or more exhaust blower(s) (2640).

Without being limited, the at least one filtered exhaust assembly(s) (2530) can include, and without limitation, at least one of any various suitable and effective parts and components that suitably and effectively connect and communicate with each other, such as, but not limited to any, at least one chamber outlet(s) (2592) that connect and communicate with the one or more interior space(s) of the one or more treatment chamber(s) (2026), and where the at least one chamber outlet(s) (2592) connect and communicate with the at least one chamber outlet conduit(s) (2600), and where the at least one chamber outlet conduit(s) (2600) connect and communicate with the at least one chamber outlet valve(s) (2605), and where the at least one post valve conduit(s) (2610) connect and communicate with the at least one chamber outlet valve(s) (2605) and the at least one first outlet filter(s) (2615), and where the one or more first outlet filter(s) (2615) connect and communicate with at least one vapor absorbing outlet filter(s) (2620), and where the at least one vapor absorbing outlet filter(s) (2620) connect and communicate with at least one primary post absorption filter(s) (2625), and where the primary post absorption filter(s) (2625) connect and communicate with at least one secondary post absorption filter(s) (2630), and where at least one pre-outbound blower conduit(s) (2635) connect and communicate with the at least one primary post absorption filter(s) (2625) and/or post absorption filter(s) (2630) and the at least one exhaust blower(s) (2640), and where the at least one post outbound blower outlet conduit(s) (2652) connect and communicate with at least one exhaust blower(s) (2640) and at least one exhaust outlet filter(s) (2645), and where the at least one exhaust outlet filter(s) (2645) connect and communicate with the at least one exhaust outlet(s) (2650), and where the air/gas(s), fresh air/gas(s), heated air/gas(s), heated fresh air/gas(s), humidity, vapor(s), gas(s), aerosol(s), chemical(s), and/or deployed agent(s) (2100) is exhausted from and/or leaves the at least one exhaust outlet(s) (2650) and flows and/or moves into the surrounding environment (2900) and/or into the environment and/or atmosphere that surrounds the outside of the treatment cabinet(s) (2519), treatment and processing cabinet(s) (2860), and/or the cabinet outer enclosure(s) (2865).

Without being limited, the various said parts and components of the filtered and heated inbound air/gas(s) assembly (2525) and filtered exhaust assembly(s) (2530) can be located at one or more of any suitable and effective location(s) and/or position(s), and can be located in one or more of any suitable and effective order(s) and/or one or more of any suitable and effective combination(s) of position(s) and/or order(s) of location(s) and/or position(s). The said various parts and components of the said filtered exhaust assembly(s) (2530) can effectively connect and communicate with each other so that any air, gas(s), and/or substance(s) such as, but not limited to any, air/gas(s), fresh air/gas(s), heated air/gas(s), heated fresh air/gas(s), humidity, vapor(s), gas(s), aerosol(s), chemical(s), and/or deployed agent(s) (2100), can flow effectively out of the treatment chamber(s) (2026) and flow effectively into, through, and/or be exhausted out of and/or from, the said filtered exhaust assembly(s) (2530). Without being limited, the air/gas(s), fresh air/gas(s), heated air/gas(s), heated fresh air/gas(s), humidity, vapor(s), gas(s), aerosol(s), chemical(s), and/or deployed agent(s) (2100), can flow into and through the filtered exhaust assembly(s) (2530) and any of its various parts and components, at one or more of any suitable and effective, speed(s), velocity(s), quantity(s), flow rate(s), and/or cubic feet per minute(s) (CFM). Also, and without being limited, air/gas(s), fresh air/gas(s), heated air/gas(s), heated fresh air/gas(s), humidity, vapor(s), gas(s), aerosol(s), chemical(s), and/or deployed agent(s) (2100), can be both pushed and moved into and through the filtered exhaust assembly(s) (2530) with any suitable and effective pressure(s) and force(s) created by the one or more inbound blower(s) (2550) and also pulled and moved through the said filtered exhaust assembly(s) (2530) with any suitable and effective pressure(s), negative pressure(s), vacuum(s), and/or force(s), created by the one or more exhaust blower(s) (2640).

Generally, and without being limited, the filtered exhaust assembly(s) (2530) can include, and without limitation, at least one first suitable and effective filter(s), and more specifically, one or more of any suitable and effective first outlet filter(s) (2615) that can effectively filter one or more of any, air/gas(s), vapor(s), humidity(s), particle(s), and/or foreign object debris(s), that can either flow and move out of the treatment chamber(s) (2026) and/or flow and move back towards the said treatment chamber(s) (2026). In one example, and without limitation, the first outlet filter(s) (2615) can filter, trap, and/or remove, any particle(s) and/or foreign object debris(s), such as, but not limited to any, material(s), fabric particle(s), packaging material(s), packaging particle(s), lint(s), dust(s), skin particle(s), and/or hair(s), and stop or prohibit it from flowing or moving into any one or more of any other part(s) of the filtered exhaust assembly(s) (2530) such as, but not limited to, one or more of any, activated charcoal filter(s), and/or any other filter(s), further along the exhaust path out of the treatment chamber(s) (2026) and filtered exhaust assembly(s) (2530). In another and preferred example, and without limitation, the first outlet filter(s) (2615) can also filter, trap, and/or remove, any particle(s) and/or foreign object debris(s), such as, but not limited to any, filter media(s) particle(s), filter particle(s), charcoal dust or particle(s), and/or activated charcoal dust or particle(s), that can or may be released from one or more of any filter(s) in the filtered exhaust assembly(s) (2530) such as, but not limited to, one or more of any vapor absorbing outlet filter(s) (2620), that can or may flow, drift, or move, back into the treatment chamber(s) (2026) at one or more of any time(s) and for any reason(s) known to those skilled in the art.

Without being limited, the first outlet filter(s) (2615) can have one or more of any suitable and effective, performance rating(s), filter rating(s), DOP filter rating(s), MERV filter rating(s), HEPA filter rating(s), and/or ULPA filter rating(s), all in a manner known to those skilled in the art for any given use and/or application. Without being limited, the one or more first outlet filter(s) (2615) can include and/or be one or more of any suitable and effective, DOP, HEPA, and/or ULPA, rated filters, all in a manner known to those skilled in the art. It is preferred, without limitation, that the first outlet filter(s) (2615) has at least a MERV 1 or higher rating. It is more preferred, without limitation, that the first outlet filter(s) (2615) has any MERV rating between about 1 MERV to about 20 MERV. It is even more preferred, without limitation, that the first outlet filter(s) (2615) has a MERV rating between about 3 MERV to about 10 MERV. It is very preferred, without limitation, that the said first outlet filter(s) (2615) is any suitable and effective filter(s) that has a MERV rating between about 0 MERV to about 20 MERV. It is extremely preferred, without limitation, that the first outlet filter(s) (2615) is at least any suitable and effective DOP type and/or DOP rated filter, all in a manner known to those skilled in the art.

Without being limited, the first outlet filter(s) (2615) can have any suitable and effective, flow resistance, airflow resistance, airflow filter resistance, and/or air resistance, at any airflow rate, airflow speed, and/or airflow measurement in cubic feet per minute (CFM), but it is preferred, without limitation, that the said first outlet filter(s) (2615) at least has as effectively low or minimal of air resistance as possible. Also, without being limited, the said first outlet filter(s) (2615) can have any suitable and effective, length, width, height, and/or diameter, and preferably, and without limitation, a diameter and/or length, width and/or height, between about 1 inch to about 48 inch, and even more preferably, and without limitation, a diameter and/or length, width, and/or height, between about 3 inch to about 10 inch.

The filtered exhaust assembly(s) (2530) can also include, and without limitation, at least one or more of any suitable and effective second filter(s) that is located after and communicates with the first outlet filter(s) (2615), and where the said second filter(s) can include filter(s) such as, but not limited to, one or more of any suitable and effective vapor absorbing outlet filter(s) (2620), that can suitably and effectively remove one or more of any suitable and effective amount(s) of one or more of any, gas(s), vapor(s), molecule(s), deployed agent(s) (2100), and/or chemistry(s), from any air/gas(s), fresh air/gas(s), heated air/gas(s), heated fresh air/gas(s), humidity(s), vapor(s), and/or deployed agent(s) (2100), that are flowed into and through the filtered exhaust assembly(s) (2530) and into and through the said vapor absorbing outlet filter(s) (2620). It is preferred, without limitation, that the vapor absorbing outlet filter(s) (2620) is any suitable and effective activated charcoal filter(s) known to those skilled in the art. Without being limited, the vapor absorbing outlet filter(s) (2620) can be any suitable and effective design and construction known to those skilled in the art. It is also preferred, without limitation, that the one or more of any, activated charcoal(s), filter material(s), and/or filter media, that is present in the vapor absorbing outlet filter(s) (2620), is any suitable and effective filter(s) and/or filter type(s) known to those skilled in the art that can effectively remove and/or filter one or more of any desired and/or targeted amount(s) of the one or more of any, gas(s), vapor(s), molecule(s), deployed agent(s) (2100), and/or chemistry(s), from any air/gas(s), fresh air/gas(s), heated air/gas(s), heated fresh air/gas(s), humidity(s), vapor(s), and/or deployed agent(s) (2100), that are flowed into and through the filtered exhaust assembly(s) (2530) and into and through the said vapor absorbing outlet filter(s) (2620).

Without being limited, the vapor absorbing outlet filter(s) (2620) can have one or more of any suitable and effective, performance rating(s), filter rating(s), absorption performance(s), absorption property(s), absorption characteristics, DOP filter rating(s), MERV filter rating(s), HEPA filter rating(s), and/or ULPA filter rating(s), all in a manner known to those skilled in the art for any given use and/or application. Without being limited, the one or more vapor absorbing outlet filter(s) (2620) can include one or more of any suitable and effective, filter(s), filter design(s), charcoal filter(s), activated charcoal filter(s), activated carbon(s) absorbent(s), activated carbon filter(s), filter media(s), and/or filter media(s), that can suitably and effectively filter, capture, and/or absorb any suitable and effective, quantity(s), amount(s), and/or concentration(s), of one or more of any gas(s), vapor(s), molecule(s), deployed agent(s) (2100), and/or chemistry(s), from any of the air/gas(s), fresh air/gas(s), heated air/gas(s), heated fresh air/gas(s), humidity(s), vapor(s), and/or deployed agent(s) (2100), that are flowed from the treatment chamber(s) (2026) into and through the filtered exhaust assembly(s) (2530) and said vapor absorbing outlet filter(s) (2620), all in a manner known to those skilled in the art. Also, without being limited, the said vapor absorbing outlet filter(s) (2620) can also include one or more of any suitable and effective, DOP, HEPA, and/or ULPA, rated filters, all in a manner known to those skilled in the art.

Without being limited, the vapor absorbing outlet filter(s) (2620) can have any suitable and effective, flow resistance, airflow resistance, airflow filter resistance, and/or air resistance, at any airflow rate, airflow speed, and/or airflow measurement in cubic feet per minute (CFM), but it is preferred, without limitation, that the said vapor absorbing outlet filter(s) (2620) at least has as effectively low or minimal of air resistance as possible. Also, without being limited, the said vapor absorbing outlet filter(s) (2620) can have any suitable and effective, length, width, height, and/or diameter, and preferably, and without limitation, a diameter and/or length, width and/or height, between about 1 inch to about 48 inch, and even more preferably, and without limitation, a diameter and/or length, width, and/or height, between about 3 inch to about 10 inch.

Without being limited, the vapor absorbing outlet filter(s) (2620) can be designed, built, and constructed, so that any, filter material(s), filter media(s), loose fill filter media(s), charcoal, and/or activated carbon, is suitably and effectively retained in, within, inside and/or kept as a part of, the said vapor absorbing outlet filter(s) (2620), all in a manner known to those skilled in the art.

The filtered exhaust assembly(s) (2530) can also include, and without limitation, at least one or more of any suitable and effective third and fourth filter(s) that can be located after and communicates with the second and vapor absorbing outlet filter(s) (2620), and where the said third and fourth filter(s) can include filter(s) such as, but not limited to, one or more of any suitable and effective primary post absorption filter(s) (2625) and secondary post absorption filter(s) (2630), that can be any suitable and effective filter(s) and/or filter(s) type(s) known to those skilled in the art that can effectively remove and/or filter one or more of any, substance(s), particle(s), dust(s), and/or foreign object debris(s), such as, but not limited to any, charcoal dust(s), charcoal(s), filter particle(s), fabric particle(s), packaging particle(s), hair(s), skin particle(s), fiber(s), from any air/gas(s), fresh air/gas(s), heated air/gas(s), heated fresh air/gas(s), humidity(s), vapor(s), and/or deployed agent(s) (2100), that are flowed into and through the filtered exhaust assembly(s) (2530) and into and through the said primary post absorption filter(s) (2625) and secondary post absorption filter(s) (2630).

Without being limited, any air/gas(s), fresh air/gas(s), heated air/gas(s), heated fresh air/gas(s), humidity(s), vapor(s), and/or deployed agent(s) (2100) can pass through one or more of any suitable and effective third and fourth air/gas(s) filter(s) or inbound air filter(s) (2560) before being pulled, vacuumed, suctioned, blown, moved, and/or flowed, into and through the one or more primary post absorption filter(s) (2625) and secondary post absorption filter(s) (2630).

Without being limited, the primary post absorption filter(s) (2625) and secondary post absorption filter(s) (2630) can have one or more of any suitable and effective, performance rating(s), filter rating(s), filtering performance, DOP filter rating(s), MERV rating(s), HEPA rating(s), and/or ULPA rating(s), all in a manner known to those skilled in the art for any given use and/or application. Without being limited, the one or more primary post absorption filter(s) (2625) and secondary post absorption filter(s) (2630) can also include one or more of any suitable and effective, DOP, HEPA, and/or ULPA, rated filters, all in a manner known to those skilled in the art. It is preferred, without limitation, that the primary post absorption filter(s) (2625) and secondary post absorption filter(s) (2630) has at least a MERV 1 or higher rating. It is more preferred, without limitation, that the primary post absorption filter(s) (2625) and secondary post absorption filter(s) (2630) has any MERV rating between about 0.25 MERV to at least 20 MERV. It is even more preferred, without limitation, that the one or more primary post absorption filter(s) (2625) and secondary post absorption filter(s) (2630) is any suitable and/or effective HEPA filter(s) and/or ULPA filter(s).

Without being limited, the primary post absorption filter(s) (2625) and secondary post absorption filter(s) (2630) can have any suitable and effective, flow resistance, airflow resistance, airflow filter resistance, and/or air resistance, at any suitable and effective airflow rate, airflow speed, and/or airflow measurement in cubic feet per minute (CFM), but it is preferred, without limitation, that the said primary post absorption filter(s) (2625) and secondary post absorption filter(s) (2630) at least has as effectively low or minimal of flow resistance, airflow resistance, airflow filter resistance, and/or air resistance as possible. Also, without being limited, the said primary post absorption filter(s) (2625) and secondary post absorption filter(s) (2630) can have any suitable and effective, length, width, height, and/or diameter, and preferably, and without limitation, a diameter and/or length, width and/or height, between about 1 inch to about 48 inch, and even more preferably, and without limitation, a diameter and/or length, width, and/or height, between about 3 inch to about 10 inch.

Without being limited, in certain uses, situations, applications, and/or circumstances, known to those skilled in the art, only just the primary post absorption filter(s) (2625) or only just the secondary post absorption filter(s) (2630) may be needed, desired, and/or included in the design of the filtered exhaust assembly(s) (2530), to suitably and effectively filter any air/gas(s), fresh air/gas(s), heated air/gas(s), heated fresh air/gas(s), humidity(s), vapor(s), and/or deployed agent(s) (2100), before it is exhausted from and/or exits the filtered exhaust assembly(s) (2530), all in a manner known to those skilled in the art. However, in certain uses, situations, applications, and/or circumstances, known to those skilled in the art, both the primary post absorption filter(s) (2625) and secondary post absorption filter(s) (2630) may be needed and/or desired to suitably and effectively filter any air/gas(s), fresh air/gas(s), heated air/gas(s), heated fresh air/gas(s), humidity(s), vapor(s), and/or deployed agent(s) (2100), before it is exhausted from and/or exits the filtered exhaust assembly(s) (2530), all in a manner known to those skilled in the art. It is preferred, without limitation, that only the primary post absorption filter(s) (2625) is included in the construct of the filtered exhaust assembly(s) (2530) for most uses, situations, applications, and/or circumstances, all in a manner known to those skilled in the art.

After flowing, moving, and/or passing, through the one or more, first outlet filter(s) (2615), vapor absorbing outlet filter(s) (2620), primary post absorption filter(s) (2625) and/or secondary post absorption filter(s) (2630), the effectively filtered air/gas(s), fresh air/gas(s), heated air/gas(s), heated fresh air/gas(s), humidity(s), vapor(s), and/or deployed agent(s) (2100), can flow into and through one or more of any suitable and effective, fan(s), air pump(s), and/or blower(s), known to those skilled in the art, such as, but not limited to, one or more of any suitable and effective exhaust blower(s) (2640).

Without being limited, the at least one exhaust blower(s) (2640) can be any suitable and effective, fan(s), air pump(s), and/or blower(s), known to those skilled in the art, and can be located at one or more of any suitable and effective location(s). It is preferred, without limitation, that the one or more exhaust blower(s) (2640) is any suitable and effective blower(s) known to those skilled in the art, and more preferred, without limitation, is any suitable and effective fan(s) known to those skilled in the art. Without being limited, the said exhaust blower(s) (2640) can have any suitable and effective output, airflow, and/or cubic feet per minute (CFM), rating. It is preferred, without limitation, that the said exhaust blower(s) (2640) has an output and/or is rated at least at about 1 cubic feet per minute or more. It is more preferred, without limitation, that the said exhaust blower(s) (2640) has an output and/or is rated between about 5 and about 1,000 cubic feet per minute. It is even more preferred, without limitation, that the said exhaust blower(s) (2640) has an output and/or is rated between about 200 and about 700 cubic feet per minute. Without being limited, the said exhaust blower(s) (2640) can have any suitable and effective, length, width, height, and/or diameter, and preferably, and without limitation, a diameter between about 1 inch to about 24 inch, and even more preferably, and without limitation, a diameter between about 3 inch to about 8 inch.

Without limitation, the exhaust blower(s) (2640) can move and/or flow the the air/gas(s), fresh air/gas(s), heated air/gas(s), heated fresh air/gas(s), humidity, vapor(s), gas(s), aerosol(s), chemical(s), and/or deployed agent(s) (2100), and/or assist with the movement and/or flow of, the air/gas(s), fresh air/gas(s), heated air/gas(s), heated fresh air/gas(s), humidity, vapor(s), gas(s), aerosol(s), chemical(s), and/or deployed agent(s) (2100), with the assistance of the one or more inbound blower(s) (2550), into, through, within, and/or out of, various locations, parts, and components, such as, but not limited to, the filtered and heated inbound air/gas(s) assembly (2525), treatment chamber(s) (2026), and filtered exhaust assembly (2530), at any suitable and effective, speed(s), velocity(s), quantity(s) per unit of time, and/or cubic feet per minute (CFM).

It is preferred, without limitation, that the air/gas(s), fresh air/gas(s), heated air/gas(s), heated fresh air/gas(s), humidity, vapor(s), gas(s), aerosol(s), chemical(s), and/or deployed agent(s) (2100) are flowed and/or moved into, through, within, and/or out of, various locations, parts, and components, such as, but not limited to, the one or more, filtered and heated inbound air/gas(s) assembly(s) (2525), treatment chamber(s) (2026), and filtered exhaust assembly (2530), with a cubic feet per minute value or measurement that is at least suitable and effective. It is more preferred, without limitation, that the air/gas(s), fresh air/gas(s), heated air/gas (s), heated fresh air/gas(s), humidity, vapor(s), gas(s), aerosol(s), chemical(s), and/or deployed agent(s) (2100) are flowed and/or moved into, through, within, and/or out of, various locations, parts, and components, such as, but not limited to, the one or more, filtered and heated inbound air/gas(s) assembly(s) (2525), treatment chamber(s) (2026), and filtered exhaust assembly (2530), with a cubic feet per minute value or measurement of at least 2 or more cubic feet per minute (CFM). It is even more preferred, without limitation, that the air/gas(s), fresh air/gas(s), heated air/gas(s), heated fresh air/gas(s), humidity, vapor(s), gas(s), aerosol(s), chemical(s), and/or deployed agent(s) (2100) are flowed and/or moved into, through, within, and/or out of, various locations, parts, and components, such as, but not limited to, the filtered and heated inbound air/gas(s) assembly (2525), treatment chamber(s) (2026), and filtered exhaust assembly (2530), with a cubic feet per minute value or measurement between at least 10 to 950 or more cubic feet per minute (CFM). It is very preferred, without limitation, that the air/gas(s), fresh air/gas(s), heated air/gas(s), heated fresh air/gas(s), humidity, vapor(s), gas(s), aerosol(s), chemical(s), and/or deployed agent(s) (2100) are flowed and/or moved into, through, within, and/or out of, various locations, parts, and components, such as, but not limited to, the filtered and heated inbound air/gas(s) assembly (2525), treatment chamber(s) (2026), and filtered exhaust assembly (2530), with a cubic feet per minute value or measurement between at least about 10 to about 1,000 cubic feet per minute (CFM).

Without being limited, the air/gas(s), fresh air/gas(s), heated air/gas(s), heated fresh air/gas(s), humidity, vapor(s), gas(s), aerosol(s), chemical(s), and/or deployed agent(s) (2100), can flow and/or move into, through, and out of, the filtered exhaust assembly (2530) at one or more of any suitable and effective, speed(s), velocity(s), quantity(s), flow rate(s), and/or cubic feet per minute(s) (CFM).

Also, without being limited, the said air/gas(s), fresh air/gas(s), heated air/gas(s), heated fresh air/gas(s), humidity, vapor(s), gas(s), aerosol(s), chemical(s), and/or deployed agent(s) (2100), is pushed and/or pulled out of the treatment chamber(s) (2026) and enters the filtered exhaust assembly (2530) and moves or flows through at least one of any, chamber outlet(s) (2592), chamber outlet conduit(s) (2600), chamber outlet valve(s) (2605), post valve conduit(s) (2610), first outlet filter(s) (2615), vapor absorbing outlet filter(s) (2620), primary post absorption filter(s) (2625), secondary post absorption filter(s) (2630), and pre-outbound blower conduit(s) (2635), before the said air/gas(s), fresh air/gas(s), heated air/gas(s), heated fresh air/gas(s), humidity, vapor(s), gas(s), aerosol(s), chemical(s), and/or deployed agent(s) (2100) moves or flows into and through the said one or more exhaust blower(s) (2640) that is a part of and located at one or more of any suitable and effective location(s) and/or position(s) of the filtered exhaust assembly (2530), and where the said air/gas(s), fresh air/gas(s), heated air/gas(s), heated fresh air/gas(s), humidity, vapor(s), gas(s), aerosol(s), chemical(s), and/or deployed agent(s) (2100), is then blown, pushed, forced, flowed, and/or moved, with any suitable and effective, and without limitation, force(s), pressure(s), and/or positive pressure(s), created by the said exhaust blower(s) (2640), through one or more of any suitable and effective exhaust outlet filter(s) (2645).

Without being limited, the said one or more exhaust blower(s) (2640) can exert, cause, create, induce, and/or form, any suitable and effective, negative pressure(s), vacuum(s), pressure(s), and/or pulling force(s), on the filtered and heated inbound air/gas(s) assembly (2525) and/or treatment chamber(s) (2026), and more specifically, and without limitation, on any of the atmosphere(s), air/gas(s), fresh air/gas(s), heated air/gas(s), heated fresh air/gas(s), humidity, vapor(s), gas(s), aerosol(s), chemical(s), and/or deployed agent(s) (2100), present within the various space(s) and/or area(s) within the said filtered and heated inbound air/gas(s) assembly (2525) and/or treatment chamber(s) (2026), to cause and/or assist with the movement and flow of the said air/gas(s), fresh air/gas(s), heated air/gas(s), heated fresh air/gas(s), humidity, vapor(s), gas(s), aerosol(s), chemical(s), and/or deployed agent(s) (2100), through and out of the said filtered and heated inbound air/gas(s) assembly (2525) and/or treatment chamber(s) (2026), and flow into and through the said filtered exhaust assembly (2530) and finally out of the filtered exhaust assembly (2530) and into the surrounding environment (2900) and/or into the environment and/or atmosphere that surrounds the outside of the treatment cabinet(s) (2519), treatment and processing cabinet(s) (2860), and/or the cabinet outer enclosure(s) (2865).

More specifically and with reference to FIG. 113, and without limitation, the air/gas(s), fresh air/gas(s), heated air/gas(s), heated fresh air/gas(s), humidity, vapor(s), gas(s), aerosol(s), chemical(s), and/or deployed agent(s) (2100), are flowed, moved, pushed, and/or pulled, into and through the, airflow system(s) (2521), filtered and heated inbound air/gas(s) assembly (2525), treatment chamber(s) (2026), and filtered exhaust assembly (2530), with the assistance and operation of both the inbound blower(s) (2550) and exhaust blower(s) (2640). Once the air/gas(s), fresh air/gas(s), heated air/gas(s), heated fresh air/gas(s), humidity, vapor(s), gas(s), aerosol(s), chemical(s), and/or deployed agent(s) (2100) have flowed into and through the filtered exhaust assembly (2530), the air/gas(s), fresh air/gas(s), heated air/gas(s), heated fresh air/gas(s), humidity, vapor(s), gas(s), aerosol(s), chemical(s), and/or deployed agent(s) (2100) is blown, pushed, sucked, suctioned, forced, flowed, and/or moved, into and through the exhaust blower(s) (2640) and then blown, pushed, forced, flowed, and/or moved, out of the exhaust blower(s) (2640) with any suitable and effective, and without limitation, force(s), pressure(s), and/or positive pressure(s), created by the said exhaust blower(s) (2640) and/or inbound blower(s) (2550), and where the said air/gas(s), fresh air/gas(s), heated air/gas(s), heated fresh air/gas(s), humidity, vapor(s), gas(s), aerosol(s), chemical(s), and/or deployed agent(s) (2100) is blown, flowed, and/or moved, into and through one or more of any suitable and effective exhaust outlet filter(s) (2645), and finally exhausted, blown, flowed, and/or moved, out of the said exhaust outlet filter(s) (2645) and the filtered exhaust assembly (2530), and into the surrounding environment (2900) and/or into the environment and/or atmosphere that surrounds the outside of the treatment cabinet(s) (2519), treatment and processing cabinet(s) (2860), and/or the cabinet outer enclosure(s) (2865).

Without being limited, the one or more inbound blower(s) (2550) and exhaust blower(s) (2640) can operate at the same time for any suitable and effective duration of time(s) and/or at one or more of any suitable and effective different time(s) for any suitable and effective duration of time(s). It is preferred, without limitation, that both the inbound blower(s) (2550) and exhaust blower(s) (2640) operate at the same time for one or more time(s) and/or effectively about at the same time for one or more time(s), and for one or more of any suitable and effective length(s) of time(s).

Also, and without being limited, any ratio, fraction, and/or percentage, of any suitable and effective, pressure(s), air/gas(s) flow(s), positive pressure(s), negative pressure(s), and vacuum(s), that is experienced, exerted upon, and/or produced within, the airflow system(s) (2521), filtered and heated inbound air/gas(s) assembly (2525), treatment chamber(s) (2026), and filtered exhaust assembly (2530), can be established between the inbound blower(s) (2550) and the exhaust blower(s) (2640). For example, and without limitation, the flow or movement of any, air/gas(s), fresh air/gas(s), heated air/gas(s), heated fresh air/gas(s), humidity, vapor(s), gas(s), aerosol(s), chemical(s), and/or deployed agent(s) (2100), can be started, maintained, established, and/or terminated, with the operation and/or control of the inbound blower(s) (2550) and/or the exhaust blower(s) (2640). Also, without being limited, the inbound blower(s) (2550) and/or the exhaust blower(s) (2640) can have and/or share one or more of any suitable and effective ratio(s) and/or percentage(s) of any force(s), vacuum(s), and/or pressure(s), exerted and/or created to move any air/gas(s), fresh air/gas(s), heated air/gas(s), heated fresh air/gas(s), humidity, vapor(s), gas(s), aerosol(s), chemical(s), and/or deployed agent(s) (2100), into, through, and out of, the airflow system(s) (2521), filtered and heated inbound air/gas(s) assembly (2525), treatment chamber(s) (2026), and/or filtered exhaust assembly(s) (2530).

It is preferred, without limitation, that the inbound blower(s) (2550) and the exhaust blower(s) (2640) at least provide and/or create any one or more of any suitable and effective positive pressure(s) air/gas(s) flows and/or negative pressure(s) air/gas(s) flows with any suitable and effective, speed(s), velocity(s), quantity(s), flow rate(s), and/or cubic feet per minute(s) (CFM). It is more preferred, without limitation, that the inbound blower(s) (2550) and the exhaust blower(s) (2640) at least provide and/or create any one or more of any suitable and effective positive pressure(s) air/gas(s) flows and/or negative pressure(s) air/gas(s) flows with any suitable and effective, speed(s), velocity(s), quantity(s), flow rate(s), and/or cubic feet per minute(s) (CFM), and where the inbound blower(s) (2550) can at least provide and/or create any positive pressure force(s) of air/gas(s) that flow out of the said inbound blower(s) (2550) and into the treatment chamber(s) (2026) that is less than any negative pressure force(s) of air/gas(s) that are created by the exhaust blower(s) (2640) causing air/gas(s) to flow out of the treatment chamber(s) (2026). It is even more preferred, without limitation, that the inbound blower(s) (2550) and the exhaust blower(s) (2640) at least provide and/or create any one or more of any suitable and effective positive pressure(s) air/gas(s) flows and/or negative pressure(s) air/gas(s) flows with any suitable and effective, speed(s), velocity(s), quantity(s), flow rate(s), and/or cubic feet per minute(s) (CFM), and where the inbound blower(s) (2550) can at least provide and/or create any positive pressure force(s) of air/gas(s) that flow out of the said inbound blower(s) (2550) and into the treatment chamber(s) (2026) that is greater than any negative pressure force(s) of air/gas(s) that are created by the exhaust blower(s) (2640) causing air/gas(s) to flow out of the treatment chamber(s) (2026). It is very preferred, without limitation, that the inbound blower(s) (2550) and the exhaust blower(s) (2640) at least provide and/or create any one or more of any suitable and effective positive pressure(s) air/gas(s) flows and/or negative pressure(s) air/gas(s) flows with any suitable and effective, speed(s), velocity(s), quantity(s), flow rate(s), and/or cubic feet per minute(s) (CFM), and where the inbound blower(s) (2550) can at least provide and/or create any positive pressure force(s) of air/gas(s) that flow out of the said inbound blower(s) (2550) and into the treatment chamber(s) (2026) that is equal to and/or about equal to any negative pressure force(s) of air/gas(s) that are created by the exhaust blower(s) (2640) causing air/gas(s) to flow out of the treatment chamber(s) (2026). It is extremely preferred, without limitation, that the one or more of any suitable and effective inbound blower(s) (2550) provides and/or creates any one or more of any suitable and effective positive pressure(s) air/gas(s) flows into the treatment chamber(s) (2026) with any suitable and effective, speed(s), velocity(s), flow quantity(s), flow rate(s), and/or cubic feet per minute(s) (CFM), and the one or more of any suitable and effective exhaust blower(s) (2640) also provides and/or creates any one or more of any suitable and effective negative pressure(s) air/gas(s) flows out of the treatment chamber(s) (2026) and into the filtered exhaust assembly(s) (2530) with any suitable and effective, speed(s), velocity(s), flow quantity(s), flow rate(s), and/or cubic feet per minute(s) (CFM), and where the inbound blower(s) (2550) and exhaust blower(s) (2640) have the same or equal and/or have about the same or equal air/gas(s) flow output characteristics such as, but not limited to any, cubic feet per minute(s) (CFM) output(s), air/gas(s) flow quantity output(s), air/gas(s) output flow velocity(s), air/gas(s) output flow rate(s), air/gas(s) output flow speed(s).

Without being limited, the inbound blower(s) (2550) can be suitably and effectively located at one or more of any suitable and effective location(s) and/or position(s) of, in, and/or within, the filtered and heated inbound air/gas(s) assembly (2525) and/or treatment chamber(s) (2026). Also, and without limitation, the inbound blower(s) (2550) can create and/or exert any suitable and effective negative air/gas(s) pressure(s) and/or vacuum(s) to pull any air/gas(s) and/or fresh air/gas(s) from any suitable and effective location(s) such as, but not limited to, the surrounding environment (2900), the atmosphere that surrounds the outside of the treatment cabinet(s) (2519), treatment and processing cabinet(s) (2860), and/or the cabinet outer enclosure(s) (2865), and/or the outside of the filtered and heated inbound air/gas(s) assembly (2525) into the filtered and heated inbound air/gas(s) assembly (2525) and into and through the inbound blower(s) (2550). Without being limited, the inbound blower(s) (2550) can also create and/or exert any suitable and effective positive pressures and air/gas(s) flows to push the said air/gas(s) and/or fresh air/gas(s) through the filtered and heated inbound air/gas(s) assembly (2525) and into and through the treatment chamber(s) (2026) and filtered exhaust assembly (2530), as well as suitably and effectively push and/or assist the exhaust blower(s) (2640) with moving, any, air/gas(s), fresh air/gas(s), heated air/gas(s), heated fresh air/gas(s), humidity, vapor(s), gas(s), aerosol(s), chemical(s), and/or deployed agent(s) (2100), out of the treatment chamber(s) (2026) and suitably and effectively into, through, and out of, the filtered exhaust assembly(s) (2530), at one or more of any suitable and effective time(s).

Without being limited, the various parts and components of the filtered and heated inbound air/gas(s) assembly (2525), such as, but not limited to, the airflow inlet prefilter(s) (2540), inbound blower(s) (2550), inbound air filter(s) (2560), heated air/gas(s) system(s) (2568), and chamber inlet valve(s) (2585), can be positioned and/or located in one or more of any suitable and effective order(s), position(s), and/or location(s). It is preferred, without limitation, that any air/gas(s) and/or fresh air/gas(s), that flows into and then through the filtered and heated inbound air/gas(s) assembly (2525), generally and without limitation, first flows through the airflow inlet prefilter(s) (2540), then second through the inbound blower(s) (2550), then third through the inbound air filter(s) (2560), then fourth through the heated air/gas(s) system(s) (2568), then fifth through the chamber inlet valve(s) (2585), as well as through the various connecting pipes, conduits, inlet(s), and fittings (2535)(2545)(2555)(2565)(2570)(2580)(2590), known to those skilled in the art, that can suitably and effectively connect these various said parts and components. Without being limited, any one or more of suitable and effective parts of the filtered and heated inbound air/gas(s) assembly (2525) can also be suitably and effectively located and connected in the treatment chamber(s) (2026).

Also, without being limited, the exhaust blower(s) (2640) can be suitably and effectively located at one or more of any suitable and effective location(s) and/or position(s) of, in, and/or within, the filtered exhaust assembly(s) (2530) and/or treatment chamber(s) (2026). Also, and without limitation, the exhaust blower(s) (2640) can create and/or exert any suitable and effective air/gas(s) flows, negative air/gas(s) pressure(s) and/or vacuum(s) to suitably and effectively pull any air/gas(s), fresh air/gas(s), heated air/gas(s), heated fresh air/gas(s), humidity, vapor(s), gas(s), aerosol(s), chemical(s), and/or deployed agent(s) (2100) from the inside of the treatment chamber(s) (2026) and into the filtered exhaust assembly(s) (2530) and into the exhaust blower(s) (2640) that can be a part of the said filtered exhaust assembly(s) (2530). Without being limited, the said any air/gas(s), fresh air/gas(s), heated air/gas(s), heated fresh air/gas(s), humidity, vapor(s), gas(s), aerosol(s), chemical(s), and/or deployed agent(s) (2100), is pulled into the said exhaust blower(s) (2640) and is then forced out of the exhaust blower(s) (2640) creating and/or exerting any suitable and effective positive pressures and air/gas(s) flows on the back side of the said exhaust blower(s) (2640), all in a manner known to those skilled in the art, that can also suitably and effectively push the said any air/gas(s), fresh air/gas(s), heated air/gas(s), heated fresh air/gas(s), humidity, vapor(s), gas(s), aerosol(s), chemical(s), and/or deployed agent(s) (2100), through any remaining part(s) and component(s) of the filtered exhaust assembly(s) (2530), such as, but not limited to any exhaust outlet filter(s) (2645), and where the said any air/gas(s), fresh air/gas(s), heated air/gas(s), heated fresh air/gas(s), humidity(s), vapor(s), gas(s), aerosol(s), chemical(s), and/or deployed agent(s) (2100), can then flow and/or move under one or more of any suitable and effective positive pressure(s) created by either and/or both the said inbound blower(s) (2550) and exhaust blower(s) (2640), out of the said filtered exhaust assembly(s) (2530) and into the surrounding environment (2900) and/or into the environment and/or atmosphere that surrounds the outside of the treatment cabinet(s) (2519), treatment and processing cabinet(s) (2860), and/or the cabinet outer enclosure(s) (2865).

Without being limited, the various parts and components of the filtered exhaust assembly(s) (2530), such as, but not limited to, the chamber outlet valve(s) (2605), first outlet filter(s) (2615), vapor absorbing outlet filter(s) (2620), primary post absorption filter(s) (2625), secondary post absorption filter(s) (2630), exhaust blower(s) (2640), and exhaust outlet filter(s) (2645), can be positioned and/or located in one or more of any suitable and effective order(s) and/or position(s). It is preferred, without limitation, that any air/gas(s), fresh air/gas(s), heated air/gas(s), heated fresh air/gas(s), humidity(s), vapor(s), gas(s), aerosol(s), chemical(s), and/or deployed agent(s) (2100), that flows through the filtered exhaust assembly(s) (2530), generally and without limitation, first flows through the chamber outlet valve(s) (2605), then second through the first outlet filter(s) (2615), then third through the vapor absorbing outlet filter(s) (2620), then fourth through the primary post absorption filter(s) (2625), then fifth through the secondary post absorption filter(s) (2630), then sixth through the exhaust blower(s) (2640), and then seventh through the exhaust outlet filter(s) (2645), as well as through the various connecting pipes, conduits, outlet(s), and fittings (2600)(2610)(2635)(2652)(2650), known to those skilled in the art, that can suitably and effectively connect these various said parts and components. Without being limited, any one or more of suitable and effective parts of the filtered exhaust assembly(s) (2530) can also be suitably and effectively located and connected, in the treatment chamber(s) (2026).

Without being limited, after passing through the one or more of any suitable and effective exhaust blower(s) (2640), the said air/gas(s), fresh air/gas(s), heated air/gas(s), heated fresh air/gas(s), humidity(s), vapor(s), gas(s), aerosol(s), chemical(s), and/or deployed agent(s) (2100), can pass through one or more of any suitable and effective exhaust outlet filter(s) (2645) that is also a part of the filtered exhaust assembly(s) (2530), before being moved, pushed, flowed, and/or exhausted from and/or out of the filtered exhaust assembly(s) (2530) and into the surrounding environment (2900) and/or into the environment and/or atmosphere that surrounds the outside of the treatment cabinet(s) (2519), treatment and processing cabinet(s) (2860), and/or the cabinet outer enclosure(s) (2865).

Without being limited, the exhaust outlet filter(s) (2645) can have one or more of any suitable and effective, performance rating(s), filter rating(s), DOP filter rating(s), MERV filter rating(s), HEPA filter rating(s), and/or ULPA filter rating(s), all in a manner known to those skilled in the art for any given use and/or application. Without being limited, the one or more exhaust outlet filter(s) (2645) can also include and/or be one or more of any suitable and effective, DOP, HEPA, and/or ULPA, rated filters, all in a manner known to those skilled in the art. Also, and without being limited, the exhaust outlet filter(s) (2645) can be used and/or provide one or more of any suitable and effective purposes, uses, and/or functions, such as, but not limited to, providing one or more easily replaceable and/or cheaper exhaust filter(s) that can assist with keeping the exhaust blower(s) (2640) effectively and/or suitably clean.

It is preferred, without limitation, that the exhaust outlet filter(s) (2645) is at least one or more of any effective filter(s), sponge(s), and/or screen(s), material(s) that is commonly supplied with various muffin type fans in a manner known to those skilled in the art, and the said exhaust outlet filter(s) (2645) has a MERV rating between about 0 MERV to about 20 MERV. It is more preferred, without limitation, that the exhaust outlet filter(s) (2645) has at least a MERV 0.25 or higher rating. It is even more preferred, without limitation, that the exhaust outlet filter(s) (2645) has any MERV rating between about 1 MERV to about 20 MERV. It is very preferred, without limitation, that the exhaust outlet filter(s) (2645) is any suitable and effective filter that has a MERV rating between about 3 MERV to about 10 MERV.

Without being limited, the exhaust outlet filter(s) (2645) can have any suitable and effective, flow resistance, airflow resistance, airflow filter resistance, and/or air resistance, at any suitable and effective airflow rate, airflow speed, and/or airflow measurement in cubic feet per minute (CFM), but it is preferred, without limitation, that the said exhaust outlet filter(s) (2645) at least has as effectively low or minimal of flow resistance, airflow resistance, airflow filter resistance, and/or air resistance as possible. Also, without being limited, the said exhaust outlet filter(s) (2645) can have any suitable and effective, length, width, height, and/or diameter, and preferably, and without limitation, a diameter and/or length, width and/or height, between about 1 inch to about 48 inch, and even more preferably, and without limitation, a diameter and/or length, width, and/or height, between about 3 inch to about 10 inch.

Without being limited, the one or more treatment chamber(s) and/or treatment enclosure(s) (2026) can have any suitable and effective, construct(s), design(s), size(s), shape(s), geometry(s), measurement(s), dimension(s), diameter(s), length(s), width(s), height(s), area(s), and/or volume(s). It is preferred, without limitation, that at least the volume(s) and/or area(s) of the said treatment chamber(s) (2026) is at least suitable and effective. It is more preferred, without limitation, that the volume(s) and/or area(s) of the said treatment chamber(s) (2026) is at least between about 0.25 and 500,000 cubic feet.

Without being limited, the improved cabinet mounted treatment chamber processing system and/or "treatment cabinet" (2519), can include, and without limitation, at least one of any suitable and effective microcontroller(s), PLC(s), programmable logic controller(s), computer(s), and/or processor(s), (Herein called "Micro-controller(s)") (2920). Without being limited, the microcontroller(s) (2920) can be located at any one or more of any suitable and effective location(s), such as, but not limited to, at one or more of any suitable and effective location(s) inside of and/or any part of the treatment cabinet(s) (2519), any one or more of any suitable and effective location(s) of and/or related to the treatment cabinet(s) (2519), and/or any suitable and effective remote location(s), all in a manner known to those skilled in the art.

Also, without being limited, the microcontroller(s) (2920) can suitably and effectively control one or more of any parts and components of the treatment cabinet(s) (2519) and/or one or more of any parts, components, and/or hardware(s), that are directly and/or indirectly connected to and/or a part of the said treatment cabinet(s) (2519), such as, but not limited to any, inbound blower(s) (2550), heated air/gas(s) system(s) (2568) and one or more of any air/gas(s) heater(s) (2575), chamber inlet valve(s) (2585), circulation input valve(s) (2905), circulation blower(s) (2715), circulation output valve(s) (2910), deployed agent(s) inlet valve(s) (2685), agent blower(s) (2660), decontamination system(s) (2040) and any related and/or associated part(s), component(s), and/or hardware(s), deployed agent(s) outlet valve(s) (2690), chamber outlet valve(s) (2605), exhaust blower(s) (2640), one or more of any means, hardware(s), equipment(s), and/or component(s) to hold or temporarily hold one or more of any objects, one or more of any means, hardware(s), equipment(s), and/or component(s) to grip and/or temporarily grip one or more of any objects, and/or one or more of any means, hardware(s), equipment(s), and/or component(s) to package one or more of any objects.

With reference to FIGS. 113-119 and without limitation, a general example of the operation and method of the present invention and more specifically, and without limitation, the improved cabinet mounted treatment chamber processing system (2519) is given. Without limitation, the one or more treated object(s) (2300) are suitably and effectively, placed, gripped, held, supported, and/or located, within the treatment chamber(s) (2026) all in a manner known to those skilled in the art, and the one or more chamber door(s) (2036) is then effectively closed. It is preferred, without limitation, that the one or more treated object(s) (2300) are at least suitably and effectively, placed, gripped, held, supported, and/or located, inside the said treatment chamber(s) (2026) so that the various treated object(s) (2300) surfaces and/or any other surface(s) inside of the treatment chamber(s) (2026), are not shadowed during the various processing step(s) and thus preventing one or more of any surface(s) within the treatment chamber(s) (2026) and/or one or more of any surface(s) of the treated object(s) (2300) from becoming, untreated with the deployed agent(s) (2100), ineffectively treated with the deployed agent(s) (2100), ineffectively dried, and/or any ineffective removal of the deployed agent(s) (2100) from one or more of any surface(s) inside of the treatment chamber(s) (2026) and/or one or more of any surface(s) of the treated object(s) (2300) located inside of the treatment chamber(s) (2026), after one or more of any treatment cycle(s) with the deployed agent(s) (2100) and/or drying cycle(s), and/or otherwise after any processing cycle(s) are completed that are used to treat and/or dry the various surface(s) of the treated object(s) (2300) and/or any other surface(s) inside of the treatment chamber(s) (2026).

After the chamber door(s) (2036) are effectively closed, and without limitation, at least two different courses of actions can take place. Without being limited, the first and preferred course of action, is that after the treated object(s) (2300) are placed within the treatment chamber(s) (2026), the chamber door(s) (2036) are effectively closed, the machine operator starts the operation of the treatment cabinet(s) (2519), the chamber inlet valve(s) (2585) and chamber outlet valve(s) (2605) are effectively closed if they aren't already effectively closed, and the one or more processing and/or treatment cycle(s) with the deployed agent(s) (2100) begins. If needed, and without limitation, the decontamination system(s) (2040) and/or treatment agent deployment apparatus(s) (2654), is prepared for deployment of the deployed agent(s) (2100), and the deployed agent(s) (2100) are effectively deployed into the treatment chamber(s) (2026), all in a manner known to those skilled in the art.

Without being limited, the second alternative course of action includes effectively filtered, unheated air/gas(s), unheated fresh air/gas(s), heated air/gas(s), and/or heated fresh air/gas(s), and/or one or more of any suitable and effective combination(s) at one or more of any suitable and effective time(s), of the effectively filtered, unheated air/gas(s), unheated fresh air/gas(s), heated air/gas(s), and/or heated fresh air/gas(s), can be moved and/or flowed into, through, and out of, the treatment chamber(s) (2026) before any deployment of the deployed agent(s) (2100) into the treatment chamber(s) (2026). Without being limited, the flow and/or movement of any suitable and effective quantity(s) of heated and/or unheated air/gas(s) and/or fresh air/gas(s), for one or more of any suitable and effective lengths of time(s), and at one or more of any suitable and effective temperature(s), and that is effectively filtered, into, through, and then out of, the treatment chamber(s) (2026) before any movement, flow, and/or deployment, of the deployed agent(s) (2100) into the treatment chamber(s) (2026), can provide various advantages such as, but not limited to, (a) suitably and effectively drying the various surfaces inside of the treatment chamber(s) (2026) if they have one or more of any liquid(s) on them such as, but not limited to any, cleaner(s), drying agent(s), disinfectant(s), sterilant(s), sanitizer(s), water(s), moisture(s), and/or one or more of any liquid chemical residue(s) and/or chemical(s) in liquid form(s), on any of the said surface(s), (b) suitably and effectively drying the one or more of any surfaces of the one or more treated object(s) (2300) located inside of the treatment chamber(s) (2026) if they have one or more of any liquid(s) on them such as, but not limited to any, cleaner(s), drying agent(s), disinfectant(s), sterilant(s), sanitizer(s), water(s), moisture(s), and/or any one or more liquid chemical(s) residue(s) and/or chemical(s) in liquid form(s), on them, (c) suitably and effectively removing one or more of any liquid(s) such as, but not limited to any, cleaner(s), drying agent(s), disinfectant(s), sterilant(s), sanitizer(s), water(s), moisture(s), and/or any one or more liquid chemical(s) residue(s) and/or chemical(s) in liquid form(s), from any surface(s) within the treatment chamber(s) (2026) and/or one or more of any surfaces of the one or more of any treated object(s) (2300) located inside of the treatment chamber(s), (d) suitably and effectively reducing the temperature of one or more of any parts and/or surface(s) of the treated object(s) (2300) and/or any other surface(s) within the treatment chamber(s) (2026), to one or more of any suitable and effective temperature(s) before the deployed agent(s) (2100) are deployed into the said treatment chamber(s) (2026), and/or (e) removing any airborne foreign object debris and/or any unwanted airborne particles from the atmosphere and/or air/gas(s) that may be present inside of the treatment chamber(s) (2026) before any movement and/or deployment of the deployed agent(s) (2100) into the treatment chamber(s) (2026).

If the second course of action is taken to flow suitably and effectively filtered and heated and/or unheated air/gas(s) and/or fresh air/gas(s) into, through, and out of, the treatment chamber(s) (2026) before any deployment and/or movement of the deployed agent(s) (2100) into the treatment chamber(s) (2026), then the chamber inlet valve(s) (2585) and chamber outlet valve(s) (2605) can be effectively opened if they are closed, and both and/or either, the inbound blower(s) (2550) and exhaust blower(s) (2640) can be turned on and/or effectively operated and flow and/or move air/gas(s) and/or fresh air/gas(s) into and through the filtered and heated inbound air/gas(s) assembly(s) (2525) where it can be, and without limitation, suitably and effectively filtered, and optionally effectively heated if desired and/or necessary, to one or more of any suitable and effective temperature(s), and the said air/gas(s), heated air/gas(s), fresh air/gas(s), and/or heated fresh air/gas(s), then leave the filtered and heated inbound air/gas(s) assembly(s) (2525) and is flowed into, through, and out of, the treatment chamber(s) (2026) for one or more of any suitable and effective duration(s) of time(s).

More specifically, and without limitation, the said air/gas(s) and/or fresh air/gas(s) that are flowed into, through, and out of, the filtered and heated inbound air/gas(s) assembly(s) (2525), and then flowed into, through, and out of, the treatment chamber(s) (2026) for one or more of any suitable and effective purpose(s) and/or during the various steps at one or more of any suitable and effective time(s) such as, but not limited to, effectively, processing, drying, removing any liquid(s) from, removing the deployed agent(s) (2100) from, cooling, and/or reducing the temperature of, the various surface(s) within the treatment chamber(s) (2026) and/or the one or more surface(s) of the treated object(s) (2300), are sourced and/or pulled from one or more of any suitable and effective location(s) such as, but not limited to, inside of, outside of, directly from, and/or about, one or more of any suitable and effective area(s) and/or location(s) such as, but not limited to any, environment(s) and/or atmosphere(s) that are outside of the treatment chamber(s) (2026), environment(s) and/or atmosphere(s) that surrounds the outside of the treatment cabinet(s) (2519), treatment and processing cabinet(s) (2860), one or more of any suitable and effective location(s) inside of the treatment cabinet(s) (2519) and/or treatment and processing cabinet(s) (2860), surrounding environment(s) (2900), and/or any cabinet outer enclosure(s) (2865).

Also, without being limited, the said air/gas(s) and/or fresh air/gas(s) can be suitably and effectively pulled, sourced, moved, and/or flowed, into, through, and then out of, the one or more of any suitable and effective, filtered and heated inbound air/gas(s) assembly(s) (2525) by the operation of both and/or either, the one or more of any inbound blower(s) (2550) and/or exhaust blower(s) (2640), but preferably and without limitation, at least primarily and/or effectively by the operation of the one or more inbound blower(s) (2550) while the exhaust blower(s) (2640) is also simultaneously effectively operated, and where the said air/gas(s) and/or fresh air/gas(s) are preferably and without limitation, flowed through one or more of any suitable and effective, sequence(s), order(s), and/or combination(s), of the one or more of any suitable and effective part(s) and component(s) such as, but not limited to any, air/gas(s) filter(s), filter(s), blower(s), air/gas heater(s), and valve(s), of the filtered and heated inbound air/gas(s) assembly(s) (2525), such as, but not limited to, the following four examples, (a) in a first example of possible sequence(s), order(s), and/or combination(s), of various parts and components of the filtered and heated inbound air/gas(s) assembly(s) (2525), where the said air/gas(s) and/or fresh air/gas(s) can first flow into, through, and then out of, one or more of any suitable and effective first air filter(s) and/or airflow inlet prefilter(s) (2540), but preferably and without limitation, where the said airflow inlet prefilter(s) (2540) can be, without limitation, at least any suitable and effective, general airborne dust and debris filter(s), MERV rated air/gas(s) filter(s), DOP rated air/gas(s) filter(s), HEPA rated air/gas(s) filter(s), and/or ULPA rated air/gas(s) filter(s), known to those skilled in the art, and more preferably and without limitation, at least any air/gas(s) filter(s) with a MERV rating between and including about 0 to 20 MERV, and even more preferably and without limitation, at least any air/gas(s) filter(s) with a MERV rating between about 0 to 12 MERV, and where the said air/gas(s) and/or fresh air/gas(s) can then flow into, through, and then out of, one or more of any suitable and effective inbound blower(s) (2550) at and/or with, any suitable and effective, speed(s), velocity(s), quantity(s) per minute, and/or cubic feet per minute (CFM).

Without being limited, the said air/gas(s) and/or fresh air/gas(s) can then flow into, through, and then out of, one or more of any suitable and effective second air filter(s) and/or inbound air filter(s) (2560), and preferably and without limitation, where the said inbound air filter(s) (2560) can be, without limitation, any suitable and effective, MERV rated air/gas(s) filter(s), DOP rated air/gas(s) filter(s), HEPA rated air/gas(s) filter(s), and/or ULPA rated air/gas(s) filter(s), known to those skilled in the art, and more preferably and without limitation, any suitable and effective HEPA and/or ULPA rated air/gas(s) filter(s). Also, without being limited, the said air/gas(s) and/or fresh air/gas(s) can flow into, through, and then out of, the said second air filter(s) and/or inbound air filter(s) (2560) at and/or with, any suitable and effective, speed(s), velocity(s), quantity(s) per minute, and/or cubic feet per minute (CFM).

Still also, and without being limited, the said air/gas(s) and/or fresh air/gas(s) can then flow into, through, and then out of, one or more of any suitable and effective heated air/gas(s) system(s) (2568), and where the said air/gas(s) and/or fresh air/gas(s) can be heated in any suitable and effective manner and/or with one or more of any suitable and effective apparatus(s) known to those skilled in the art that can suitably and effectively heat the flow and/or movement of one or more of any air/gas(s) and/or fresh air/gas(s), such as, but not limited to, one or more of any suitable and effective heater element(s) (2575), as the said air/gas(s) and/or fresh air/gas(s) flows through the heated air/gas(s) system(s) (2568), and can be suitably and effectively heated to one or more of any suitable and effective temperature(s), when heated air/gas(s) and/or fresh air/gas(s) is needed and/or desired to be flowed into, through, and out of, the treatment chamber(s) (2026), at one or more of any suitable and effective time(s) and for any suitable and effective duration(s) of time(s) during any one or more of any step(s) such as, but not limited to, heating, drying, and/or otherwise removing the deployed agent(s) (2100) from, the one or more of any surface(s) of the one or more of any treated object(s) (2300) and/or one or more of any other surface(s) inside of the treatment chamber(s) (2026).

Also, and without being limited, the said air/gas(s), fresh air/gas(s), heated air/gas(s), and/or heated fresh air/gas(s), can then flow into, through, and then out of, one or more of any suitable and effective open chamber inlet valve(s) (2585) before the said air/gas(s) and/or fresh air/gas(s) flow and/or move into the treatment chamber(s) (2026), and where the said chamber inlet valve(s) (2585) can suitably and effectively open and close at any one or more of any suitable and effective time(s) and for any suitable and effective duration(s) of time(s), controlling the flow and movement of the said air/gas(s), fresh air/gas(s), heated air/gas(s), and/or heated fresh air/gas(s), into the treatment chamber(s), all in a manner known to those skilled in the art.

(b) in a second example of possible sequence(s), order(s), and/or combination(s), of various parts and components of the filtered and heated inbound air/gas(s) assembly(s) (2525), and without limitation, where the said air/gas(s) and/or fresh air/gas(s) can first flow into, through, and then out of, one or more of any suitable and effective first air filter(s) and/or airflow inlet prefilter(s) (2540), but preferably and without limitation, where the said airflow inlet prefilter(s) (2540) can be, without limitation, at least any suitable and effective, general airborne dust and debris filter(s), MERV rated air/gas(s) filter(s), DOP rated air/gas(s) filter(s), HEPA rated air/gas(s) filter(s), and/or ULPA rated air/gas(s) filter(s), known to those skilled in the art, and more preferably and without limitation, at least any air/gas(s) filter(s) with a MERV rating between and including about 0 to 20 MERV, and even more preferably and without limitation, at least any air/gas(s) filter(s) with a MERV rating between about 0 to 12 MERV, and where the said air/gas(s) and/or fresh air/gas(s) can then flow into, through, and then out of, one or more of any suitable and effective inbound blower(s) (2550) at and/or with, any suitable and effective, speed(s), velocity(s), quantity(s) per minute, and/or cubic feet per minute (CFM).

Without being limited, the said air/gas(s) and/or fresh air/gas(s) can then flow into, through, and then out of, one or more of any suitable and effective heated air/gas(s) system(s) (2568), where the said air/gas(s) and/or fresh air/gas(s) can be heated in any suitable and effective manner and/or with one or more of any suitable and effective apparatus(s) to heat air/gas(s) and/or moving air/gas(s), such as, but not limited to, one or more of any suitable and effective heater element(s) (2575), all in a manner known to those skilled in the art, as the said air/gas(s) and/or fresh air/gas(s) flows through the heated air/gas(s) system(s) (2568), and is heated to one or more of any suitable and effective temperature(s), when heated air/gas(s) and/or fresh air/gas(s) is needed and/or desired to be flowed into the treatment chamber(s) (2026) at one or more of any suitable and effective time(s) and for any suitable and effective duration(s) of time(s), and with any suitable and effective quantities of air/gas(s), fresh air/gas(s), heated air/gas(s), and/or heated fresh air/gas(s), during any one or more of any step(s) of heating, drying, and/or otherwise removing the deployed agent(s) (2100) from, the one or more of any surface(s) of the one or more of any treated object(s) (2300) and/or one or more of any other surface(s) inside of the treatment chamber(s) (2026).

Also, and without being limited, the said air/gas(s), fresh air/gas(s), heated air/gas(s), and/or heated fresh air/gas(s), can then flow into, through, and then out of, one or more of any suitable and effective second air filter(s) and/or inbound air filter(s) (2560), and preferably and without limitation, where the said inbound air filter(s) (2560) can be, without limitation, any suitable and effective, MERV rated air/gas(s) filter(s), DOP rated air/gas(s) filter(s), HEPA rated air/gas(s) filter(s), and/or ULPA rated air/gas(s) filter(s), known to those skilled in the art, and more preferably and without limitation, any suitable and effective HEPA and/or ULPA rated air/gas(s) filter(s). Also, without being limited, the said air/gas(s) and/or fresh air/gas(s) can flow into, through, and then out of, the said second air filter(s) and/or inbound air filter(s) (2560) at and/or with, any suitable and effective, speed(s), velocity(s), quantity(s) per minute, and/or cubic feet per minute (CFM).

Still also, and without limitation, the said air/gas(s), fresh air/gas(s), heated air/gas(s), and/or heated fresh air/gas(s), can then flow into, through, and then out of, one or more of any suitable and effective chamber inlet valve(s) (2585) before the said air/gas(s) and/or fresh air/gas(s) flow into the treatment chamber(s) (2026), and where the said chamber inlet valve(s) (2585) can suitably and effectively open and close at any one or more of any suitable and effective time(s) and for any suitable and effective duration(s) of time(s), controlling the flow and movement of the said air/gas(s), fresh air/gas(s), heated air/gas(s), and/or heated fresh air/gas(s), into the treatment chamber(s), all in a manner known to those skilled in the art.

(c) in a third example of possible sequence(s), order(s), and/or combination(s) of various parts and components of the filtered and heated inbound air/gas(s) assembly(s) (2525), and without limitation, where the said air/gas(s) and/or fresh air/gas(s) can first flow into, through, and then out of, one or more of any suitable and effective first air filter(s) and/or airflow inlet prefilter(s) (2540), and preferably and without limitation, where the said airflow inlet prefilter(s) (2540) can be, without limitation, at least any suitable and effective, general airborne dust and debris filter(s), MERV rated air/gas(s) filter(s), DOP rated air/gas(s) filter(s), HEPA rated air/gas(s) filter(s), and/or ULPA rated air/gas(s) filter(s), known to those skilled in the art, and more preferably and without limitation, at least any suitable and effective air/gas(s) filter(s) with any MERV rating between and including about 0 to 20 MERV, and even more preferably, and without limitation, at least any suitable and effective air/gas(s) filter(s) with any suitable and effective DOP rating, and even more preferably, and without limitation, at least any suitable and effective air/gas(s) filter(s) with any suitable and effective HEPA rating, and very preferably, and without limitation, at least any suitable and effective air/gas(s) filter(s) with any suitable and effective ULPA rating, and where the said air/gas(s) and/or fresh air/gas(s) can then flow into, through, and then out of, one or more of any suitable and effective inbound blower(s) (2550) at and/or with, any suitable and effective, speed(s), velocity(s), quantity(s) per minute, and/or cubic feet per minute (CFM).

Without being limited, the said air/gas(s) and/or fresh air/gas(s) can then flow into, through, and then out of, one or more of any suitable and effective heated air/gas(s) system(s) (2568), where the said air/gas(s) and/or fresh air/gas(s) can be heated in any suitable and effective manner and/or with one or more of any suitable and effective apparatus(s) known to those skilled in the art, such as, but not limited to, one or more of any suitable and effective heater element(s) (2575), as the said air/gas(s) and/or fresh air/gas(s) flows through the heated air/gas(s) system(s) (2568), and is heated to one or more of any suitable and effective temperature(s) when heated air/gas(s) and/or fresh air/gas(s) is needed and/or desired to be flowed into, through, and out of, the treatment chamber(s) (2026) at one or more of any suitable and effective time(s) and for any suitable and effective duration(s) of time(s) during any step(s) of heating, drying, and/or otherwise removing the deployed agent(s) (2100) from, the one or more of any surface(s) of the one or more of any treated object(s) (2300) and/or one or more of any other surface(s) inside of the treatment chamber(s) (2026).

Also, and without being limited, the said air/gas(s), fresh air/gas(s), heated air/gas(s), and/or heated fresh air/gas(s), can then flow into, through, and then out of, one or more of any suitable and effective chamber inlet valve(s) (2585) before the said air/gas(s) and/or fresh air/gas(s) flow into the treatment chamber(s) (2026), and where the said chamber inlet valve(s) (2585) can suitably and effectively open and close at any one or more of any suitable and effective time(s) and for any suitable and effective duration(s) of time(s), controlling the flow and movement of the said air/gas(s), fresh air/gas(s), heated air/gas(s), and/or heated fresh air/gas(s), into the treatment chamber(s), all in a manner known to those skilled in the art.

(d) in a fourth example of possible sequence(s), order(s), and/or combination(s), of various parts and components of the filtered and heated inbound air/gas(s) assembly(s) (2525), where the said air/gas(s) and/or fresh air/gas(s) can first flow into, through, and then out of, one or more of any suitable and effective first air filter(s) and/or airflow inlet prefilter(s) (2540), but preferably and without limitation, where the said airflow inlet prefilter(s) (2540) can be, without limitation, at least any suitable and effective, general airborne dust and debris filter(s), MERV rated air/gas(s) filter(s), DOP rated air/gas(s) filter(s), HEPA rated air/gas(s) filter(s), and/or ULPA rated air/gas(s) filter(s), known to those skilled in the art, and more preferably and without limitation, at least any air/gas(s) filter(s) with a MERV rating between and including about 0 to 20 MERV. However, it is even more preferred, and without limitation, that the first air filter(s) and/or airflow inlet prefilter(s) (2540) is any suitable and effective HEPA rated and/or ULPA rated air/gas(s) filter(s).

After the said air/gas(s) and/or fresh air/gas(s) pass through the first air filter(s) and/or airflow inlet prefilter(s) (2540), and without being limited, the said air/gas(s) and/or fresh air/gas(s) can then flow into, through, and then out of, one or more of any suitable and effective inbound blower(s) (2550) at and/or with, any suitable and effective, speed(s), velocity(s), quantity(s) per minute, and/or cubic feet per minute (CFM).

Also, and without being limited, the said air/gas(s) and/or fresh air/gas(s) can then flow into, through, and then out of, one or more of any suitable and effective heated air/gas(s) system(s) (2568), where the said air/gas(s) and/or fresh air/gas(s) can be heated in any suitable and effective manner and/or with one or more of any suitable and effective apparatus(s) known to those skilled in the art that can suitably and effectively heat the flow and/or movement of one or more of any air/gas(s) and/or fresh air/gas(s) flows, such as, but not limited to, one or more of any suitable and effective heater element(s) (2575), as the said air/gas(s) and/or fresh air/gas(s) flows through the heated air/gas(s) system(s) (2568), and can be suitably and effectively heated to one or more of any suitable and effective temperature(s), when heated air/gas(s) and/or fresh air/gas(s) is needed and/or desired to be flowed into the treatment chamber(s) (2026), at one or more of any suitable and effective time(s) and for any suitable and effective duration(s) of time(s) during any one or more of any step(s) such as, but not limited to, heating, drying, and/or otherwise removing the deployed agent(s) (2100) from, the one or more of any surface(s) of the one or more of any treated object(s) (2300) and/or one or more of any other surface(s) inside of the treatment chamber(s) (2026).

Also, and without being limited, the said air/gas(s), fresh air/gas(s), heated air/gas(s), and/or heated fresh air/gas(s), can then flow into, through, and then out of, one or more of any suitable and effective open chamber inlet valve(s) (2585) before the said air/gas(s) and/or fresh air/gas(s) flow into the treatment chamber(s) (2026), and where the said chamber inlet valve(s) (2585) can suitably and effectively open and close at any one or more of any suitable and effective time(s) and for any suitable and effective duration(s) of time(s), controlling the flow and movement of the said air/gas(s), fresh air/gas(s), heated air/gas(s), and/or heated fresh air/gas(s), into the treatment chamber(s), all in a manner known to those skilled in the art.

Without being limited, if any various surface(s) within the treatment chamber(s) (2026) and/or any various surface(s) of the treated object(s) (2300), exceed one or more of any suitable and effective temperature(s) before they are treated with and/or exposed to the deployed agent(s) (2100), and/or the treated object(s) (2300) are heated to any temperature(s) and then exceed one or more of any suitable and effective temperature(s) before the various surface(s) inside of the treatment chamber(s) (2026) and/or the various surface(s) of the treated object(s) (2300) are treated with and/or exposed to the deployed agent(s) (2100), they can first be cooled and/or have their surface(s) temperature(s) reduced to one or more of any suitable and effective temperature(s) by flowing effectively filtered unheated air/gas(s) and/or effectively filtered unheated fresh air/gas(s), from the filtered and heated inbound air/gas(s) assembly(s) (2525), and at one or more of any suitable and effective temperature(s) for the said air/gas(s) and/or fresh air/gas(s), into, through, and out of, the treatment chamber(s) (2026), and into, through, and out of, the filtered exhaust assembly(s) (2530), for one or more of any suitable and effective number(s) and duration(s) of time(s), and at any suitable and effective, speed(s), velocity(s), quantity(s) per minute, and/or cubic feet per minute (CFM).

Without being limited, any suitable and effective quantity of air/gas(s) and/or fresh air/gas(s) that is heated and/or unheated can be flowed into the treatment chamber(s) (2026) at any suitable and effective temperature(s) and at any suitable and effective time(s), and can be flowed into, through, and then out of, the treatment chamber(s) (2026) for one or more of any suitable and effective duration(s) of time(s), and the flow of the said heated air/gas(s), heated fresh air/gas(s), unheated air/gas(s), and/or unheated fresh air/gas(s), can be stopped and/or terminated at any suitable and effective time(s) and/or after the various surfaces within the treatment chamber(s) (2026) and/or the treated object(s) (2300) are effectively dry and/or the one or more of any deployed agent(s) (2100), liquid(s), cleaner(s), drying agent(s), disinfectant(s), sterilant(s), sanitizer(s), water(s), moisture(s), and/or any one or more of any liquid chemical residue(s) and/or chemical(s) in liquid form, on any of the surface(s) within the treatment chamber(s) (2026) and/or any surface(s) of the treated object(s) (2300) inside of the treatment chamber(s) (2026), are effectively removed from the one or more surface(s) of the treated object(s) (2300) and/or the various surface(s) within the treatment chamber(s) (2026), and/or the one or more surface(s) of the treated object(s) (2300) and/or the various surfaces within the treatment chamber(s) (2026), are effectively cooled and/or reduced in temperature(s) to any suitable and effective temperature(s), all before the treated object(s) (2300) are exposed to and/or treated with the deployed agent(s) (2100).

Also, and without being limited, after the various surfaces within the treatment chamber(s) (2026) and/or the treated object(s) (2300) surface(s) are effectively dry and/or the one or more of any deployed agent(s) (2100), liquid(s), cleaner(s), drying agent(s), disinfectant(s), sterilant(s), sanitizer(s), water(s), moisture(s), and/or any one or more of any liquid chemical residue(s) and/or chemical(s) in liquid form, on any of the surface(s) within the treatment chamber(s) (2026) and/or any surface(s) of the treated object(s) (2300) inside of the treatment chamber(s) (2026), are effectively removed from the one or more surface(s) of the treated object(s) (2300) and/or the various surface(s) within the treatment chamber(s) (2026), and/or the one or more surface(s) of the treated object(s) (2300) and/or the various surfaces within the treatment chamber(s) (2026), are effectively cooled and/or reduced in temperature(s) to any suitable and effective temperature(s), the said inbound blower(s) (2550) and exhaust blower(s) (2640) can be turned off or not operated, and the chamber inlet valve(s) (2585) and chamber outlet valve(s) (2605) can be effectively closed.

Without limitation, the efficacy and/or effectiveness of any, activity(s), action(s), method(s), and/or procedure(s), that are engaged, executed, taken, and/or carried out, such as, but not limited to, the drying and/or removal of the one or more of any deployed agent(s) (2100), liquid(s), cleaner(s), drying agent(s), disinfectant(s), sterilant(s), sanitizer(s), alcohol(s), water(s), moisture(s), and/or any one or more of any liquid chemical residue(s) and/or chemical(s) in any vapor and/or liquid form(s), on any surface(s) within the treatment chamber(s) (2026) and/or any surface(s) of the treated object(s) (2300) inside of the treatment chamber(s) (2026), as well as any cooling and/or reduction of any one or more temperature(s) of the various surfaces within the treatment chamber(s) (2026) and/or the treated object(s) (2300), at one or more of any time(s) during the operation of the improved cabinet mounted treatment chamber processing system (2519), can be sensed, detected, measured, and/or reported, by one or more of any suitable and effective sensor(s) known to those skilled in the art such as, but not limited to any, (a) air/gas(s) temperature sensor(s) (2926) that can be located at and/or communicate with, one or more of any suitable and effective location(s) inside of the treatment chamber(s) (2026) and/or any other communicating area(s) to the treatment chamber(s) (2026), and sense, monitor, and report, to one or more of any microcontroller(s) (2920), one or more of any temperature(s) of any air/gas(s) and/or atmosphere(s) inside of and/or communicating with the treatment chamber(s) (2026), (b) surface temperature sensor(s) (2929) that can be located at one or more of any suitable and effective location(s) indirectly and/or directly communicating with and/or inside of the treatment chamber(s) (2026) and/or any other communicating area(s) to the treatment chamber(s) (2026), and sense and report to one or more of any microcontroller(s) (2920), one or more of any temperature(s) of any surface(s) and/or surface(s) of any treated object(s) (2300) and/or any other surface(s) located within the treatment chamber(s) (2026) and/or communicating with the treatment chamber(s) (2026), (c) humidity sensor(s) (2927) that can be located at and/or communicate with, one or more of any suitable and effective location(s) inside of the treatment chamber(s) (2026) and/or any other communicating area(s) to the treatment chamber(s) (2026), and sense, monitor, and report, to one or more of any microcontroller(s) (2920), one or more of any humidity(s) data(s), percent humidity(s), and/or humidity level(s), that may be present in any air/gas(s) and/or atmosphere(s) inside of and/or communicating with the treatment chamber(s) (2026), and/or (d) chemical sensor(s) (2928) that can be located at and/or communicate with, one or more of any suitable and effective location(s) inside the treatment chamber(s) (2026) and/or any other communicating area(s) to the treatment chamber(s) (2026), and sense, monitor, and report, to one or more of any microcontroller(s) (2920), one or more of any humidity(s) data(s), percent humidity(s), and/or humidity level(s), that may be present in any air/gas(s) and/or atmosphere(s) inside of and/or communicating with the treatment chamber(s) (2026).

Without limitation, the various data reported and/or communicated by the various said sensor(s) (2926)(2929)(2927)(2928), can be reported and/or communicated to one or more of any suitable and effective microcontroller(s) (2920) and the various data(s) can be interpreted by the said microcontroller(s) (2920) to determine when various activity(s), action(s), method(s), and/or procedure(s), that are engaged, executed, taken, and/or carried out, such as, but not limited to, any drying and/or removal of the one or more of any deployed agent(s) (2100), liquid(s), cleaner(s), drying agent(s), disinfectant(s), sterilant(s), sanitizer(s), alcohol(s), water(s), moisture(s), and/or any one or more liquid chemical residue(s) and/or chemical(s) in any vapor and/or liquid form(s), on any surface(s) within the treatment chamber(s) (2026) and/or any surface(s) of the treated object(s) (2300) inside of the treatment chamber(s) (2026), as well as any cooling and/or reduction of any one or more temperature(s) of the various surfaces within the treatment chamber(s) (2026) and/or the treated object(s) (2300), at one or more of any time(s) during the operation of the improved cabinet mounted treatment chamber processing system (2519), are suitable and effective, and/or the outcomes and/or resultant condition(s) of these said various activity(s), action(s), method(s), and/or procedure(s), have met one or more of any preestablished criteria(s) known to those skilled in the art to be determined as suitable, effective, and/or efficacious.

Also, and without limitation, the efficacy and/or effectiveness of any cooling and/or any reduction of the temperature of any surface(s) within the treatment chamber(s) (2026) and/or any surface(s) of the treated object(s) (2300) inside of the treatment chamber(s) (2026), at any time(s), can be sensed, detected, measured, and/or reported, by one or more of any suitable and effective sensor(s) known to those skilled in the art such as, but not limited to any, (a) air/gas(s) temperature sensor(s) (2926) that can be located at and/or communicate with, one or more of any suitable and effective location(s) inside of the treatment chamber(s) (2026) and/or any other communicating area(s) to the treatment chamber(s) (2026), and sense, monitor, and report, to one or more of any microcontroller(s) (2920), one or more of any temperature(s) of any air/gas(s) and/or atmosphere(s) inside of and/or communicating with the treatment chamber(s) (2026), (b) surface temperature sensor(s) (2929) that can be located at one or more of any suitable and effective location(s) indirectly and/or directly communicating with and/or inside of the treatment chamber(s) (2026) and/or any other communicating area(s) to the treatment chamber(s) (2026), and sense and report to one or more of any microcontroller(s) (2920), one or more of any temperature(s) of any surface(s) and/or surface(s) of any treated object(s) (2300) and/or any other surface(s) located within the treatment chamber(s) (2026) and/or communicating with the treatment chamber(s) (2026).

Without being limited, after the chamber inlet valve(s) (2585) and chamber outlet valve(s) (2605) are effectively closed, if they aren't already effectively closed, the deployed agent(s) inlet valve(s) (2685) and the deployed agent(s) outlet valve(s) (2690) can be effectively opened, if they aren't already open, and the one or more deployed agent(s) (2100) are moved and/or flowed from one or more of any suitable and effective treatment agent deployment apparatus(s) (2654) and more specifically, and without limitation, the at least one of any suitable and effective decontamination system(s) (2040), and into the treatment chamber(s) (2026) for one or more of any suitable and effective number of time(s) and for one or more of any suitable and effective duration(s) of time(s). It is preferred, without limitation, that the treatment chamber(s) (2026) are at least suitably and effectively filled with the deployed agent(s) (2100) when the treatment chamber(s) (2026) is treated and/or filled with the deployed agent(s) (2100). Without being limited, the deployed agent(s) (2100) can suitably and effectively fill the treatment chamber(s) (2026) to and/or with one or more of any suitable and effective, concentration(s) of the deployed agent(s) (2100) within the treatment chamber(s) (2026), parts per million measurements of the deployed agent(s) (2100) within the treatment chamber(s) (2026), opacity of the deployed agent(s) (2100) within the treatment chamber(s) (2026), opaqueness of the deployed agent(s) (2100) within the treatment chamber(s) (2026), and/or one or more of any condition(s), method(s), and/or data(s), that can indicate that the treatment chamber(s) (2026) are suitably and effectively filled with the deployed agent(s) (2100), all in a manner known to those skilled in the art. It is more preferred, without limitation, that the one or more treatment chamber(s) (2026) are suitably and effectively completely filled with the deployed agent(s) (2100).

It is also preferred, without limitation, that the one or more decontamination system(s) (2040) and/or the one or more of any agent blower(s) (2660) that communicate with the decontamination system(s) (2040) are isolated from the treatment chamber(s) (2026) with one or more of any suitable and effective deployed agent(s) inlet valve(s) (2685) and deployed agent(s) outlet valve(s) (2690), that allow the one or more of any decontamination system(s) (2040), and also allow the one or more of any agent blower(s) (2660) if it is included in the design of the treatment agent deployment apparatus(s) (2654), to effectively communicate with the treatment chamber(s) (2026) when the deployed agent(s) inlet valve(s) (2685) and deployed agent(s) outlet valve(s) (2690) are effectively open. It is also preferred, without limitation, that the deployed agent(s) inlet valve(s) (2685) and the deployed agent(s) outlet valve(s) (2690) are effectively open when the said decontamination system(s) (2040) and/or agent blower(s) (2660) are operated, and effectively closed when the said decontamination system(s) (2040) and/or agent blower(s) (2660) are not operated.

However, and without limitation, the said deployed agent(s) inlet valve(s) (2685) and deployed agent(s) outlet valve(s) (2690) can also be effectively open during the deployment and/or movement of the deployed agent(s) (2100) into the treatment chamber(s) (2026) and also during any movements of any air/gas(s), heated air/gas(s), fresh air/gas(s), and/or heated air/gas(s), into, through, and out of, the treatment chamber(s) (2026) for purposes such as, but not limited to, effectively drying the various surface(s) of the treatment agent deployment apparatus(s) (2654) that communicate with the treatment chamber(s) (2026), effectively removing the deployed agent(s) (2100) from various targeted surface(s) of the treatment agent deployment apparatus(s) (2654) that communicate with the treatment chamber(s) (2026), removing the deployed agent(s) (2100) from inside of the treatment chamber(s) (2026), drying the various surface(s) and treated object(s) (2300) surface(s) inside of the treatment chamber(s) (2026), and/or removing the deployed agent(s) (2100) from the various surface(s) and treated object(s) (2300) surface(s) located within the treatment chamber(s) (2026), and then the said deployed agent(s) inlet valve(s) (2685) and deployed agent(s) outlet valve(s) (2690) can then suitably and effectively close at any suitable and effective time(s) and/or step(s).

Alternatively, and without limitation, the deployed agent(s) inlet valve(s) (2685) and deployed agent(s) outlet valve(s) (2690) can also not be included in the design and construction of the improved cabinet mounted treatment chamber processing system (2519) and its treatment agent deployment apparatus(s) (2654). For example, and without being limited, in various situations known to those skilled in the art, the one or more of any, location(s), emitter(s), part(s), component(s), and/or area(s), where the deployed agent(s) are emitted into the treatment chamber(s) (2026), such as, but not limited to one or more of any, nozzle(s), aerosol output nozzle(s), aerosol generating nozzle(s), output orifice(s), and/or tube opening(s), that are a part of the one or more decontamination system(s) (2040), can also interface with, indirectly communicate with, and/or directly communicate with, one or more of any suitable and effective area(s) and/or location(s) inside of the treatment chamber(s) and/or any one or more connecting area(s) with the treatment chamber(s), all in a manner known to those skilled in the art.

However, and without limitation, the deployed agent(s) inlet valve(s) (2685) and deployed agent(s) outlet valve(s) (2690) can be included in the design of the improved cabinet mounted treatment chamber processing system (2519) and can at least remain effectively open at one or more of any suitable and effective time(s) and for any suitable and effective duration(s) of time(s), and/or the said deployed agent(s) inlet valve(s) (2685) and deployed agent(s) outlet valve(s) (2690) can also at least be closed at one or more of any suitable and effective time(s) and for any suitable and effective duration(s) of time(s) for various other operations such as, but not limited to, spraying, jetting, and/or immersing, the one or more treated object(s) (2300) with one or more of any suitable and effective cleaning agent(s) and/or deployed agent(s) (2100) that are in any suitable and effective liquid form(s) known to those skilled in the art, flooding the treatment chamber(s) (2026) to any suitable and effective depth(s) with one or more of any suitable and effective cleaning solution(s), cleaning enzyme(s) in liquid solution(s), cleaning liquid(s), and/or deployed agent(s) (2100) in liquid form(s), all in a manner known to those skilled in the art, that can be used for any suitable uses and/or operations such as, but not limited to any, cleaning, soaking, sanitizing, disinfecting, high level disinfecting, and/or sterilizing, the various surface(s) of the said treated object(s) (2300) and/or any other surface(s) inside of the said treatment chamber(s) (2026), before they are suitably and effectively dried, cooled, and/or then treated with any suitable and effective airborne deployed agent(s) (2100) as taught in the current invention.

Without being limited, the deployed and/or emitted airborne deployed agent(s) (2100) that are located inside of the said treatment chamber(s) (2026) can be suitably and effectively stirred, mixed, and/or homogenized, within the said treatment chamber(s) (2026) at one or more of any suitable and effective time(s), for any suitable and effective number of time(s), and for one or more of any suitable and effective duration(s) of time(s), using one or more of any suitable and effective means such as, but not limited to any, fan(s), blower(s), air pump(s), and/or chamber circulation apparatus(s)) (2695). It is preferred, without limitation that at least one chamber circulation apparatus(s) (2695) and/or circulation blower(s) (2715) effectively communicates with the one or more treatment chamber(s) (2026), and is effectively operated to effectively, stir, mix, move, disrupt, and/or homogenize, the deployed agent(s) (2100) within the said treatment chamber(s) (2026). In addition, and without limitation, the deployed agent(s) (2100) can be suitably and effectively stirred, mixed, disrupted, moved, and/or homogenized, within the said treatment chamber(s) (2026) when one or more of any amount(s) and/or quantity(s) of the said deployed agent(s) (2100) has been deployed, moved, and/or flowed into the said treatment chamber(s) (2026). For example, and without limitation, the air/gas(s) and/or atmosphere(s) within the treatment chamber(s) (2026) can be disrupted, stirred, moved, mixed, and/or homogenized, first when between about 0.25 percent to about 50 percent of the internal area and/or internal volume of and/or inside of the treatment chamber(s) (2026) is filled with the deployed agent(s) (2100), and then the air/gas(s) and/or atmosphere(s) within the treatment chamber(s) (2026) can be disrupted, stirred, mixed, moved, and/or homogenized again, when between about 50 percent to about 100 percent of the internal area and/or internal volume of and/or inside of the treatment chamber(s) (2026) is filled with the deployed agent(s) (2100), and then any one or more suitable and effective number of time(s) after.

Without being limited, the circulation blower(s) (2715) can operate for one or more time(s) and for any suitable and effective duration(s) of time(s). It is preferred, without limitation, that the circulation blower(s) (2715) are operated and suitably and effectively stir, mix, move, and/or homogenize, the deployed agent(s) (2100) within the said treatment chamber(s) (2026) for at least about 0.10 second to about 30 minutes, each time they are energized and/or operated. It is more preferred, without limitation, that the circulation blower(s) (2715) are operated and suitably and effectively stir, mix, move, and/or homogenize, the deployed agent(s) (2100) within the said treatment chamber(s) (2026) for at least about 0.25 second to about 60 seconds each time they are energized and/or operated. It is even more preferred, without limitation, that the circulation blower(s) (2715) are operated and suitably and effectively stir, mix, move, and/or homogenize, the deployed agent(s) (2100) within the said treatment chamber(s) (2026) for at least about 1 seconds to about 30 seconds each time they are energized and/or operated. It is very preferred, without limitation, that the circulation blower(s) (2715) are operated and suitably and effectively stir, mix, move, and/or homogenize, the deployed agent(s) (2100) within the said treatment chamber(s) (2026) for at least about 1 seconds to about 8 seconds each time they are energized and/or operated.

Without being limited, any output from the one or more chamber circulation apparatus(s) (2695) and/or circulation blower(s) (2715) can flow, move, and/or exit, out of one or more of any suitable and effective, orifice(s), outlet(s), and/or circulation outlet(s) (2705), and into and/or on one or more of any suitable and effective location(s) inside of the treatment chamber(s) (2026). Also, and without being limited, the one or more said circulation outlet(s) (2705) can be one or more of any suitable and effective, length, width, height, shape, angle, number, and/or geometry, and can be suitably and effectively angled in one or more of any direction(s) and/or angle(s) and/or have any suitable and effective angled outlet(s). Without being limited, the one or more circulation outlet(s) (2705) can suitably and effectively communicate with the treatment chamber(s) (2026) and/or one or more of any effective communicating area(s).

It is preferred, without limitation, that the circulation outlet(s) (2705) are suitably and effectively interfaced with and/or located inside of, the treatment chamber(s) (2026) and are also suitably and effectively located suitably and effectively close to the chamber floor(s) (2885) and the output of the one or more of any substance(s) from the said chamber circulation apparatus(s) (2695) and/or circulation blower(s) (2715) such as, but not limited to any, deployed agent(s) (2100), air/gas(s), fresh air/gas(s), heated air/gas(s), and/or heated fresh air/gas(s), is suitably and effectively directed at, along, and/or about horizontally along, the chamber floor(s) (2885) inside of the treatment chamber(s) (2026) at one or more of any suitable and effective, temperature(s), speed(s), velocity(s), and/or cubic feet per minute (CFM) value(s). Without being limited, the operation of the one or more chamber circulation apparatus(s) (2695) and/or circulation blower(s) (2715) while air/gas(s), fresh air/gas(s), heated air/gas(s), and/or heated fresh air/gas(s), is flowed into, through, and out of, the treatment chamber(s) (2026) can also assist with the removal of the deployed agent(s) (2100) from the various surface(s) inside of the treatment chamber(s) (2026) and/or the drying of various surface(s) within the treatment chamber(s) such as, but not limited to any, chamber floor(s) (2885) inside of the treatment chamber(s) (2026), various surface(s) within the treatment chamber(s) (2026), and/or any surface(s) of the treated object(s) (2300).

Without being limited, the one or more chamber circulation apparatus(s) (2695) and/or any one or more of any circulation blower(s) (2715) can be isolated from the treatment chamber(s) (2026) with one or more of any suitable and effective circulation input valve(s) (2905) and circulation output valve(s) (2910), and the said valves can control the connection and/or communication of the one or more of any chamber circulation apparatus(s) (2695) and/or circulation blower(s) (2715) with the said treatment chamber(s) (2026), by suitably and effectively opening and closing the said valve(s) (2905) (2910). It is also preferred, without limitation, that the circulation input valve(s) (2905) and circulation output valve(s) (2910) are effectively open when the one or more of any chamber circulation apparatus(s) (2695) and/or the one or more of any circulation blower(s) (2715) are operated, and effectively closed when the one or more of any chamber circulation apparatus(s) (2695) and/or the one or more of any circulation blower(s) (2715) are not operated.

Further, is also preferred, without limitation, that the circulation input valve(s) (2905) and circulation output valve(s) (2910) are effectively open and the circulation blower(s) (2715) are at least effectively operated, effectively operated continuously, and/or effectively operated non-stop, when both the chamber inlet valve(s) (2585) and chamber outlet valve(s) (2605) are open and either and/or both the inbound blower(s) (2550) and/or exhaust blower(s) (2640)

are operated. Without being limited, the operation of the circulation blower(s) (2715) while both the chamber inlet valve(s) (2585) and chamber outlet valve(s) (2605) are effectively open and either and/or both the inbound blower(s) (2550) and/or exhaust blower(s) (2640) are operated, can increase the performance of various activities such as, but not limited to, effectively reducing the time to reduce and/or dry the deployed agent(s) (2100) from the various surface(s) inside of the treatment chamber(s) (2026) and/or the various surface(s) of the various treated object(s) (2300) located inside of the treatment chamber(s), drying and/or removing any liquid(s) and/or deployed agent(s) (2100) from the one or more floor(s) (2885) inside of the treatment chamber(s) (2026).

It is also preferred, without being limited, that the one or more circulation blower(s) (2715) are suitably and effectively operated when both the one or more circulation input valve(s) (2905) and the one or more circulation output valve(s) (2910) are effectively open, and both the one or more chamber inlet valve(s) (2585) and the one or more chamber outlet valve(s) (2605) are effectively open, and either and/or both the one or more inbound blower(s) (2550) and/or one or more exhaust blower(s) (2640) are effectively operated, for purposes such as, but not limited to, (a) removing, reducing, and/or purging, any deployed agent(s) (2100) from the inside of the treatment chamber(s) (2026) to any suitable and effective, measurement(s), level(s), concentration(s), and/or parts per million (PPM), known to those skilled in the art, (b) drying, reducing, and/or removing, the deployed agent(s) (2100) and/or any other liquid(s) and/or substance(s) from the various surface(s) inside of the treatment chamber(s) (2026) and/or one or more of any area(s) that may communicate with the treatment chamber(s) (2026) to any suitable and effective, measurement(s), level(s), concentration(s), and/or parts per million (PPM), known to those skilled in the art, (c) drying, reducing, and/or removing, any deployed agent(s) (2100) and/or any other liquid(s) and/or substance(s) from the various surface(s) of any treated object(s) (2300) located inside of the treatment chamber(s) (2026) to any suitable and effective, measurement(s), level(s), concentration(s), and/or parts per million (PPM), known to those skilled in the art, (d) cooling and/or reducing the temperature(s) of the various surface(s) located inside of the treatment chamber(s) (2026) and/or one or more of any area(s) that may communicate with the treatment chamber(s) (2026) to one or more of any suitable and effective, measurement(s), level(s), and/or temperature(s), known to those skilled in the art, (e) cooling and/or reducing the temperature(s) of the various surface(s) of any treated object(s) (2300) located inside of the treatment chamber(s) (2026) to one or more of any suitable and effective, measurement(s), level(s), and/or temperature(s), known to those skilled in the art.

Alternatively, and without limitation, the circulation input valve(s) (2905) and circulation output valve(s) (2910) can also not be included in the design and construction of the improved cabinet mounted treatment chamber processing system (2519) and its chamber circulation apparatus(s) (2695) for purposes such as, but not limited to, simplifying the design and complexity of the chamber circulation apparatus(s) (2695). Without being limited, the one or more agent blower(s) (2660) and their accompanying deployed agent(s) inlet valve(s) (2685) and deployed agent(s) outlet valve(s) (2690) can also replace the purpose and functionality of the one or more circulation blower(s) (2715) and the accompanying circulation input valve(s) (2905) and circulation output valve(s) (2910).

However, it is preferred, without limitation, that the circulation blower(s) (2715), the circulation input valve(s) (2905), and the circulation output valve(s) (2910), are included in the design of the improved cabinet mounted treatment chamber processing system (2519) and can at least remain effectively open at least at one or more of any suitable and effective time(s) and for any suitable and effective duration(s) of time(s). Without being limited, the various valves such as, but not limited to the, circulation input valve(s) (2905), circulation output valve(s) (2910), deployed agent(s) inlet valve(s) (2685), and deployed agent(s) outlet valve(s) (2690), can also at least be closed at one or more of any suitable and effective time(s) and for any suitable and effective duration(s) of time(s) for various other operations and/or purposes such as, but not limited to, spraying, jetting, and/or immersing, the one or more treated object(s) (2300) with one or more of any suitable and effective cleaning agent(s) and/or deployed agent(s) (2100) that are in any suitable and effective liquid form(s) known to those skilled in the art, flooding the treatment chamber(s) (2026) to any suitable and effective depth(s) with one or more of any suitable and effective cleaning solution(s), cleaning enzyme(s) in liquid solution(s), cleaning liquid(s), and/or deployed agent(s) (2100) in liquid form(s), all in a manner known to those skilled in the art, that can be used for any suitable uses and/or operations such as, but not limited to any, cleaning, soaking, sanitizing, disinfecting, high level disinfecting, and/or sterilizing, of the various surface(s) of the said treated object(s) (2300) and/or any other surface(s) inside of the said treatment chamber(s) (2026), before they are suitably and effectively dried and/or then treated with any airborne deployed agent(s) (2100) as taught in the current invention.

Without limitation, after the treated object(s) (2300) are effectively exposed to and/or treated with one or more of any suitable and effective amount(s), quantity(s), and/or concentration(s), of the deployed agent(s) (2100), the flow of the deployed agent(s) (2100) into the treatment chamber(s) (2026) is stopped and/or terminated, and one or more of any dwell time(s) and stirring and/or homogenizing of the deployed agent(s) (2100) activities can take place within the said treatment chamber(s) (2026) for any suitable and effective number(s) and duration(s) of time(s). Alternatively, and without limitation, the treatment chamber(s) (2026) are suitably and effectively filled with the deployed agent(s) (2100), the flow of the deployed agent(s) (2100) into the treatment chamber(s) (2026) is stopped and/or terminated, and one or more of any steps and/or activities such as, but not limited to any, dwell time(s), and/or stirring, mixing, and/or homogenizing, of the deployed agent(s) (2100), can take place within the said treatment chamber(s) (2026) for any suitable and effective number(s) and duration(s) of time(s).

Without being limited, the said stirring, mixing, and/or homogenizing of the deployed agent(s) (2100) activities can also occur for one or more of any suitable and effective number(s) and duration(s) of time(s) while the deployed agent(s) (2100) are flowed and/or moved into the treatment chamber(s) (2026). Without being limited, the deployed agent(s) (2100) can also be suitably and effectively stirred, mixed, moved, and/or homogenized, inside of the treatment chamber(s) (2026) one or more time(s) during any one or more dwell time(s) or one or more time(s) the flow and/or movement of the deployed agent(s) (2100) into the treatment chamber(s) (2026) is stopped and the deployed agent(s) (2100) are given one or more of any suitable and effective time(s) and any suitable and effective duration(s) of time(s)

to be present inside of the treatment chamber(s) and suitably and effectively, interact with, interface with, and/or act upon, the various surface(s) within the treatment chamber(s) (2026) and/or the one or more surface(s) of the treated object(s) (2300).

Without being limited, the deployed agent(s) (2100) can be deployed and/or moved into the one or more treatment chamber(s) (2026) one or more of any suitable and effective number(s) and duration(s) of time(s) during the operation of the improved cabinet mounted treatment chamber processing system (2519), to effectively treat the various surfaces inside of the treatment chamber(s) (2026) and effectively treat the various surface(s) of the treated object(s) (2300), and can all be determined in a manner known to those skilled in the art.

Still also, and without being limited, the one or more of any suitable and effective dwell time(s) that can be used and/or employed, can have any suitable and effective length(s) and/or duration(s) of time(s). Without being limited, the dwell time(s) can also include, and without limitation, any suitable and effective pause(s) in any deployment(s) of the deployed agent(s) (2100) into the treatment chamber(s) (2026), and any pause(s) of flowing any air/gas(s), fresh air/gas(s), heated air/gas(s), and/or heated fresh air/gas(s), into, through, and out of, the treatment chamber(s). However, and without limitation, one or more of any effective additional deployment(s) of any deployed agent(s) (2100) for any suitable and effective number(s) and duration(s) of time(s) can also occur during any dwell time(s). Without being limited, the dwell time(s) can be used for various purposes known to those skilled in the art, such as, but not limited to, effectively exposing the various surface(s) inside of the treatment chamber(s) to the deployed agent(s) (2100) for any suitable and effective duration(s) of time(s). It is preferred, without limitation, that each one or more dwell time(s) is between about 0 minutes to about 60 minutes in duration(s). It is more preferred, without limitation, that the dwell time(s) is between about 2 seconds to about 10 minutes in duration(s). It is even more preferred, without limitation, that the dwell time(s) is between about 30 seconds to about 7 minutes in duration(s). Without limitation, the duration(s) and number(s) of the one or more effective dwell time(s) can be determined all in a manner known to those skilled in the art.

Without being limited, the effective treatment and/or exposure of the various surface(s) inside the treatment chamber(s) (2026) and/or any of the various surface(s) of the treated object(s) (2300), to and/or with the deployed agent(s) (2100), at one or more of any suitable and effective time(s) during the operation of the improved cabinet mounted treatment chamber processing system (2519), can be sensed, measured, monitored, recorded, and/or reported, by one or more of any suitable and effective sensor(s) such as, but not limited to any, air/gas(s) temperature sensor(s) (2926), surface temperature sensor(s) (2929), humidity sensor(s) (2927), and/or chemical sensor(s) (2928), and reported to one or more of any suitable and effective microcontroller(s) (2920), all in a manner known to those skilled in the art.

For example, and without limitation, effectively filling the treatment chamber(s) (2026) with the deployed agent(s) (2100) can be sensed by one or more of any suitable and effective air/gas(s) temperature sensor(s) (2926) and/or surface temperature sensor(s) (2929), effectively located in and/or communicating with the treatment chamber(s) (2026) and can be indicated by one or more of any suitable and effective data(s) that is reported such as, but not limited to any, change(s) in one or more of any temperature(s) sensed inside of the treatment chamber(s) and/or any communicating area(s), temperature value(s) sensed inside of the treatment chamber(s) (2026) and/or any communicating area(s), and/or increase(s) and/or decrease(s) and/or then leveling off of any temperature(s) to one or more of any suitable and effective temperature(s) sensed inside of the treatment chamber(s) and/or any communicating area(s).

In another example, and without limitation, effectively filling the treatment chamber(s) (2026) with the deployed agent(s) (2100) can be sensed by one or more of any suitable and effective humidity sensor(s) (2927) effectively located in and/or communicating with the treatment chamber(s) (2026) and can be indicated by one or more of any suitable and effective data(s) that is reported such as, but not limited to any, change(s) in one or more of any humidity level(s) and/or relative humidity data(s) sensed inside of the treatment chamber(s) and/or any communicating area(s), humidity value(s) sensed inside of the treatment chamber(s) (2026) and/or any communicating area(s), and/or increase(s) and/or decrease(s) and then leveling off of any humidity level(s) and/or relative humidity data(s) to one or more of any suitable and effective humidity level(s) and/or relative humidity data(s) sensed inside of the treatment chamber(s) and/or any communicating area(s).

In still another example, and without limitation, effectively filling the treatment chamber(s) (2026) with the deployed agent(s) (2100) can be sensed by one or more of any effective chemical sensor(s) (2928) effectively located in and/or communicating with the treatment chamber(s) (2026) and can be indicated by one or more of any suitable and effective data(s) that is reported such as, but not limited to any, change(s) in one or more of any chemical concentration(s) sensed inside of the treatment chamber(s) and/or any communicating area(s), chemical concentration value(s) sensed inside of the treatment chamber(s) (2026) and/or any communicating area(s), and/or any increase(s) and then leveling off of any chemical concentration(s) to one or more of any suitable and effective chemical concentration(s) sensed inside of the treatment chamber(s) and/or any communicating area(s).

In still even another example, and without limitation, effectively filling the treatment chamber(s) (2026) with the deployed agent(s) (2100) can be sensed by one or more of any suitable and effective optical sensor(s) (not shown), known to those skilled in the art, and effectively located in and/or communicating with the treatment chamber(s) (2026), and where the various signal(s) sent from the said optical sensor(s) (not shown) can be interpreted by one or more microcontroller(s) (2920) to determine when the treatment chamber(s) (2026) are suitably and effectively filled with the deployed agent(s) (2100), all in a manner known to those skilled in the art.

In addition, and without limitation, various one or more, order(s), number(s), and/or combination(s), of various steps, processing steps, and/or various actions, taken during any one or more entire processing cycle(s) for the improved cabinet mounted treatment chamber processing system (2519) can include, and without limitation, effectively deploying the deployed agent(s) (2100) into the treatment chamber(s) (2026) one or more time(s) and for any effective duration(s) of time(s), effectively stirring and/or homogenizing the deployed agent(s) (2100) inside of the treatment chamber(s) (2026) with the chamber circulation apparatus(s) (2695) one or more time(s) and for any effective duration(s) of time(s), allowing the deployed agent(s) (2100) that are moved into the treatment chamber(s) (2026) to effectively dwell for one or more time(s) and for any effective duration(s) of time(s), and effectively drying and/or effectively removing the deployed agent(s) (2100) from the various surfaces inside of the treatment chamber(s) (2026) and/or any of the various surface(s) of the treated object(s) (2300) one or more time(s) and for any effective duration(s) of time(s).

Without limitation, after the flow and/or movement of the deployed agent(s) (2100) into the treatment chamber(s) (2026) is stopped and/or terminated, and any dwell time(s) have elapsed and/or finished, and the various steps taken to treat the various surface(s) of the treated object(s) (2300) is suitably and effectively complete, the one or more chamber inlet valve(s) (2585) and chamber outlet valve(s) (2605) can be effectively opened, and both the one or more inbound blower(s) (2550) and one or more exhaust blower(s) (2640) can be turned on and/or effectively operated, preferably and without limitation, at about the same time, but at least at any suitable and effective time(s). Also, and without being limited, air/gas(s) and/or fresh air/gas(s) are pulled into the filtered and heated inbound air/gas(s) assembly (2525) where the said air/gas(s) and/or fresh air/gas(s) can be effectively filtered one or more times, but preferably and without limitation, suitably and effectively filtered with at least two different filter(s), with at least any suitable and effective first filter(s) such as, but not limited to any, airflow inlet prefilter(s) (2540) and at least any suitable and effective second filter(s) such as, but not limited to any, inbound air filter(s) (2560), using any suitable and effective filter(s) known to those skilled in the art, and then preferably, and without limitation. Without being limited, the said air/gas(s) and/or fresh air/gas(s) are effectively heated to one or more of any suitable and effective temperature(s), before being pushed by at least the said inbound blower(s) (2550) and preferably, and without limitation, also pulled by the said exhaust blower(s) (2640), past the said chamber inlet valve(s) (2585) and into, through, and out of the said treatment chamber(s) (2026). It is also preferred, without limitation, that the air/gas(s) and/or fresh air/gas(s) are suitably and effectively filtered by at least one high efficiency and/or HEPA rated filter(s) (2560) before being moved and/or flowed into the said treatment chamber(s) (2026). Without being limited, the suitable and effective operation of both the one or more inbound blower(s) (2550) and the one or more exhaust blower(s) (2640), suitably and effectively moves the air/gas(s), fresh air/gas(s), heated air/gas(s), and/or heated fresh air/gas(s), into, through, and out of, the one or more treatment chamber(s) (2026). Without being limited, a more detailed description of filtering and heating the air/gas(s) and/or fresh air/gas(s) before they are moved into the treatment chamber(s) (2026) is given both above and further below in greater detail.

It is preferred, without limitation, that the suitable and effective operation of both the one or more inbound blower(s) (2550) and the one or more exhaust blower(s) (2640), can suitably and effectively move the air/gas(s), fresh air/gas(s), heated air/gas(s), and/or heated fresh air/gas(s), into, through, and out of, various parts and components such as, but not limited to, the one or more of any suitable and effective filtered and heated inbound air/gas(s) assembly(s) (2525), the one or more of any suitable and effective treatment chamber(s) (2026), and the one or more of any suitable and effective filtered exhaust assembly(s) (2530), at one or more of any suitable and effective time(s) during one or more of any suitable and effective steps of operating the improved cabinet mounted treatment chamber processing system (2519).

Also, and without being limited, any quantity of the effectively heated and filtered air/gas(s) and/or fresh air/gas(s) can be moved into, through, and out of, the said treatment chamber(s) (2026) at one or more of any suitable and effective, temperature(s), speed(s), velocity(s), cubic feet per minute (CFM) value(s), and for any suitable and effective length(s) of time(s) and number of time(s), to suitably and effectively dry and/or remove the one or more deployed agent(s) from the various surface(s) located inside of the treatment chamber(s) and/or the one or more surface(s) of the one or more treated object(s) (2300) that may be located in the treatment chamber(s) (2026), at one or more of any suitable and effective time(s) and for one or more of any suitable and effective number of time(s), during the operation of the improved cabinet mounted treatment chamber processing system (2519). It is preferred, without limitation, that one or more of any suitable and effective flow(s) and/or supply(s) of effectively filtered air/gas(s) and/or fresh air/gas(s) that can be suitably and effectively heated to one or more of any suitable and effective temperature(s) at one or more of any suitable and effective time(s), is moved and/or flowed into, through, and out of, the treatment chamber(s) (2026) for purposes such as, but not limited to, suitably and effectively removing and/or reducing the deployed agent(s) from the various surface(s) located within and/or communicating with the treatment chamber(s) (2026), suitably and effectively removing and/or reducing the deployed agent(s) from the various surface(s) of the treated object(s) (2300) located within the treatment chamber(s) (2026), suitably and effectively removing and/or reducing the deployed agent(s) from the air/gas(s) and/or atmosphere(s) located within and/or communicating with the treatment chamber(s) (2026), at one or more of any suitable and effective time(s) during any suitable and effective steps of operating the improved cabinet mounted treatment chamber processing system (2519), but at least after the treated object(s) (2300) have been suitable and effectively exposed to and treated with the deployed agent(s) (2100).

Without being limited, the surface temperature(s), air/gas(s) temperature(s), humidity(s), water vapor concentration(s), and/or chemical concentration(s), of and/or measured within, the air/gas(s) and/or atmosphere(s) inside of the treatment chamber(s) (2026), and/or the one or more of any surface(s) located inside the treatment chamber(s) and/or one or more of any surface(s) of the treated object(s) (2300) located within the treatment chamber(s) (2026), can be suitably and effectively sensed, monitored, and reported, at one or more of any suitable and effective time(s) and for any suitable and effective number(s) of time(s), with one or more of any suitable and effective sensor(s), such as, but not limited to any suitable and effective, air/gas(s) temperature sensor(s) (2926), surface temperature sensor(s) (2929), humidity sensor(s) (2927), chemical sensor(s) (2928), all in a manner known to those skilled in the art, and reported to one or more of any suitable and effective microcontroller(s) (2920) also in a manner known to those skilled in the art, during one or more of any step(s) and/or part(s) of any operation(s) of and/or any partial operation(s) of the improved cabinet mounted treatment chamber processing system (2519) and any parts of any steps and/or procedures taken in any parts of any processing cycle(s) to effectively process various location(s), surface(s), air/gas(s), and/or area(s), inside of the treatment chamber(s) and/or any communicating area(s) such as, but not limited to any, atmosphere(s) and/or air/gas(s) within the treatment chamber(s) (2026), various surface(s) within the treatment chamber(s), and/or any treated object(s) (2300) surface(s) located inside of the treatment chamber(s) (2026) such as, but not limited to any, surface(s) treatment step(s) and/or operation(s) used to treat any surface(s) and/or treated object(s) (2300) surface(s) inside of any treatment chamber(s) (2026) with any deployed agent(s) (2100), step(s) and/or operation(s) for the removal of any deployed agent(s) (2100) from any surface(s) located inside of the treatment chamber(s) (2026) and/or any treated object (2300) surface(s) within any treatment chamber(s) (2026), surface(s) drying step(s) and/or operation(s), step(s) for the stirring, mixing, and/or homogenizing the air/gas(s) and/or deployed agent(s) (2100) inside of the treatment chamber(s) (2026), airflow step(s) and/or operation(s) where any air/gas(s), heated air/gas(s), fresh air/gas(s), and/or heated fresh air/gas(s), is flowed into, through, and out of the treatment chamber(s) (2026).

Without limitation, the temperature(s) of any, air/gas(s), atmosphere(s), various surface(s), and/or surface(s) of any treated object(s) (2300), located inside of the the treatment chamber(s) (2026) and/or in any one or more area(s) that communicate with the treatment chamber(s) (2026), can also be suitably and effectively, sensed, monitored, and reported, in a manner known to those skilled in the art, by one or more of any suitable and effective air/gas(s) temperature sensor(s) (2926) that can sense and report any temperature(s) of any air/gas(s) and/or atmosphere(s) inside of and/or communicating with the treatment chamber(s) (2026), and/or by one or more of any surface temperature sensor(s) (2929) that can sense the temperature(s) of any surface(s) and/or surface(s) of any treated object(s) (2300) located within the treatment chamber(s) (2026) and/or in any communicating area(s), and reported to one or more of any suitable and effective microcontroller(s) (2920), and can be used for various purposes such as, but not limited to, (a) determining and/or sensing if or when any suitable and effective quantity(s) and/or concentration(s) of the deployed agent(s) (2100) is flowed and/or moved into the treatment chamber(s) (2026), (b) determining and/or sensing if or when the treatment chamber(s) (2026) is effectively filled with any suitable and effective quantity(s) and/or concentration(s) of the deployed agent(s) (2100) that is flowed and/or moved into the treatment chamber(s) (2026), (c) determining and/or sensing if or when the treatment chamber(s) (2026) are suitably and effectively purged of the deployed agent(s) (2100), (d) determining and/or sensing if or when the deployed agent(s) (2100) are suitably and effectively removed from the various surface(s) inside of the treatment chamber(s) (2026) and/or the one or more surface(s) of the one or more treated object(s) (2300) that may be located in the treatment chamber(s) (2026), (e) determining and/or sensing if or when the said various surface(s) inside of the treatment chamber(s) and/or the various treated object(s) (2300) surface(s) are suitably and effectively dry, (f) determining and/or sensing if or when the deployed agent(s) (2100) are suitably and effectively removed and/or reduced from the air/gas(s) and/or atmosphere(s) located inside of the treatment chamber(s) (2026), (g) determining and/or sensing if or when the deployed agent(s) (2100) are suitably and effectively removed and/or reduced from the air/gas(s) and/or atmosphere(s) located inside of the treatment chamber(s) (2026) indicating that the deployed agent(s) (2100) are suitably and effectively removed and/or reduced from various location(s) within the treatment chamber(s) (2026) such as, but not limited to any, one or more of any surface(s) within the treatment chamber(s) (2026), one or more of any surface(s) of any treated object(s) (2300), and/or any air/gas(s) and/or atmosphere(s) located inside of the treatment chamber(s) (2026), (h) determining and/or sensing if or when the heated air/gas(s) and/or heated fresh air/gas(s) are at and/or maintained at any suitable and effective temperature(s), (i) determining and/or sensing if or when any effective quantity(s) of air/gas(s), fresh air/gas(s), heated air/gas(s), and/or heated fresh air/gas(s), is flowed and/or moved into, through, and out of, the treatment chamber(s) (2026), (j) determining and/or sensing if or when it is time to stop heating the air/gas(s) and/or fresh air/gas(s) that are moved and/or flowed into, through, and out of the treatment chamber(s) (2026), and start cooling, if necessary, the various surface(s) and/or the various treated object (2300) surface(s) located within the treatment chamber(s) (2026), (k) determining and/or sensing if or when the various surface(s) and/or various treated object (2300) surface(s) located within the treatment chamber(s) (2026) are effectively cooled, effectively reduced in temperature, and/or effectively maintained at any suitable and effective temperature(s), (l) determining and/or sensing if or when the air/gas(s) and/or fresh air/gas(s) that are moved into, through, and out of, the treatment chamber(s) (2026), are effectively cooled and/or reduced to any suitable and effective temperature(s) to suitably and effectively cool and/or reduce the temperature(s) of the various surface(s) within the treatment chamber(s) and/or the surface(s) of the one or more treated object(s) (2300) located inside of the treatment chamber(s) (2026), to any suitable and effective temperature(s), and (m) determining and/or sensing if or when any unheated air/gas(s) and/or fresh air/gas(s) that are moved into, through, and out of, the treatment chamber(s) (2026), have suitably and effectively cooled and/or reduced in temperature(s) the various surface(s) within the treatment chamber(s) and/or the one or more surface(s) of the one or more treated object(s) (2300) located inside of the treatment chamber(s) (2026) to one or more of any suitable and effective temperature(s).

In addition, and without limitation, the humidity(s), relative humidity(s), water vapor content(s), and/or moisture level(s), sensed within any air/gas(s) and/or atmosphere(s) located inside of the treatment chamber(s) (2026) and/or in one or more of any area(s) that communicate with the treatment chamber(s) (2026), can also be suitably and effectively, sensed, monitored, and reported, in a manner known to those skilled in the art, by one or more of any suitable and effective humidity sensor(s) (2927) located in or at any suitable and effective location(s) within the treatment chamber(s) (2026) and/or in any communicating area(s), and reported to one or more of any suitable and effective microcontroller(s) (2920), and can be used for various purposes such as, but not limited to, (a) determining and/or sensing if or when any suitable and effective quantity(s) and/or concentration(s) of the deployed agent(s) (2100) is flowed and/or moved into the treatment chamber(s) (2026), (b) determining and/or sensing if or when the treatment chamber(s) (2026) is effectively filled with any suitable and effective quantity(s) and/or concentration(s) of the deployed agent(s) (2100) that is flowed and/or moved into the treatment chamber(s) (2026), (c) determining and/or sensing if or when the treatment chamber(s) (2026) are suitably and effectively purged and/or removed of the deployed agent(s) (2100), (d) determining and/or sensing if or when the deployed agent(s) (2100) are suitably and effectively removed from the various surface(s) inside of the treatment chamber(s) (2026) and/or the one or more surface(s) of the one or more treated object(s) (2300) that may be located in the treatment chamber(s) (2026), (e) determining and/or sensing if or when the said various surface(s) inside of the treatment chamber(s) and/or the various treated object(s)

(2300) surface(s) are suitably and effectively dry, (f) determining and/or sensing if or when the deployed agent(s) (2100) are suitably and effectively removed and/or reduced from the air/gas(s) and/or atmosphere(s) located inside of the treatment chamber(s) (2026), (g) determining and/or sensing if or when the deployed agent(s) (2100) are suitably and effectively removed and/or reduced from the air/gas(s) and/or atmosphere(s) located inside of the treatment chamber(s) (2026) indicating that the deployed agent(s) (2100) are suitably and effectively removed and/or reduced from various location(s) within the treatment chamber(s) (2026) such as, but not limited to any, one or more of any surface(s) within the treatment chamber(s) (2026), one or more of any surface(s) of any treated object(s) (2300), and/or any air/gas(s) and/or atmosphere(s) located inside of the treatment chamber(s) (2026), (h) determining and/or sensing if or when the heated air/gas(s) and/or heated fresh air/gas(s) are at and/or maintained at any suitable and effective temperature(s), (i) determining and/or sensing if or when any effective quantity(s) of air/gas(s), fresh air/gas(s), heated air/gas(s), and/or heated fresh air/gas(s), is flowed and/or moved into, through, and out of, the treatment chamber(s) (2026), (j) determining and/or sensing if or when it is time to stop heating the air/gas(s) and/or fresh air/gas(s) that are moved and/or flowed into, through, and out of the treatment chamber(s) (2026), and start cooling, if necessary, the various surface(s) and/or the various treated object (2300) surface(s) located within the treatment chamber(s) (2026), and (k) determining and/or sensing if or when the various surface(s) and/or various treated object (2300) surface(s) located within the treatment chamber(s) (2026) are effectively cooled, effectively reduced in temperature, and/or effectively maintained at any suitable and effective temperature(s).

Further, and without limitation, the one or more of any, chemical concentration(s) of the deployed agent(s) (2100) and/or the parts per million (PPM) measurement(s) of the deployed agent(s) (2100), of or within any air/gas(s) and/or atmosphere(s) inside of the treatment chamber(s) (2026) and/or in any one or more area(s) that communicate with the treatment chamber(s) (2026), can also be suitably and effectively, sensed, monitored, and reported, in a manner known to those skilled in the art, by one or more of any suitable and effective chemical sensor(s) (2928), located in or at any suitable and effective location(s) within the treatment chamber(s) (2026) and/or in any communicating area(s), and reported to one or more of any suitable and effective microcontroller(s) (2920), and used for various purposes such as, but not limited to, (a) determining and/or sensing if or when any suitable and effective quantity(s) and/or concentration(s) of the deployed agent(s) (2100) is flowed and/or moved into the treatment chamber(s) (2026), (b) determining and/or sensing if or when the treatment chamber(s) (2026) is effectively filled with any suitable and effective quantity(s) and/or concentration(s) of the deployed agent(s) (2100) that is flowed and/or moved into the treatment chamber(s) (2026), (c) determining and/or sensing if or when the treatment chamber(s) (2026) are suitably and effectively purged of the deployed agent(s) (2100), (d) determining and/or sensing if or when the deployed agent(s) (2100) are suitably and effectively removed from the various surface(s) inside of the treatment chamber(s) (2026) and/or the one or more surface(s) of the one or more treated object(s) (2300) that may be located in the treatment chamber(s) (2026), (e) determining and/or sensing if or when the said various surface(s) inside of the treatment chamber(s) and/or the various treated object(s) (2300) surface(s) are suitably and effectively dry, (f) determining and/or sensing if or when the deployed agent(s) (2100) are suitably and effectively removed and/or reduced from the air/gas(s) and/or atmosphere(s) located inside of the treatment chamber(s) (2026), (g) determining and/or sensing if or when the deployed agent(s) (2100) are suitably and effectively removed and/or reduced from the air/gas(s) and/or atmosphere(s) located inside of the treatment chamber(s) (2026) indicating that the deployed agent(s) (2100) are suitably and effectively removed and/or reduced from various location(s) within the treatment chamber(s) (2026) such as, but not limited to any, one or more of any surface(s) within the treatment chamber(s) (2026), one or more of any surface(s) of any treated object(s) (2300), and/or any air/gas(s) and/or atmosphere(s) located inside of the treatment chamber(s) (2026), (h) determining and/or sensing if or when the heated air/gas(s) and/or heated fresh air/gas(s) are at and/or maintained at any suitable and effective temperature(s), (i) determining and/or sensing if or when any effective quantity(s) of air/gas(s), fresh air/gas(s), heated air/gas(s), and/or heated fresh air/gas(s), is flowed and/or moved into, through, and out of, the treatment chamber(s) (2026), (j) determining and/or sensing if or when it is time to stop heating the air/gas(s) and/or fresh air/gas(s) that are moved and/or flowed into, through, and out of the treatment chamber(s) (2026), and start cooling, if necessary, the various surface(s) and/or the various treated object (2300) surface(s) located within the treatment chamber(s) (2026), and (k) determining and/or sensing if or when the various surface(s) and/or various treated object (2300) surface(s) located within the treatment chamber(s) (2026) are effectively cooled, effectively reduced in temperature, and/or effectively maintained at any suitable and effective temperature(s).

It is preferred, without limitation, that after the various surface(s) within the treatment chamber(s) (2026) and/or any various surface(s) of the treated object(s) (2300) located in the treatment chamber(s) (2026) are effectively treated with the deployed agent(s) (2100), effectively filtered air/gas(s) and/or fresh air/gas(s), are at least moved into, through, and out of, the treatment chamber(s) (2026) until the various surface(s) within the treatment chamber(s) (2026) and/or any various surface(s) of the treated object(s) (2300) located in the treatment chamber(s) (2026), are at least suitably and effectively dry and/or the said deployed agent(s) (2100) are effectively and suitably reduced and/or removed from the various surface(s) and/or any targeted surface(s) of the said treated object(s) (2300) and/or from inside of the treatment chamber(s) (2026).

However, it is more preferred, without limitation, that after the various surface(s) within the treatment chamber(s) (2026) and/or any various surface(s) of the treated object(s) (2300) located in the treatment chamber(s) (2026) are effectively treated with the deployed agent(s) (2100), effectively filtered and effectively heated air/gas(s) and/or fresh air/gas(s), are at least moved into, through, and out of, the treatment chamber(s) (2026) until the various surface(s) within the treatment chamber(s) (2026) and/or any various surface(s) of the treated object(s) (2300) located in the treatment chamber(s) (2026), are at least suitably and effectively dry and/or the said deployed agent(s) (2100) are effectively and suitably reduced and/or removed from the various surface(s) and/or any targeted surface(s) of the said treated object(s) (2300) and/or from inside of the treatment chamber(s) (2026).

Without being limited, the effective drying of the various surface(s) within the treatment chamber(s) (2026) and/or any various surface(s) of the treated object(s) (2300) located in the treatment chamber(s) (2026), and/or the effective and suitable reduction and/or removal of the deployed agent(s) (2100) from the various surface(s) within the treatment chamber(s) (2026) and/or any various surface(s) of the treated object(s) (2300) located in the treatment chamber(s) (2026), at one or more of any suitable and effective time(s) during the operation of the improved cabinet mounted treatment chamber processing system (2519), can be can be sensed, measured, monitored, recorded, and/or reported, by one or more of any suitable and effective sensor(s) such as, but not limited to any, air/gas(s) temperature sensor(s) (2926), surface temperature sensor(s) (2929), humidity sensor(s) (2927), and/or chemical sensor(s) (2928), and reported to one or more of any suitable and effective microcontroller(s) (2920), all in a manner known to those skilled in the art.

For example, and without limitation, the effective drying of the various surface(s) within the treatment chamber(s) (2026) and/or any various surface(s) of the treated object(s) (2300) located in the treatment chamber(s) (2026), and/or the effective and suitable reduction and/or removal of the deployed agent(s) (2100) from the various surface(s) within the treatment chamber(s) (2026) and/or any various surface(s) of the treated object(s) (2300) located in the treatment chamber(s) (2026) can be sensed by one or more of any suitable and effective air/gas(s) temperature sensor(s) (2926) effectively located in and/or communicating with the treatment chamber(s) (2026) and can be indicated by one or more of any suitable and effective data(s) that is reported such as, but not limited to any, change(s) in one or more of any air/gas(s) temperature(s) sensed inside of the treatment chamber(s) and/or any communicating area(s), effective increase(s) in temperature(s) to one or more of any suitable and effective temperature(s) sensed inside of the treatment chamber(s) and/or any communicating area(s), and/or any increase(s) in temperature(s) and then leveling off of the said temperature(s) to one or more of any suitable and effective temperature(s) sensed inside of the treatment chamber(s) and/or any communicating area(s).

In another example, and without limitation, the effective drying of the various surface(s) within the treatment chamber(s) (2026) and/or any various surface(s) of the treated object(s) (2300) located in the treatment chamber(s) (2026), and/or the effective and suitable reduction and/or removal of the deployed agent(s) (2100) from the various surface(s) within the treatment chamber(s) (2026) and/or any various surface(s) of the treated object(s) (2300) located in the treatment chamber(s) (2026) can be sensed by one or more of any suitable and effective surface temperature sensor(s) (2929) effectively located in and/or communicating with the treatment chamber(s) (2026) and can be indicated by one or more of any suitable and effective data(s) that is reported such as, but not limited to any, change(s) in one or more of any surface(s) temperature(s) sensed inside of the treatment chamber(s) and/or any communicating area(s), increase(s) in the measured surface(s) temperature(s) to one or more of any suitable and effective temperature(s) sensed inside of the treatment chamber(s) and/or any communicating area(s), and/or any increase(s) in the measured surface(s) temperature(s) and then leveling off of the said temperature(s) to one or more of any suitable and effective temperature(s) sensed inside of the treatment chamber(s) and/or any communicating area(s).

In still another example, and without limitation, the effective drying of the various surface(s) within the treatment chamber(s) (2026) and/or any various surface(s) of the treated object(s) (2300) located in the treatment chamber(s) (2026), and/or the effective and suitable reduction and/or removal of the deployed agent(s) (2100) from the various surface(s) within the treatment chamber(s) (2026) and/or any various surface(s) of the treated object(s) (2300) located in the treatment chamber(s) (2026) can be sensed by one or more of any suitable and effective humidity sensor(s) (2927) effectively located in and/or communicating with the treatment chamber(s) (2026) and can be indicated by one or more of any suitable and effective data(s) that is reported such as, but not limited to any, change(s) in one or more of any measured, humidity level(s), relative humidity(s), and/or humidity data(s) sensed inside of the treatment chamber(s) and/or any communicating area(s), effective decrease(s) in the measured, humidity level(s), relative humidity(s), and/or humidity data(s), to one or more of any suitable and effective humidity level(s), relative humidity(s), humidity data(s), sensed inside of the treatment chamber(s) and/or any communicating area(s), and/or any decrease(s) in the measured humidity level(s), relative humidity(s), and/or humidity data(s), and then leveling off of the said humidity level(s), relative humidity(s), and/or humidity data(s) to one or more of any suitable and effective humidity level(s), relative humidity(s), humidity data(s), sensed inside of the treatment chamber(s) and/or any communicating area(s).

In still even another example, and without limitation, the effective drying of the various surface(s) within the treatment chamber(s) (2026) and/or any various surface(s) of the treated object(s) (2300) located in the treatment chamber(s) (2026), and/or the effective and suitable reduction and/or removal of the deployed agent(s) (2100) from the the various surface(s) within the treatment chamber(s) (2026) and/or any various surface(s) of the treated object(s) (2300) located in the treatment chamber(s) (2026) can be sensed by one or more of any suitable and effective chemical sensor(s) (2928) effectively located in and/or communicating with the treatment chamber(s) (2026) and can be indicated by one or more of any suitable and effective data(s) that is reported such as, but not limited to any, change(s) in one or more of any chemical concentration(s) sensed inside of the treatment chamber(s) and/or any communicating area(s), decrease(s) in any measured chemical concentration(s) sensed inside of the treatment chamber(s) and/or any communicating area(s) to one or more of any suitable and effective chemical concentration(s), and/or any decrease(s) in the measured chemical concentration(s) and then leveling off of the said chemical concentration(s) to one or more of any suitable and effective chemical concentration(s), sensed inside of the treatment chamber(s) and/or any communicating area(s).

In addition, and without limitation, various variables and data(s) and one or more of any suitable and effective combination(s) of various variable(s) and data(s) such as, but not limited to any, amount(s) and/or quantity(s) of the deployed agent(s) (2100) moved, deployed, and/or flowed, into the treatment chamber(s) (2026) at any time(s), concentration(s) and/or parts-per-million data(s) of the deployed agent(s) (2100) located inside of the treatment chamber(s) (2026) during its deployment and/or after being deployed into the treatment chamber(s) (2026), relative humidity of the air/gas(s) and/or atmosphere(s) inside of the treatment chamber(s) (2026) during and/or after the deployment of the deployed agent(s) (2100) into the said treatment chamber(s) (2026), temperature(s) of the air/gas(s) and/or atmosphere(s) inside of the treatment chamber(s) (2026) during and/or after the deployment of the deployed agent(s) (2100) into the said treatment chamber(s) (2026), temperature(s) and/or relative humidity(s) of the air/gas(s), heated air/gas(s), heated fresh air/gas(s), and/or fresh air/gas(s), that are flowed into, through, and/or out of, the treatment chamber(s) (2026) at any time(s) but at least during and/or after any drying and/or removal of the deployed agent(s) process(s), any duration(s) of time(s) used for flowing any deployed agent(s) (2100) into the treatment chamber(s) (2026), as well as any number and duration(s) of time(s) used for flowing any unheated and/or heated air/gas(s) and/or fresh air/gas(s) into, through, and/or and out of various locations such as, but not limited to any, treatment chamber(s) (2026), filtered and heated inbound air/gas(s) assembly(s) (2525), and/or filtered exhaust assembly(s) (2530), at any time(s), can be used in any suitable and effective combination(s) and with any suitable and effective value(s) to establish and/or set one or more of any suitable and effective operating parameters and/or operating algorithms that can be tested, established, and proven, in a manner known to those skilled in the art, and used to deliver and/or provide any suitable and effective performance(s) and outcome(s) considering various operational scenarios that may be encountered.

Without limitation, after the said treated object(s) (2300) are at least suitably and effectively dry and/or the said deployed agent(s) (2100) are suitably and effectively reduced and/or removed from the various surface(s) within the treatment chamber(s) (2026) and/or any various surface(s) of the treated object(s) (2300) located in the treatment chamber(s) (2026), the flow and/or movement of any filtered and heated air/gas(s) and/or fresh air/gas(s), into, through, and out of, location(s) such as, but not limited to any, treatment chamber(s) (2026), filtered and heated inbound air/gas(s) assembly(s) (2525), and/or filtered exhaust assembly(s) (2530), can be stopped, and various one or more of any suitable and effective additional step(s) and/or action(s) can be taken, such as, but not limited to, (a) in a first example, and without limitation, after the flow of the heated air/gas(s) and/or heated fresh air/gas(s) into the treatment chamber(s) (2026) is stopped, both the inbound blower(s) (2550) and the exhaust blower(s) (2640) can be shut down, and the circulation input valve(s) (2905), circulation output valve(s) (2910), deployed agent(s) inlet valve(s) (2685), and deployed agent(s) outlet valve(s) (2690) can be in any effectively open position(s), and the chamber inlet valve(s) (2585) and chamber outlet valve(s) (2605) can also be left effectively open, and the one or more treated object(s) (2300) can be removed and/or retrieved by the machine operator(s) at any suitable and effective time(s), (b) in a second example, and without limitation, after the flow of the heated air/gas(s) and/or heated fresh air/gas(s) into the treatment chamber(s) (2026) is stopped, both the inbound blower(s) (2550) and the exhaust blower(s) (2640) can be shut down, and the circulation input valve(s) (2905), circulation output valve(s) (2910), deployed agent(s) inlet valve(s) (2685), and deployed agent(s) outlet valve(s) (2690) can be in any effectively closed position(s), and the chamber inlet valve(s) (2585) and chamber outlet valve(s) (2605) can also be in any effectively closed position, and the one or more treated object(s) (2300) can be removed and/or retrieved by the machine operator at any suitable and effective time(s), (c) in a third example, and without limitation, after the flow of the heated air/gas(s) and/or heated fresh air/gas(s) into the treatment chamber(s) (2026) is stopped, both the inbound blower(s) (2550) and the exhaust blower(s) (2640) can be shut down, and the circulation input valve(s) (2905) and circulation output valve(s) (2910) can be in any effectively closed position(s), however the deployed agent(s) inlet valve(s) (2685), deployed agent(s) outlet valve(s) (2690), chamber inlet valve(s) (2585), and chamber outlet valve(s) (2605), can be in any effectively open position(s), and the one or more treated object(s) (2300) can be removed and/or retrieved by the machine operator at any suitable and effective time(s), (d) in a fourth example, and without limitation, after the flow of the heated air/gas(s) and/or heated fresh air/gas(s) into the treatment chamber(s) (2026) is stopped, the circulation input valve(s) (2905), circulation output valve(s) (2910), can be in any effectively closed position(s), and the deployed agent(s) inlet valve(s) (2685), deployed agent(s) outlet valve(s) (2690), chamber inlet valve(s) (2585), and chamber outlet valve(s) (2605), can be in any effectively open position(s), and the one or more inbound blower(s) (2550) and/or the one or more exhaust blower(s) (2640), but preferably, and without limitation both the inbound blower(s) (2550) and the exhaust blower(s) (2640), can be effectively operated and suitably and effectively move unheated and effectively filtered air/gas(s) and/or fresh air/gas(s) into, through, and out of, the treatment chamber(s) (2026) until the treated object(s) (2300) are removed and/or retrieved by the machine operator at any suitable and effective time(s) or at least until the one or more door(s) (2036) that access the treatment chamber(s) (2026) are opened and then closed, (e) in a fifth example, and without limitation, after the flow of the heated air/gas(s) and/or heated fresh air/gas(s) into the treatment chamber(s) (2026) is stopped, the circulation input valve(s) (2905), circulation output valve(s) (2910), deployed agent(s) inlet valve(s) (2685), and deployed agent(s) outlet valve(s) (2690) can be in any effectively open position(s), and the chamber inlet valve(s) (2585) and chamber outlet valve(s) (2605) can also be in an effectively open position(s), and the one or more inbound blower(s) (2550) and/or the one or more exhaust blower(s) (2640), but preferably, and without limitation both the inbound blower(s) (2550) and the exhaust blower(s) (2640), can be operated and suitably and effectively move unheated and effectively filtered air/gas(s) and/or fresh air/gas(s) into, through, and out of, the treatment chamber(s) (2026) until the treated object(s) (2300) are removed and/or retrieved by the machine operator at any suitable and effective time(s) or at least until the one or more door(s) (2036) that access the treatment chamber(s) (2026) are opened and then closed, (f) in a sixth example, and without limitation, after the flow of the heated air/gas(s) and/or heated fresh air/gas(s) into the treatment chamber(s) (2026) is stopped, the circulation input valve(s) (2905), circulation output valve(s) (2910), deployed agent(s) inlet valve(s) (2685), and deployed agent(s) outlet valve(s) (2690) can be in any effectively closed position(s), and the chamber inlet valve(s) (2585) and chamber outlet valve(s) (2605) can be in an effectively open position(s), and the one or more inbound blower(s) (2550) and/or the one or more exhaust blower(s) (2640), but preferably, and without limitation both the inbound blower(s) (2550) and the exhaust blower(s) (2640), can be operated and suitably and effectively move unheated and effectively filtered air/gas(s) and/or fresh air/gas(s) into, through, and out of, the treatment chamber(s) (2026) at least until the various surface(s) within the treatment chamber(s) (2026) and/or any of the one or more surface(s) of the treated object(s) (2300) located in the treatment chamber(s) (2026), are effectively cooled and/or the temperature(s) of any of the various said surface(s) are reduced to any suitable and effective temperature(s), (g) in a seventh example, and without limitation, after the flow of the heated air/gas(s) and/or heated fresh air/gas(s) into the treatment chamber(s) (2026) is stopped, the circulation input valve(s) (2905), circulation output valve(s)

(2910), deployed agent(s) inlet valve(s) (2685), and deployed agent(s) outlet valve(s) (2690) can be in any effectively open position(s), and the chamber inlet valve(s) (2585) and chamber outlet valve(s) (2605) can also be in any effectively open position(s), and the one or more inbound blower(s) (2550) and/or the one or more exhaust blower(s) (2640), but preferably, and without limitation both the inbound blower(s) (2550) and the exhaust blower(s) (2640), can be operated and suitably and effectively move unheated and effectively filtered air/gas(s) and/or fresh air/gas(s) into, through, and out of, the treatment chamber(s) (2026) at least until the various surface(s) within the treatment chamber(s) (2026) and/or any various surface(s) of the treated object(s) (2300) located in the treatment chamber(s) (2026), are effectively cooled and/or the temperature(s) of any of the various said surface(s) are reduced to any suitable and effective temperature(s).

Without being limited, after the temperature(s) of the air/gas(s) and/or atmosphere(s) within the treatment chamber(s) are increased to and then maintained at one or more of any suitable and effective temperature(s) for any one or more of any suitable and effective duration(s) of time(s), and/or the said treated object(s) (2300) are at least suitably and effectively dry, and/or the said deployed agent(s) (2100) are suitably and effectively reduced and/or removed from the various surface(s) within the treatment chamber(s) (2026) and/or any various surface(s) of the treated object(s) (2300) located in the treatment chamber(s) (2026), the flow and/or movement of any heated air/gas(s) and/or heated fresh air/gas(s), into, through, and out of, the said treatment chamber(s) (2026), can be stopped, and any suitable and effective quantity of unheated air/gas(s) and/or unheated fresh air/gas(s), at one or more of any suitable and effective temperature(s) can be moved into, through, and out of, the treatment chamber(s) (2026), for various purposes such as, but not limited to, effectively cooling and/or effectively reducing the temperature(s) of the various surface(s) within the treatment chamber(s) (2026) and/or any various surface(s) of the treated object(s) (2300) located in the treatment chamber(s) (2026), to one or more of any suitable and effective temperature(s). Without being limited, the said unheated air/gas(s) and/or unheated fresh air/gas(s) can flow into, through, and out of, the treatment chamber(s) (2026), for one or more of any suitable and effective duration(s) of time(s), and at any suitable and effective, speed(s), velocity(s), quantity(s) per minute, and/or cubic feet per minute (CFM).

It is preferred, without limitation, that the unheated and effectively filtered air/gas(s) and/or fresh air/gas(s), is moved and/or flowed into, through, and out of, the treatment chamber(s) (2026) at least until the temperature(s) of the various surface(s) within the treatment chamber(s) (2026) and/or any various surface(s) of the treated object(s) (2300) located in the treatment chamber(s) (2026), are suitably and effectively cooled and/or reduced to any suitable and effective temperature(s), after the steps to move any heated air/gas(s) and/or heated fresh air/gas(s) are completed. It is also preferred, without limitation, that the one or more treated object(s) (2300) are not removed from the treatment chamber(s) (2026) until their various surface(s) are at least at, about, and/or below, any suitable and effective temperature(s) and/or temperature range(s), any maximum established temperature(s), and/or any maximum allowed temperature(s), known to those skilled in the art.

Without being limited, the temperature(s) of the various surface(s) within the treatment chamber(s) (2026) and/or any various surface(s) of the treated object(s) (2300) located in the treatment chamber(s) (2026), can also be sensed, measured, monitored, recorded, and/or reported, during any of the said step(s), action(s), and/or method(s), to effectively cool and/or reduce the temperature(s) of the various surface(s) within the treatment chamber(s) (2026) and/or any various surface(s) of the treated object(s) (2300) located in the treatment chamber(s) (2026), by one or more of any suitable and effective sensor(s) such as, but not limited to any, air/gas(s) temperature sensor(s) (2926), surface temperature sensor(s) (2929), and reported to one or more of any suitable and effective microcontroller(s) (2920), all in a manner known to those skilled in the art.

Alternatively, and without being limited, after the said flow and/or movement of any heated air/gas(s) and/or heated fresh air/gas(s), into, through, and out of, the said treatment chamber(s) (2026), is stopped, any suitable and effective quantity(s) of unheated air/gas(s) and/or unheated fresh air/gas(s), at one or more of any suitable and effective temperature(s) can be moved into, through, and out of, the treatment chamber(s) (2026), at least until the one or more chamber door(s) (2036) are opened. Without being limited, it can be foreseeable to those skilled in the art, that in certain situations, the temperature(s) of the said heated air/gas(s) and/or heated fresh air/gas(s) that is moved into, through, and out of, the treatment chamber(s) (2026), for various purpose(s), may not be high enough to warrant any activities, steps, methods, and/or actions, such as, but not limited to, effectively cooling and/or effectively reducing the temperature(s) of the various surface(s) within the treatment chamber(s) (2026) and/or any various surface(s) of the treated object(s) (2300) located in the treatment chamber(s) (2026), before the said treated object(s) (2300) are removed from the treatment chamber(s) (2026). However, any suitable and effective quantity(s) of unheated air/gas(s) and/or unheated fresh air/gas(s), can be flowed into, through, and out of, the treatment chamber(s) (2026) for any suitable and effective number of time(s) and any suitable and effective duration(s) of time(s), and at one or more of any suitable and effective temperature(s), after the flow and/or movement of any heated air/gas(s) and/or heated fresh air/gas(s), into, through, and out of, the said treatment chamber(s) (2026), is stopped.

Without being limited, the flow and/or movement of any suitable and effective quantity(s) of any unheated air/gas(s) and/or unheated fresh air/gas(s), at one or more of any suitable and effective temperature(s), and for one or more of any suitable and effective time(s) and for any suitable and effective duration(s) of time(s), and at any suitable and effective, speed(s), velocity(s), quantity(s) per minute, and/or cubic feet per minute (CFM), into, through, and out of, the treatment chamber(s) (2026), after the flow and/or movement of the said heated air/gas(s) and/or heated fresh air/gas(s), into, through, and out of, the said treatment chamber(s) (2026), has stopped, can provide various purposes such as, but not limited to, (a) effectively removing any remaining and/or residual deployed agent(s) (2100) and/or any gas(s) and/or vapor(s) of the deployed agent(s) (2100) from inside of location(s) such as, but not limited to any, treatment chamber(s) (2026), filtered and heated inbound air/gas(s) assembly(s) (2525), and/or filtered exhaust assembly(s) (2530), (b) effectively removing any airborne dust(s) and/or foreign object debris from the air/gas(s) and/or atmosphere inside of the treatment chamber(s) (2026) that can be introduced into the treatment chamber(s) (2026) when the chamber door(s) (2036) are opened, (c) providing an effective means for humidity control and/or removing any water vapor and/or humidity from the inside of the treatment chamber(s) (2026) at one or more of any suitable and effective time(s), inside one or more of any location(s) such as, but not limited to any, treatment chamber(s) (2026), filtered and heated inbound air/gas(s) assembly(s) (2525), and/or filtered exhaust assembly(s) (2530), and/or (d) further reducing the temperature(s) of the various surface(s) within the treatment chamber(s) (2026) and/or any various surface(s) of the treated object(s) (2300) located in the treatment chamber(s) (2026), if needed or desired.

In one example, and without being limited, when the flow and/or movement of any suitable and effective quantity(s) of any heated air/gas(s) and/or heated fresh air/gas(s), used for purposes such as, but not limited to, drying and/or removing the deployed agent(s) (2100) from the various surface(s) and/or treated object(s) (2300) surface(s) inside of the treatment chamber(s) (2026), has stopped flowing into, through, and out of, the said treatment chamber(s) (2026), additional suitable and effective heated air/gas(s) and/or heated fresh air/gas(s), and more preferably, and without limitation, any unheated air/gas(s) and/or unheated fresh air/gas(s), can flow into, through, and out of, the treatment chamber(s) (2026), for one or more of any suitable and effective number of time(s), and for any suitable and effective lengths of time(s), at one or more of any suitable and effective temperature(s), and at any suitable and effective, speed(s), velocity(s), quantity(s) per minute, and/or cubic feet per minute (CFM), and where the length of time(s) that the movement and/or flow of the said additional heated air/gas(s), heated fresh air/gas(s), unheated air/gas(s), and/or unheated fresh air/gas(s) can be predetermined, pre-programmed, and/or preset, to any suitable and effective length(s) of time(s).

Without being limited, after the one or more flow(s) and/or movement(s) of the heated air/gas(s), heated fresh air/gas(s), unheated air/gas(s), and/or unheated fresh air/gas(s), is stopped, the chamber inlet valve(s) (2585) and chamber outlet valve(s) (2605) can be effectively closed, however they can also be effectively reopened before, during, and/or effectively about, any one or more time(s) the inbound blower(s) (2550) and/or the one or more exhaust blower(s) (2640) are later operated, and the said valve(s) (2585) (2605) can also be effectively re-closed before, during, after, and/or effectively about, any one or more time(s) the inbound blower(s) (2550) and/or the one or more exhaust blower(s) (2640) are later stopped and/or their operation is ceased. However, and without being limited, the one or more said valve(s) (2585)(2605) can also remain effectively open at one or more of any suitable and effective time(s) and for any suitable and effective duration(s) of time(s) after the inbound blower(s) (2550) and/or the one or more exhaust blower(s) (2640) are not operated.

In another example, and without being limited, after the flow and/or movement of any heated air/gas(s) and/or heated fresh air/gas(s), used for purposes such as, but not limited to any, drying and/or removing the deployed agent(s) (2100) from the various surface(s) and/or treated object(s) (2300) surface(s) inside of the treatment chamber(s) (2026) has stopped flowing into, through, and out of, the said treatment chamber(s) (2026), additional heated air/gas(s) and/or heated fresh air/gas(s) and/or preferably, and without any limitation, any effective unheated air/gas(s) and/or unheated fresh air/gas(s), can flow into, through, and out of, the treatment chamber(s) (2026), for one or more of any suitable and effective number of time(s), and for any suitable and effective lengths of time(s), at one or more of any suitable and effective temperature(s), and at any suitable and effective, speed(s), velocity(s), quantity(s) per minute, and/or cubic feet per minute (CFM), and with any suitable and effective duration(s) of time(s) between not flowing and/or moving the additional heated air/gas(s), heated fresh air/gas(s), unheated air/gas(s), and/or unheated fresh air/gas(s), into, through, and out of, the treatment chamber(s) (2026) and then flowing and/or moving any additional heated air/gas(s), heated fresh air/gas(s), unheated air/gas(s), and/or unheated fresh air/gas(s), into, through, and out of, the treatment chamber(s) (2026).

More specifically, and without limitation, the flow and/or movement of any suitable and effective quantity(s) of any additional heated air/gas(s) and/or heated fresh air/gas(s) and/or preferably, and without any limitation, any effective unheated air/gas(s) and/or unheated fresh air/gas(s), at one or more of any suitable and effective temperature(s), and for one or more of any suitable and effective time(s) and for any suitable and effective duration(s) of time(s), and at any suitable and effective, speed(s), velocity(s), quantity(s) per minute, and/or cubic feet per minute (CFM), can flow and/or move one or more time(s) after one or more of any suitable and effective delay(s) of time(s), after the one or more flow(s) and/or movement(s) of the heated air/gas(s) and/or heated fresh air/gas(s) that is used for drying and/or removal of the deployed agent(s) (2100) from the various surface(s) inside of the treatment chamber(s) (2026) and/or the various treated object(s) (2300) surface(s) located inside of the said treatment chamber(s) (2026) has stopped, and where the said one or more delay(s) of time(s) can have any suitable and effective length(s) of time(s) where the inbound blower(s) (2550) and/or the one or more exhaust blower(s) (2640) are not operating and there is no flow and/or movement of the said unheated air/gas(s), unheated fresh air/gas(s), heated air/gas(s), and/or heated fresh air/gas(s) into, through, and out of, the treatment chamber(s) (2026).

In another example, and without limitation, after the flow and/or movement of any suitable and effective unheated air/gas(s) and/or unheated fresh air/gas(s), and preferably, and without limitation, any suitable and effective heated air/gas(s) and/or heated fresh air/gas(s), used for purposes such as, but not limited to, drying and/or removal of the deployed agent(s) (2100) from the various surface(s) inside of the treatment chamber(s) (2026) and/or the various treated object(s) (2300) surface(s) located inside of the said treatment chamber(s) (2026), the flow of any unheated air/gas(s), unheated fresh air/gas(s), heated air/gas(s), and/or heated fresh air/gas(s), can be stopped and the movement and/or flow of any suitable and effective unheated air/gas(s) and/or unheated fresh air/gas(s) at any suitable and effective temperature(s), and at any suitable and effective, speed(s), velocity(s), quantity(s) per minute, and/or cubic feet per minute (CFM), can flow into, through, and out of, various parts and component(s) such as, but limited to one or more of any, treatment chamber(s) (2026), filtered and heated inbound air/gas(s) assembly(s) (2525), and/or filtered exhaust assembly(s) (2530), for any suitable and effective duration(s) of time(s), and once this said duration of time(s) is over and/or ended for operating the inbound blower(s) (2550) and/or the exhaust blower(s) (2640), the said inbound blower(s) (2550) and/or the exhaust blower(s) (2640), but preferably, and without limitation, both the inbound blower(s) (2550) and the exhaust blower(s) (2640), are stopped.

Also, and without being limited, once the inbound blower(s) (2550) and/or the exhaust blower(s) (2640) are stopped, the chamber inlet valve(s) (2585) and chamber outlet valve(s) (2605) can effectively close. After one or more of any suitable and effective length of time(s), that is preferably, and without limitation, preset, predetermined, effected by, and/or caused by, one or more of any situation(s) and/or condition(s) such as, but not limited to, any suitable and effective increase(s) in humidity(s) and/or deployed agent(s) in various area(s) such as, but not limited to one or more of any, treatment chamber(s) (2026), filtered and heated inbound air/gas(s) assembly(s) (2525), and/or filtered exhaust assembly(s) (2530), the chamber inlet valve(s) (2585) and chamber outlet valve(s) (2605) can effectively open, and preferably and without limitation, the inbound blower(s) (2550) and/or the exhaust blower(s) (2640), but preferably, and without limitation, both the inbound blower(s) (2550) and the exhaust blower(s) (2640), can suitably and effectively operate, and again move and/or flow any suitable and effective heated air/gas(s), heated fresh air/gas(s), unheated air/gas(s), and/or unheated fresh air/gas(s), at any suitable and effective temperature(s), and at any suitable and effective, speed(s), velocity(s), quantity(s) per minute, and/or cubic feet per minute (CFM), into, through, and out of, various parts and component(s) such as, but limited to one or more of any, treatment chamber(s) (2026), filtered and heated inbound air/gas(s) assembly(s) (2525), and/or filtered exhaust assembly(s) (2530), for any suitable and effective duration(s) of time(s), and where the said inbound blower(s) (2550) and/or the exhaust blower(s) (2640) will again stop operating, and the said chamber inlet valve(s) (2585) and chamber outlet valve(s) (2605) can effectively close again if needed and/or desired. Without being limited, these various said activities, series of action(s), and/or event(s), can repeat for one or more of any suitable and effective number(s) of times such as, but not limited to, preferably and without limitation, at least about every 5 minutes to about every 30 days, and more preferably and without limitation, at least about every one day to about every 14 days. Without being limited, when the one or more inbound blower(s) (2550) and/or the exhaust blower(s) (2640) are not operated, the one or more of various valves, such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and/or circulation output valve(s) (2910), can also remain effectively open and/or closed.

Without limitation, various other examples are given below for flowing and/or moving the said unheated air/gas(s) and/or unheated fresh air/gas(s) into, through, and out of, the treatment chamber(s) (2026), after the flow and/or movement of any, unheated air/gas(s) and/or unheated fresh air/gas(s), and preferably, and without limitation, after any heated air/gas(s) and/or heated fresh air/gas(s), is flowed and/or moved into, through, and out of, the treatment chamber(s) (2026), for purposes such as, but not limited to, removing any deployed agent(s) (2100) and/or residual deployed agent(s)(2100) from one or more of any location(s) including, but not limited to any treatment chamber(s) (2026), removing any particles and/or foreign object debris that may enter the treatment chamber(s) (2026) when the one or more door(s) (2036) that access the said treatment chamber(s) (2026) are opened, and drying and/or removal of the deployed agent(s) (2100) from the various surface(s) inside of the treatment chamber(s) (2026) and/or the various treated object(s) (2300) surface(s) located inside of the said treatment chamber(s) (2026), such as, but not limited to, in a first example, and without limitation, the various surface(s) within the treatment chamber(s) (2026) and/or any various surface(s) of the treated object(s) (2300) located in the treatment chamber(s) (2026), are suitably and effectively treated with the deployed agent(s) (2100), and then after, the chamber inlet valve(s) (2585) and chamber outlet valve(s) (2605) are effectively opened, and the inbound blower(s) (2550) and/or the exhaust blower(s) (2640) are suitably and effectively operated for one or more of any suitable and effective duration of time(s).

Without being limited, the flow and/or movement of any suitable and effective unheated air/gas(s) and/or unheated fresh air/gas(s), and preferably, and without limitation, any suitable and effective heated air/gas(s) and/or heated fresh air/gas(s), used for purposes such as, but not limited to, drying and/or removal of the deployed agent(s) (2100) from the various surface(s) inside of the treatment chamber(s) (2026) and/or the various treated object(s) (2300) surface(s) located inside of the said treatment chamber(s) (2026), can be stopped after any suitable and effective length(s) of operation time(s) has ended, and preferably, and without limitation, after the deployed agent(s) have been effectively removed from the various surface(s) inside of the treatment chamber(s) (2026) and/or at least the various treated object(s) (2300) surface(s) located inside of the said treatment chamber(s) (2026) are effectively dry.

Without limitation, the inbound blower(s) (2550) and the exhaust blower(s) (2640) can also be preferably, and without limitation, both effectively operated after the deployed agent(s) have been effectively removed from the various surface(s) inside of the treatment chamber(s) (2026) and/or at least the various treated object(s) (2300) surface(s) located inside of the said treatment chamber(s) (2026) are effectively dry, and unheated air/gas(s) and/or unheated fresh air/gas(s) can then be flowed and/or moved into, through, and out of, the treatment chamber(s) (2026), filtered and heated inbound air/gas(s) assembly(s) (2525), and/or filtered exhaust assembly(s) (2530), for one or more of any suitable and effective length(s) of time(s), and the said length(s) of time(s) is preferably, and without limitation, preset and/or predetermined and preferably, and without limitation, controlled by the one or more microcontroller(s) (2920). Without limitation, when the said operation time(s) for the inbound blower(s) (2550) and the exhaust blower(s) (2640) has ended, the operation of the said inbound blower(s) (2550) and the exhaust blower(s) (2640) is stopped, and one or more of various valves, such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and/or circulation output valve(s) (2910), but preferably, and without limitation, at least the chamber inlet valve(s) (2585) and chamber outlet valve(s) (2605), and even more preferably all of the said valve(s) such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and circulation output valve(s) (2910), are suitably and effectively closed.

In a second example, and without limitation, the various surface(s) within the treatment chamber(s) (2026) and/or any various surface(s) of the treated object(s) (2300) located in the treatment chamber(s) (2026), are suitably and effectively treated with the deployed agent(s) (2100), and then after, the chamber inlet valve(s) (2585) and chamber outlet valve(s) (2605) are effectively opened, and the inbound blower(s) (2550) and/or the exhaust blower(s) (2640) are suitably and effectively operated for one or more of any suitable and effective duration of time(s).

Without being limited, the flow and/or movement of any suitable and effective unheated air/gas(s) and/or unheated fresh air/gas(s), and preferably, and without limitation, any suitable and effective heated air/gas(s) and/or heated fresh air/gas(s), used for purposes such as, but not limited to, drying and/or removal of the deployed agent(s) (2100) from the various surface(s) inside of the treatment chamber(s) (2026) and/or the various treated object(s) (2300) surface(s) located inside of the said treatment chamber(s) (2026), can be stopped after any suitable and effective length(s) of operation time(s) has ended, and preferably, and without limitation, after the deployed agent(s) have been effectively removed from the various surface(s) inside of the treatment chamber(s) (2026) and/or at least the various treated object(s) (2300) surface(s) located inside of the said treatment chamber(s) (2026) are effectively dry.

Without limitation, the inbound blower(s) (2550) and the exhaust blower(s) (2640) can also be preferably, and without limitation, both effectively operated after the deployed agent(s) have been effectively removed from the various surface(s) inside of the treatment chamber(s) (2026) and/or at least the various treated object(s) (2300) surface(s) located inside of the said treatment chamber(s) (2026) are effectively dry, and unheated air/gas(s) and/or unheated fresh air/gas(s) can then be flowed and/or moved into, through, and out of, the treatment chamber(s) (2026), filtered and heated inbound air/gas(s) assembly(s) (2525), and/or filtered exhaust assembly(s) (2530), for one or more of any suitable and effective length(s) of time(s), and the said length(s) of time(s) is preferably, and without limitation, preset and/or predetermined and preferably, and without limitation, controlled by the one or more microcontroller(s) (2920). Without limitation, when the said operation time(s) for the inbound blower(s) (2550) and the exhaust blower(s) (2640) has ended, the operation of the said inbound blower(s) (2550) and the exhaust blower(s) (2640) is stopped, and one or more of various valves, such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and/or circulation output valve(s) (2910), but preferably, and without limitation, at least the chamber inlet valve(s) (2585) and chamber outlet valve(s) (2605), and even more preferably all of the said valve(s) such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and circulation output valve(s) (2910), are suitably and effectively open.

In third example, and without limitation, the various surface(s) within the treatment chamber(s) (2026) and/or any various surface(s) of the treated object(s) (2300) located in the treatment chamber(s) (2026), are suitably and effectively treated with the deployed agent(s) (2100), and then after, the chamber inlet valve(s) (2585) and chamber outlet valve(s) (2605) are effectively opened, and the inbound blower(s) (2550) and/or the exhaust blower(s) (2640) are suitably and effectively operated for one or more of any suitable and effective duration of time(s).

Without being limited, the flow and/or movement of any suitable and effective unheated air/gas(s) and/or unheated fresh air/gas(s), and preferably, and without limitation, any suitable and effective heated air/gas(s) and/or heated fresh air/gas(s), used for purposes such as, but not limited to, drying and/or removal of the deployed agent(s) (2100) from the various surface(s) inside of the treatment chamber(s) (2026) and/or the various treated object(s) (2300) surface(s) located inside of the said treatment chamber(s) (2026), can be stopped after any suitable and effective length(s) of operation time(s) has ended, and preferably, and without limitation, after the deployed agent(s) have been effectively removed from the various surface(s) inside of the treatment chamber(s) (2026) and/or at least the various treated object(s) (2300) surface(s) located inside of the said treatment chamber(s) (2026) are effectively dry.

Without limitation, the inbound blower(s) (2550) and the exhaust blower(s) (2640) can also be preferably, and without limitation, both effectively operated after the deployed agent(s) have been effectively removed from the various surface(s) inside of the treatment chamber(s) (2026) and/or at least the various treated object(s) (2300) surface(s) located inside of the said treatment chamber(s) (2026) are effectively dry, and unheated air/gas(s) and/or unheated fresh air/gas(s) can then be flowed and/or moved into, through, and out of, the treatment chamber(s) (2026), filtered and heated inbound air/gas(s) assembly(s) (2525), and/or filtered exhaust assembly(s) (2530), for one or more of any suitable and effective length(s) of time(s), and the said length(s) of time(s) is preferably, and without limitation, preset and/or predetermined and preferably, and without limitation, controlled by the one or more microcontroller(s) (2920). Without limitation, when the said operation time(s) for the inbound blower(s) (2550) and the exhaust blower(s) (2640) has ended, the operation of the said inbound blower(s) (2550) and the exhaust blower(s) (2640) is stopped, and one or more of various valves, such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and/or circulation output valve(s) (910), but preferably, and without limitation, at least the chamber inlet valve(s) (2585) and chamber outlet valve(s) (2605), and even more preferably all of the said valve(s) such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and circulation output valve(s) (2910), are suitably and effectively closed.

However, and without limitation, the operation of the inbound blower(s) (2550) and the exhaust blower(s) (2640) can also, and without limitation, be stopped after one or more of any suitable and effective length(s) of time(s) after the one or more chamber door(s) (2036) are opened and then re-closed, and/or immediately stopped when the one or more chamber door(s) (2036) are opened and/or then re-closed. Without limitation, when the said operation time(s) for the inbound blower(s) (2550) and the exhaust blower(s) (2640) has ended and/or the one or more door(s) (2036) that access the treatment chamber(s) (2026) are closed, the operation of the said inbound blower(s) (2550) and the exhaust blower(s) (2640) is stopped, and one or more of various valves, such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and/or circulation output valve(s) (2910), but preferably, and without limitation, at least the chamber inlet valve(s) (2585) and chamber outlet valve(s) (2605), and even more preferably all of the said valve(s) such as, but not limited to any, chamber inlet valve(s) (2585), chamber outlet valve(s) (2605), deployed agent(s) inlet valve(s) (2685), deployed agent(s) outlet valve(s) (2690), circulation input valve(s) (2905), and circulation output valve(s) (2910), are effectively closed.

Without being limited, after the treated object(s) (2300) have been suitably and effectively, treated, dried, and/or processed, and the treated object(s) (2300) are ready for removal from the treatment chamber(s) (2026), and the said flow of any heated and/or unheated air/gas(s) and/or fresh air/gas(s) has finally stopped, it is preferred, without limitation, that both the chamber inlet valve(s) (2585) and chamber outlet valve(s) (2605) are suitably and effectively closed.

The effective operation of both the one or more inbound blower(s) (2550) and the one or more exhaust blower(s) (2640), and without limitation, causes air/gas(s), fresh air/gas(s), heated air/gas(s), and/or heated fresh air/gas(s) to flow and/or move into, through, and out of, the one or more of any, filtered and heated inbound air/gas(s) assembly(s) (2525) and treatment chamber(s) (2026), and then into, through, and exhausted out of, the one or more filtered exhaust assembly(s) (2530). Also, and without being limited, the operation of both the one or more inbound blower(s) (2550) and the one or more exhaust blower(s) (2640), can also cause any, humidity(s), vapor(s), chemical(s), gas(s), and deployed agent(s) (2100), to flow and/or move out of the said treatment chamber(s) (2026) and into, through, and exhausted out of, the one or more filtered exhaust assembly(s) (2530).

More specifically, and without limitation, the said air/gas(s), fresh air/gas(s), heated air/gas(s), heated fresh air/gas(s), humidity(s), vapor(s), chemical(s), gas(s), and/or deployed agent(s) (2100), are moved, flowed, pushed, and/or pulled, from the one or more treatment chamber(s) (2026) and are moved and/or flowed into, through, and then out of, one or more of any suitable and effective chamber outlet valve(s) (2605) before the said air/gas(s), fresh air/gas(s), heated air/gas(s), heated fresh air/gas(s), humidity(s), vapor(s), chemical(s), gas(s), and/or deployed agent(s) (2100), flow into the one or more filtered exhaust assembly(s) (2530), and where the one or more said chamber outlet valve(s) (2605) can suitably and effectively open and close at any one or more of any suitable and effective time(s) and for any suitable and effective duration(s) of time(s), controlling the flow and movement of the said air/gas(s), fresh air/gas(s), heated air/gas(s), heated fresh air/gas(s), humidity(s), vapor(s), chemical(s), gas(s), and/or deployed agent(s) (2100), out of the treatment chamber(s), and where the said air/gas(s), fresh air/gas(s), heated air/gas(s), heated fresh air/gas(s), humidity(s), vapor(s), chemical(s), gas(s), and/or deployed agent(s) (2100), are flowed and/or moved into the one or more of any suitable and effective filtered exhaust assembly(s) (2530) by the operation of both and/or either the one or more of any suitable and effective inbound blower(s) (2550) and/or exhaust blower(s) (2640), but preferably and without limitation, at least primarily and/or effectively by the operation of the one or more exhaust blower(s) (2640) while the inbound blower(s) (2550) is also simultaneously operated. Alternatively, and without limitation, the flow and/or movement of any air/gas(s), fresh air/gas(s), heated air/gas(s), and/or heated fresh air/gas(s), into, through, and out of, the one or more of any, filtered and heated inbound air/gas(s) assembly(s) (2525), at any suitable and effective, speed(s), velocity(s), quantity(s) per minute, and/or cubic feet per minute (CFM), and the flow and/or movement of any air/gas(s), fresh air/gas(s), heated air/gas(s), heated fresh air/gas(s), humidity(s), vapor(s), chemical(s), gas(s), and/or deployed agent(s) (2100), into, through, and out of, the one or more of any, treatment chamber(s) (2026) and filtered exhaust assembly(s) (2530), at any suitable and effective, speed(s), velocity(s), quantity(s) per minute, and/or cubic feet per minute (CFM), can be shared, equally shared, and/or at least effectively shared, by the effective operation of both the inbound blower(s) (2550) and the exhaust blower(s) (2640).

Without being limited, the said any, air/gas(s), fresh air/gas(s), heated air/gas(s), heated fresh air/gas(s), humidity(s), vapor(s), chemical(s), gas(s), and/or deployed agent(s) (2100), can be flowed and/or moved through one or more of any suitable and effective, sequence(s), order(s), and/or combination(s), of the one or more of any suitable and effective part(s) and component(s) of the filtered exhaust assembly(s) (2530), such as, but not limited to, (a) a first and preferred, and without limitation, possible sequence(s), order(s), and/or combination(s), of various parts and components of the filtered exhaust assembly(s) (2530), and shown in FIG. 113, and without limitation, where the said any, air/gas(s), fresh air/gas(s), heated air/gas(s), heated fresh air/gas(s), humidity(s), vapor(s), chemical(s), gas(s), and/or deployed agent(s) (2100), can first flow into, through, and then out of, one or more of any suitable and effective chamber outlet valve(s) (2605) that is suitably and effectively open, and into the one or more of any suitable and effective filtered exhaust assembly(s) (2530) that the chamber outlet valve(s) (2605) is preferably, and without limitation, a part and/or a component of.

Without being limited, the said any, air/gas(s), fresh air/gas(s), heated air/gas(s), heated fresh air/gas(s), humidity(s), vapor(s), chemical(s), gas(s), and/or deployed agent(s) (2100), can then flow into, through, and then out of, one or more of any suitable and effective first air/gas(s) filter(s) and/or first outlet filter(s) (2615), where the said first outlet filter(s) (2615) can be, without limitation, at least any suitable and effective, MERV rated air/gas(s) filter(s), DOP rated air/gas(s) filter(s), HEPA rated air/gas(s) filter(s), and/or ULPA rated air/gas(s) filter(s), and preferably and without limitation, at least any suitable and effective air/gas(s) filter(s) with a MERV rating between and including about 0 to 20 MERV, and more preferably and without limitation, at least any suitable and effective air/gas(s) filter(s) that is any HEPA rated filter(s), and even more preferably and without limitation, at least any suitable and effective air/gas(s) filter(s) that is any DOP rated filter(s).

Also, without being limited, the said any, air/gas(s), fresh air/gas(s), heated air/gas(s), heated fresh air/gas(s), humidity(s), vapor(s), chemical(s), gas(s), and/or deployed agent(s) (2100), can then flow into, through, and then out of, one or more of any suitable and effective second air/gas(s) filter(s) and/or vapor absorbing outlet filter(s) (2620), where the vapor absorbing outlet filter(s) (2620) can have any suitable and effective, attribute(s), performance(s), and/or be, and without limitation, one or more of any suitable and effective, air filter(s), chemical absorbing filter(s), vapor capturing filter(s), chemical removing filter(s), vapor removing filter(s), molecule(s) removing filter(s), one or more targeted molecule(s) removing air filter(s), and where the said vapor absorbing outlet filter(s) (2620) can at least be, and without limitation, any suitable and effective air/gas(s) filter(s) that can suitably and effectively, absorb, adsorb, remove, and/or filter, one or more of any, chemical(s), vapor(s), gas(s), substance(s), compound(s), molecule(s), deployed agent(s) (2100), and/or chemical agent(s), and where the vapor absorbing outlet filter(s) (2620) can have any suitable and effective performance(s) and/or filter attributes known to those skilled in the art, and where the vapor absorbing outlet filter(s) (2620) can have one or more of any suitable and effective design(s) and construction(s) known to those skilled in the art, and where the vapor absorbing outlet filter(s) (2620) can have, and without limitation, one or more of any suitable and effective filter media(s) and/or one or more of any suitable and effective filter component(s), material(s), and/or part(s), that can, and without limitation, filter, absorb, adsorb, and/or remove, one or more of any, chemical(s), vapor(s), gas(s), substance(s), compound(s), molecule(s), deployed agent(s) (2100), and/or chemical agent(s), all in a manner known to those skilled in the art.

Without being limited, the one or more vapor absorbing outlet filter(s) (2620) can be, and without limitation, effectively, impregnated, blended, compounded, and/or constructed, of and/or with, as well as effectively contain, one or more of any suitable and effective, filter(s), air/gas(s) filter(s), filter media(s), chemical absorbing and/or adsorbing media and/or material(s), and/or filter material(s), that can absorb, collect, adsorb, and/or remove, one or more of any deployed agent(s) (2100), gas(s), molecule(s), targeted molecule(s), and/or vapor(s), from any flow and/or movement of any air/gas(s), all in a manner known to those skilled in the art.

In addition, it is preferred, without limitation, that the vapor absorbing outlet filter(s) (2620) at least contains one or more of any suitable and effective, charcoal(s) and/or activated charcoal filter(s), charcoal and/or activated charcoal filter bed(s), charcoal and/or activated charcoal filtration media(s), and/or charcoal and/or activated charcoal filtration material(s), known to those skilled in the art, and where the vapor absorbing outlet filter(s) (2620) can filter, remove, adsorb, and/or absorb, any suitable and effective amount(s) and/or concentration(s) of one or more of any, chemical(s), vapor(s), gas(s), substance(s), compound(s), molecule(s), deployed agent(s) (2100), chemical agent(s), and/or element(s), at or per one or more of any suitable and effective unit(s), length(s), and/or segment(s) of time(s) and/or at any given moment(s) and/or range(s) of time(s).

Without being limited, the said any, air/gas(s), fresh air/gas(s), heated air/gas(s), heated fresh air/gas(s), and/or any remaining humidity(s), gas(s), vapor(s), and/or deployed agent(s) (2100), can then flow into, through, and then out of, one or more of any suitable and effective third air/gas(s) filter(s) and/or primary post absorption filter(s) (2625), where the said primary post absorption filter(s) (2625) can be, and without limitation, at least any suitable and effective, MERV rated air/gas(s) filter(s), DOP rated air/gas(s) filter(s), HEPA rated air/gas(s) filter(s), and/or ULPA rated air/gas(s) filter(s), and preferably and without limitation, at least any suitable and effective air/gas(s) filter(s) with a MERV rating between and including about 0 to 20 MERV, and more preferably and without limitation, at least any suitable and effective air/gas(s) filter(s) that is any DOP rated filter(s), and even more preferably and without limitation, at least any suitable and effective air/gas(s) filter(s) that is any ULPA rated filter(s), and very preferably and without limitation, at least any suitable and effective air/gas(s) filter(s) that is any HEPA rated filter(s).

Also, without being limited, the said any, air/gas(s), fresh air/gas(s), heated air/gas(s), heated fresh air/gas(s), and/or any remaining humidity(s), gas(s), vapor(s), and/or deployed agent(s) (2100), can then flow into, through, and then out of, one or more of any suitable and effective fourth air/gas(s) filter(s) and/or secondary post absorption filter(s) (2630), where the said secondary post absorption filter(s) (2630) can be, without limitation, at least any suitable and effective, MERV rated air/gas(s) filter(s), DOP rated air/gas(s) filter(s), HEPA rated air/gas(s) filter(s), and/or ULPA rated air/gas(s) filter(s), and preferably and without limitation, at least any suitable and effective air/gas(s) filter(s) with a MERV rating between and including about 0 to 20 MERV, and more preferably and without limitation, at least any suitable and effective air/gas(s) filter(s) that is any DOP rated filter(s), and even more preferably and without limitation, at least any suitable and effective air/gas(s) filter(s) that is any ULPA rated filter(s), and very preferably and without limitation, at least any suitable and effective air/gas(s) filter(s) that is any HEPA rated filter(s).

Without being limited, the said any, air/gas(s), fresh air/gas(s), heated air/gas(s), heated fresh air/gas(s), and/or any remaining humidity(s), gas(s), vapor(s), and/or deployed agent(s) (2100), can then flow into, through, and then out of, one or more of any suitable and effective exhaust blower(s) (2640) at and/or with, any suitable and effective, speed(s), velocity(s), quantity(s) per minute, and/or cubic feet per minute (CFM).

Without being limited, the said any, air/gas(s), fresh air/gas(s), heated air/gas(s), heated fresh air/gas(s), and/or any remaining humidity(s), gas(s), vapor(s), and/or deployed agent(s) (2100), can flow into, through, and then out of, one or more of any suitable and effective fifth air/gas(s) filter(s) and/or exhaust outlet filter(s) (2645), and where the said exhaust outlet filter(s) (2645) can at least be any suitable and effective, general airborne dust and debris filter(s), MERV rated air/gas(s) filter(s), DOP rated air/gas(s) filter(s), HEPA rated air/gas(s) filter(s), and/or ULPA rated air/gas(s) filter(s), and preferably and without limitation, at least any air/gas(s) filter(s) with a MERV rating between and including about 0 to 20 MERV, and more preferably and without limitation, at least any air/gas(s) filter(s) with a MERV rating between about 0 to 12 MERV.

Finally, and without being limited, the said any, air/gas(s), fresh air/gas(s), heated air/gas(s), heated fresh air/gas(s), and/or any remaining humidity(s), gas(s), vapor(s), and/or deployed agent(s) (2100), can then flow, and without limitation, out of the one or more exhaust outlet(s) (2650) and out of the filtered exhaust assembly(s) (2530) and into one or more of any suitable and effective location(s) such as, but not limited to, the surrounding environment(s) (2900), and/or any environment(s) and/or atmosphere(s) that surrounds the outside of the treatment cabinet(s) (2519), treatment and processing cabinet(s) (2860), and/or the cabinet outer enclosure(s) (2865).

(b) a second possible sequence(s), order(s), and/or combination(s), of various parts and components of a modified filtered exhaust assembly(s) (2530) (not shown), and without limitation, where the said any, air/gas(s), fresh air/gas(s), heated air/gas(s), heated fresh air/gas(s), humidity(s), vapor(s), chemical(s), gas(s), and/or deployed agent(s) (2100), can first flow into, through, and then out of, one or more of any suitable and effective chamber outlet valve(s) (2605) that is suitably and effectively open, and into the one or more of any suitable and effective modified filtered exhaust assembly(s) (2530) (not shown), that the chamber outlet valve(s) (2605) is preferably, and without limitation, a part and/or a component of, and where the said any, air/gas(s), fresh air/gas(s), heated air/gas(s), heated fresh air/gas(s), humidity(s), vapor(s), chemical(s), gas(s), and/or deployed agent(s) (2100), can then flow into, through, and then out of, one or more of any suitable and effective exhaust blower(s) (2640) at and/or with, any suitable and effective, speed(s), velocity(s), quantity(s) per minute, and/or cubic feet per minute (CFM).

Without being limited, the said any, air/gas(s), fresh air/gas(s), heated air/gas(s), heated fresh air/gas(s), humidity(s), vapor(s), chemical(s), gas(s), and/or deployed agent(s) (2100), can then flow into, through, and then out of, one or more of any suitable and effective first air/gas(s)

filter(s) and/or first outlet filter(s) (2615), where the said first outlet filter(s) (2615) can be, without limitation, at least any suitable and effective, MERV rated air/gas(s) filter(s), DOP rated air/gas(s) filter(s), HEPA rated air/gas(s) filter(s), and/or ULPA rated air/gas(s) filter(s), and preferably and without limitation, at least any suitable and effective air/gas(s) filter(s) with a MERV rating between and including about 0 to 20 MERV, and more preferably and without limitation, at least any suitable and effective air/gas(s) filter(s) that is any HEPA rated filter(s), and even more preferably and without limitation, at least any suitable and effective air/gas(s) filter(s) that is any DOP rated filter(s).

Also, without being limited, the said any, air/gas(s), fresh air/gas(s), heated air/gas(s), heated fresh air/gas(s), humidity(s), vapor(s), chemical(s), gas(s), and/or deployed agent(s) (2100), can then flow into, through, and then out of, one or more of any suitable and effective second air/gas(s) filter(s) and/or vapor absorbing outlet filter(s) (2620), where the vapor absorbing outlet filter(s) (2620) can have any suitable and effective, attribute(s), performance(s), and/or be, and without limitation, one or more of any suitable and effective, air filter(s), chemical absorbing filter(s), vapor capturing filter(s), chemical removing filter(s), vapor removing filter(s), molecule(s) removing filter(s), one or more targeted molecule(s) removing air filter(s), and where the said vapor absorbing outlet filter(s) (2620) can at least be, and without limitation, any suitable and effective air/gas(s) filter(s) that can suitably and effectively, absorb, adsorb, remove, and/or filter, one or more of any, chemical(s), vapor(s), gas(s), substance(s), compound(s), molecule(s), deployed agent(s) (2100), and/or chemical agent(s), and where the vapor absorbing outlet filter(s) (2620) can have any suitable and effective performance(s) and/or filter attributes known to those skilled in the art, and where the vapor absorbing outlet filter(s) (2620) can have one or more of any suitable and effective design(s) and construction(s) known to those skilled in the art, and where the vapor absorbing outlet filter(s) (2620) can have, and without limitation, one or more of any suitable and effective filter media(s) and/or one or more of any suitable and effective filter component(s), material(s), and/or part(s), that can, and without limitation, filter, absorb, adsorb, and/or remove, one or more of any, chemical(s), vapor(s), gas(s), substance(s), compound(s), molecule(s), deployed agent(s) (2100), and/or chemical agent(s), all in a manner known to those skilled in the art.

Without being limited, the one or more vapor absorbing outlet filter(s) (2620) can be, and without limitation, effectively, impregnated, blended, compounded, and/or constructed, of and/or with, as well as effectively contain, one or more of any suitable and effective, filter(s), air/gas(s) filter(s), filter media(s), chemical absorbing and/or adsorbing media and/or material(s), and/or filter material(s), that can absorb, collect, adsorb, and/or remove, one or more of any deployed agent(s) (2100), gas(s), molecule(s), targeted molecule(s), and/or vapor(s), from any flow and/or movement of any air/gas(s), all in a manner known to those skilled in the art.

In addition, it is preferred, without limitation, that the vapor absorbing outlet filter(s) (2620) at least contains one or more of any suitable and effective, charcoal(s) and/or activated charcoal filter(s), charcoal and/or activated charcoal filter bed(s), charcoal and/or activated charcoal filtration media(s), and/or charcoal and/or activated charcoal filtration material(s), known to those skilled in the art, and where the vapor absorbing outlet filter(s) (2620) can filter, remove, adsorb, and/or absorb, any suitable and effective amount(s) and/or concentration(s) of one or more of any, chemical(s), vapor(s), gas(s), substance(s), compound(s), molecule(s), deployed agent(s) (2100), chemical agent(s), and/or element(s), at or per one or more of any suitable and effective unit(s), length(s), and/or segment(s) of time(s) and/or at any given moment(s) and/or range(s) of time(s).

Without being limited, the said any, air/gas(s), fresh air/gas(s), heated air/gas(s), heated fresh air/gas(s), and/or any remaining humidity(s) and/or deployed agent(s) (2100), can then flow into, through, and then out of, one or more of any suitable and effective third air/gas(s) filter(s) and/or primary post absorption filter(s) (2625), where the said primary post absorption filter(s) (2625) can be, without limitation, at least any suitable and effective, MERV rated air/gas(s) filter(s), DOP rated air/gas(s) filter(s), HEPA rated air/gas(s) filter(s), and/or ULPA rated air/gas(s) filter(s), and preferably and without limitation, at least any suitable and effective air/gas(s) filter(s) with a MERV rating between and including about 0 to 20 MERV, and more preferably and without limitation, at least any suitable and effective air/gas(s) filter(s) that is any DOP rated filter(s), and even more preferably and without limitation, at least any suitable and effective air/gas(s) filter(s) that is any ULPA rated filter(s), and very preferably and without limitation, at least any suitable and effective air/gas(s) filter(s) that is any HEPA rated filter(s).

Also, without being limited, the said any, air/gas(s), fresh air/gas(s), heated air/gas(s), heated fresh air/gas(s), and/or any remaining humidity(s) and/or deployed agent(s) (2100), can then flow into, through, and then out of, one or more of any suitable and effective fourth air/gas(s) filter(s) and/or secondary post absorption filter(s) (2630), where the said secondary post absorption filter(s) (2630) can be, without limitation, at least any suitable and effective, MERV rated air/gas(s) filter(s), DOP rated air/gas(s) filter(s), HEPA rated air/gas(s) filter(s), and/or ULPA rated air/gas(s) filter(s), and preferably and without limitation, at least any suitable and effective air/gas(s) filter(s) with a MERV rating between and including about 0 to 20 MERV, and more preferably and without limitation, at least any suitable and effective air/gas(s) filter(s) that is any DOP rated filter(s), and even more preferably and without limitation, at least any suitable and effective air/gas(s) filter(s) that is any ULPA rated filter(s), and very preferably and without limitation, at least any suitable and effective air/gas(s) filter(s) that is any HEPA rated filter(s).

Finally, and without limitation, the said any, air/gas(s), fresh air/gas(s), heated air/gas(s), heated fresh air/gas(s), and/or any remaining humidity(s) and/or deployed agent(s) (2100), can then flow, and without limitation, out of the one or more exhaust outlet(s) (2650) and out of the modified filtered exhaust assembly(s) (2530) (not shown) and into one or more of any suitable and effective location(s) such as, but not limited to, the surrounding environment(s) (2900), and/or any environment(s) and/or atmosphere(s) that surrounds the outside of the treatment cabinet(s) (2519), treatment and processing cabinet(s) (2860), and/or the cabinet outer enclosure(s) (2865).

(c) a third possible sequence(s), order(s), and/or combination(s), of various parts and components of a modified filtered exhaust assembly(s) (2530) (not shown), and without limitation, where the said any, air/gas(s), fresh air/gas(s), heated air/gas(s), heated fresh air/gas(s), humidity(s), vapor(s), chemical(s), gas(s), and/or deployed agent(s) (2100), can first flow into, through, and then out of, one or more of any suitable and effective chamber outlet valve(s) (2605) that is suitably and effectively open, and into the one or more of any suitable and effective modified filtered exhaust assembly(s) (2530) (not shown), that the chamber outlet valve(s) (2605) is preferably, and without limitation, a part and/or a component of, and where the said any, air/gas(s), fresh air/gas(s), heated air/gas(s), heated fresh air/gas(s), humidity(s), vapor(s), chemical(s), gas(s), and/or deployed agent(s) (2100), can then flow into, through, and then out of, one or more of any suitable and effective exhaust blower(s) (2640) at and/or with, any suitable and effective, speed(s), velocity(s), quantity(s) per minute, and/or cubic feet per minute (CFM). Without being limited, the one or more exhaust blower(s) (2640) can also be suitably and effectively located closest to the one or more treatment chamber(s) (2026) and/or suitably and effectively located before the one or more chamber outlet valve(s) (2605).

Without being limited, the said any, air/gas(s), fresh air/gas(s), heated air/gas(s), heated fresh air/gas(s), humidity(s), vapor(s), chemical(s), gas(s), and/or deployed agent(s) (2100), can then flow into, through, and then out of, one or more of any suitable and effective first outlet filter(s) (2615), where the said first outlet filter(s) (2615) can be, without limitation, at least any suitable and effective, MERV rated air/gas(s) filter(s), DOP rated air/gas(s) filter(s), HEPA rated air/gas(s) filter(s), and/or ULPA rated air/gas(s) filter(s), and preferably and without limitation, at least any suitable and effective air/gas(s) filter(s) with a MERV rating between and including about 0 to 20 MERV, and more preferably and without limitation, at least any suitable and effective air/gas(s) filter(s) that is any DOP rated filter(s), and even more preferably and without limitation, at least any suitable and effective air/gas(s) filter(s) that is any ULPA rated filter(s), and very preferably and without limitation, at least any suitable and effective air/gas(s) filter(s) that is any HEPA rated filter(s).

Also, without being limited, the said any, air/gas(s), fresh air/gas(s), heated air/gas(s), heated fresh air/gas(s), humidity(s), vapor(s), chemical(s), gas(s), and/or deployed agent(s) (2100), can then flow into, through, and then out of, one or more of any suitable and effective second air/gas(s) filter(s) and/or vapor absorbing outlet filter(s) (2620), where the vapor absorbing outlet filter(s) (2620) can have any suitable and effective, attribute(s), performance(s), and/or be, and without limitation, one or more of any suitable and effective, air filter(s), chemical absorbing filter(s), vapor capturing filter(s), chemical removing filter(s), vapor removing filter(s), molecule(s) removing filter(s), one or more targeted molecule(s) removing air filter(s), and where the said vapor absorbing outlet filter(s) (2620) can at least be, and without limitation, any suitable and effective air/gas(s) filter(s) that can suitably and effectively, absorb, adsorb, remove, and/or filter, one or more of any, chemical(s), vapor(s), gas(s), substance(s), compound(s), molecule(s), deployed agent(s) (2100), and/or chemical agent(s), and where the vapor absorbing outlet filter(s) (2620) can have any suitable and effective performance(s) and/or filter attributes known to those skilled in the art, and where the vapor absorbing outlet filter(s) (2620) can have one or more of any suitable and effective design(s) and construction(s) known to those skilled in the art, and where the vapor absorbing outlet filter(s) (2620) can have, and without limitation, one or more of any suitable and effective filter media(s) and/or one or more of any suitable and effective filter component(s), material(s), and/or part(s), that can, and without limitation, filter, absorb, adsorb, and/or remove, one or more of any, chemical(s), vapor(s), gas(s), substance(s), compound(s), molecule(s), deployed agent(s) (2100), and/or chemical agent(s), all in a manner known to those skilled in the art.

Without being limited, the one or more vapor absorbing outlet filter(s) (2620) can be, and without limitation, effectively, impregnated, blended, compounded, and/or constructed, of and/or with, as well as effectively contain, one or more of any suitable and effective, filter(s), air/gas(s) filter(s), filter media(s), chemical absorbing and/or adsorbing media and/or material(s), and/or filter material(s), that can absorb, collect, adsorb, and/or remove, one or more of any deployed agent(s) (2100), gas(s), molecule(s), targeted molecule(s), and/or vapor(s), from any flow and/or movement of any air/gas(s), all in a manner known to those skilled in the art.

In addition, it is preferred, without limitation, that the vapor absorbing outlet filter(s) (2620) at least contains one or more of any suitable and effective, charcoal(s) and/or activated charcoal filter(s), charcoal and/or activated charcoal filter bed(s), charcoal and/or activated charcoal filtration media(s), and/or charcoal and/or activated charcoal filtration material(s), known to those skilled in the art, and where the vapor absorbing outlet filter(s) (2620) can filter, remove, adsorb, and/or absorb, any suitable and effective amount(s) and/or concentration(s) of one or more of any, chemical(s), vapor(s), gas(s), substance(s), compound(s), molecule(s), deployed agent(s) (2100), chemical agent(s), and/or element(s), at or per one or more of any suitable and effective unit(s), length(s), and/or segment(s) of time(s) and/or at any given moment(s) and/or range(s) of time(s).

Also, and without being limited, the said any, air/gas(s), fresh air/gas(s), heated air/gas(s), heated fresh air/gas(s), and/or any remaining humidity(s) and/or deployed agent(s) (2100), can then flow into, through, and then out of, one or more of any suitable and effective third air/gas(s) filter(s) and/or primary post absorption filter(s) (2625), where the said primary post absorption filter(s) (2625) can be, without limitation, at least any suitable and effective, MERV rated air/gas(s) filter(s), DOP rated air/gas(s) filter(s), HEPA rated air/gas(s) filter(s), and/or ULPA rated air/gas(s) filter(s), and preferably and without limitation, at least any suitable and effective air/gas(s) filter(s) with a MERV rating between and including about 0 to 20 MERV, and more preferably and without limitation, at least any suitable and effective air/gas(s) filter(s) that is any DOP rated filter(s), and even more preferably and without limitation, at least any suitable and effective air/gas(s) filter(s) that is any HEPA rated filter(s), and very preferably and without limitation, at least any suitable and effective air/gas(s) filter(s) that is any ULPA rated filter(s).

Finally, and without limitation, the said any, air/gas(s), fresh air/gas(s), heated air/gas(s), heated fresh air/gas(s), and/or any remaining humidity(s) and/or deployed agent(s) (2100), can then flow, and without limitation, out of the one or more exhaust outlet(s) (2650) and out of the modified filtered exhaust assembly(s) (2530) (not shown) and into one or more of any suitable and effective location(s) such as, but not limited to, the surrounding environment(s) (2900), and/or any environment(s) and/or atmosphere(s) that surrounds the outside of the treatment cabinet(s) (2519), treatment and processing cabinet(s) (2860), and/or the cabinet outer enclosure(s) (2865).

In these said one or more sequences, and without limitation, the various one or more of any suitable and effective filter(s) such as, but not limited to any suitable and effective, DOP, HEPA, MERV, coarse, general, and/or ULPA, rated and/or configured air/gas(s) filter(s) and/or any one or more combination(s) of various air/gas(s) filter(s) known to those skilled in the art, that are located between the one or more of any vapor absorbing outlet filter(s) (2620) and the one or more valve(s) (2605) and/or the one or more treatment chamber(s) (2026), can serve various function(s) such as, but not limited to, suitably and effectively, preventing, prohibiting, stopping, and/or limiting, any, charcoal(s), activated charcoal(s), and/or any other filter media(s) in various forms such as, but not limited to any, granulated, chip, particle, pellet, and/or powder, filter media(s), and/or any other filter material(s) debris, from migrating and/or moving into and/or through the one or more valve(s) (2605) and/or into the one or more treatment chamber(s) (2026), as well as suitably and effectively, preventing, prohibiting, stopping, and/or limiting, any foreign object debris from migrating and/or moving from any one or more location(s) in the treatment chamber(s) (2026) and into various location(s) such as, but not limited to, the one or more filtered exhaust assembly(s) (2530) and/or vapor absorbing outlet filter(s) (2620). Without being limited, the one or more first outlet filter(s) (2615) can also be located before the chamber outlet valve(s) (2605) and/or closest to the one or more treatment chamber(s) (2026).

Also, and without being limited, the one or more vapor absorbing outlet filter(s) (2620) can also include in its design and construction, and located on the side where the chamber outlet valve(s) (2605) and/or treatment chamber(s) (2026) are located, and/or also located on the other side of the vapor absorbing outlet filter(s) (2620) where the one or more exhaust outlet(s) (2650) are located, one or more of any suitable and effective filter(s) that can suitably and effectively filter any flows and/or movements of any air/gas(s) such as, but not limited to any suitable and effective, DOP, HEPA, MERV, coarse, general, and/or ULPA, rated and/or configured air/gas(s) filter(s), and/or any suitable and effective combination(s) of the said air/gas(s) filter(s), known to those skilled in the art, but preferably, and without limitation at least any DOP rated filter(s) and/or any other effective filter material(s) on the side of the vapor absorbing outlet filter(s) (2620) closest to the treatment chamber(s) (2026) and at least any HEPA and/or ULPA rated filter(s) and/or any other effective filter materials on the side of the vapor absorbing outlet filter(s) (2620) closest to the exhaust outlet(s) (2650).

Without being limited, after the one or more of any surface(s) inside of the one or more treatment chamber(s) (2026) and/or the one or more of any targeted surface(s) of the treated object(s) (2300) and/or all of the surfaces of the treated object(s) (2300) located inside of the said treatment chamber(s) (2026), are effectively treated with the deployed agent(s) (2100), and the deployed agent(s) (2100) are suitably and effectively dried, removed, and/or are suitably and effectively reduced, from the one or more of any surface(s) and/or the one or more surface(s) of the treated object(s) (2300) located inside of the one or more treatment chamber(s) (2026), and/or additionally, the deployed agent(s) (2100) are suitably and effectively removed and/or reduced from the atmosphere(s) and/or air/gas(s) within the said treatment chamber(s) (2026), various activities can then take place, happen, and/or transpire, such as, but not limited to, (a) effectively filtered, air/gas(s), fresh air/gas(s), heated air/gas(s), and/or heated fresh air/gas(s), can flow and/or move into, through, and out of, the treatment chamber(s) (2026) for any suitable and effective length(s) and number(s) of time(s) and is then stopped. Without being limited, the various suitable and effective valve(s) that connect and communicate to and/or with the said treatment chamber(s) (2026) such as, but not limited to any, chamber inlet valve(s) (2585), chamber outlet valve(s) (2605), circulation input valve(s) (2905), circulation output valve(s) (2910), deployed agent(s) inlet valve(s) (2685), and/or deployed agent(s) outlet valve(s) (2690), can be preferably, and without limitation, suitably and effectively closed, however one or more of these said valve(s) (2585)(2605)(2905)(2910)(2685)(2690) can also, and without limitation, remain effectively open for any suitable and effective length(s) of time(s). Also, and without being limited, the machine operator(s) can then be alerted that the entire processing cycle(s) for the various object(s) (2300) and/or surface(s) within the treatment chamber(s) is complete, and the treated object(s) (2300) can then be removed from the treatment chamber(s) (2026) at one or more of any suitable and effective time(s), (b) effectively filtered and unheated, air/gas(s) and/or unheated fresh air/gas(s), can flow and/or move into, through, and out of, the treatment chamber(s) (2026) for any suitable and effective length(s) and number(s) of time(s) and is then stopped. Without being limited, once this flow and/or movement of the said unheated air/gas(s) and/or unheated fresh air/gas(s) into, through, and out of, the treatment chamber(s) (2026) is stopped, the various suitable and effective valve(s) that connect and communicate to and/or with the said treatment chamber(s) (2026) such as, but not limited to any, chamber inlet valve(s) (2585), chamber outlet valve(s) (2605), circulation input valve(s) (2905), circulation output valve(s) (2910), deployed agent(s) inlet valve(s) (2685), and/or deployed agent(s) outlet valve(s) (2690), can be preferably, and without limitation, suitably and effectively closed, however one or more of the said valve(s) (2585)(2605)(2905)(2910) (2685)(2690) can also, and without limitation, remain effectively open for any suitable and effective length(s) of time(s). Also, and without being limited, the machine operator can be alerted that the entire processing cycle(s) for the various object(s) (2300) and/or surface(s) within the treatment chamber(s) is complete, and the treated object(s) (2300) can then be removed from the treatment chamber(s) (2026) at one or more of any suitable and effective time(s), (c) the flow and/or movement of filtered unheated air/gas(s) and/or unheated fresh air/gas(s) can flow and/or move into, through, and out of, the treatment chamber(s) (2026) for one or more of any suitable and effective amount(s), number(s), and/or length(s) of time(s) before it is stopped, and the said amount(s) and/or length(s) of time(s) can be established, set, and/or determined, by any, needed, desired, suitable, and/or effective, situation(s), event(s), criteria, and/or condition(s), such as, but not limited to, (i) the temperature(s) of the air/gas(s) and/or atmosphere(s) within and/or exiting the treatment chamber(s) (2026) reaches and/or is maintained at any one or more suitable and effective temperature(s) sensed and/or measured by one or more of any suitable and effective temperature sensor(s) such as, but not limited to any, air/gas(s) temperature sensor(s) (2926) and/or surface temperature sensor(s) (2929), for any suitable and effective duration(s) and/or number(s) of time(s), all in a manner known to those skilled in the art, and reported to one or more of any suitable and effective microcontroller(s) (2920) also in a manner known to those skilled in the art, (ii) the percent humidity data(s), relative humidity data(s), humidity level(s) data(s), water vapor data(s), and/or chemical concentration(s) data(s) within and/or exiting the treatment chamber(s) (2026) reaches, decreases to, decreases below, and/or is maintained at, one or more of any suitable and effective humidity and/or water vapor data point(s), humidity ranges, and/or chemical concentration(s), sensed and/or measured by one or more of any suitable and effective sensor(s) such as, but not limited to any, humidity sensor(s) (2927) and/or chemical sensor(s) (2928), for any suitable and effective duration(s) and/or number(s) of time(s), all in a manner known to those skilled in the art, and reported to one or more of any suitable and effective microcontroller(s) (2920) also in a manner known to those skilled in the art, (iii) the one or more of any surface(s) of the treated object(s) (2300) and/or one or more of any other surface(s) inside of the treatment chamber(s) (2026) are suitably and effectively cooled, reduced to one or more of any suitable and effective temperature(s), and/or are maintained at, to, and/or below, any suitable and effective temperature(s) that is desired, needed, and/or known to those skilled in the art, and the temperature(s) of the one or more surface(s) of the said treated object(s) (2300) and/or any surface(s) inside of the treatment chamber(s) (2026) is sensed and/or measured by one or more of any suitable and effective, temperature sensor(s) air/gas(s) temperature sensor(s) (2926) and/or surface temperature sensor(s) (2929) all in a manner known to those skilled in the art, and reported to one or more of any suitable and effective microcontroller(s) (2920) also in a manner known to those skilled in the art, (iv) one or more of any suitable and effective preset, pre-configured, validated, proven, and/or per-established, duration(s) and/or amount(s) of time(s) is met. Without being limited, when the flow and/or movement of the said unheated air/gas(s) and/or unheated fresh air/gas(s) is stopped, the various suitable and effective valve(s) that connect and communicate to and/or with the said treatment chamber(s) (2026) such as, but not limited to any, chamber inlet valve(s) (2585), chamber outlet valve(s) (2605), circulation input valve(s) (2905), circulation output valve(s) (2910), deployed agent(s) inlet valve(s) (2685), and/or deployed agent(s) outlet valve(s) (2690), can be preferably, and without limitation, suitably and effectively closed, however one or more of the said valve(s) (2585) (2605)(2905)(2910)(2685)(2690) can also, and without limitation, remain effectively open for any suitable and effective length(s) of time(s). Also, and without being limited, the machine operator can be alerted that the entire processing cycle(s) for the various object(s) (2300) and/or surface(s) within the treatment chamber(s) is complete, and the treated object(s) (2300) can then be removed from the treatment chamber(s) (2026) at one or more of any suitable and effective time(s), (d) the flow and/or movement of the said air/gas(s), fresh air/gas(s), heated air/gas(s), and/or heated fresh air/gas(s), and preferably and without limitation, at least any suitable and effective filtered flows of unheated air/gas(s) and/or unheated fresh air/gas(s), can flow and/or move into, through, and out of, the treatment chamber(s) (2026) until the machine operator or any individual opens the one or more chamber door(s) (2036), and when the said chamber door(s) (2036) is opened and/or then closed, the said flow and/or movement of the filtered air/gas(s), fresh air/gas(s), heated air/gas(s), and/or heated fresh air/gas(s), is stopped, and the various suitable and effective valve(s) that connect and communicate to and/or with the said treatment chamber(s) (2026) such as, but not limited to any, chamber inlet valve(s) (2585), chamber outlet valve(s) (2605), circulation input valve(s) (2905), circulation output valve(s) (2910), deployed agent(s) inlet valve(s) (2685), and/or deployed agent(s) outlet valve(s) (2690), can be preferably, and without limitation, suitably and effectively closed, however one or more of the said valve(s) (2585)(2605) (2905) (2910)(2685)(2690) can also and without limitation remain effectively open for any suitable and effective length(s) of time(s). Also, and without being limited, the machine opera-tor can be alerted that the entire processing cycle(s) for the various object(s) (2300) and/or surface(s) within the treatment chamber(s) is complete, and the treated object(s) (2300) can then be removed from the treatment chamber(s) (2026) at one or more of any suitable and effective time(s).

Without being limited, the one or more chamber inlet valve(s) (2585) and the one or more chamber outlet valve(s) (2605) can also be separate part(s) and do not have to be considered a part of any component assembly group and/or part assembly group. For example, and without limitation, the one or more chamber inlet valve(s) (2585) does not have to be considered a part of the one or more filtered and heated inbound air/gas(s) assembly(s) (2525) and the one or more chamber outlet valve(s) (2605) does not have to be considered a part of the one or more filtered exhaust assembly(s) (2530). However, it is preferred, without limitation, that the one or more chamber inlet valve(s) (2585) is considered a part of the one or more filtered and heated inbound air/gas(s) assembly(s) (2525) and the one or more chamber outlet valve(s) (2605) is also considered a part of the one or more filtered exhaust assembly(s) (2530).

Without being limited, after the various surface(s) inside of the treatment chamber(s) (2026) and/or the one or more surface(s) of the treated object(s) (2300) are suitably and effectively dry and/or the deployed agent(s) (2100) are suitably and effectively removed and/or reduced from one or more of any surface(s) and/or treated object(s) (2300) surface(s), the one or more treated object(s) (2300) can also be suitably and effectively packaged inside of the treatment chamber(s) (2026), all in a manner known to those skilled in the art. However, it is preferred, without limitation, that the treated object(s) (2300) are packaged at least after the one or more surface(s) of the treated object(s) (2300) are at, meet, and/or are below, one or more of any suitable and effective temperature(s) and/or temperature range(s), and/or are suitably and effectively cooled and/or reduced in temperature(s), to one or more of any suitable and effective temperature(s), if they were heated by any suitable and effective means such as, but not limited to any, heated air/gas(s) and/or heated fresh air/gas(s). It is also preferred, without limitation, that after the one or more object(s) are packaged, they can be removed and/or retrieved by one or more machine operator(s) and/or any other suitable and effective means known to those skilled in the art, at one or more of any suitable and effective time(s).

Without being limited, the one or more microcontroller(s) (2920) can suitably and effectively communicate with and control one or more of any apparatuses and/or device(s), such as, but not limited to any, inbound blower(s) (2550), heater element(s) (2575), chamber inlet valve(s) (2585), circulation blower(s) (2715), decontamination system(s) (2040), agent blower(s) (2660), chamber outlet valve(s) (2605), and/or exhaust blower(s) (2640), all in a manner known to those skilled in the art.

In addition, and without being limited, the one or more microcontroller(s) (2920) can also suitably and effectively communicate with and/or control one or more of various sensor(s) known to those skilled in the art, and in any suitable and effective manner known to those skilled in the art, such as, but not limited to any, air/gas(s) temperature sensor(s) (2926), humidity sensor(s) (2927), chemical sensor(s) (2928), surface temperature sensor(s) (2929), and/or door position sensor(s) (not shown). Without being limited, the said door position sensor(s) (not shown) can sense, determine, and/or report, if the one or more chamber(s) doors (2036) are effectively closed and/or open. Without being limited, the one or more microcontroller(s) (2920) can also control one or more of any suitable and effective chamber light(s) (2925) all in a manner known to those skilled in the art.

Without being limited, one or more of any suitable and effective light(s) (Herein called Chamber Light(s)) (2925) can be shined into the said treatment chamber(s) (2026) at one or more of any time(s), but at least any suitable and effective time(s), and for any suitable and effective duration(s) of time(s). It is preferred, without limitation, that the chamber light(s) (2925) are at least directed into and/or shined into the treatment chamber(s) (2026) while the deployed agent(s) (2100) are present inside of the treatment chamber(s) (2026), and with one or more of any suitable and effective color(s) of light(s).

It is also preferred, without limitation, that the one or more of any suitable and effective door(s) (2036) that access the treatment chamber(s) (2026) can have one or more of any suitable and effective window(s) (2880) and/or one or more of any suitable and effective transparent window(s) (2880) known to those skilled in the art, and the machine operator(s) can look through the window(s) (2880) and see the status of the various treatment cycle(s) and/or which step(s) are taking place during any processing cycle(s), by observing the various colors of the chamber light(s) (2925) that can be shined into the treatment chamber(s) (2026) during each part and/or various parts of any processing cycle(s). Without limitation, the said chamber light(s) (2925) can include and/or emit one or more of any suitable and effective color(s) and/or emit light(s) having one or more of any suitable and effective light spectrum(s) and/or electromagnetic frequency(s) in the viable light spectrum.

Also, and without limitation, any one or more of any color(s) of the said chamber light(s) (2925) can be assigned to one or more of any, part(s), step(s), and/or activity(s), of the one or more of any processing cycle(s). It is preferred, without limitation, that at least one or more of any suitable and effective shade(s) of colored lights such as, but not limited to any, white, red, yellow, orange, bronze, green, blue, purple, turquoise, and/or aqua marine, colored light(s) (2925) and/or about these colors and/or light spectrum(s), is suitably and effectively, emitted, shined, used, and/or displayed, during the various steps of operating the improved cabinet mounted treatment chamber processing system(s) (2519). Without being limited, the chamber light(s) (2925) can be shined into the treatment chamber(s) (2026) during any of the one or more step(s) of the entire one or more processing cycle(s) for any treated object(s) (2300) located inside of the treatment chamber(s) (2026).

Without limitation, at least one or more of any suitable and effective shade(s) of blue, purple, turquoise, and/or aqua marine, colored chamber light(s) (2925) and/or about these colored chamber light(s) (2925) can be shined into the treatment chamber(s) (2026) when any deployed agent(s) (2100) is present, moved, and/or flowed, into and/or within the said treatment chamber(s) (2026). Without limitation, at least one or more of any suitable and effective shade(s) of orange, yellow, and/or bronze, colored light(s) (2925) and/or about these colored chamber light(s) (2925) can be shined into the treatment chamber(s) (2026) during one or more of any drying step(s) and/or step(s) to remove the deployed agent(s) (2100) from the various surface(s) inside of the treatment chamber(s) (2026) and/or the one or more surface(s) of the treated object(s) (2300). Without limitation, at least one or more of any suitable and effective shade(s) of green colored chamber light(s) (2925) and/or about these colored chamber light(s) (2925) can be shined into the treatment chamber(s) (2026) when the one or more step(s) for the one or more processing cycle(s) for any treated object(s) (2300) located inside of the treatment chamber(s) (2026) and/or the entire processing cycle, is suitably and effectively complete and/or any packaging activities and/or step(s), that might be taken, are also complete, and the said treated object(s) (2300) is ready for removal from the said treatment chamber(s) (2026). Without being limited, after one or more of any suitable, effective, and/or desired, processing cycle(s) for any treated object(s) (2300) located inside of the treatment chamber(s) (2026) is suitably and effectively complete and the said object(s) (2300) is removed from the said treatment chamber(s) (2026) and/or the one or more door(s) (2036) is opened, one or more of any suitable and effective shade(s) of white colored chamber light(s) (2925) and/or about these colored chamber light(s) (2925) can be shined into the treatment chamber(s) (2026).

Also, and without being limited, one or more of any suitable and effective shade(s) of red colored light(s) (2925) and/or about these colored chamber light(s) (2925) can also be shined into the treatment chamber(s) (2026) to indicate to anyone and/or indicate to the machine operator(s), one or more of any, non-conformance(s), error(s), failed step(s), system failure(s), and/or malfunction(s), at any time(s) and during any one or more part(s) and/or steps(s) of any entire processing cycle(s) such as, but not limited to, treating the various surface(s) inside of the treatment chamber(s) (2026) with the deployed agent(s) (2100), treating the one or more surface(s) of the treated object(s) (2300) with the deployed agent(s) (2100), drying and/or removing the deployed agent(s) (2100) from the various surface(s) inside of the treatment chamber(s) (2026), drying and/or removing the deployed agent(s) (2100) from the various surface(s) of the treated object(s) (2300), flowing and/or moving unheated air/gas(s) and/or unheated fresh air/gas(s) into, through, and out of, the treatment chamber(s) (2026). Without being limited, the said red colored chamber light(s) (2925) can also, and without limitation, suitably and effectively, strobe, pulse, and/or flash, at one or more of any suitable and effective rate(s) and/or intensity(s), at one or more of any suitable and effective time(s) and for any suitable and effective duration(s) of time(s).

Various other embodiments of the present invention are contemplated as being within the scope of the following claims.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. An enhanced decontamination enclosure for treating at least one object, comprising:
a holding chamber;
at least one inlet gas pathway communicates with said holding chamber, each one of said at least one inlet gas pathway includes a first inlet filter, an inlet blower communicates with an exhaust of said first inlet filter and a second inlet filter communicates with an exhaust of said inlet blower; and
at least one outlet gas pathway communicates with said holding chamber, each one of said at least one outlet gas pathway includes a first outlet filter, a charcoal filter communicates with an exhaust of said first outlet filter, a second outlet filter communicates with an exhaust of said charcoal filter and an outlet blower communicates with an exhaust of said second outlet filter; and a treatment device emits an airborne treatment substance into said holding chamber for treating the at least one object.

2. The enhanced decontamination enclosure for treating at least one object of claim 1, further comprising:
an exit of said at least one inlet gas pathway is located near a ceiling of said holding chamber, an entrance of said at least one outlet gas pathway is located near a floor of said holding chamber.

3. The enhanced decontamination enclosure for treating at least one object of claim 1, further comprising:
a circulation blower includes a circulation inlet and a circulation outlet, said circulation inlet communicates with said holding chamber, said circulation outlet communicates with said holding chamber.

4. The enhanced decontamination enclosure for treating at least one object of claim 3 wherein:
said circulation inlet is located near a ceiling of said holding chamber, said circulation outlet is located near a floor of said holding chamber.

5. The enhanced decontamination enclosure for treating at least one object of claim 1 wherein:
said second outlet filter is a HEPA rated filter, a ULPA rated filter or a MERV rated liter.

6. The enhanced decontamination enclosure for treating at least one object of claim 1, further comprising:
said treatment device includes a treatment inlet and treatment outlet, said treatment inlet is closed with a treatment inlet valve, said treatment outlet is closed with a treatment outlet valve.

7. The enhanced decontamination enclosure for treating at least one object of claim 1, further comprising:
an inlet heater communicates with an exhaust of said second inlet filter.

8. An enhanced decontamination enclosure for treating at least one object, comprising:
a holding chamber;
at least one inlet gas pathway communicates with said holding chamber, each one of said at least one inlet gas pathway includes an inlet valve and an inlet blower, said inlet valve is located proximate an exit of said at least one inlet gas pathway;
at least one outlet gas pathway communicates with said holding chamber, each one of said at least one outlet gas pathway includes an outlet valve and an outlet blower, said outlet valve is located proximate an entrance of said at least one outlet gas pathway;
a treatment device emits an airborne treatment substance into said holding chamber for treating the at least one object;
a circulation blower includes a circulation inlet in which gas enters from said holding chamber into said circulation blower and a circulation outlet in which gas is exhausted from said circulation blower into said holding chamber, said circulation inlet communicates with said holding chamber, said circulation outlet communicates with said holding chamber, said circulation inlet is located near a ceiling of said holding chamber, said circulation outlet is located proximate a floor of said holding chamber; and a controller operates opening and closing of said inlet valve and said outlet valve, wherein said controller closes said inlet and outlet valves when the at least object is treated with said treatment substance, said controller opens said inlet and outlet valves after treatment of the least one object to clear said holding chamber with said inlet and outlet blowers.

9. The enhanced decontamination enclosure for treating at least one object of claim 8 wherein:
a circulation inlet valve is located near said circulation inlet, a circulation outlet valve is located proximate said circulation outlet.

10. The enhanced decontamination enclosure for treating at least one object of claim 8, further comprising:
said treatment device includes a treatment inlet and treatment outlet, said treatment inlet is closed with a treatment inlet valve, said treatment outlet is closed with a treatment outlet valve.

11. The enhanced decontamination enclosure for treating at least one object of claim 8, further comprising:
an inlet heater is retained in said inlet gas pathway.

12. The enhanced decontamination enclosure for treating at least one object of claim 8, further comprising:
at least one inlet filter is retained in said inlet gas pathway, at least one outlet filter is retained in said outlet gas pathway.

13. An enhanced decontamination enclosure for treating at least one object, comprising:
a holding chamber;
at least one inlet gas pathway communicates with said holding chamber, each one of said at least one inlet gas pathway includes an inlet filter and an inlet blower, an inlet valve is located proximate an exit of said at least one inlet gas pathway; and
at least one outlet gas pathway communicates with said holding chamber, each one of said at least one outlet gas pathway includes an outlet filter and an outlet blower, an outlet valve is located proximate an entrance of said at least one outlet gas pathway;
a circulation blower includes a circulation inlet in which gas enters from said holding chamber into said circulation blower and a circulation outlet in which gas is exhausted from said circulation blower into said holding chamber, said circulation inlet communicates with said holding chamber, said circulation outlet communicates with said holding chamber, said circulation inlet is located near a ceiling of said holding chamber, said circulation outlet is located proximate a floor of said holding chamber; and
a treatment device emits an airborne treatment substance into said holding chamber, the airborne treatment substance treats the at least one object.

14. The enhanced decontamination enclosure for treating at least one object of claim 13 wherein:
a circulation inlet valve is located near said circulation inlet, a circulation outlet valve is located near said circulation outlet.

15. The enhanced decontamination enclosure for treating at least one object of claim 13, further comprising:
exhaust from said holding chamber is not fed back into said at least one gas inlet pathway of said holding chamber.

* * * * *